(12) United States Patent
Barany et al.

(10) Patent No.: US 11,466,311 B2
(45) Date of Patent: *Oct. 11, 2022

(54) METHOD FOR IDENTIFICATION AND QUANTIFICATION OF NUCLEIC ACID EXPRESSION, SPLICE VARIANT, TRANSLOCATION, COPY NUMBER, OR METHYLATION CHANGES

(71) Applicant: CORNELL UNIVERSITY, Ithaca, NY (US)

(72) Inventors: Francis Barany, New York, NY (US); John William Efcavitch, San Carlos, CA (US); Cristian Ruiz Rueda, Northridge, CA (US); Jianmin Huang, Elmhurst, NY (US); Philip B. Feinberg, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 427 days.

This patent is subject to a terminal disclaimer.

(21) Appl. No.: 16/433,971

(22) Filed: Jun. 6, 2019

(65) Prior Publication Data

US 2019/0316187 A1 Oct. 17, 2019

Related U.S. Application Data

(63) Continuation of application No. 15/517,727, filed as application No. PCT/US2015/054759 on Oct. 8, 2015, now Pat. No. 10,344,321.

(60) Provisional application No. 62/103,894, filed on Jan. 15, 2015, provisional application No. 62/061,376, filed on Oct. 8, 2014.

(51) Int. Cl.
*C12Q 1/6827* (2018.01)

(52) U.S. Cl.
CPC ...... *C12Q 1/6827* (2013.01); *C12Q 2600/118* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| 5,683,896 | A | 11/1997 | Hartley et al. | |
|---|---|---|---|---|
| 7,687,247 | B1 | 3/2010 | Hartley et al. | |
| 2003/0119004 | A1 | 6/2003 | Wenz et al. | |
| 2004/0219565 | A1* | 11/2004 | Kauppinen | C07H 19/16 435/5 |
| 2008/0299609 | A1 | 12/2008 | Kwon et al. | |
| 2010/0006437 | A1 | 1/2010 | Barany et al. | |
| 2010/0248228 | A1 | 9/2010 | Wang et al. | |
| 2011/0287436 | A1 | 11/2011 | Shannon et al. | |

FOREIGN PATENT DOCUMENTS

| CN | 1632132 A | 6/2005 |
|---|---|---|
| CN | 101329250 A | 12/2008 |
| CN | 101613730 A | 12/2009 |
| EP | 0522884 A1 | 7/1992 |
| JP | H6-90755 | 7/1991 |
| JP | 2000514659 A | 11/2000 |
| JP | 2006500034 A | 1/2006 |
| JP | 2000511060 A | 8/2008 |
| WO | 97/45559 A1 | 12/1997 |
| WO | 98/03673 | 1/1998 |
| WO | 2004/027082 A2 | 4/2004 |
| WO | 2005/092038 A2 | 10/2005 |
| WO | 2008/135512 A2 | 11/2008 |
| WO | 2013123220 A1 | 8/2013 |
| WO | 2014160199 A1 | 10/2014 |

OTHER PUBLICATIONS

Notice of Reasons for Rejection for Japanese Patent Application No. 2017-519282 (dated Jun. 3, 2020) with English Translation.
Notice of Reasons for Rejection for Japanese Patent Application No. 2017-519282 (dated Sep. 26, 2019) with English Translation.
Khanna et al., "Ligase Detection Reaction for Identification of Low Abundance Mutations," Clin. Biochem. 32 (4):287-290 (1999).
Wabuyele et al., "Approaching Real-Time Molecular Diagnostics: Single-Pair Fluorescence Resonance Energy Transfer (spFRET) Detection for the Analysis of Low Abundant Point Mutations in K-ras Oncogenes," J. Am. Chem. Soc. 125(23):6937-6945 (2003).
2010-2011 Applied Biosystems Molecular and Cell Biology Product Catalog p. 56 (2010).
Office Action for Canadian Patent Application No. 2963687 (dated Sep. 17, 2021).
International Search Report and Written Opinion for corresponding Application No. PCT/US2015/054759 (dated Apr. 1, 2016).
Extended European Search Report and Opinion For Corresponding EP Patent Application No. 15849301.5 (dated Feb. 1,2018).
English Translation and First Office Action for China Application No. 201580066531.3 (dated Apr. 24, 2020).
Extended European Search Report EP Patent Application No. 20150354.7 (dated May 29, 2020).
Schmittgen et al., "Real-Time PCR Quantification of Precursor and Mature MicroRNA," Methods 44(1):31-38 (2007).
Maroney et al., "A Rapid, Quantification Assay for Direct Detection of MicroRNAs and Other Small RNAs Using Splinted Ligation," RNA 13(6):930-936 (2007).

(Continued)

*Primary Examiner* — Amanda Haney
(74) *Attorney, Agent, or Firm* — Troutman Pepper Hamilton Sanders LLP

(57) ABSTRACT

The present invention relates to methods and devices for identifying and quantifying, including low abundance, nucleotide base mutations, insertions, deletions, translocations, splice variants, miRNA variants, alternative transcripts, alternative start sites, alternative coding sequences, alternative non-coding sequences, alternative splicings, exon insertions, exon deletions, intron insertions, or other rearrangement at the genome level and/or methylated nucleotide bases.

3 Claims, 182 Drawing Sheets

Specification includes a Sequence Listing.

(56) References Cited

OTHER PUBLICATIONS

Xiao et al., "Molecular Diagnosis of HIV and Relevant Novel Technologies in Mutation Analysis," Biotechnology Advances 26:389-397 (2008).
Mingmin et al., "Hanghai Scientific and Technological Literature Press," Medical Genetics, 3rd Edition p. 328-330 (2013).
Office Action for Australian Patent Application No. 2015330844 (dated Jan. 27, 2021).
Office Action for Brazilian Patent Application No. 112017007033-2 and informal translation (dated Dec. 17, 2019).
Office Action for EP Patent Application No. 15849301.5 (dated May 2, 2019).
Yamane et al., "X Chromosome Methylation-Based Chimerism Assay for Sex-Mismatched Hematopoietic Stem Cell Transplantation," Bone Marrow Transplantation Nature Publishing Group 28(10):1969-973 (2001).
Wyn-Jones et al., "Surveillance of Adenoviruses and Noroviruses in European Recreational Waters," Water Research 45(3):1025-1038 (2011).
Yap et al., "False-Positives and Contamination in PCR," CRC Press pp. 249-258 (1994).
Schmittgen et al., "Real-Time PCR Quantification of Precursor and Mature MicroRNA," Methods 44(1):131-38 (2008).
Maroney et al., "A Rapid, Quantitative Assay for Direct Detection of MicroRNAs and Other Small RNAs Using Splinted Ligation," RNA 13(6):1930-936 (2007).
EP Search Report and Written Opinion for EP 21202762.7, dated Jun. 7, 2022.
Office Action for Israel Application No. 286496 and English Translation (dated Apr. 24, 2022).
Office Action for JP Patent Application No. 2021-068936 and English Translation (dated Jun. 13, 2022).

\* cited by examiner (Multiplexed PCR & RT-PCR; LDR w/Tags, 24 samples)

Real-Time PCR results, 24 samples (Distribute 1 sample into 24 tubes (wells), then Multiplexed PCR; LDR w/Tags)

Real-Time PCR results, 1 sample
w/ "Pixel" Enumeration

Dilute 1 sample into 24 tubes (wells), then Multiplexed RT-PCR; LDR w/Tags (Dilute 1 sample into 24 tubes (wells), then Multiplexed RT-PCR; LDR w/Tags)

Real-Time PCR results, 1 sample
w/ "Pixel" Enumeration (Multiplexed PCR & RT-PCR; 24 samples)

LDR-FRET results, 24 samples

Distribute 1 sample into 24 tubes (wells), then Multiplexed PCR

PCR Products Captured on Solid Support (Distribute 1 sample into 24 tubes (wells), then Multiplexed PCR)

LDR-FRET results, 1 sample
w/ "Pixel" Enumeration

Dilute 1 sample into 24 tubes (wells), then Multiplexed RT-PCR

RT-PCR Products Captured on Solid Support (Dilute 1 sample into 24 tubes (wells), then Multiplexed RT-PCR)

LDR-FRET results, 1 sample
w/ "Pixel" Enumeration

Poisson Distribution of 6 to 48 molecules in 24 wells

| Wells with | 6 | 12 | 18 | 24 | 30 | 36 | 42 | 48 |
|---|---|---|---|---|---|---|---|---|
| 0 | 19 | 15 | 11 | 9 | 7 | 5 | 4 | 3 |
| 1 | 5 | 7 | 9 | 9 | 9 | 8 | 7 | 6 |
| 2 | 1 | 2 | 3 | 4 | 5 | 6 | 6 | 6 |
| 3 | 0 | 0 | 1 | 1 | 2 | 3 | 4 | 4 |
| 4 | 0 | 0 | 0 | 0 | 1 | 1 | 2 | 2 |
| 5 | 0 | 0 | 0 | 0 | 0 | 0 | 1 | 1 |
| 6 | 0 | 0 | 0 | 0 | 0 | 0 | 0 | 0 |
| 7 | 0 | 0 | 0 | 0 | 0 | 0 | 0 | 0 |
| 8 | 0 | 0 | 0 | 0 | 0 | 0 | 0 | 0 |
| 9 | 0 | 0 | 0 | 0 | 0 | 0 | 0 | 0 |
| 10 | 0 | 0 | 0 | 0 | 0 | 0 | 0 | 0 |
| 11 | 0 | 0 | 0 | 0 | 0 | 0 | 0 | 0 |
| 12 | 0 | 0 | 0 | 0 | 0 | 0 | 0 | 0 |
| 13 | 0 | 0 | 0 | 0 | 0 | 0 | 0 | 0 |
| 14 | 0 | 0 | 0 | 0 | 0 | 0 | 0 | 0 |
| 15 | 0 | 0 | 0 | 0 | 0 | 0 | 0 | 0 |
| 16 | 0 | 0 | 0 | 0 | 0 | 0 | 0 | 0 |
| 17 | 0 | 0 | 0 | 0 | 0 | 0 | 0 | 0 |
| 18 | 0 | 0 | 0 | 0 | 0 | 0 | 0 | 0 |
| 19 | 0 | 0 | 0 | 0 | 0 | 0 | 0 | 0 |
| 20 | 0 | 0 | 0 | 0 | 0 | 0 | 0 | 0 |
| 21 | 0 | 0 | 0 | 0 | 0 | 0 | 0 | 0 |
| 22 | 0 | 0 | 0 | 0 | 0 | 0 | 0 | 0 |
| 23 | 0 | 0 | 0 | 0 | 0 | 0 | 0 | 0 |

Poisson Distribution of 12 to 96 molecules in 24 wells

| Wells with | 12 | 24 | 36 | 48 | 60 | 72 | 84 | 96 |
|---|---|---|---|---|---|---|---|---|
| 0 | 15 | 9 | 5 | 3 | 2 | 1 | 1 | 0 |
| 1 | 7 | 9 | 8 | 6 | 5 | 4 | 3 | 2 |
| 2 | 2 | 4 | 6 | 6 | 6 | 5 | 4 | 4 |
| 3 | 0 | 1 | 3 | 4 | 5 | 5 | 5 | 5 |
| 4 | 0 | 0 | 1 | 2 | 3 | 4 | 5 | 5 |
| 5 | 0 | 0 | 0 | 1 | 2 | 2 | 3 | 4 |
| 6 | 0 | 0 | 0 | 0 | 1 | 1 | 2 | 3 |
| 7 | 0 | 0 | 0 | 0 | 0 | 1 | 1 | 1 |
| 8 | 0 | 0 | 0 | 0 | 0 | 0 | 0 | 1 |
| 9 | 0 | 0 | 0 | 0 | 0 | 0 | 0 | 0 |
| 10 | 0 | 0 | 0 | 0 | 0 | 0 | 0 | 0 |
| 11 | 0 | 0 | 0 | 0 | 0 | 0 | 0 | 0 |
| 12 | 0 | 0 | 0 | 0 | 0 | 0 | 0 | 0 |
| 13 | 0 | 0 | 0 | 0 | 0 | 0 | 0 | 0 |
| 14 | 0 | 0 | 0 | 0 | 0 | 0 | 0 | 0 |
| 15 | 0 | 0 | 0 | 0 | 0 | 0 | 0 | 0 |
| 16 | 0 | 0 | 0 | 0 | 0 | 0 | 0 | 0 |
| 17 | 0 | 0 | 0 | 0 | 0 | 0 | 0 | 0 |
| 18 | 0 | 0 | 0 | 0 | 0 | 0 | 0 | 0 |
| 19 | 0 | 0 | 0 | 0 | 0 | 0 | 0 | 0 |
| 20 | 0 | 0 | 0 | 0 | 0 | 0 | 0 | 0 |
| 21 | 0 | 0 | 0 | 0 | 0 | 0 | 0 | 0 |
| 22 | 0 | 0 | 0 | 0 | 0 | 0 | 0 | 0 |
| 23 | 0 | 0 | 0 | 0 | 0 | 0 | 0 | 0 |

Poisson Distribution of 12 to 96 molecules in 48 wells

| Wells with | 12 | 24 | 36 | 48 | 60 | 72 | 84 | 96 |
|---|---|---|---|---|---|---|---|---|
| 0 | 37 | 29 | 23 | 18 | 14 | 11 | 8 | 6 |
| 1 | 9 | 15 | 17 | 18 | 17 | 16 | 15 | 13 |
| 2 | 1 | 4 | 6 | 9 | 11 | 12 | 13 | 13 |
| 3 | 0 | 1 | 2 | 3 | 4 | 6 | 7 | 9 |
| 4 | 0 | 0 | 0 | 1 | 1 | 2 | 3 | 4 |
| 5 | 0 | 0 | 0 | 0 | 0 | 1 | 1 | 2 |
| 6 | 0 | 0 | 0 | 0 | 0 | 0 | 0 | 1 |
| 7 | 0 | 0 | 0 | 0 | 0 | 0 | 0 | 0 |
| 8 | 0 | 0 | 0 | 0 | 0 | 0 | 0 | 0 |
| 9 | 0 | 0 | 0 | 0 | 0 | 0 | 0 | 0 |
| 10 | 0 | 0 | 0 | 0 | 0 | 0 | 0 | 0 |
| 11 | 0 | 0 | 0 | 0 | 0 | 0 | 0 | 0 |
| 12 | 0 | 0 | 0 | 0 | 0 | 0 | 0 | 0 |
| 13 | 0 | 0 | 0 | 0 | 0 | 0 | 0 | 0 |
| 14 | 0 | 0 | 0 | 0 | 0 | 0 | 0 | 0 |
| 15 | 0 | 0 | 0 | 0 | 0 | 0 | 0 | 0 |
| 16 | 0 | 0 | 0 | 0 | 0 | 0 | 0 | 0 |
| 17 | 0 | 0 | 0 | 0 | 0 | 0 | 0 | 0 |
| 18 | 0 | 0 | 0 | 0 | 0 | 0 | 0 | 0 |
| 19 | 0 | 0 | 0 | 0 | 0 | 0 | 0 | 0 |
| 20 | 0 | 0 | 0 | 0 | 0 | 0 | 0 | 0 |
| 21 | 0 | 0 | 0 | 0 | 0 | 0 | 0 | 0 |
| 22 | 0 | 0 | 0 | 0 | 0 | 0 | 0 | 0 |
| ... | ... | ... | ... | ... | ... | ... | ... | ... |
| 47 | 0 | 0 | 0 | 0 | 0 | 0 | 0 | 0 |

Poisson Distribution of 24 to 192 molecules in 48 wells

| Wells with | 24 | 48 | 72 | 96 | 120 | 144 | 168 | 192 |
|---|---|---|---|---|---|---|---|---|
| 0 | 29 | 18 | 11 | 6 | 4 | 2 | 1 | 1 |
| 1 | 15 | 18 | 16 | 13 | 10 | 7 | 5 | 4 |
| 2 | 4 | 9 | 12 | 13 | 12 | 11 | 9 | 7 |
| 3 | 1 | 3 | 6 | 9 | 10 | 11 | 10 | 9 |
| 4 | 0 | 1 | 2 | 4 | 6 | 8 | 9 | 9 |
| 5 | 0 | 0 | 1 | 2 | 3 | 5 | 6 | 8 |
| 6 | 0 | 0 | 0 | 1 | 1 | 2 | 4 | 5 |
| 7 | 0 | 0 | 0 | 0 | 0 | 1 | 2 | 3 |
| 8 | 0 | 0 | 0 | 0 | 0 | 0 | 1 | 1 |
| 9 | 0 | 0 | 0 | 0 | 0 | 0 | 0 | 1 |
| 10 | 0 | 0 | 0 | 0 | 0 | 0 | 0 | 0 |
| 11 | 0 | 0 | 0 | 0 | 0 | 0 | 0 | 0 |
| 12 | 0 | 0 | 0 | 0 | 0 | 0 | 0 | 0 |
| 13 | 0 | 0 | 0 | 0 | 0 | 0 | 0 | 0 |
| 14 | 0 | 0 | 0 | 0 | 0 | 0 | 0 | 0 |
| 15 | 0 | 0 | 0 | 0 | 0 | 0 | 0 | 0 |
| 16 | 0 | 0 | 0 | 0 | 0 | 0 | 0 | 0 |
| 17 | 0 | 0 | 0 | 0 | 0 | 0 | 0 | 0 |
| 18 | 0 | 0 | 0 | 0 | 0 | 0 | 0 | 0 |
| 19 | 0 | 0 | 0 | 0 | 0 | 0 | 0 | 0 |
| 20 | 0 | 0 | 0 | 0 | 0 | 0 | 0 | 0 |
| 21 | 0 | 0 | 0 | 0 | 0 | 0 | 0 | 0 |
| 22 | 0 | 0 | 0 | 0 | 0 | 0 | 0 | 0 |
| ... | ... | ... | ... | ... | ... | ... | ... | ... |
| 47 | 0 | 0 | 0 | 0 | 0 | 0 | 0 | 0 |

Poisson Distribution of 1 to 8 molecules in 8 wells

| Wells with | 1 | 2 | 3 | 4 | 5 | 6 | 7 | 8 |
|---|---|---|---|---|---|---|---|---|
| 0 | 7 | 6 | 5 | 5 | 4 | 4 | 3 | 3 |
| 1 | 1 | 2 | 2 | 2 | 3 | 3 | 3 | 3 |
| 2 | 0 | 0 | 0 | 1 | 1 | 1 | 1 | 1 |
| 3 | 0 | 0 | 0 | 0 | 0 | 0 | 0 | 0 |
| 4 | 0 | 0 | 0 | 0 | 0 | 0 | 0 | 0 |
| 5 | 0 | 0 | 0 | 0 | 0 | 0 | 0 | 0 |
| 6 | 0 | 0 | 0 | 0 | 0 | 0 | 0 | 0 |
| 7 | 0 | 0 | 0 | 0 | 0 | 0 | 0 | 0 |

Poisson Distribution of 2 to 16 molecules in 8 wells

| Wells with | 2 | 4 | 6 | 8 | 10 | 12 | 14 | 16 |
|---|---|---|---|---|---|---|---|---|
| 0 | 6 | 5 | 4 | 3 | 2 | 2 | 1 | 1 |
| 1 | 2 | 2 | 3 | 3 | 3 | 3 | 2 | 2 |
| 2 | 0 | 1 | 1 | 1 | 2 | 2 | 2 | 2 |
| 3 | 0 | 0 | 0 | 0 | 1 | 1 | 1 | 1 |
| 4 | 0 | 0 | 0 | 0 | 0 | 0 | 1 | 1 |
| 5 | 0 | 0 | 0 | 0 | 0 | 0 | 0 | 0 |
| 6 | 0 | 0 | 0 | 0 | 0 | 0 | 0 | 0 |
| 7 | 0 | 0 | 0 | 0 | 0 | 0 | 0 | 0 |

Poisson Distribution of 4 to 32 molecules in 8 wells

| Wells with | 4 | 8 | 12 | 16 | 20 | 24 | 28 | 32 |
|---|---|---|---|---|---|---|---|---|
| 0 | 5 | 3 | 2 | 1 | 1 | 0 | 0 | 0 |
| 1 | 2 | 3 | 3 | 2 | 2 | 1 | 1 | 1 |
| 2 | 1 | 1 | 2 | 2 | 2 | 2 | 1 | 1 |
| 3 | 0 | 0 | 1 | 1 | 2 | 2 | 2 | 2 |
| 4 | 0 | 0 | 0 | 1 | 1 | 1 | 2 | 2 |
| 5 | 0 | 0 | 0 | 0 | 1 | 1 | 1 | 1 |
| 6 | 0 | 0 | 0 | 0 | 0 | 0 | 1 | 1 |
| 7 | 0 | 0 | 0 | 0 | 0 | 0 | 0 | 0 |
| 8 | 0 | 0 | 0 | 0 | 0 | 0 | 0 | 0 |
| 9 | 0 | 0 | 0 | 0 | 0 | 0 | 0 | 0 |
| 10 | 0 | 0 | 0 | 0 | 0 | 0 | 0 | 0 |
| 11 | 0 | 0 | 0 | 0 | 0 | 0 | 0 | 0 |
| 12 | 0 | 0 | 0 | 0 | 0 | 0 | 0 | 0 |
| 13 | 0 | 0 | 0 | 0 | 0 | 0 | 0 | 0 |
| 14 | 0 | 0 | 0 | 0 | 0 | 0 | 0 | 0 |
| 15 | 0 | 0 | 0 | 0 | 0 | 0 | 0 | 0 |
| 16 | 0 | 0 | 0 | 0 | 0 | 0 | 0 | 0 |
| 17 | 0 | 0 | 0 | 0 | 0 | 0 | 0 | 0 |
| 18 | 0 | 0 | 0 | 0 | 0 | 0 | 0 | 0 |
| 19 | 0 | 0 | 0 | 0 | 0 | 0 | 0 | 0 |
| 20 | 0 | 0 | 0 | 0 | 0 | 0 | 0 | 0 |
| 21 | 0 | 0 | 0 | 0 | 0 | 0 | 0 | 0 |
| 22 | 0 | 0 | 0 | 0 | 0 | 0 | 0 | 0 |
| 23 | 0 | 0 | 0 | 0 | 0 | 0 | 0 | 0 |

Poisson Distribution of 8 to 64 molecules in 8 wells

| Wells with | 8 | 16 | 24 | 32 | 40 | 48 | 56 | 64 |
|---|---|---|---|---|---|---|---|---|
| 0 | 3 | 1 | 0 | 0 | 0 | 0 | 0 | 0 |
| 1 | 3 | 2 | 1 | 1 | 0 | 0 | 0 | 0 |
| 2 | 1 | 2 | 2 | 1 | 1 | 0 | 0 | 0 |
| 3 | 0 | 1 | 2 | 2 | 1 | 1 | 0 | 0 |
| 4 | 0 | 1 | 1 | 2 | 1 | 1 | 1 | 0 |
| 5 | 0 | 0 | 1 | 1 | 1 | 1 | 1 | 1 |
| 6 | 0 | 0 | 0 | 1 | 1 | 1 | 1 | 1 |
| 7 | 0 | 0 | 0 | 0 | 1 | 1 | 1 | 1 |
| 8 | 0 | 0 | 0 | 0 | 1 | 1 | 1 | 1 |
| 9 | 0 | 0 | 0 | 0 | 0 | 1 | 1 | 1 |
| 10 | 0 | 0 | 0 | 0 | 0 | 0 | 1 | 1 |
| 11 | 0 | 0 | 0 | 0 | 0 | 0 | 0 | 1 |
| 12 | 0 | 0 | 0 | 0 | 0 | 0 | 0 | 0 |
| 13 | 0 | 0 | 0 | 0 | 0 | 0 | 0 | 0 |
| 14 | 0 | 0 | 0 | 0 | 0 | 0 | 0 | 0 |
| 15 | 0 | 0 | 0 | 0 | 0 | 0 | 0 | 0 |
| 16 | 0 | 0 | 0 | 0 | 0 | 0 | 0 | 0 |
| 17 | 0 | 0 | 0 | 0 | 0 | 0 | 0 | 0 |
| 18 | 0 | 0 | 0 | 0 | 0 | 0 | 0 | 0 |
| 19 | 0 | 0 | 0 | 0 | 0 | 0 | 0 | 0 |
| 20 | 0 | 0 | 0 | 0 | 0 | 0 | 0 | 0 |
| 21 | 0 | 0 | 0 | 0 | 0 | 0 | 0 | 0 |
| 22 | 0 | 0 | 0 | 0 | 0 | 0 | 0 | 0 |
| 23 | 0 | 0 | 0 | 0 | 0 | 0 | 0 | 0 |

Poisson Distribution of 16 to 128 molecules in 8 wells

| Wells with | 16 | 32 | 48 | 64 | 80 | 96 | 112 | 128 |
|---|---|---|---|---|---|---|---|---|
| 0 | 1 | 0 | 0 | 0 | 0 | 0 | 0 | 0 |
| 1 | 2 | 1 | 0 | 0 | 0 | 0 | 0 | 0 |
| 2 | 2 | 1 | 0 | 0 | 0 | 0 | 0 | 0 |
| 3 | 1 | 2 | 1 | 0 | 0 | 0 | 0 | 0 |
| 4 | 1 | 2 | 1 | 0 | 0 | 0 | 0 | 0 |
| 5 | 0 | 1 | 1 | 1 | 0 | 0 | 0 | 0 |
| 6 | 0 | 1 | 1 | 1 | 1 | 0 | 0 | 0 |
| 7 | 0 | 0 | 1 | 1 | 1 | 0 | 0 | 0 |
| 8 | 0 | 0 | 1 | 1 | 1 | 1 | 0 | 0 |
| 9 | 0 | 0 | 1 | 1 | 1 | 1 | 0 | 0 |
| 10 | 0 | 0 | 0 | 1 | 1 | 1 | 1 | 0 |
| 11 | 0 | 0 | 0 | 1 | 1 | 1 | 1 | 0 |
| 12 | 0 | 0 | 0 | 0 | 1 | 1 | 1 | 1 |
| 13 | 0 | 0 | 0 | 0 | 1 | 1 | 1 | 1 |
| 14 | 0 | 0 | 0 | 0 | 0 | 1 | 1 | 1 |
| 15 | 0 | 0 | 0 | 0 | 0 | 1 | 1 | 1 |
| 16 | 0 | 0 | 0 | 0 | 0 | 0 | 1 | 1 |
| 17 | 0 | 0 | 0 | 0 | 0 | 0 | 1 | 1 |
| 18 | 0 | 0 | 0 | 0 | 0 | 0 | 0 | 1 |
| 19 | 0 | 0 | 0 | 0 | 0 | 0 | 0 | 1 |
| 20 | 0 | 0 | 0 | 0 | 0 | 0 | 0 | 0 |
| 21 | 0 | 0 | 0 | 0 | 0 | 0 | 0 | 0 |
| 22 | 0 | 0 | 0 | 0 | 0 | 0 | 0 | 0 |
| 23 | 0 | 0 | 0 | 0 | 0 | 0 | 0 | 0 |

A. PCR-LDR-qPCR carryover prevention reaction to detect mutation. Isolate genomic or cfDNA.

B. Treat with UDG (uracil DNA glycosylase) for carryover prevention, and amplify mutation containing regions using PCR (and dUTP) with locus-specific primers. Perform limited cycle amplification (12-20) to maintain relative ratios of different amplicons. (Optional: aliquot into 12, 24, 48, or 96 wells prior to PCR step.)

C. PCR products incorporate dU, allowing for carryover prevention.

D. Mutation-specific ligation oligonucleotides contain tags (Ai, Ci') for subsequent PCR amplification. Ligase covalently seals the two oligonucleotides together. Aliquot into separate wells for detection. (LDR products are not amplified by either original PCR or LDR primers, providing additional protection.)

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

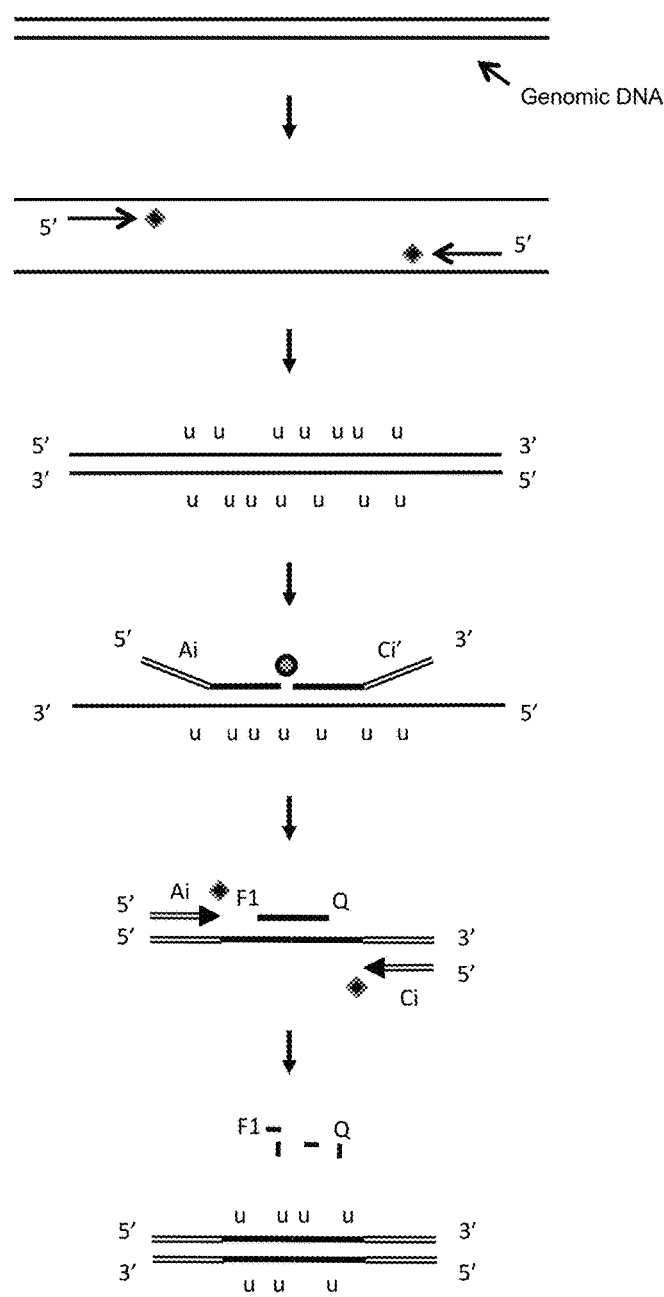

Figure 38

A. PCR-qLDR carryover prevention reaction to detect mutation. Isolate genomic or cfDNA.

B. Treat with UDG (uracil DNA glycosylase) for carryover prevention, aliquot into 12, 24, 48, or 96 wells, and amplify mutation containing regions using PCR (and dUTP) with locus-specific primers. Perform limited cycle amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Mutation-specific ligation oligonucleotides contain complementary tails for subsequent FRET detection. Ligase covalently seals the two oligonucleotides together. (LDR products are not amplified by either original PCR or LDR primers, providing additional protection.)

E. Wash away unligated primers. Denature product from target, allowing tails to hybridize and bringing donor (D) and fluorescent group (F1) in close proximity. Then detect, and enumerate FRET signal.

Or

F. Mutation-specific ligation oligonucleotides contain complementary tails for subsequent fluorescent detection. Ligase covalently seals the two oligonucleotides together.

G. Denature product from target, allowing tails to hybridize and separate quencher (Q) from fluorescent reporter (F1). Then detect, and enumerate un-quenched fluorescent signal.

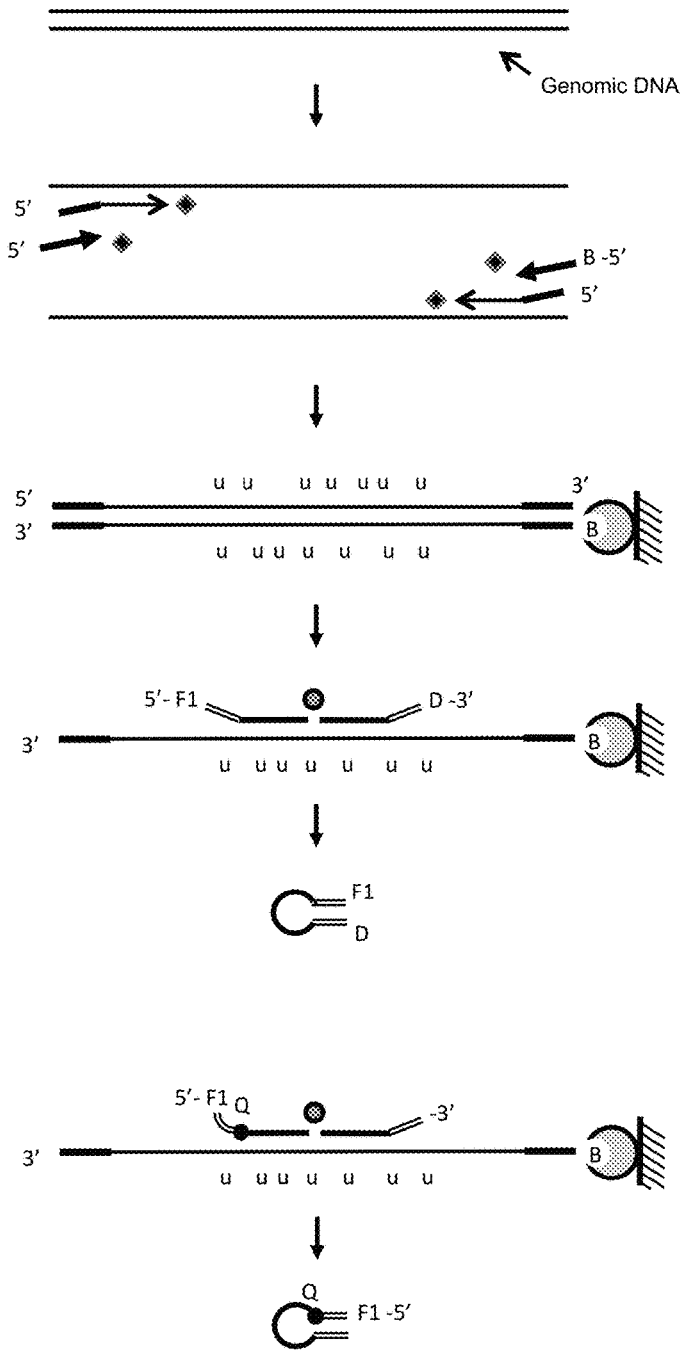

Figure 39

A. PCR-LDR-qPCR carryover prevention reaction to detect mutation. Isolate genomic or cfDNA.

B. Treat with UDG (uracil DNA glycosylase) for carryover prevention. Locus-specific primers are unblocked with RNaseH2 only when bound to target. Amplify mutation containing regions using PCR (and dUTP). Perform limited cycle amplification (12-20) to maintain relative ratios of different amplicons. (Optional: aliquot into 12, 24, 48, or 96 wells prior to PCR.)

C. PCR products incorporate dU, allowing for carryover prevention.

D. Mutation-specific ligation oligonucleotides contain tags (Ai, Ci') for subsequent PCR amplification. Ligase covalently seals the two oligonucleotides together. Aliquot into separate wells for detection. (LDR products are not amplified by either original PCR or LDR primers, providing additional protection.)

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

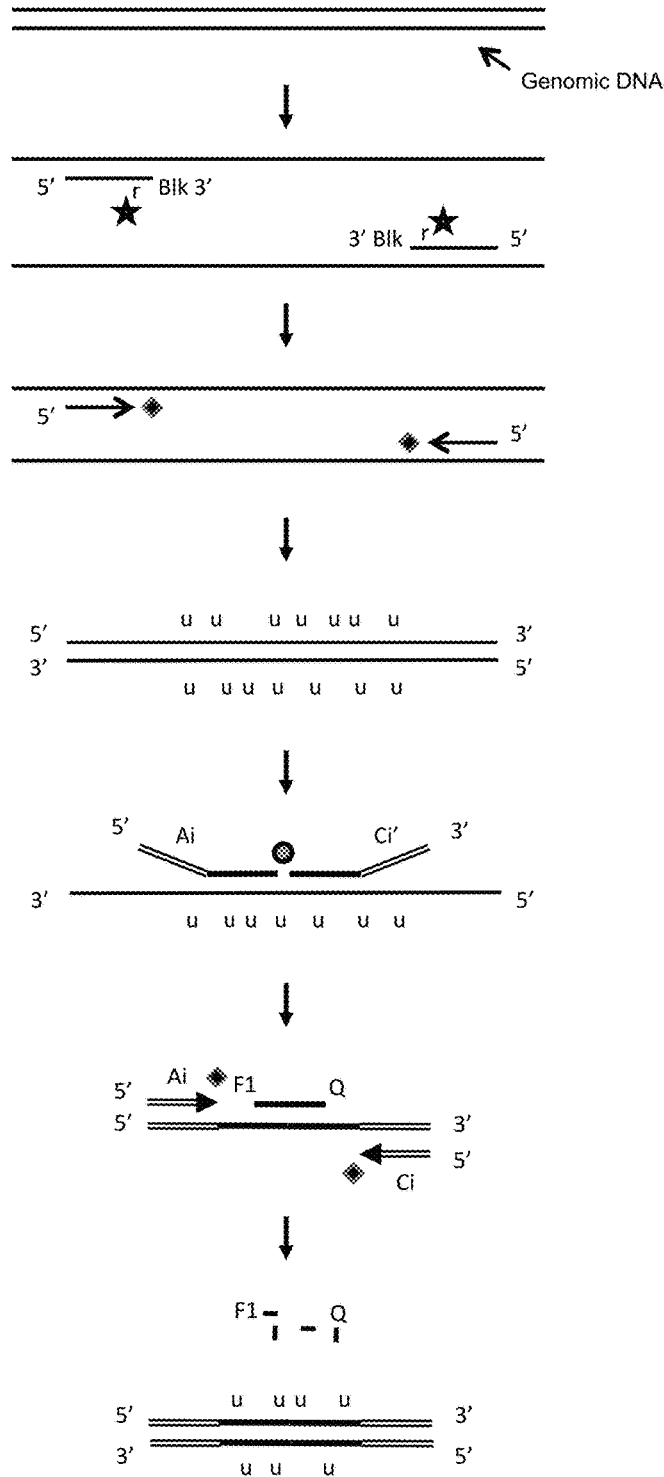

Figure 40

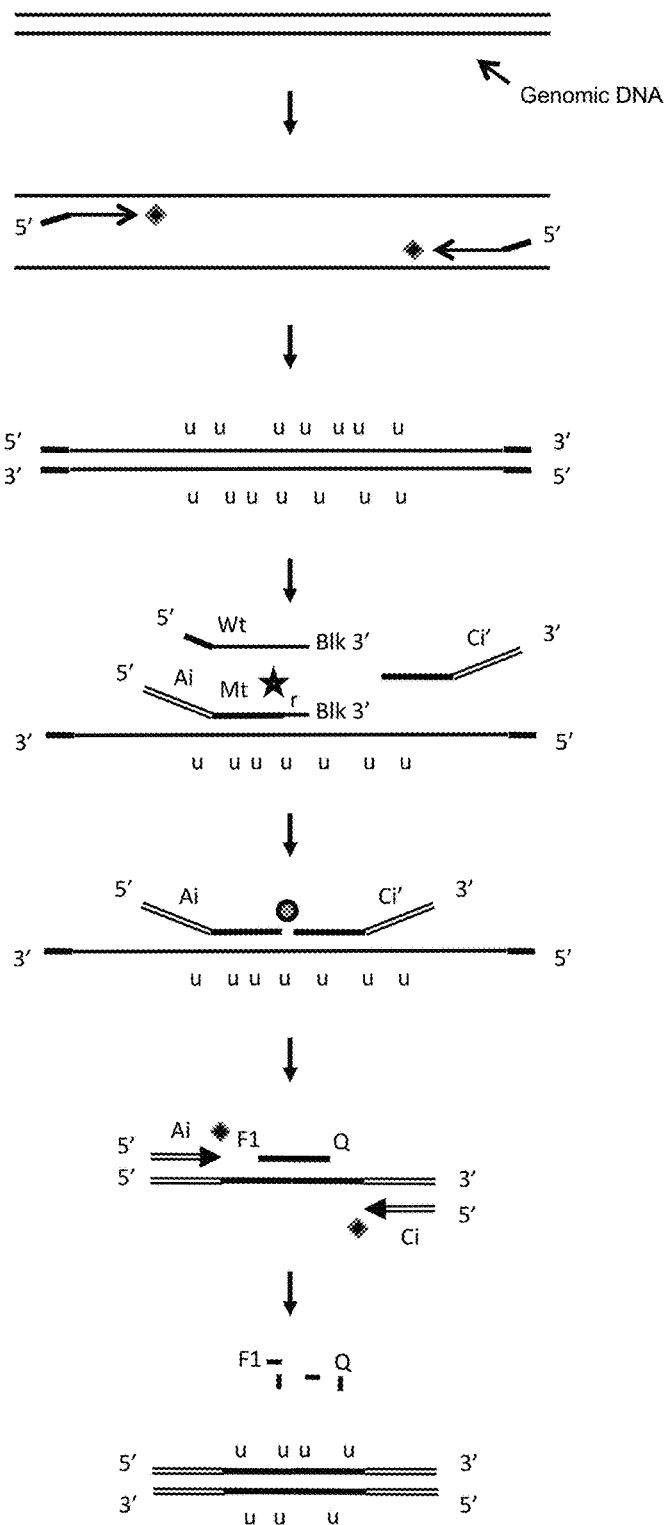

A. PCR-LDR-qPCR carryover prevention reaction to detect mutation. Isolate genomic or cfDNA.

B. Treat with UDG for carryover prevention, and amplify mutation containing regions using PCR (and dUTP) with locus-specific primers. Perform limited cycle amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Mutation-specific ligation oligonucleotides (Mt) contain tags (Ai, Ci') for subsequent PCR amplification, while wild-type probe (Wt) does not. Upstream ligation primer contains block, which may be removed by cleaving ribose base with RNaseH2 only when hybridized to target.

E. Ligase covalently seals the unblocked upstream and phosphorylated downstream oligonucleotides together. Aliquot into separate wells for detection.

F. Treat with UDG for carryover prevention, which also destroys original target amplicons. Only authentic LDR products will amplify, when using PCR (and dUTP) with tag-specific primers (Ai, Ci'). Each Taqman probe spans the ligation junction.

G. The 5'->3' nuclease activity of Taq polymerase liberates the fluorescent group to generate signal. (PCR products incorporate dU, allowing for carryover prevention.)

Figure 41

A. PCR-qLDR carryover prevention reaction to detect mutation. Isolate genomic or cfDNA.

B. Treat with UDG (uracil DNA glycosylase) for carryover prevention, aliquot into 12, 24, 48, or 96 wells, and amplify mutation containing regions using PCR (and dUTP) with locus-specific primers. Perform limited cycle amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Mutation-specific ligation oligonucleotides (Mt) contain tails for subsequent FRET detection, while wild-type probe (Wt) does not. Upstream ligation primer contains block, which may be removed by cleaving ribose base with RNaseH2 only when hybridized to target.

E. Ligase covalently seals the unblocked upstream and phosphorylated downstream oligonucleotides together.

F. Wash away unligated primers. Denature product from target, then detect, and enumerate FRET signal.

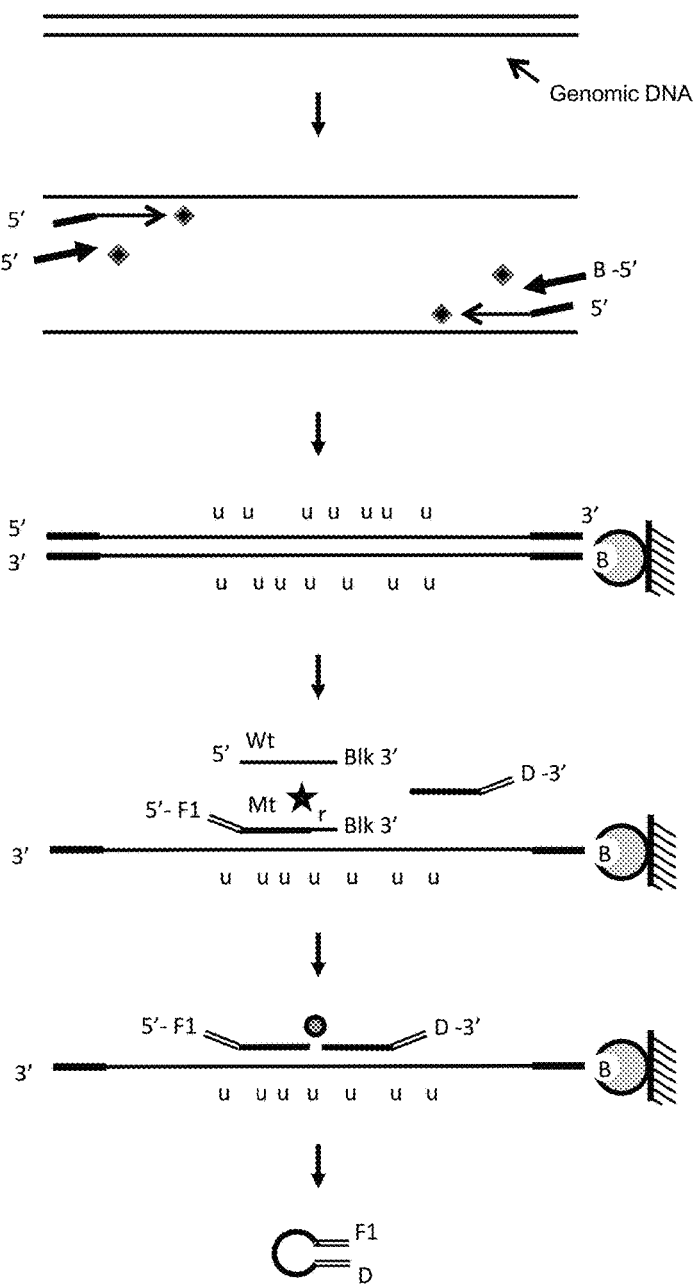

Figure 42

A. PCR-qLDR carryover prevention reaction to detect mutation. Isolate genomic or cfDNA.

B. Treat with UDG (uracil DNA glycosylase) for carryover prevention, aliquot into 12, 24, 48, or 96 wells, and amplify mutation containing regions using PCR (and dUTP) with locus-specific primers. Perform limited cycle amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Mutation-specific ligation oligonucleotides (Mt) overlap at the mutation base, and contain tails for subsequent FRET detection, while wild-type probe (Wt) does not. 5'-nuclease activity of polymerase cleaves off only matching 5'-overlapping base and additional flap, leaving ligation-competent 5-phosphate.

E. Ligase covalently seals the upstream and unblocked phosphorylated downstream oligonucleotides together.

F. Wash away unligated primers. Denature product from target, then detect, and enumerate FRET signal.

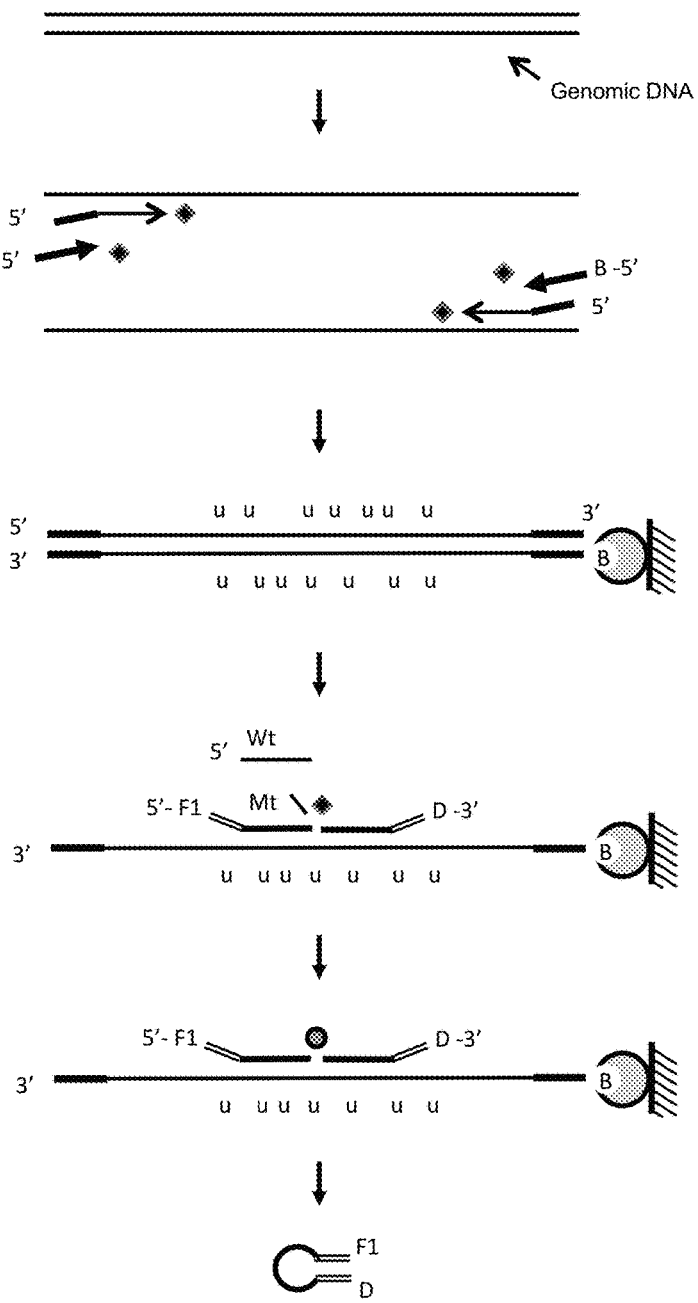

Figure 43

A. PCR-LDR-qPCR carryover prevention reaction to detect mutation. Isolate genomic or cfDNA.

B. Treat with UDG for carryover prevention, and amplify mutation containing regions using PCR (and dUTP) with locus-specific primers. Perform limited cycle amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Mutation-specific ligation oligonucleotides contain tags (Ai, Bi'-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal. (PCR products incorporate dU, allowing for carryover prevention.)

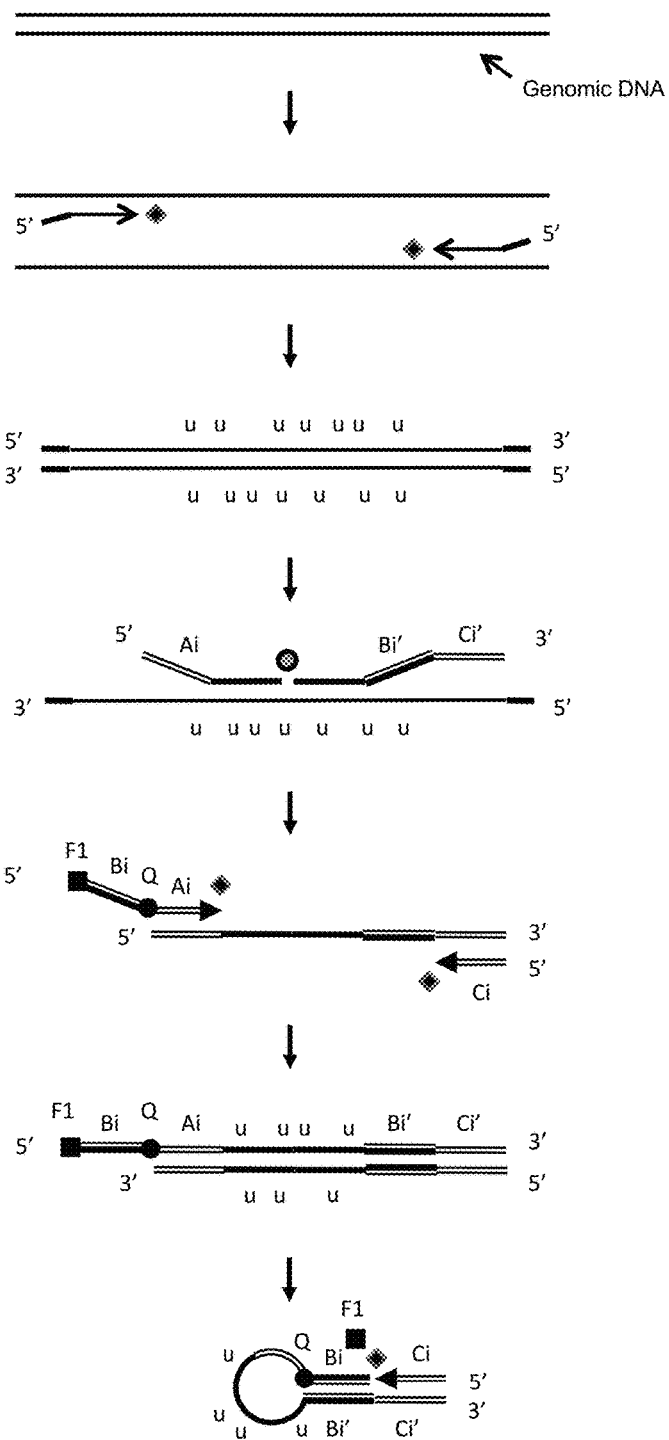

Figure 44

A. PCR-LDR-qPCR carryover prevention reaction to detect methylation. Isolate genomic or cfDNA. Optional: enrich for methylated DNA using antibodies. Treat with methyl-sensitive restriction endonucleases Bsh1236I (CG^CG) and HinP1I (G^CGC), and UNG (37oC, 30-60 minutes) to completely digest unmethylated DNA and prevent carryover.

B. Amplify methyl containing regions using PCR (and dUTP) with locus-specific primers. Perform limited cycle amplification (12-20) to maintain relative ratios of different amplicons. (Optional: aliquot into 12, 24, 48, or 96 wells prior to PCR.)

C. PCR products incorporate dU, allowing for carryover prevention. (Products lack methyl groups, providing additional protection.)

D. Methyl region-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

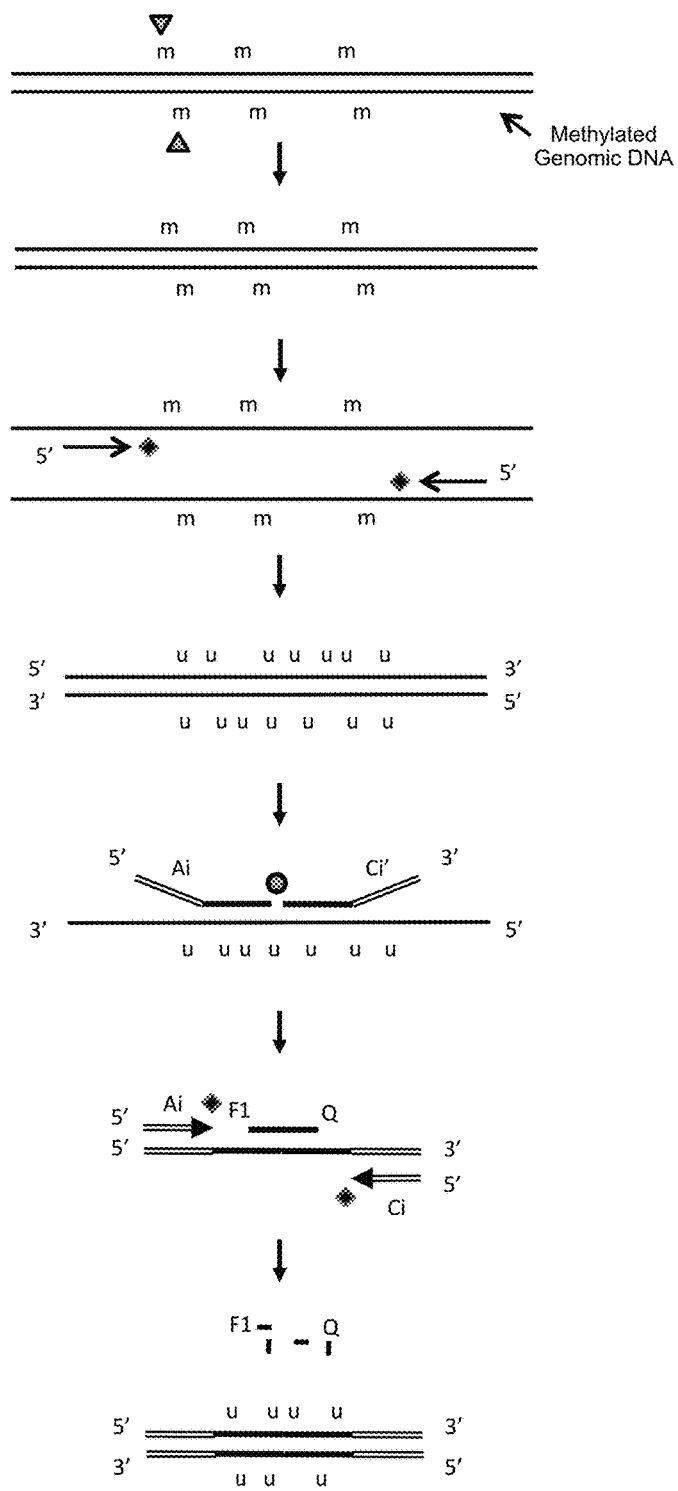

Figure 45

A. PCR-LDR-qPCR carryover prevention reaction to detect methylation. Isolate genomic or cfDNA. Treat with Bsh1236I (CG^CG) and HinP1I (G^CGC), and UNG (37oC, 30-60 minutes) to completely digest unmethylated DNA and prevent carryover.

B. Amplify methyl containing regions using PCR (and dUTP) with locus-specific primers. Perform limited cycle amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Methyl region-specific ligation oligonucleotides contain tags (Ai, Bi'-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal. (PCR products incorporate dU, allowing for carryover prevention.)

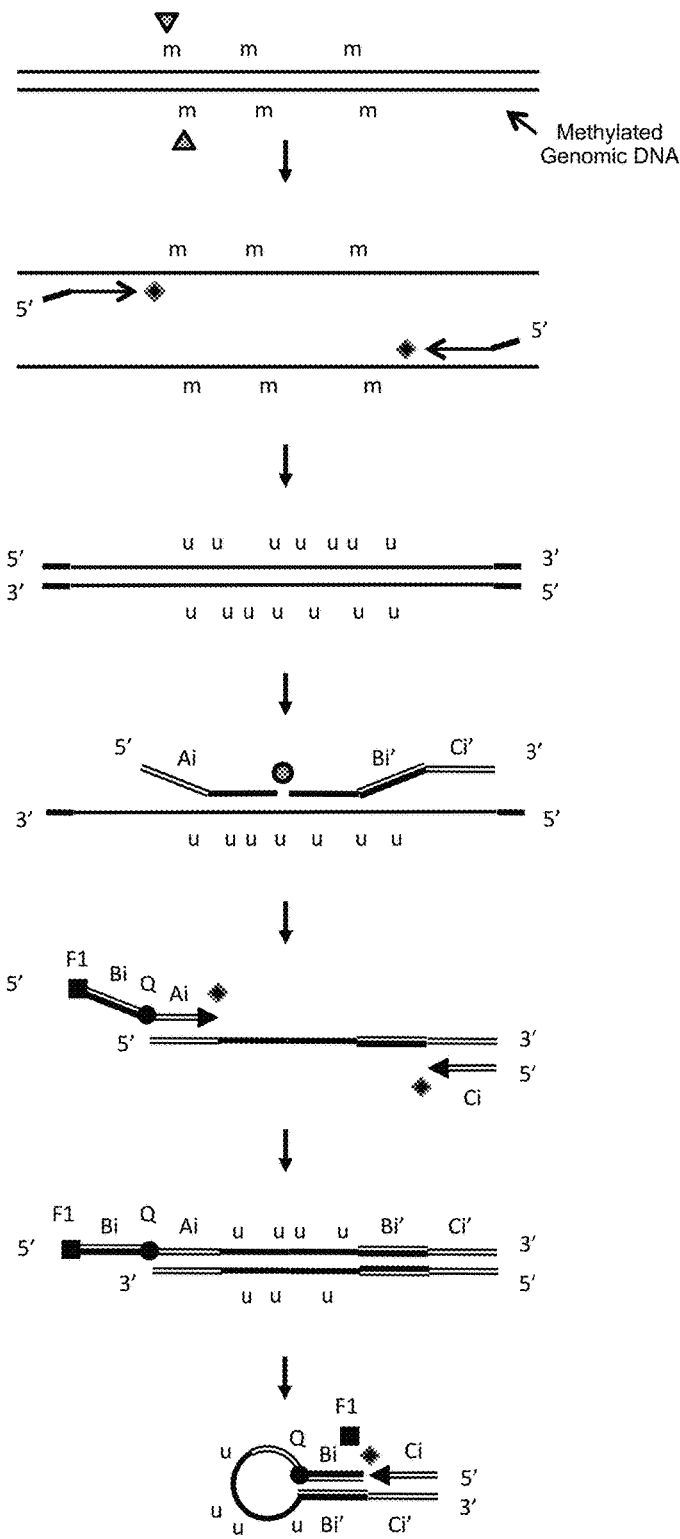

Figure 46

A. PCR-qLDR carryover prevention reaction to detect methylation. Isolate genomic or cfDNA. Optional: enrich for methylated DNA using antibodies. Treat with methyl-sensitive restriction endonucleases Bsh1236I (CG^CG) and HinP1I (G^CGC), and UNG (37oC, 30-60 minutes) to completely digest unmethylated DNA and prevent carryover.

B. Aliquot into 12, 24, 48, or 96 wells, and amplify methyl containing regions using PCR (and dUTP) with locus-specific primers. Perform limited cycle amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. (Products lack methyl groups, providing additional protection.) Separate product from primers and capture biotinylated product on solid support.

D. Methyl region-specific ligation oligonucleotides contain tails for subsequent FRET detection. Ligase covalently seals the two oligonucleotides together.

E. Wash away unligated primers. Denature product from target, then detect, and enumerate FRET signal.

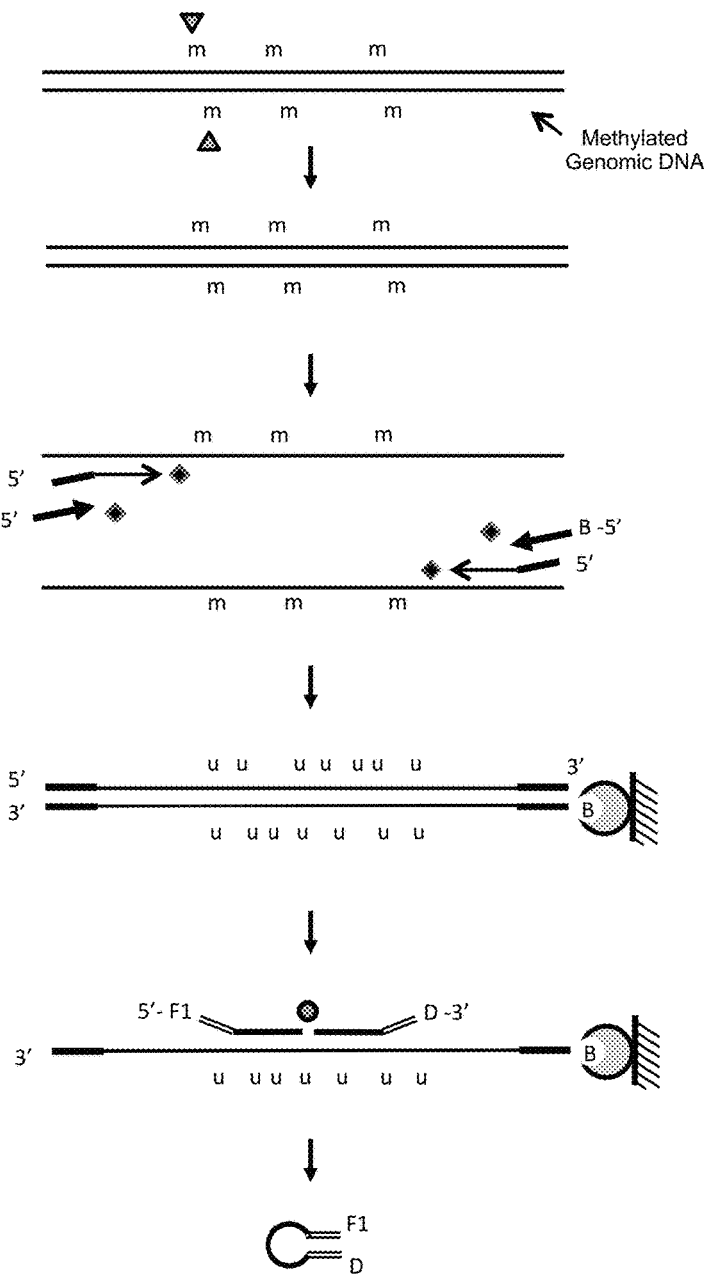

Figure 47

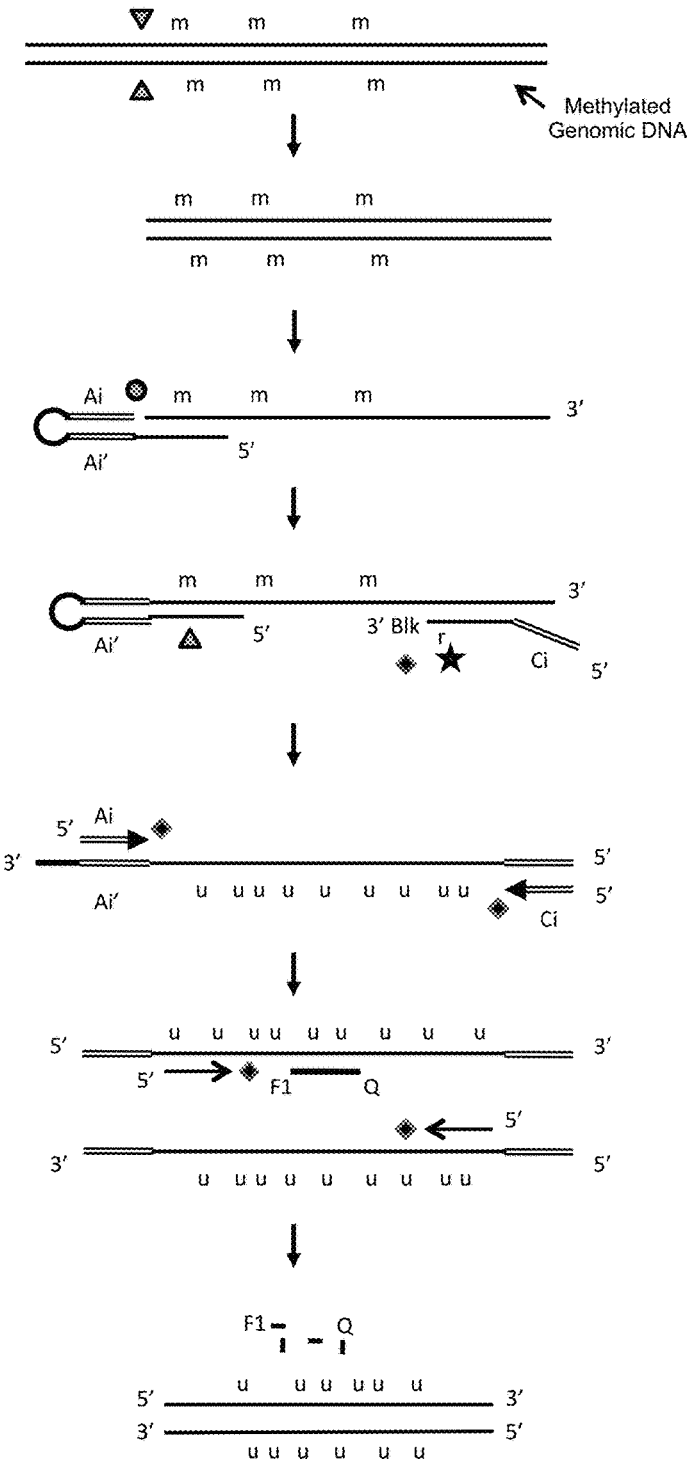

A. Nuclease-Ligation-PCR-qPCR carryover prevention reaction to detect methylation. Isolate genomic or cfDNA. Treat with HaeIII (GG^CC) and methyl-sensitive restriction endonucleases Bsh1236I (CG^CG) and HinP1I (G^CGC), and UNG (37oC, 30-60 minutes) to completely digest unmethylated DNA and prevent carryover.

B. Ligate hairpin oligonucleotide containing tag sequence (Ai') to newly liberated phosphate of template strand.

C. Treat with HinP1I and Bsh1236I at 37oC, then heat kill endonucleases while activating Taq polymerase. Locus-specific primers (containing Ci tag sequence) are unblocked with RNaseH2 only when bound to target, and extended with polymerase, whose 5' nuclease activity digests 5' portion of hairpin to generate target complement with Ai' sequence. Unligated hairpin extends on itself.

D. Amplify methyl containing regions using PCR (and dUTP) with tag-primers Ai and Ci. Perform limited cycle amplification (12-20) to maintain relative ratios of different amplicons. (Optional: aliquot into 12, 24, 48, or 96 wells prior to PCR.)

E. PCR products incorporate dU, allowing for carryover prevention. (Products lack methyl groups, providing additional protection.) Aliquot into separate wells for Taqman detection using locus-specific primers and Taqman probe.

F. The 5'->3' nuclease activity of Taq polymerase liberates the fluorescent group to generate signal. (PCR products incorporate dU, allowing for carryover prevention.)

Figure 48

A. Nuclease-Ligation-PCR-qPCR carryover prevention reaction to detect methylation. Isolate genomic or cfDNA. Treat with HaeIII (GG^CC), Bsh1236I (CG^CG) and HinP1I (G^CGC), and UNG.

B. Ligate hairpin oligonucleotide containing tag sequence (Ai') to newly liberated phosphate of template strand.

C. Treat with HinP1I and Bsh1236I at 37oC, then heat kill endonucleases while activating Taq polymerase. Locus-specific primers (containing Ci tag sequence) are unblocked with RNaseH2 only when bound to target, and extended with polymerase, whose 5' nuclease activity digests 5' portion of hairpin to generate target complement with Ai' sequence.

D. Amplify methyl containing regions using PCR (and dUTP) with tag-primers Ai and Ci. Perform limited cycle amplification (12-20) to maintain relative ratios of different amplicons. (Optional: aliquot into 12, 24, 48, or 96 wells prior to PCR.)

E. PCR products incorporate dU, allowing for carryover prevention. Aliquot into separate wells for UniTaq detection, and amplify using locus-specific primers tailed with Aj, and Bj-Cj, as well as Unitaq-specific primers (F1-Bj-Q-Aj, and Cj).

F. Double-stranded DNA products of PCR; the polymerase blocker stops extension of the bottom strand.

G. After the denaturation step, as the temperature decreases, a hairpin forms between Bj and Bj'. The 5'->3' nuclease activity of Taq polymerase extends primer Cj and liberates the fluorescent group to generate signal. (PCR products incorporate dU, allowing for carryover prevention.)

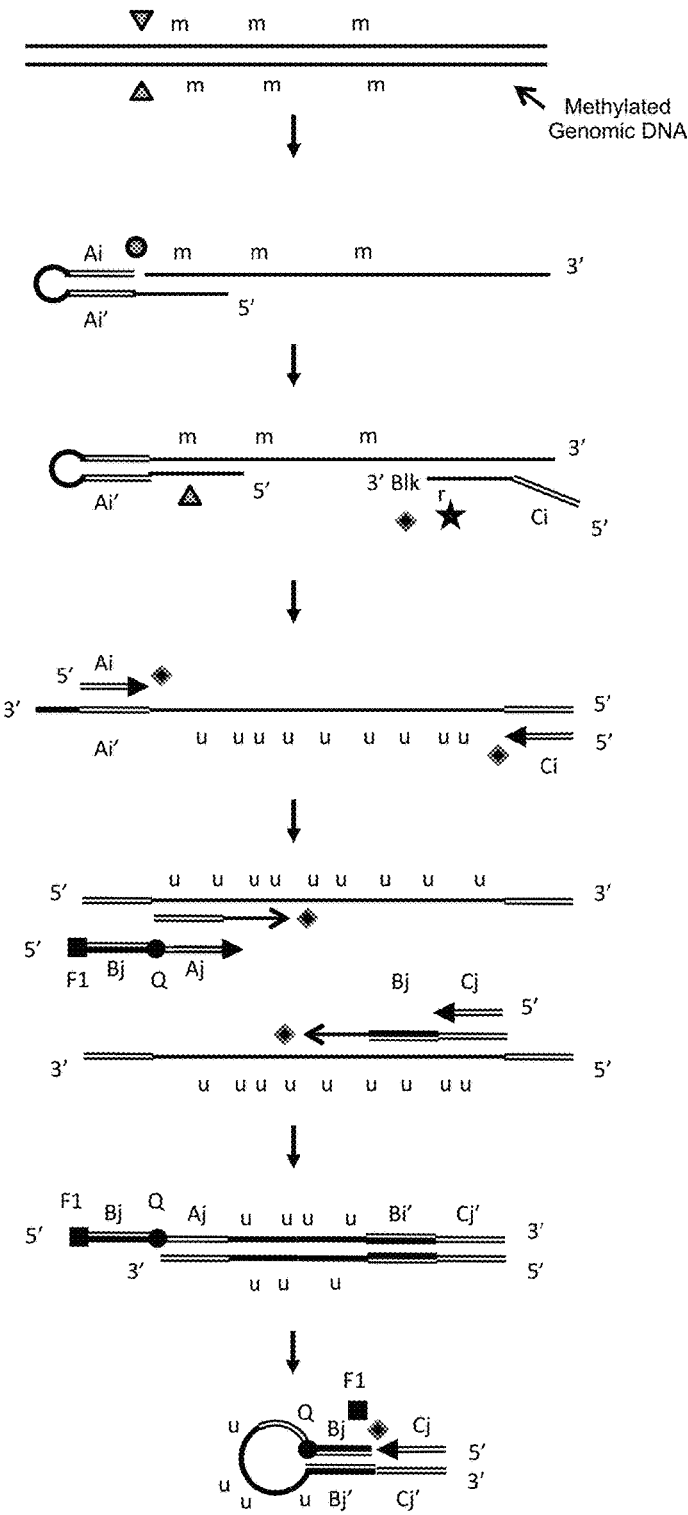

Figure 49

A. PCR-LDR-qPCR carryover prevention reaction to detect methylation. Isolate genomic or cfDNA. Treat with Bsh1236I (CG^CG) and UNG (37oC, 30-60 minutes) to completely digest unmethylated DNA and prevent carryover. Treat with bisulfite, which renders the strands non-complementary.

B. Hybridize locus-specific primers in presence of BstU1 (CG^CG), will cleave carryover DNA. Primers are unblocked with RNaseH2 only when bound to target. Amplify methyl containing regions using PCR (and dUTP). Perform limited cycle amplification (12-20) to maintain relative ratios of different amplicons. Blocking oligo may be used to limit amplification of originally un-methylated DNA (Optional: aliquot into 12, 24, 48, or 96 wells prior to PCR.)

C. PCR products incorporate dU, allowing for carryover prevention. (Products lack methyl groups, providing additional protection.)

D. Methyl region-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

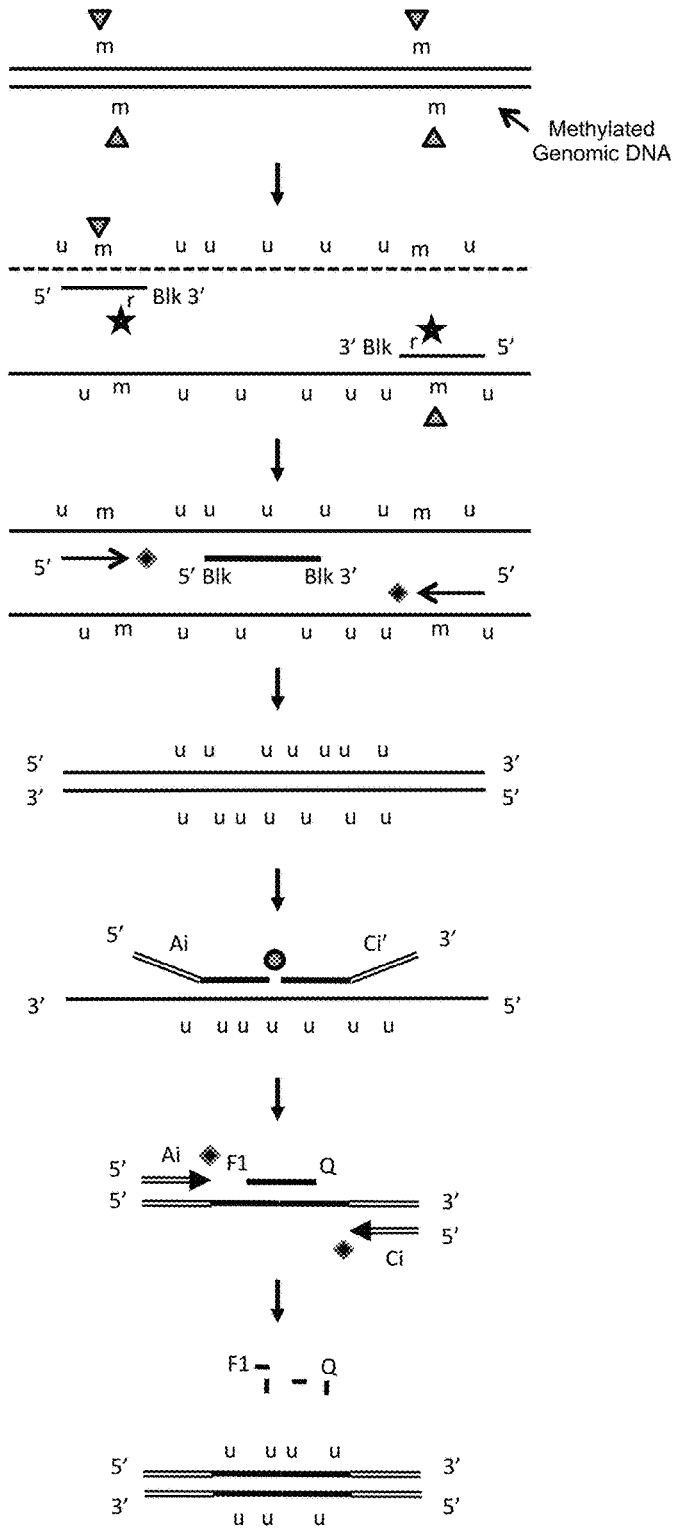

Figure 50

A. PCR-LDR-qPCR carryover prevention reaction to detect methylation. Isolate genomic or cfDNA. Treat with Bsh1236I (CG^CG) and UNG (37oC, 30-60 minutes) to completely digest unmethylated DNA and prevent carryover. Treat with bisulfite, which renders the strands non-complementary.

B. Hybridize locus-specific primers in presence of BstU1 (CG^CG), will cleave carryover DNA. Primers are unblocked with RNaseH2 only when bound to target. Amplify methyl containing regions using PCR (and dUTP). Perform limited cycle amplification (12-20) to maintain relative ratios of different amplicons. Blocking oligo may be used to limit amplification of originally unmethylated DNA (Optional: aliquot into 12, 24, 48, or 96 wells prior to PCR.)

C. PCR products incorporate dU, allowing for carryover prevention.

D. Methyl region-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

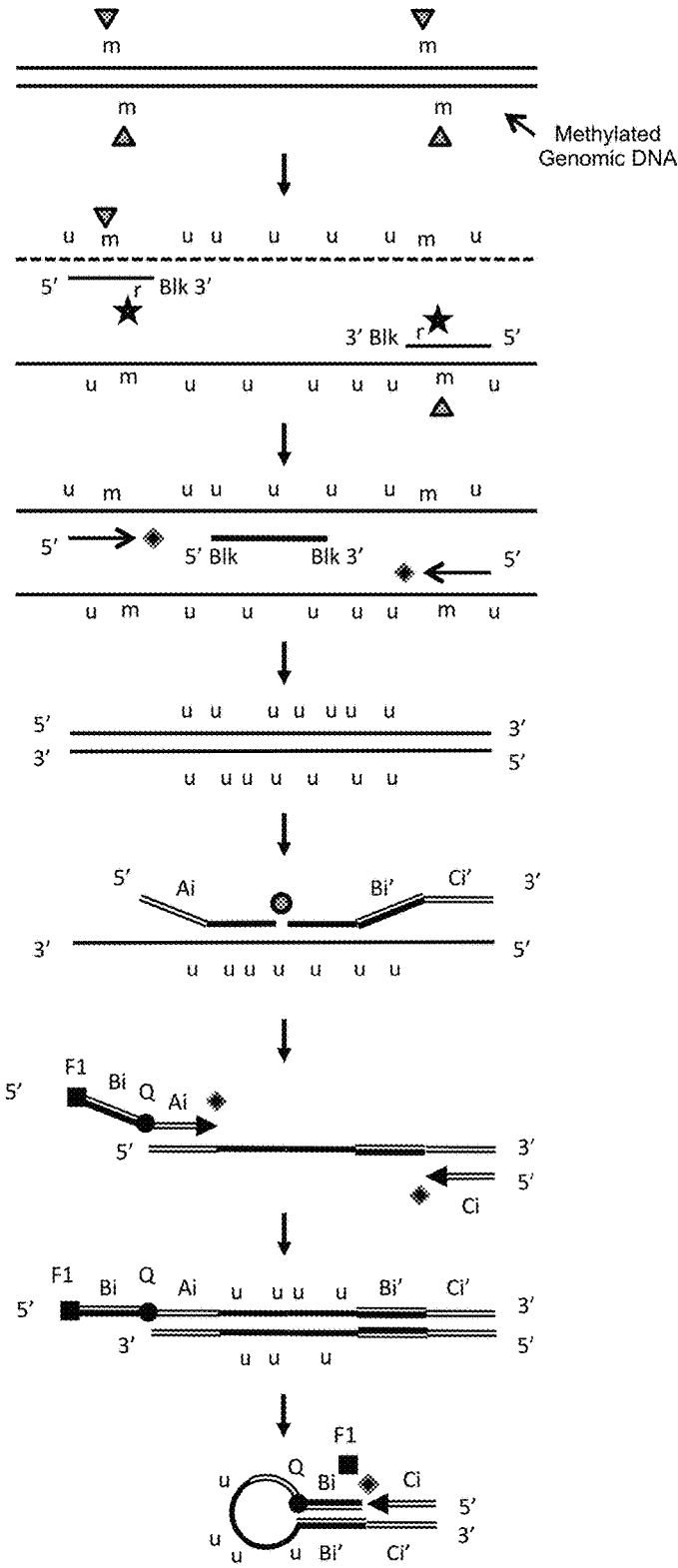

Figure 51

A. PCR-qLDR carryover prevention reaction to detect methylation. Isolate genomic or cfDNA. Treat with Bsh1236I (CG^CG) and UNG (37oC, 30-60 minutes) to completely digest unmethylated DNA and prevent carryover. Treat with bisulfite, which renders the strands non-complementary.

B. Hybridize locus-specific primers in presence of BstU1 (CG^CG), will cleave carryover DNA. Primers are unblocked with RNaseH2 only when bound to target. Aliquot into 12, 24, 48, or 96 wells, and amplify methyl containing regions using PCR (and dUTP) with locus-specific primers. Perform limited cycle amplification (12-20) to maintain relative ratios of different amplicons. Primers contain universal tails (with identical 8-11 bases to prevent primer dimers), also enabling universal primer amplification to append a 5' biotin. Blocking oligo may be used to limit amplification of originally unmethylated DNA.

C. PCR products incorporate dU, allowing for carryover prevention. (Products lack methyl groups, providing additional protection.) Separate product from primers and capture biotinylated product on solid support.

D. Methyl region-specific ligation oligonucleotides contain tails for subsequent FRET detection. Ligase covalently seals the two oligonucleotides together.

E. Wash away unligated primers. Denature product from target, then detect, and enumerate FRET signal.

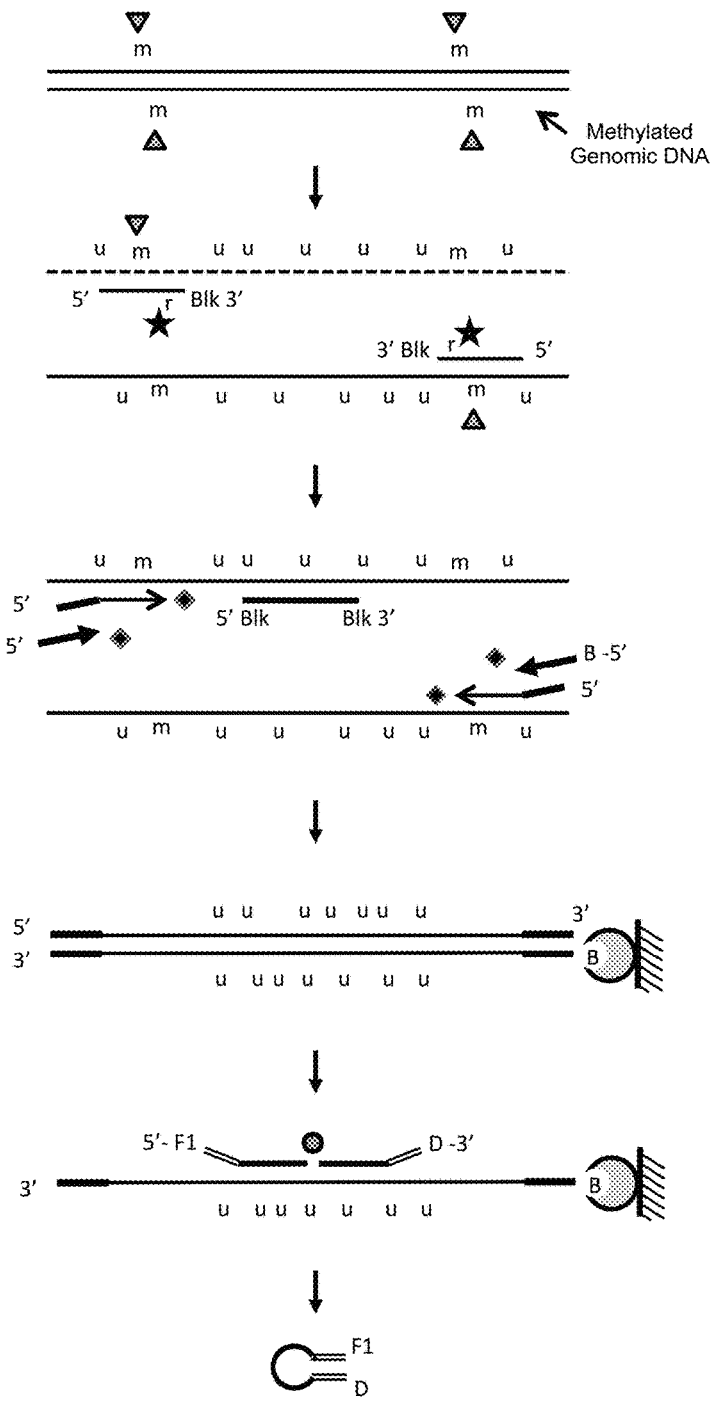

Figure 52

A. PCR-qPCR carryover prevention reaction to detect methylation. Isolate genomic or cfDNA. Treat Bsh1236I (CG^CG) and UNG (37oC, 30-60 minutes) to completely digest unmethylated DNA and prevent carryover. Treat with bisulfite, which renders the strands non-complementary.

B. Hybridize locus-specific primers in presence of BstU1 (CG^CG), will cleave carryover DNA. Primers are unblocked with RNaseH2 only when bound to target. Amplify methyl containing regions using PCR with dNTPs. Perform limited cycle amplification (12-20) to maintain relative ratios of different amplicons. Blocking oligos may be used to limit amplification of wild-type DNA. (Optional: aliquot into 12, 24, 48, or 96 wells prior to PCR.)

C. PCR products are unmethylated providing carryover protection.

D. Aliquot into separate wells for Taqman detection using locus-specific primers and Taqman probe. Optional blocking oligonucleotide is used to limit amplification of wild-type DNA E. The 5'->3' nuclease activity of Taq polymerase liberates the fluorescent group to generate signal. (PCR products incorporate dU, allowing for carryover prevention.)

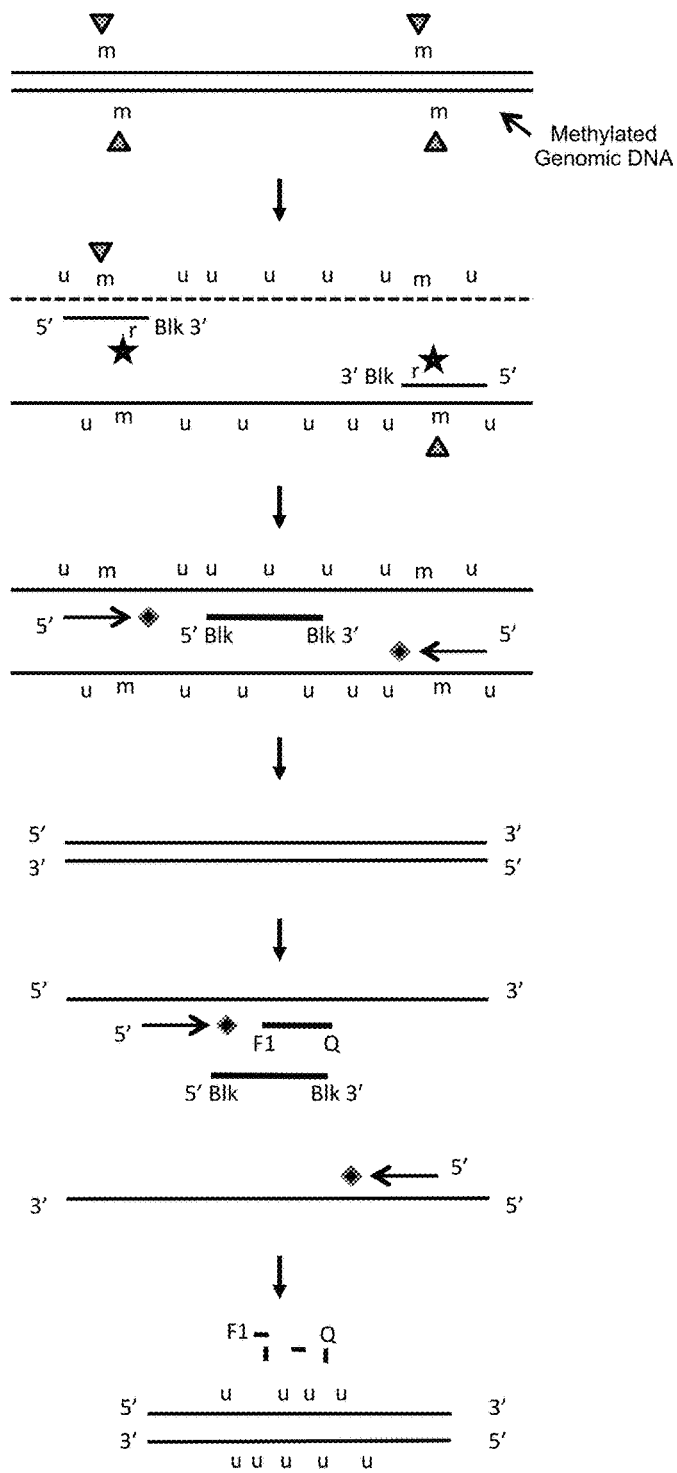

Figure 53

A. Overview: RT-PCR-LDR-qPCR carryover prevention reaction to detect translocation at the mRNA level. Illustration of translocations between two genes shown at the DNA level.

B. Examples of fusion junctions between exons 1-b, 2-b, and 3-b in mRNAs are illustrated. Isolate mRNA from whole blood cells, exosomes, or CTCs. Generate cDNA using reverse transcriptase and primer complementary to exon b. PCR amplify using forward primers to exons 1, 2, and 3. Independent of translocation breakpoint, the primers will amplify the smallest fragment containing the exon junction region.

C. Exon junction-specific ligation oligonucleotides contain tags (Ai, Ci' for individual Taqman probes; or Ai, Bi-Ci for UniTaq probes) for subsequent PCR amplification. Ligase covalently seals the two oligonucleotides together, if there is perfect complementarity at the junction. Aliquot into separate wells for detection using real-time PCR.

D. When using tag-specific primers (Ai, Ci) for amplifying LDR products of the upper set, each Taqman probe spans the ligation junction, and can be scored individually. When using UniTaq-specific primers (F1-Bi-Q-Ai, Ci), for amplifying LDR products of the lower set, the same primer set scores for the given translocation, independent of the specific exon junction.

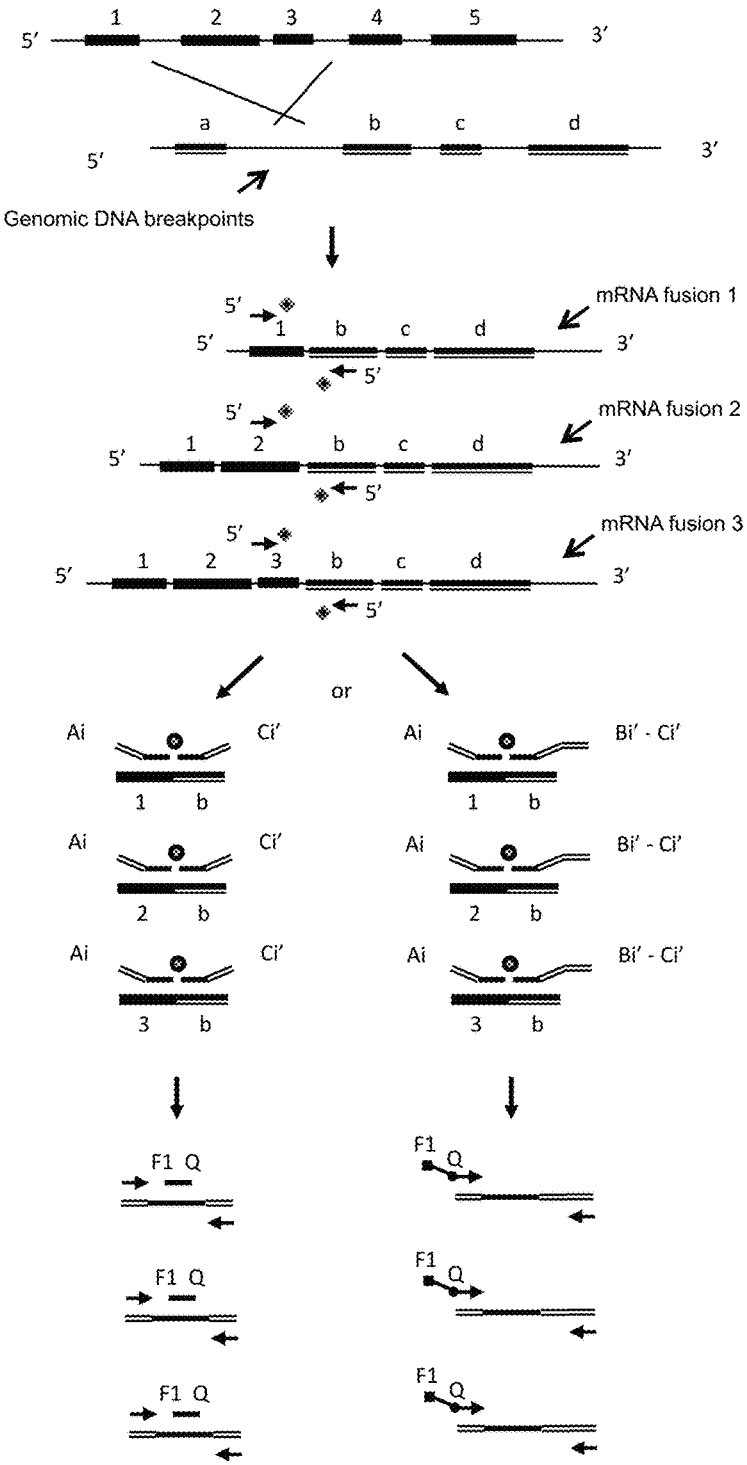

Figure 54

A. RT-PCR-LDR-qPCR carryover prevention reaction to detect translocation at the mRNA level. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection. (LDR products are not amplified by either original PCR or LDR primers, providing additional protection.)

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

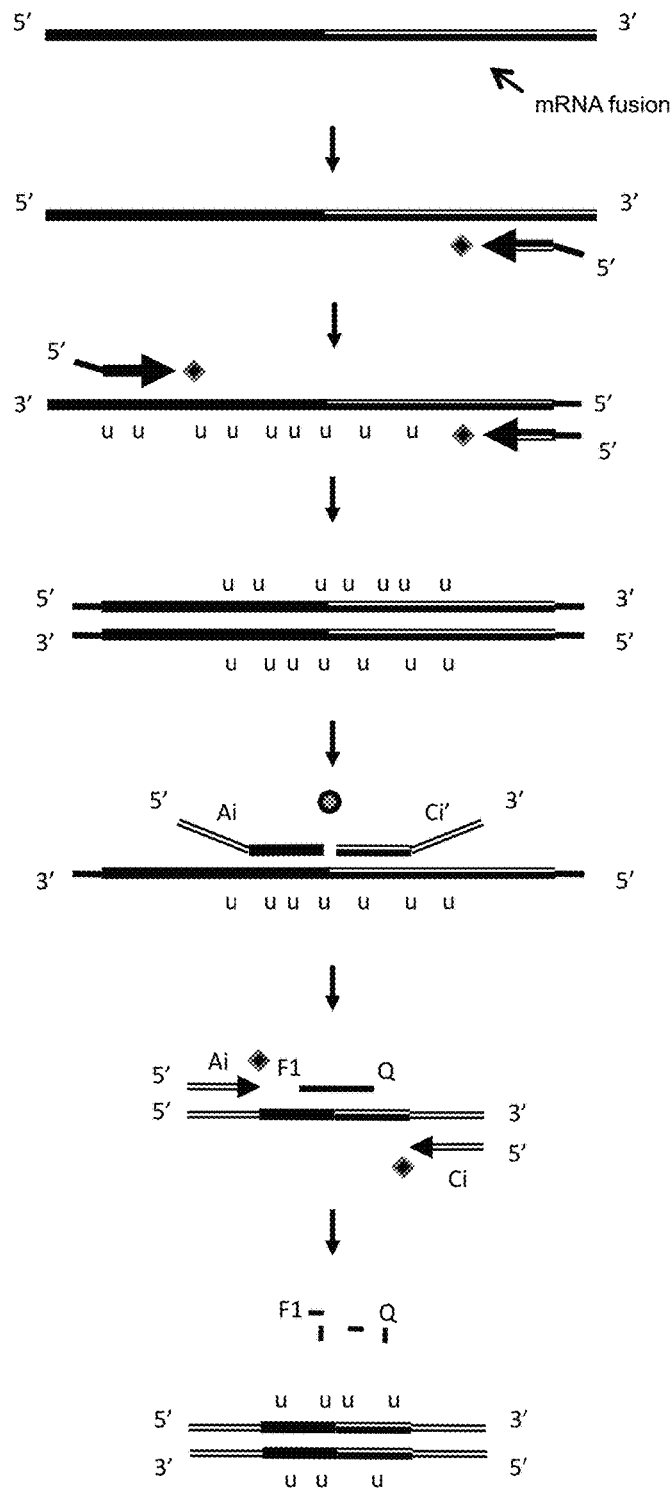

Figure 55

A. RT-PCR-LDR-qPCR carryover prevention reaction to detect translocation at the mRNA level. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

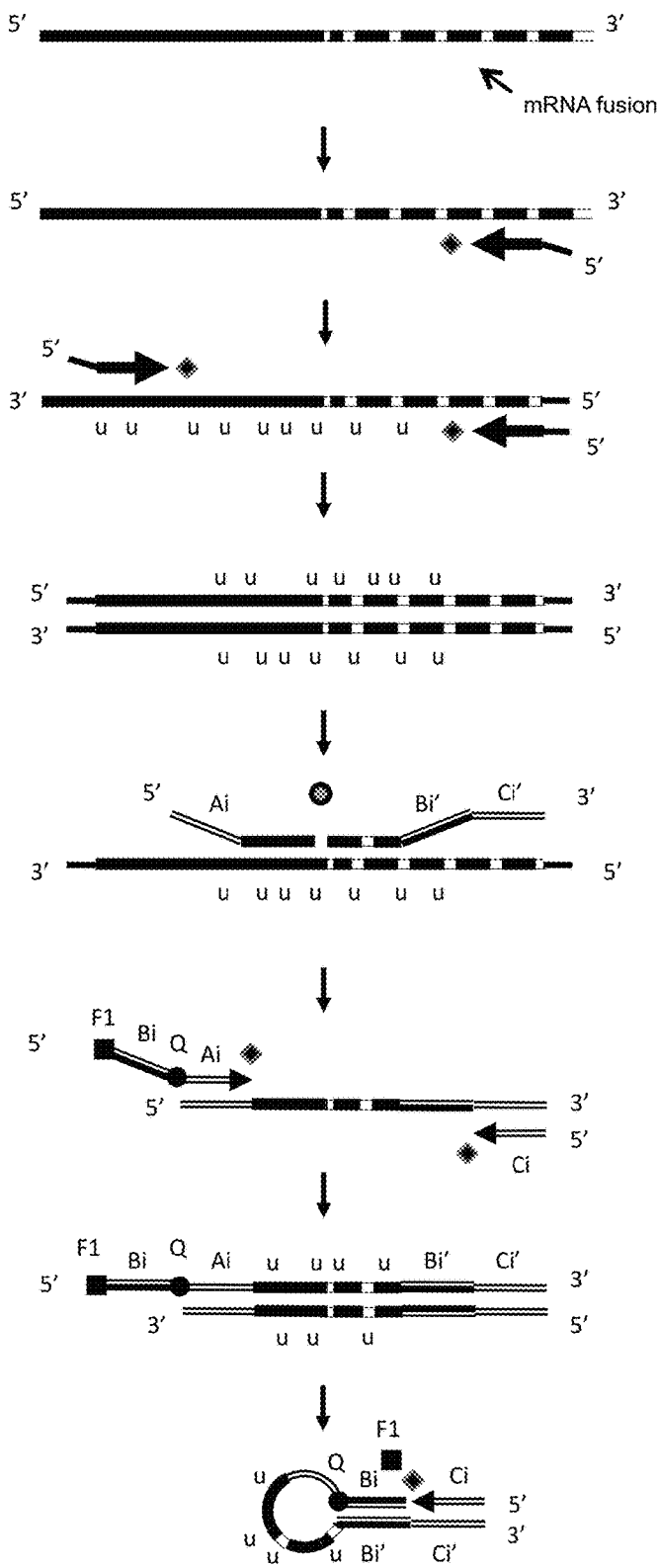

Figure 56

A. RT-PCR-qLDR carryover prevention reaction to detect translocation at the mRNA level. Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

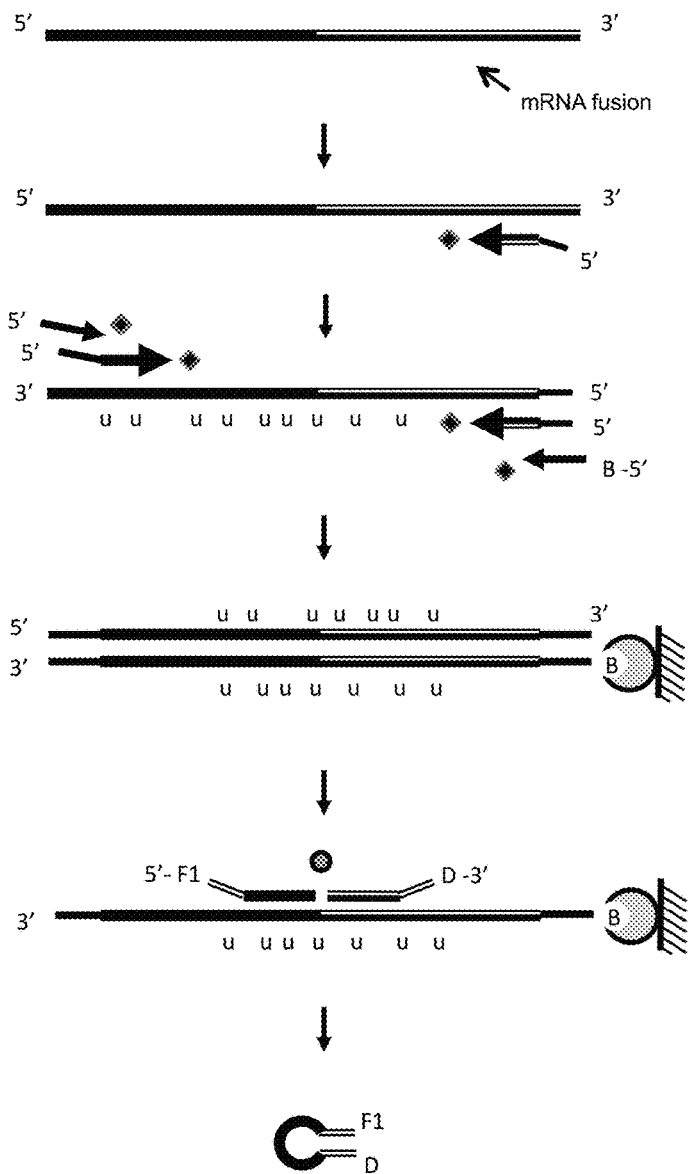

Figure 57

A. Overview: RT-PCR-LDR-qPCR carryover prevention reaction to detect alternative splicing. Illustration of gene with 5 exons shown at the DNA level.

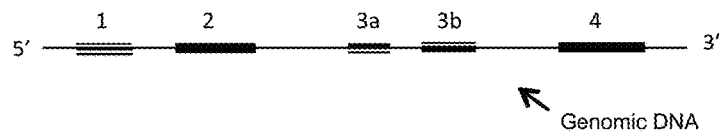

B. Examples of normal (1-2-3a-4), alternative splice variant (1-2-3b-4) mRNAs are illustrated. Isolate mRNA from whole blood cells, exosomes, or CTCs. Generate cDNA using reverse transcriptase and primer complementary to exon 4. PCR amplify using forward primer to exon 2, generating amplicons of both splice variants.

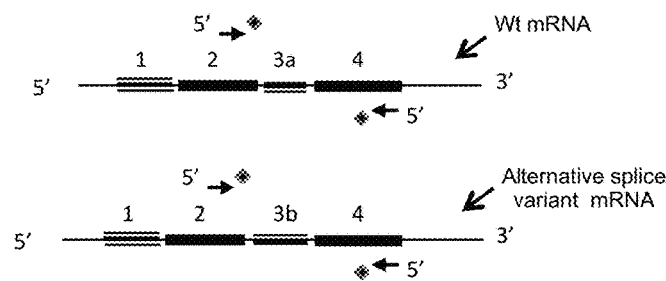

C. Exon junction-specific ligation oligonucleotides contain tags (Ai, Ci' for individual Taqman probes; or Ai, Bi-Ci for UniTaq probes) for subsequent PCR amplification. Ligase covalently seals the two oligonucleotides together, if there is perfect complementarity at the junction. Aliquot into separate wells for detection using real-time PCR.

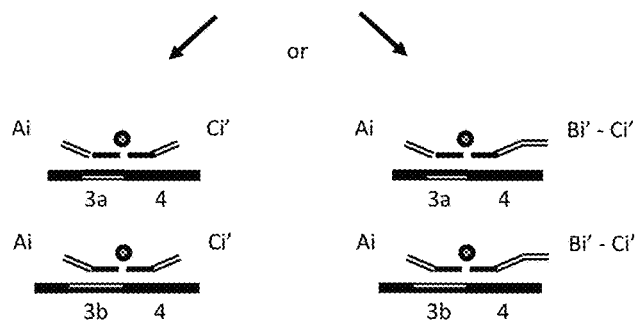

D. When using tag-specific primers (Ai, Ci) for amplifying LDR products of the upper set, each Taqman probe spans the ligation junction, and can be scored individually. When using UniTaq-specific primers (F1-Bi-Q-Ai, Ci), for amplifying LDR products of the lower set, a given primer set scores for a given ligation junction.

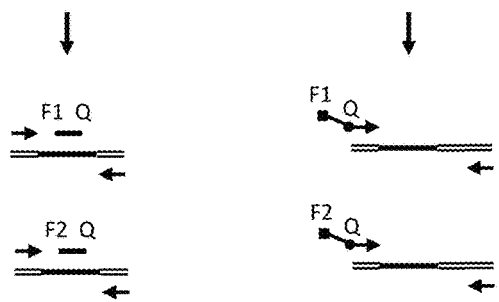

Figure 58

A. RT-PCR-LDR-qPCR carryover prevention reaction to quantify wt and alternatively spliced (3a vs. 3b) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection. (LDR products are not amplified by either original PCR or LDR primers, providing additional protection.)

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. The relative Ct values reflects the relative amount of each transcript.

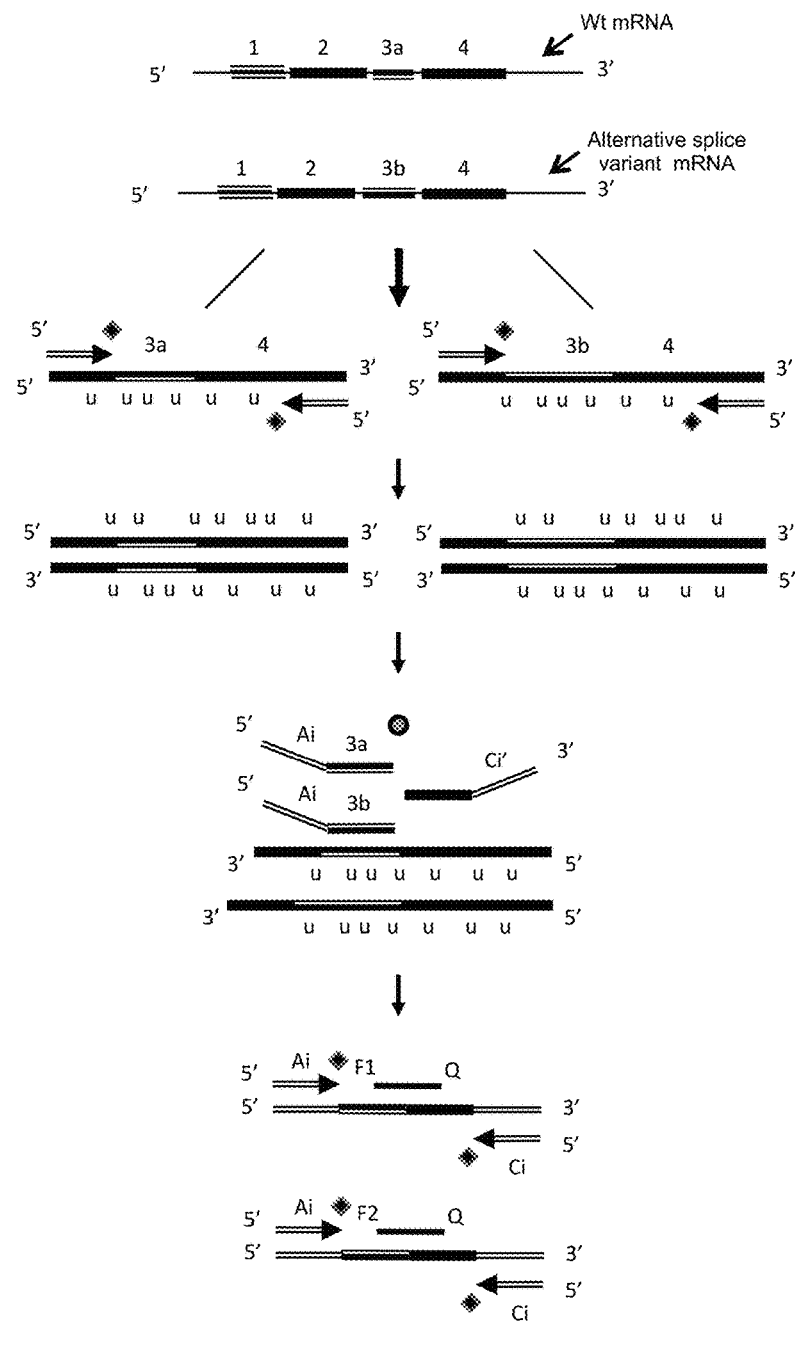

Figure 59

A. RT-PCR-LDR-qPCR carryover prevention reaction to quantify wt and alternatively spliced (3a vs. 3b) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR (not shown); the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal. The relative Ct values reflects the relative amount of each transcript.

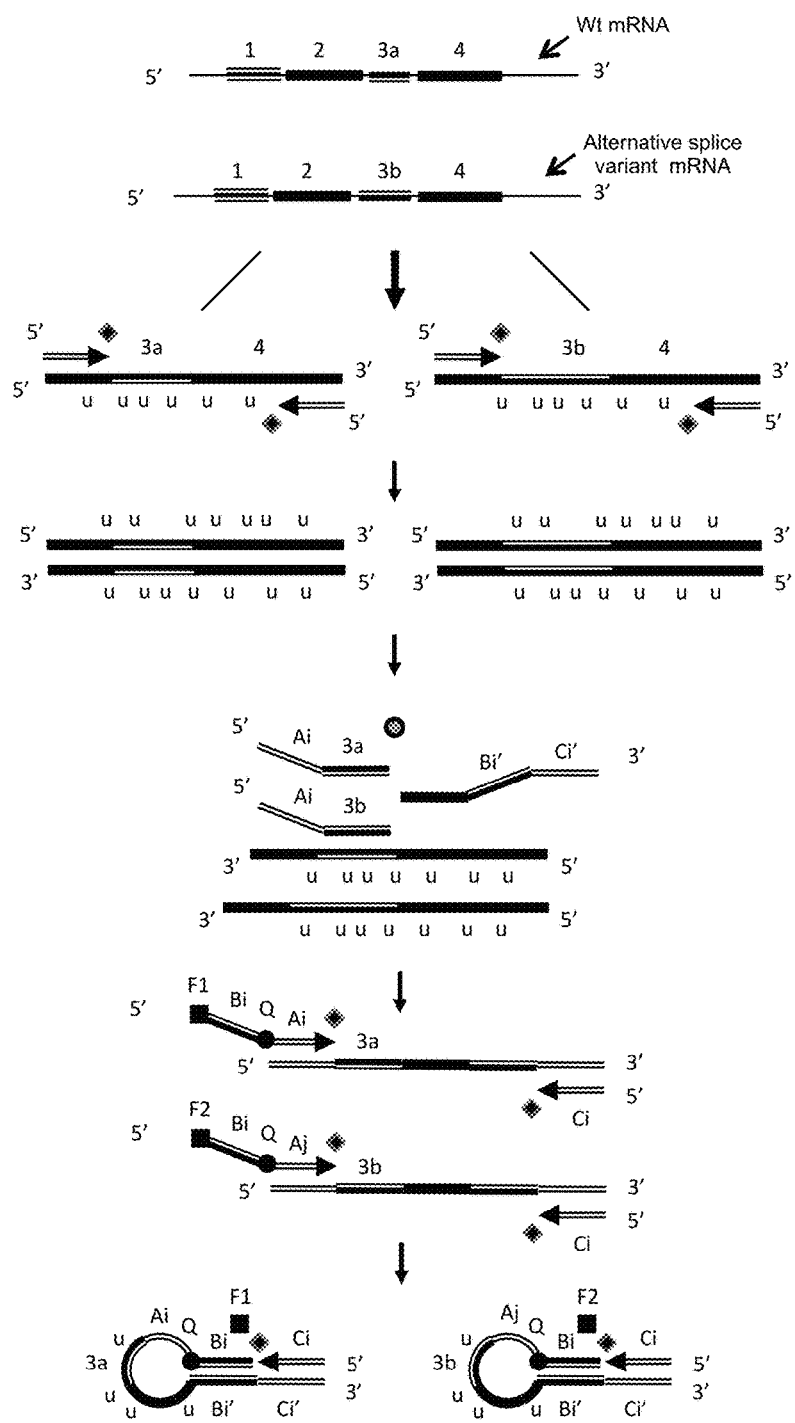

Figure 60

A. RT-PCR-qLDR carryover prevention reaction to quantify wt and alternatively spliced (3a vs. 3b) transcript. Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

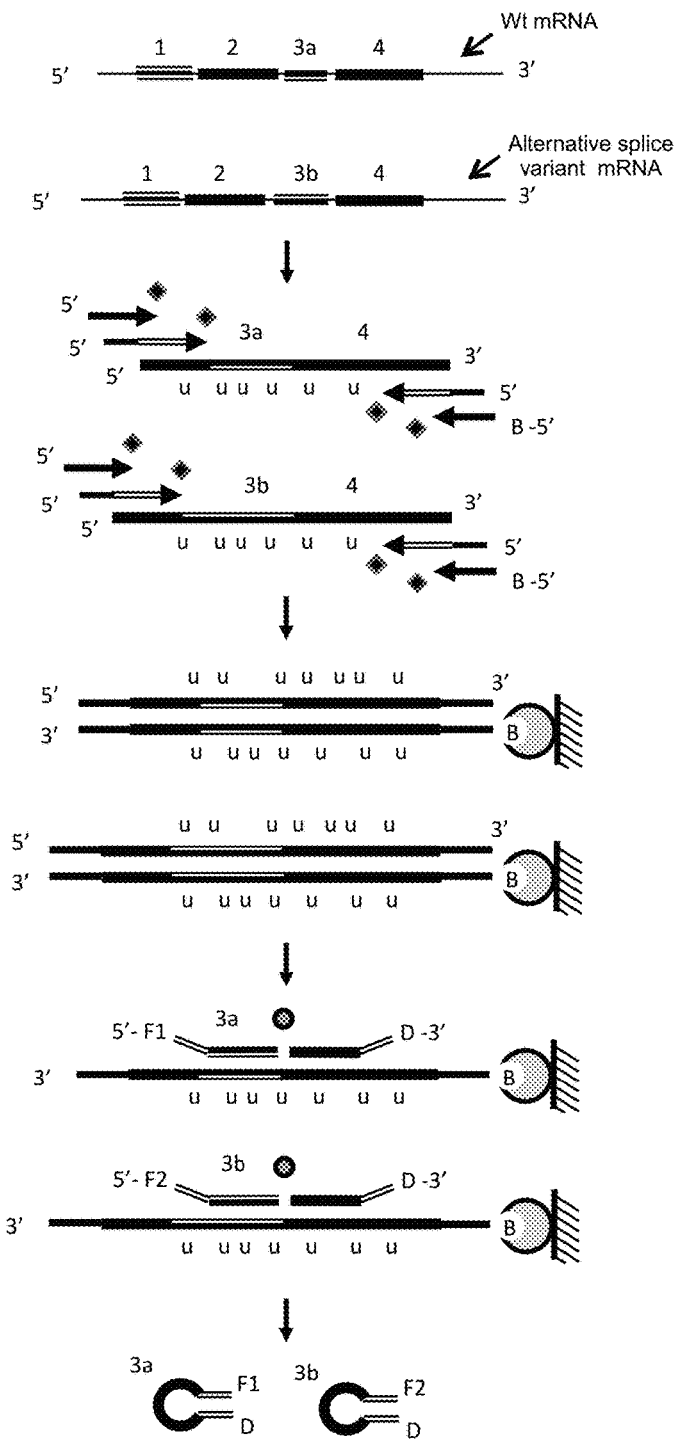

Figure 61

A. RT-PCR-LDR-qPCR carryover prevention reaction to detect low-level alternatively spliced (e.g. 3b) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Exon-specific primer does not amplify wt transcript. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

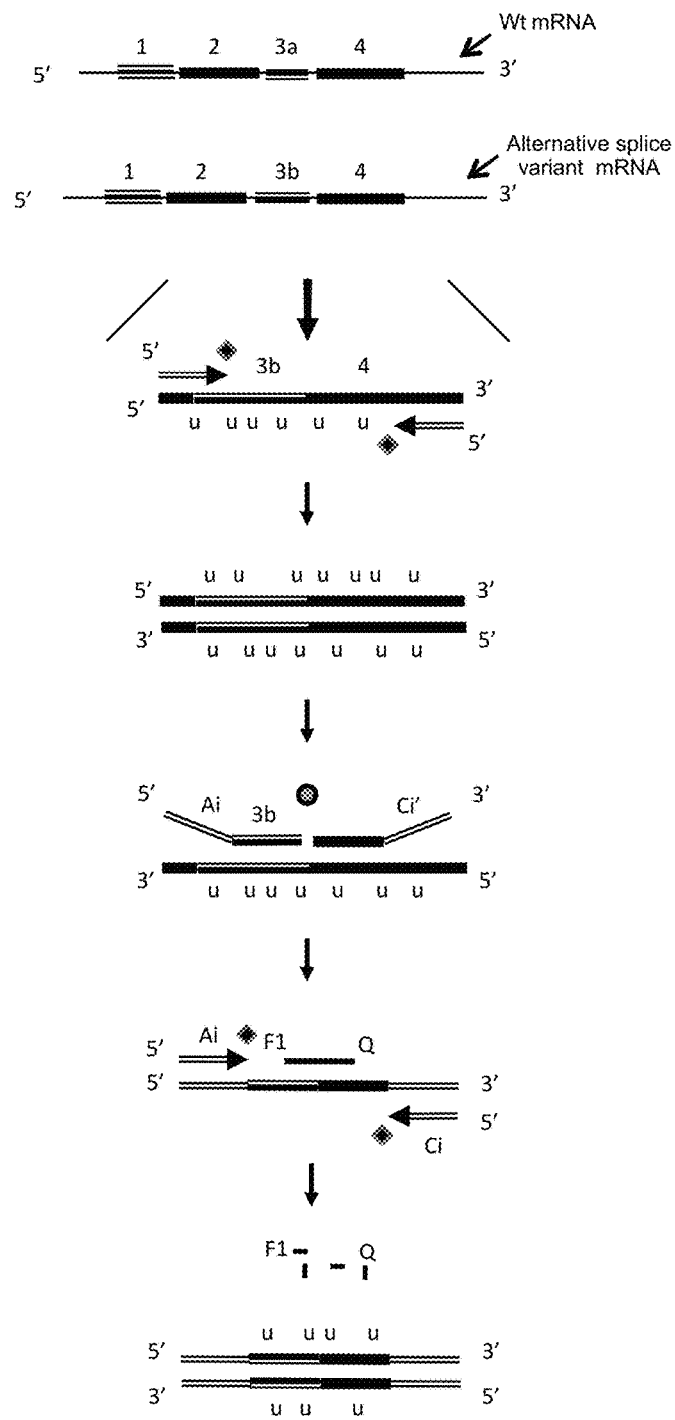

Figure 62

A. PCR-LDR carryover prevention reaction to detect low-level alternatively spliced (e.g. 3b) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Exon-specific primer does not amplify wt transcript. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

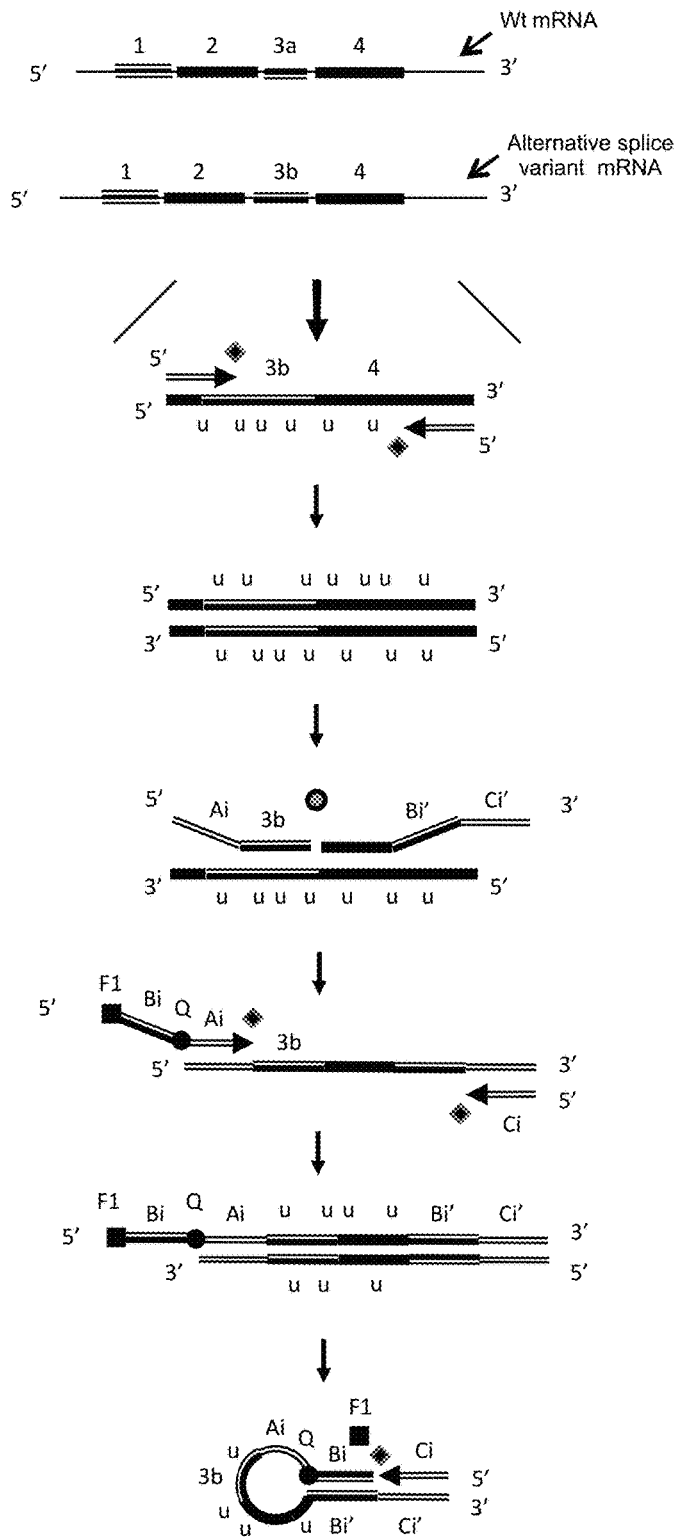

Figure 63

A. PCR-LDR carryover prevention reaction to detect low-level alternatively spliced (e.g. 3b) transcript. Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

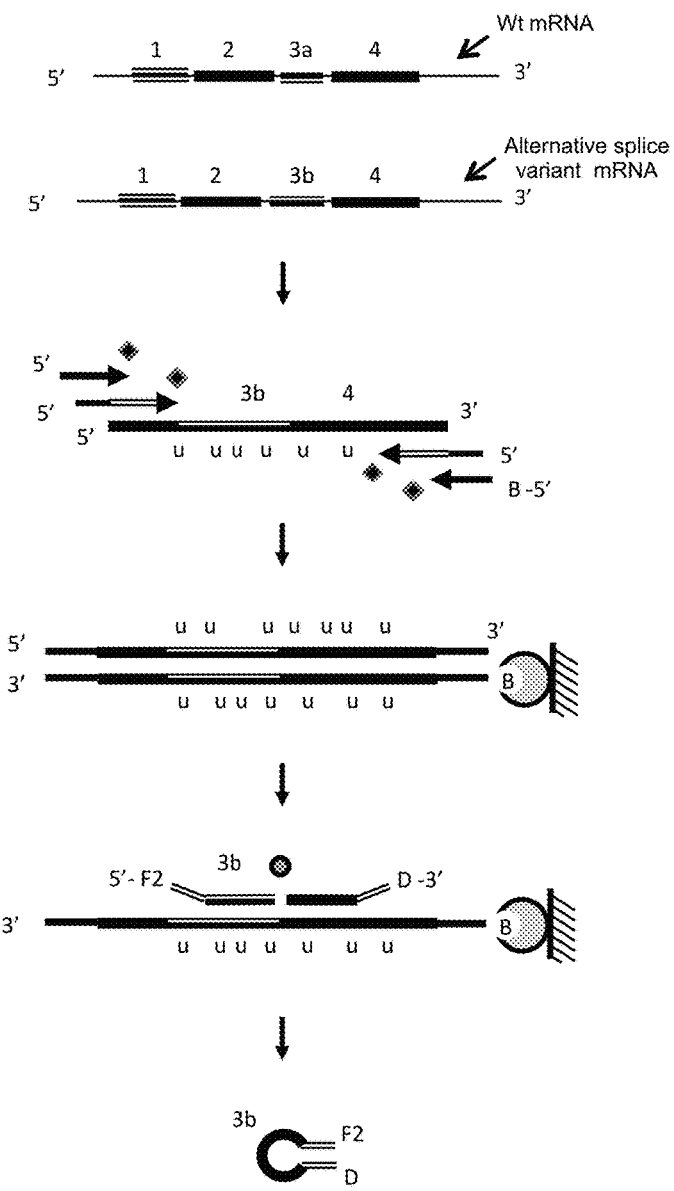

Figure 64

A. Overview: RT-PCR-LDR-qPCR carryover prevention reaction to detect alternative splicing. Illustration of gene with 3 exons, and an alternative start site and first exon, shown at the DNA level.

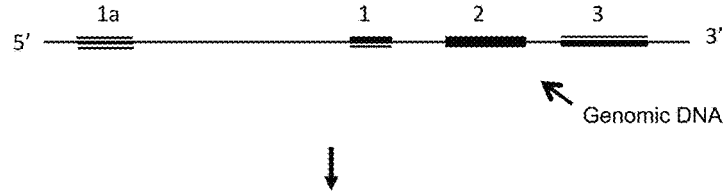

B. Examples of normal (1-2-3), alternative splice variant (1a-2-3) mRNAs are illustrated. Isolate mRNA from whole blood cells, exosomes, or CTCs. Generate cDNA using reverse transcriptase and primer complementary to exon 2. PCR amplify using forward primers to exons 1 and 1a, generating amplicons of both splice variants.

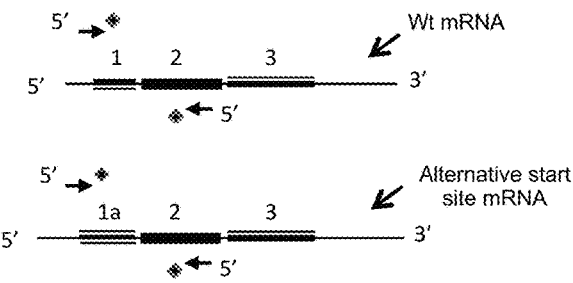

C. Exon junction-specific ligation oligonucleotides contain tags (Ai, Ci' for individual Taqman probes; or Ai, Bi-Ci for UniTaq probes) for subsequent PCR amplification. Ligase covalently seals the two oligonucleotides together, if there is perfect complementarity at the junction. Aliquot into separate wells for detection using real-time PCR.

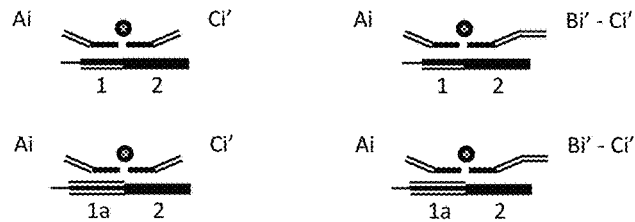

D. When using tag-specific primers (Ai, Ci) for amplifying LDR products of the upper set, each Taqman probe spans the ligation junction, and can be scored individually. When using UniTaq-specific primers (F1-Bi-Q-Ai, Ci), for amplifying LDR products of the lower set, a given primer set scores for a given ligation junction.

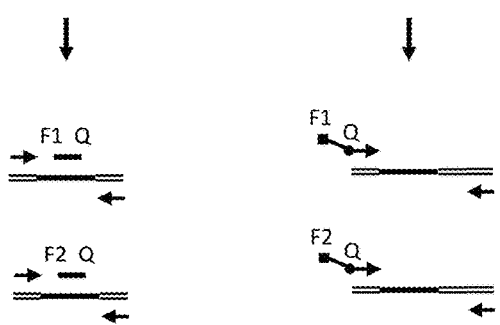

Figure 65

A. RT-PCR-LDR-qPCR carryover prevention reaction to quantify wt and alternative transcript start site (1 vs. 1a). Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection. (LDR products are not amplified by either original PCR or LDR primers, providing additional protection.)

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. The relative Ct values reflects the relative amount of each transcript.

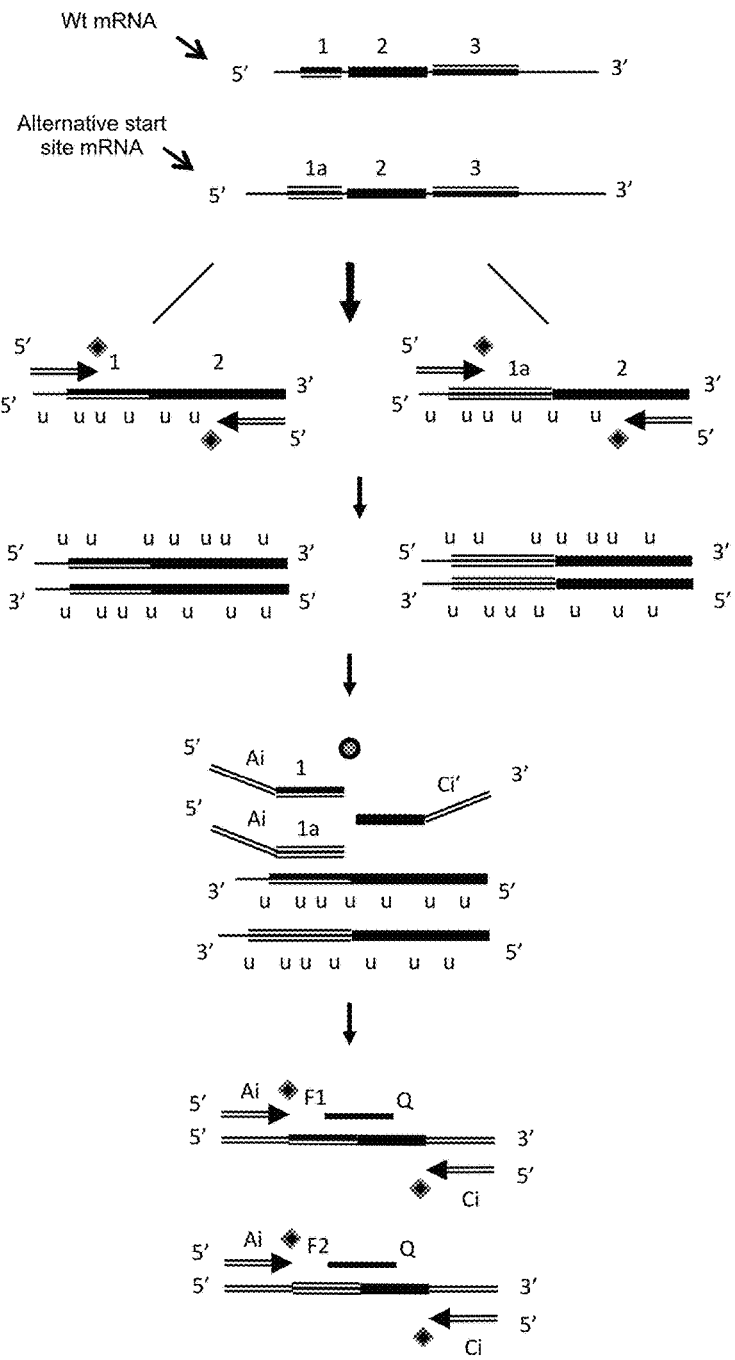

Figure 66

A. RT-PCR-LDR-qPCR carryover prevention reaction to quantify wt and alternative transcript start site (1 vs. 1a). Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection. (LDR products are not amplified by either original PCR or LDR primers, providing additional protection.)

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. The relative Ct values reflects the relative amount of each transcript.

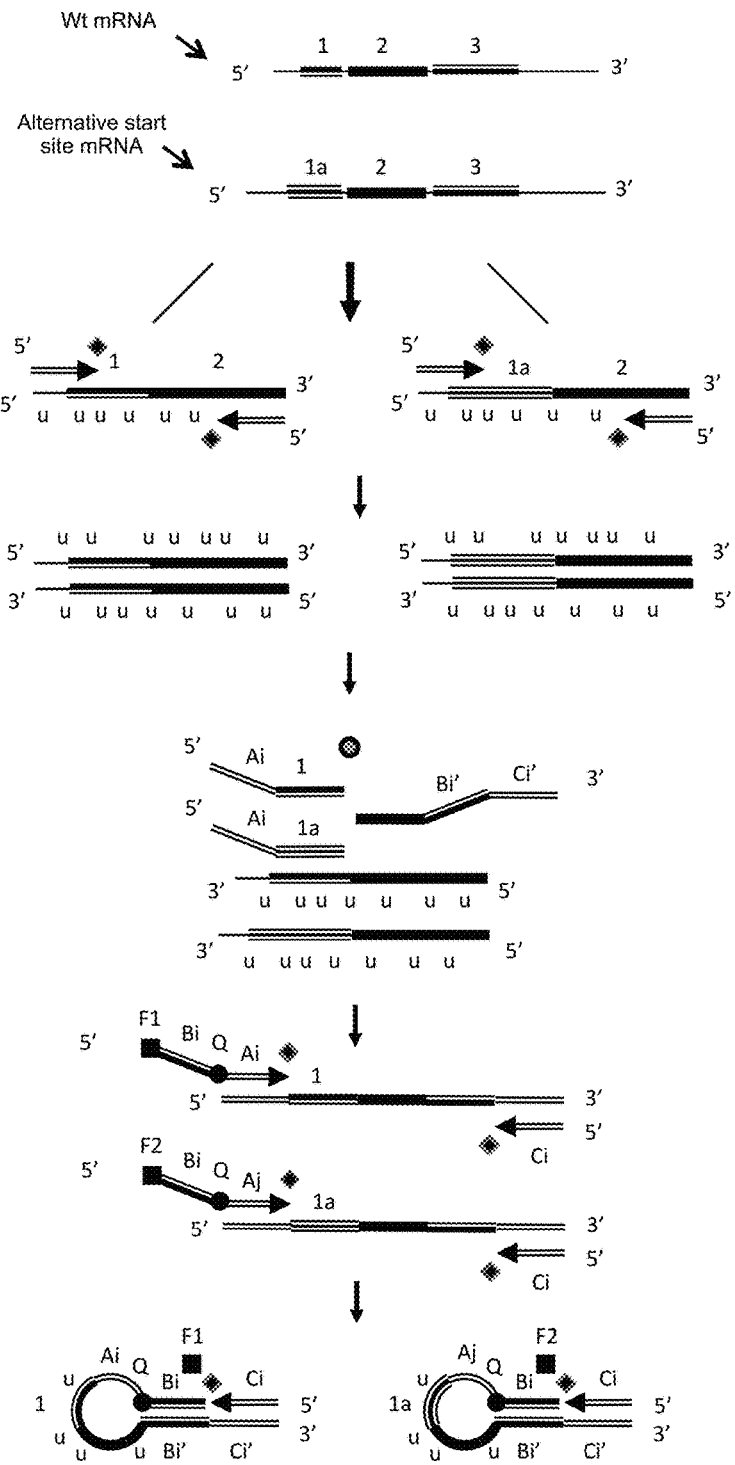

Figure 67

A. RT-PCR-qLDR carryover prevention reaction to quantify wt and alternative transcript start site (1 vs. 1a). Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

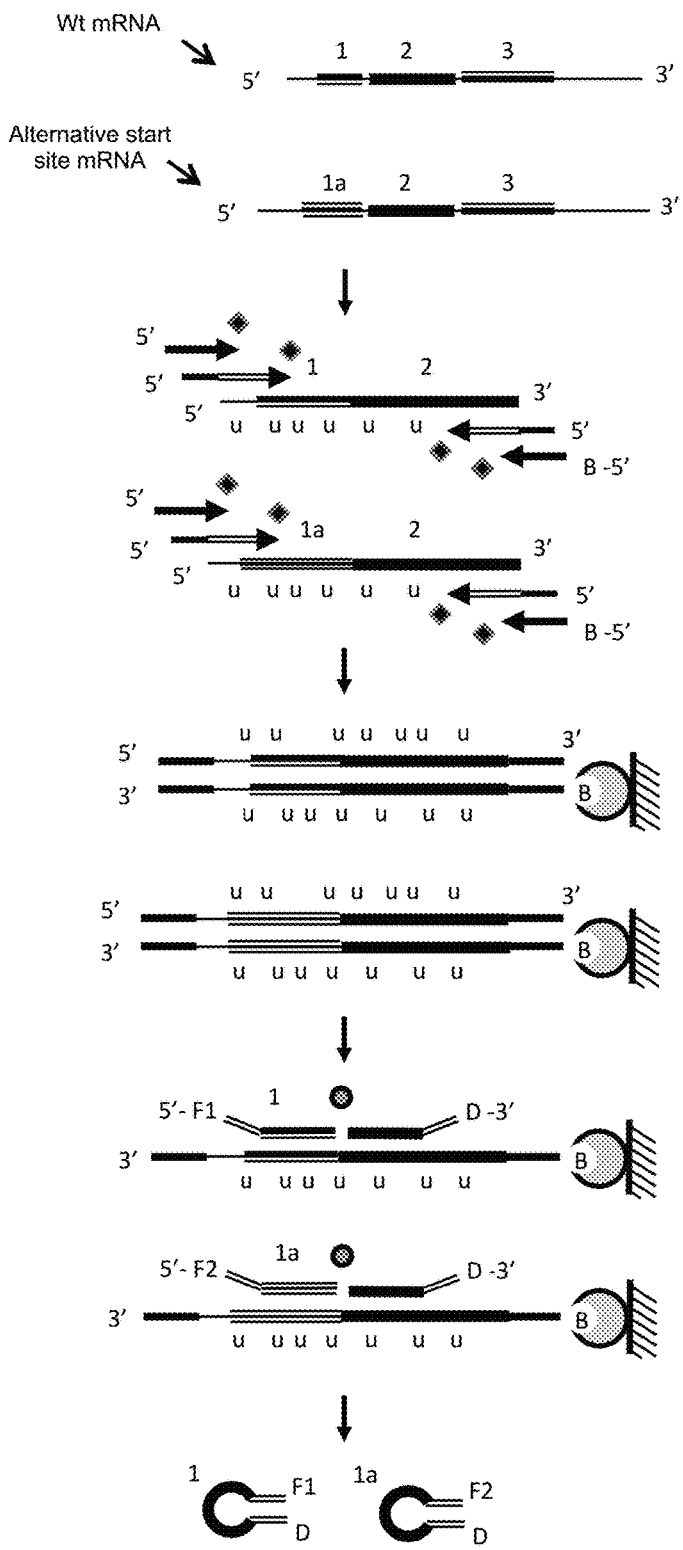

Figure 68

A. RT-PCR-LDR-qPCR carryover prevention reaction to detect low level of alternative transcript start site (1 vs. 1a). Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Exon-specific primer does not amplify wt transcript. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

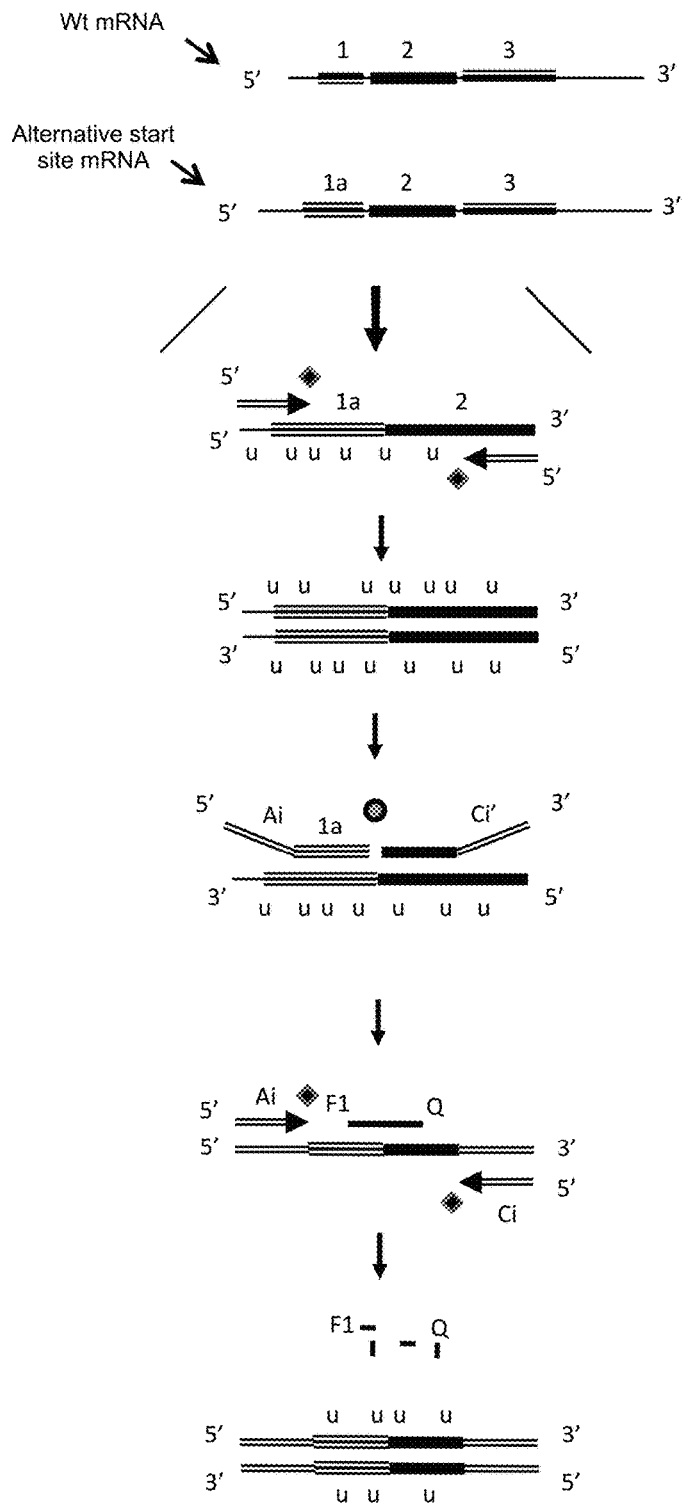

Figure 69

A. RT-PCR-LDR-qPCR carryover prevention reaction to detect low level of alternative transcript start site (1 vs. 1a). Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Exon-specific primer does not amplify wt transcript. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

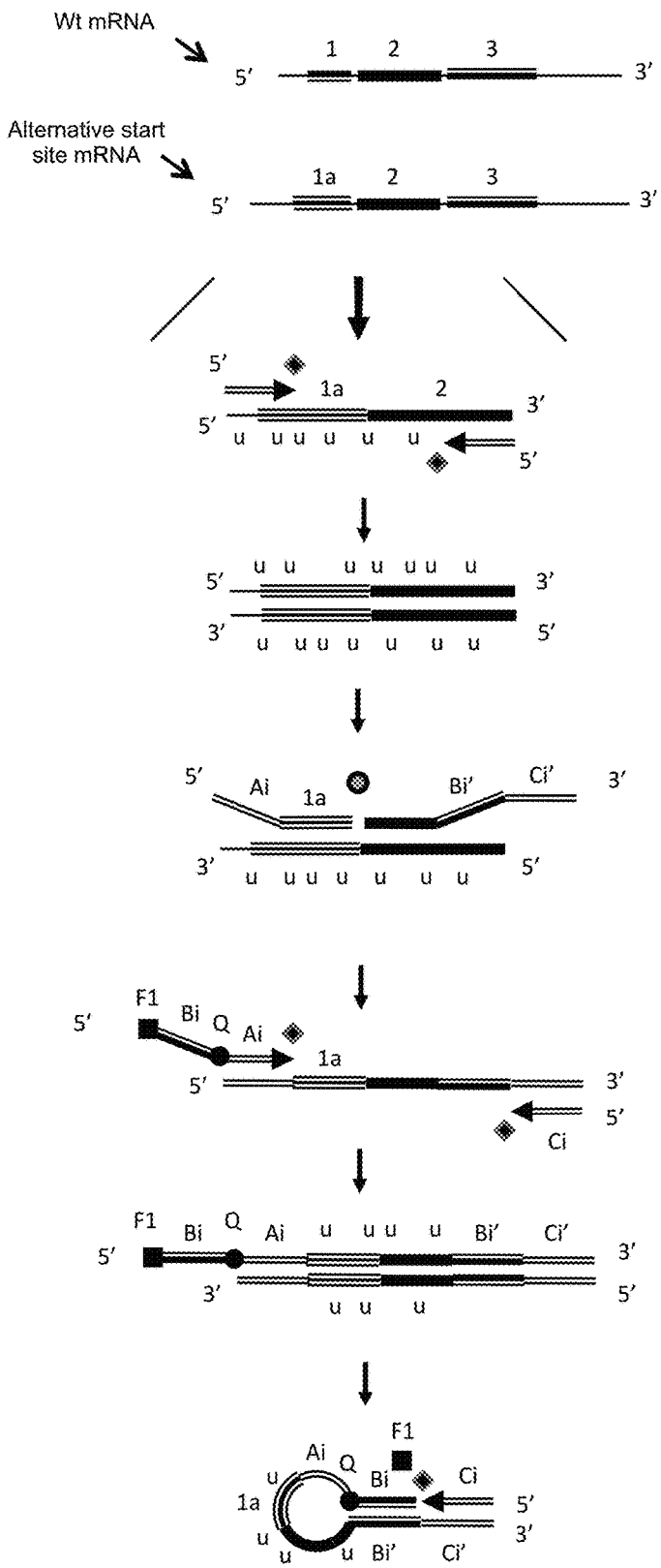

Figure 70

A. RT-PCR-qLDR carryover prevention reaction to detect low level of alternative transcript start site (1 vs. 1a). Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

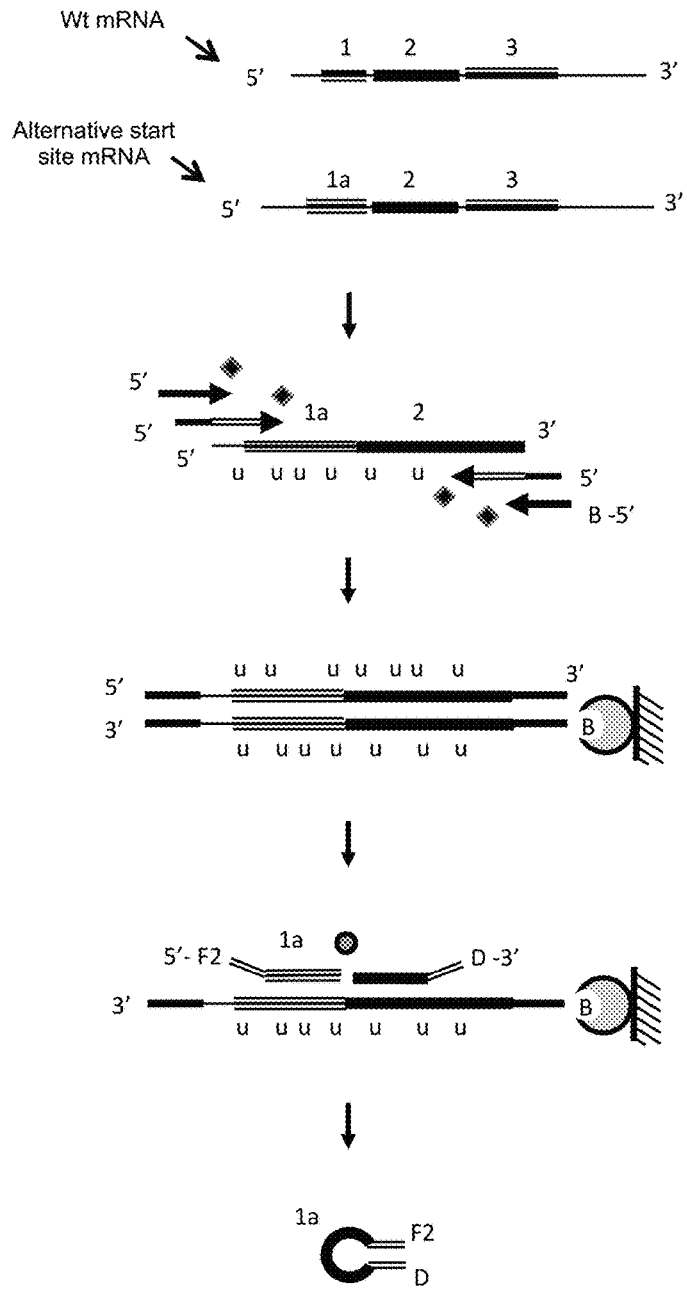

Figure 71

A. Overview: RT-PCR-LDR-qPCR carryover prevention reaction to detect exon deletion. Illustration of gene with 5 exons and 4 introns shown at the DNA level.

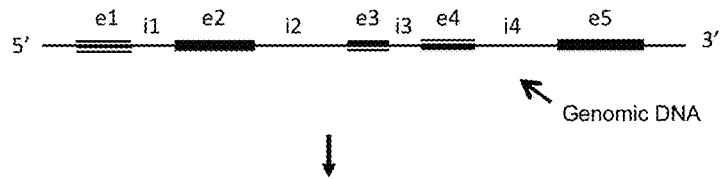

B. Example of normal (e1-e2-e3-e4-e5) and exon deletion (e1-e2-e3-e5) mRNAs are illustrated. Isolate mRNA from whole blood cells, exosomes, or CTCs. Generate cDNA using reverse transcriptase and primer complementary to exon e5. PCR amplify using forward primers to exons e3, and e4, generating amplicons of both splice variants.

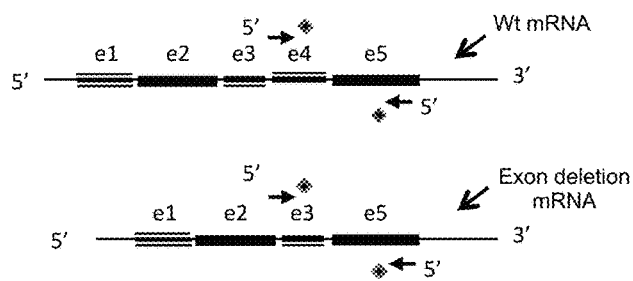

C. Exon junction-specific ligation oligonucleotides contain tags (Ai, Ci' for individual Taqman probes; or Ai, Bi-Ci for UniTaq probes) for subsequent PCR amplification. Ligase covalently seals the two oligonucleotides together, if there is perfect complementarity at the junction. Aliquot into separate wells for detection using real-time PCR.

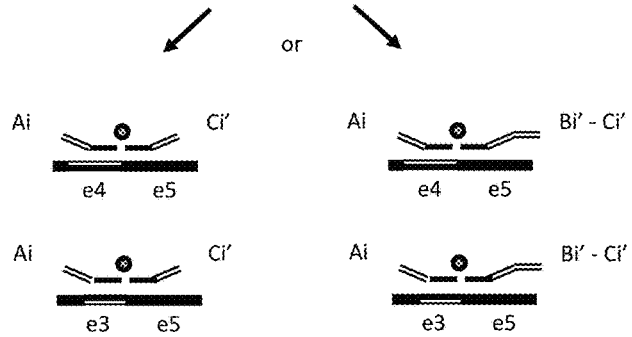

D. When using tag-specific primers (Ai, Ci) for amplifying LDR products of the upper set, each Taqman probe spans the ligation junction, and can be scored individually. When using UniTaq-specific primers (F1-Bi-Q-Ai, Ci), for amplifying LDR products of the lower set, a given primer set scores for a given ligation junction.

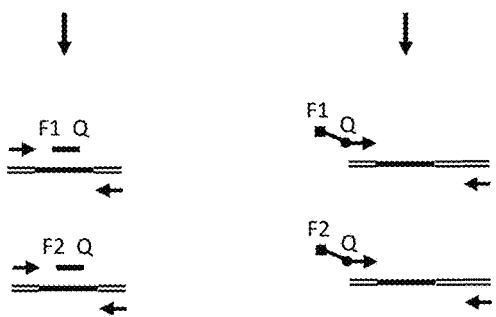

Figure 72

A. RT-PCR-LDR-qPCR carryover prevention reaction to quantify wt and alternatively spliced (exon deletion) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection. (LDR products are not amplified by either original PCR or LDR primers, providing additional protection.)

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. The relative Ct values reflects the relative amount of each transcript.

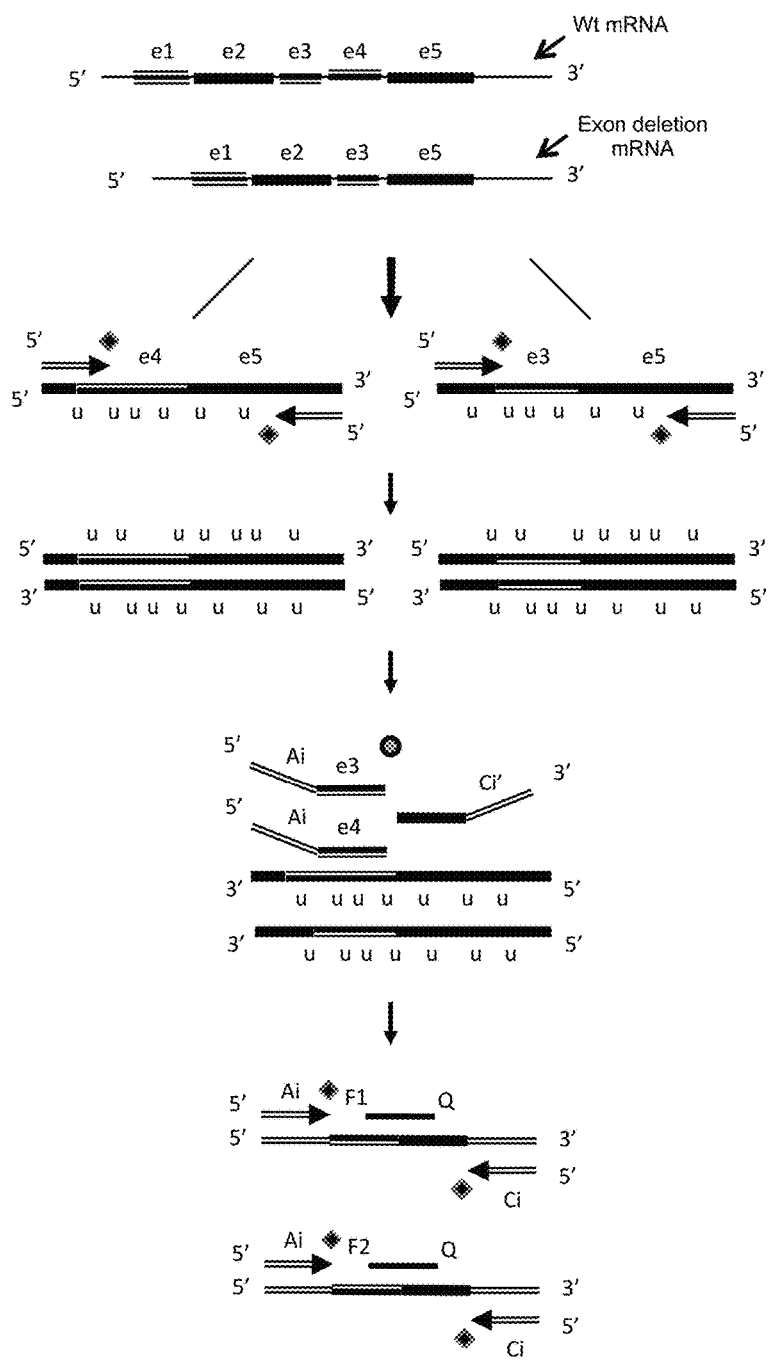

Figure 73

A. RT-PCR-LDR-qPCR carryover prevention reaction to quantify wt and alternatively spliced (exon deletion) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR (not shown); the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal. The relative Ct values reflects the relative amount of each transcript.

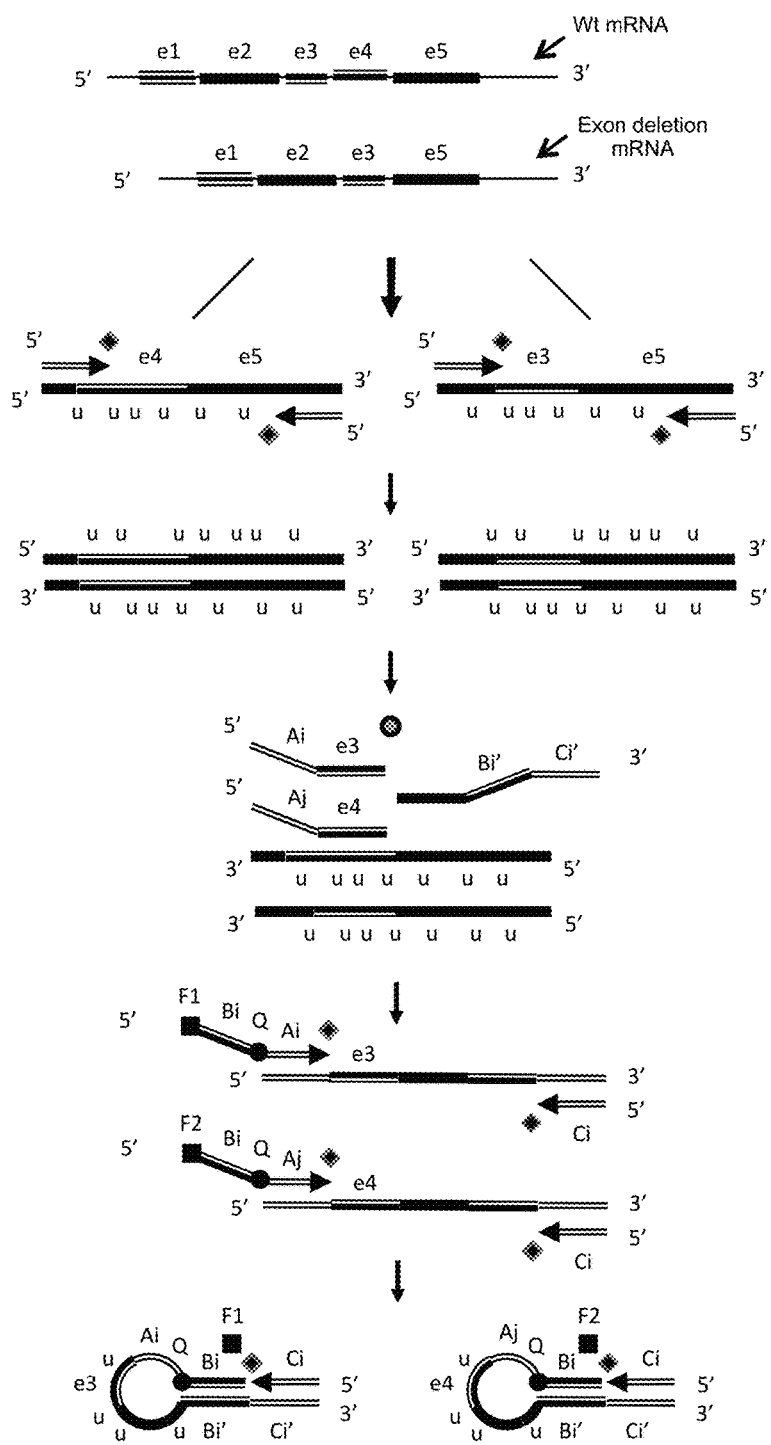

Figure 74

A. RT-PCR-qLDR carryover prevention reaction to quantify wt and alternatively spliced (exon deletion) transcript. Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

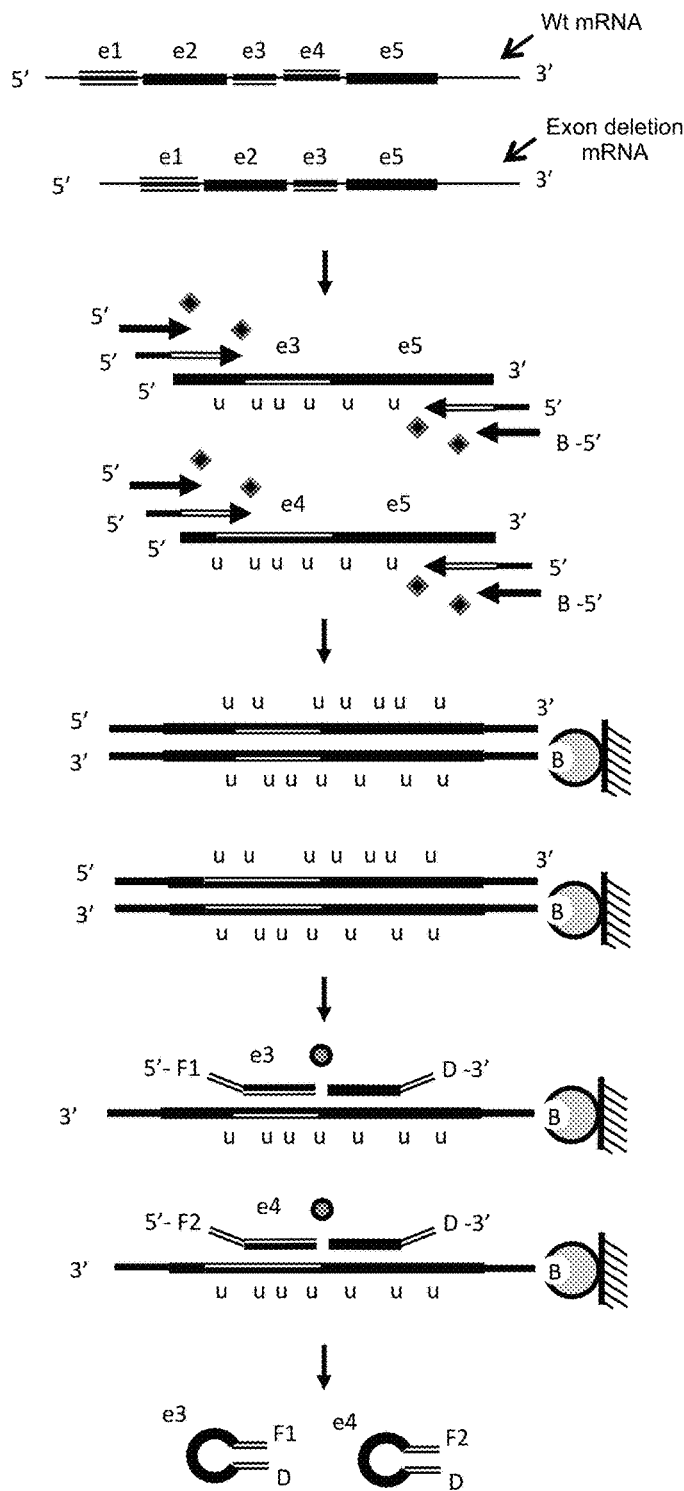

Figure 75

A. RT-PCR-LDR-qPCR carryover prevention reaction to detect low-level alternatively spliced (exon deletion) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Blocking oligo suppresses amplification of wt transcript. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

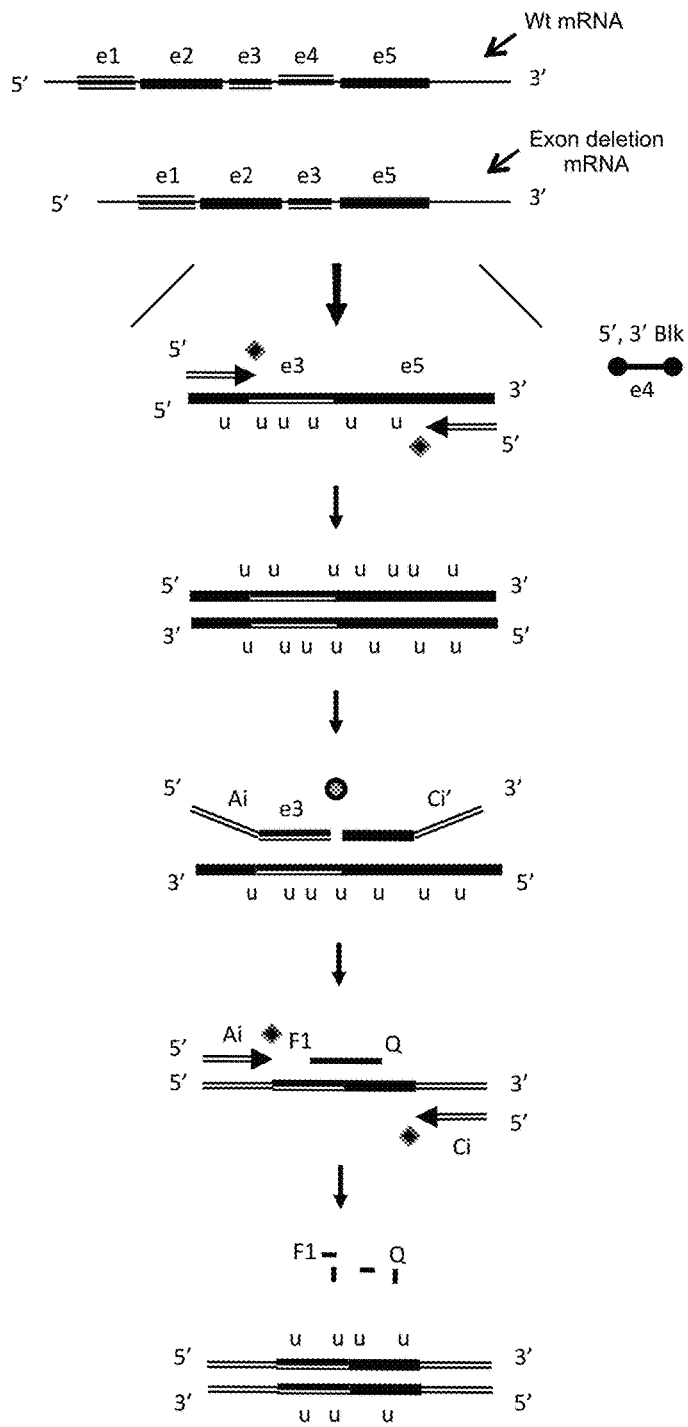

Figure 76

A. RT-PCR-LDR-qPCR carryover prevention reaction to detect low-level alternatively spliced (exon deletion) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Blocking oligo suppresses amplification of wt transcript. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

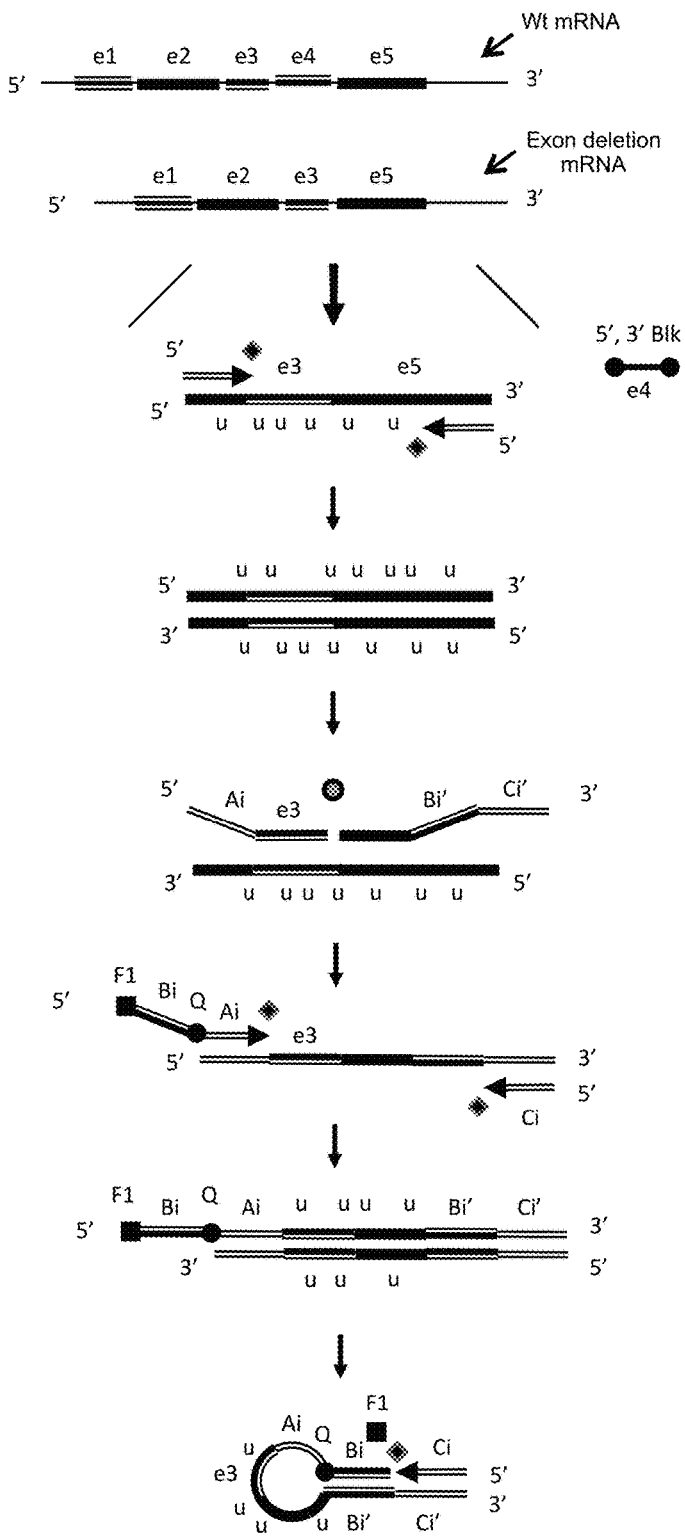

Figure 77

A. RT-PCR-qLDR carryover prevention reaction to detect low-level alternatively spliced (exon deletion) transcript. Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Blocking oligo suppresses amplification of wt transcript. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

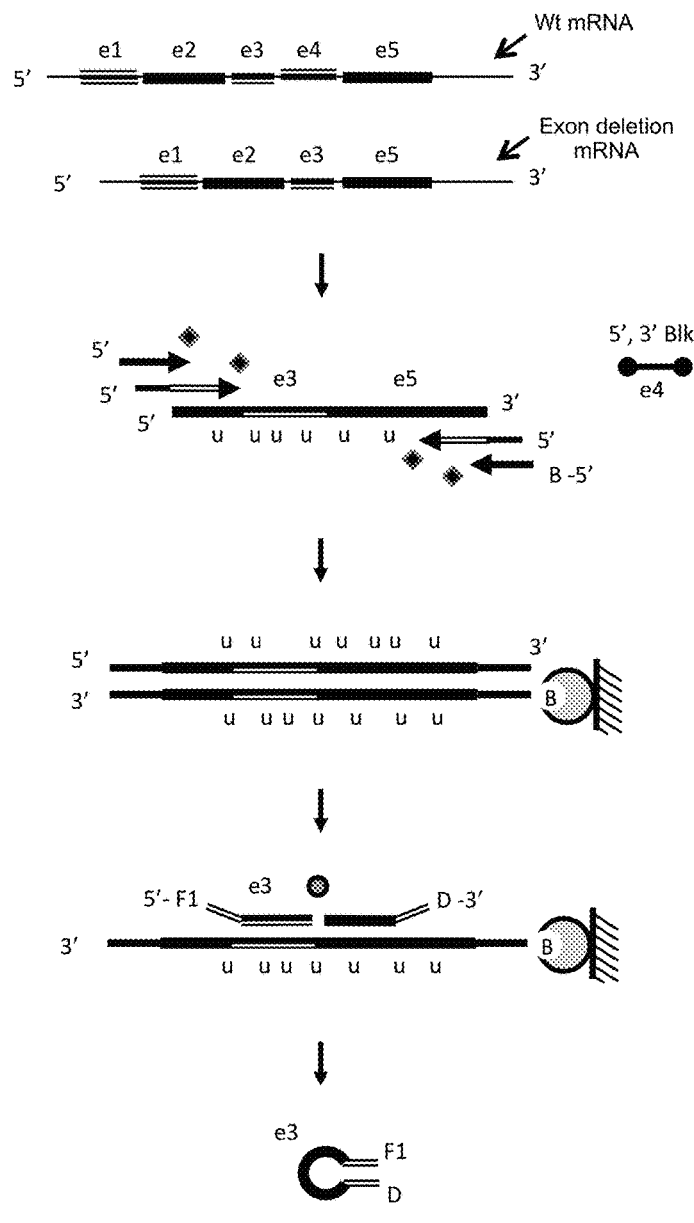

Figure 78

A. Overview: RT-PCR-LDR-qPCR carryover prevention reaction to detect alternative splicing with intron insertion. Illustration of gene with 5 exons and 4 introns shown at the DNA level.

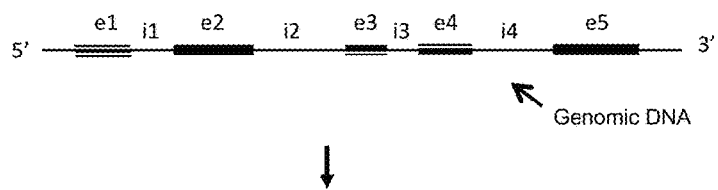

B. Examples of normal (e1-e2-e3-e4-e5) and intron insertion (e1-i1-e2-e3-e4-e5) mRNAs are illustrated. Isolate mRNA from whole blood cells, exosomes, or CTCs. Generate cDNA using reverse transcriptase and primer complementary to exon e2. PCR amplify using forward primers to exon e1, generating amplicons of both splice variants.

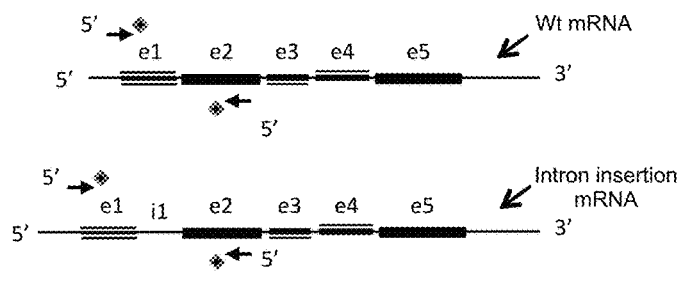

C. Exon junction-specific ligation oligonucleotides contain tags (Ai, Ci' for individual Taqman probes; or Ai, Bi-Ci for UniTaq probes) for subsequent PCR amplification. Ligase covalently seals the two oligonucleotides together, if there is perfect complementarity at the junction. Aliquot into separate wells for detection using real-time PCR.

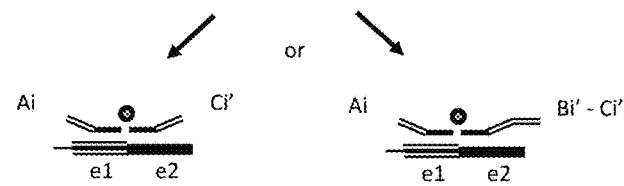

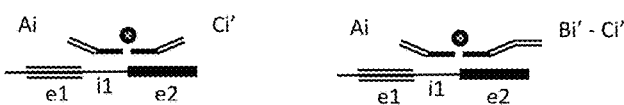

D. When using tag-specific primers (Ai, Ci) for amplifying LDR products of the upper set, each Taqman probe spans the ligation junction, and can be scored individually. When using UnTtaq-specific primers (F1-Bi-Q-Ai, Ci), for amplifying LDR products of the lower set, a given primer set scores for a given ligation junction.

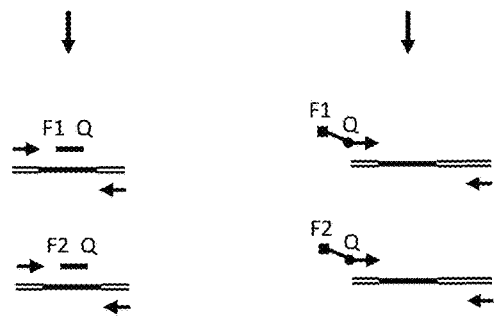

Figure 79

A. RT-PCR-LDR-qPCR carryover prevention reaction to quantify wt and alternatively spliced (intron insertion) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection. (LDR products are not amplified by either original PCR or LDR primers, providing additional protection.)

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. The relative Ct values reflects the relative amount of each transcript.

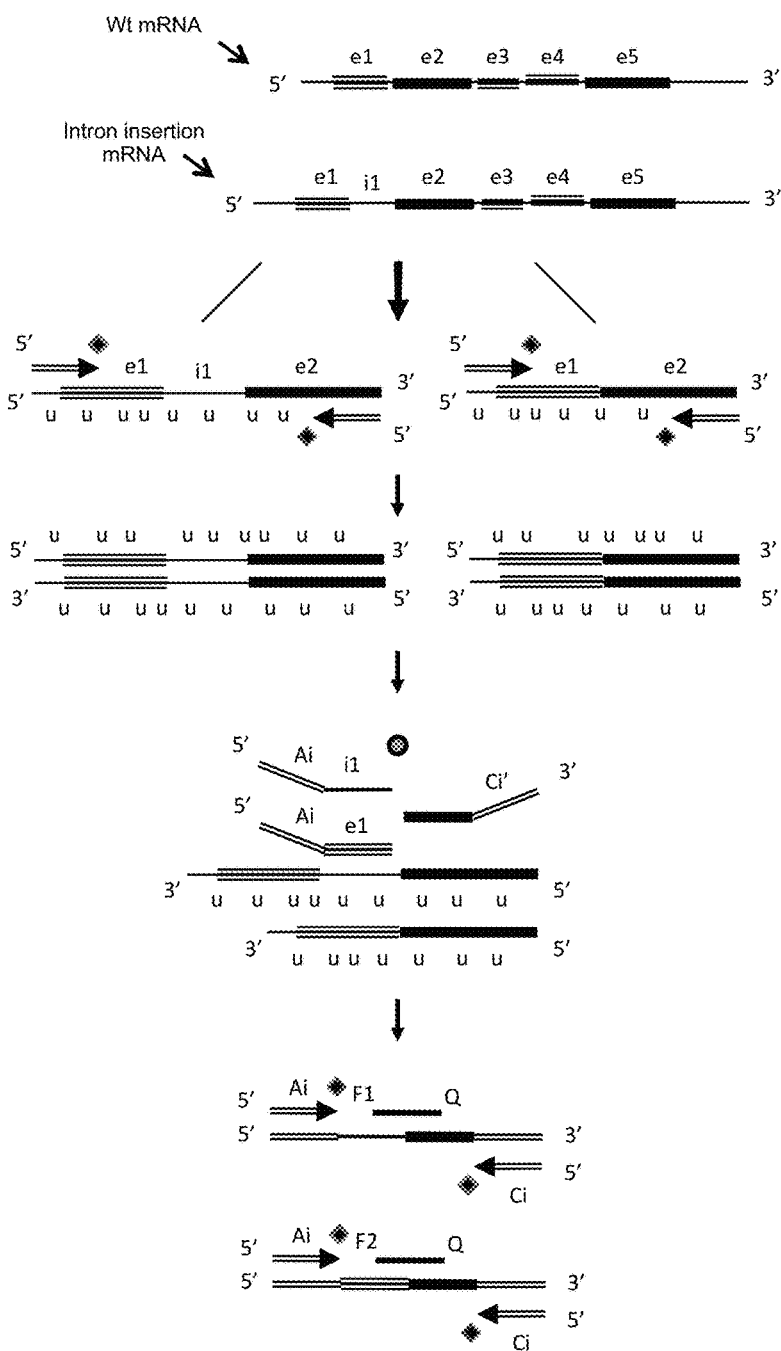

Figure 80

A. RT-PCR-LDR-qPCR carryover prevention reaction to quantify wt and alternatively spliced (intron insertion) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR (not shown); the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal. The relative Ct values reflects the relative amount of each transcript.

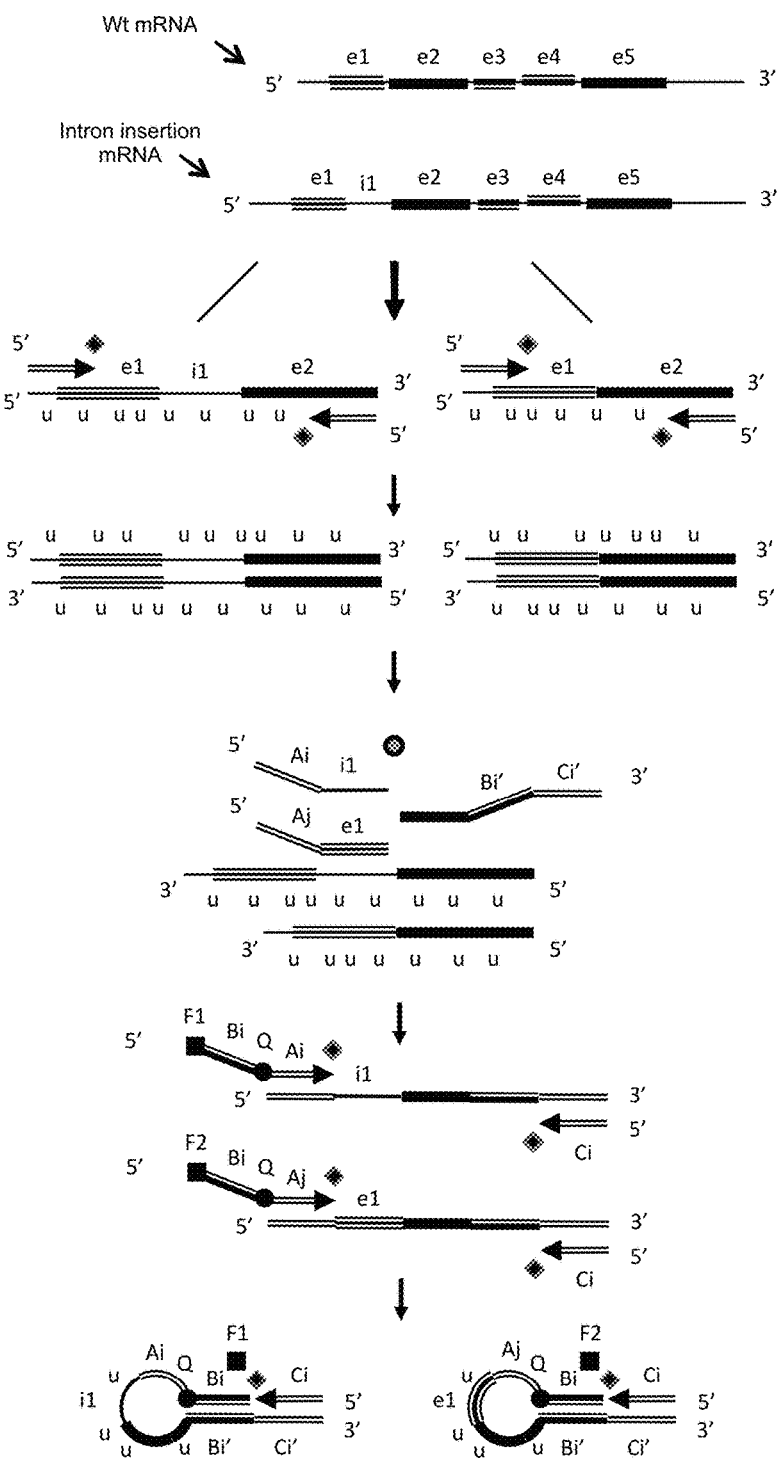

Figure 81

A. RT-PCR-qLDR carryover prevention reaction to quantify wt and alternatively spliced (intron insertion) transcript. Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

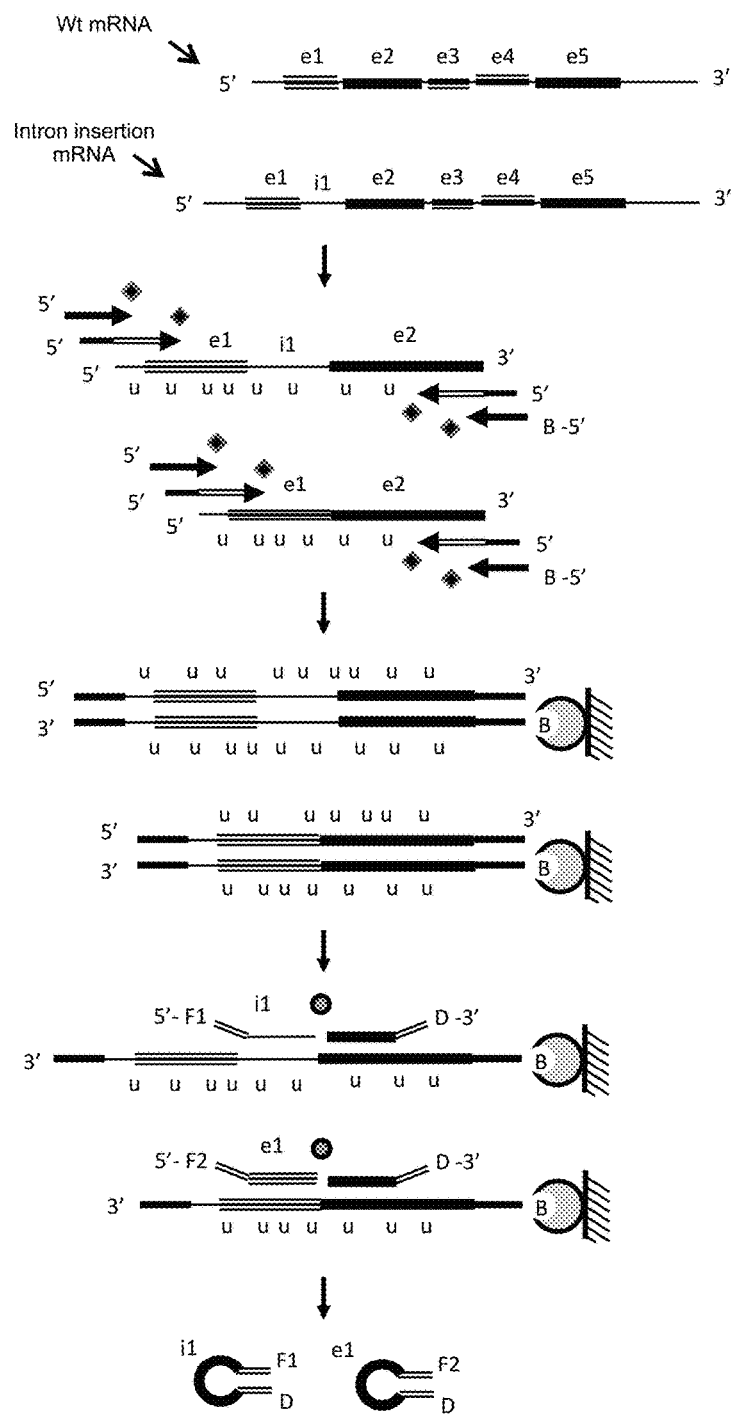

Figure 82

A. RT-PCR-LDR-qPCR carryover prevention reaction to detect low-level alternatively spliced (intron insertion) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Intron-specific primer does not amplify wt transcript. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

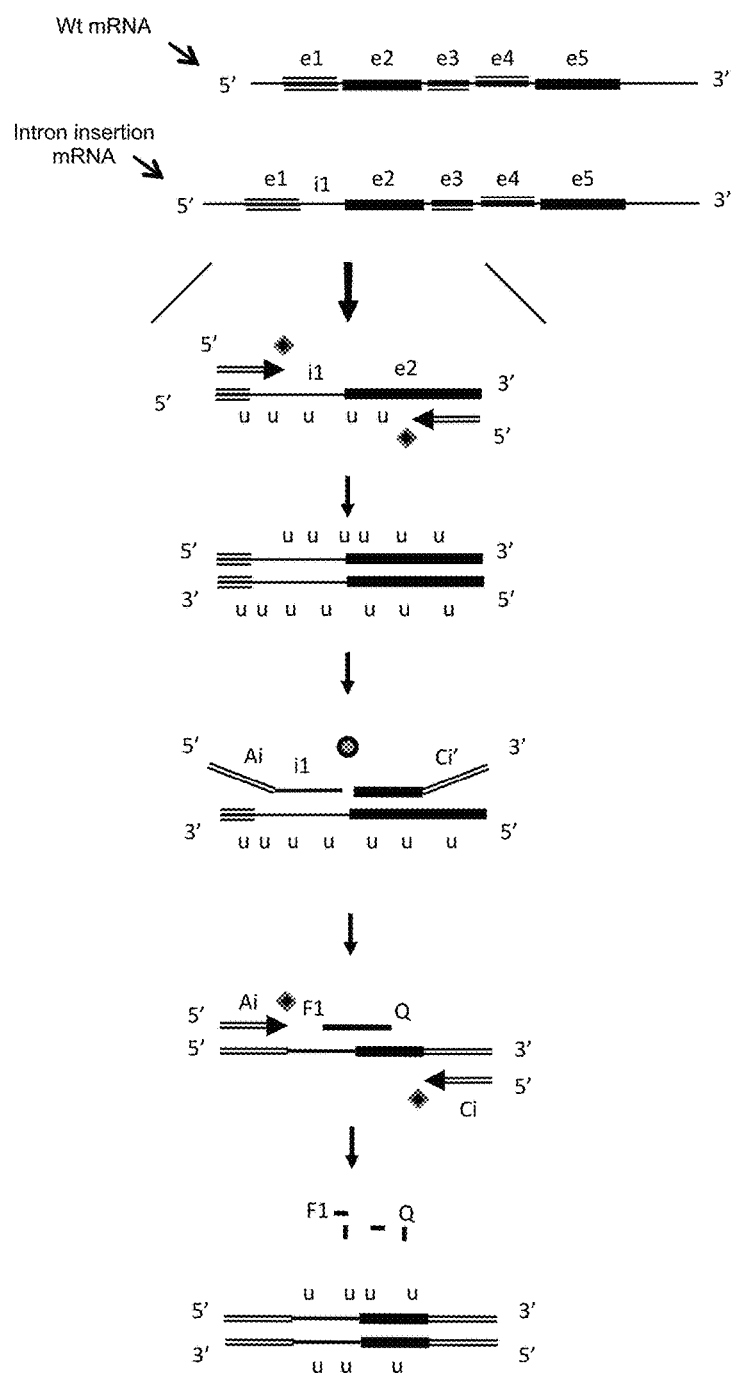

Figure 83

A. RT-PCR-LDR-qPCR carryover prevention reaction to detect low-level alternatively spliced (intron insertion) transcript. Isolate mRNA.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Intron-specific primer does not amplify wt transcript. Primers contain identical 8-11 base tails to prevent primer dimers. (Optional: aliquot into 12, 24, 48, or 96 wells prior to PCR.)

C. PCR products incorporate dU, allowing for carryover prevention.

D. Exon junction-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

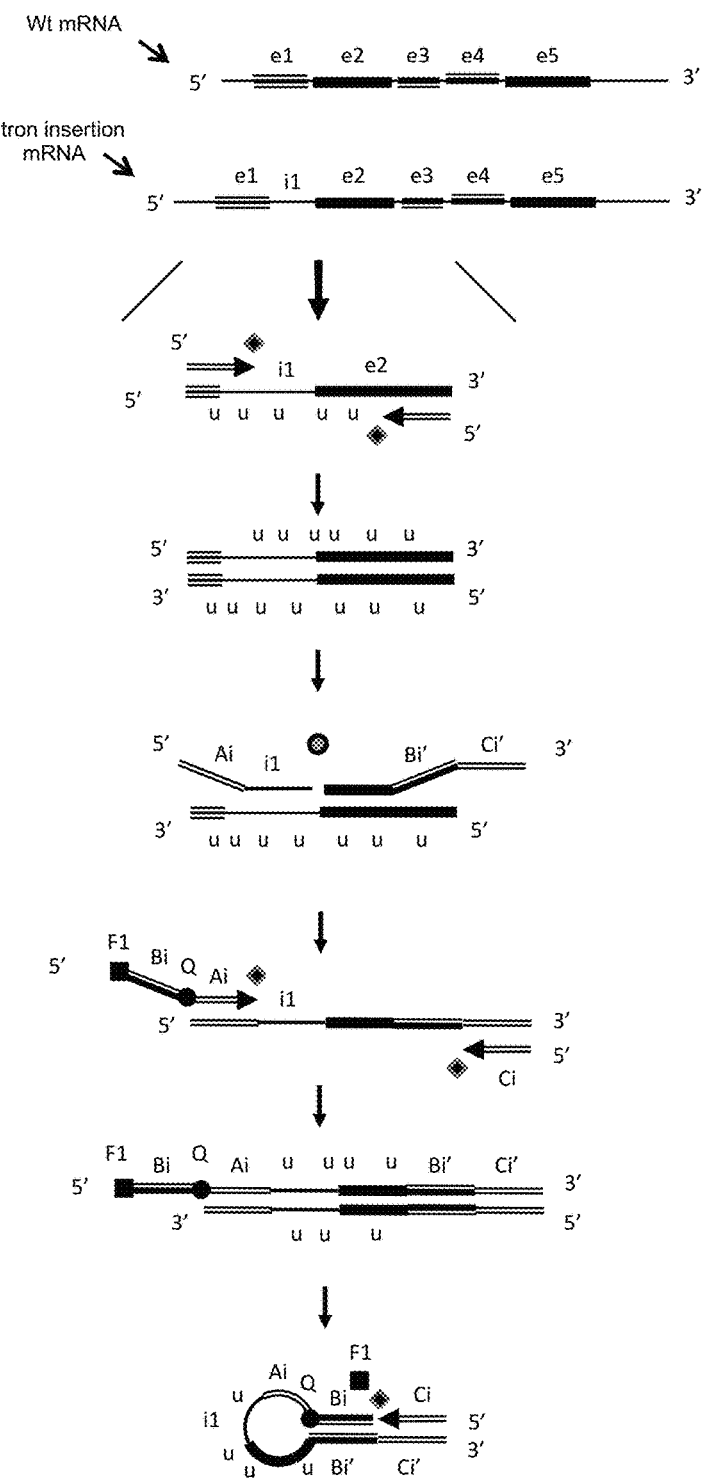

Figure 84

A. PCR-LDR carryover prevention reaction to detect low-level alternatively spliced (intron insertion) transcript. Isolate mRNA.

B. Treat with UDG (uracil DNA glycosylase) for carryover prevention, aliquot into 12, 24, 48, or 96 wells, and heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Intron-specific primer does not amplify wt transcript. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Exon junction-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

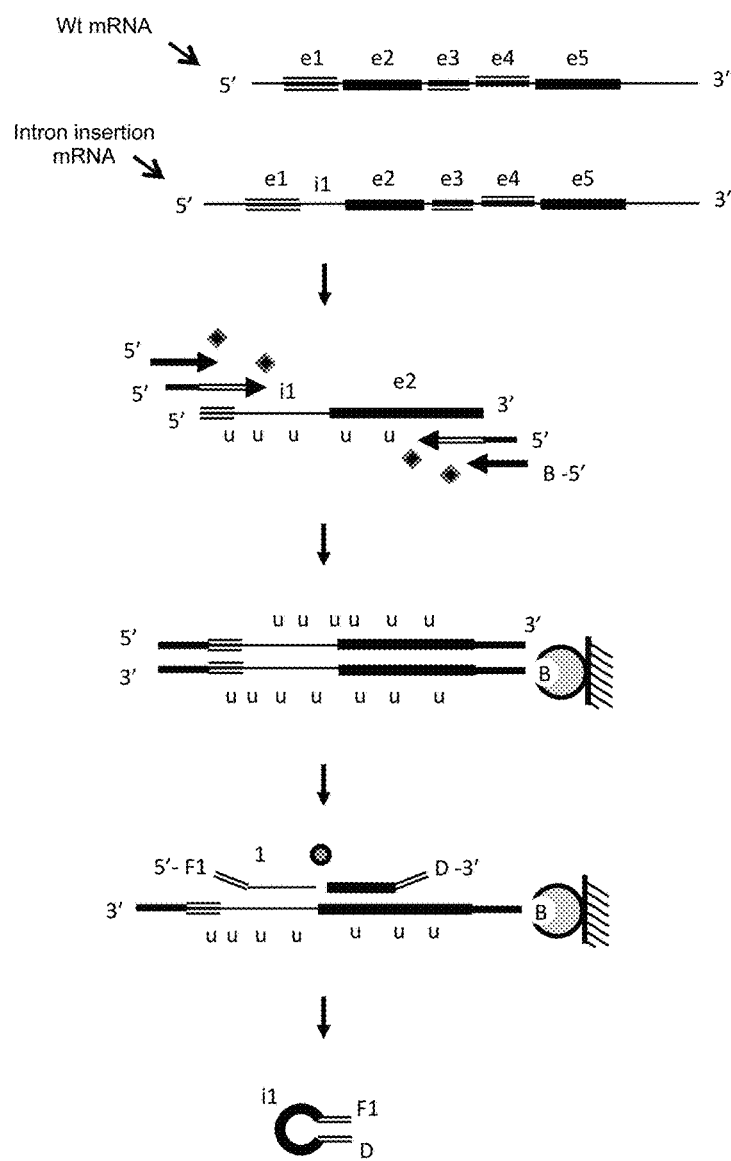

Figure 85

A. PCR-LDR-qPCR carryover prevention reaction to enumerate DNA copy number. Isolate tumor DNA from CTCs or tumor-specific exosomes.

B. Treat with UDG (uracil DNA glycosylase) for carryover prevention, and amplify chromosomal regions using PCR (and dUTP) with locus-specific primers. Perform limited cycle amplification (12-20) to maintain relative ratios of different amplicons. Primers contain identical 8-11 base tails to prevent primer dimers. For accurate enumeration, aliquot into 12, 24, 48, or 96 wells prior to PCR.

C. PCR products incorporate dU, allowing for carryover prevention.

D. Locus-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. Determine copy number based on signal from wells where original distribution was one copy/ well.

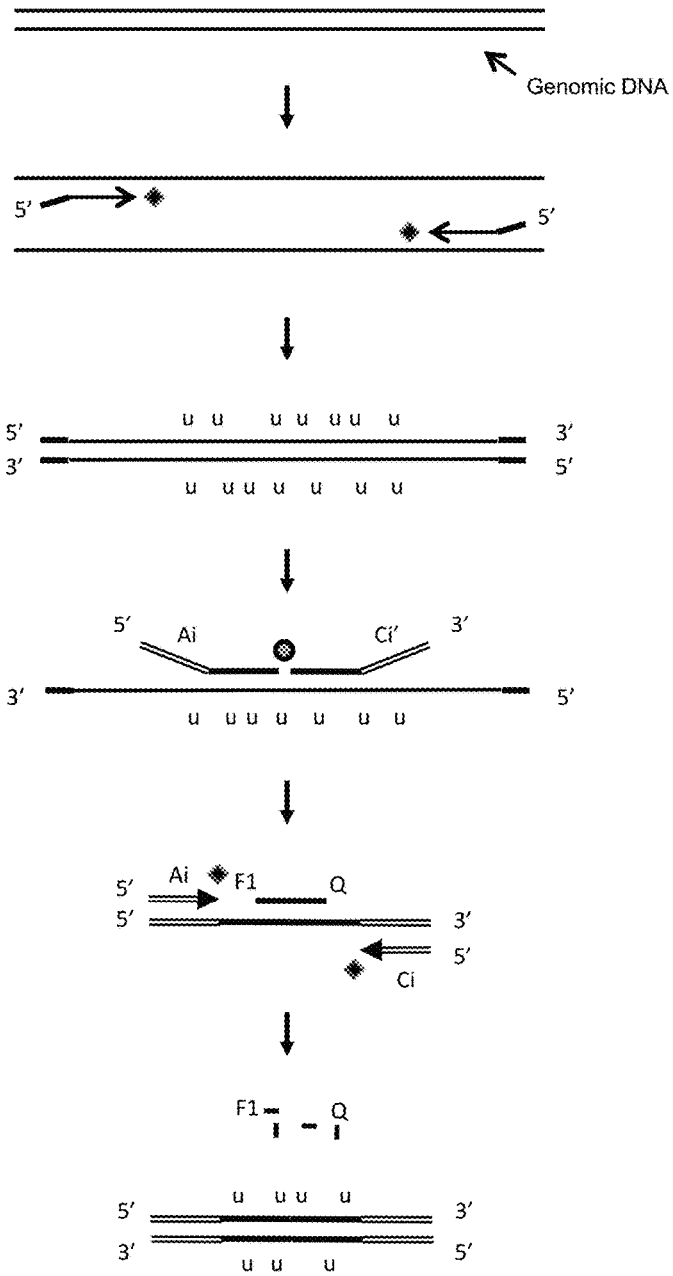

Figure 86

A. PCR-LDR-qPCR carryover prevention reaction to enumerate DNA copy number. Isolate tumor DNA from CTCs or tumor-specific exosomes.

B. Treat with UDG (uracil DNA glycosylase) for carryover prevention, and amplify chromosomal regions using PCR (and dUTP) with locus-specific primers. Perform limited cycle amplification (12-20) to maintain relative ratios of different amplicons. Primers contain identical 8-11 base tails to prevent primer dimers. For accurate enumeration, aliquot into 12, 24, 48, or 96 wells prior to PCR.

C. PCR products incorporate dU, allowing for carryover prevention.

D. Locus-specific ligation oligonucleotides contain tags (Ai, Bi'-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal. Determine copy number based on signal from wells where original distribution was one copy/well.

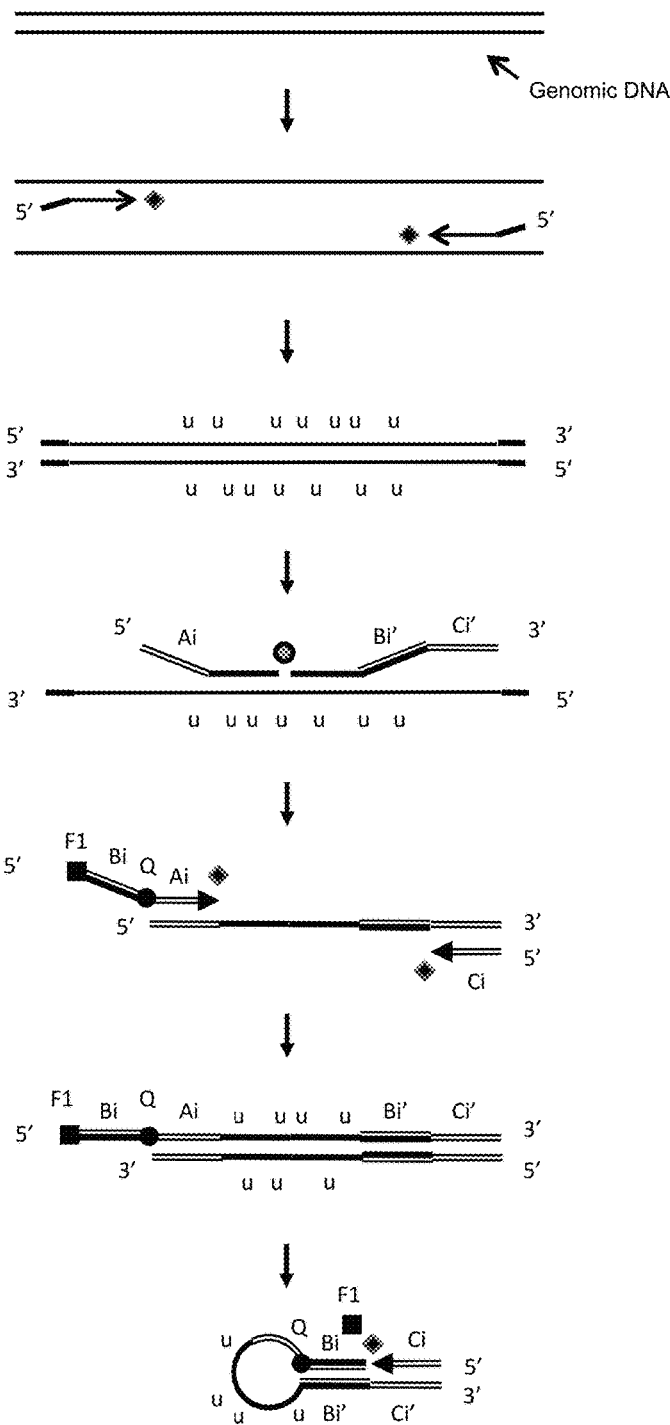

Figure 87

A. PCR-qLDR carryover prevention reaction to enumerate DNA copy number. Isolate tumor DNA from CTCs or tumor-specific exosomes.

B. Treat with UDG (uracil DNA glycosylase) for carryover prevention, aliquot into 12, 24, 48, or 96 wells, and amplify mutation containing regions using PCR (and dUTP) with locus-specific primers. Perform limited cycle amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Locus-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal. Determine copy number based on signal from wells where original distribution was one copy/well.

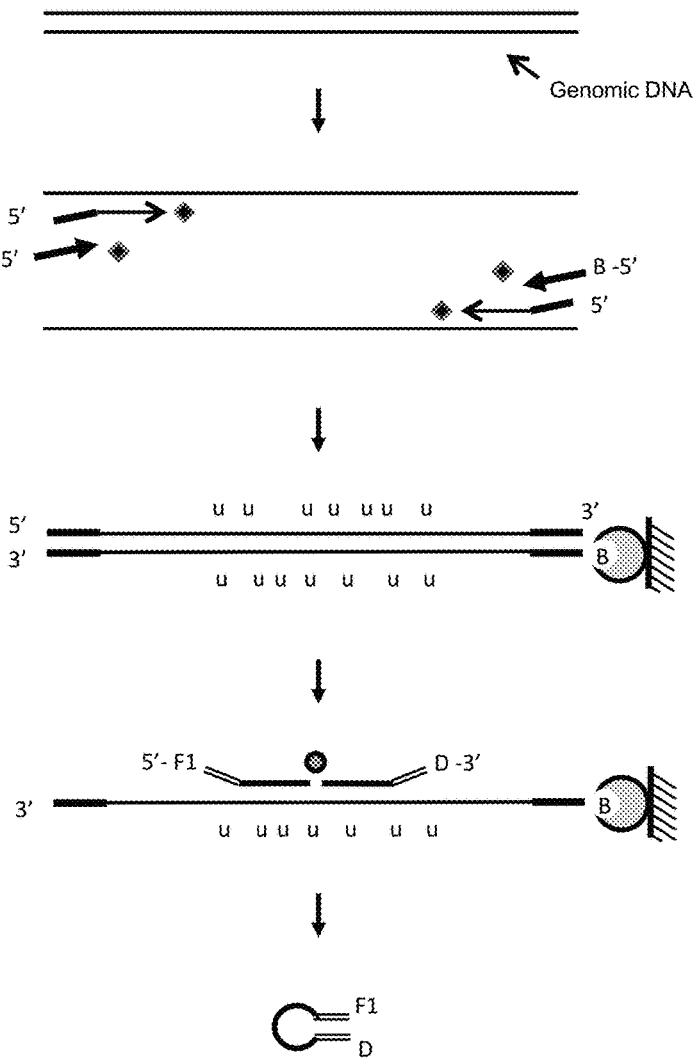

Figure 88

A. RT-PCR-LDR-qPCR carryover prevention reaction to enumerate RNA copy number. Isolate RNA from whole blood cells, exosomes, or CTCs..

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. For accurate enumeration, aliquot into 12, 24, 48, or 96 wells prior to PCR.

C. PCR products incorporate dU, allowing for carryover prevention.

D. Locus-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. Determine copy number based on signal from wells where original distribution was one copy/well.

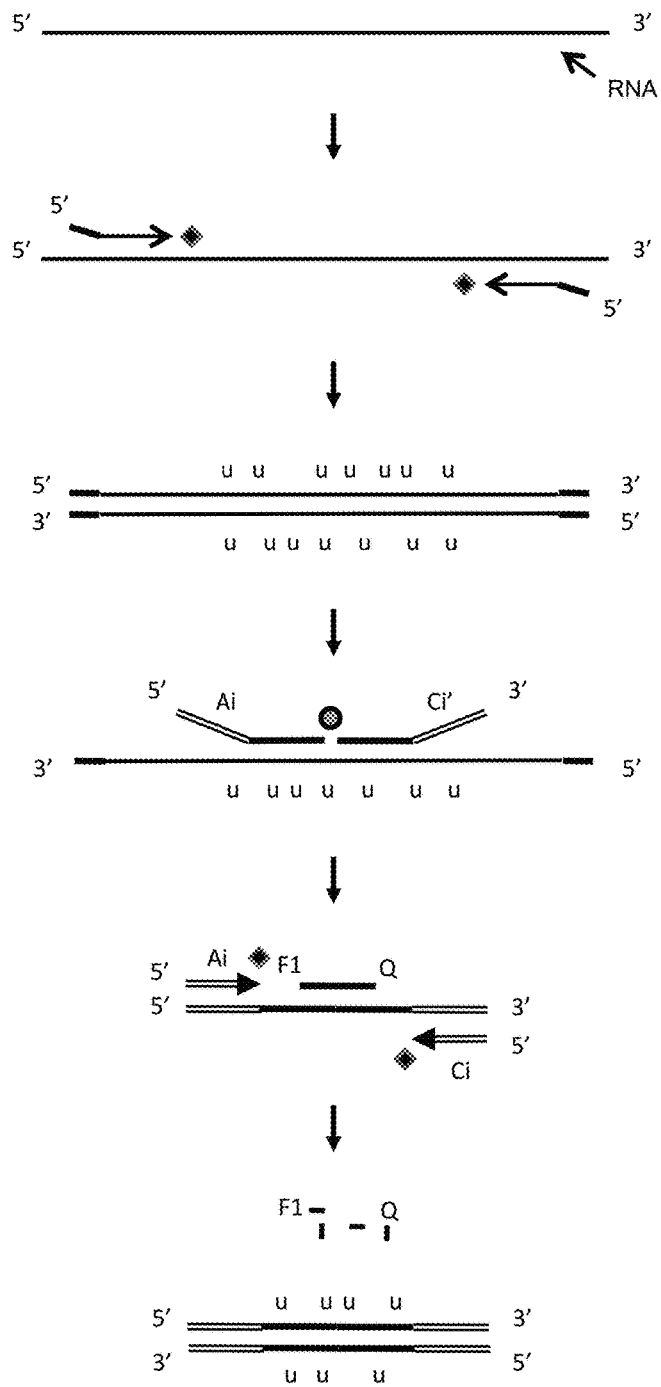

Figure 89

A. RT-PCR-LDR-qPCR carryover prevention reaction to enumerate RNA copy number. Isolate RNA from whole blood cells, exosomes, or CTCs.

B. Treat with UDG (uracil DNA glycosylase) for carryover prevention, heat kill. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain identical 8-11 base tails to prevent primer dimers. For accurate enumeration, aliquot into 12, 24, 48, or 96 wells prior to PCR.

C. PCR products incorporate dU, allowing for carryover prevention.

D. Locus-specific ligation oligonucleotides contain tags (Ai, Bi'-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal. Determine copy number based on signal from wells where original distribution was one copy/well.

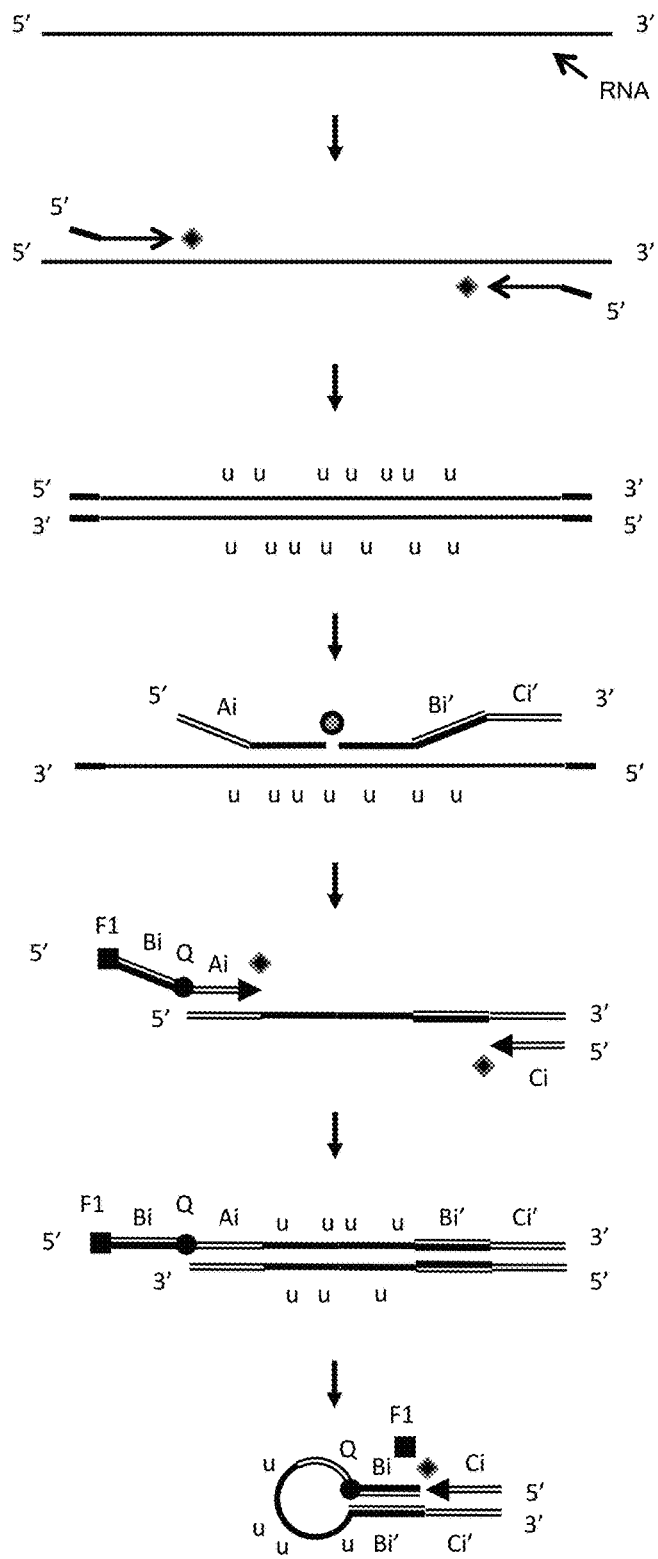

Figure 90

A. RT-PCR-qLDR carryover prevention reaction to enumerate RNA copy number. Isolate RNA from whole blood cells, exosomes, or CTCs.

B. Treat with UDG (uracil DNA glycosylase) for carryover prevention, and aliquot into 12, 24, 48, or 96 wells. Use reverse-transcriptase to make cDNA copy (using dUTP) with 3' transcript-specific primers. Activate Taq polymerase and perform limited cycle PCR amplification (12-20) to maintain relative ratios of different amplicons. Primers contain universal tails (with identical 8-11 bases to prevent primer dimers), also enabling universal primer amplification to append a 5' biotin.

C. PCR products incorporate dU, allowing for carryover prevention. Separate product from primers and capture biotinylated product on solid support.

D. Locus-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal. Determine copy number based on signal from wells where original distribution was one copy/well.

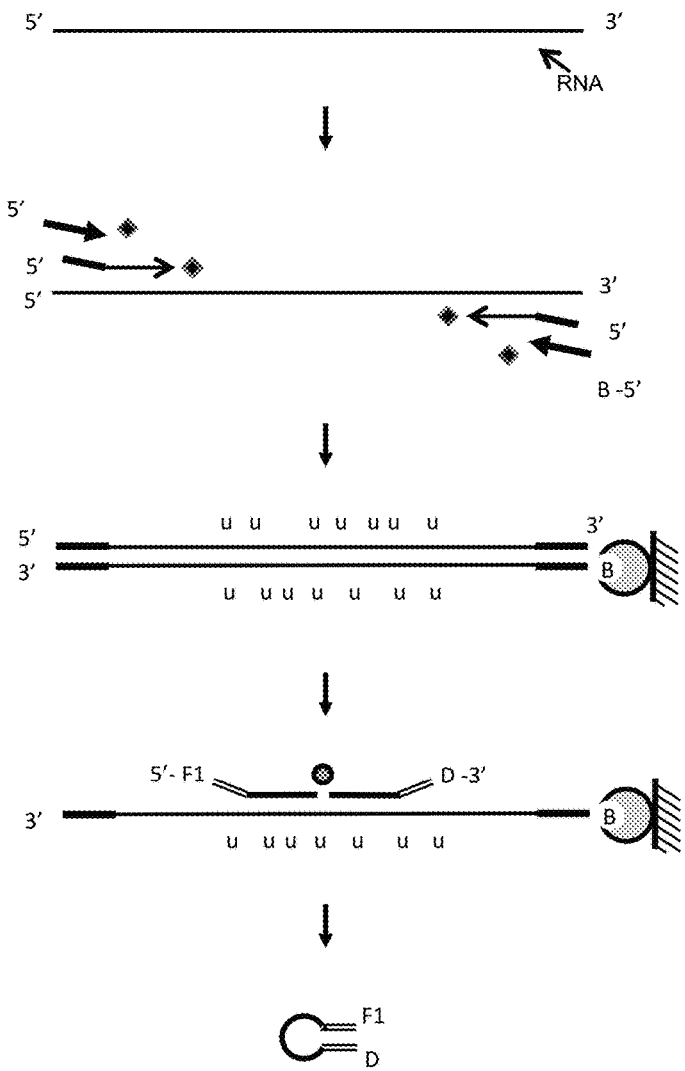

Figure 91

A. RT-PCR-LDR-qPCR carryover prevention reaction to quantify miRNA. Isolate miRNA from exosomes.

B. Treat with UDG (uracil DNA glycosylase) for carryover prevention, heat kill. Hybridize probe complementary to 3' end of target miRNA, containing a stem-loop, tag (Tj), and blocking group. Extend 3' end of loop primer with reverse transcriptase (using dUTP). Activate Taq polymerase and perform limited cycle PCR amplification (12-20), using bridge and tag primers (Ti, Tj), to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. miRNA sequence-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

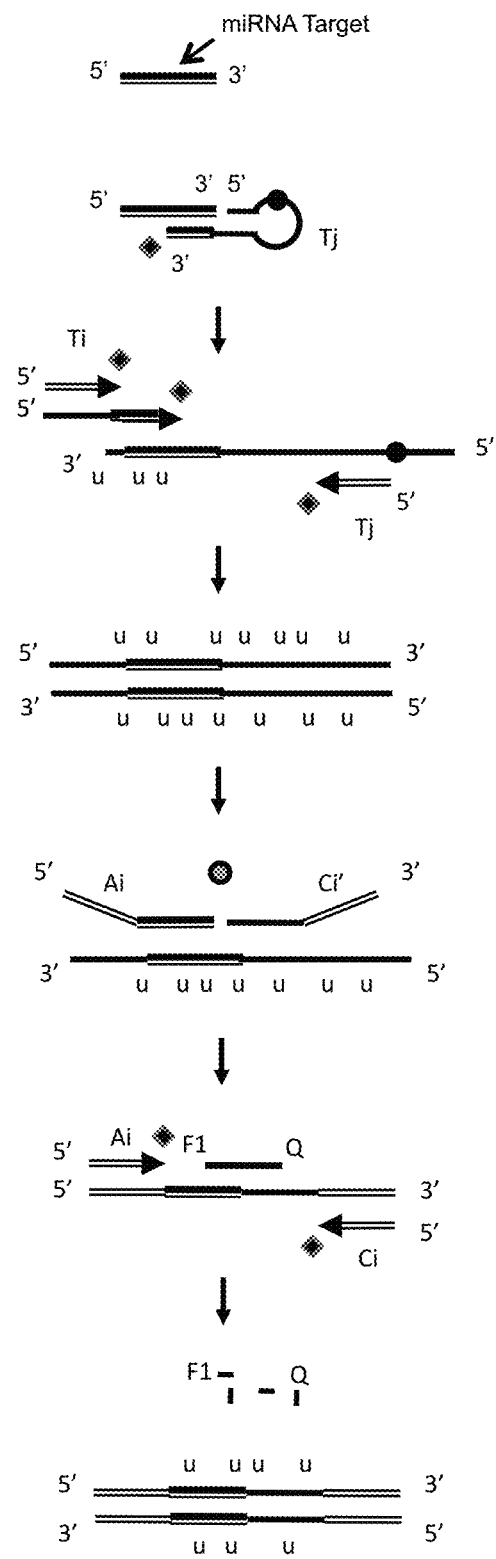

Figure 92

A. RT-PCR-LDR-qPCR carryover prevention reaction to quantify miRNA. Isolate miRNA from exosomes.

B. Treat with UDG (uracil DNA glycosylase) for carryover prevention, heat kill. Hybridize probe complementary to 3' end of target miRNA, containing a stem-loop, tag (Tj), and blocking group. Extend 3' end of loop primer with reverse transcriptase (using dUTP). Activate Taq polymerase and perform limited cycle PCR amplification (12-20), using bridge and tag primers (Ti, Tj), to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. miRNA sequence-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

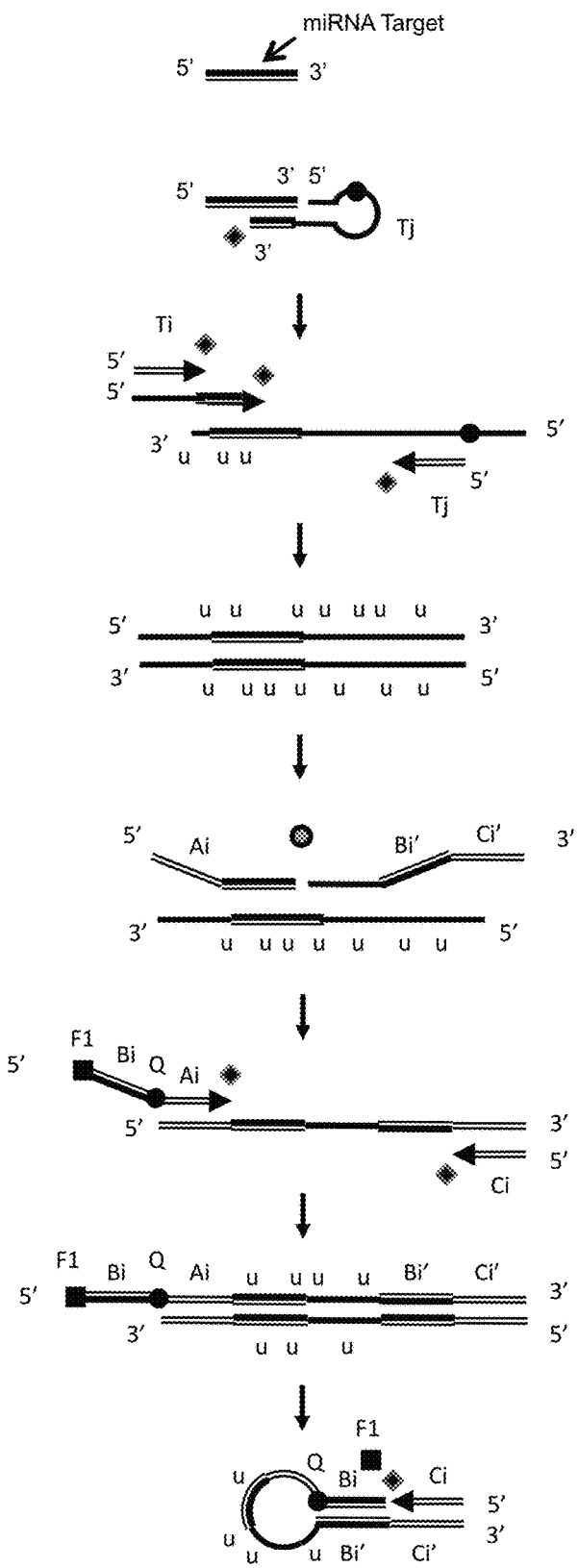

Figure 93

A. RT-PCR-qLDR carryover prevention reaction to quantify miRNA. Isolate miRNA from exosomes.

B. Treat with UDG (uracil DNA glycosylase) for carryover prevention, and aliquot into 12, 24, 48, or 96 wells. Hybridize probe complementary to 3' end of target miRNA, containing a stem-loop, tag (Tj), and blocking group. Extend 3' end of loop primer with reverse transcriptase (using dUTP). Activate Taq polymerase and perform limited cycle PCR amplification (12-20), using bridge and tag primers (Ti, Tj), to maintain relative ratios of different amplicons. Primers contain identical 8-11 base tails to prevent primer dimers, with one primer containing a 5' biotin.

C. PCR products incorporate dU, allowing for carryover prevention. Separate product from primers and capture biotinylated product on solid support.

D. miRNA-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

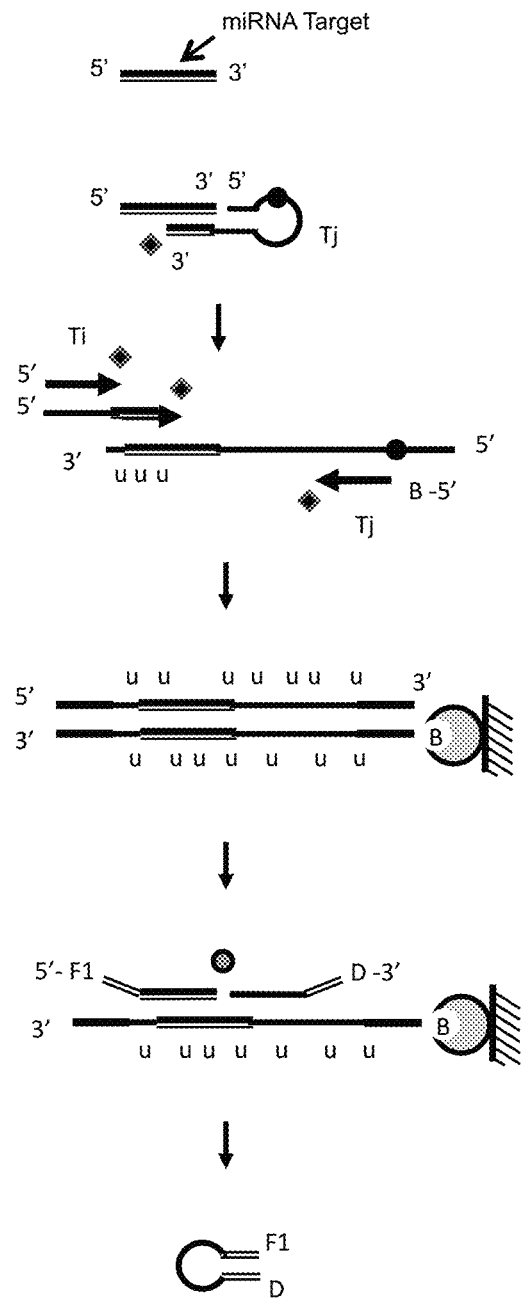

Figure 94

A. Ligation-RT-PCR-LDR-qPCR carryover prevention reaction to quantify miRNA. Isolate miRNA from exosomes.

B. Treat with UDG (uracil DNA glycosylase) for carryover prevention, heat kill. Ligate probe complementary to 3' end of target miRNA, containing a stem-loop, Tag (Tj'), and blocking group. Extend with primer Tj and reverse transcriptase (using dUTP). Activate Taq polymerase and perform limited cycle PCR amplification (12-20), using bridge and tag primers (Ti, Tj), to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. miRNA sequence-specific ligation oligonucleotides contain tags (Ai, Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with tag-specific primers (Ai, Ci). Each Taqman probe spans the ligation junction.

F. The 5'->3' nuclease activity of Taq polymerase liberates the fluorescent group to generate signal. (PCR products incorporate dU, allowing for carryover prevention.)

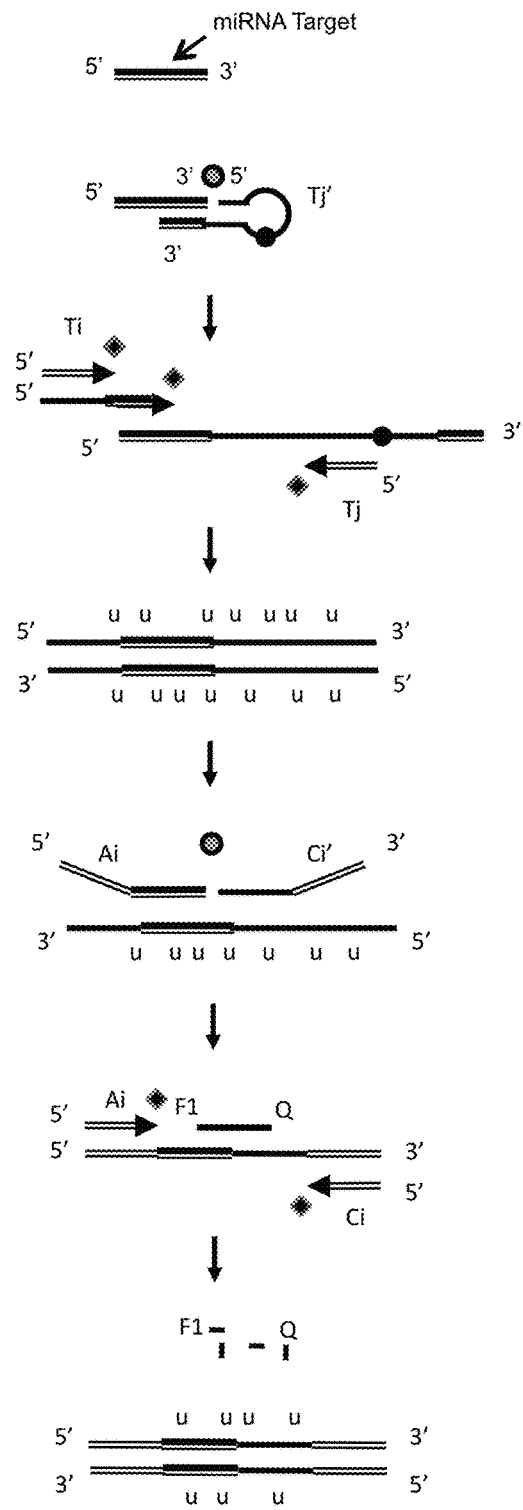

Figure 95

A. Ligation-RT-PCR-LDR-qPCR carryover prevention reaction to quantify miRNA. Isolate miRNA from exosomes.

B. Treat with UDG (uracil DNA glycosylase) for carryover prevention, heat kill. Ligate probe complementary to 3' end of target miRNA, containing a stem-loop, Tag (Tj'), and blocking group. Extend with primer Tj and reverse transcriptase (using dUTP). Activate Taq polymerase and perform limited cycle PCR amplification (12-20), using bridge and tag primers (Ti, Tj), to maintain relative ratios of different amplicons. Primers contain identical 8-11 base tails to prevent primer dimers. (Optional: aliquot into 12, 24, 48, or 96 wells prior to PCR.)

C. PCR products incorporate dU, allowing for carryover prevention.

D. miRNA sequence-specific ligation oligonucleotides contain tags (Ai, Bi-Ci') for subsequent PCR amplification. Ligase covalently seals the two oligonucleotides together. Aliquot into separate wells for detection.

E. Treat with UDG for carryover prevention, which also destroys original target amplicons. Only authentic LDR products will amplify, when using PCR (and dUTP) with Unitaq-specific primers (F1-Bi-Q-Ai, Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

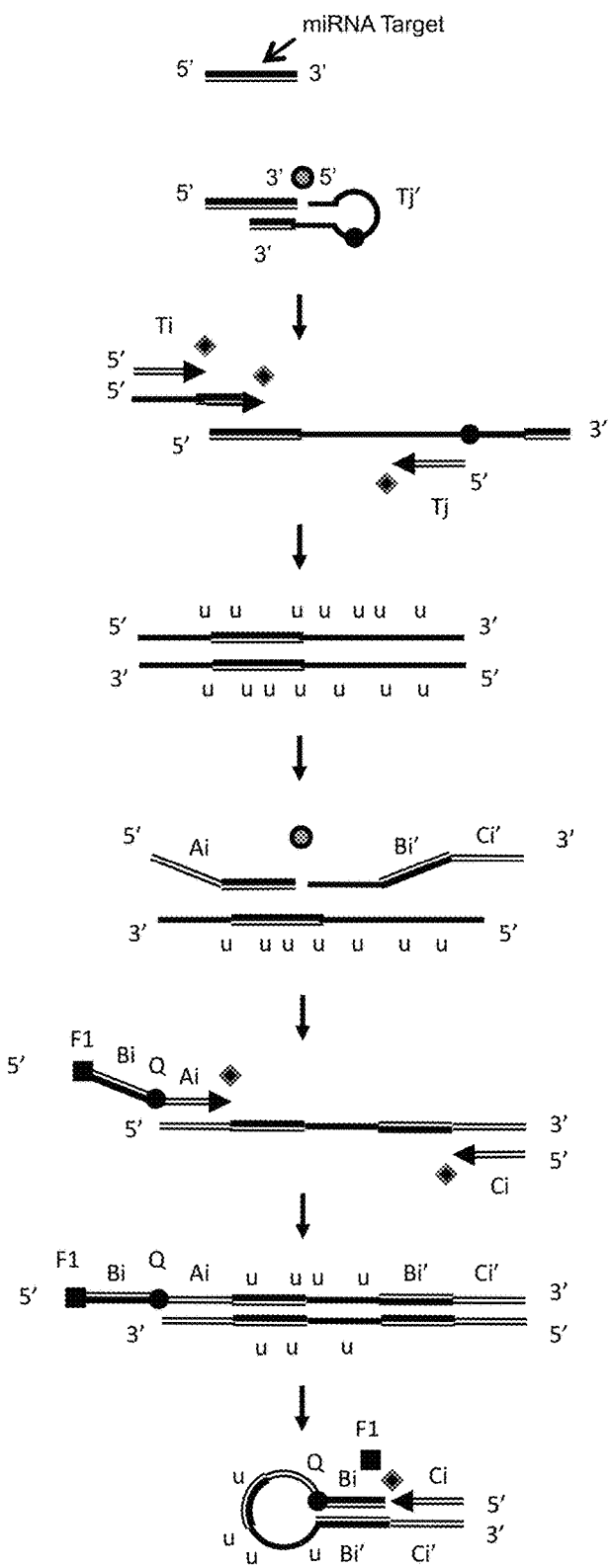

Figure 96

A. Ligation-RT-PCR-qLDR carryover prevention reaction to quantify miRNA. Isolate miRNA from exosomes.

B. Treat with UDG (uracil DNA glycosylase) for carryover prevention, and aliquot into 12, 24, 48, or 96 wells. Ligate probe complementary to 3' end of target miRNA, containing a stem-loop, Tag (Tj'), and blocking group. Extend with primer Tj and reverse transcriptase (using dUTP). Activate Taq polymerase and perform limited cycle PCR amplification (12-20), using bridge and tag primers (Ti, Tj), to maintain relative ratios of different amplicons. Primers contain identical 8-11 base tails to prevent primer dimers, with one primer containing a 5' biotin.

C. PCR products incorporate dU, allowing for carryover prevention. Separate product from primers and capture biotinylated product on solid support.

D. miRNA-specific ligation oligonucleotides contain tails for subsequent FRET detection. Ligase covalently seals the two oligonucleotides together. (LDR products are not amplified by either original PCR or LDR primers, providing additional protection.)

E. Wash away unligated primers. Denature product from target, then detect, and enumerate FRET signal.

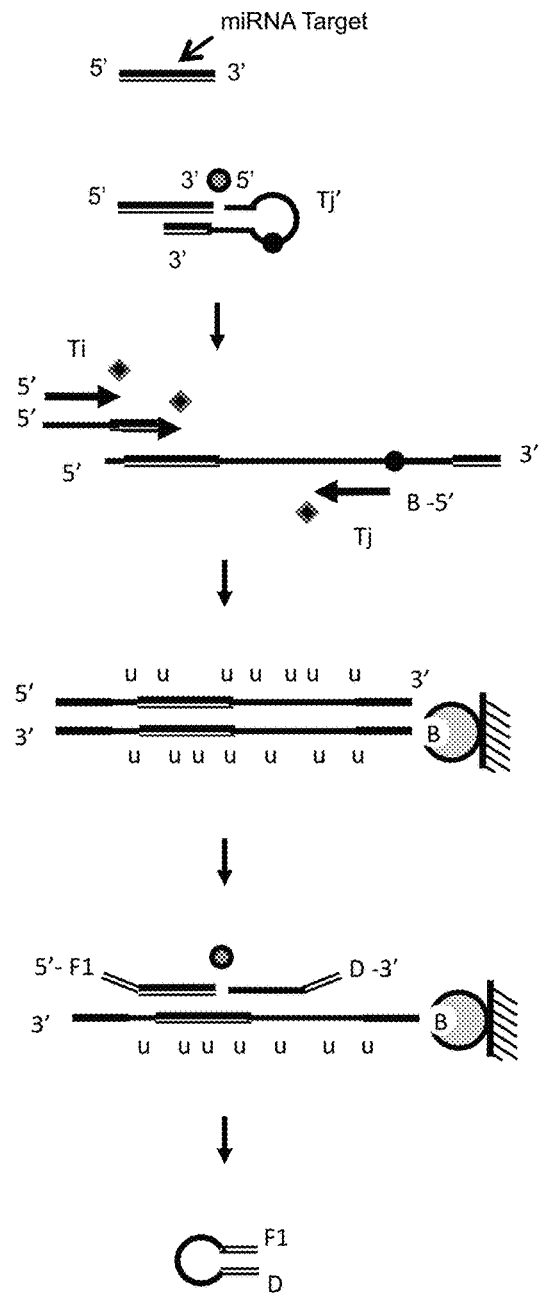

Figure 97

A. Ligation-RT-PCR-LDR-qPCR carryover prevention reaction to quantify miRNA. Isolate miRNA from exosomes.

B. Treat with UDG (uracil DNA glycosylase) for carryover prevention, heat kill. Ligate probe complementary to 3' end of target miRNA, containing a stem-loop, Tag (Tj'), and blocking group. Extend with primer Tj and reverse transcriptase (using dUTP).

C. miRNA-specific bridge primers are unblocked with RNaseH2 only when bound to target. Perform limited cycle PCR amplification (12-20), using tag primers (Ti, Tj), to maintain relative ratios of different amplicons. Primers contain identical 8-11 base tails to prevent primer dimers. (Optional: aliquot into 12, 24, 48, or 96 wells prior to PCR.)

D. PCR products incorporate dU, allowing for carryover prevention.

E. miRNA sequence-specific ligation oligonucleotides contain tags (Ai, Ci') for subsequent PCR amplification. Ligase covalently seals the two oligonucleotides together. Aliquot into separate wells for detection.

F. Treat with UDG for carryover prevention, which also destroys original target amplicons. Only authentic LDR products will amplify, when using PCR (and dUTP) with tag-specific primers (Ai, Ci). Each Taqman probe spans the ligation junction.

G. The 5'->3' nuclease activity of Taq polymerase liberates the fluorescent group to generate signal. (PCR products incorporate dU, allowing for carryover prevention.)

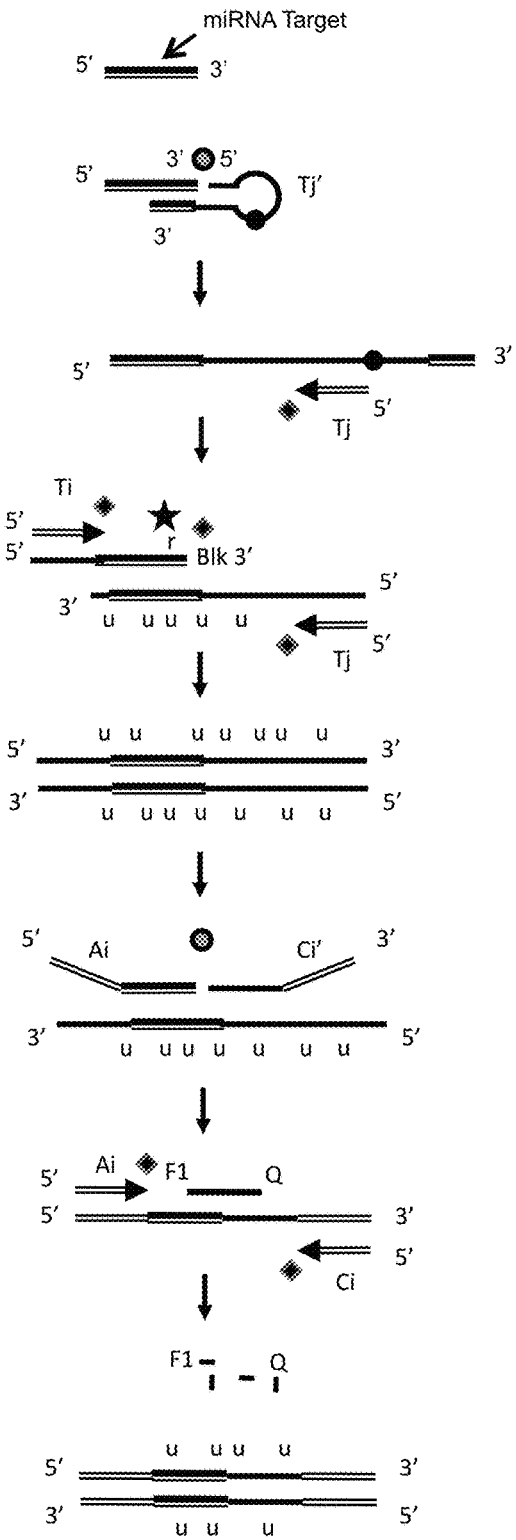

Figure 98

A. Ligation-RT-PCR-LDR-qPCR carryover prevention reaction to quantify miRNA. Isolate miRNA from exosomes.

B. Treat with UDG (uracil DNA glycosylase) for carryover prevention, heat kill. Ligate probe complementary to 3' end of target miRNA, containing a stem-loop, Tag (Tj'), and blocking group. Extend with primer Tj and reverse transcriptase (using dUTP).

C. miRNA-specific bridge primers are unblocked with RNaseH2 only when bound to target. Perform limited cycle PCR amplification (12-20), using tag primers (Ti, Tj), to maintain relative ratios of different amplicons. Primers contain identical 8-11 base tails to prevent primer dimers. (Optional: aliquot into 12, 24, 48, or 96 wells prior to PCR.)

D. PCR products incorporate dU, allowing for carryover prevention.

E. miRNA sequence-specific ligation oligonucleotides contain tags (Ai, Bi-Ci') for subsequent PCR amplification. Ligase covalently seals the two oligonucleotides together. Aliquot into separate wells for detection.

F. Treat with UDG for carryover prevention, which also destroys original target amplicons. Only authentic LDR products will amplify, when using PCR (and dUTP) with Unitaq-specific primers (F1-Bi-Q-Ai, Ci).

G. Double-stranded DNA products of PCR; the polymerase blocker stops extension of the bottom strand.

H. After the denaturation step, as the temperature decreases, a hairpin forms between Bi and Bi'. The 5'->3' nuclease activity of Taq polymerase extends primer Ci and liberates the fluorescent group to generate signal.

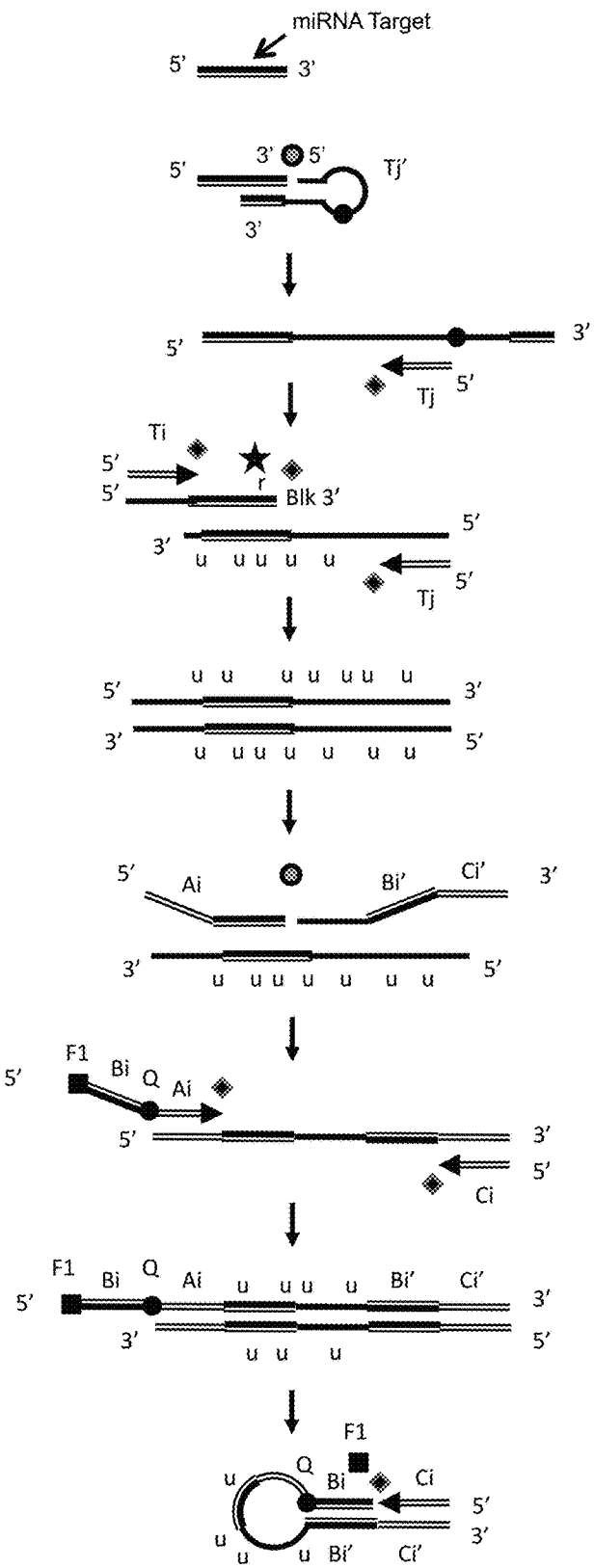

Figure 99

A. Ligation-RT-PCR-qLDR carryover prevention reaction to quantify miRNA. Isolate miRNA from exosomes.

B. Treat with UDG (uracil DNA glycosylase) for carryover prevention, and aliquot into 12, 24, 48, or 96 wells. Ligate probe complementary to 3' end of target miRNA, containing a stem-loop, Tag (Tj'), and blocking group. Extend with primer Tj and reverse transcriptase (using dUTP).

C. miRNA-specific bridge primers are unblocked with RNaseH2 only when bound to target. Perform limited cycle PCR amplification (12-20), using tag primers (Ti, Tj), to maintain relative ratios of different amplicons. Primers contain identical 8-11 base tails to prevent primer dimers, with one primer containing a 5' biotin.

D. PCR products incorporate dU, allowing for carryover prevention. Separate product from primers and capture biotinylated product on solid support.

E. miRNA-specific ligation oligonucleotides contain tails for subsequent FRET detection. Ligase covalently seals the two oligonucleotides together. (LDR products are not amplified by either original PCR or LDR primers, providing additional protection.)

F. Wash away unligated primers. Denature product from target, then detect, and enumerate FRET signal.

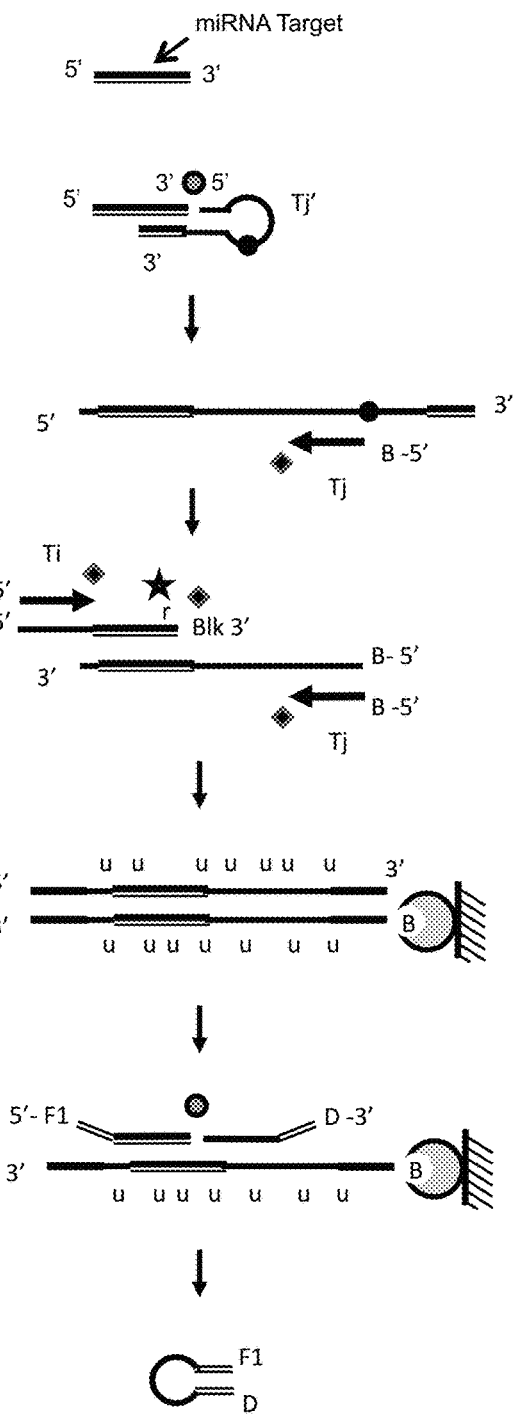

Figure 100

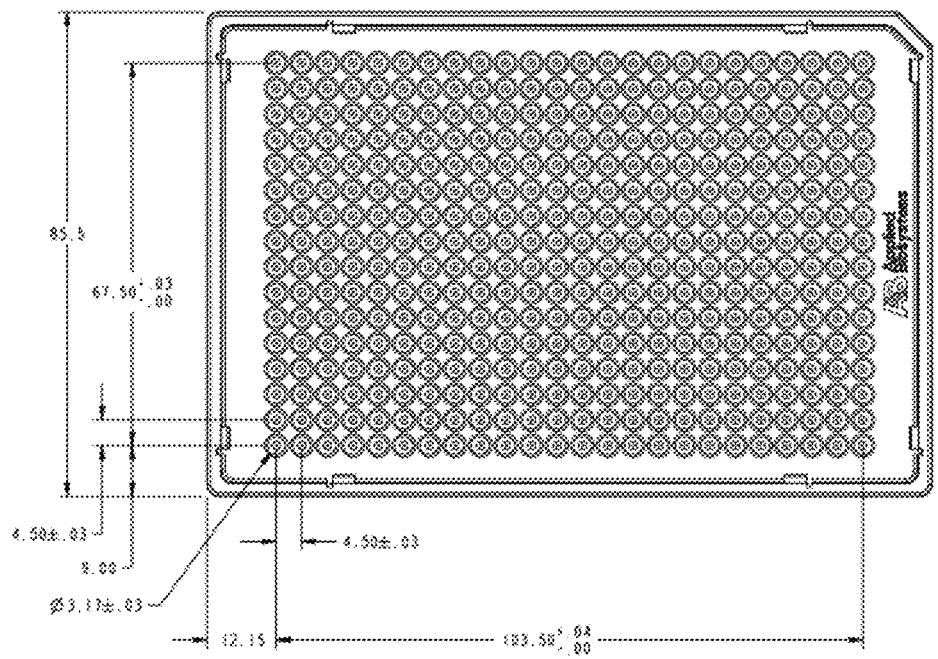
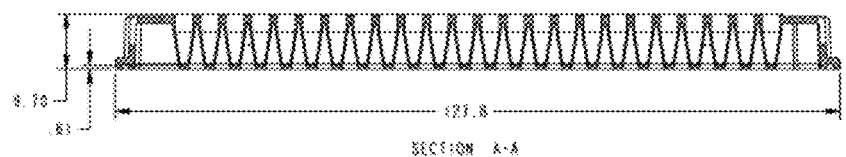
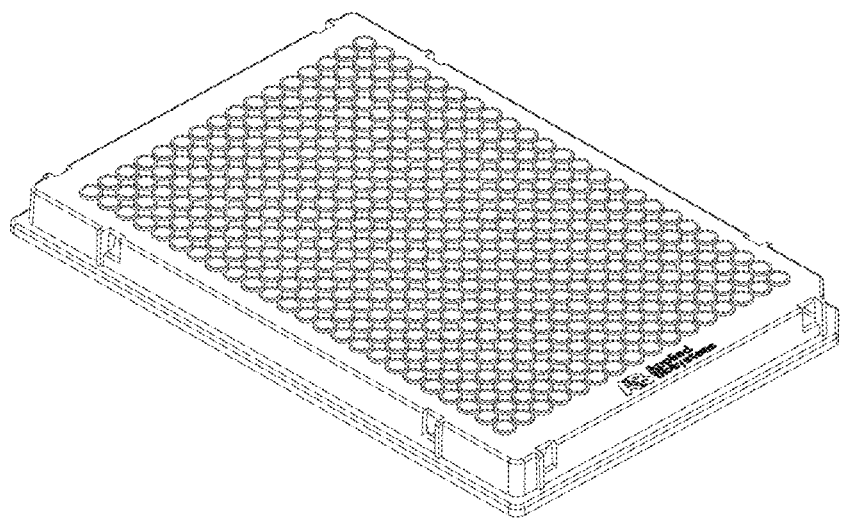
Figure 102

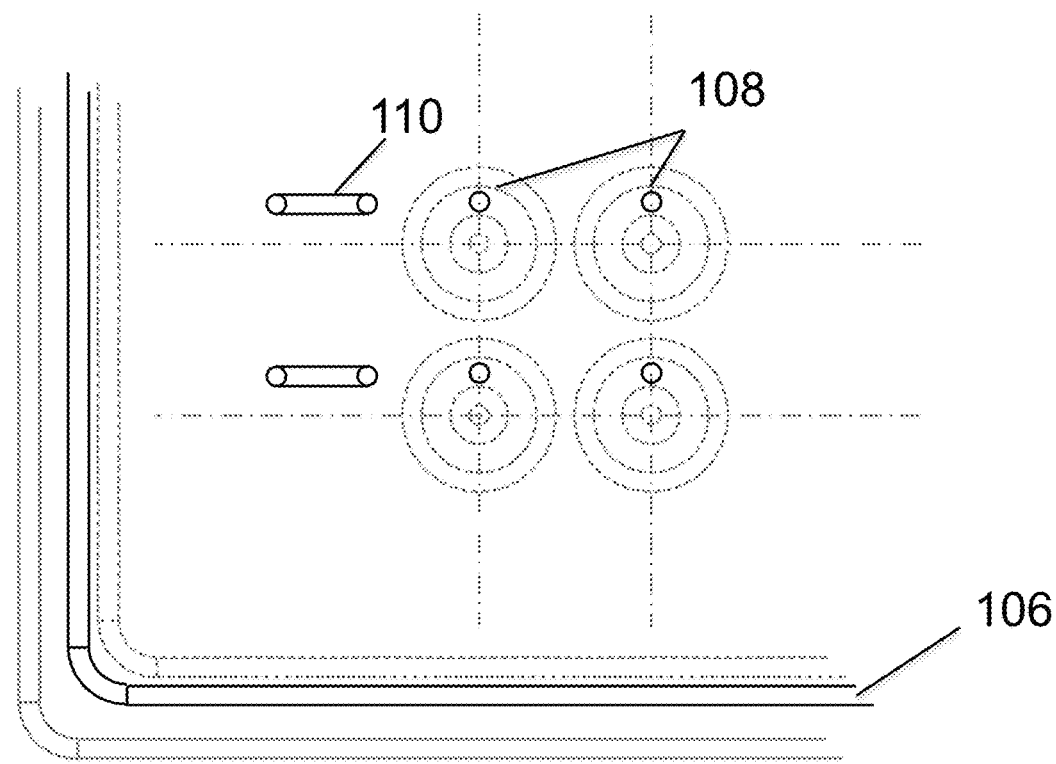
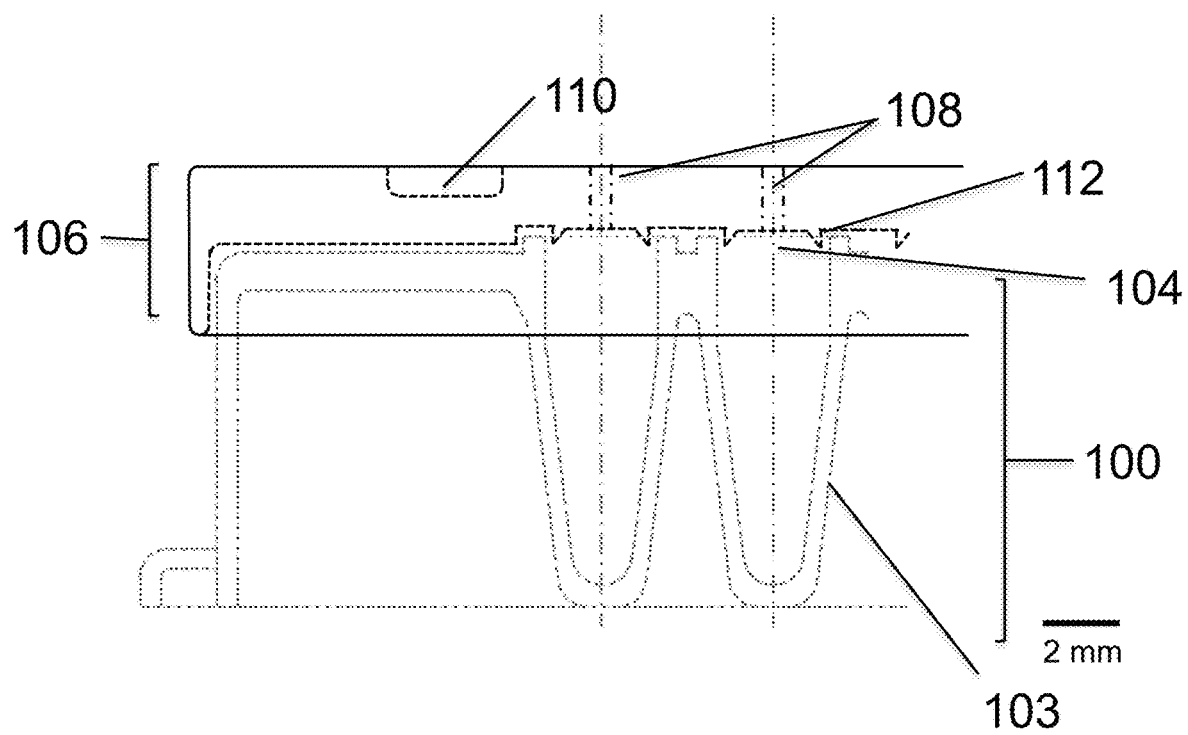
Figure 105

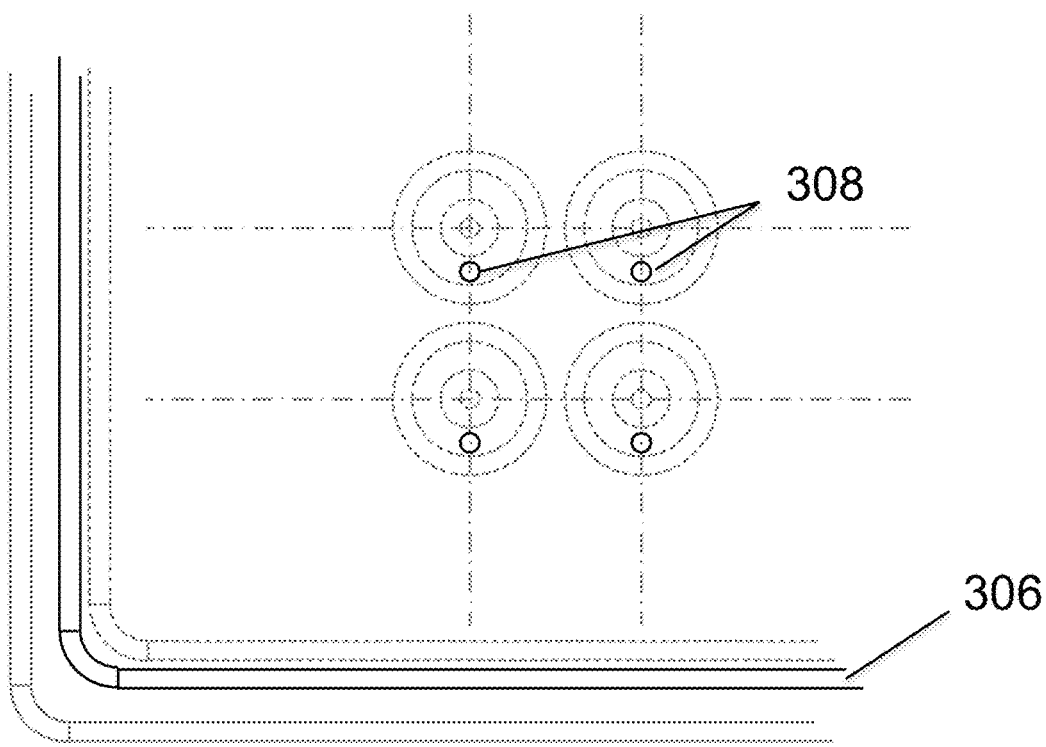
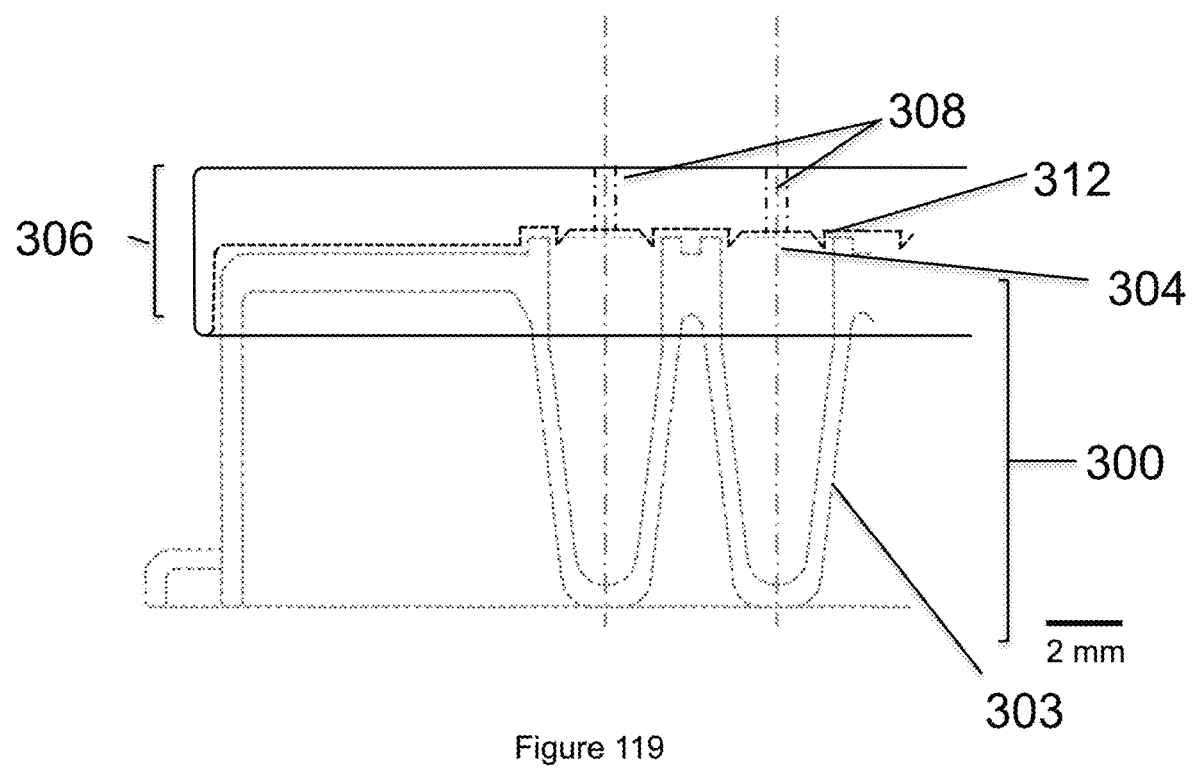
Figure 119

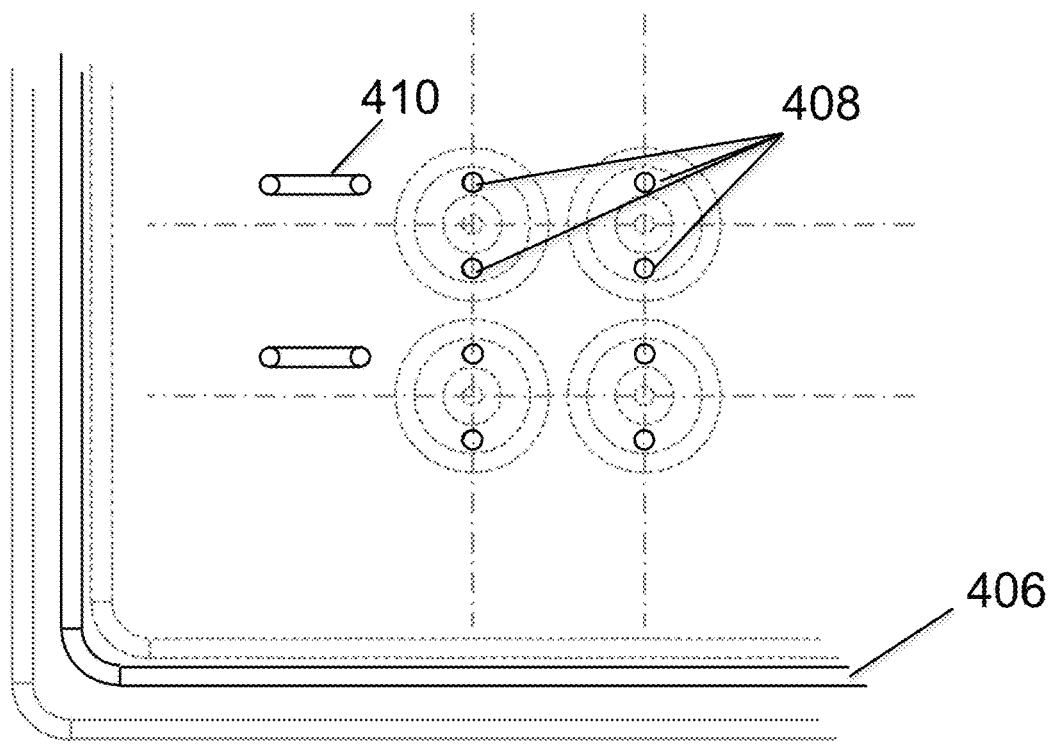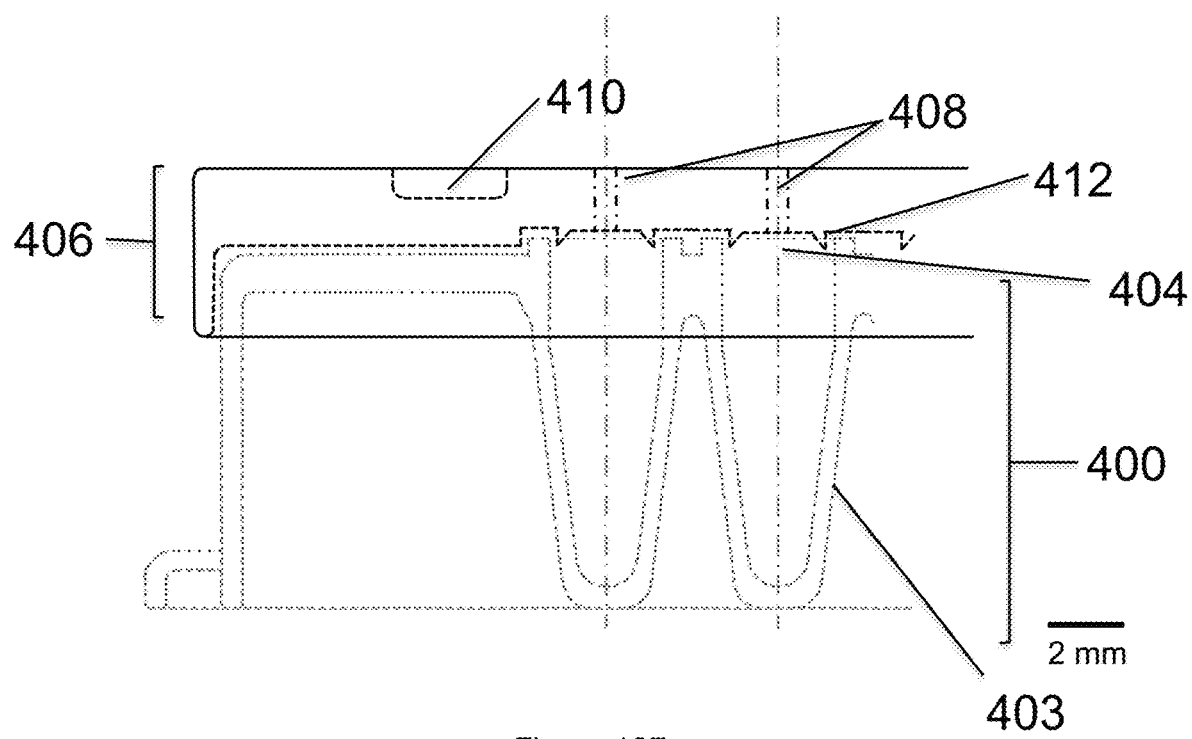
Figure 127

A. PCR-LDR-qPCR carryover prevention reaction to detect low-level mutation. Isolate genomic or cfDNA.

B. Treat with UDG for carryover prevention. Upstream locus primers contain mutation-specific ribose bases (mr), which are removed with RNaseH2 only when bound to target, thus unblocking primer. Primers with Wt sequence remain blocked. Preferentially amplify mutation containing regions using PCR (and dUTP). Downstream primers contain identical 8-11 base tails to prevent primer dimers. (Optional: aliquot into 12, 24, 48, or 96 wells prior to PCR.)

C. PCR products incorporate dU, allowing for carryover prevention.

D. Mutation-specific ligation oligonucleotides (Mt) contain tags (Ai, Ci') for subsequent PCR amplification, while wild-type probe (Wt) does not. Upstream ligation primer contains block, which may be removed by cleaving ribose base with RNaseH2 only when hybridized to target.

E. Ligase covalently seals the unblocked mutation-specific upstream and phosphorylated downstream oligonucleotides together. Aliquot into separate wells for detection.

F. Treat with UDG for carryover prevention, which also destroys original target amplicons. Only authentic LDR products will amplify, when using PCR (and dUTP) with tag-specific primers (Ai, Ci'). Each Taqman probe spans the ligation junction.

G. The 5'->3' nuclease activity of Taq polymerase liberates the fluorescent group to generate signal. (PCR products incorporate dU, allowing for carryover prevention.)

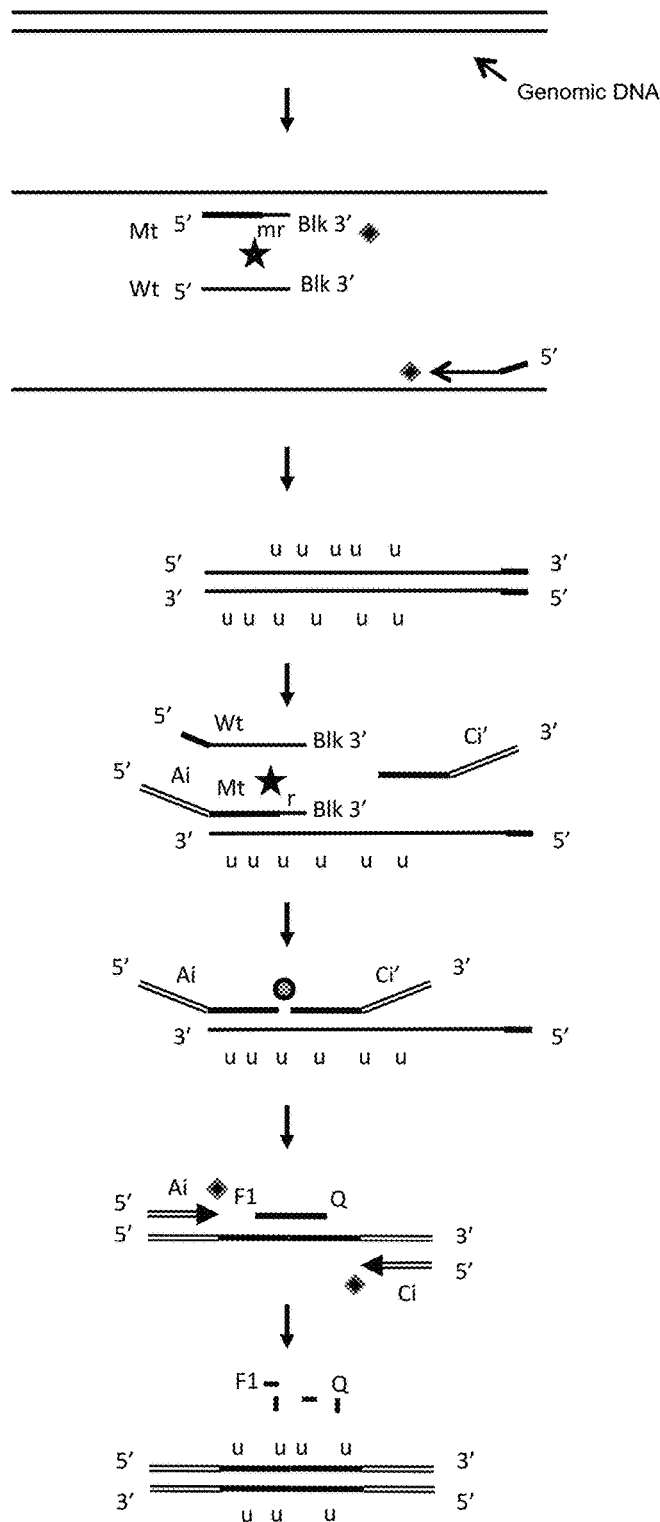

Figure 145

A. PCR-LDR-qPCR carryover prevention reaction to detect low-level mutation. Isolate genomic or cfDNA.

B. Treat with UDG for carryover prevention. Upstream locus primers contain mutation-specific ribose bases (mr), which are removed with RNaseH2 only when bound to target, thus unblocking primer. Primers with Wt sequence remain blocked. Preferentially amplify mutation containing regions using PCR (and dUTP). Downstream primers contain identical 8-11 base tails to prevent primer dimers. (Optional: aliquot into 12, 24, 48, or 96 wells prior to PCR.)

C. PCR products incorporate dU, allowing for carryover prevention.

D. Mutation-specific ligation oligonucleotides (Mt) contain tags (Ai, Bi', Ci') for subsequent PCR amplification, while wild-type probe (Wt) does not. Upstream ligation primer contains block, which may be removed by cleaving ribose base with RNaseH2 only when hybridized to target.

E. Ligase covalently seals the unblocked mutation-specific upstream and phosphorylated downstream oligonucleotides together. Aliquot into separate wells for detection.

F. Treat with UDG for carryover prevention, which also destroys original target amplicons. Only authentic LDR products will amplify, when using PCR (and dUTP) with Unitaq-specific primers (F1-Bi-Q-Ai, Ci).

G. Double-stranded DNA products of PCR; the polymerase blocker stops extension of the bottom strand.

H. After the denaturation step, as the temperature decreases, a hairpin forms between Bi and Bi'. The 5'->3' nuclease activity of Taq polymerase extends primer Ci and liberates the fluorescent group to generate signal. (PCR products incorporate dU, allowing for carryover prevention.)

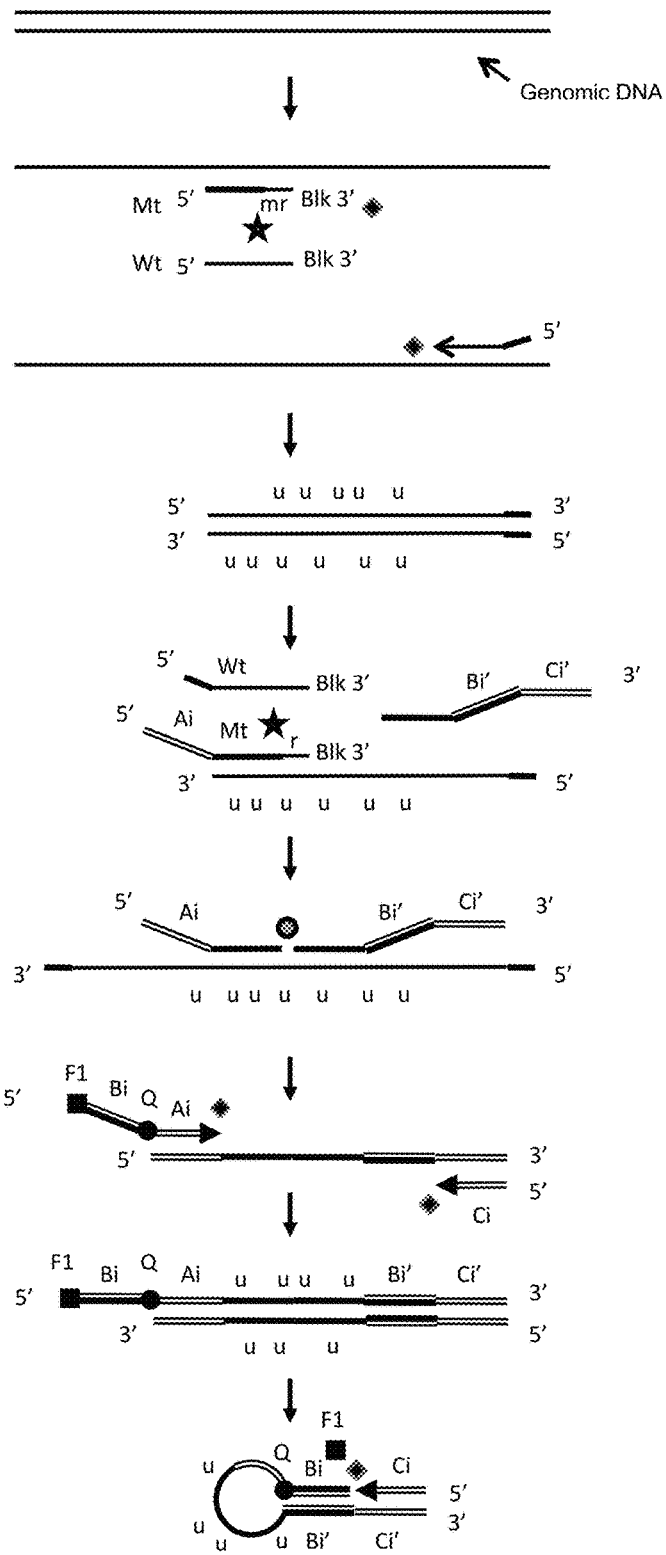

Figure 146

A. PCR-qLDR carryover prevention reaction to detect low-level mutation. Isolate genomic or cfDNA.

B. Treat with UDG for carryover prevention. Upstream locus primers contain mutation-specific ribose bases (mr), which are removed with RNaseH2 only when bound to target, thus unblocking primer. Primers with Wt sequence remain blocked. Preferentially amplify mutation containing regions using PCR (and dUTP). Downstream primers contain universal tails to enable universal primer amplification to append a 5' biotin.

C. PCR products incorporate dU, allowing for carryover prevention. Separate product from primers and capture biotinylated product on solid support.

D. Mutation-specific ligation oligonucleotides (Mt) contain tails for subsequent FRET detection, while wild-type probe (Wt) does not. Upstream ligation primer contains block, which may be removed by cleaving ribose base with RNaseH2 only when hybridized to target.

E. Ligase covalently seals the unblocked upstream and phosphorylated downstream oligonucleotides together.

F. Wash away unligated primers. Denature product from target, then detect, and enumerate FRET signal.

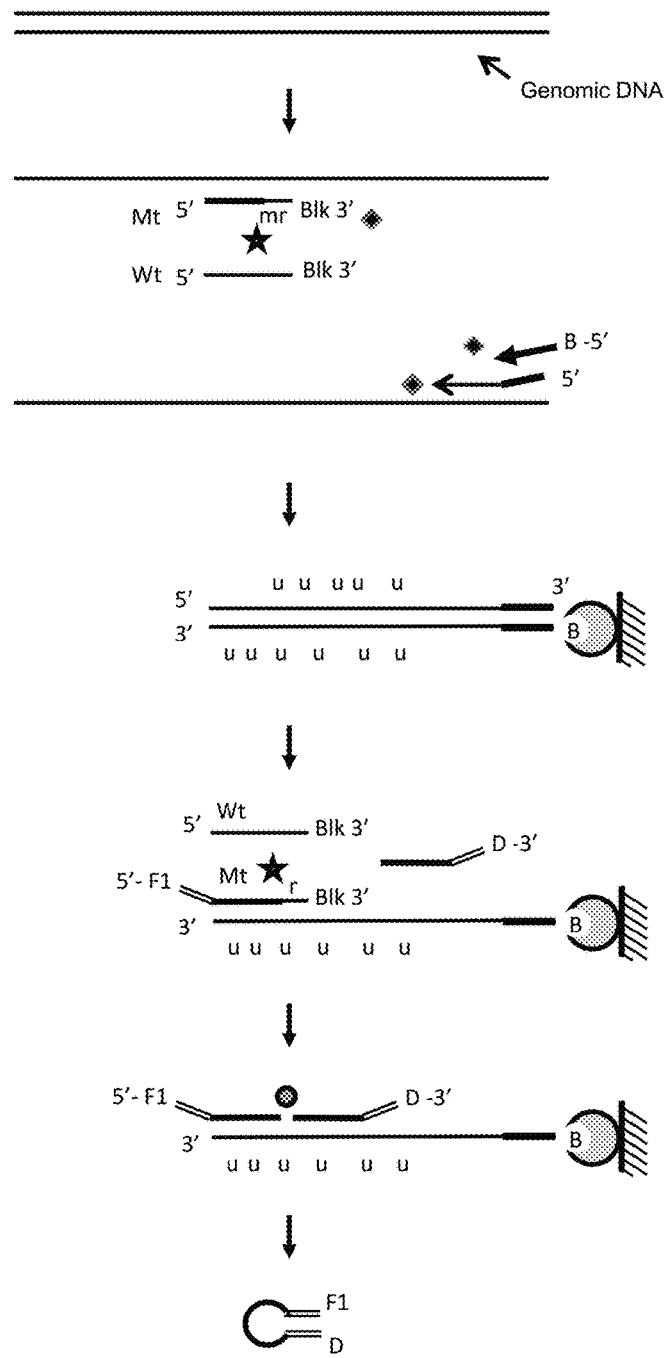

Figure 147

A. PCR-LDR-qPCR carryover prevention reaction to detect low-level mutation. Isolate genomic or cfDNA.

B. Treat with UDG for carryover prevention. Upstream locus primers contain ribose bases (r), which are removed with RNaseH2 only when bound to target, thus unblocking primer. Blocking LNA or PNA Wt probes facilitate preferential amplification of mutation containing regions using PCR (and dUTP). Downstream primers contain identical 8-11 base tails to prevent primer dimers. (Optional: aliquot into 12, 24, 48, or 96 wells prior to PCR.)

C. PCR products incorporate dU, allowing for carryover prevention.

D. Mutation-specific ligation oligonucleotides (Mt) contain tags (Ai, Ci') for subsequent PCR amplification. Blocking LNA or PNA Wt probes suppress ligation to Wt sequence. Upstream ligation primer contains block, which may be removed by cleaving ribose base with RNaseH2 only when hybridized to target.

E. Ligase covalently seals the unblocked mutation-specific upstream and phosphorylated downstream oligonucleotides together. Aliquot into separate wells for detection.

F. Treat with UDG for carryover prevention, which also destroys original target amplicons. Only authentic LDR products will amplify, when using PCR (and dUTP) with tag-specific primers (Ai, Ci'). Each Taqman probe spans the ligation junction.

G. The 5'->3' nuclease activity of Taq polymerase liberates the fluorescent group to generate signal. (PCR products incorporate dU, allowing for carryover prevention.)

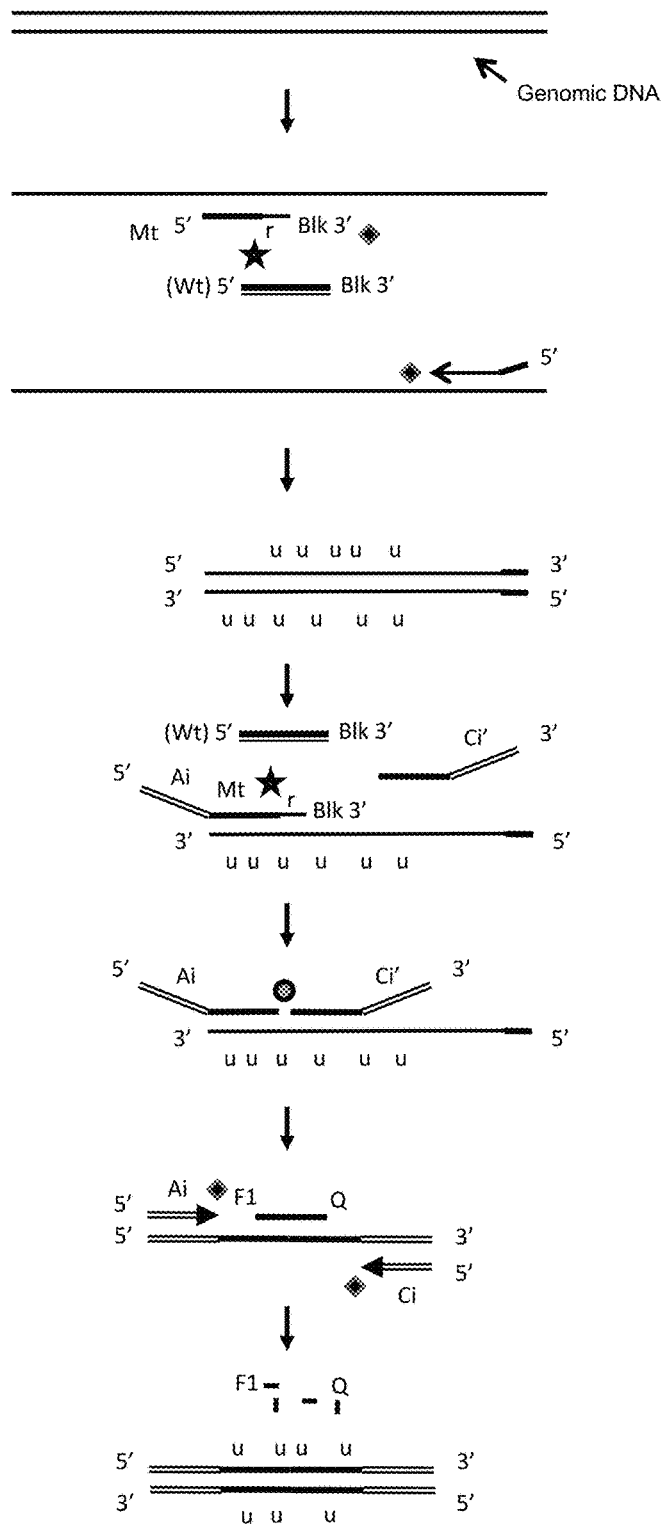

Figure 148

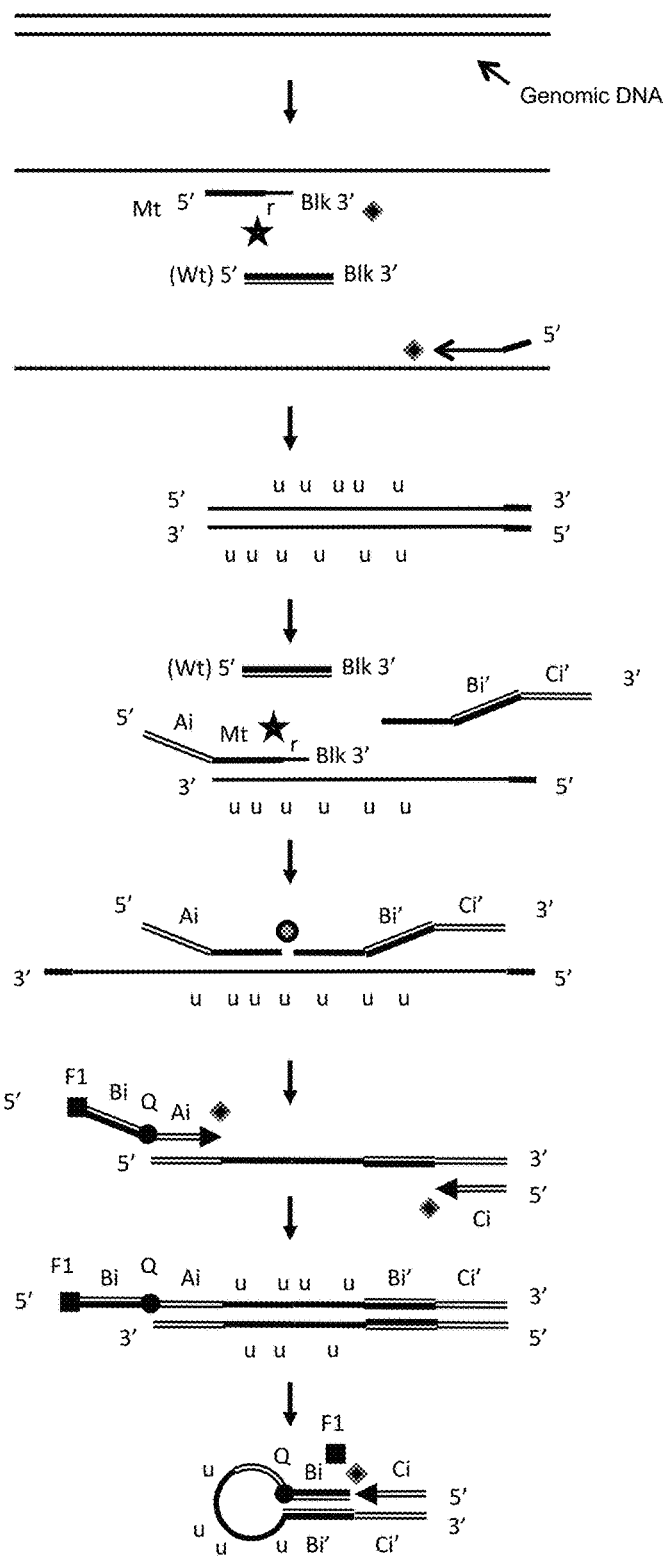

A. PCR-LDR-qPCR carryover prevention reaction to detect low-level mutation. Isolate genomic or cfDNA.

B. Treat with UDG for carryover prevention. Upstream locus primers contain ribose bases (r), which are removed with RNaseH2 only when bound to target, thus unblocking primer. Blocking LNA or PNA Wt probes facilitate preferential amplification of mutation containing regions using PCR (and dUTP). Downstream primers contain identical 8-11 base tails to prevent primer dimers. (Optional: aliquot into 12, 24, 48, or 96 wells prior to PCR.)

C. PCR products incorporate dU, allowing for carryover prevention.

D. Mutation-specific ligation oligonucleotides (Mt) contain tags (Ai, Bi', Ci') for subsequent PCR amplification. Blocking LNA or PNA Wt probes suppress ligation to Wt sequence. Upstream ligation primer contains block, which may be removed by cleaving ribose base with RNaseH2 only when hybridized to target.

E. Ligase covalently seals the unblocked mutation-specific upstream and phosphorylated downstream oligonucleotides together. Aliquot into separate wells for detection.

F. Treat with UDG for carryover prevention, which also destroys original target amplicons. Only authentic LDR products will amplify, when using PCR (and dUTP) with Unitaq-specific primers (F1-Bi-Q-Ai, Ci).

G. Double-stranded DNA products of PCR; the polymerase blocker stops extension of the bottom strand.

H. After the denaturation step, as the temperature decreases, a hairpin forms between Bi and Bi'. The 5'->3' nuclease activity of Taq polymerase extends primer Ci and liberates the fluorescent group to generate signal. (PCR products incorporate dU, allowing for carryover prevention.)

Figure 149

A. PCR-qLDR carryover prevention reaction to detect low-level mutation. Isolate genomic or cfDNA.

B. Treat with UDG for carryover prevention. Upstream locus primers contain ribose bases (r), which are removed with RNaseH2 only when bound to target, thus unblocking primer. Blocking LNA or PNA Wt probes facilitate preferential amplification of mutation containing regions using PCR (and dUTP). Downstream primers contain universal tails to enable universal primer amplification to append a 5' biotin. (Optional: aliquot into 12, 24, 48, or 96 wells prior to PCR.)

C. PCR products incorporate dU, allowing for carryover prevention. Separate product from primers and capture biotinylated product on solid support.

D. Mutation-specific ligation oligonucleotides (Mt) contain tails for subsequent FRET detection. Blocking LNA or PNA Wt probes suppress ligation to Wt sequence. Upstream ligation primer contains block, which may be removed by cleaving ribose base with RNaseH2 only when hybridized to target.

E. Ligase covalently seals the unblocked upstream and phosphorylated downstream oligonucleotides together.

F. Wash away unligated primers. Denature product from target, then detect, and enumerate FRET signal.

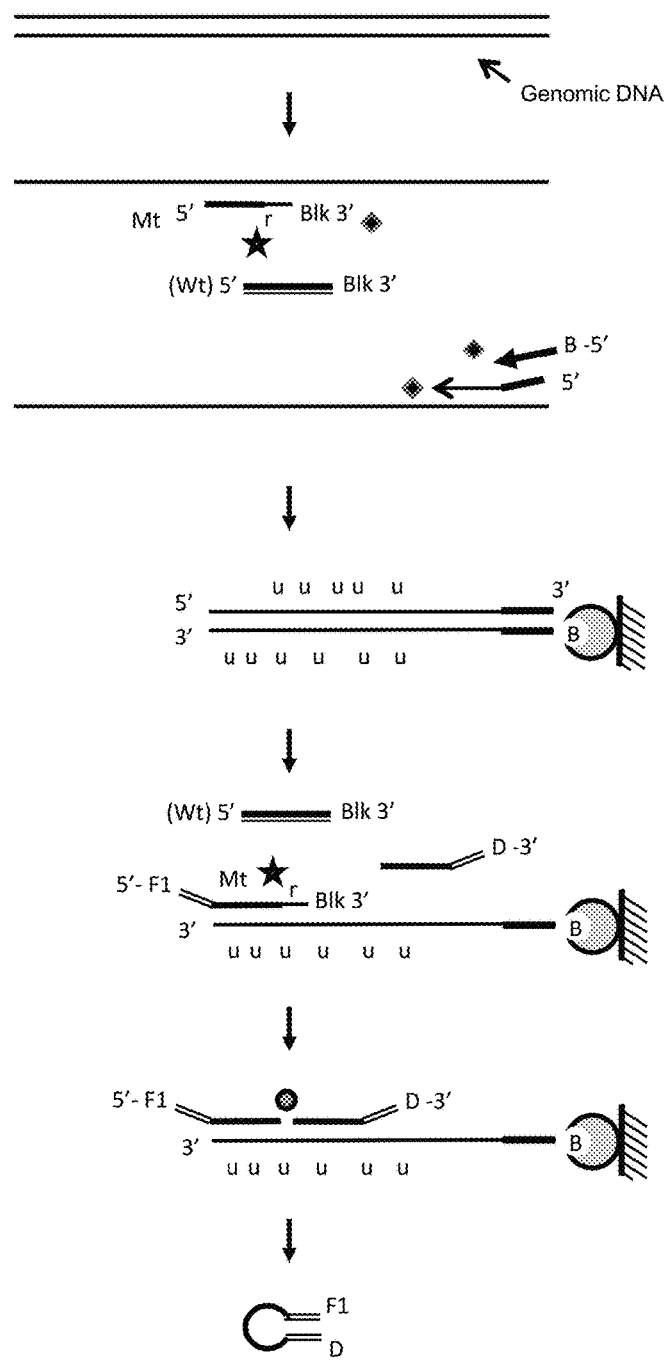

Figure 150

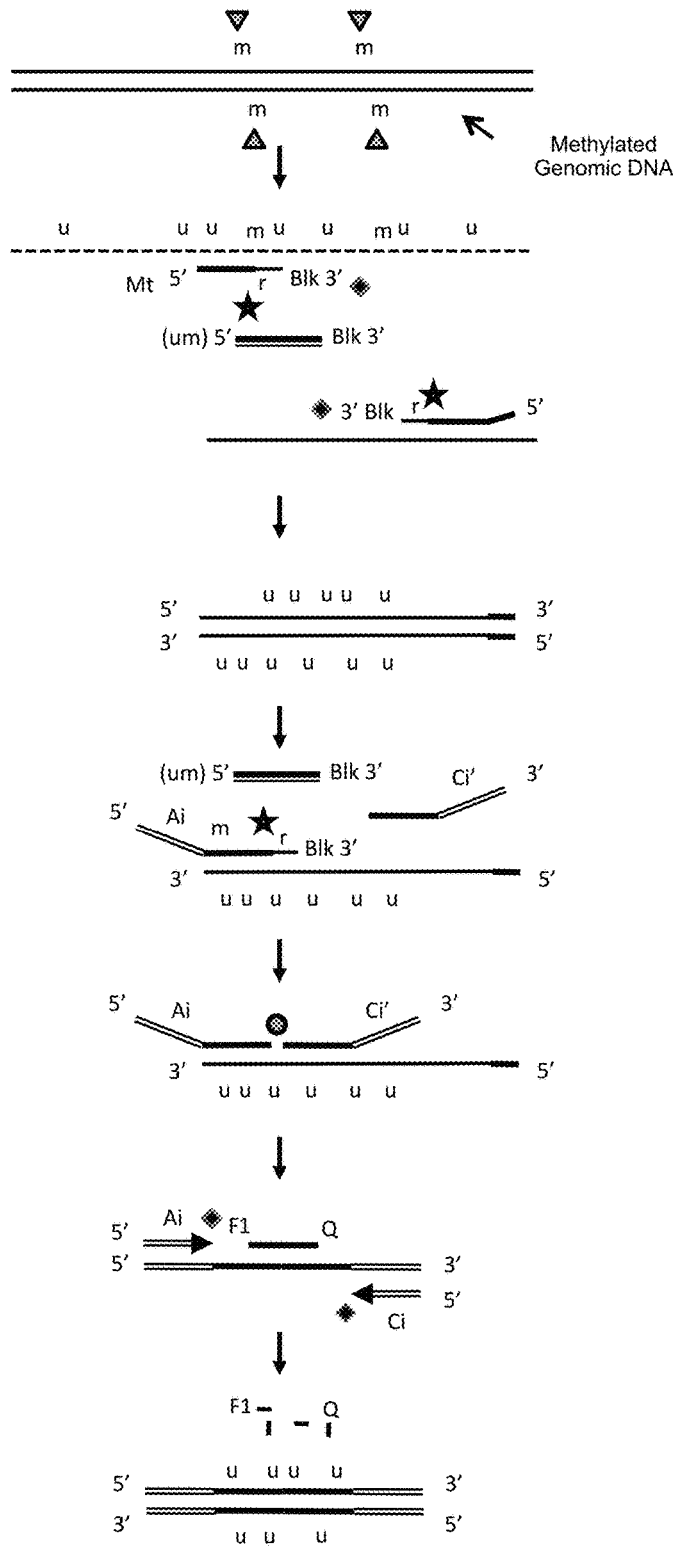

A. PCR-LDR-qPCR carryover prevention reaction to detect low-level methylation. Isolate genomic or cfDNA. Treat with Bsh1236I (CG^CG) and UNG (37oC, 30-60 minutes) to completely digest un-methylated DNA and prevent carryover. Treat with bisulfite, which renders the strands non-complementary.

B. Locus primers contain ribose bases (r), which are removed with RNaseH2 only when bound to target, thus unblocking primer. Blocking LNA or PNA probes may be used to limit amplification of originally un-methylated DNA using PCR (and dUTP). Downstream primers contain identical 8-11 base tails to prevent primer dimers. (Optional: aliquot into 12, 24, 48, or 96 wells prior to PCR.)

C. PCR products incorporate dU, allowing for carryover prevention.

D. Methyl region-specific ligation oligonucleotides (m) contain tags (Ai, Ci') for subsequent PCR amplification. Blocking LNA or PNA probes suppress ligation to originally un-methylated DNA sequence. Upstream ligation primer contains block, which may be removed by cleaving ribose base with RNaseH2 only when hybridized to target.

E. Ligase covalently seals the unblocked methyl region-specific upstream and phosphorylated downstream oligonucleotides together. Aliquot into separate wells for detection.

F. Treat with UDG for carryover prevention, which also destroys original target amplicons. Only authentic LDR products will amplify, when using PCR (and dUTP) with tag-specific primers (Ai, Ci'). Each Taqman probe spans the ligation junction.

G. The 5'->3' nuclease activity of Taq polymerase liberates the fluorescent group to generate signal. (PCR products incorporate dU, allowing for carryover prevention.)

Figure 151

A. PCR-LDR-qPCR carryover prevention reaction to detect low-level methylation. Isolate genomic or cfDNA. Treat with Bsh1236I (CG^CG) and UNG (37oC, 30-60 minutes) to completely digest un-methylated DNA and prevent carryover. Treat with bisulfite, which renders the strands non-complementary.

B. Locus primers contain ribose bases (r), which are removed with RNaseH2 only when bound to target, thus unblocking primer. Blocking LNA or PNA probes may be used to limit amplification of originally un-methylated DNA using PCR (and dUTP). Downstream primers contain identical 8-11 base tails to prevent primer dimers. (Optional: aliquot into 12, 24, 48, or 96 wells prior to PCR.)

C. PCR products incorporate dU, allowing for carryover prevention.

D. Methyl region-specific ligation oligonucleotides (m) contain tags (Ai, Bi', Ci') for subsequent PCR amplification. Blocking LNA or PNA probes suppress ligation to originally un-methylated DNA sequence. Upstream ligation primer contains block, which may be removed by cleaving ribose base with RNaseH2 only when hybridized to target.

E. Ligase covalently seals the unblocked methyl region-specific upstream and phosphorylated downstream oligonucleotides together. Aliquot into separate wells for detection.

F. Treat with UDG for carryover prevention, which also destroys original target amplicons. Only authentic LDR products will amplify, when using PCR (and dUTP) with Unitaq-specific primers (F1-Bi-Q-Ai, Ci).

G. Double-stranded DNA products of PCR; the polymerase blocker stops extension of the bottom strand.

H. After the denaturation step, as the temperature decreases, a hairpin forms between Bi and Bi'. The 5'->3' nuclease activity of Taq polymerase extends primer Ci and liberates the fluorescent group to generate signal. (PCR products incorporate dU, allowing for carryover prevention.)

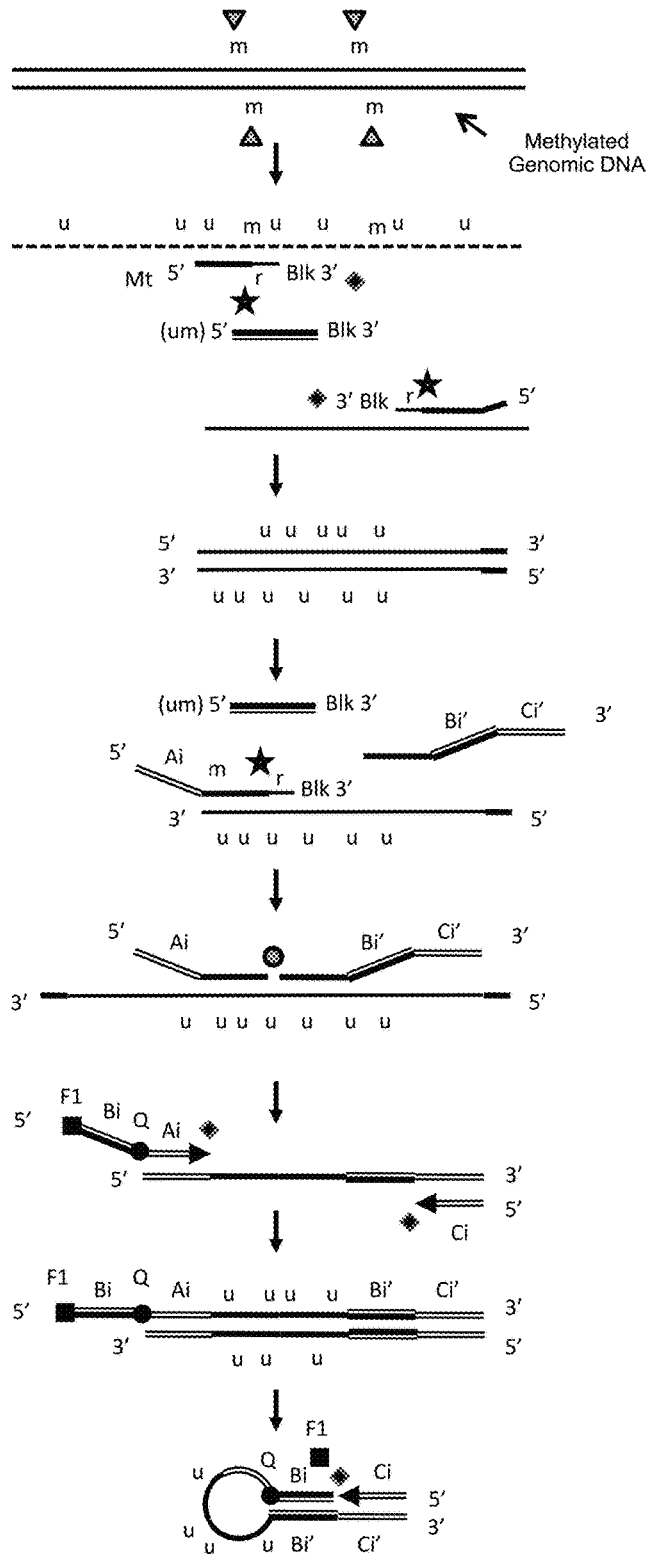

Figure 152

A. PCR-LDR-qPCR carryover prevention reaction to detect low-level methylation. Isolate genomic or cfDNA. Treat with Bsh1236I (CG^CG) and UNG (37oC, 30-60 minutes) to completely digest un-methylated DNA and prevent carryover. Treat with bisulfite, which renders the strands non-complementary.

B. Locus primers contain ribose bases (r), which are removed with RNaseH2 only when bound to target, thus unblocking primer. Blocking LNA or PNA probes may be used to limit amplification of originally un-methylated DNA using PCR (and dUTP). Downstream primers contain universal tails to enable universal primer amplification to append a 5' biotin. (Optional: aliquot into 12, 24, 48, or 96 wells prior to PCR.)

C. PCR products incorporate dU, allowing for carryover prevention. Separate product from primers and capture biotinylated product on solid support.

D. Methyl region-specific ligation oligonucleotides (m) contain tails for subsequent FRET detection. Blocking LNA or PNA probes suppress ligation to originally un-methylated DNA sequence. Upstream ligation primer contains block, which may be removed by cleaving ribose base with RNaseH2 only when hybridized to target.

E. Ligase covalently seals the unblocked upstream and phosphorylated downstream oligonucleotides together.

F. Wash away unligated primers. Denature product from target, then detect, and enumerate FRET signal.

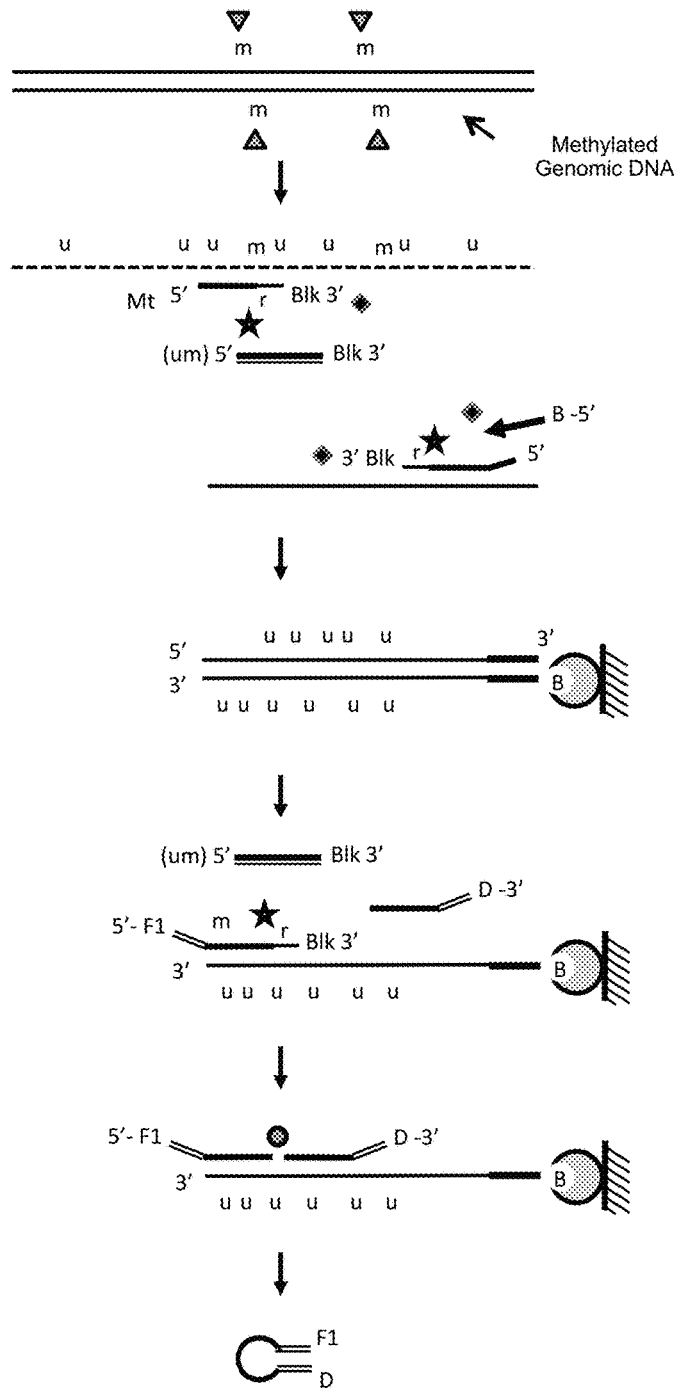

Figure 153

A. Loop-PCR-LDR-qPCR carryover prevention reaction to detect low-level mutation. Isolate genomic or cfDNA.

B. Treat with UDG for carryover prevention. Upstream locus-specific primers also contain 5' sequences complementary to Wt sequence of top strand, and are unblocked with RNaseH2 only when bound to target. Amplify mutation containing regions using PCR (and dUTP). Downstream primers contain identical 8-11 base tails to prevent primer dimers. (Optional: aliquot into 12, 24, 48, or 96 wells prior to PCR.)

C. (PCR products incorporate dU, allowing for carryover prevention.)

D. In detail: PCR is performed with a polymerase lacking 5' nuclease, 3' nuclease, and strand-displacement activity. (i) Denaturation of Wt bottom strand results in hairpin with perfect match at 3' end, which is extended by polymerase. (ii) Denaturation of Mt bottom strand results in hairpin with mismatch at 3' end, which generally is not extended by polymerase. (iii) Denaturation of top strand results in hairpin on 5' side, which denatures during the extend step of PCR (72oC).

E. (i) After extension of hairpin on wild-type DNA, extended hairpin sequence does not denature at 72oC and prevents upstream primer from generating full-length top strand. (ii) Hairpin sequence of mutant DNA does not extend, and thus denatures at 72oC, enabling upstream primer to generate full-length top strand. (iii) Likewise, top strand product denatures at 72oC, allowing polymerase to generate full-length bottom strand. The difference in hairpin extension preference of upstream primers with (i) wild-type and (ii) mutant template results in preferential amplification of mutant DNA.

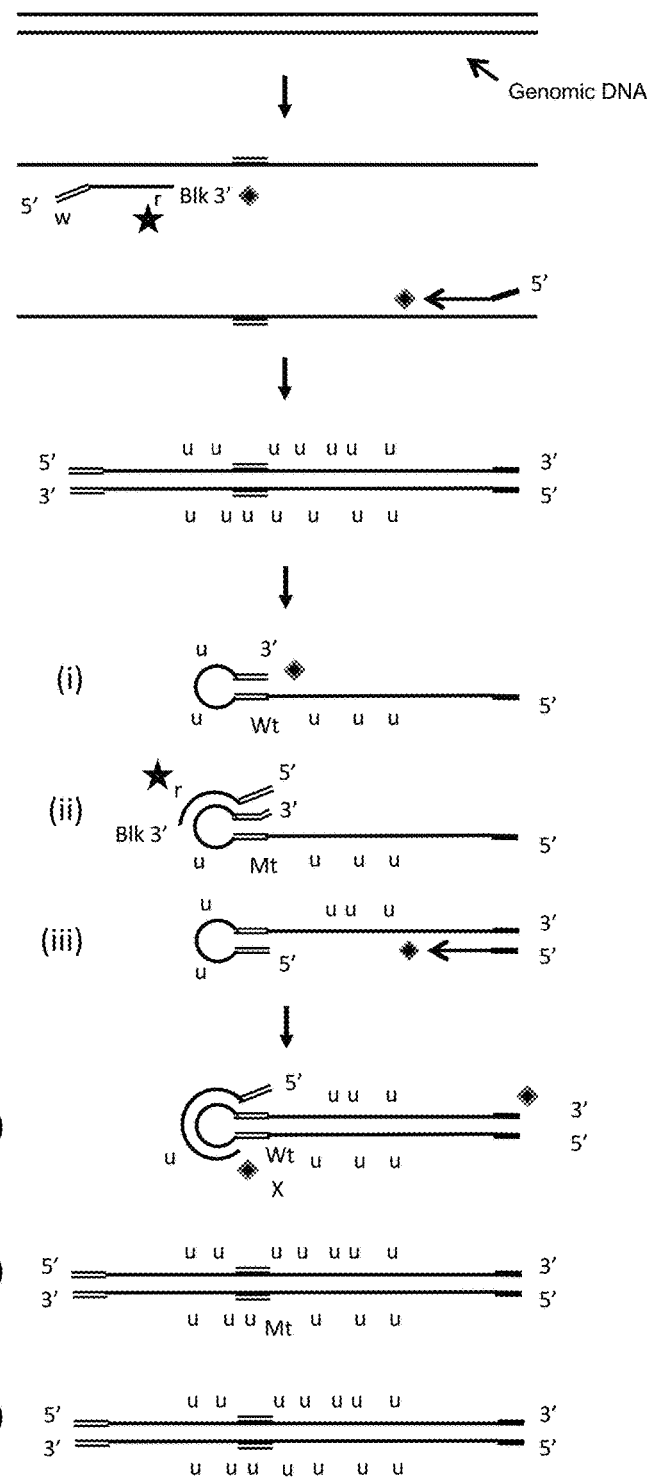

Figure 154

F. (PCR products incorporate dU, allowing for carryover prevention. Optional: wild-type sequence on end may be clipped off with restriction endonuclease.)

G. Mutation-specific ligation oligonucleotides (Mt) contain tags (Ai, Ci') for subsequent PCR amplification, while (optional) wild-type probe (Wt) does not. Upstream ligation primer contains block, which may be removed by cleaving ribose base with RNaseH2 only when hybridized to target. (Optional: wild-type sequence on 3' end may be clipped off with exonuclease III)

H. Ligase covalently seals the unblocked upstream and phosphorylated downstream oligonucleotides together. Aliquot into separate wells for detection.

I. Treat with UDG for carryover prevention, which also destroys original target amplicons. Only authentic LDR products will amplify, when using PCR (and dUTP) with tag-specific primers (Ai, Ci'). Each Taqman probe spans the ligation junction.

J. The 5'->3' nuclease activity of Taq polymerase liberates the fluorescent group to generate signal. (PCR products incorporate dU, allowing for carryover prevention.)

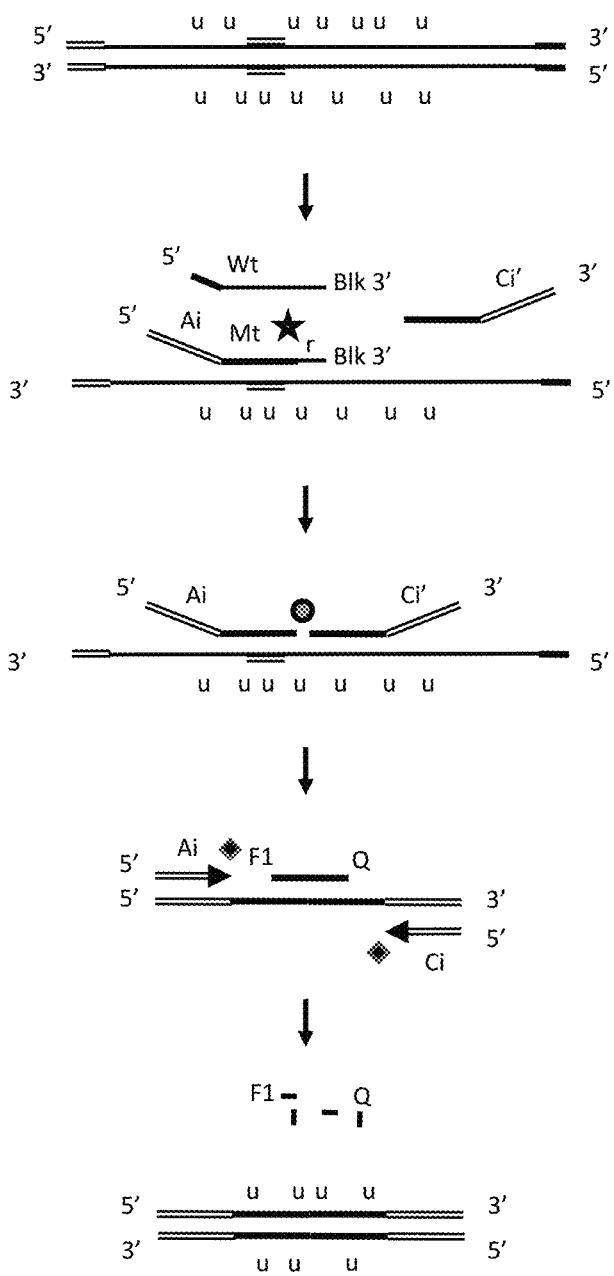

Figure 154 (Cont.)

A. Loop-PCR-qLDR carryover prevention reaction to detect low-level mutation. Isolate genomic or cfDNA.

B. Treat with UDG for carryover prevention. Upstream locus-specific primers also contain 5' sequences complementary to Wt sequence of top strand, and are unblocked with RNaseH2 only when bound to target. Amplify mutation containing regions using PCR (and dUTP). Downstream primers contain universal tails to enable universal primer amplification to append a 5' biotin. (Optional: aliquot into 12, 24, 48, or 96 wells prior to PCR.)

C. (PCR products incorporate dU, allowing for carryover prevention.)

D. In detail: PCR is performed with a polymerase lacking 5' nuclease, 3' nuclease, and strand-displacement activity. (i) Denaturation of Wt bottom strand results in hairpin with perfect match at 3' end, which is extended by polymerase. (ii) Denaturation of Mt bottom strand results in hairpin with mismatch at 3' end, which generally is not extended by polymerase. (iii) Denaturation of top strand results in hairpin on 5' side, which denatures during the extend step of PCR (72oC).

E. (i) After extension of hairpin on wild-type DNA, extended hairpin sequence does not denature at 72oC and prevents upstream primer from generating full-length top strand. (ii) Hairpin sequence of mutant DNA does not extend, and thus denatures at 72oC, enabling upstream primer to generate full-length top strand. (iii) Likewise, top strand product denatures at 72oC, allowing polymerase to generate full-length bottom strand. The difference in hairpin extension preference of upstream primers with (i) wild-type and (ii) mutant template results in preferential amplification of mutant DNA.

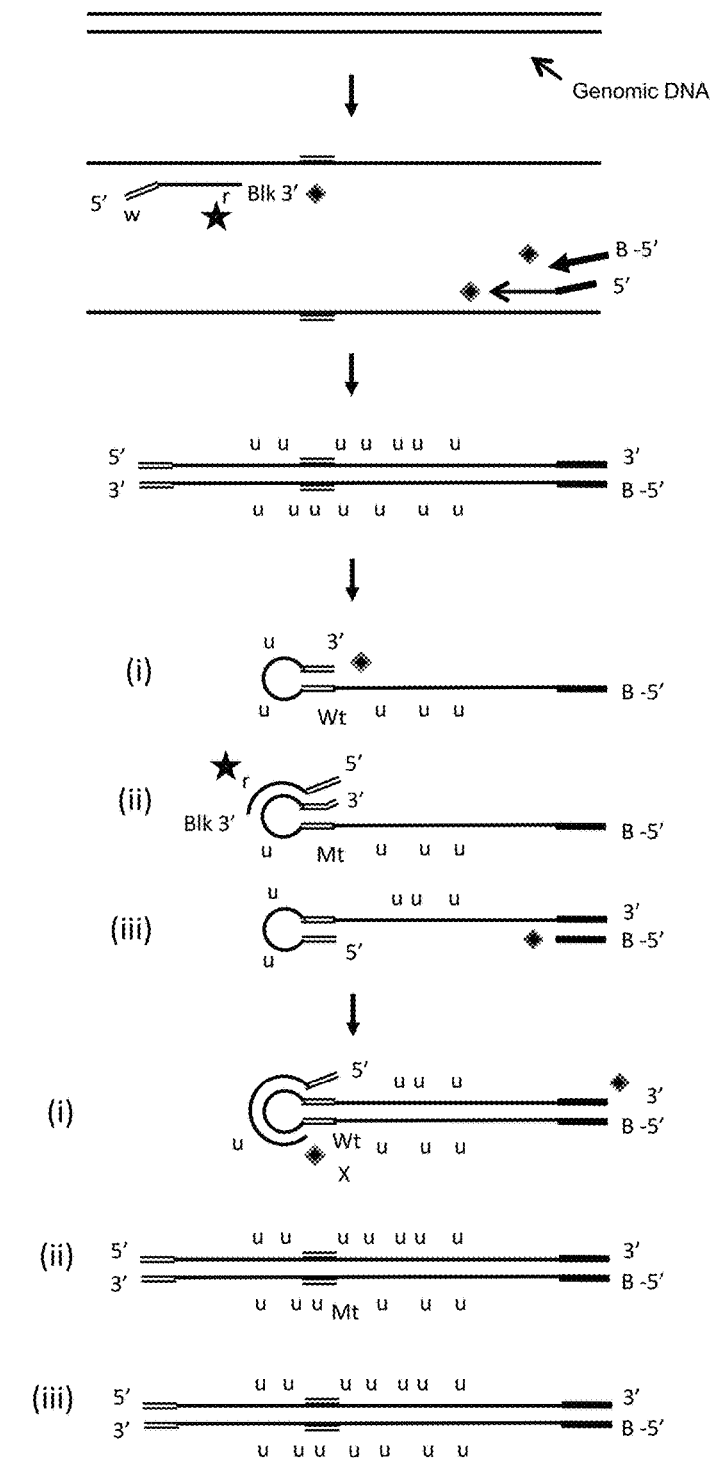

Figure 155

F. PCR products incorporate dU, allowing for carryover prevention. Separate product from primers and capture biotinylated product on solid support. Optional: wild-type sequence on end may be clipped off with restriction endonuclease.

G. Mutation-specific ligation oligonucleotides (Mt) contain tails for subsequent FRET detection, while (optional) wild-type probe (Wt) does not. Upstream ligation primer contains block, which may be removed by cleaving ribose base with RNaseH2 only when hybridized to target. (Optional: wild-type sequence on 3' end may be clipped off with exonuclease III)

H. Ligase covalently seals the unblocked upstream and phosphorylated downstream oligonucleotides together.

I. Wash away unligated primers. Denature product from target, then detect, and enumerate FRET signal.

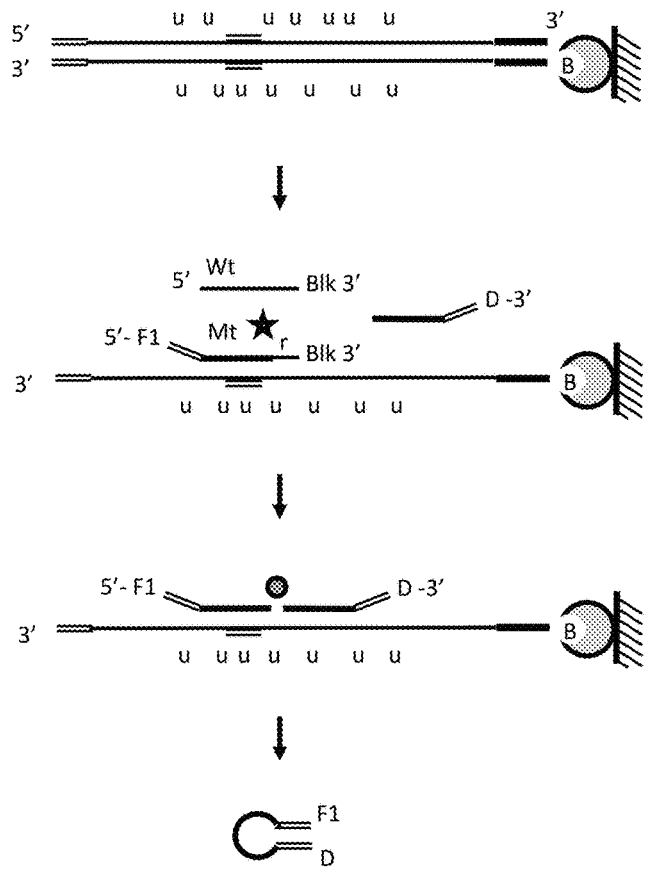

Figure 155 (Cont.)

A. Loop-PCR-LDR-qPCR carryover prevention reaction to detect low-level methylation. Isolate genomic or cfDNA. Treat with Bsh1236I (CG^CG) and UDG (37oC, 30-60 minutes) to completely digest unmethylated DNA and prevent carryover. Treat with bisulfite, which renders the strands non-complementary.

B. Upstream locus-specific primers also contain 5' sequences complementary to bisulfite-treated unmethylated sequence of top strand, and are unblocked with RNaseH2 only when bound to target. Amplify methylation containing regions using PCR (and dUTP). Downstream primers contain identical 8-11 base tails to prevent primer dimers. (Optional: aliquot into 12, 24, 48, or 96 wells prior to PCR.)

C. (PCR products incorporate dU, allowing for carryover prevention.)

D. In detail: PCR is performed with a polymerase lacking 5' nuclease, 3' nuclease, and strand-displacement activity. (i) Denaturation of unmethylated bottom strand results in hairpin with perfect match at 3' end, which is extended by polymerase. (ii) Denaturation of methylated bottom strand results in hairpin with mismatches, which generally is not extended by polymerase. (iii) Denaturation of top strand results in hairpin on 5' side, which denatures during the extend step of PCR (72oC).

E. (i) After extension of hairpin on unmethylated DNA, extended hairpin sequence does not denature at 72oC and prevents upstream primer from generating full-length top strand. (ii) Hairpin sequence of methylated DNA does not extend, and thus denatures at 72oC, enabling upstream primer to generate full-length top strand. (iii) Likewise, top strand product denatures at 72oC, allowing polymerase to generate full-length bottom strand. The difference in hairpin extension preference of upstream primers with (i) unmethylated and (ii) methylated template results in preferential amplification of methylated DNA.

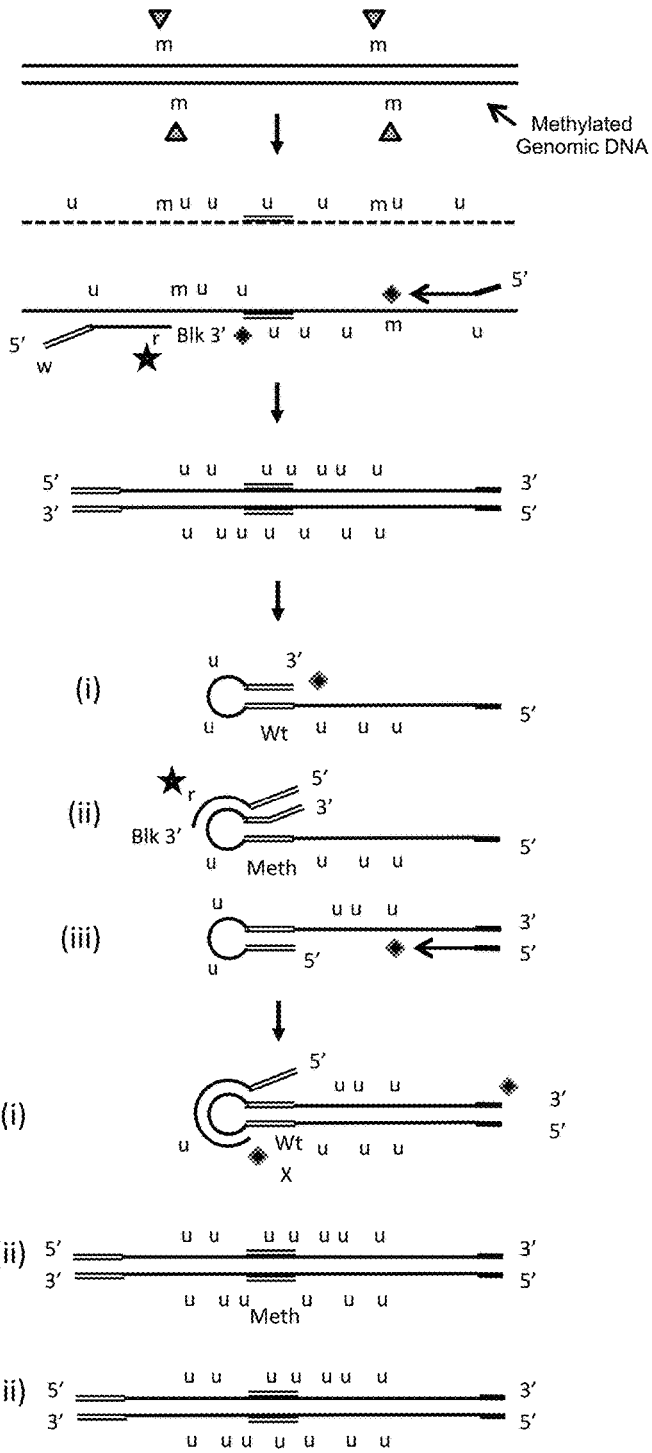

Figure 156

F. PCR products incorporate dU, allowing for carryover prevention. Optional: sequence on end complementary to unmethylated region may be clipped off with restriction endonuclease.

G. Methylation-specific ligation oligonucleotides (Meth) contain tags (Ai, Ci') for subsequent PCR amplification, while (optional) unmethylated probe (Umet) does not. Upstream ligation primer contains block, which may be removed by cleaving ribose base with RNaseH2 only when hybridized to target. (Optional: wild-type sequence on 3' end may be clipped off with exonuclease III)

H. Ligase covalently seals the unblocked upstream and phosphorylated downstream oligonucleotides together. Aliquot into separate wells for detection.

I. Treat with UDG for carryover prevention, which also destroys original target amplicons. Only authentic LDR products will amplify, when using PCR (and dUTP) with tag-specific primers (Ai, Ci'). Each Taqman probe spans the ligation junction.

J. The 5'->3' nuclease activity of Taq polymerase liberates the fluorescent group to generate signal. (PCR products incorporate dU, allowing for carryover prevention.)

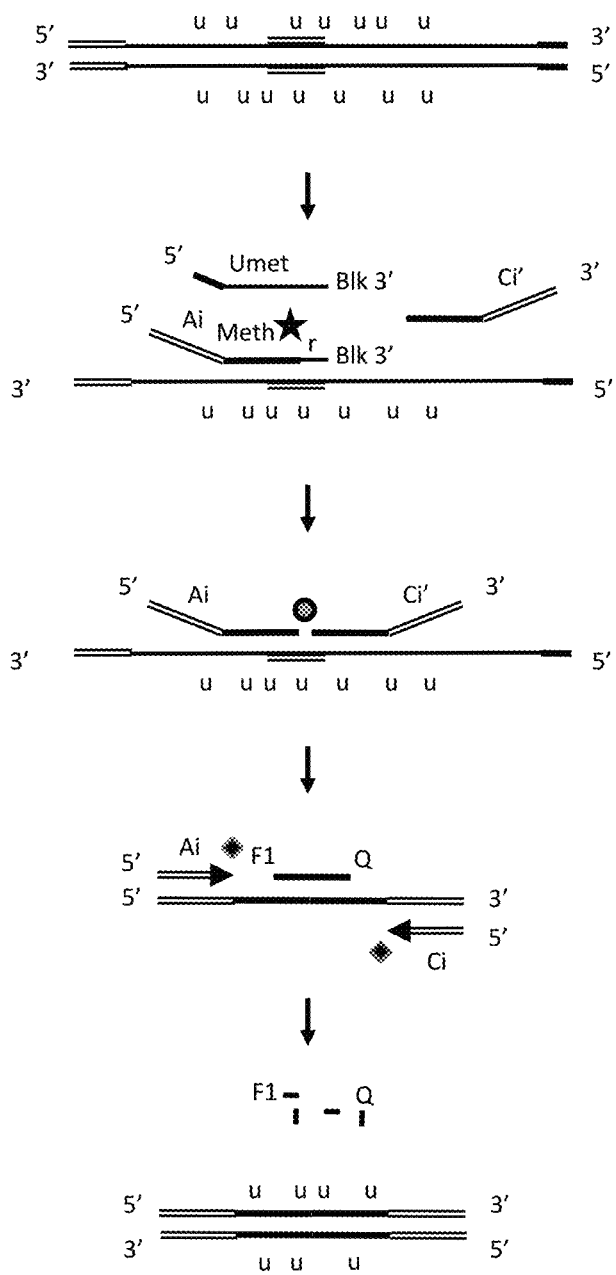

Figure 156 (Cont.)

A. Loop-PCR-qLDR carryover prevention reaction to detect low-level methylation. Isolate genomic or cfDNA. Treat with Bsh1236I (CG^CG) and UDG (37oC, 30-60 minutes) to completely digest unmethylated DNA and prevent carryover. Treat with bisulfite, which renders the strands non-complementary.

B. Upstream locus-specific primers also contain 5' sequences complementary to bisulfite-treated unmethylated sequence of bottom strand, and are unblocked with RNaseH2 only when bound to target. Amplify methylation containing regions using PCR (and dUTP). Downstream primers contain universal tails to enable universal primer amplification to append a 5' biotin. (Optional: aliquot into 12, 24, 48, or 96 wells prior to PCR.)

C. (PCR products incorporate dU, allowing for carryover prevention.)

D. In detail: PCR is performed with a polymerase lacking 5' nuclease, 3' nuclease, and strand-displacement activity. (i) Denaturation of unmethylated bottom strand results in hairpin with perfect match at 3' end, which is extended by polymerase. (ii) Denaturation of methylated bottom strand results in hairpin with mismatches, which generally is not extended by polymerase. (iii) Denaturation of top strand results in hairpin on 5' side, which denatures during the extend step of PCR (72oC).

E. (i) After extension of hairpin on unmethylated DNA, extended hairpin sequence does not denature at 72oC and prevents upstream primer from generating full-length top strand. (ii) Hairpin sequence of methylated DNA does not extend, and thus denatures at 72oC, enabling upstream primer to generate full-length top strand. (iii) Likewise, top strand product denatures at 72oC, allowing polymerase to generate full-length bottom strand. The difference in hairpin extension preference of upstream primers with (i) unmethylated and (ii) methylated template results in preferential amplification of methylated DNA.

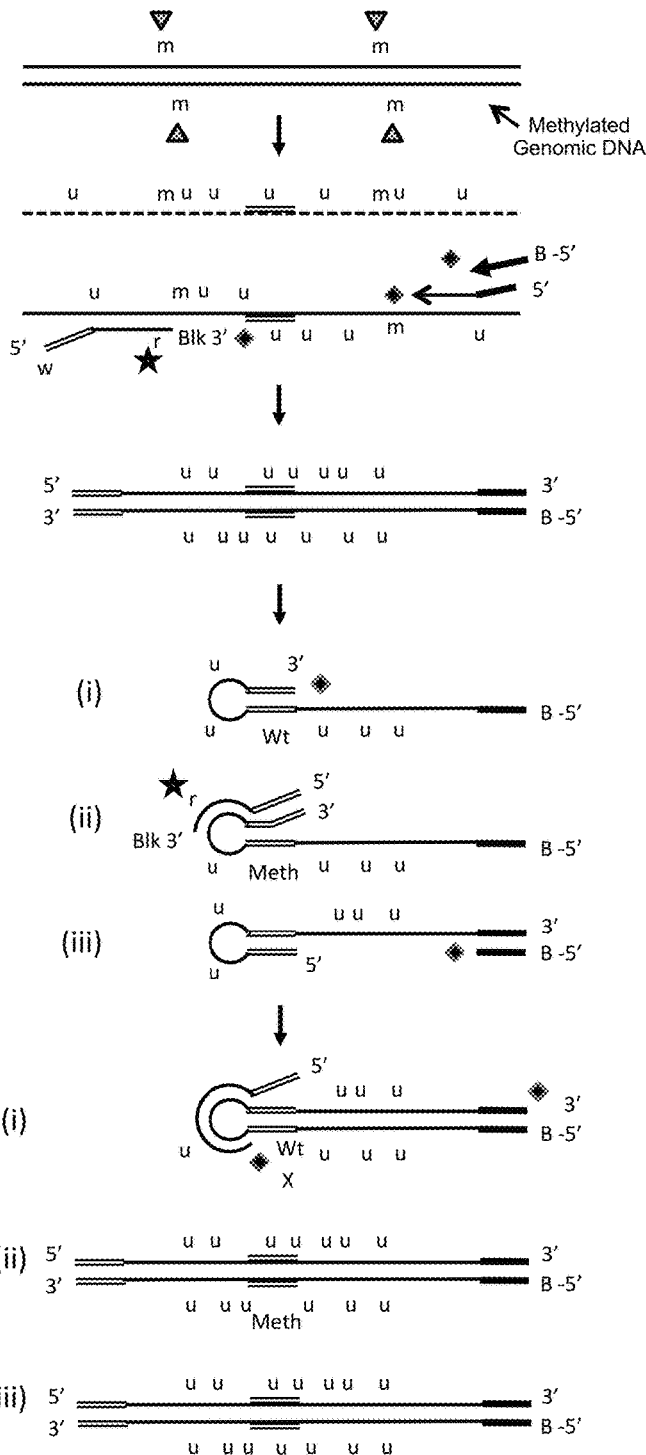

Figure 157

F. PCR products incorporate dU, allowing for carryover prevention. Separate product from primers and capture biotinylated product on solid support. Optional: sequence on end complementary to unmethylated region may be clipped off with restriction endonuclease.

G. Methytion-specific ligation oligonucleotides (Meth) contain tails for subsequent FRET detection, while (optional) unmethylated probe (Umet) does not. Upstream ligation primer contains block, which may be removed by cleaving ribose base with RNaseH2 only when hybridized to target. (Optional: wild-type sequence on 3' end may be clipped off with exonuclease III)

H. Ligase covalently seals the unblocked upstream and phosphorylated downstream oligonucleotides together.

I. Wash away unligated primers. Denature product from target, then detect, and enumerate FRET signal.

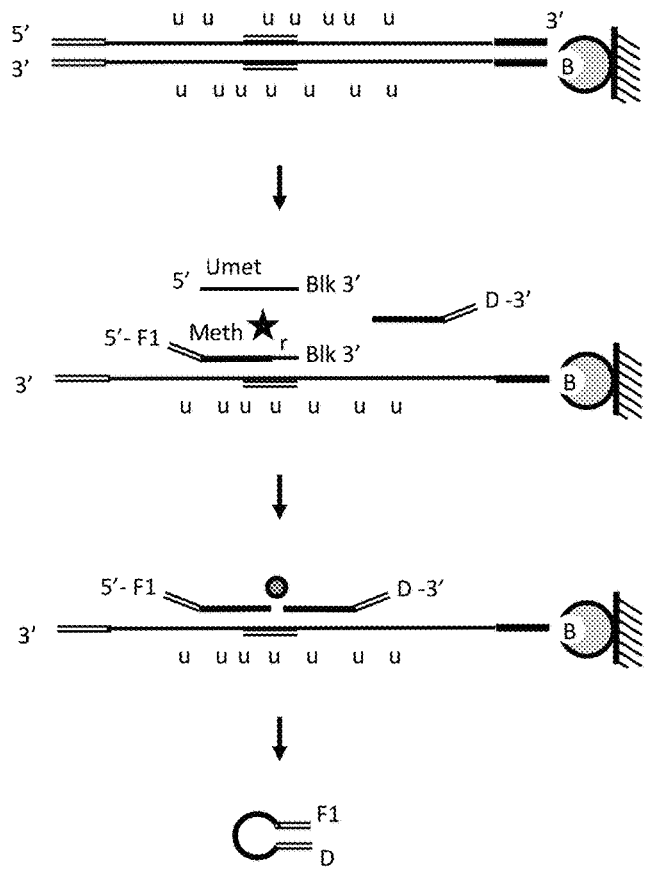

Figure 157 (Cont.)

A. PCR-qPCR carryover prevention reaction to detect low-level methylation. Isolate genomic or cfDNA. Optional: enrich for methylated DNA using antibodies. Treat with methyl-sensitive restriction endonucleases Bsh1236I (CG^CG) and HinP1I (G^CGC), and UNG (37oC, 30-60 minutes) to completely digest unmethylated DNA and prevent carryover.

B. Amplify methyl containing regions using PCR (and dUTP) with locus-specific primers. Perform limited cycle amplification (12-20) to maintain relative ratios of different amplicons. (Optional: aliquot into 12, 24, 48, or 96 wells prior to PCR.)

C. PCR products incorporate dU, allowing for carryover prevention. (Products lack methyl groups, providing additional protection.)

D. Optional: Aliquot into separate wells for detection. Amplify methyl containing regions using PCR (and dUTP) with nested locus-specific primers and internal Taqman probes.

E. The 5'->3' nuclease activity of Taq polymerase liberates the fluorescent group to generate signal. (PCR products incorporate dU, allowing for carryover prevention.)

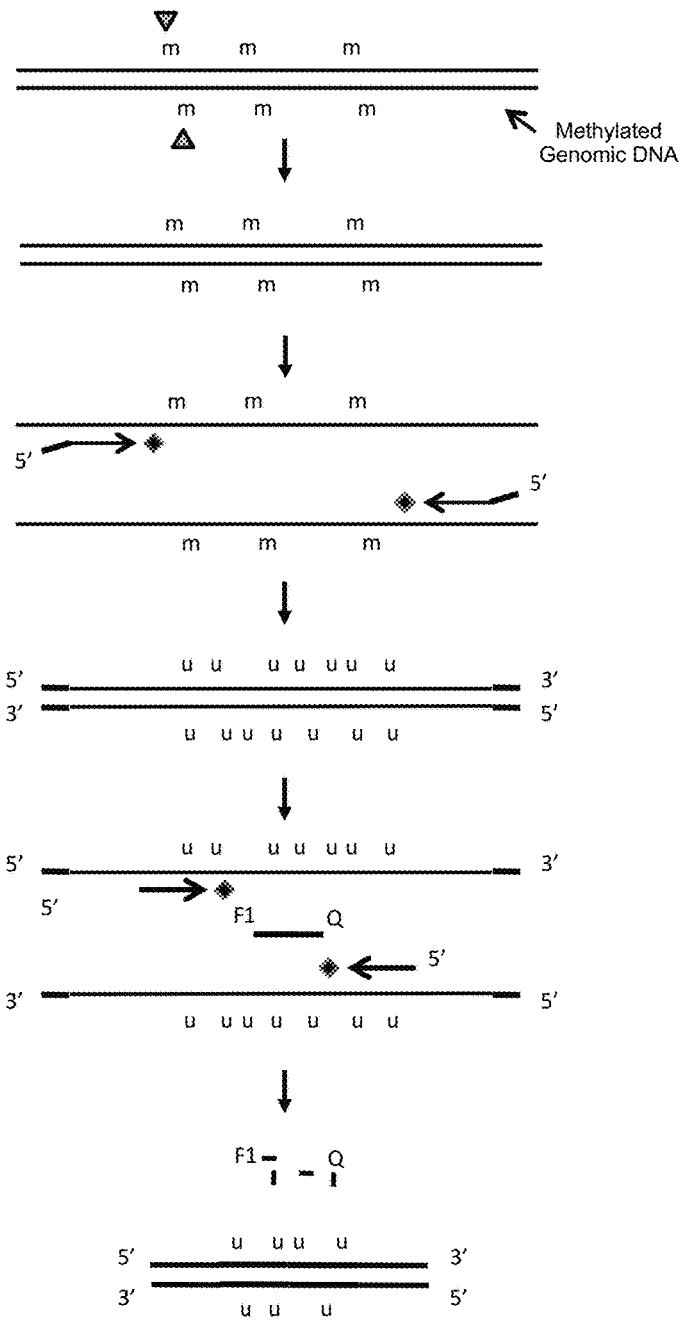

Figure 158

SEQUENCE LISTING

```
<160> NUMBER OF SEQ ID NOS: 138

<210> SEQ ID NO 1
<211> LENGTH: 36
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (32)..(32)
<223> OTHER INFORMATION: N at position 32 is riboguanosine

<400> SEQUENCE: 1
cctcacagta aaataggtg attttggtct anctat                          36

<210> SEQ ID NO 2
<211> LENGTH: 39
<212> TYPE: DNA
<213> ORGANISM: Artificial
<220> FEATURE:
<223> OTHER INFORMATION: Primer

<400> SEQUENCE: 2
ggtgtcgtgg tcaaaatgga tccagacaac tgttcaaac                      39

<210> SEQ ID NO 3
<211> LENGTH: 17
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (5)..(5)
<223> OTHER INFORMATION: N at position 5 is locked nucleic acid cytosine
<220> FEATURE:
<221> NAME/KEY: misc_feature
<222> LOCATION: (6)..(6)
<223> OTHER INFORMATION: N at position 6 is locked nucleic acid
      adenosine
<220> FEATURE:
<221> NAME/KEY: misc_feature
<222> LOCATION: (8)..(8)
<223> OTHER INFORMATION: N at position 8 is locked nucleic acid
      thymidine
<220> FEATURE:
<221> NAME/KEY: misc_feature
<222> LOCATION: (9)..(9)
<223> OTHER INFORMATION: N at position 9 is locked nucleic acid
      guanosine
<220> FEATURE:
<221> NAME/KEY: misc_feature
<222> LOCATION: (10)..(10)
<223> OTHER INFORMATION: N at position 10 is locked nucleic acid
      adenosine
<220> FEATURE:
<221> NAME/KEY: misc_feature
<222> LOCATION: (14)..(14)
<223> OTHER INFORMATION: N at position 14 is locked nucleic acid
      cytosine

<400> SEQUENCE: 3
gctanngnnn aatntcg                                              17

<210> SEQ ID NO 4
<211> LENGTH: 60
<212> TYPE: DNA
<213> ORGANISM: Artificial
<220> FEATURE:
<223> OTHER INFORMATION: Primer
<220> FEATURE:
```

```
<221> NAME/KEY: misc_feature
<222> LOCATION: (56)..(56)
<223> OTHER INFORMATION: N at position 56 is riboguanosine

<400> SEQUENCE: 4
tagcgatagt accgacagtc acgtcctaaa taggtgattt tggtctagct acgganaaac    60

<210> SEQ ID NO 5
<211> LENGTH: 50
<212> TYPE: DNA
<213> ORGANISM: Artificial
<220> FEATURE:
<223> OTHER INFORMATION: Primer

<400> SEQUENCE: 5
gaaatctcga tggagtgggt cccatttggt gtgcggaaac ctatcgtcga               50

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
tagcgatagt accgacagtc ac                                             22

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
tcgacgatag gtttccgcac                                                20

<210> SEQ ID NO 8
<211> LENGTH: 26
<212> TYPE: DNA
<213> ORGANISM: Artificial
<220> FEATURE:
<223> OTHER INFORMATION: Primer

<400> SEQUENCE: 8
tacggagaaa tctcgatgga gtgggt                                         26

<210> SEQ ID NO 9
<211> LENGTH: 22
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (18)..(18)
<223> OTHER INFORMATION: N at position 18 is riboadenosine

<400> SEQUENCE: 9
cctgcatggg cggcatgnac cg                                             22

<210> SEQ ID NO 10
<211> LENGTH: 31
<212> TYPE: DNA
<213> ORGANISM: Artificial
<220> FEATURE:
<223> OTHER INFORMATION: Primer
```

```
<400> SEQUENCE: 10
ggtgtcgtgg aagtggcaag tggctcctga c                                 31

<210> SEQ ID NO 11
<211> LENGTH: 10
<212> TYPE: DNA
<213> ORGANISM: Artificial
<220> FEATURE:
<223> OTHER INFORMATION: Primer

<400> SEQUENCE: 11
gaaccggagg                                                         10

<210> SEQ ID NO 12
<211> LENGTH: 11
<212> TYPE: DNA
<213> ORGANISM: Artificial
<220> FEATURE:
<223> OTHER INFORMATION: Primer

<400> SEQUENCE: 12
tgaaccggag g                                                       11

<210> SEQ ID NO 13
<211> LENGTH: 50
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (46)..(46)
<223> OTHER INFORMATION: N at position 46 is riboguanosine

<400> SEQUENCE: 13
tcactatcgg cgtagtcacc acagacgcat gggcggcatg aatcanaggt             50

<210> SEQ ID NO 14
<211> LENGTH: 49
<212> TYPE: DNA
<213> ORGANISM: Artificial
<220> FEATURE:
<223> OTHER INFORMATION: Primer

<400> SEQUENCE: 14
gaggcccatc ctcaccatca tcacgttgtt ggtgacttta cccggagga              49

<210> SEQ ID NO 15
<211> LENGTH: 21
<212> TYPE: DNA
<213> ORGANISM: Artificial
<220> FEATURE:
<223> OTHER INFORMATION: Primer

<400> SEQUENCE: 15
tcactatcgg cgtagtcacc a                                            21

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
```
tcctccgggt aaagtcacca                                                          20

<210> SEQ ID NO 17
<211> LENGTH: 23
<212> TYPE: DNA
<213> ORGANISM: Artificial
<220> FEATURE:
<223> OTHER INFORMATION: Primer

<400> SEQUENCE: 17
cggcatgaat cagaggccca tcc                                                      23

<210> SEQ ID NO 18
<211> LENGTH: 34
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (30)..(30)
<223> OTHER INFORMATION: N at position 30 is riboguanosine

<400> SEQUENCE: 18
tgactgaata taaacttgtg gtagttggan ctgg                                          34

<210> SEQ ID NO 19
<211> LENGTH: 40
<212> TYPE: DNA
<213> ORGANISM: Artificial
<220> FEATURE:
<223> OTHER INFORMATION: Primer

<400> SEQUENCE: 19
ggtgtcgtgg cgtccacaaa atgattctga attagctgta                                    40

<210> SEQ ID NO 20
<211> LENGTH: 11
<212> TYPE: DNA
<213> ORGANISM: Artificial
<220> FEATURE:
<223> OTHER INFORMATION: Primer

<400> SEQUENCE: 20
gagctggtgg c                                                                   11

<210> SEQ ID NO 21
<211> LENGTH: 11
<212> TYPE: DNA
<213> ORGANISM: Artificial
<220> FEATURE:
<223> OTHER INFORMATION: Primer

<400> SEQUENCE: 21
agctggtggc g                                                                   11

<210> SEQ ID NO 22
<211> LENGTH: 60
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (56)..(56)
<223> OTHER INFORMATION: N at position 56 is riboguanosine

<400> SEQUENCE: 22
ttcgtacctc ggcacaccaa cataactgaa tataaacttg tggtagttgg agtthntgat      60

<210> SEQ ID NO 23
<211> LENGTH: 51
<212> TYPE: DNA
<213> ORGANISM: Artificial
<220> FEATURE:
<223> OTHER INFORMATION: Primer

<400> SEQUENCE: 23
gtggcgtagg caagagtgcc ttgacggcgt gtggctccgt tactctgtcg a      51

<210> SEQ ID NO 24
<211> LENGTH: 19
<212> TYPE: DNA
<213> ORGANISM: Artificial
<220> FEATURE:
<223> OTHER INFORMATION: Primer

<400> SEQUENCE: 24
ttcgtacctc ggcacacca      19

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
tcgacagagt aacggagcca      20

<210> SEQ ID NO 26
<211> LENGTH: 24
<212> TYPE: DNA
<213> ORGANISM: Artificial
<220> FEATURE:
<223> OTHER INFORMATION: Primer

<400> SEQUENCE: 26
ttggagtthg tggcgtaggc aaga      24

<210> SEQ ID NO 27
<211> LENGTH: 59
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (55)..(55)
<223> OTHER INFORMATION: N at position 55 is ribouridine

<400> SEQUENCE: 27
ttcgtacctc ggcacaccaa catatgaata taaacttgtg gtagttggag ccghnggca      59

<210> SEQ ID NO 28
<211> LENGTH: 59
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (55)..(55)
<223> OTHER INFORMATION: N at position 55 is ribouridine

```
<400> SEQUENCE: 28
ttcgtacctc ggcacaccaa catatgaata taaacttgtg gtagttggag ccghnggta        59

<210> SEQ ID NO 29
<211> LENGTH: 50
<212> TYPE: DNA
<213> ORGANISM: Artificial
<220> FEATURE:
<223> OTHER INFORMATION: Primer

<400> SEQUENCE: 29
tggcgtaggc aagagtgcct tgacggcgtg tggctccgtt actctgtcga                  50

<210> SEQ ID NO 30
<211> LENGTH: 22
<212> TYPE: DNA
<213> ORGANISM: Artificial
<220> FEATURE:
<223> OTHER INFORMATION: Primer

<400> SEQUENCE: 30
tagttggagc cghtggcgta gg                                                22

<210> SEQ ID NO 31
<211> LENGTH: 28
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (24)..(24)
<223> OTHER INFORMATION: N at position 24 is ribocytosine

<400> SEQUENCE: 31
gaactccaac cgaaactacg taantaca                                          28

<210> SEQ ID NO 32
<211> LENGTH: 33
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is riboguanosine

<400> SEQUENCE: 32
ggtgtcgtgg acgaggcgta gaggttgcng tta                                    33

<210> SEQ ID NO 33
<211> LENGTH: 18
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: N at position 3 is locked nucleic acid
      thymidine
<220> FEATURE:
<221> NAME/KEY: misc_feature
<222> LOCATION: (6)..(6)
<223> OTHER INFORMATION: N at position 6 is locked nucleic acid cytosine
<220> FEATURE:
<221> NAME/KEY: misc_feature
<222> LOCATION: (8)..(8)
```

```
<223> OTHER INFORMATION: N at position 8 is locked nucleic acid
      adenosine
<220> FEATURE:
<221> NAME/KEY: misc_feature
<222> LOCATION: (10)..(10)
<223> OTHER INFORMATION: N at position 10 is locked nucleic acid
      adenosine
<220> FEATURE:
<221> NAME/KEY: misc_feature
<222> LOCATION: (12)..(12)
<223> OTHER INFORMATION: N at position 12 is locked nucleic acid
      cytosine
<220> FEATURE:
<221> NAME/KEY: misc_feature
<222> LOCATION: (14)..(14)
<223> OTHER INFORMATION: N at position 14 is locked nucleic acid
      adenosine
<220> FEATURE:
<221> NAME/KEY: misc_feature
<222> LOCATION: (16)..(16)
<223> OTHER INFORMATION: N at position 16 is locked nucleic acid
      cytosine

<400> SEQUENCE: 33
canaantncn tncncnca                                                 18

<210> SEQ ID NO 34
<211> LENGTH: 18
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: N at position 3 is locked nucleic acid
      thymidine
<220> FEATURE:
<221> NAME/KEY: misc_feature
<222> LOCATION: (6)..(6)
<223> OTHER INFORMATION: N at position 6 is locked nucleic acid cytosine
<220> FEATURE:
<221> NAME/KEY: misc_feature
<222> LOCATION: (8)..(8)
<223> OTHER INFORMATION: N at position 8 is locked nucleic acid
      adenosine
<220> FEATURE:
<221> NAME/KEY: misc_feature
<222> LOCATION: (10)..(10)
<223> OTHER INFORMATION: N at position 10 is locked nucleic acid
      adenosine
<220> FEATURE:
<221> NAME/KEY: misc_feature
<222> LOCATION: (12)..(13)
<223> OTHER INFORMATION: N at position 12-13 is locked nucleic acid
      cytosine
<220> FEATURE:
<221> NAME/KEY: misc_feature
<222> LOCATION: (14)..(14)
<223> OTHER INFORMATION: N at position 14 is locked nucleic acid
      adenosine
<220> FEATURE:
<221> NAME/KEY: misc_feature
<222> LOCATION: (16)..(16)
<223> OTHER INFORMATION: N at position 16 is locked nucleic acid
      cytosine

<400> SEQUENCE: 34
canaantncn tnnncnca                                                 18

<210> SEQ ID NO 35
<211> LENGTH: 19
<212> TYPE: DNA
<213> ORGANISM: Artificial
<220> FEATURE:
```

<223> OTHER INFORMATION: Primer

<400> SEQUENCE: 35
acataactac atccaccca                                               19

<210> SEQ ID NO 36
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (47)..(47)
<223> OTHER INFORMATION: N at position 47 is ribouridine

<400> SEQUENCE: 36
tagacacgag cgaggtcaca actccaaccg aaactacgta actgcgnccg t           51

<210> SEQ ID NO 37
<211> LENGTH: 50
<212> TYPE: DNA
<213> ORGANISM: Artificial
<220> FEATURE:
<223> OTHER INFORMATION: Primer

<400> SEQUENCE: 37
tccacccgca cctacaacct aaacaacgcg tgcaaaattc aggctgtgca             50

<210> SEQ ID NO 38
<211> LENGTH: 23
<212> TYPE: DNA
<213> ORGANISM: Artificial
<220> FEATURE:
<223> OTHER INFORMATION: Primer

<400> SEQUENCE: 38
taactgcgtc cacccgcacc tac                                          23

<210> SEQ ID NO 39
<211> LENGTH: 19
<212> TYPE: DNA
<213> ORGANISM: Artificial
<220> FEATURE:
<223> OTHER INFORMATION: Primer

<400> SEQUENCE: 39
tagacacgag cgaggtcac                                               19

<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
tgcacagcct gaattttgca c                                            21

<210> SEQ ID NO 41
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (47)..(47)
<223> OTHER INFORMATION: N at position 47 is ribouridine

<400> SEQUENCE: 41
tagacacgag cgaggtcaca actccaaccg aaactacgta actgcgnccg t    51

<210> SEQ ID NO 42
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (47)..(47)
<223> OTHER INFORMATION: N at position 47 is ribouridine

<400> SEQUENCE: 42
tagacacgag cgaggtcaca actccaaccg aaactacgta actgcgncta t    51

<210> SEQ ID NO 43
<211> LENGTH: 53
<212> TYPE: DNA
<213> ORGANISM: Artificial
<220> FEATURE:
<223> OTHER INFORMATION: Primer

<400> SEQUENCE: 43
tccgcccgca cctacaacct aaacaacgcg ctgtgcaaaa ttcaggctgt gca    53

<210> SEQ ID NO 44
<211> LENGTH: 25
<212> TYPE: DNA
<213> ORGANISM: Artificial
<220> FEATURE:
<223> OTHER INFORMATION: Primer

<400> SEQUENCE: 44
tttaactgcg tccacccgca cctac    25

<210> SEQ ID NO 45
<211> LENGTH: 25
<212> TYPE: DNA
<213> ORGANISM: Artificial
<220> FEATURE:
<223> OTHER INFORMATION: Primer

<400> SEQUENCE: 45
tttaactgcg tccgcccgca cctac    25

<210> SEQ ID NO 46
<211> LENGTH: 24
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (20)..(20)
<223> OTHER INFORMATION: N at position 20 is ribocytosine

<400> SEQUENCE: 46
accactctcg ctccgaaatn ccca    24

<210> SEQ ID NO 47
<211> LENGTH: 38
<212> TYPE: DNA

<213> ORGANISM: Artificial
<220> FEATURE:
<223> OTHER INFORMATION: Primer
<220> FEATURE:
<221> NAME/KEY: misc_feature
<222> LOCATION: (34)..(34)
<223> OTHER INFORMATION: N at position 34 is ribocytosine

<400> SEQUENCE: 47
ggtgtcgtgg cggattggtt ttcggagaag aggngaat                    38

<210> SEQ ID NO 48
<211> LENGTH: 44
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (40)..(40)
<223> OTHER INFORMATION: N at position 40 is ribocytosine

<400> SEQUENCE: 48
taccctccta gctccgtaca tctcgctccg aaatcctcgn gctg            44

<210> SEQ ID NO 49
<211> LENGTH: 39
<212> TYPE: DNA
<213> ORGANISM: Artificial
<220> FEATURE:
<223> OTHER INFORMATION: Primer

<400> SEQUENCE: 49
cgccaaaaac gcaaccgcgc tgtgttgtct ggtggtgca                  39

<210> SEQ ID NO 50
<211> LENGTH: 19
<212> TYPE: DNA
<213> ORGANISM: Artificial
<220> FEATURE:
<223> OTHER INFORMATION: Primer

<400> SEQUENCE: 50
atcctcgcgc caaaaacgc                                        19

<210> SEQ ID NO 51
<211> LENGTH: 23
<212> TYPE: DNA
<213> ORGANISM: Artificial
<220> FEATURE:
<223> OTHER INFORMATION: Primer

<400> SEQUENCE: 51
ccgaaatcct cgcgccaaaa acg                                   23

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
taccctccta gctccgtaca                                       20

<210> SEQ ID NO 53
<211> LENGTH: 19

```
<212> TYPE: DNA
<213> ORGANISM: Artificial
<220> FEATURE:
<223> OTHER INFORMATION: Primer

<400> SEQUENCE: 53
tgcaccacca gacaacaca                                                    19

<210> SEQ ID NO 54
<211> LENGTH: 14
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (2)..(2)
<223> OTHER INFORMATION: N at position 2 is locked nucleic acid
      adenosine
<220> FEATURE:
<221> NAME/KEY: misc_feature
<222> LOCATION: (4)..(4)
<223> OTHER INFORMATION: N at position 4 is locked nucleic acid cytosine
<220> FEATURE:
<221> NAME/KEY: misc_feature
<222> LOCATION: (6)..(6)
<223> OTHER INFORMATION: N at position 6 is locked nucleic acid cytosine
<220> FEATURE:
<221> NAME/KEY: misc_feature
<222> LOCATION: (8)..(8)
<223> OTHER INFORMATION: N at position 8 is locked nucleic acid
      adenosine
<220> FEATURE:
<221> NAME/KEY: misc_feature
<222> LOCATION: (10)..(10)
<223> OTHER INFORMATION: N at position 10 is locked nucleic acid
      adenosine
<220> FEATURE:
<221> NAME/KEY: misc_feature
<222> LOCATION: (12)..(12)
<223> OTHER INFORMATION: N at position 12 is locked nucleic acid
      cytosine
<220> FEATURE:
<221> NAME/KEY: misc_feature
<222> LOCATION: (14)..(14)
<223> OTHER INFORMATION: N at position 14 is locked nucleic acid
      adenosine

<400> SEQUENCE: 54
antncncncn cnan                                                         14

<210> SEQ ID NO 55
<211> LENGTH: 14
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (2)..(2)
<223> OTHER INFORMATION: N at position 2 is locked nucleic acid
      adenosine
<220> FEATURE:
<221> NAME/KEY: misc_feature
<222> LOCATION: (4)..(4)
<223> OTHER INFORMATION: N at position 5 is locked nucleic acid cytosine
<220> FEATURE:
<221> NAME/KEY: misc_feature
<222> LOCATION: (6)..(6)
<223> OTHER INFORMATION: N at position 6 is locked nucleic acid cytosine
<220> FEATURE:
<221> NAME/KEY: misc_feature
<222> LOCATION: (8)..(8)
<223> OTHER INFORMATION: N at position 8 is locked nucleic acid
      adenosine
```

```
<220> FEATURE:
<221> NAME/KEY: misc_feature
<222> LOCATION: (9)..(9)
<223> OTHER INFORMATION: N at position 9 is locked nucleic acid cytosine
<220> FEATURE:
<221> NAME/KEY: misc_feature
<222> LOCATION: (10)..(10)
<223> OTHER INFORMATION: N at position 10 is locked nucleic acid
      adenosine
<220> FEATURE:
<221> NAME/KEY: misc_feature
<222> LOCATION: (12)..(12)
<223> OTHER INFORMATION: N at position 12 is locked nucleic acid
      cytosine
<220> FEATURE:
<221> NAME/KEY: misc_feature
<222> LOCATION: (14)..(14)
<223> OTHER INFORMATION: N at position 14 is locked nucleic acid
      adenosine

<400> SEQUENCE: 55
antncncnnn cnan                                                   14

<210> SEQ ID NO 56
<211> LENGTH: 15
<212> TYPE: DNA
<213> ORGANISM: Artificial
<220> FEATURE:
<223> OTHER INFORMATION: Primer

<400> SEQUENCE: 56
aatccccaca ccaaa                                                  15

<210> SEQ ID NO 57
<211> LENGTH: 34
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (30)..(30)
<223> OTHER INFORMATION: N at position 30 is riboguanosine

<400> SEQUENCE: 57
gttagatatt ggtcgcgggt tattatttgn acga                             34

<210> SEQ ID NO 58
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (27)..(27)
<223> OTHER INFORMATION: N at position 27 is ribothymidine

<400> SEQUENCE: 58
ggtgtcgtgg gcaacccgcg cgaaaanaac t                                31

<210> SEQ ID NO 59
<211> LENGTH: 45
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (41)..(41)
<223> OTHER INFORMATION: N at position 41 is riboguanosine
```

<400> SEQUENCE: 59
tgcttaccca cgatgcaccc gcgggttatt atttggaagc natcc    45

<210> SEQ ID NO 60
<211> LENGTH: 45
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (41)..(41)
<223> OTHER INFORMATION: N at position 41 is riboguanosine

<400> SEQUENCE: 60
tgcttaccca cgatgcaccc gcgggttatt atttggaagc nactc    45

<210> SEQ ID NO 61
<211> LENGTH: 45
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (41)..(41)
<223> OTHER INFORMATION: N at position 41 is riboguanosine

<400> SEQUENCE: 61
tgcttaccca cgatgcaccc gcgggttatt atttggaagc natcc    45

<210> SEQ ID NO 62
<211> LENGTH: 62
<212> TYPE: DNA
<213> ORGANISM: Artificial
<220> FEATURE:
<223> OTHER INFORMATION: Primer

<400> SEQUENCE: 62
gatctttcgt tagggttttt ttggtttggg ttaaagttgg tgggtcgtat gacttgctcg    60
ca    62

<210> SEQ ID NO 63
<211> LENGTH: 58
<212> TYPE: DNA
<213> ORGANISM: Artificial
<220> FEATURE:
<223> OTHER INFORMATION: Primer

<400> SEQUENCE: 63 gattttcgt tagggttttt ttggtttggg ttaaagttgg tcgtatgact tgctcgca    58

<210> SEQ ID NO 64
<211> LENGTH: 32
<212> TYPE: DNA
<213> ORGANISM: Artificial
<220> FEATURE:
<223> OTHER INFORMATION: Primer

<400> SEQUENCE: 64
aatggaagcg atctttcgtt agggtttttt tg    32

<210> SEQ ID NO 65
<211> LENGTH: 29
<212> TYPE: DNA

```
<213> ORGANISM: Artificial
<220> FEATURE:
<223> OTHER INFORMATION: Primer

<400> SEQUENCE: 65
atttggaagc gatttttcgt tagggtttt                                    29

<210> SEQ ID NO 66
<211> LENGTH: 19
<212> TYPE: DNA
<213> ORGANISM: Artificial
<220> FEATURE:
<223> OTHER INFORMATION: Primer

<400> SEQUENCE: 66
tgcttaccca cgatgcacc                                               19

<210> SEQ ID NO 67
<211> LENGTH: 20
<212> TYPE: DNA
<213> ORGANISM: Artificial
<220> FEATURE:
<223> OTHER INFORMATION: Primer

<400> SEQUENCE: 67
tgcgagcaag tcatacgacc                                              20

<210> SEQ ID NO 68
<211> LENGTH: 23
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: N at position 3 is locked nucleic acid
      thymidine
<220> FEATURE:
<221> NAME/KEY: misc_feature
<222> LOCATION: (5)..(5)
<223> OTHER INFORMATION: N at position 5 is locked nucleic acid
      guanosine
<220> FEATURE:
<221> NAME/KEY: misc_feature
<222> LOCATION: (7)..(7)
<223> OTHER INFORMATION: N at position 7 is locked nucleic acid
      adenosine
<220> FEATURE:
<221> NAME/KEY: misc_feature
<222> LOCATION: (8)..(8)
<223> OTHER INFORMATION: N at position 8 is locked nucleic acid
      thymidine
<220> FEATURE:
<221> NAME/KEY: misc_feature
<222> LOCATION: (9)..(9)
<223> OTHER INFORMATION: N at position 9 is locked nucleic acid
      guanosine
<220> FEATURE:
<221> NAME/KEY: misc_feature
<222> LOCATION: (10)..(10)
<223> OTHER INFORMATION: N at position 10 is locked nucleic acid
      thymidine
<220> FEATURE:
<221> NAME/KEY: misc_feature
<222> LOCATION: (11)..(11)
<223> OTHER INFORMATION: N at position 11 is locked nucleic acid
      guanosine
<220> FEATURE:
<221> NAME/KEY: misc_feature
<222> LOCATION: (13)..(13)
<223> OTHER INFORMATION: N at position 13 is locked nucleic acid
      thymidine
```

```
<220> FEATURE:
<221> NAME/KEY: misc_feature
<222> LOCATION: (18)..(18)
<223> OTHER INFORMATION: N at position 18 is locked nucleic acid
      thymidine
<220> FEATURE:
<221> NAME/KEY: misc_feature
<222> LOCATION: (19)..(19)
<223> OTHER INFORMATION: N at position 19 is locked nucleic acid
      guanosine
<220> FEATURE:
<221> NAME/KEY: misc_feature
<222> LOCATION: (22)..(22)
<223> OTHER INFORMATION: N at position 22 is locked nucleic acid
      adenosine

<400> SEQUENCE: 68
atntngnnnn nantttnnnt tng                                        23

<210> SEQ ID NO 69
<211> LENGTH: 31
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (27)..(27)
<223> OTHER INFORMATION: N at position 27 is riboadenosine

<400> SEQUENCE: 69 tttggttgt attttggtgt tttgttnttt a                                31

<210> SEQ ID NO 70
<211> LENGTH: 36
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (32)..(32)
<223> OTHER INFORMATION: N at position 32 is ribouridine

<400> SEQUENCE: 70
ggtgtcgtgg ctaactccgc tacgctctca antcta                          36

<210> SEQ ID NO 71
<211> LENGTH: 53
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (49)..(49)
<223> OTHER INFORMATION: N at position 49 is riboguanosine

<400> SEQUENCE: 71
ttcgcctacc gcagtgaact gggttgtatt ttggtgtttt gttatctcng gga       53

<210> SEQ ID NO 72
<211> LENGTH: 53
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (49)..(49)
<223> OTHER INFORMATION: N at position 49 is riboguanosine
```

```
<400> SEQUENCE: 72
ttcgcctacc gcagtgaact gggttgtatt ttggtgtttt gttatctcng aaa          53

<210> SEQ ID NO 73
<211> LENGTH: 53
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (49)..(49)
<223> OTHER INFORMATION: N at position 49 is riboguanosine

<400> SEQUENCE: 73
ttcgcctacc gcagtgaact gggttgtatt ttggtgtttt gttatctcng gga          53

<210> SEQ ID NO 74
<211> LENGTH: 47
<212> TYPE: DNA
<213> ORGANISM: Artificial
<220> FEATURE:
<223> OTHER INFORMATION: Primer

<400> SEQUENCE: 74
gggtgacgcg aagggttgt tgtgcgaagt tgagacatgg gctcgca                  47

<210> SEQ ID NO 75
<211> LENGTH: 43
<212> TYPE: DNA
<213> ORGANISM: Artificial
<220> FEATURE:
<223> OTHER INFORMATION: Primer

<400> SEQUENCE: 75
gggagacgcg aagggttgt tgtggttgag acatgggctc gca                       43

<210> SEQ ID NO 76
<211> LENGTH: 24
<212> TYPE: DNA
<213> ORGANISM: Artificial
<220> FEATURE:
<223> OTHER INFORMATION: Primer

<400> SEQUENCE: 76
aattatctcg ggagacgcga aggg                                           24

<210> SEQ ID NO 77
<211> LENGTH: 24
<212> TYPE: DNA
<213> ORGANISM: Artificial
<220> FEATURE:
<223> OTHER INFORMATION: Primer

<400> SEQUENCE: 77
aattatctcg ggtgacgcga aggg                                           24

<210> SEQ ID NO 78
<211> LENGTH: 27
<212> TYPE: DNA
<213> ORGANISM: Artificial
<220> FEATURE:
<223> OTHER INFORMATION: Primer

<400> SEQUENCE: 78
```

```
ttttgttatc tcgggagacg cgaaggg                                        27
```

<210> SEQ ID NO 79
<211> LENGTH: 19
<212> TYPE: DNA
<213> ORGANISM: Artificial
<220> FEATURE:
<223> OTHER INFORMATION: Primer

<400> SEQUENCE: 79

```
ttcgcctacc gcagtgaac                                                 19
```

<210> SEQ ID NO 80
<211> LENGTH: 19
<212> TYPE: DNA
<213> ORGANISM: Artificial
<220> FEATURE:
<223> OTHER INFORMATION: Primer

<400> SEQUENCE: 80

```
tgcgagccca tgtctcaac                                                 19
```

<210> SEQ ID NO 81
<211> LENGTH: 23
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (9)..(10)
<223> OTHER INFORMATION: N at position 9-10 is locked nucleic acid
      thymidine
<220> FEATURE:
<221> NAME/KEY: misc_feature
<222> LOCATION: (11)..(11)
<223> OTHER INFORMATION: N at position 11 is locked nucleic acid
      guanosine
<220> FEATURE:
<221> NAME/KEY: misc_feature
<222> LOCATION: (17)..(17)
<223> OTHER INFORMATION: N at position 17 is locked nucleic acid
      thymidine
<220> FEATURE:
<221> NAME/KEY: misc_feature
<222> LOCATION: (18)..(18)
<223> OTHER INFORMATION: N at position 18 is locked nucleic acid
      guanosine
<220> FEATURE:
<221> NAME/KEY: misc_feature
<222> LOCATION: (19)..(19)
<223> OTHER INFORMATION: N at position 19 is locked nucleic acid
      thymidine
<220> FEATURE:
<221> NAME/KEY: misc_feature
<222> LOCATION: (20)..(20)
<223> OTHER INFORMATION: N at position 20 is locked nucleic acid
      guanosine

<400> SEQUENCE: 81

```
ttgttattnn nggagannnn aag                                            23
```

<210> SEQ ID NO 82
<211> LENGTH: 36
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (32)..(32)
<223> OTHER INFORMATION: N at position 32 is ribouridine

<400> SEQUENCE: 82
ggtttagttt tttgttattt tcgtttcgag gnttta                              36

<210> SEQ ID NO 83
<211> LENGTH: 36
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (32)..(32)
<223> OTHER INFORMATION: N at position 32 is ribocytosine

<400> SEQUENCE: 83
ggtgtcgtgg gacgataacg cgaactaact cncgag                              36

<210> SEQ ID NO 84
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (50)..(50)
<223> OTHER INFORMATION: N at position 50 is riboguanosine

<400> SEQUENCE: 84
ttgcaacagg ctaccgaccg ttttttgtta ttttcgtttc gaggttctcn cgcc          54

<210> SEQ ID NO 85
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (50)..(50)
<223> OTHER INFORMATION: N at position 50 is riboguanosine

<400> SEQUENCE: 85
ttgcaacagg ctaccgaccg ttttttgtta ttttcgtttc gaggttctcn cgcc          54

<210> SEQ ID NO 86
<211> LENGTH: 65
<212> TYPE: DNA
<213> ORGANISM: Artificial
<220> FEATURE:
<223> OTHER INFORMATION: Primer

<400> SEQUENCE: 86
gcgttagaga cgtagtcgcg tttttattat ttatatttat cgcgggtagg taaggaagtc    60
acgca                                                                65

<210> SEQ ID NO 87
<211> LENGTH: 26
<212> TYPE: DNA
<213> ORGANISM: Artificial
<220> FEATURE:
<223> OTHER INFORMATION: Primer

<400> SEQUENCE: 87
aggttctcgc gttagagacg tagtcg                                         26

```
<210> SEQ ID NO 88
<211> LENGTH: 30
<212> TYPE: DNA
<213> ORGANISM: Artificial
<220> FEATURE:
<223> OTHER INFORMATION: Primer

<400> SEQUENCE: 88
attttcgttt cgaggttctc gcgttagaga                                      30

<210> SEQ ID NO 89
<211> LENGTH: 19
<212> TYPE: DNA
<213> ORGANISM: Artificial
<220> FEATURE:
<223> OTHER INFORMATION: Primer

<400> SEQUENCE: 89
ttgcaacagg ctaccgacc                                                  19

<210> SEQ ID NO 90
<211> LENGTH: 21
<212> TYPE: DNA
<213> ORGANISM: Artificial
<220> FEATURE:
<223> OTHER INFORMATION: Primer

<400> SEQUENCE: 90
tgcgtgactt ccttacctac c                                               21

<210> SEQ ID NO 91
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (4)..(4)
<223> OTHER INFORMATION: N at position 4 is locked nucleic acid
      thymidine
<220> FEATURE:
<221> NAME/KEY: misc_feature
<222> LOCATION: (5)..(5)
<223> OTHER INFORMATION: N at position 5 is locked nucleic acid
      guanosine
<220> FEATURE:
<221> NAME/KEY: misc_feature
<222> LOCATION: (8)..(8)
<223> OTHER INFORMATION: N at position 8 is locked nucleic acid
      guanosine
<220> FEATURE:
<221> NAME/KEY: misc_feature
<222> LOCATION: (13)..(13)
<223> OTHER INFORMATION: N at position 13 is locked nucleic acid
      thymidine
<220> FEATURE:
<221> NAME/KEY: misc_feature
<222> LOCATION: (14)..(14)
<223> OTHER INFORMATION: N at position 14 is locked nucleic acid
      guanosine
<220> FEATURE:
<221> NAME/KEY: misc_feature
<222> LOCATION: (15)..(15)
<223> OTHER INFORMATION: N at position 15 is locked nucleic acid
      thymidine
<220> FEATURE:
<221> NAME/KEY: misc_feature
<222> LOCATION: (16)..(16)
<223> OTHER INFORMATION: N at position 16 is locked nucleic acid
      guanosine
<220> FEATURE:
```

```
<221> NAME/KEY: misc_feature
<222> LOCATION: (24)..(24)
<223> OTHER INFORMATION: N at position 24 is locked nucleic acid
      thymidine
<220> FEATURE:
<221> NAME/KEY: misc_feature
<222> LOCATION: (25)..(25)
<223> OTHER INFORMATION: N at position 25 is locked nucleic acid
      guanosine

<400> SEQUENCE: 91
tttnnagntt ttnnnnttag aganntta                                      27

<210> SEQ ID NO 92
<211> LENGTH: 30
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (26)..(26)
<223> OTHER INFORMATION: N at position 26 is riboadenosine

<400> SEQUENCE: 92
gtcgagtttt agtcggagtt acgtgnttaa                                    30

<210> SEQ ID NO 93
<211> LENGTH: 43
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (39)..(39)
<223> OTHER INFORMATION: N at position 39 is ribouridine

<400> SEQUENCE: 93
ggtgtcgtgg gaaaacgaaa cgtaaaaact acgactaana ctg                     43

<210> SEQ ID NO 94
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (50)..(50)
<223> OTHER INFORMATION: N at position 50 is riboguanosine

<400> SEQUENCE: 94
tggatcgaga cggaatgcaa ccgagtttta gtcggagtta cgtgatcacn ttcg         54

<210> SEQ ID NO 95
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (50)..(50)
<223> OTHER INFORMATION: N at position 50 is riboguanosine

<400> SEQUENCE: 95
tggatcgaga cggaatgcaa ccgagtttta gtcggagtta cgtgatcacn tctg         54
```

```
<210> SEQ ID NO 96
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (50)..(50)
<223> OTHER INFORMATION: N at position 50 is riboguanosine

<400> SEQUENCE: 96
tggatcgaga cggaatgcaa ccgagttttta gtcggagtta cgtgatcacn ttcg      54

<210> SEQ ID NO 97
<211> LENGTH: 62
<212> TYPE: DNA
<213> ORGANISM: Artificial
<220> FEATURE:
<223> OTHER INFORMATION: Primer

<400> SEQUENCE: 97
gttcattcgt atttatagtt tgggtagcgc gttgcgtttt gtttccctga ttgatacccg  60
ca                                                                62

<210> SEQ ID NO 98
<211> LENGTH: 58
<212> TYPE: DNA
<213> ORGANISM: Artificial
<220> FEATURE:
<223> OTHER INFORMATION: Primer

<400> SEQUENCE: 98
gtttattcgt atttatagtt tgggtagcgc gttgcggttt ccctgattga tacccgca    58

<210> SEQ ID NO 99
<211> LENGTH: 39
<212> TYPE: DNA
<213> ORGANISM: Artificial
<220> FEATURE:
<223> OTHER INFORMATION: Primer

<400> SEQUENCE: 99
tttgatcacg tttattcgta tttatagttt gggtagcgc                        39

<210> SEQ ID NO 100
<211> LENGTH: 39
<212> TYPE: DNA
<213> ORGANISM: Artificial
<220> FEATURE:
<223> OTHER INFORMATION: Primer

<400> SEQUENCE: 100
tttgatcacg ttcattcgta tttatagttt gggtagcgc                        39

<210> SEQ ID NO 101
<211> LENGTH: 38
<212> TYPE: DNA
<213> ORGANISM: Artificial
<220> FEATURE:
<223> OTHER INFORMATION: Primer

<400> SEQUENCE: 101
agtcggagtt acgtgatcac gtttattcgt atttatag                         38

<210> SEQ ID NO 102
```

```
<211> LENGTH: 21
<212> TYPE: DNA
<213> ORGANISM: Artificial
<220> FEATURE:
<223> OTHER INFORMATION: Primer

<400> SEQUENCE: 102
tggatcgaga cggaatgcaa c                                              21

<210> SEQ ID NO 103
<211> LENGTH: 22
<212> TYPE: DNA
<213> ORGANISM: Artificial
<220> FEATURE:
<223> OTHER INFORMATION: Primer

<400> SEQUENCE: 103
tgcgggtatc aatcagggaa ac                                             22

<210> SEQ ID NO 104
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (4)..(4)
<223> OTHER INFORMATION: N at position 4 is locked nucleic acid
      adenosine
<220> FEATURE:
<221> NAME/KEY: misc_feature
<222> LOCATION: (5)..(5)
<223> OTHER INFORMATION: N at position 5 is locked nucleic acid
      thymidine
<220> FEATURE:
<221> NAME/KEY: misc_feature
<222> LOCATION: (6)..(6)
<223> OTHER INFORMATION: N at position 6 is locked nucleic acid
      guanosine
<220> FEATURE:
<221> NAME/KEY: misc_feature
<222> LOCATION: (8)..(8)
<223> OTHER INFORMATION: N at position 8 is locked nucleic acid
      guanosine
<220> FEATURE:
<221> NAME/KEY: misc_feature
<222> LOCATION: (9)..(9)
<223> OTHER INFORMATION: N at position 9 is locked nucleic acid
      adenosine
<220> FEATURE:
<221> NAME/KEY: misc_feature
<222> LOCATION: (12)..(12)
<223> OTHER INFORMATION: N at position 12 is locked nucleic acid
      adenosine
<220> FEATURE:
<221> NAME/KEY: misc_feature
<222> LOCATION: (13)..(13)
<223> OTHER INFORMATION: N at position 13 is locked nucleic acid
      thymidine
<220> FEATURE:
<221> NAME/KEY: misc_feature
<222> LOCATION: (14)..(14)
<223> OTHER INFORMATION: N at position 14 is locked nucleic acid
      guanosine
<220> FEATURE:
<221> NAME/KEY: misc_feature
<222> LOCATION: (16)..(16)
<223> OTHER INFORMATION: N at position 16 is locked nucleic acid
      thymidine
<220> FEATURE:
<221> NAME/KEY: misc_feature
<222> LOCATION: (18)..(18)
<223> OTHER INFORMATION: N at position 18 is locked nucleic acid
      adenosine
```

```
<220> FEATURE:
<221> NAME/KEY: misc_feature
<222> LOCATION: (20)..(21)
<223> OTHER INFORMATION: N at position 20-21 is locked nucleic acid
      thymidine
<220> FEATURE:
<221> NAME/KEY: misc_feature
<222> LOCATION: (22)..(22)
<223> OTHER INFORMATION: N at position 22 is locked nucleic acid
      guanosine
<220> FEATURE:
<221> NAME/KEY: misc_feature
<222> LOCATION: (24)..(24)
<223> OTHER INFORMATION: N at position 24 is locked nucleic acid
      adenosine

<400> SEQUENCE: 104
gttnnntnnt tnnntntntn nntnttt                                             27

<210> SEQ ID NO 105
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (23)..(23)
<223> OTHER INFORMATION: N at position 23 is riboadenosine

<400> SEQUENCE: 105
ctaaccgcga accaccatct aancgct                                             27

<210> SEQ ID NO 106
<211> LENGTH: 33
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is ribouridine

<400> SEQUENCE: 106
ggtgtcgtgg ttcgcgcgaa ggtggttant aac                                      33

<210> SEQ ID NO 107
<211> LENGTH: 47
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (43)..(43)
<223> OTHER INFORMATION: N at position 43 is riboadenosine

<400> SEQUENCE: 107
ttgcatttcg ttagcgacac agcgaaccac catctaaaca cgntctt                       47

<210> SEQ ID NO 108
<211> LENGTH: 47
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (43)..(43)
<223> OTHER INFORMATION: N at position 43 is riboadenosine
```

```
<400> SEQUENCE: 108
ttgcatttcg ttagcgacac agcgaaccac catctaaaca cgnttct                    47

<210> SEQ ID NO 109
<211> LENGTH: 47
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (43)..(43)
<223> OTHER INFORMATION: N at position 43 is riboadenosine

<400> SEQUENCE: 109
ttgcatttcg ttagcgacac agcgaaccac catctaaaca cgntctt                    47

<210> SEQ ID NO 110
<211> LENGTH: 59
<212> TYPE: DNA
<213> ORGANISM: Artificial
<220> FEATURE:
<223> OTHER INFORMATION: Primer

<400> SEQUENCE: 110
atctcccgct aaaacctccc taatctaaac caaaattaat gtgagtcgat ctacccgca       59

<210> SEQ ID NO 111
<211> LENGTH: 51
<212> TYPE: DNA
<213> ORGANISM: Artificial
<220> FEATURE:
<223> OTHER INFORMATION: Primer

<400> SEQUENCE: 111
atcccccgct aaaacctccc taatctaaac ctgtgagtcg atctacccgc a               51

<210> SEQ ID NO 112
<211> LENGTH: 26
<212> TYPE: DNA
<213> ORGANISM: Artificial
<220> FEATURE:
<223> OTHER INFORMATION: Primer

<400> SEQUENCE: 112
aaaaacacga tcccccgcta aaacct                                           26

<210> SEQ ID NO 113
<211> LENGTH: 28
<212> TYPE: DNA
<213> ORGANISM: Artificial
<220> FEATURE:
<223> OTHER INFORMATION: Primer

<400> SEQUENCE: 113
aaaaacacga tctcccgcta aaacctcc                                         28

<210> SEQ ID NO 114
<211> LENGTH: 24
<212> TYPE: DNA
<213> ORGANISM: Artificial
<220> FEATURE:
<223> OTHER INFORMATION: Primer

<400> SEQUENCE: 114
```
catctaaaca cgatcccccg ctaa                                              24

<210> SEQ ID NO 115
<211> LENGTH: 21
<212> TYPE: DNA
<213> ORGANISM: Artificial
<220> FEATURE:
<223> OTHER INFORMATION: Primer

<400> SEQUENCE: 115
ttgcatttcg ttagcgacac a                                                 21

<210> SEQ ID NO 116
<211> LENGTH: 20
<212> TYPE: DNA
<213> ORGANISM: Artificial
<220> FEATURE:
<223> OTHER INFORMATION: Primer

<400> SEQUENCE: 116
tgcgggtaga tcgactcaca                                                   20

<210> SEQ ID NO 117
<211> LENGTH: 19
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is locked nucleic acid cytosine
<220> FEATURE:
<221> NAME/KEY: misc_feature
<222> LOCATION: (7)..(7)
<223> OTHER INFORMATION: N at position 7 is locked nucleic acid
      adenosine
<220> FEATURE:
<221> NAME/KEY: misc_feature
<222> LOCATION: (8)..(8)
<223> OTHER INFORMATION: N at position 8 is locked nucleic acid cytosine
<220> FEATURE:
<221> NAME/KEY: misc_feature
<222> LOCATION: (9)..(10)
<223> OTHER INFORMATION: N at position 9-10 is locked nucleic acid
      adenosine
<220> FEATURE:
<221> NAME/KEY: misc_feature
<222> LOCATION: (16)..(16)
<223> OTHER INFORMATION: N at position 16 is locked nucleic acid
      cytosine
<220> FEATURE:
<221> NAME/KEY: misc_feature
<222> LOCATION: (17)..(17)
<223> OTHER INFORMATION: N at position 17 is locked nucleic acid
      adenosine
<220> FEATURE:
<221> NAME/KEY: misc_feature
<222> LOCATION: (18)..(18)
<223> OTHER INFORMATION: N at position 18 is locked nucleic acid
      cytosine

<400> SEQUENCE: 117 ctaaannnn tcccnnnt                                                      19

<210> SEQ ID NO 118
<211> LENGTH: 36
<212> TYPE: DNA
<213> ORGANISM: Artificial
<220> FEATURE:
<223> OTHER INFORMATION: Primer
<220> FEATURE:

```
<221> NAME/KEY: misc_feature
<222> LOCATION: (32)..(32)
<223> OTHER INFORMATION: N at position 32 is ribocytosine

<400> SEQUENCE: 118
ctaacctaaa ctacacctta ataccttacc anccct                                36

<210> SEQ ID NO 119
<211> LENGTH: 41
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (37)..(37)
<223> OTHER INFORMATION: N at position 37 is ribocytosine

<400> SEQUENCE: 119
ggtgtcgtgg ttttgttggg tagtttggtt tcgttangtt c                          41

<210> SEQ ID NO 120
<211> LENGTH: 52
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (48)..(48)
<223> OTHER INFORMATION: N at position 48 is riboadenosine

<400> SEQUENCE: 120
tggatcgaga cggaatgcaa cctacacctt aataccttac cacctcgnaa gg              52

<210> SEQ ID NO 121
<211> LENGTH: 52
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (48)..(48)
<223> OTHER INFORMATION: N at position 48 is riboadenosine

<400> SEQUENCE: 121
tggatcgaga cggaatgcaa cctacacctt aataccttac cacctcgnag ag              52

<210> SEQ ID NO 122
<211> LENGTH: 52
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (48)..(48)
<223> OTHER INFORMATION: N at position 48 is riboadenosine

<400> SEQUENCE: 122
tggatcgaga cggaatgcaa cctacacctt aataccttac cacctcgnaa gg              52

<210> SEQ ID NO 123
<211> LENGTH: 78
<212> TYPE: DNA
<213> ORGANISM: Artificial
<220> FEATURE:
<223> OTHER INFORMATION: Primer
```

<400> SEQUENCE: 123
aaagacgcga aaaaactact atacgaattc gataaaaact aataaaaccg aaaactgttt        60
ccctgattga tacccgca                                                       78

<210> SEQ ID NO 124
<211> LENGTH: 71
<212> TYPE: DNA
<213> ORGANISM: Artificial
<220> FEATURE:
<223> OTHER INFORMATION: Primer

<400> SEQUENCE: 124
aaaaacgcga aaaactact atacgaattc gataaaaact aataaaaccg tttccctgat        60
tgatacccgc a                                                              71

<210> SEQ ID NO 125
<211> LENGTH: 29
<212> TYPE: DNA
<213> ORGANISM: Artificial
<220> FEATURE:
<223> OTHER INFORMATION: Primer

<400> SEQUENCE: 125
ttcacctcga aaacgcgaa aaaactact                                            29

<210> SEQ ID NO 126
<211> LENGTH: 34
<212> TYPE: DNA
<213> ORGANISM: Artificial
<220> FEATURE:
<223> OTHER INFORMATION: Primer

<400> SEQUENCE: 126
ttcacctcga aagacgcgaa aaaactacta tacg                                     34

<210> SEQ ID NO 127
<211> LENGTH: 24
<212> TYPE: DNA
<213> ORGANISM: Artificial
<220> FEATURE:
<223> OTHER INFORMATION: Primer

<400> SEQUENCE: 127
ccttaccacc tcgaaaaacg cgaa                                                24

<210> SEQ ID NO 128
<211> LENGTH: 21
<212> TYPE: DNA
<213> ORGANISM: Artificial
<220> FEATURE:
<223> OTHER INFORMATION: Primer

<400> SEQUENCE: 128
tggatcgaga cggaatgcaa c                                                   21

<210> SEQ ID NO 129
<211> LENGTH: 22
<212> TYPE: DNA
<213> ORGANISM: Artificial
<220> FEATURE:
<223> OTHER INFORMATION: Primer

<400> SEQUENCE: 129
tgcgggtatc aatcagggaa ac                                                22

<210> SEQ ID NO 130
<211> LENGTH: 19
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (8)..(8)
<223> OTHER INFORMATION: N at position 8 is locked nucleic acid cytosine
<220> FEATURE:
<221> NAME/KEY: misc_feature
<222> LOCATION: (9)..(10)
<223> OTHER INFORMATION: N at position 9-10 is locked nucleic acid
      adenosine
<220> FEATURE:
<221> NAME/KEY: misc_feature
<222> LOCATION: (15)..(15)
<223> OTHER INFORMATION: N at position 15 is locked nucleic acid
      cytosine
<220> FEATURE:
<221> NAME/KEY: misc_feature
<222> LOCATION: (16)..(16)
<223> OTHER INFORMATION: N at position 16 is locked nucleic acid
      adenosine
<220> FEATURE:
<221> NAME/KEY: misc_feature
<222> LOCATION: (17)..(17)
<223> OTHER INFORMATION: N at position 18 is locked nucleic acid
      cytosine
<220> FEATURE:
<221> NAME/KEY: misc_feature
<222> LOCATION: (18)..(18)
<223> OTHER INFORMATION: N at position 18 is locked nucleic acid
      adenosine

<400> SEQUENCE: 130
accacccnnn aaaannnna                                                    19

<210> SEQ ID NO 131
<211> LENGTH: 137
<212> TYPE: DNA
<213> ORGANISM: Artificial
<220> FEATURE:
<223> OTHER INFORMATION: Fragment of VIM S3 bisulfite converted genomic
      DNA

<400> SEQUENCE: 131
aaccgaccga actccaaccg aaactacgta actacgtcca cccgcaccta caacctaaac       60
aacgcgctac gccccaacac caaccgcaac ctctacgcct cgtccccgaa cgacgtatat      120
accacgcgct cctctac                                                    137

<210> SEQ ID NO 132
<211> LENGTH: 32
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (28)..(28)
<223> OTHER INFORMATION: N at position 28 is ribouridine

<400> SEQUENCE: 132
aactccaacc gaaactacgt aactgcgncc gt                                     32

<210> SEQ ID NO 133
<211> LENGTH: 51

<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (47)..(47)
<223> OTHER INFORMATION: N at position 47 is ribouridine

<400> SEQUENCE: 133
tagacacgag cgaggtcaca actccaaccg aaactacgta actgcgnccg t          51

<210> SEQ ID NO 134
<211> LENGTH: 29
<212> TYPE: DNA
<213> ORGANISM: Artificial
<220> FEATURE:
<223> OTHER INFORMATION: Primer

<400> SEQUENCE: 134
tccacccgca cctacaacct aaacaacgc                                    29

<210> SEQ ID NO 135
<211> LENGTH: 53
<212> TYPE: DNA
<213> ORGANISM: Artificial
<220> FEATURE:
<223> OTHER INFORMATION: Primer

<400> SEQUENCE: 135
tccacccgca cctacaacct aaacaacgcg ctgtgcaaaa ttcaggctgt gca         53

<210> SEQ ID NO 136
<211> LENGTH: 23
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (19)..(19)
<223> OTHER INFORMATION: N at position 19 is riboguanosine

<400> SEQUENCE: 136
acgaggcgta gaggttgcng tta                                          23

<210> SEQ ID NO 137
<211> LENGTH: 137
<212> TYPE: DNA
<213> ORGANISM: Artificial
<220> FEATURE:
<223> OTHER INFORMATION: Fragment of VIM S3 genomic DNA

<400> SEQUENCE: 137
agccggccga gctccagccg gagctacgtg actacgtcca cccgcaccta cagcctgggc    60
agcgcgctgc gccccagcac cagccgcagc ctctacgcct cgtccccggg cggcgtgtat   120
gccacgcgct cctctgc                                                  137

<210> SEQ ID NO 138
<211> LENGTH: 32
<212> TYPE: DNA
<213> ORGANISM: Artificial

```
<220> FEATURE:
<223> OTHER INFORMATION: Primer

<400> SEQUENCE: 138
aatggaagcg atttttcgtt agggtttttt tg                              32
```

METHOD FOR IDENTIFICATION AND QUANTIFICATION OF NUCLEIC ACID EXPRESSION, SPLICE VARIANT, TRANSLOCATION, COPY NUMBER, OR METHYLATION CHANGES

This application is a continuation of U.S. patent application Ser. No. 15/517,727, filed Apr. 7, 2017, which is a national stage application under 35 U.S.C. § 371 of International Application No. PCT/US2015/054759, filed, Oct. 8, 2015, which claims the benefit of U.S. Provisional Patent Application Ser. No. 62/061,376, filed Oct. 8, 2014, and U.S. Provisional Patent Application Ser. No. 62/103,894, filed Jan. 15, 2015, which are hereby incorporated by reference in their entirety.

FIELD OF THE INVENTION

The present invention relates to methods for identifying and quantifying nucleic acid sequence, expression, splice variant, translocation, copy number, and/or methylation changes using combined nuclease, ligation, and polymerase reactions with carryover prevention.

BACKGROUND OF THE INVENTION

Blood carries oxygen, nutrients, and physiological signals to every cell in the body, while simultaneously providing immunity and protection against outside pathogens. Yet the same ability of blood to spread sustenance also allows for dissemination of disease, be it cancer cells metastasizing to the liver, Ebola virus ravaging the capillaries, *Streptococcus pyogenes* liquefying flesh, or HIV eluding detection within the very CD4 cells that aim to eliminate infections.

The universal propensity of pathogens and cancers alike to spread via the blood also creates an opportunity for identification and early detection—allowing physicians to better treat and manage patient care. The evolution of AIDS treatments went hand-in-hand with improvements in nucleic acid diagnostics, from initial reverse-transcription PCR assays to protect the nations' blood supply, to sequencing drug-resistant variants, to RT-PCR quantification of viral load to determine treatment efficacy over time. To date, those infected have not been cured, but sophisticated diagnostic tools have guided treatment, epidemiological, and political decisions to stem this global epidemic.

Cancer is the leading cause of death in developed countries and the second leading cause of death in developing countries. Cancer has now become the biggest cause of mortality worldwide, with an estimated 8.2 million deaths from cancer in 2012. Cancer cases worldwide are forecast to rise by 75% and reach close to 25 million over the next two decades. A recent report by the world health organization concludes: "(The) Global battle against cancer won't be won with treatment alone. Effective prevention measures (are) urgently needed to prevent (a) cancer crisis". Detection of early cancer in the blood is the best means of effective prevention. It will save lives by enabling earlier and better treatment, as well as reduce the cost of cancer care.

Plasma or serum from a cancer patient contains nucleic acids released from cancers cells undergoing abnormal physiological processes. These nucleic acids have already demonstrated diagnostic utility (Diaz and Bardelli, *J Clin Oncol* 32: 579-586 (2014); Bettegowda et al., *Sci Transl Med* 6: 224 (2014); Newman et al., *Nat Med* 20: 548-554 (2014); Thierry et al., *Nat Med* 20: 430-435 (2014)). A further source of nucleic acids is within circulating tumor cells (CTCs), although early stage and a significant fraction of localized tumors send out very few to no CTC's per ml. Normal plasma or serum contains nucleic acids released from normal cells undergoing normal physiological processes (i.e. exosome secretion, apoptosis). There may be additional release of nucleic acids under conditions of stress, inflammation, infection, or injury.

The challenge to develop reliable diagnostic and screening tests is to distinguish those markers emanating from the tumor that are indicative of disease (e.g., early cancer) vs. presence of the same markers emanating from normal tissue (which would lead to a false-positive signal). There is also a need to balance the number of markers examined and the cost of the test, with the specificity and sensitivity of the assay. Comprehensive molecular profiling (mRNA, methylation, copy number, miRNA, mutations) of thousands of tumors by The Cancer Genome Atlas Consortium (TCGA), has revealed that colorectal tumors are as different from each other as they are from breast, prostrate, or other epithelial cancers (TCGA "Comprehensive Molecular Characterization of Human Colon and Rectal Cancer *Nature* 487: 330-337 (2014)). Further, those few markers they share in common (e.g., KRAS mutations,) are also present in multiple cancer types, hindering the ability to pinpoint the tissue of origin. For early cancer detection, the nucleic acid assay should serve primarily as a screening tool, requiring the availability of secondary diagnostic follow-up (e.g., colonoscopy for colorectal cancer).

Compounding the biological problem is the need to reliably quantify mutation, promoter methylation, or DNA or RNA copy number from either a very small number of initial cells (i.e. from CTCs), or when the cancer signal is from cell-free DNA (cfDNA) in the blood and diluted by an excess of nucleic acid arising from normal cells, or inadvertently released from normal blood cells during sample processing (Mateo et al., *Genome Biol* 15: 448 (2014)).

Likewise, an analogous problem of identifying rare target is encountered when using nucleic-acid-based techniques to detect infectious diseases directly in the blood. Briefly, either the pathogen may be present at 1 or less colony forming units (cfu)/ml, and/or there are many potential pathogens and sequence variations responsible for virulence or drug resistance. While these issues are exemplified with cancer, it is recognized that the solutions are equally applicable to infectious diseases.

A continuum of Diagnostic Needs Require a Continuum of Diagnostic Tests.

The majority of current molecular diagnostics efforts in cancer have centered on:
(i) prognostic and predictive genomics, e.g., identifying inherited mutations in cancer predisposition genes, such as BrCA1, BrCA2, (Ford et al. *Am J Hum Genet* 62: 676-689 (1998))
(ii) individualized treatment, e.g., mutations in the EGFR gene guiding personalized medicine (Sequist and Lynch, *Ann Rev Med,* 59: 429-442 (2008), and (iii) recurrence monitoring, e.g., detecting emerging KRAS mutations in patients developing resistance to drug treatments (Hiley et al., *Genome Biol* 15: 453 (2014); Amado et al., *J Clin Oncol* 26: 1626-1634 (2008)). Yet, this misses major opportunities in the cancer molecular diagnostics continuum: (i) more frequent screening of those with a family history, (ii) screening for detection of early disease, and (iii) monitoring treatment efficacy. To address these three unmet needs, a new metric for blood-based detection termed "cancer marker load", analogous to viral load is herein proposed.

DNA sequencing provides the ultimate ability to distinguish all nucleic acid changes associated with disease. However, the process still requires multiple up-front sample and template preparation, and is not always cost-effective. DNA microarrays can provide substantial information about multiple sequence variants, such as SNPs or different RNA expression levels, and are less costly then sequencing; however, they are less suited for obtaining highly quantitative results, nor for detecting low abundance mutations. On the other end of the spectrum is the TaqMan™ reaction, which provides real-time quantification of a known gene, but is less suitable for distinguishing multiple sequence variants or low abundance mutations.

It is critical to match each unmet diagnostic need with the appropriate diagnostic test—one that combines the divergent goals of achieving both high sensitivity (i.e., low false-negatives) and high specificity (i.e., low false-positives) at a low cost. For example, direct sequencing of EGFR exons from a tumor biopsy to determine treatment for non-small cell lung cancer (NSCLC) is significantly more accurate and cost effective than designing TaqMan™ probes for the over 180 known mutations whose drug response is already catalogued (Jia et al. *Genome Res* 23: 1434-1445 (2013)). The most sensitive technique for detecting point mutations, BEAMing (Dressman et al., *Proc Natl Acad Sci USA* 100: 8817-8822 (2003)), rely on prior knowledge of which mutations to look for, and thus are best suited for monitoring for disease recurrence, rather than for early detection. Likewise, to monitor blood levels of Bcr-Abl translocations when treating CML patients with Gleevec (Jabbour et al., *Cancer* 112: 2112-2118 (2008)), a simple quantitative reverse-transcription PCR assay is far preferable to sequencing the entire genomic DNA in 1 ml of blood (9 million cells×3 GB=27 million Gb of raw data).

Sequencing 2.1 Gb each of cell-free DNA (cfDNA) isolated from NSCLC patients was used to provide 10,000-fold coverage on 125 kb of targeted DNA (Kandoth et al. *Nature* 502: 333-339 (2013)). This approach correctly identified mutations present in matched tumors, although only 50% of stage 1 tumors were covered. The approach has promise for NSCLC, where samples average 5 to 20 mutations/Mb, however would not be cost effective for other cancers such as breast and ovarian, that average less than 1 to 2 mutations per Mb. Current up-front ligation, amplification, and/or capture steps required for highly accurate targeted deep sequencing are still more complex than multiplexed PCR-TaqMan™ or PCR-LDR assays.

A comprehensive data analysis of over 600 colorectal cancer samples that takes into account tumor heterogeneity, tumor clusters, and biological/technical false-positives ranging from 3% to 10% per individual marker showed that the optimal early detection screen for colorectal cancer would require at least 5 to 6 positive markers out of 24 markers tested (Bacolod et al, *Cancer Res* 69:723-727 (2009); Tsafrir et al. *Cancer Res* 66: 2129-2137 (2006), Weinstein et al., *Nat Genet* 45: 1113-1120 (2013); Navin N. E. *Genome Biol* 15: 452 (2014); Hiley et al., *Genome Biol* 15: 453 (2014)); Esserman et al. *Lancet Oncol* 15: e234-242 (2014)). Further, marker distribution is biased into different tumor clades, e.g., some tumors are heavily methylated, while others are barely methylated, and indistinguishable from age-related methylation of adjacent tissue. Consequently, a multidimensional approach using combinations of 3-5 sets of mutation, methylation, miRNA, mRNA, copy-variation, alternative splicing, or translocation markers is needed to obtain sufficient coverage of all different tumor clades. Analogous to non-invasive prenatal screening for trisomy, based on sequencing or performing ligation detection on random fragments of cfDNA (Benn et al., *Ultrasound Obstet Gynecol.* 42(1):15-33 (2013); Chiu et al., *Proc Natl Acad Sci USA* 105: 20458-20463 (2008); Juneau et al., *Fetal Diagn Ther.* 36(4) (2014)), the actual markers scored in a cancer screen are secondary to accurate quantification of those positive markers in the plasma.

Technical Challenges of Cancer Diagnostic Test Development.

Diagnostic tests that aim to find very rare or low-abundance mutant sequences face potential false-positive signal arising from: (i) polymerase error in replicating wild-type target, (ii) DNA sequencing error, (iii) mis-ligation on wild-type target, (iii) target independent PCR product, and (iv) carryover contamination of PCR products arising from a previous positive sample. The profound clinical implications of a positive test result when screening for cancer demand that such a test use all means possible to virtually eliminate false-positives.

Central to the concept of nucleic acid detection is the selective amplification or purification of the desired cancer-specific markers away from the same or closely similar markers from normal cells. These approaches include: (i) multiple primer binding regions for orthogonal amplification and detection, (ii) affinity selection of CTC's or exosomes, and (iii) spatial dilution of the sample.

The success of PCR-LDR, which uses 4 primer-binding regions to assure sensitivity and specificity, has previously been demonstrated. Desired regions are amplified using pairs or even tandem pairs of PCR primers, followed by orthogonal nested LDR primer pairs for detection. One advantage of using PCR-LDR is the ability to perform proportional PCR amplification of multiple fragments to enrich for low copy targets, and then use quantitative LDR to directly identify cancer-specific mutations. Biofire/bioMerieux has developed a similar technology termed "film array"; wherein initial multiplexed PCR reaction products are redistributed into individual wells, and then nested real-time PCR performed with SYBR Green Dye detection.

Affinity purification of CTC's using antibody or aptamer capture has been demonstrated (Adams et al., *J Am Chem Soc* 130: 8633-8641 (2008); Dharmasiri et al., *Electrophoresis* 30: 3289-3300 (2009); Soper et al. *Biosens Bioelectron* 21: 1932-1942 (2006)). Peptide affinity capture of exosomes has been reported in the literature. Enrichment of these tumor-specific fractions from the blood enables copy number quantification, as well as simplifying screening and verification assays.

The last approach, spatial dilution of the sample, is employed in digital PCR as well as its close cousin known as BEAMing (Vogelstein and Kinzler, *Proc Natl Acad Sci USA*. 96(16):9236-41 (1999); Dressman et al., *Proc Natl Acad Sci USA* 100: 8817-8822 (2003)). The rational for digital PCR is to overcome the limit of enzymatic discrimination when the sample comprises very few target molecules containing a known mutation in a 1,000 to 10,000-fold excess of wild-type DNA. By diluting input DNA into 20,000 or more droplets or beads to distribute less than one molecule of target per droplet, the DNA may be amplified via PCR, and then detected via probe hybridization or TaqMan™ reaction, giving in essence a 0/1 digital score. The approach is currently the most sensitive for finding point mutations in plasma, but it does require prior knowledge of the mutations being scored, as well as a separate digital dilution for each mutation, which would deplete the entire sample to score just a few mutations.

Real-Time PCR & Microfluidic Instrumentation

A number of PCR assays/microfabricated devices have been designed for rapid detection of pathogens and disease-associated translocations and mutations. Each assay/hardware combination has particular strengths, but when combined with the real world problem of multidimensional and multiplexed markers required for cancer detection, the flexibility of PCR-LDR with microfluidics provides certain advantages.

Instrumentation, assay design, and microfluidic architecture need to be seamlessly integrated. Some PCR instrumentation use real-time fluorescence or end-point fluorescence to quantify initial template molecules by cycling chambers, wells, or droplets through different temperatures. Yet other instrumentation comprises addressable microfluidic plates for real-time PCR detection. However the high cost of both the instruments and consumables has limited the widespread use of these machines for clinical applications.

In a different architecture, termed continuous-flow PCR, the reaction mix moves through channels that are neatly arranged in a radiator pattern, and flow over heating elements that are at fixed temperatures. This architecture allows the entire amplification reaction to be completed in a few minutes, and is ideal for capillary separation and readout. For ligase detection reactions, the readout may be achieved by taking advantage of LDR-FRET or electronic detection. In LDR-FRET, one primer has a donor, the other has an acceptor group, and after ligation they form a hairpin. This allows for counting single ligation events to obtain highly quantitative readouts of input DNA copy number. Alternatively, by appending gold-nanoparticles on each primer, the ligation product will contain two nano-particles, and these may be distinguished using electronic readout.

In considering various degrees of automation, the approach described herein is guided by the principles of "modularity" and "scalability". Firstly, the process should be separated into modular steps that may initially be optimized on separate instruments. For example, the device may be comprised of a first module for purification of DNA from plasma cfDNA as well as RNA from exosomes, a second module for multiplexed reverse transcription and/or limited amplification of various targets, and a third module for generating and detecting ligation products. Such a modular architecture allows for swapping in improved modules that keep pace with technological developments. For the modularity approach to work, it is critical that products from one module can be moved seamlessly into the next module, without leakage and without worry of crossover contamination.

Secondly, the modular design should be amenable to scalable manufacture in high volumes at low cost. The manufacturing costs and how primers/reagents/samples are deposited into the device must be taken into consideration.

The present invention is directed at overcoming these and other deficiencies in the art.

SUMMARY OF THE INVENTION

A first aspect of the present invention is directed to a method for identifying, in a sample, one or more nucleic acid molecules containing a target nucleotide sequence differing from nucleotide sequences in other nucleic acid molecules in the sample, or other samples, by one or more nucleotides, one or more copy numbers, one or more transcript sequences, and/or one or more methylated residues. This method involves providing a sample potentially containing one or more nucleic acid molecules containing the target nucleotide sequence differing from the nucleotide sequences in other nucleic acid molecules by one or more nucleotides, one or more copy numbers, one or more transcript sequences, and/or one or more methylated residues, and contacting the sample with one or more enzymes capable of digesting deoxyuracil (dU) containing nucleic acid molecules present in the sample. One or more primary oligonucleotide primer sets are provided, each primary oligonucleotide primer set comprising (a) a first primary oligonucleotide primer that comprises a nucleotide sequence that is complementary to a sequence adjacent to the target nucleotide sequence, and (b) a second primary oligonucleotide primer that comprises a nucleotide sequence that is complementary to a portion of an extension product formed from the first primary oligonucleotide primer. The contacted sample is blended with the one or more primary oligonucleotide primer sets, a deoxynucleotide mix including dUTP, and a DNA polymerase to form a polymerase chain reaction mixture, and the polymerase chain reaction mixture is subjected to one or more polymerase chain reaction cycles comprising a denaturation treatment, a hybridization treatment, and an extension treatment, thereby forming primary extension products comprising the target nucleotide sequence or a complement thereof. The method further involves blending the primary extension products with a ligase and one or more oligonucleotide probe sets to form a ligation reaction mixture. Each oligonucleotide probe set comprises (a) a first oligonucleotide probe having a target nucleotide sequence-specific portion, and (b) a second oligonucleotide probe having a target nucleotide sequence-specific portion, and wherein the first and second oligonucleotide probes of a probe set are configured to hybridize, in a base specific manner, on a complementary target nucleotide sequence of a primary extension product. The first and second oligonucleotide probes of the one or more oligonucleotide probe sets are ligated together to form ligated product sequences in the ligation reaction mixture, and the ligated product sequences in the sample are detected and distinguished to identify the presence of one or more nucleic acid molecules containing target nucleotide sequences differing from nucleotide sequences in other nucleic acid molecules in the sample by one or more nucleotides, one or more copy numbers, one or more transcript sequences, and/or one or more methylated residues.

Another aspect of the present invention is directed to a method for identifying, in a sample, one or more nucleic acid molecules containing a target nucleotide sequence differing from nucleotide sequences in other nucleic acid molecules in the sample, or other samples, by one or more nucleotides, one or more copy numbers, one or more transcript sequences, and/or one or more methylated residues. This method involves providing a sample containing one or more nucleic acid molecules potentially containing the target nucleotide sequence differing from the nucleotide sequences in other nucleic acid molecules by one or more nucleotides, one or more copy numbers, one or more transcript sequences, and/or one or more methylated residues. The method further involves providing one or more enzymes capable of digesting deoxyuracil (dU) containing nucleic acid molecules present in the sample, and providing one or more primary oligonucleotide primer sets, each primary oligonucleotide primer set comprising (a) a first primary oligonucleotide primer that comprises a nucleotide sequence that is complementary to a sequence adjacent to the target nucleotide sequence and (b) a second primary oligonucleotide primer that comprises a nucleotide sequence that is complementary to a portion of an extension product formed from the first primary oligonucleotide primer. The sample is blended with the one or more primary oligonucleotide primer sets, the one or more enzymes capable of digesting deoxyuracil (dU) containing nucleic acid molecules in the sample, a deoxynucleotide mix including dUTP, and a DNA polymerase to form a polymerase chain reaction mixture. The polymerase chain reaction mixture is subjected to conditions suitable for digesting deoxyuracil (dU) containing nucleic acid molecules present in the polymerase chain reaction mixture, and for one or more polymerase chain reaction cycles comprising a denaturation treatment, a hybridization treatment, and an extension treatment, thereby forming primary extension products comprising the target nucleotide sequence or a complement thereof. The method further involves blending the primary extension products with a ligase and one or more oligonucleotide probe sets to form a ligation reaction mixture, wherein each oligonucleotide probe set comprises (a) a first oligonucleotide probe having a 5' primer-specific portion and a 3' target nucleotide sequence-specific portion, and (b) a second oligonucleotide probe having a 5' target nucleotide sequence-specific portion and a 3' primer-specific portion. The first and second oligonucleotide probes of a probe set are configured to hybridize, in a base specific manner, on a complementary target nucleotide sequence of a primary extension product. The ligation reaction mixture is subjected to one or more ligation reaction cycles whereby the first and second oligonucleotide probes of the one or more oligonucleotide probe sets are ligated together to form ligated product sequences in the ligation reaction mixture where each ligated product sequence comprises the 5' primer-specific portion, the target-specific portions, and the 3' primer-specific portion. The method further involves providing one or more secondary oligonucleotide primer sets, each secondary oligonucleotide primer set comprising (a) a first secondary oligonucleotide primer comprising the same nucleotide sequence as the 5' primer-specific portion of the ligated product sequence and (b) a second secondary oligonucleotide primer comprising a nucleotide sequence that is complementary to the 3' primer-specific portion of the ligated product sequence, and blending the ligated product sequences, the one or more secondary oligonucleotide primer sets, the one or more enzymes capable of digesting deoxyuracil (dU) containing nucleic acid molecules, a deoxynucleotide mix including dUTP, and a DNA polymerase to form a second polymerase chain reaction mixture. The second polymerase chain reaction mixture is subjected to conditions suitable for digesting deoxyuracil (dU) containing nucleic acid molecules present in the second polymerase chain reaction mixture, and one or more polymerase chain reaction cycles comprising a denaturation treatment, a hybridization treatment, and an extension treatment thereby forming secondary extension products. The secondary extension products are detected and distinguished in the sample to identify the presence of one or more nucleic acid molecules containing target nucleotide sequences differing from nucleotide sequences in other nucleic acid molecules in the sample by one or more nucleotides, one or more copy numbers, one or more transcript sequences, and/or one or more methylated residues.

Another aspect of the present invention is directed to a method for identifying, in a sample, one or more nucleic acid molecules containing a target nucleotide sequence differing from nucleotide sequences in other nucleic acid molecules in the sample, or other samples, by one or more nucleotides, one or more copy numbers, one or more transcript sequences, and/or one or more methylated residues. This method involves providing a sample containing one or more nucleic acid molecules potentially containing the target nucleotide sequence differing from the nucleotide sequences in other nucleic acid molecules by one or more nucleotides, one or more copy numbers, one or more transcript sequences, and/or one or more methylated residues; providing one or more enzymes capable of digesting deoxyuracil (dU) containing nucleic acid molecules present in the sample; and providing one or more primary oligonucleotide primer sets, each primary oligonucleotide primer set comprising (a) a first primary oligonucleotide primer that comprises a nucleotide sequence that is complementary to a sequence adjacent to the target nucleotide sequence and (b) a second primary oligonucleotide primer that comprises a nucleotide sequence that is complementary to a portion of an extension product formed from the first primary oligonucleotide primer. The method further involves blending the sample, the one or more primary oligonucleotide primer sets, the one or more enzymes capable of digesting deoxyuracil (dU) containing nucleic acid molecules in the sample, a deoxynucleotide mix including dUTP, and a DNA polymerase to form a polymerase chain reaction mixture. The polymerase chain reaction mixture is subjected to conditions suitable for digesting deoxyuracil (dU) containing nucleic acid molecules present in the polymerase chain reaction mixture, and for one or more polymerase chain reaction cycles comprising a denaturation treatment, a hybridization treatment, and an extension treatment, thereby forming primary extension products comprising the target nucleotide sequence or a complement thereof. The primary extension products are blended with a ligase and one or more oligonucleotide probe sets to form a ligation reaction mixture, wherein each oligonucleotide probe set comprises (a) a first oligonucleotide probe having a 5' portion and a 3' target nucleotide sequence-specific portion, and (b) a second oligonucleotide probe having a 5' target nucleotide sequence-specific portion and a 3' portion, where the 5' portion of the first oligonucleotide probe of the probe set is complementary to a portion of the 3' portion of the second oligonucleotide probe, where one probe of the probe set comprises a detectable signal generating moiety, and where the first and second oligonucleotide probes of a probe set are configured to hybridize, in a base specific manner, on a complementary target nucleotide sequence of a primary extension product. The method further involves subjecting the ligation reaction mixture to one or more ligation reaction cycles whereby the first and second oligonucleotide probes of the one or more oligonucleotide probe sets are ligated together to form ligated product sequences in the ligation reaction mixture where each ligated product sequence comprises the 5' portion, the target-specific portions, the 3' portion, and the detectable signal generating moiety. The 5' portion of the ligated product sequence is hybridized to its complementary 3' portion and signal from the detectable signal generating moiety that is produced upon said hybridizing is detected. The ligated product sequences are distinguished in the sample based on said detecting to identify the presence of one or more nucleic acid molecules containing target nucleotide sequences differing from nucleotide sequences in other nucleic acid molecules in the sample by one or more nucleotides, one or more copy numbers, one or more transcript sequences, and/or one or more methylated residues.

Another aspect of the present invention is directed to a method for identifying, in a sample, one or more nucleic acid molecules containing a target nucleotide sequence differing from nucleotide sequences in other nucleic acid molecules in the sample, or other samples, by one or more methylated residue. This method involves providing a sample potentially containing one or more nucleic acid molecules comprising the target nucleotide sequence differing from the nucleotide sequences in other nucleic acid molecules by one or more methylated residues and contacting the sample with one or more enzymes capable of digesting deoxyuracil (dU) containing nucleic acid molecules present in the sample. The method further involves contacting the sample with one or more methylation sensitive enzymes to form a restriction enzyme reaction mixture, wherein the one or more methylation sensitive enzyme cleaves nucleic acid molecules in the sample that contain one or more unmethylated residues within at least one methylation sensitive enzyme recognition sequence. One or more primary oligonucleotide primer sets are provided, each primary oligonucleotide primer set comprising (a) first primary oligonucleotide primer comprising a nucleotide sequence that is complementary to a region of the target nucleotide sequence that is upstream of the one or more methylated residues and (b) a second primary oligonucleotide primer comprising a nucleotide sequence that is the same as a region of the target nucleotide sequence that is downstream of the one or more methylated residues. The restriction enzyme reaction mixture is blended with the one or more primary oligonucleotide primer sets, a deoxynucleotide mix including dUTP, and a DNA polymerase to form a primary polymerase chain reaction mixture. The method further involves subjecting the primary polymerase chain reaction mixture to one or more polymerase chain reaction cycles comprising a denaturation treatment, a hybridization treatment, and an extension treatment, thereby forming primary extension products comprising the target nucleotide sequence or a complement thereof. One or more secondary oligonucleotide primer sets are provided, each secondary oligonucleotide primer set comprising first and second nested oligonucleotide primers capable of hybridizing to the primary extension products The primary extension products are blended with the one or more secondary oligonucleotide primer sets, a deoxynucleotide mix including dUTP, and a DNA polymerase to form a secondary polymerase chain reaction mixture, and the secondary polymerase chain reaction mixture is subjected to one or more polymerase chain reaction cycles comprising a denaturation treatment, a hybridization treatment, and an extension treatment thereby forming secondary extension products. The secondary extension products in the sample are detected and distinguished to identify the presence of one or more nucleic acid molecules containing target nucleotide sequences differing from nucleotide sequences in other nucleic acid molecules in the sample by one or more methylated residues.

Another aspect of the present invention is directed to a method for identifying in a sample, one or more target ribonucleic acid molecules differing in sequence from other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level. This method involves providing a sample containing one or more target ribonucleic acid molecules potentially containing a sequence differing from other ribonucleic acid molecules, and contacting the sample with one or more enzymes capable of digesting dU containing nucleic acid molecules potentially present in the sample. One or more oligonucleotide primers are provided, each primer being complementary to the one or more target ribonucleic acid molecule. The contacted sample is blended with the one or more oligonucleotide primers, and a reverse-transcriptase to form a reverse-transcription mixture, and complementary deoxyribonucleic acid (cDNA) molecules are generated in the reverse transcription mixture. Each cDNA molecule comprises a nucleotide sequence that is complementary to the target ribonucleic acid molecule sequence and contains dU. The method further involves providing one or more oligonucleotide primer sets, each primer set comprising (a) a first oligonucleotide primer comprising a nucleotide sequence that is complementary to a portion of a cDNA nucleotide sequence adjacent to the target ribonucleic acid molecule sequence complement of the cDNA, and (b) a second oligonucleotide primer comprising a nucleotide sequence that is complementary to a portion of an extension product formed from the first oligonucleotide primer. The reverse transcription mixture containing the cDNA molecules is blended with the one or more oligonucleotide primer sets, and a polymerase to form a polymerase reaction mixture, and the polymerase chain reaction mixture is subjected to one or more polymerase chain reaction cycles comprising a denaturation treatment, a hybridization treatment, and an extension treatment thereby forming one or more different primary extension products. The method further involves providing one or more oligonucleotide probe sets. Each probe set comprises (a) a first oligonucleotide probe having a target sequence-specific portion, and (b) a second oligonucleotide probe having a target sequence-specific portion, wherein the first and second oligonucleotide probes of a probe set are configured to hybridize, in a base specific manner, on a complementary portion of a primary extension product corresponding to the target ribonucleic acid molecule sequence. The primary extension products are contacted with a ligase and the one or more oligonucleotide probe sets to form a ligation reaction mixture and the first and second probes of the one or more oligonucleotide probe sets are ligated together to form ligated product sequences in the ligase reaction mixture. The ligated product sequences in the sample are detected and distinguished thereby identifying the presence of one or more target ribonucleic acid molecules differing in sequence from other ribonucleic acid molecules in the sample due to alternative splicing, alternative transcript, alternative start site, alternative coding sequence, alternative non-coding sequence, exon insertion, exon deletion, intron insertion, translocation, mutations, or other rearrangement at the genome level.

Another aspect of the present invention is directed to a method for identifying in a sample, one or more target ribonucleic acid molecules differing in sequence from other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level. This method involves providing a sample containing one or more target ribonucleic acid molecules potentially differing in sequence from other ribonucleic acid molecules, and contacting the sample with one or more enzymes capable of digesting dU containing nucleic acid molecules potentially present in the sample. One or more oligonucleotide primers is provided, each primer being complementary to the one or more target ribonucleic acid molecules, and the contacted sample is blended with the one or more oligonucleotide primers, a deoxynucleotide mix including dUTP, and a reverse-transcriptase to form a reverse-transcription mixture. Complementary deoxyribonucleic acid (cDNA) molecules are generated in the reverse transcription mixture, each cDNA molecule comprising a nucleotide sequence that is complementary to the target ribonucleic acid molecule and contains dU. The method further involves providing one or more oligonucleotide primer sets, each primer set comprising (a) a first oligonucleotide primer comprising a nucleotide sequence that is complementary to a portion of a cDNA nucleotide sequence adjacent to the target ribonucleic acid molecule sequence complement of the cDNA, and (b) a second oligonucleotide primer comprising a nucleotide sequence that is complementary to a portion of an extension product formed from the first oligonucleotide primer. The reverse transcription mixture containing the cDNA molecules is blended with the one or more oligonucleotide primer sets, a deoxynucleotide mix including dUTP, and a polymerase to form a polymerase reaction mixture, and the polymerase chain reaction mixture is subjected to one or more polymerase chain reaction cycles comprising a denaturation treatment, a hybridization treatment, and an extension treatment thereby forming one or more different primary extension products. The method further involves providing one or more oligonucleotide probe sets, each probe set comprising (a) a first oligonucleotide probe having a 5' primer-specific portion and a 3' target sequence-specific portion, and (b) a second oligonucleotide probe having a 5' target sequence-specific portion and a 3' primer-specific portion, where the first and second oligonucleotide probes of a probe set are configured to hybridize, in a base specific manner, on complementary portions of a primary extension product corresponding to the target ribonucleic acid molecule sequence. The primary extension products are contacted with a ligase and the one or more oligonucleotide probe sets to form a ligation reaction mixture, and the ligation reaction mixture is subjected to one or more ligation reaction cycles whereby the first and second probes of the one or more oligonucleotide probe sets are ligated together to form ligated product sequences in the ligase reaction mixture, where each ligated product sequence comprises the 5' primer-specific portion, the target-specific portions, and the 3' primer-specific portion. The method further involves providing one or more secondary oligonucleotide primer sets, each secondary oligonucleotide primer set comprising (a) a first secondary oligonucleotide primer comprising the same nucleotide sequence as the 5' primer-specific portion of the ligated product sequence and (b) a second secondary oligonucleotide primer comprising a nucleotide sequence that is complementary to the 3' primer-specific portion of the ligated product sequence, and blending the ligated product sequences, the one or more secondary oligonucleotide primer sets with one or more enzymes capable of digesting deoxyuracil (dU) containing nucleic acid molecules, a deoxynucleotide mix including dUTP, and a DNA polymerase to form a second polymerase chain reaction mixture. The second polymerase chain reaction mixture is subjected to conditions suitable for digesting deoxyuracil (dU) containing nucleic acid molecules present in the second polymerase chain reaction mixture, and one or more polymerase chain reaction cycles comprising a denaturation treatment, a hybridization treatment, and an extension treatment thereby forming secondary extension products. The secondary extension products in the sample are detected and distinguished thereby identifying the presence of one or more ribonucleic acid molecules differing in sequence from other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level.

Another aspect of the present invention is directed to a method for identifying in a sample, one or more target ribonucleic acid molecules differing in sequence from other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level. This method involves providing a sample containing one or more target ribonucleic acid molecules potentially differing in sequence from other ribonucleic acid molecules, and contacting the sample with one or more enzymes capable of digesting dU containing nucleic acid molecules potentially present in the sample. The method further involves providing one or more oligonucleotide primers, each primer being complementary to the one or more target ribonucleic acid molecules, and blending the contacted sample, the one or more oligonucleotide primers, a deoxynucleotide mix including dUTP, and a reverse-transcriptase to form a reverse-transcription mixture. Complementary deoxyribonucleic acid (cDNA) molecules are generated in the reverse transcription mixture, each cDNA molecule comprising a nucleotide sequence that is complementary to the target ribonucleic acid molecule and contains dU. The method further involves providing one or more oligonucleotide primer sets, each primer set comprising (a) a first oligonucleotide primer comprising a nucleotide sequence that is complementary to a portion of a cDNA nucleotide sequence adjacent to the target ribonucleic acid molecule sequence complement of the cDNA, and (b) a second oligonucleotide primer comprising a nucleotide sequence that is complementary to a portion of an extension product formed from the first oligonucleotide primer. The reverse transcription mixture containing the cDNA molecules is blended with the one or more oligonucleotide primer sets, a deoxynucleotide mix including dUTP, and a polymerase to form a polymerase reaction mixture, and the polymerase chain reaction mixture is subjected to one or more polymerase chain reaction cycles comprising a denaturation treatment, a hybridization treatment, and an extension treatment thereby forming one or more different primary extension products. The method further involves providing one or more oligonucleotide probe sets, each probe set comprising (a) a first oligonucleotide probe having a 5' portion and a 3' target nucleotide sequence-specific portion, and (b) a second oligonucleotide probe having a 5' target nucleotide sequence-specific portion and a 3' portion, where the 5' portion of the first oligonucleotide probe of the probe set is complementary to a portion of the 3' portion of the second oligonucleotide probe, where one probe of the probe set comprises a detectable signal generating moiety, and where the first and second oligonucleotide probes of a probe set are configured to hybridize, in a base specific manner, on complementary portions of a primary extension product corresponding to the target ribonucleic acid molecule sequence. The primary extension products are contacted with a ligase and the one or more oligonucleotide probe sets to form a ligation reaction mixture, and the ligation reaction mixture is subjected to one or more ligation reaction cycles whereby the first and second probes of the one or more oligonucleotide probe sets are ligated together to form ligated product sequences in the ligase reaction mixture, where each ligated product sequence comprises the 5' portion, the target-specific portions, the 3' portion, and the detectable signal generating moiety. The 5' portion of the ligated product sequence is hybridized to its complementary 3' portion, and the signal from the detectable signal generating moiety that is produced upon said hybridizing is detected. The ligated product sequences in the sample are detected based on said detecting to identify the presence of one or more ribonucleic acid molecules differing in sequence from other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level.

Another aspect of the present invention is directed to a method for identifying, in a sample, one or more target micro-ribonucleic acid (miRNA) molecules differing in sequence from other miRNA molecules in the sample by one or more bases. This method involves providing a sample containing one or more target miRNA molecules potentially differing in sequence from other miRNA molecules in the sample by one or more bases, and contacting the sample with one or more enzymes capable of digesting dU containing nucleic acid molecules potentially present in the sample. One or more oligonucleotide primer sets are provided, each primer set comprising (a) a first oligonucleotide primer having a 5' stem-loop portion, a blocking group, an internal primer-specific portion within the loop region, and a 3' nucleotide sequence portion that is complementary to a 3' portion of the target miRNA molecule sequence, (b) a second oligonucleotide primer having a 3' nucleotide sequence portion that is complementary to a complement of the 5' end of the target miRNA molecule sequence, and a 5' primer-specific portion, (c) a third oligonucleotide primer comprising a nucleotide sequence that is the same as the internal primer-specific portion of the first oligonucleotide primer, and (d) a fourth oligonucleotide primer comprising a nucleotide sequence that is the same as the 5' primer-specific portion of the second oligonucleotide primer. The contacted sample is blended with the one or more first oligonucleotide primers of a primer set, a deoxynucleotide mix including dUTP, and a reverse transcriptase to form a reverse transcription reaction mixture. The first oligonucleotide primer hybridizes to the target miRNA molecule sequence, if present in the sample, and the reverse transcriptase extends the 3' end of the hybridized first oligonucleotide primer to generate an extended first oligonucleotide primer comprising the complement of the target miRNA molecule sequence. The method further involves blending the reverse transcription reaction mixture with the second, third, and fourth oligonucleotide primers of the primer set to form a polymerase reaction mixture under conditions effective for the one or more second oligonucleotide primers of a primer set to hybridize to the region of the extended first oligonucleotide primer comprising the complement of the target miRNA molecule sequence and extend to generate a primary extension product comprising the 5' primer-specific portion, a nucleotide sequence corresponding to the target miRNA molecule sequence, and the complement of the internal primer-specific portion. The polymerase chain reaction mixture is subjected to one or more polymerase chain reaction cycles comprising a denaturation treatment, a hybridization treatment, and an extension treatment thereby forming a plurality of primary extension products. The method further involves blending the plurality of primary extension products with a ligase and one or more oligonucleotide probe sets to form a ligation reaction mixture. Each oligonucleotide probe set comprises (a) a first oligonucleotide probe having a target sequence-specific portion, and (b) a second oligonucleotide probe having a target sequence-specific portion and a portion complementary to a primary extension product, wherein the first and second oligonucleotide probes of a probe set are configured to hybridize, in a base specific manner on complementary portions of a primary extension product corresponding to the target miRNA molecule sequence. The first and second oligonucleotide probes of the one or more oligonucleotide probe sets are ligated together to form ligated product sequences in the ligation reaction mixture, and the ligated product sequences in the sample are detected and distinguished thereby identifying one or more target miRNA molecules differing in sequence from other miRNA molecules in the sample by one or more bases.

Another aspect of the present invention is directed to a method for identifying, in a sample, one or more target micro-ribonucleic acid (miRNA) molecules differing in sequence from other miRNA molecules in the sample by one or more bases. This method involves providing a sample containing one or more target miRNA molecules potentially differing in sequence from other miRNA molecules in the sample by one or more bases, and contacting the sample with one or more enzymes capable of digesting dU containing nucleic acid molecules potentially present in the sample. The method further involves providing one or more oligonucleotide primer sets, each primer set comprising (a) a first oligonucleotide primer having a 5' stem-loop portion, a blocking group, an internal primer-specific portion within the loop region, and a 3' nucleotide sequence portion that is complementary to a 3' portion of the target miRNA molecule sequence, (b) a second oligonucleotide primer having a 3' nucleotide sequence portion that is complementary to a complement of the 5' end of the target miRNA molecule sequence, and a 5' primer-specific portion, (c) a third oligonucleotide primer comprising a nucleotide sequence that is the same as the internal primer-specific portion of the first oligonucleotide primer, and (d) a fourth oligonucleotide primer comprising a nucleotide sequence that is the same as the 5' primer-specific portion of the second oligonucleotide primer. The contacted sample is blended with the one or more first oligonucleotide primers of a primer set, a deoxynucleotide mix including dUTP, and a reverse transcriptase to form a reverse transcription reaction mixture where the first oligonucleotide primer hybridizes to the target miRNA molecule sequence, if present in the sample, and the reverse transcriptase extends the 3' end of the hybridized first oligonucleotide primer to generate an extended first oligonucleotide primer comprising the complement of the target miRNA molecule sequence. The reverse transcription reaction mixture is blended with the second, third, and fourth oligonucleotide primers of the primer set to form a polymerase reaction mixture under conditions effective for the one or more second oligonucleotide primers of a primer set to hybridize to the region of the extended first oligonucleotide primer comprising the complement of the target miRNA molecule sequence and extend to generate a primary extension product comprising the 5' primer-specific portion, a nucleotide sequence corresponding to the target miRNA molecule sequence, and the complement of the internal primer-specific portion. The polymerase chain reaction mixture is subjected to one or more polymerase chain reaction cycles comprising a denaturation treatment, a hybridization treatment, and an extension treatment thereby forming a plurality of primary extension products. The plurality of primary extension products are blended with a ligase and one or more oligonucleotide probe sets to form a ligation reaction mixture, where each oligonucleotide probe set comprises (a) a first oligonucleotide probe having a 5' primer-specific portion and a 3' targetsequence-specific portion, and (b) a second oligonucleotide probe having a 5' target sequence-specific portion, a portion complementary to a primary extension product, and a 3' primer-specific portion, and where the first and second oligonucleotide probes of a probe set are configured to hybridize, in a base specific manner, on complementary portions of a primary extension product corresponding to the target miRNA molecule sequence. The ligation reaction mixture is subjected to one or more ligation reaction cycles whereby the first and second oligonucleotide probes of the one or more oligonucleotide probe sets are ligated together to form ligated product sequences in the ligation reaction mixture wherein each ligated product sequence comprises the 5' primer-specific portion, the target-specific portions, and the 3' primer-specific portion. The method further involves providing one or more secondary oligonucleotide primer sets, each secondary oligonucleotide primer set comprising (a) a first secondary oligonucleotide primer comprising the same nucleotide sequence as the 5' primer-specific portion of the ligated product sequence and (b) a second secondary oligonucleotide primer comprising a nucleotide sequence that is complementary to the 3' primer-specific portion of the ligated product sequence, and blending the ligated product sequences, the one or more secondary oligonucleotide primer sets, with one or more enzymes capable of digesting deoxyuracil (dU) containing nucleic acid molecules, a deoxynucleotide mix including dUTP, and a DNA polymerase to form a second polymerase chain reaction mixture. The second polymerase chain reaction mixture is subjected to conditions suitable for digesting deoxyuracil (dU) containing nucleic acid molecules present in the second polymerase chain reaction mixture, and one or more polymerase chain reaction cycles comprising a denaturation treatment, a hybridization treatment, and an extension treatment thereby forming secondary extension product. The secondary extension products in the sample are detected and distinguished thereby identifying one or more target miRNA molecules differing in sequence from other miRNA molecules in the sample by one or more bases.

Another aspect of the present invention is directed to a method for identifying, in a sample, one or more target micro-ribonucleic acid (miRNA) molecules differing in sequence from other miRNA molecules in the sample by one or more bases. This method involves providing a sample containing one or more target miRNA molecules potentially differing in sequence from other miRNA molecules in the sample by one or more bases, and contacting the sample with one or more enzymes capable of digesting dU containing nucleic acid molecules potentially present in the sample. The method further involves providing one or more oligonucleotide primer sets, each primer set comprising (a) a first oligonucleotide primer having a 5' stem-loop portion, a blocking group, an internal primer-specific portion within the loop region, and a 3' nucleotide sequence portion that is complementary to a 3' portion of the target miRNA molecule sequence, (b) a second oligonucleotide primer having a 3' nucleotide sequence portion that is complementary to a complement of the 5' end of the target miRNA molecule sequence, and a 5' primer-specific portion, (c) a third oligonucleotide primer comprising a nucleotide sequence that is the same as the internal primer-specific portion of the first oligonucleotide primer, and (d) a fourth oligonucleotide primer comprising a nucleotide sequence that is the same as the 5' primer-specific portion of the second oligonucleotide primer. The contacted sample is blended with the one or more first oligonucleotide primers of a primer set, a deoxynucleotide mix including dUTP, and a reverse transcriptase to form a reverse transcription reaction mixture wherein the first oligonucleotide primer hybridizes to the target miRNA molecule sequence, if present in the sample, and the reverse transcriptase extends the 3' end of the hybridized first oligonucleotide primer to generate an extended first oligonucleotide primer comprising the complement of the target miRNA molecule sequence. The reverse transcription reaction mixture is blended with the second, third, and fourth oligonucleotide primers of the primer set to form a polymerase reaction mixture under conditions effective for the one or more second oligonucleotide primers of a primer set to hybridize to the region of the extended first oligonucleotide primer comprising the complement of the target miRNA molecule sequence and extend to generate a primary extension product comprising the 5' primer-specific portion, a nucleotide sequence corresponding to the target miRNA molecule sequence, and the complement of the internal primer-specific portion. The method further involves subjecting the polymerase chain reaction mixture to one or more polymerase chain reaction cycles comprising a denaturation treatment, a hybridization treatment, and an extension treatment thereby forming a plurality of primary extension products. The plurality of primary extension products are blended with a ligase and one or more oligonucleotide probe sets to form a ligation reaction mixture, wherein each oligonucleotide probe set comprises (a) a first oligonucleotide probe having a 5' portion and a 3' target nucleotide sequence-specific portion, and (b) a second oligonucleotide probe having a 5' target nucleotide sequence-specific portion and a 3' portion, where the 5' portion of the first oligonucleotide probe of the probe set is complementary to a portion of the 3' portion of the second oligonucleotide probe, where one probe of the probe set comprises a detectable signal generating moiety, and where the first and second oligonucleotide probes of a probe set are configured to hybridize, in a base specific manner, on complementary portions of a primary extension product corresponding to the target miRNA molecule sequence. The ligation reaction mixture is subjected to one or more ligation reaction cycles whereby the first and second oligonucleotide probes of the one or more oligonucleotide probe sets are ligated together to form ligated product sequences in the ligation reaction mixture wherein each ligated product sequence comprises the 5' portion, the target-specific portions, the 3' portion, and the detectable signal generating moiety. The 5' portion of the ligated product sequence is hybridized to its complementary 3' portion, and signal from the detectable signal generating moiety that is produced upon said hybridizing is detected. The ligated product sequences in the sample are distinguished based on said detecting to identify the presence one or more target miRNA molecules differing in sequence from other miRNA molecules in the sample by one or more bases.

Another aspect of the present invention is directed to a method for identifying, in a sample, one or more target micro-ribonucleic acid (miRNA) molecules differing in sequence from other miRNA molecules in the sample by one or more bases. This method involves providing a sample containing one or more target miRNA molecules potentially differing in sequence from other miRNA molecules by one or more base differences, and contacting the sample with one or more enzymes capable of digesting dU containing nucleic acid molecules potentially present in the sample. The contacted sample is blended with a ligase and a first oligonucleotide probe comprising a 5' phosphate, a 5' stem-loop portion, an internal primer-specific portion within the loop region, a blocking group, and a 3' nucleotide sequence that is complementary to a 3' portion of the target miRNA molecule sequence to form a ligation reaction. The method further involves ligating the target miRNA molecule sequence at its 3' end to the 5' phosphate of the first oligonucleotide probe to generate a chimeric nucleic acid molecule comprising the target miRNA molecule sequence, if present in the sample, appended to the first oligonucleotide probe. One or more oligonucleotide primer sets are provided, each primer set comprising (a) a first oligonucleotide primer comprising a 3' nucleotide sequence that is complementary to a complement of the 5' end of the target miRNA molecule sequence, and a 5' primer-specific portion, (b) a second oligonucleotide primer comprising a nucleotide sequence that is complementary to the internal primer-specific portion of the first oligonucleotide probe, and (c) a third oligonucleotide primer comprising a nucleotide sequence that is the same as the 5' primer-specific portion of the first oligonucleotide primer. The chimeric nucleic acid molecule is blended with the one or more second oligonucleotide primers, a deoxynucleotide mix including dUTP, and a reverse transcriptase to form a reverse transcription reaction mixture, wherein the one or more second oligonucleotide primers of a primer set hybridizes to the internal primer specific portion of the chimeric nucleic acid molecule, and extends at its 3' end to generate a complement of the chimeric nucleic acid molecule, if present in the sample. The method further involves blending the reverse transcription reaction mixture with the first and third oligonucleotide primers of a primer set to form a polymerase chain reaction mixture, and subjecting the polymerase chain reaction mixture to one or more polymerase chain reaction cycles comprising a denaturation treatment, a hybridization treatment, and an extension treatment thereby forming primary extension products. The primary extension products comprise the 5' primer-specific portion, a nucleotide sequence corresponding to the target miRNA molecule sequence, and the complement of the internal primer-specific portion. The primary extension products are blended with a ligase and one or more oligonucleotide probe sets to form a ligation reaction mixture. Each oligonucleotide probe set comprises (a) a first oligonucleotide probe having a target sequence-specific portion, and (b) a second oligonucleotide probe having a target sequence-specific portion and a portion complementary to a primary extension product, wherein the first and second oligonucleotide probes of a probe set are configured to hybridize, in a base specific manner, on complementary portions of a primary extension product corresponding to the target miRNA molecule sequence. The first and second oligonucleotide probes of the one or more oligonucleotide probe sets are ligated together to form ligated product sequences in the ligation reaction mixture, and the ligated product sequences in the sample are detected and distinguished thereby identifying one or more target miRNA molecules differing in sequence from other miRNA molecules in the sample by one or more bases.

Another aspect of the present invention method for identifying, in a sample, one or more target micro-ribonucleic acid (miRNA) molecules differing in sequence from other miRNA molecules in the sample by one or more bases. This method involves providing a sample containing one or more miRNA molecules potentially differing in sequence from other miRNA molecules by one or more base differences, and contacting the sample with one or more enzymes capable of digesting dU containing nucleic acid molecules potentially present in the sample. The contacted sample is blended with a ligase and a first oligonucleotide probe comprising a 5' phosphate, a 5' stem-loop portion, an internal primer-specific portion within the loop region, a blocking group, and a 3' nucleotide sequence that is complementary to a 3' portion of the target miRNA molecule sequence to form a ligation reaction, and the target miRNA molecule sequence at its 3' end is ligated to the 5' phosphate of the first oligonucleotide probe to generate a chimeric nucleic acid molecule comprising the target miRNA molecule sequence, if present in the sample, appended to the first oligonucleotide probe. The method further involves providing one or more oligonucleotide primer sets, each primer set comprising (a) a first oligonucleotide primer comprising a 3' nucleotide sequence that is complementary to a complement of the 5' end of the target miRNA molecule sequence, and a 5' primer-specific portion, (b) a second oligonucleotide primer comprising a nucleotide sequence that is complementary to the internal primer-specific portion of the first oligonucleotide probe, and (c) a third oligonucleotide primer comprising a nucleotide sequence that is the same as the 5' primer-specific portion of the first oligonucleotide primer. The chimeric nucleic acid molecule is blended with the one or more second oligonucleotide primers, a deoxynucleotide mix including dUTP, and a reverse transcriptase to form a reverse transcription reaction mixture, where the one or more second oligonucleotide primers of a primer set hybridizes to the internal primer specific portion of the chimeric nucleic acid molecule and extends at its 3' end to generate a complement of the chimeric nucleic acid molecule, if present in the sample. The reverse transcription reaction mixture is blended with the first and third oligonucleotide primers of a primer set to form a polymerase reaction mixture, and the polymerase chain reaction mixture is subjected to one or more polymerase chain reaction cycles comprising a denaturation treatment, a hybridization treatment, and an extension treatment thereby forming primary extension products comprising the 5' primer-specific portion, a nucleotide sequence corresponding to the target miRNA molecule sequence, and the complement of the internal primer-specific portion. The primary extension products are blended with a ligase and one or more oligonucleotide probe sets to form a ligation reaction mixture, wherein each oligonucleotide probe set comprises (a) a first oligonucleotide probe having a 5' primer-specific portion and a 3' target sequence-specific portion, and (b) a second oligonucleotide probe having a 5' target sequence-specific portion, a portion complementary to a primary extension product, and a 3' primer-specific portion, wherein the first and second oligonucleotide probes of a probe set are configured to hybridize, in a base specific manner, on complementary portions of a primary extension product corresponding to the target miRNA molecule sequence. The ligation reaction mixture is subjected to one or more ligation reaction cycles whereby the first and second oligonucleotide probes of the one or more oligonucleotide probe sets are ligated together to form ligated product sequences in the ligation reaction mixture, wherein each ligated product sequence comprises the 5' primer-specific portion, the target-specific portions, and the 3' primer-specific portion. The method further involves providing one or more secondary oligonucleotide primer sets, each secondary oligonucleotide primer set comprising (a) a first secondary oligonucleotide primer comprising the same nucleotide sequence as the 5' primer-specific portion of the ligated product sequence and (b) a second secondary oligonucleotide primer comprising a nucleotide sequence that is complementary to the 3' primer-specific portion of the ligated product sequence. The ligated product sequences are blended with the one or more secondary oligonucleotide primer sets, one or more enzymes capable of digesting deoxyuracil (dU) containing nucleic acid molecules, a deoxynucleotide mix including dUTP, and a DNA polymerase to form a second polymerase chain reaction mixture. The second polymerase chain reaction mixture is subjected to conditions suitable for digesting deoxyuracil (dU) containing nucleic acid molecules present in the second polymerase chain reaction mixture, and one or more polymerase chain reaction cycles comprising a denaturation treatment, a hybridization treatment, and an extension treatment thereby forming secondary extension products. The secondary extension products in the sample are detected and distinguished thereby identifying one or more target miRNA molecules differing in sequence from other miRNA molecules in the sample by one or more bases.

Another aspect of the present invention is directed to a method for identifying, in a sample, one or more target micro-ribonucleic acid (miRNA) molecules differing in sequence from other miRNA molecules in the sample by one or more bases. This method involves providing a sample containing one or more miRNA molecules potentially differing in sequence from other miRNA molecules by one or more base differences, and contacting the sample with one or more enzymes capable of digesting dU containing nucleic acid molecules potentially present in the sample. The contacted sample is blended with a ligase and a first oligonucleotide probe comprising a 5' phosphate, a 5' stem-loop portion, an internal primer-specific portion within the loop region, a blocking group, and a 3' nucleotide sequence that is complementary to a 3' portion of the target miRNA molecule sequence to form a ligation reaction. The target miRNA molecule sequence is ligated at its 3' end to the 5' phosphate of the first oligonucleotide probe to generate a chimeric nucleic acid molecule comprising the target miRNA molecule sequence, if present in the sample, appended to the first oligonucleotide probe. The method further involves providing one or more oligonucleotide primer sets, each primer set comprising (a) a first oligonucleotide primer comprising a 3' nucleotide sequence that is complementary to a complement of the 5' end of the target miRNA molecule sequence, and a 5' primer-specific portion, (b) a second oligonucleotide primer comprising a nucleotide sequence that is complementary to the internal primer-specific portion of the first oligonucleotide probe, and (c) a third oligonucleotide primer comprising a nucleotide sequence that is the same as the 5' primer-specific portion of the first oligonucleotide primer. The chimeric nucleic acid molecule is blended with the one or more second oligonucleotide primers, a deoxynucleotide mix including dUTP, and a reverse transcriptase to form a reverse transcription reaction mixture, wherein the one or more second oligonucleotide primers of a primer set hybridizes to the internal primer specific portion of the chimeric nucleic acid molecule and extends at its 3' end to generate a complement of the chimeric nucleic acid molecule, if present in the sample. The reverse transcription reaction mixture is blended with the first and third oligonucleotide primers of a primer set to form a polymerase reaction mixture, and the polymerase chain reaction mixture is subjected to one or more polymerase chain reaction cycles comprising a denaturation treatment, a hybridization treatment, and an extension treatment thereby forming primary extension products comprising the 5' primer-specific portion, a nucleotide sequence corresponding to the target miRNA molecule sequence, and the complement of the internal primer-specific portion. The primary extension products are blended with a ligase and one or more oligonucleotide probe sets to form a ligation reaction mixture, wherein each oligonucleotide probe set comprises (a) a first oligonucleotide probe having a 5' portion and a 3' target nucleotide sequence-specific portion, and (b) a second oligonucleotide probe having a 5' target nucleotide sequence-specific portion and a 3' portion, where the 5' portion of the first oligonucleotide probe of the probe set is complementary to a portion of the 3' portion of the second oligonucleotide probe, where one probe of the probe set comprises a detectable signal generating moiety, and where the first and second oligonucleotide probes of a probe set are configured to hybridize, in a base specific manner, on complementary portions of a primary extension product corresponding to the target miRNA molecule sequence. The ligation reaction mixture is subjected to one or more ligation reaction cycles whereby the first and second oligonucleotide probes of the one or more oligonucleotide probe sets are ligated together to form ligated product sequences in the ligation reaction mixture wherein each ligated product sequence comprises the 5' portion, the target-specific portions, the 3' portion, and the detectable signal generating moiety. The the 5' portion of the ligated product sequence is hybridized to its complementary 3' portion, and signal from the detectable signal generating moiety that is produced upon said hybridizing is detected. The ligated product sequences are distinguished in the sample based on said detecting to identify the presence one or more target miRNA molecules differing in sequence from other miRNA molecules in the sample by one or more bases.

Another aspect of the present invention is directed to a device for simultaneously adding liquids to two or more wells in a row and/or column of a microtiter plate. The device has opposed top and bottom surfaces with the top surface having openings leading into the wells and the bottom surface defining closed ends of the wells. The device comprises a first layer defined by first and second boundaries with metering chambers extending between the first and second boundaries of said first layer and in fluid communication with one another. The first layer is configured to be fitted, in an operative position, proximate to the microtiter plate with the first boundary of the first layer being closest to the top surface of the microtiter plate and each of the metering chambers being in fluid communication with an individual well in a row and/or column of the microtiter plate. The first layer further comprises a filling chamber in fluid communication with one or more of the metering chambers. The device comprises a second layer defined by first and second boundaries with a filling port extending between the first and second boundaries of the second layer. The second layer is configured to be fitted, in an operative position, on the first layer with the first boundary of the second layer adjacent to the second boundary of the first layer and the filling port being aligned with the filling chamber. When the first layer, second layer, and microtiter plate are positioned with respect to one another in their operative positions, liquid entering the device through the filling port will pass through the input chamber, the metering chambers, and into two or more wells in a row and/or column of the microtiter plate.

Another aspect of the present invention is directed to a method of adding liquids to two or more wells in a row and/or column of a microtiter plate having opposed top and bottom surfaces with the top surface having openings leading into the wells and the bottom surface defining closed ends of the wells. This method involves providing a device comprising a first layer having first and second boundaries with metering chambers extending between the first and second boundaries of the first layer and in fluid communication with one another. The first layer of the device is configured to be fitted, in an operative position, proximate to the microtiter plate with the first boundaries of the first layer being closest to the top surface of the microtiter plate and one of the metering chambers being in fluid communication with an individual well in a row and/or column of the microtiter plate. The first layer further comprising a filling chamber in fluid communication with one or more of said metering chambers. The device comprises a second layer having first and second boundaries with a filling port extending between the first and second boundaries of the second layer. The second layer is configured to be fitted, in an operative position, on the first layer with the first boundary of the second layer adjacent to the second boundary of the first layer and the filling port being aligned with the charge chamber. When the first layer, second layer, and microtiter plate are positioned with respect to one another in their operative positions, liquid entering the device through the filling port will pass through the filling chamber, the metering chambers, and into two or more wells in a row and/or column of said microtiter plate. The method further involves filling the device with liquid, and discharging liquid in the device into two or more wells in a row and/or column of said microtiter plate.

The present invention describes a number of approaches for detecting mutations, expression, splice variant, translocation, copy number, and/or methylation changes in target nucleic acid molecules using nuclease, ligase and polymerase reactions. The present invention solves the problems of carry over prevention, as well as allowing for spatial multiplexing to provide relative quantification, similar to digital PCR. Such technology may be utilized for non-invasive early detection of cancer, non-invasive prognosis of cancer, and monitoring for cancer recurrence from plasma or serum samples.

BRIEF DESCRIPTION OF THE DRAWINGS

FIG. 38 illustrates PCR-LDR-qPCR carryover prevention reaction with Taqman detection to identify or relatively quantify target(s) and/or mutations.

FIG. 39 illustrates PCR-qLDR carryover prevention reaction with FRET detection to identify or relatively quantify target(s) and/or mutations.

FIG. 40 illustrates PCR-LDR-qPCR carryover prevention reaction with Taqman detection to identify or relatively quantify target(s) and/or mutations.

FIG. 41 illustrates PCR-LDR-qPCR carryover prevention reaction with Taqman detection to identify or relatively quantify target(s) and/or mutations.

FIG. 42 illustrates PCR-qLDR carryover prevention reaction with FRET detection to identify or relatively quantify target(s) and/or mutations.

FIG. 43 illustrates PCR-qLDR carryover prevention reaction with FRET detection to identify or relatively quantify target(s) and/or mutations.

FIG. 44 illustrates PCR-LDR-qPCR carryover prevention reaction with UniTaq detection to identify or relatively quantify target(s) and/or mutations.

FIG. 45 illustrates PCR-LDR-qPCR carryover prevention reaction with Taqman detection to identify or relatively quantify target methylation.

FIG. 46 illustrates PCR-LDR-qPCR carryover prevention reaction with UniTaq detection to identify or relatively quantify target methylation.

FIG. 47 illustrates PCR-qLDR carryover prevention reaction with FRET detection to identify or relatively quantify target methylation.

FIG. 48 illustrates Nuclease-Ligation-PCR-qPCR carryover prevention reaction with Taqman detection to identify or relatively quantify target methylation.

FIG. 49 illustrates Nuclease-Ligation-PCR-qPCR carryover prevention reaction with UniTaq detection to identify or relatively quantify target methylation.

FIG. 50 illustrates PCR-LDR-qPCR carryover prevention reaction with Taqman detection to identify or relatively quantify target methylation.

FIG. 51 illustrates PCR-LDR-qPCR carryover prevention reaction with UniTaq detection to identify or relatively quantify target methylation.

FIG. 52 illustrates PCR-qLDR carryover prevention reaction with FRET detection to identify or relatively quantify target methylation.

FIG. 53 illustrates PCR-qPCR carryover prevention reaction with Taqman detection to identify or relatively quantify target methylation.

FIG. 54 illustrates an overview of PCR-LDR-qPCR carryover prevention reaction to identify or relatively quantify translocations at the mRNA level.

FIG. 55 illustrates RT-PCR-LDR-qPCR carryover prevention reaction with Taqman detection to identify or relatively quantify translocations at the mRNA level.

FIG. 56 illustrates RT-PCR-LDR-qPCR carryover prevention reaction with UniTaq detection to identify or relatively quantify translocations at the mRNA level.

FIG. 57 illustrates RT-PCR-qLDR carryover prevention reaction with FRET detection to identify or relatively quantify translocations at the mRNA level.

FIG. 58 illustrates an overview of RT-PCR-LDR-qPCR carryover prevention reaction to identify or relatively quantify alternative splicing.

FIG. 59 illustrates RT-PCR-LDR-qPCR carryover prevention reaction with Taqman detection to identify or relatively quantify wild-type and alternatively spliced transcripts.

FIG. 60 illustrates RT-PCR-LDR-qPCR carryover prevention reaction with UniTaq detection to identify or relatively quantify wild-type and alternatively spliced transcripts.

FIG. 61 illustrates RT-PCR-qLDR carryover prevention reaction with FRET detection to identify or relatively quantify wild-type and alternatively spliced transcripts.

FIG. 62 illustrates RT-PCR-LDR-qPCR carryover prevention reaction with Taqman detection to identify or relatively quantify low-level alternatively spliced transcripts.

FIG. 63 illustrates RT-PCR-LDR-qPCR carryover prevention reaction with UniTaq detection to identify or relatively quantify low-level alternatively spliced transcripts.

FIG. 64 illustrates RT-PCR-qLDR carryover prevention reaction with FRET detection to identify or relatively quantify low-level alternatively spliced transcripts.

FIG. 65 illustrates an overview of RT-PCR-LDR-qPCR carryover prevention reaction to identify or relatively quantify alternative splicing.

FIG. 66 illustrates RT-PCR-LDR-qPCR carryover prevention reaction with Taqman detection to identify or relatively quantify wild-type and alternative transcript start site.

FIG. 67 illustrates RT-PCR-LDR-qPCR carryover prevention reaction with UniTaq detection to identify or relatively quantify wild-type and alternative transcript start site.

FIG. 68 illustrates RT-PCR-qLDR carryover prevention reaction with FRET detection to identify or relatively quantify wild-type and alternative transcript start site.

FIG. 69 illustrates RT-PCR-LDR-qPCR carryover prevention reaction with Taqman detection to identify or relatively quantify low level of alternative transcript start site.

FIG. 70 illustrates RT-PCR-LDR-qPCR carryover prevention reaction with UniTaq detection to identify or relatively quantify low level of alternative transcript start site.

FIG. 71 illustrates RT-PCR-qLDR carryover prevention reaction with FRET detection to identify or relatively quantify low level of alternative transcript start site.

FIG. 72 illustrates an overview of RT-PCR-LDR-qPCR carryover prevention reaction to identify or relatively quantify exon deletion.

FIG. 73 illustrates RT-PCR-LDR-qPCR carryover prevention reaction with Taqman detection to identify or relatively quantify wild-type and alternatively spliced (exon deletion) transcript.

FIG. 74 illustrates RT-PCR-LDR-qPCR carryover prevention reaction with UniTaq detection to identify or relatively quantify wild-type and alternatively spliced (exon deletion) transcript.

FIG. 75 illustrates RT-PCR-qLDR carryover prevention reaction with FRET detection to identify or relatively quantify wild-type and alternatively spliced (exon deletion) transcript.

FIG. 76 illustrates RT-PCR-LDR-qPCR carryover prevention reaction with Taqman detection to identify or relatively quantify low-level alternatively spliced (exon deletion) transcript.

FIG. 77 illustrates RT-PCR-LDR-qPCR carryover prevention reaction with UniTaq detection to identify or relatively quantify low-level alternatively spliced (exon deletion) transcript.

FIG. 78 illustrates RT-PCR-qLDR carryover prevention reaction with FRET detection to identify or relatively quantify low-level alternatively spliced (exon deletion) transcript.

FIG. 79 illustrates an overview of RT-PCR-LDR-qPCR carryover prevention reaction to identify or relatively quantify alternative splicing with intron insertion.

FIG. 80 illustrates RT-PCR-LDR-qPCR carryover prevention reaction with Taqman detection to identify or relatively quantify wild-type and alternatively spliced (intron insertion) transcript.

FIG. 81 illustrates RT-PCR-LDR-qPCR carryover prevention reaction with UniTaq detection to identify or relatively quantify wild-type and alternatively spliced (intron insertion) transcript.

FIG. 82 illustrates RT-PCR-qLDR carryover prevention reaction with FRET detection to identify or relatively quantify wild-type and alternatively spliced (intron insertion) transcript.

FIG. 83 illustrates RT-PCR-LDR-qPCR carryover prevention reaction with Taqman detection to identify or relatively quantify low-level alternatively spliced (intron insertion) transcript.

FIG. 84 illustrates RT-PCR-LDR-qPCR carryover prevention reaction with UniTaq detection to identify or relatively quantify low-level alternatively spliced (intron insertion) transcript.

FIG. 85 illustrates RT-PCR-qLDR carryover prevention reaction with FRET detection to identify or relatively quantify low-level alternatively spliced (intron insertion) transcript.

FIG. 86 illustrates PCR-LDR-qPCR carryover prevention reaction with Taqman detection to enumerate DNA copy number.

FIG. 87 illustrates PCR-LDR-qPCR carryover prevention reaction with UniTaq detection to enumerate DNA copy number.

FIG. 88 illustrates PCR-qLDR carryover prevention reaction with FRET detection to enumerate DNA copy number.

FIG. 89 illustrates RT-PCR-LDR-qPCR carryover prevention reaction with Taqman detection to enumerate RNA copy number.

FIG. 90 illustrates RT-PCR-LDR-qPCR carryover prevention reaction with UniTaq detection to enumerate RNA copy number.

FIG. 91 illustrates RT-PCR-qLDR carryover prevention reaction with FRET detection to enumerate RNA copy number.

FIG. 92 illustrates RT-PCR-LDR-qPCR carryover prevention reaction with Taqman detection to identify or relatively quantify miRNA.

FIG. 93 illustrates RT-PCR-LDR-qPCR carryover prevention reaction with UniTaq detection to identify or relatively quantify miRNA.

FIG. 94 illustrates RT-PCR-qLDR carryover prevention reaction with FRET detection to identify or relatively quantify miRNA.

FIG. 95 illustrates Ligation-RT-PCR-LDR-qPCR carryover prevention reaction with Taqman detection to identify or relatively quantify miRNA.

FIG. 96 illustrates Ligation-RT-PCR-LDR-qPCR carryover prevention reaction with UniTaq detection to identify or relatively quantify miRNA.

FIG. 97 illustrates Ligation-RT-PCR-qLDR carryover prevention reaction with FRET detection to identify or relatively quantify miRNA.

FIG. 98 illustrates Ligation-RT-PCR-LDR-qPCR carryover prevention reaction with Taqman detection to identify or relatively quantify miRNA.

FIG. 99 illustrates Ligation-RT-PCR-LDR-qPCR carryover prevention reaction with UniTaq detection to identify or relatively quantify miRNA.

FIG. 100 illustrates Ligation-RT-PCR-qLDR carryover prevention reaction with FRET detection to identify or relatively quantify miRNA.

FIG. 102 illustrates the dimensions of another version of a commercially available 384 well microtiter plate.

FIG. 105 illustrates a top and side view of the intermediate layer of a sample dispersion device positioned above several wells of a microtiter plate.

FIG. 119 illustrates a top and side view of the intermediate layer on the exit side of a sample dispersion device that independently addresses each row of a microtiter plate.

FIG. 120 illustrates an exploded perspective view of the intermediate layer on the exit side of a sample dispersion device that independently addresses each row of a microtiter plate.

FIG. 121 illustrates a top and side view of the first and intermediate layers on the exit side of a sample dispersion device that independently addresses each row of a microtiter plate.

FIG. 122 illustrates an exploded perspective view of the first and intermediate layers on the exit side of a sample dispersion device that independently addresses each row of a microtiter plate.

FIG. 123 illustrates a top and side view of the third, first, and intermediate layers on the exit side of a sample dispersion device that independently addresses each row of a microtiter plate.

FIG. 124 illustrates an exploded perspective view of the third, first, and intermediate layers on the exit side of a sample dispersion device that independently addresses each row of a microtiter plate.

FIG. 125 illustrates a top and side view of the second, third, first, and intermediate layers on the exit side of a sample dispersion device that independently addresses each row of a microtiter plate.

FIG. 126 illustrates an exploded perspective view of the second, third, first, and intermediate layers on the exit side of a sample dispersion device that independently addresses each row of a microtiter plate.

FIG. 127 illustrates a top and side view of the intermediate layer of a sample dispersion device that independently addresses each row from both sides of a microtiter plate.

FIG. 128 illustrates an exploded perspective view of the intermediate layer a sample dispersion device that independently addresses each row from both sides of a microtiter plate.

FIG. 129 illustrates a top and side view of the first and intermediate layers of a sample dispersion device that independently addresses each row from both sides of a microtiter plate.

FIG. 130 illustrates an exploded perspective view of the first and intermediate layers of a sample dispersion device that independently addresses each row from both sides of a microtiter plate.

FIG. 131 illustrates a top and side view of the third, first, and intermediate layers of a sample dispersion device that independently addresses each row from both sides of a microtiter plate.

Figure 132:
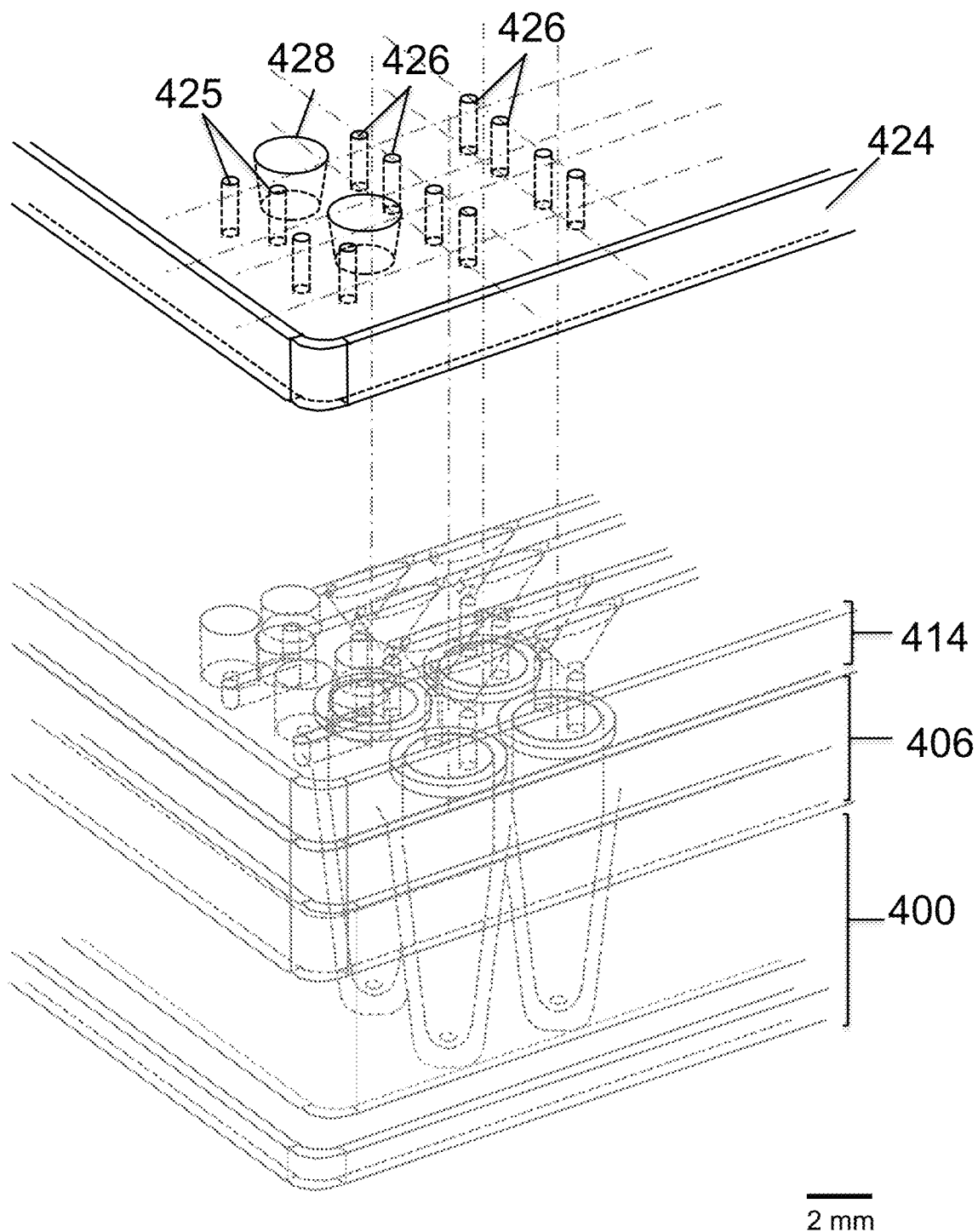

FIG. 132 illustrates an exploded perspective view of the third, first, and intermediate layers of a sample dispersion device that independently addresses each row from both sides of a microtiter plate.

Figure 133:
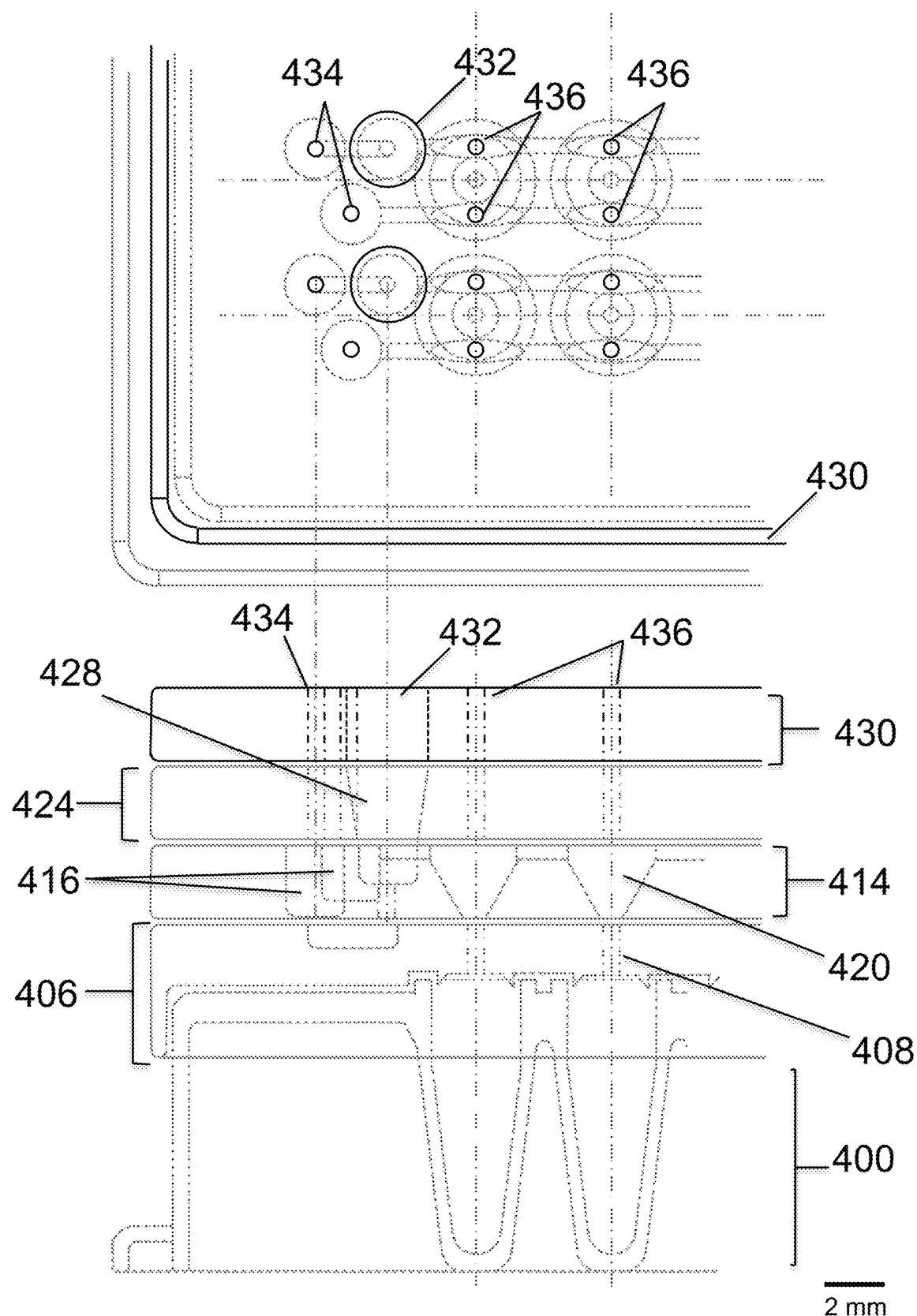

FIG. 133 illustrates a top and side view of the second, third, first, and intermediate layers of a sample dispersion device that independently addresses each row from both sides of a microtiter plate.

Figure 134:
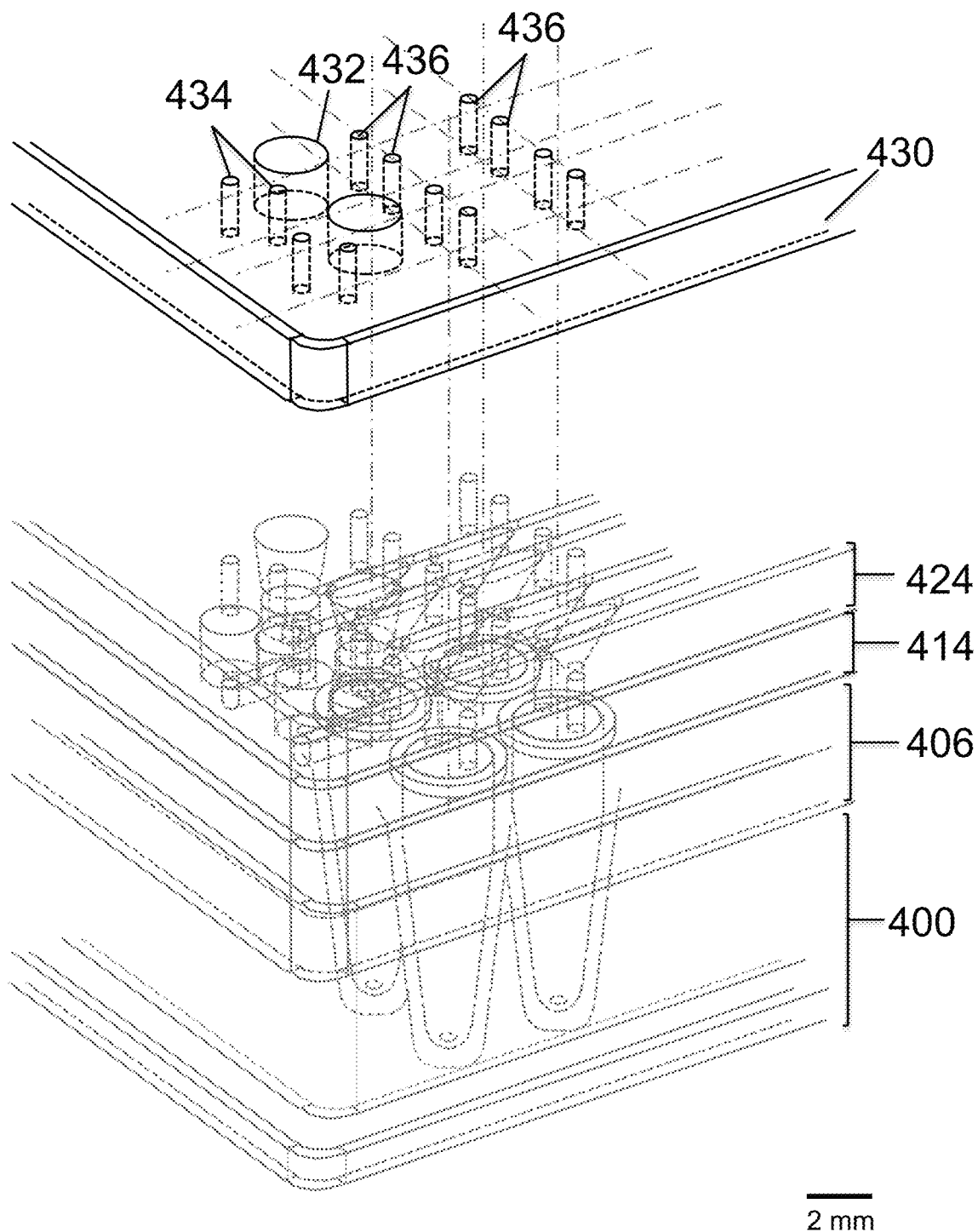

FIG. 134 illustrates an exploded perspective view of the second, third, first, and intermediate layers of a sample dispersion device that independently addresses each row from both sides of a microtiter plate.

Figure 135:
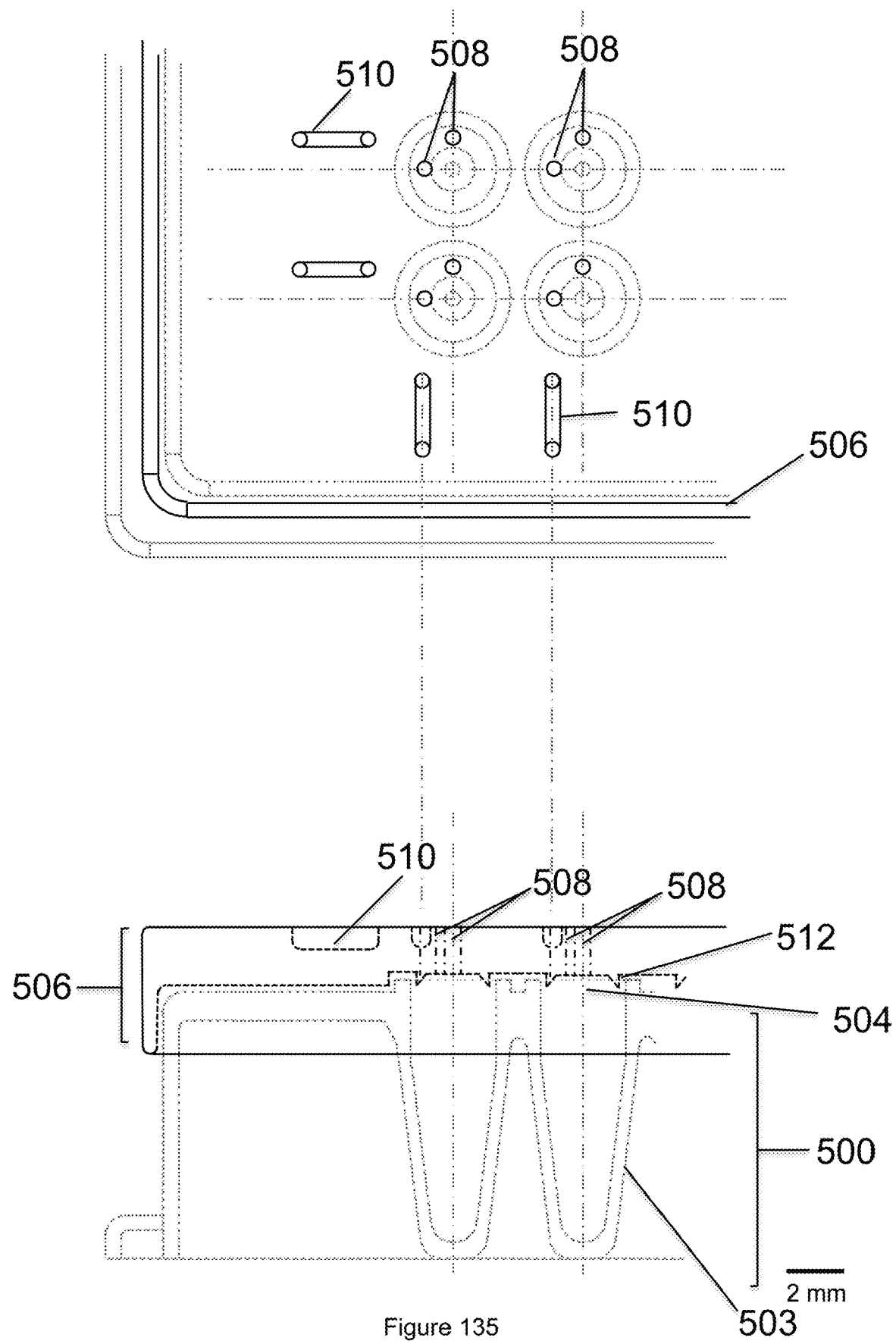

FIG. 135 illustrates a top and side view of the intermediate layer of a sample dispersion device that independently addresses each row and each column of a microtiter plate.

Figure 136:
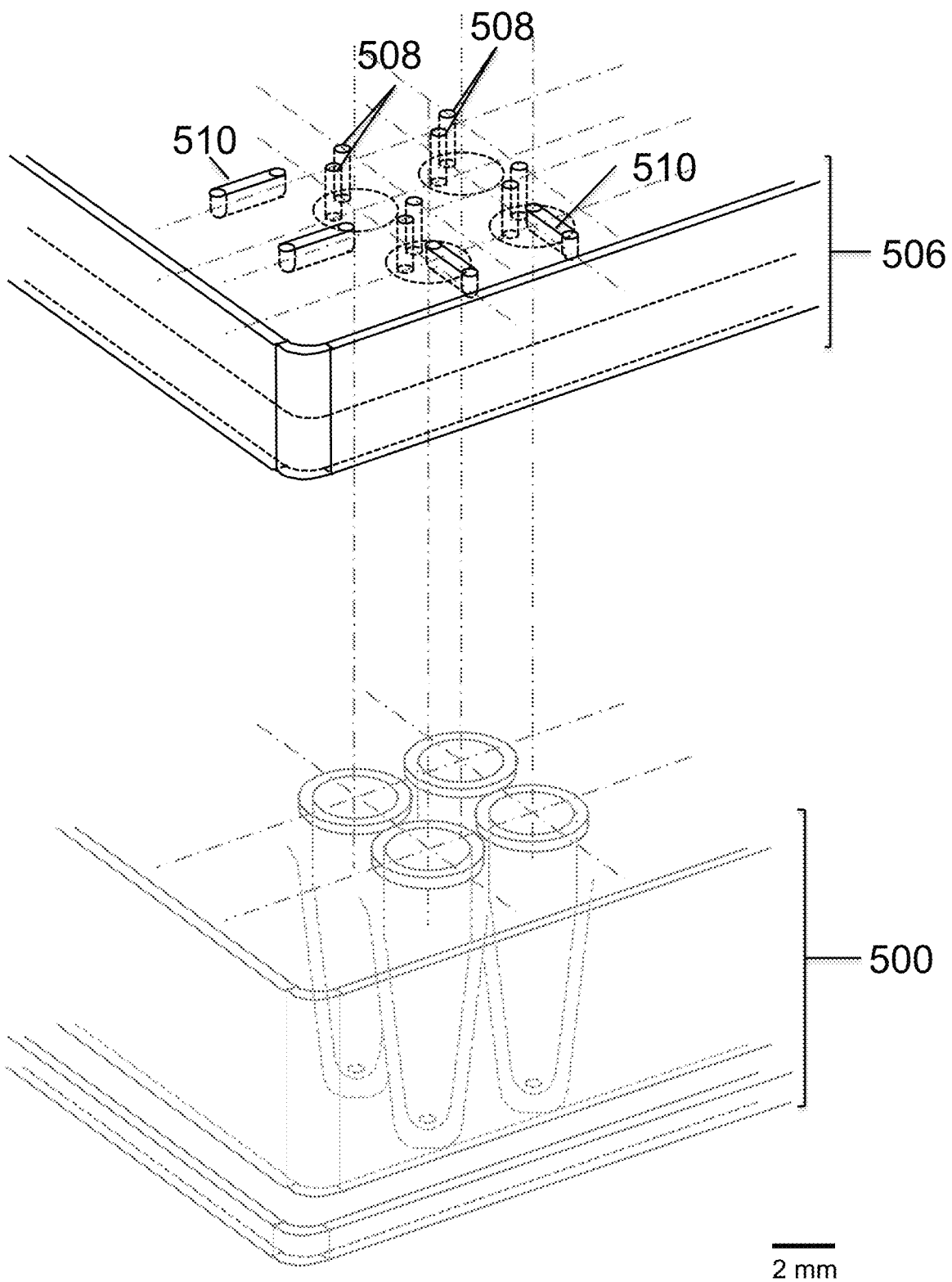

FIG. 136 illustrates an exploded perspective view of the intermediate layer of a sample dispersion device that independently addresses each row and each column of a microtiter plate.

Figure 137:
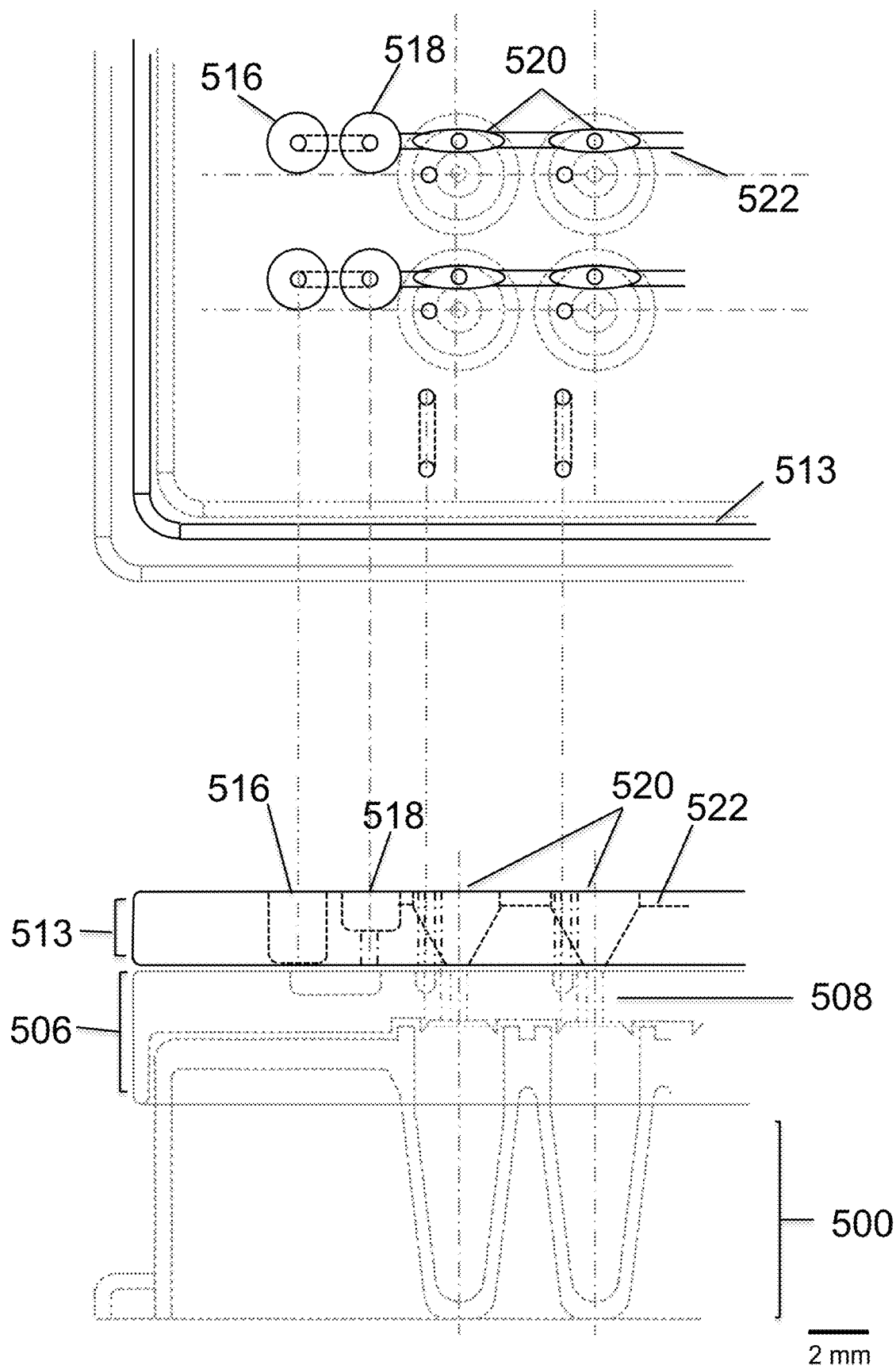

FIG. 137 illustrates a top and side view of a first region of the first layer and the intermediate layer of a sample dispersion device that independently addresses each row and each column of a microtiter plate.

Figure 138:
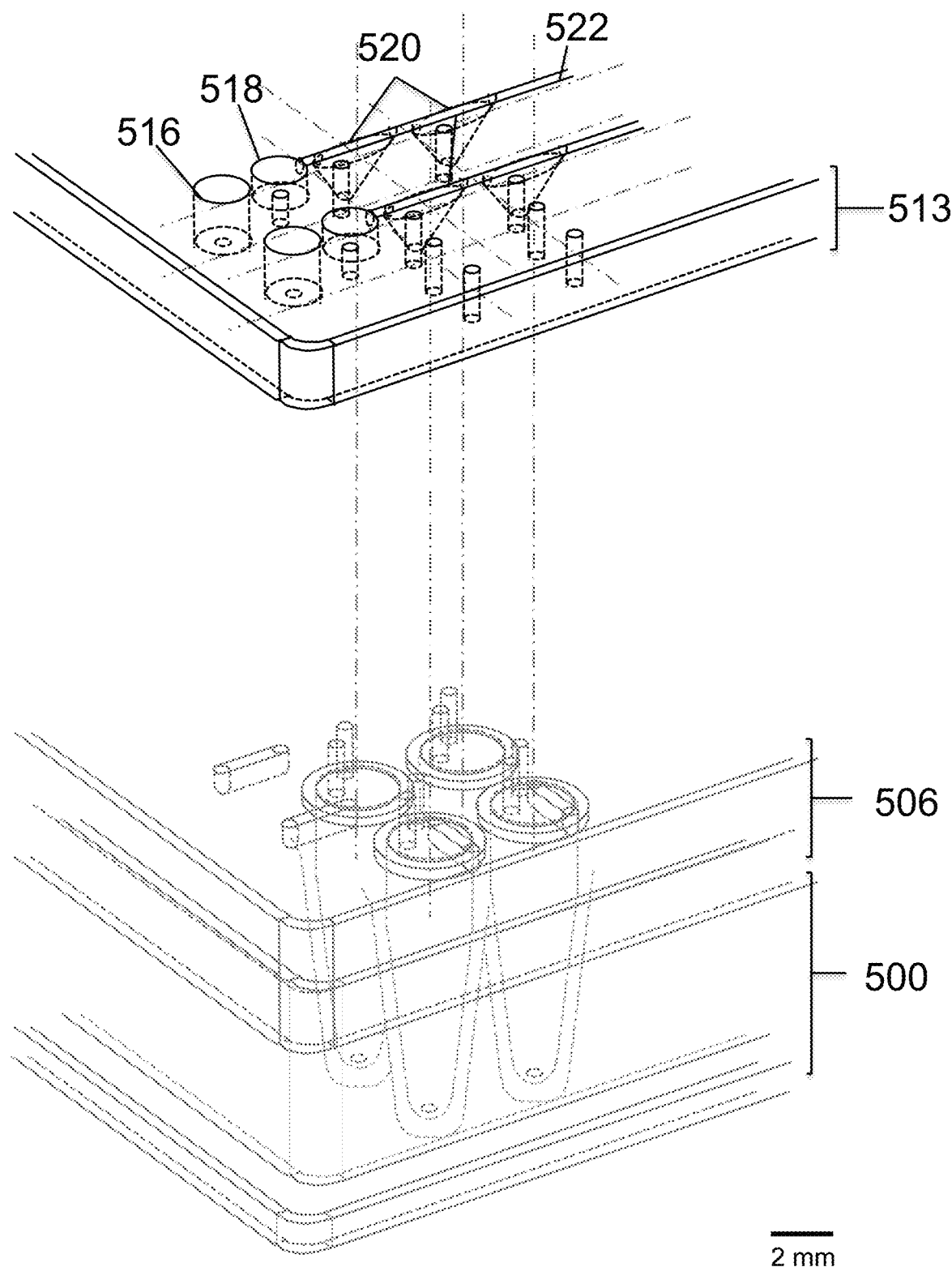

FIG. 138 illustrates an exploded perspective view of the first region of the first layer and the intermediate layer of a sample dispersion device that independently addresses each row and each column of a microtiter plate.

Figure 139:
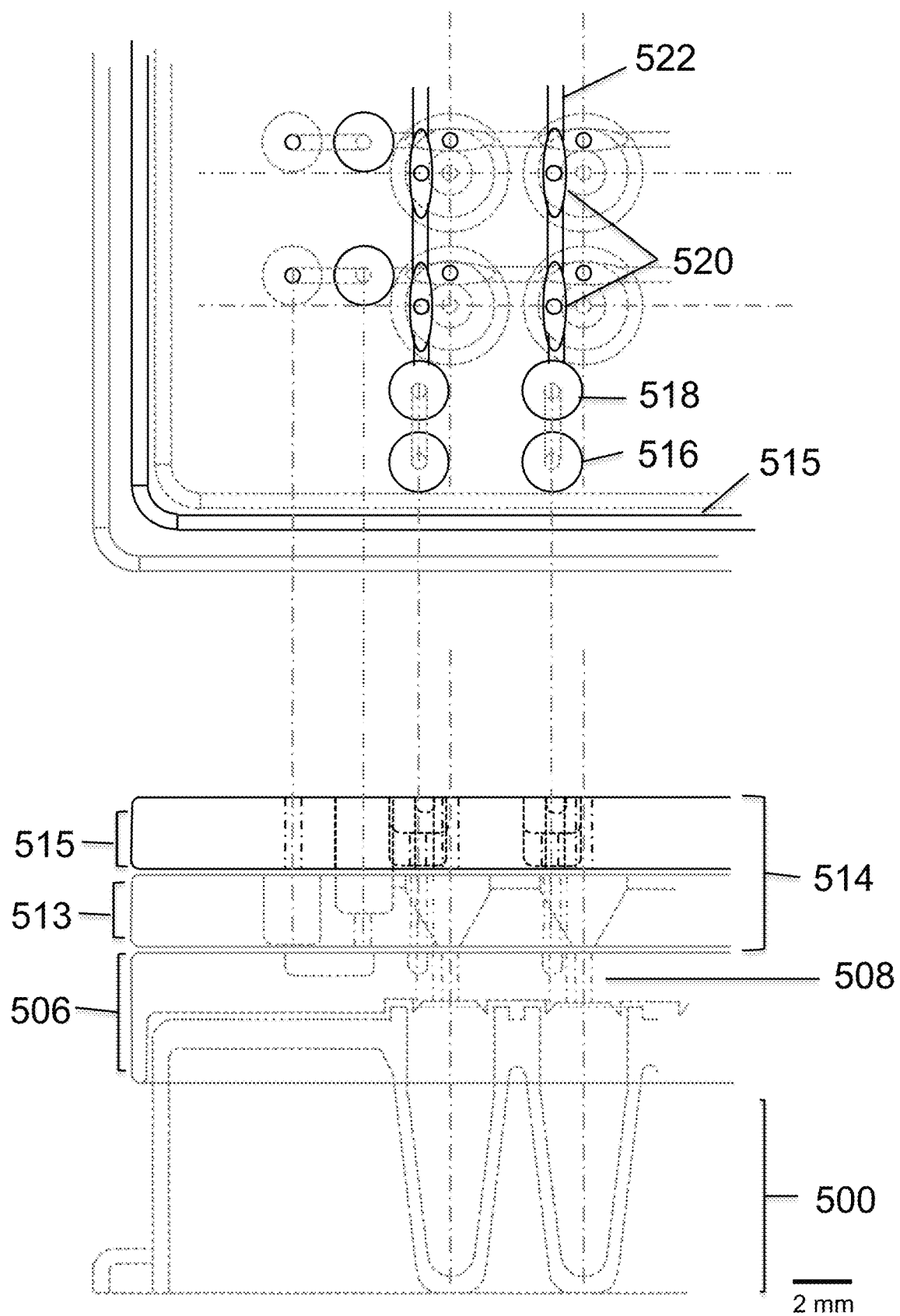

FIG. 139 illustrates a top and side view of the first and second regions of the first layer and the intermediate layer of a sample dispersion device that independently addresses each row and each column of a microtiter plate.

Figure 140:
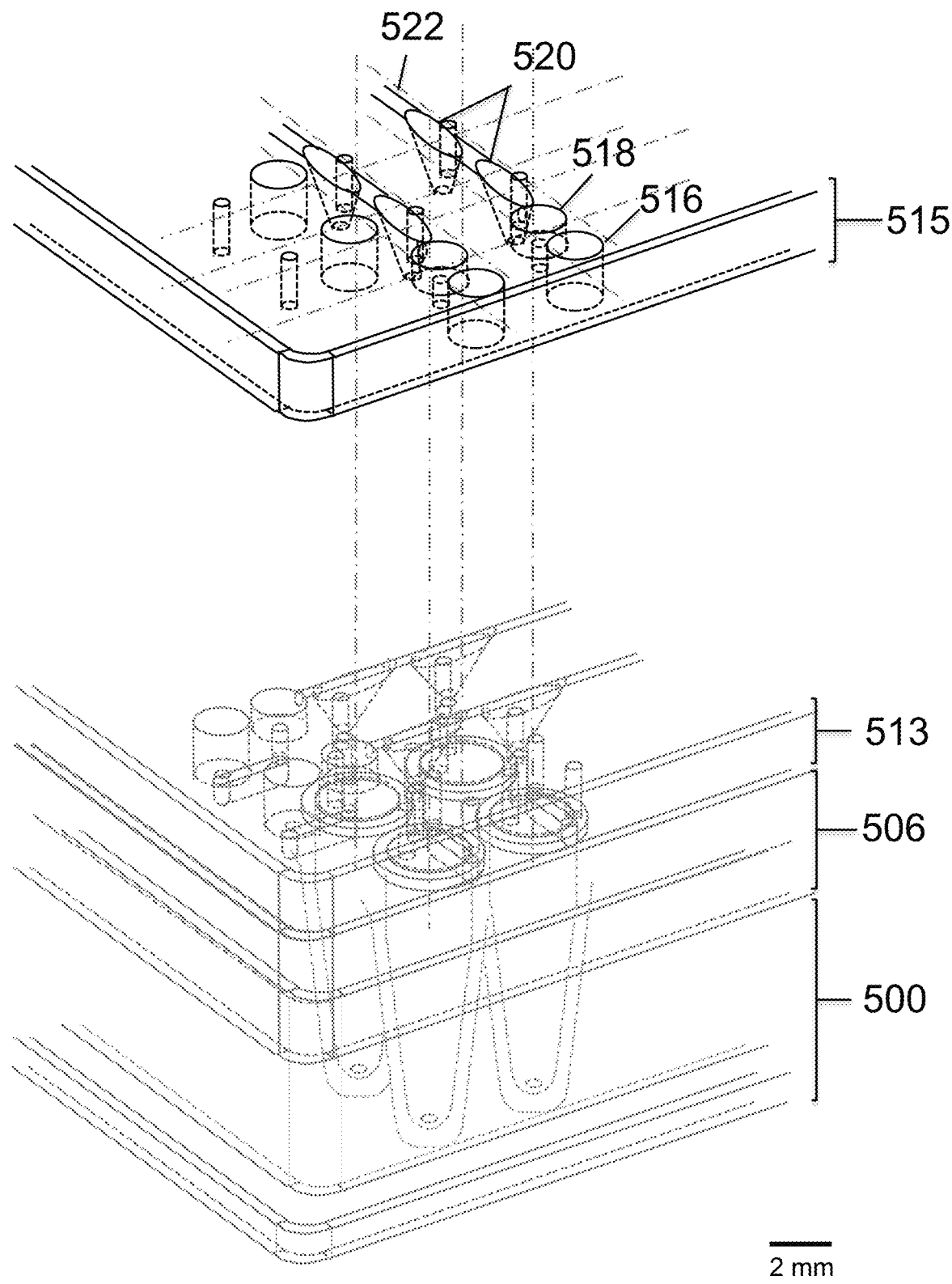

FIG. 140 illustrates an exploded perspective view of the first and second regions of the first layer and the intermediate layer of a sample dispersion device that independently addresses each row and each column of a microtiter plate.

Figure 141:
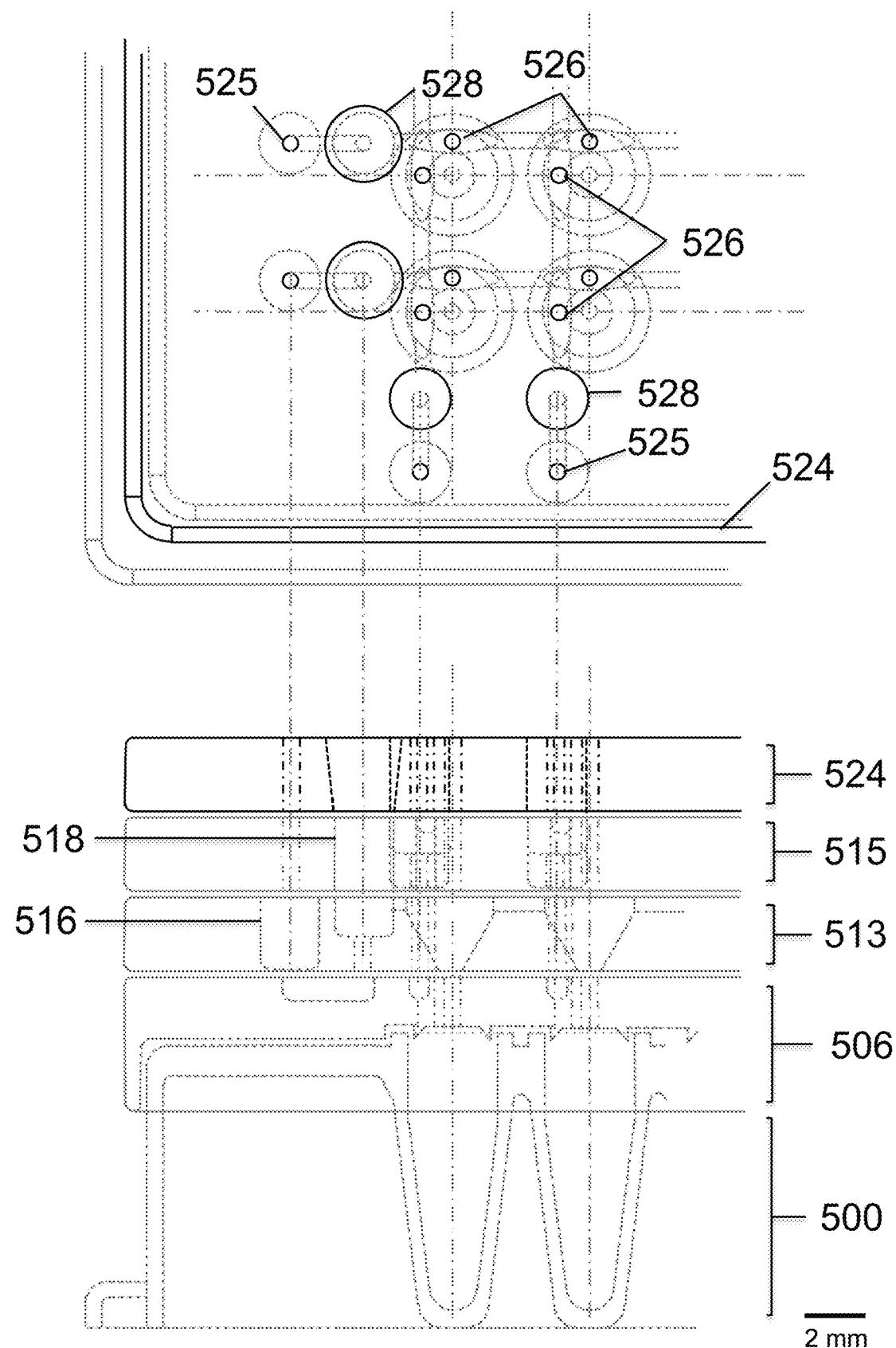

FIG. 141 illustrates a top and side view of the third layer, first layer (with first and second regions), and intermediate layer of a sample dispersion device that independently addresses each row and each column of a microtiter plate.

Figure 142:
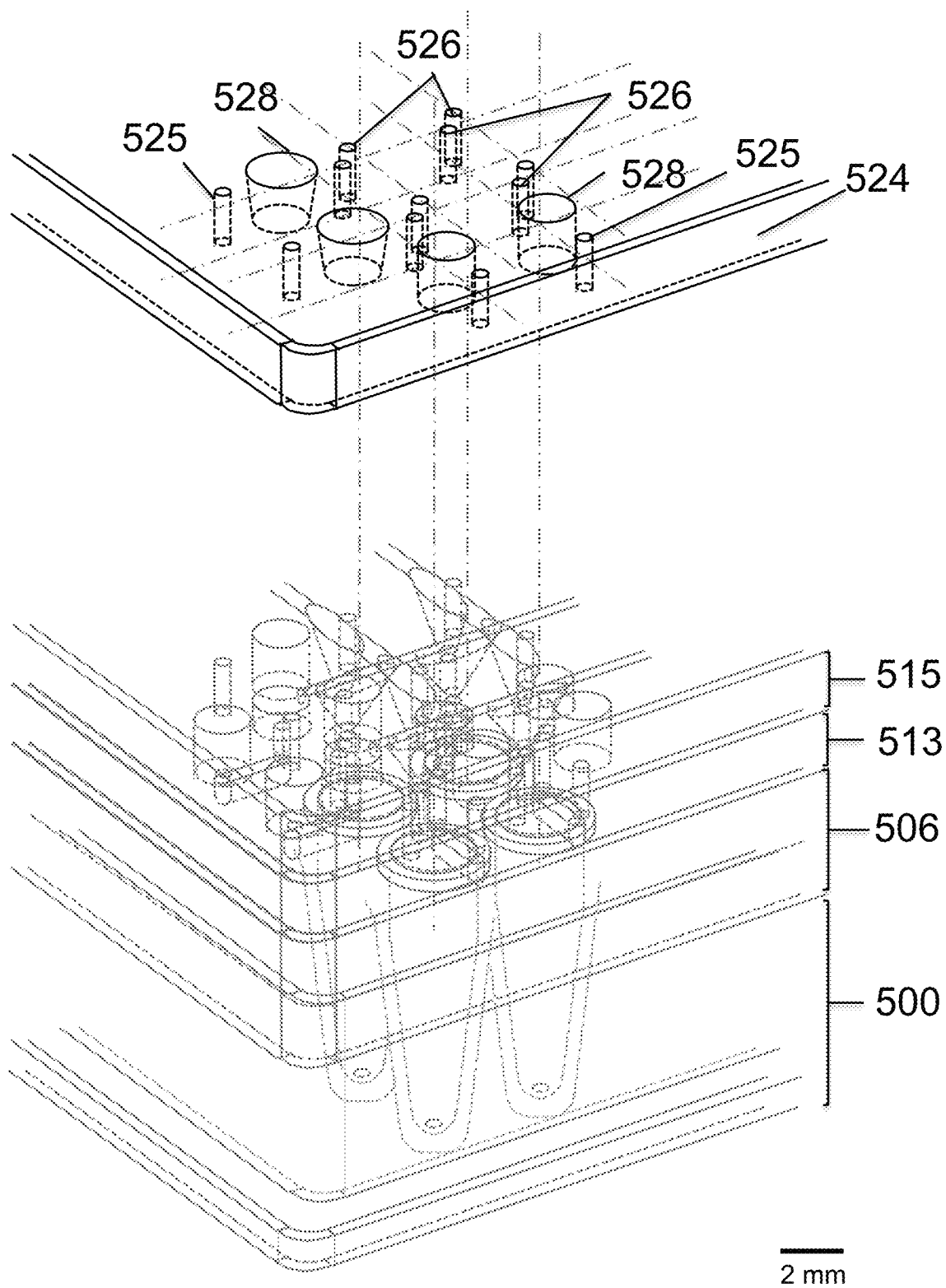

FIG. 142 illustrates an exploded perspective view of the third layer, first layer (with first and second regions), and intermediate layer of a sample dispersion device that independently addresses each row and each column of a microtiter plate.

Figure 143:
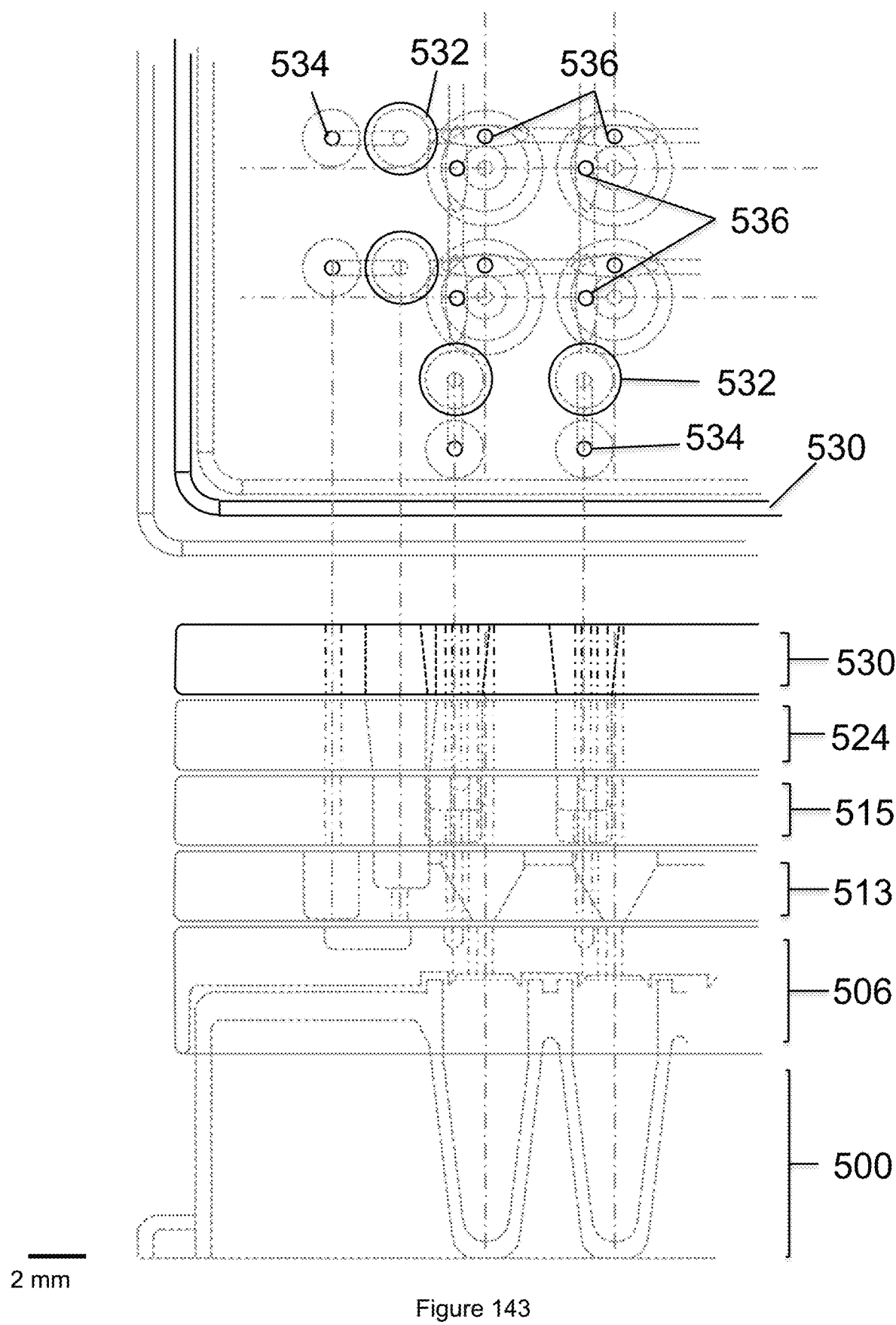

FIG. 143 illustrates a top and side view of the second layer, third layer, first layer (with first and second regions), and intermediate layer of a sample dispersion device that independently addresses each row and each column of a microtiter plate.

Figure 144:
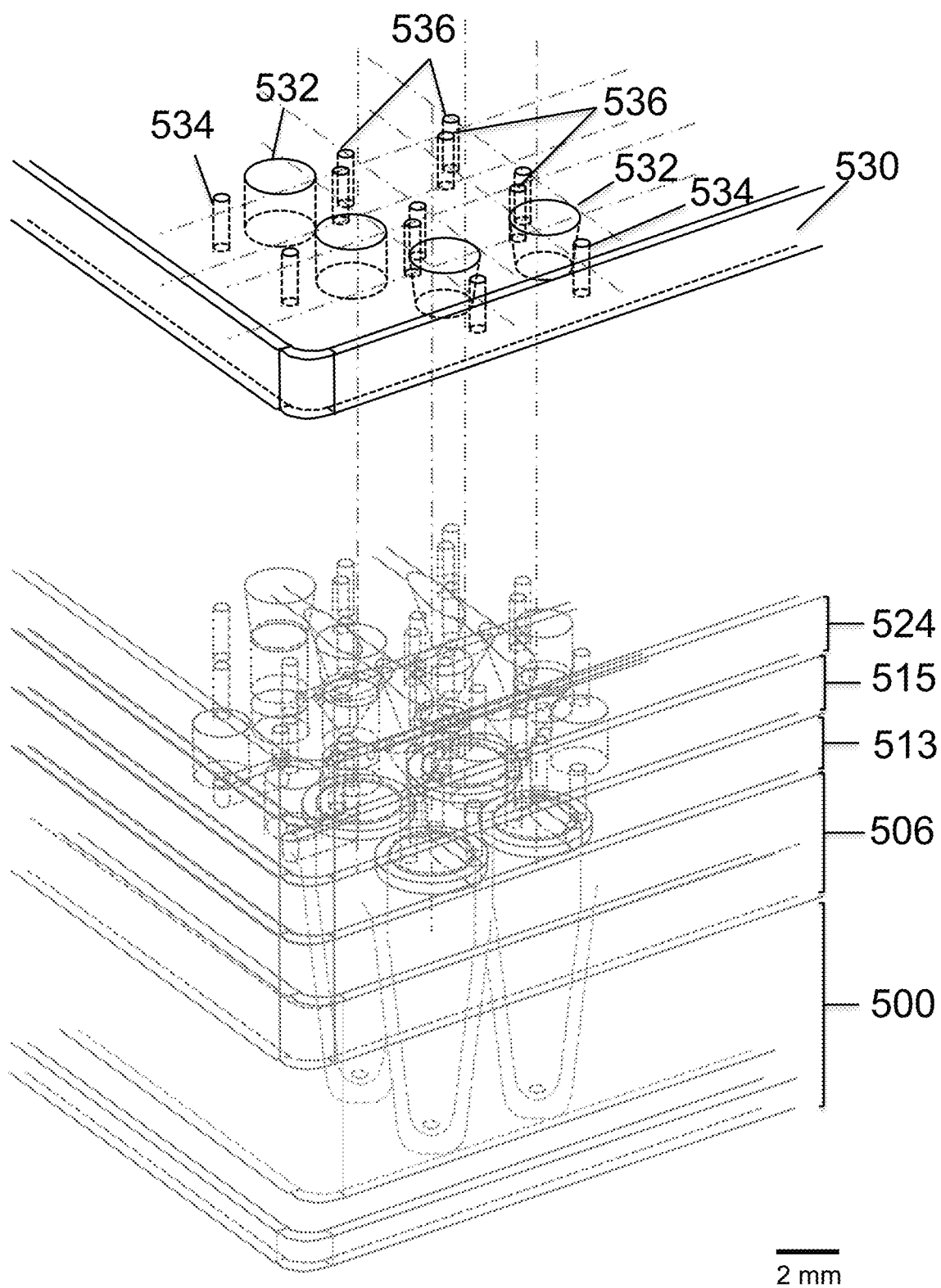

FIG. 144 illustrates an exploded perspective view of the second layer, third layer, first layer (with first and second regions), and intermediate layer of a sample dispersion device that independently addresses each row and each column of a microtiter plate.

FIG. 145 illustrates a PCR-LDR-qPCR carryover prevention reaction with Taqman readout to identify or relatively quantify low-level mutations.

FIG. 146 illustrates a PCR-LDR-qPCR carryover prevention reaction with UniTaq readout to identify or relatively quantify low-level mutations.

FIG. 147 illustrates a PCR-qLDR carryover prevention reaction with FRET readout to identify or relatively quantify low-level mutations.

FIG. 148 illustrates a PCR-LDR-qPCR carryover prevention reaction with Taqman readout to identify or relatively quantify low-level mutations.

FIG. 149 illustrates a PCR-LDR-qPCR carryover prevention reaction with UniTaq readout to identify or relatively quantify low-level mutations.

FIG. 150 illustrates a PCR-qLDR carryover prevention reaction with FRET readout to identify or relatively quantify low-level mutations.

FIG. 151 illustrates a PCR-LDR-qPCR carryover prevention reaction with Taqman readout to identify or relatively quantify low-level target methylation.

FIG. 152 illustrates a PCR-LDR-qPCR carryover prevention reaction with UniTaq readout to identify or relatively quantify low-level target methylation.

FIG. 153 illustrates a PCR-qLDR carryover prevention reaction with FRET readout to identify or relatively quantify low-level target methylation.

FIG. 154 illustrates a Loop-PCR-LDR-qPCR carryover prevention reaction with Taqman readout to identify or relatively quantify low-level target(s) and/or mutations.

FIG. 155 illustrates a Loop-PCR-qLDR carryover prevention reaction with FRET readout to identify or relatively quantify low-level mutations.

FIG. 156 illustrates a Loop-PCR-LDR-qPCR carryover prevention reaction with Taqman readout to identify or relatively quantify low-level target methylation.

FIG. 157 illustrates a Loop-PCR-qLDR carryover prevention reaction with FRET readout to identify or relatively quantify low-level target methylation.

FIG. 158 illustrates a PCR-qPCR carryover prevention reaction with Taqman readout to identify or relatively quantify low-level target methylation.

Figure 159:
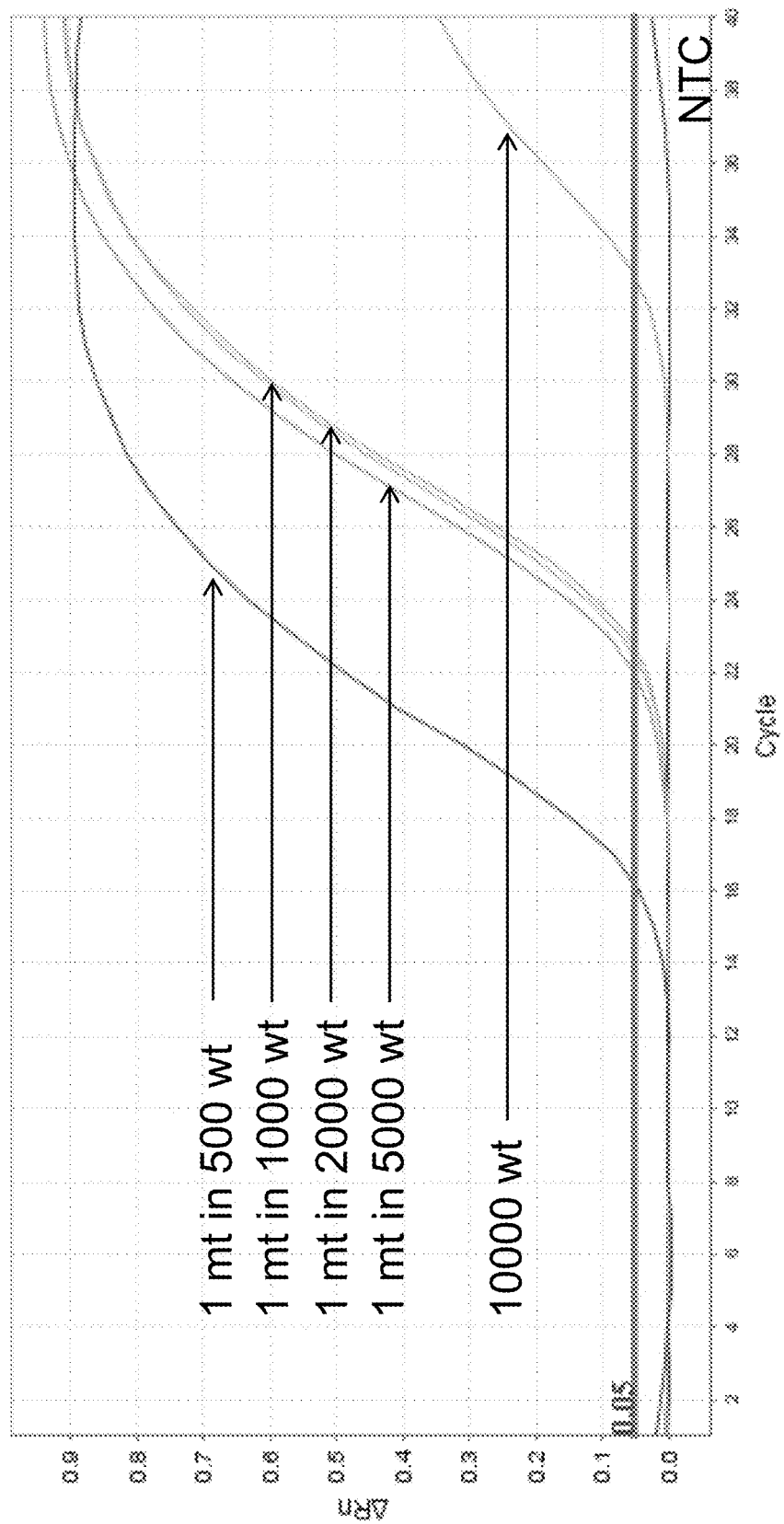

FIG. 159 illustrates the real-time PCR amplification plots obtained in the PCR-LDR-qPCR experiments to detect the BRAF V600E mutation in an excess of wild-type DNA.

Figure 160:
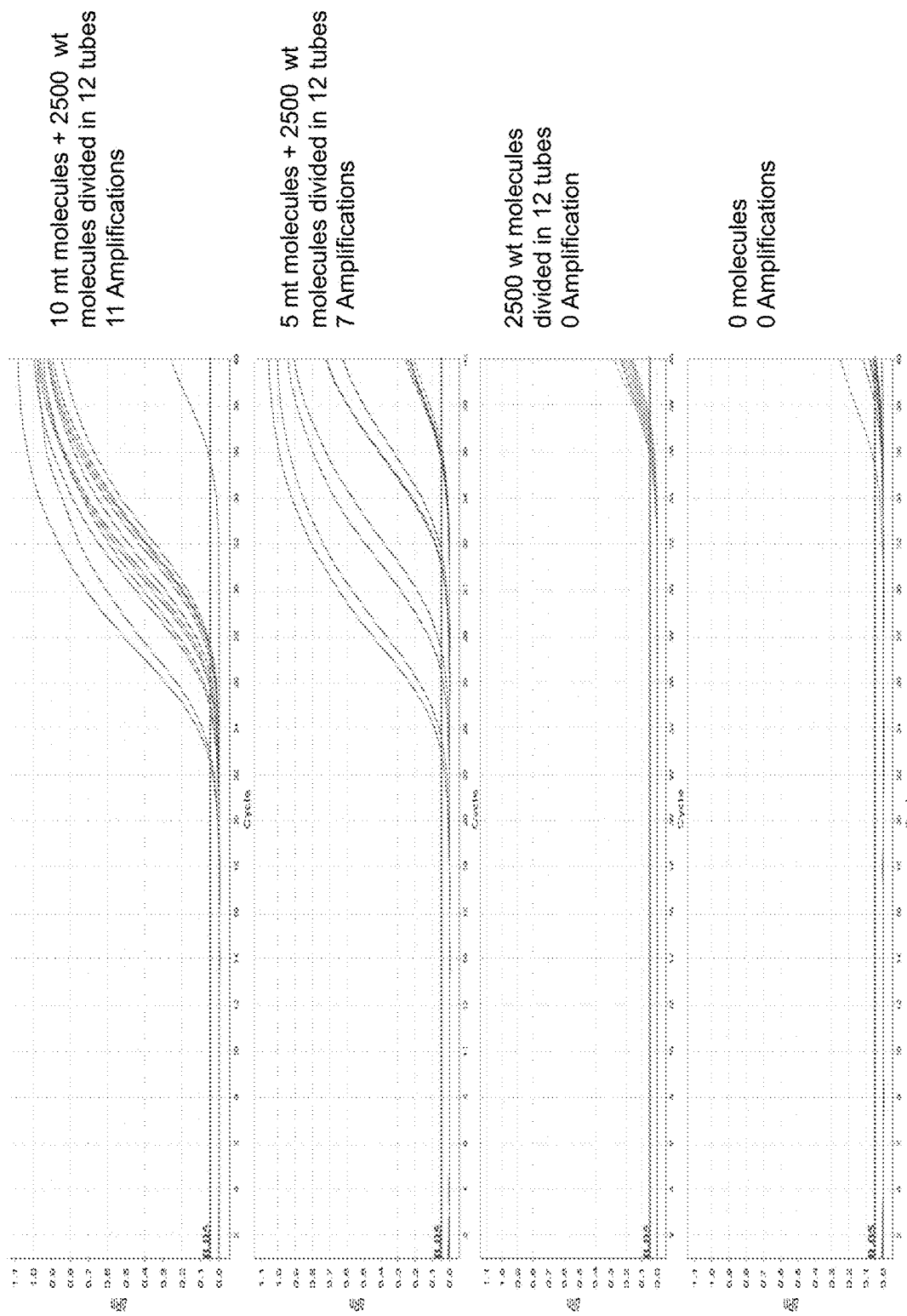

FIG. 160 illustrates the real-time PCR amplification plots obtained in the pixel PCR-LDR-qPCR experiments to enumerate single molecules of the BRAF V600E mutation.

Figure 161:
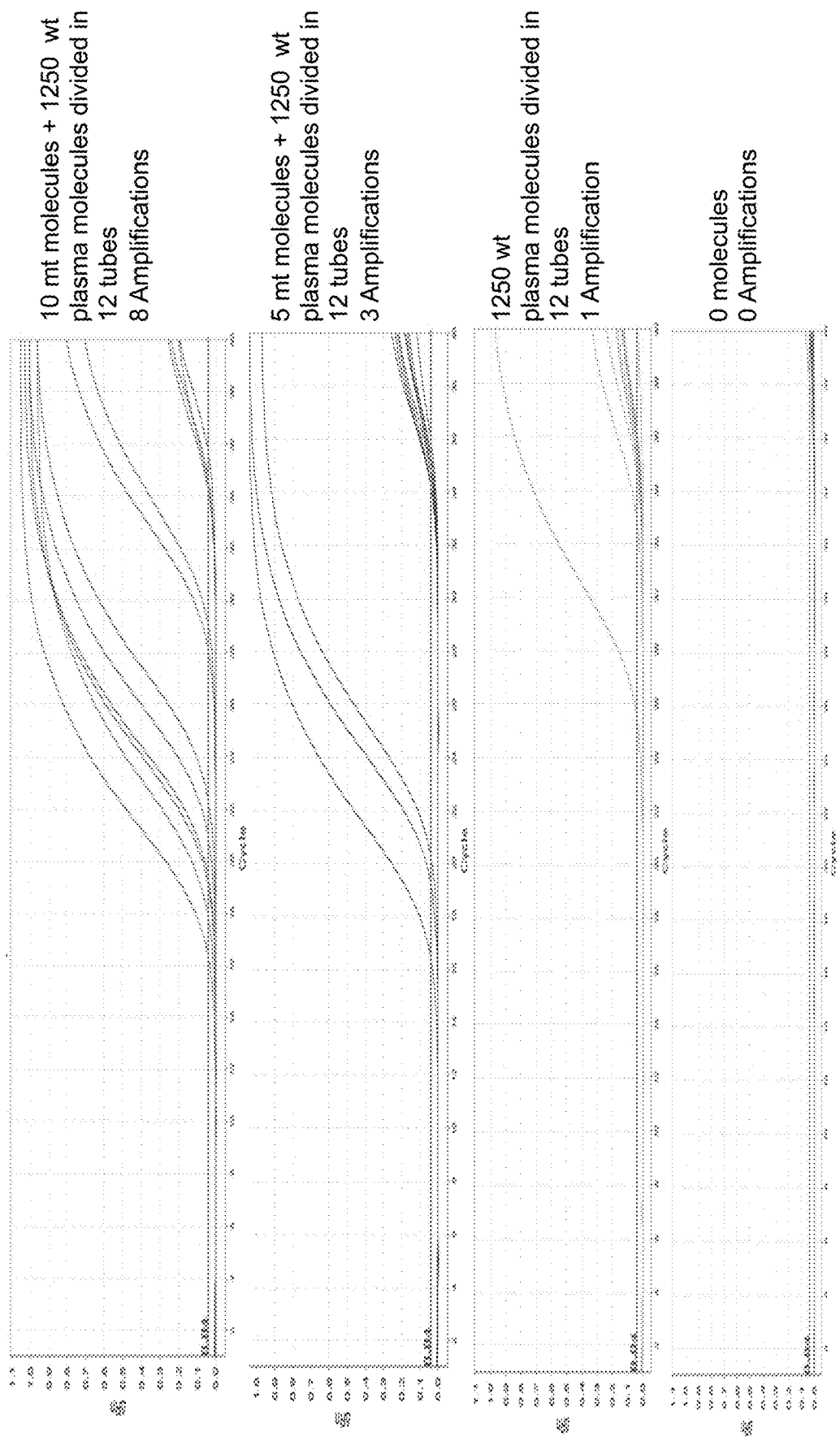

FIG. 161 illustrates the real-time PCR amplification plots obtained in the pixel PCR-LDR-qPCR experiments to enumerate single molecules of the BRAF V600E mutation in the presence of an excess of wild-type DNA from plasma.

Figure 162:
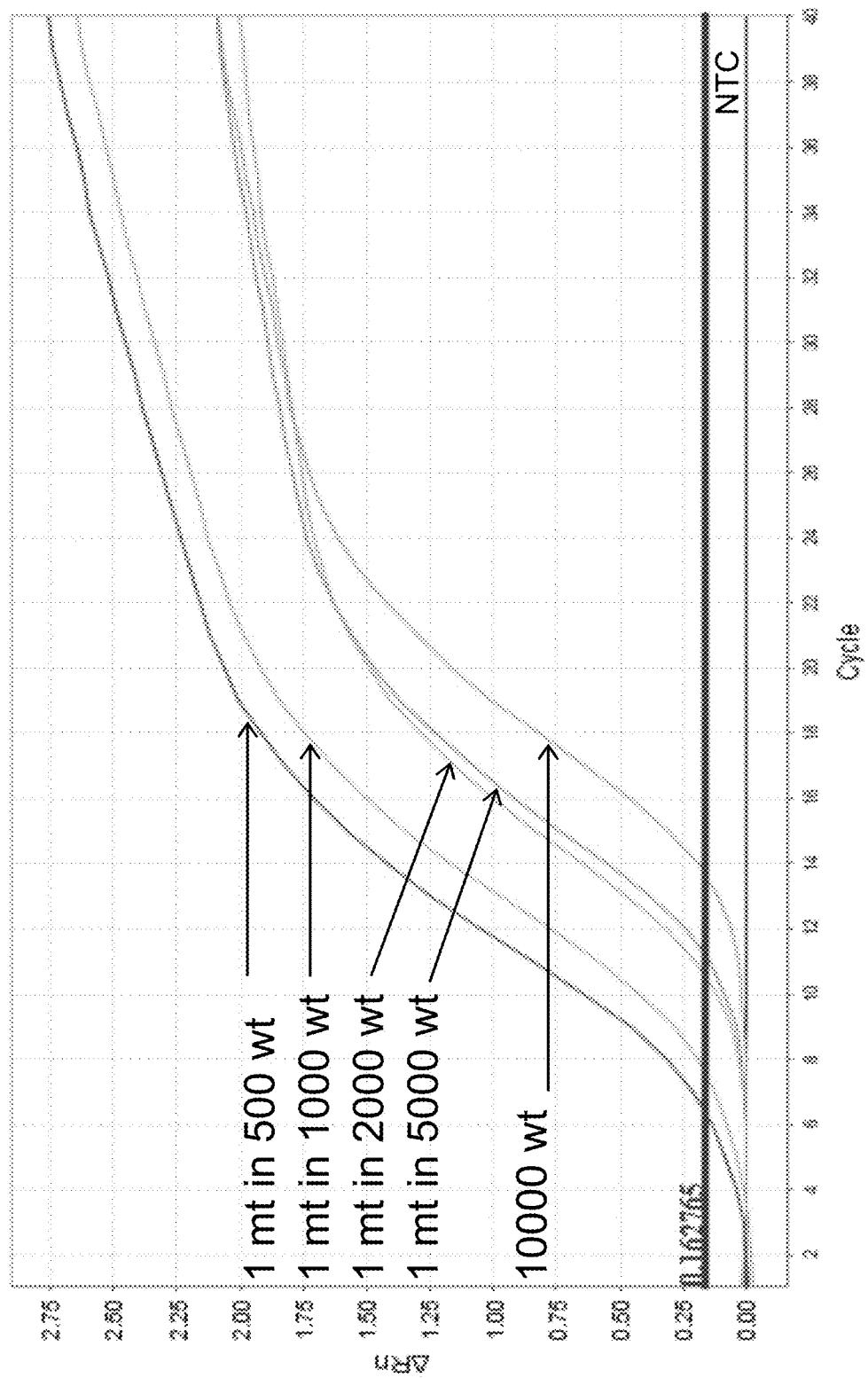

FIG. 162 illustrates the real-time PCR amplification plots obtained in the PCR-LDR-qPCR experiments to detect the TP53 R248Q mutation in the presence of an excess of wild-type DNA.

Figure 163:
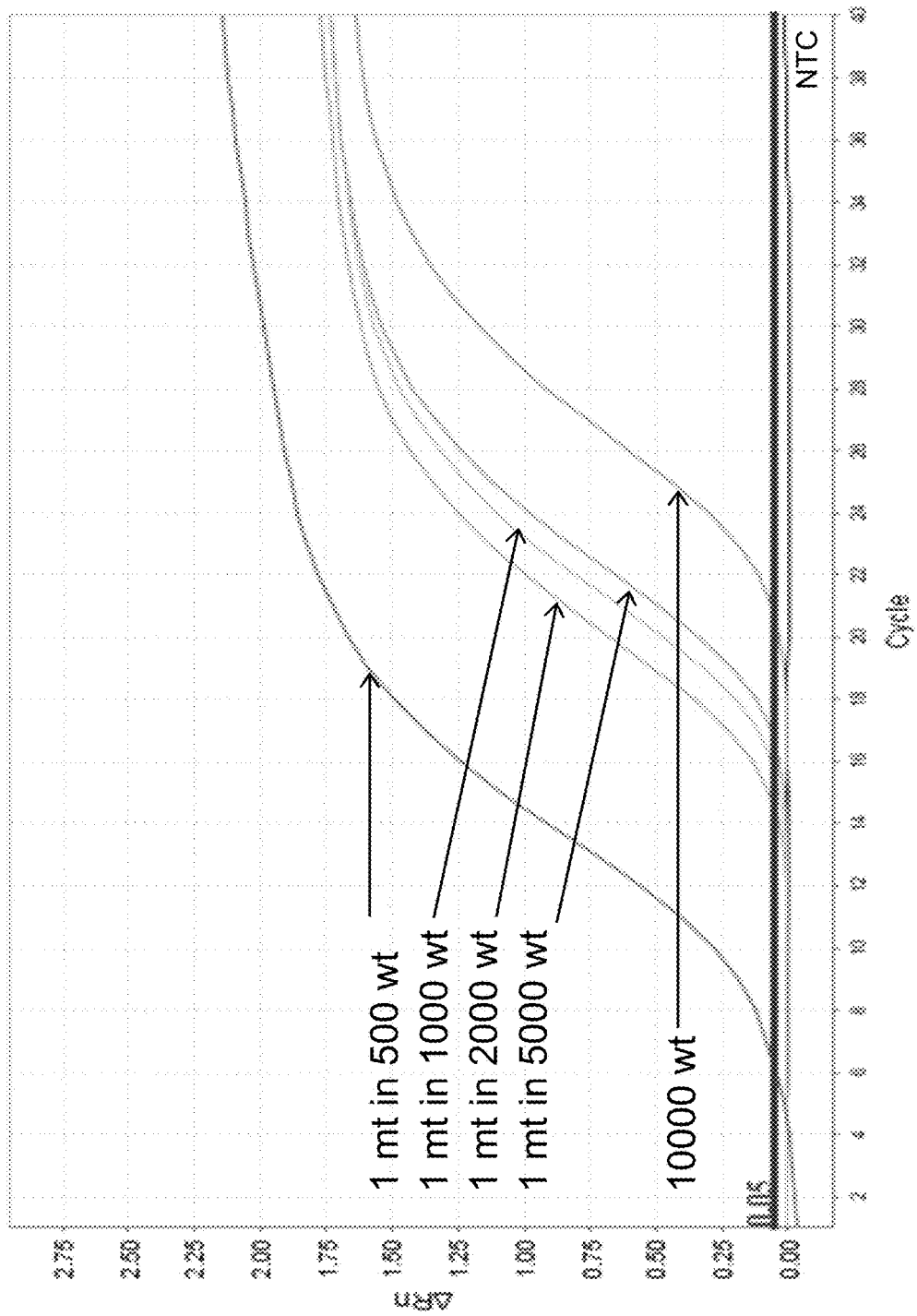

FIG. 163 illustrates the real-time PCR amplification plots obtained in the PCR-LDR-qPCR experiments to detect the TP53 R248Q mutation in the presence of an excess of wild-type DNA.

Figure 164:
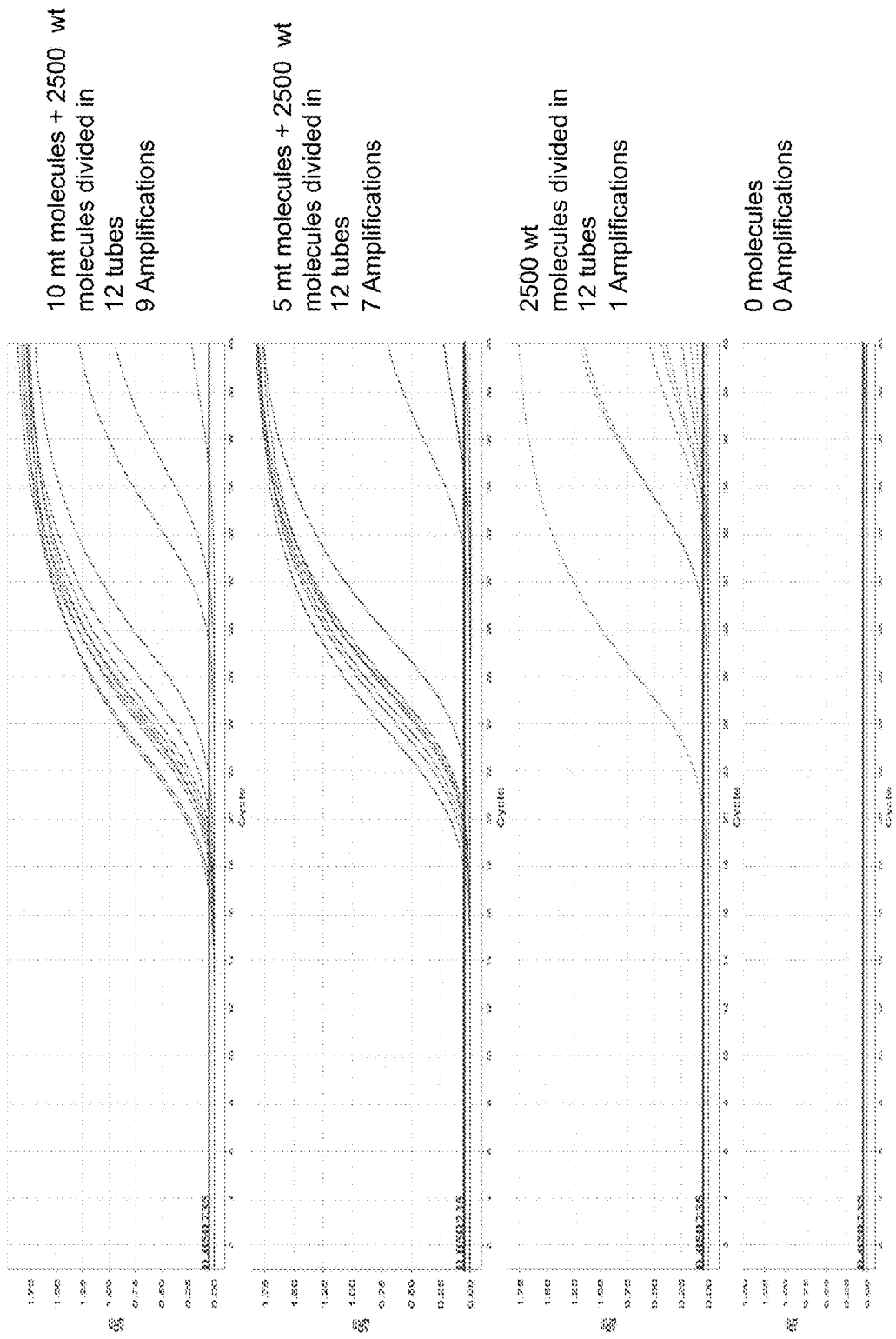

FIG. 164 illustrates the real-time PCR amplification plots obtained in the pixel PCR-LDR-qPCR experiments to enumerate single molecules of the TP53 R248Q mutation in the presence of an excess of wild-type DNA.

Figure 165:
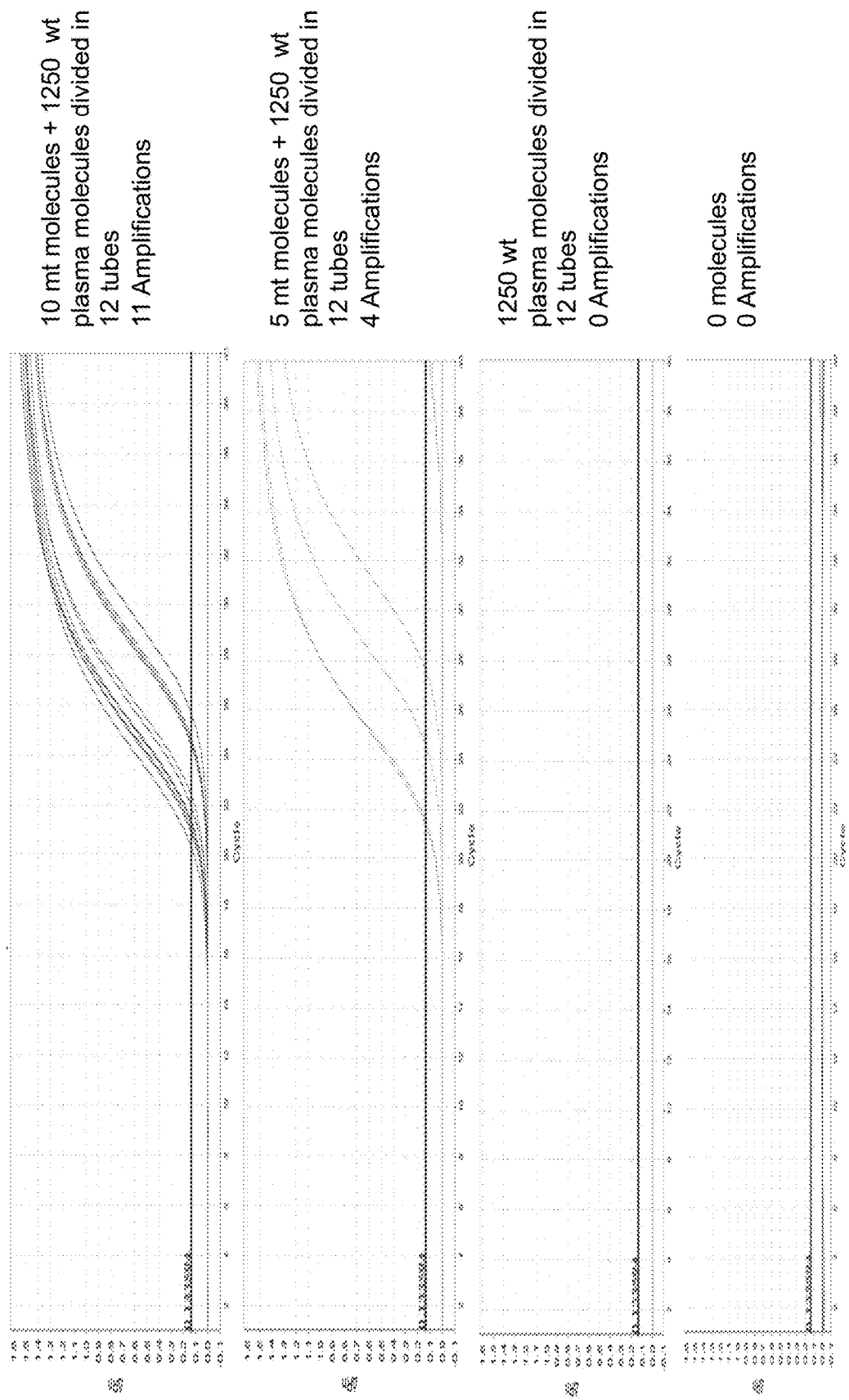

FIG. 165 illustrates the real-time PCR amplification plots obtained in the pixel PCR-LDR-qPCR experiments to enumerate single molecules of the TP53 R248Q mutation in the presence of an excess of wild-type DNA from plasma.

Figure 166:
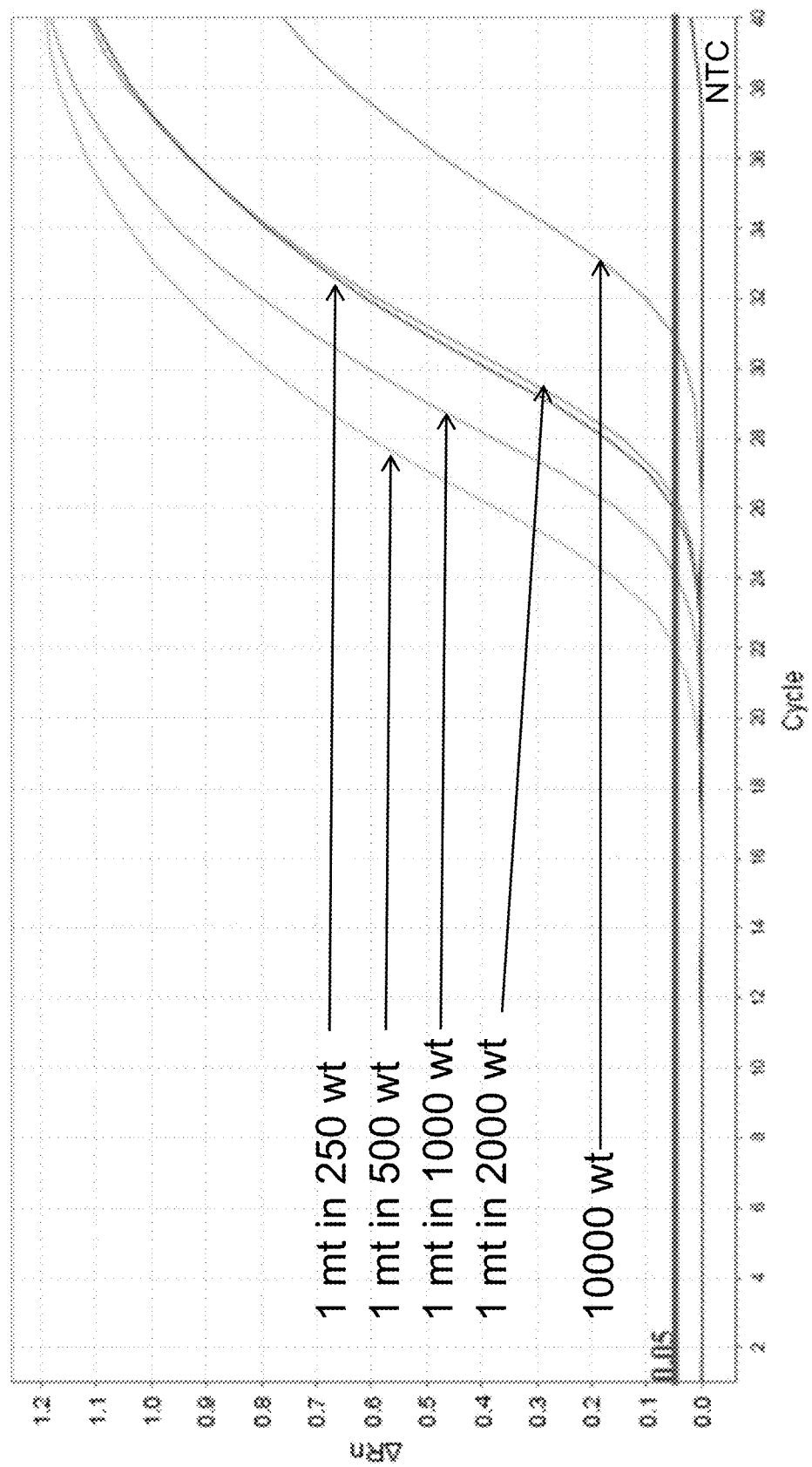

FIG. 166 illustrates the real-time PCR amplification plots obtained in the PCR-LDR-qPCR experiments to detect the KRAS G12C mutation in the presence of an excess of wild-type DNA.

Figure 167:
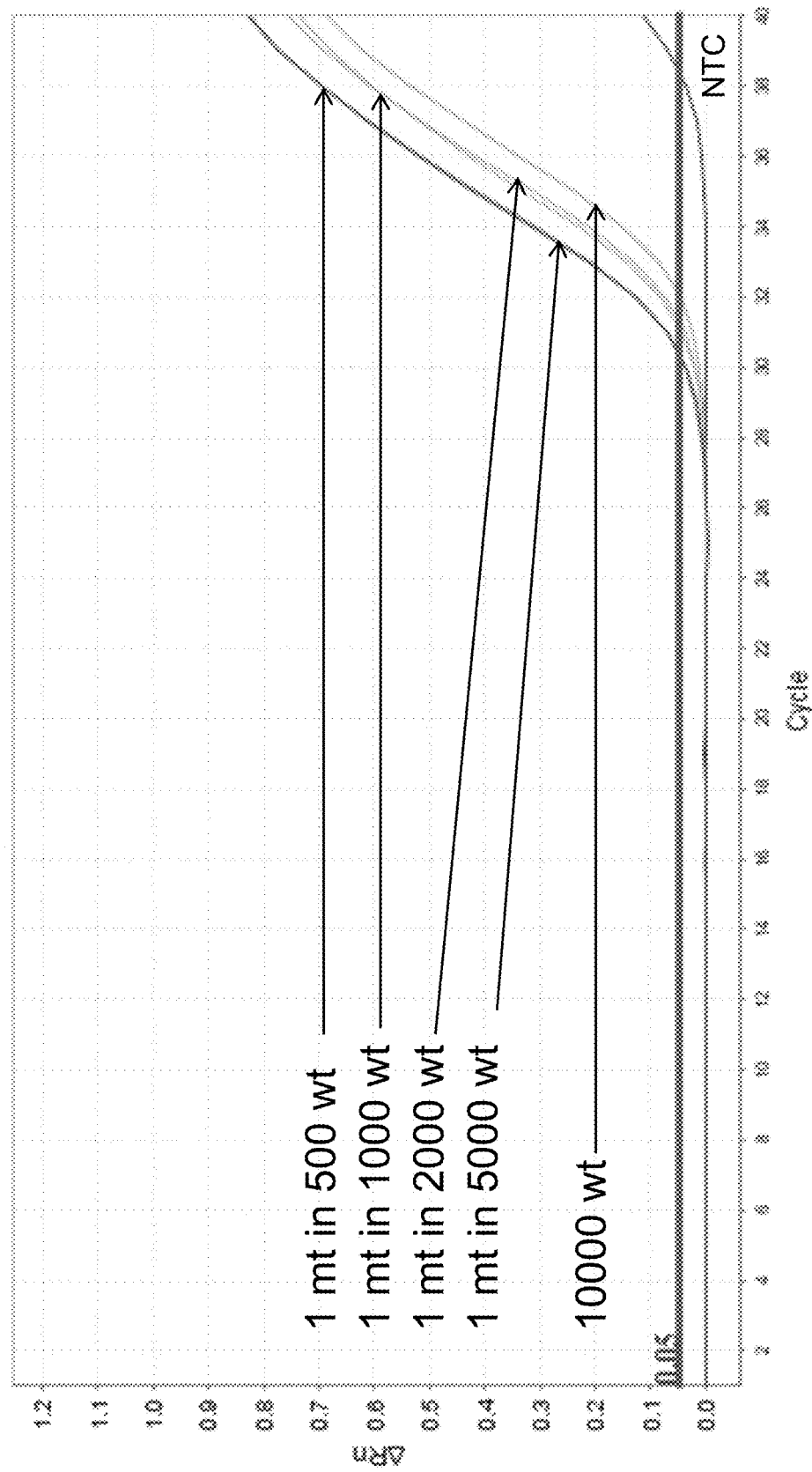

FIG. 167 illustrates the real-time PCR amplification plots obtained in the PCR-LDR-qPCR experiments to detect the KRAS G12S mutation in the presence of an excess of wild-type DNA.

Figure 168:
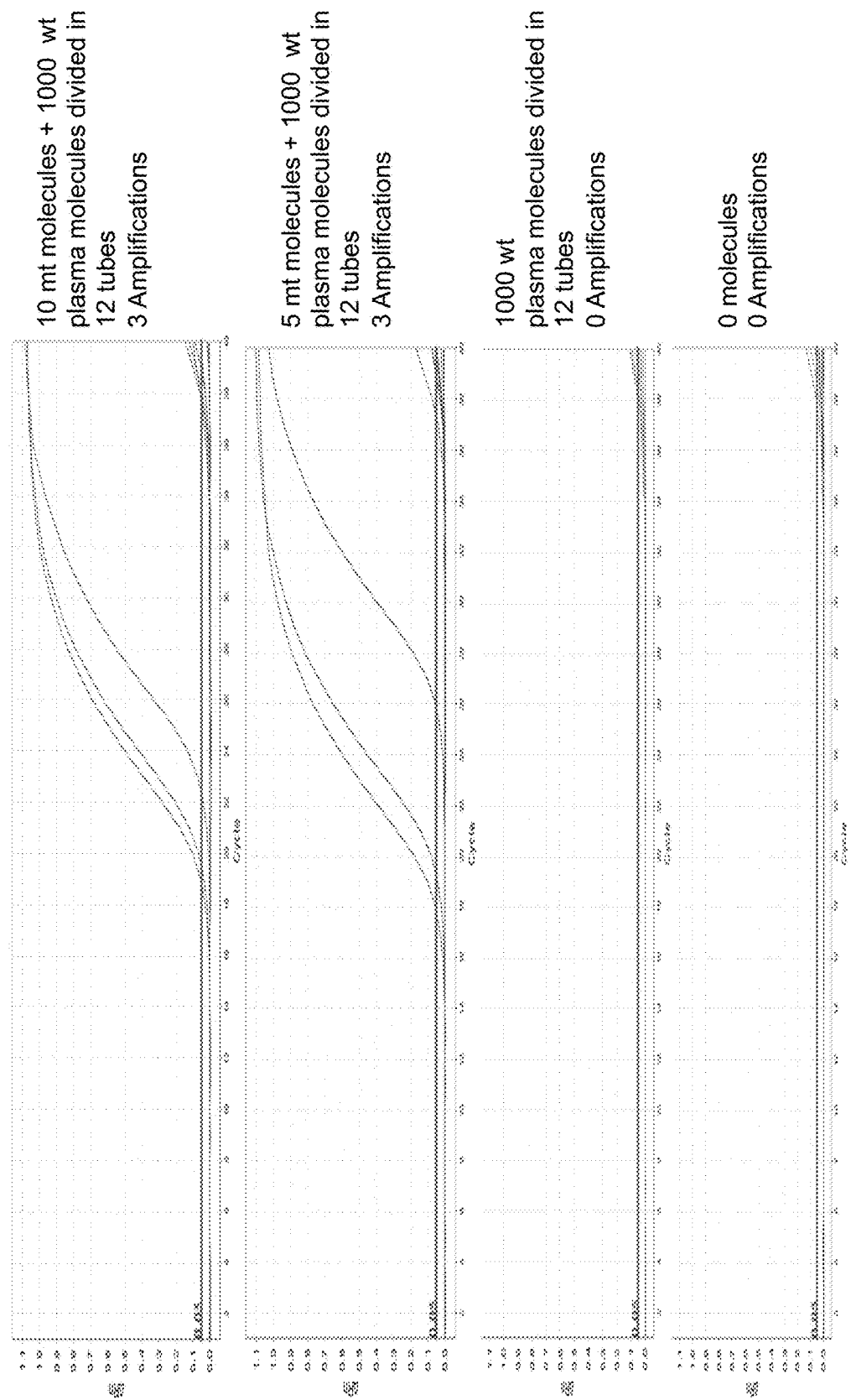

FIG. 168 illustrates the real-time PCR amplification plots obtained in the pixel PCR-LDR-qPCR experiments to enumerate single molecules of the KRAS G12C mutation in the presence of an excess of wild-type DNA from plasma.

Figure 169:
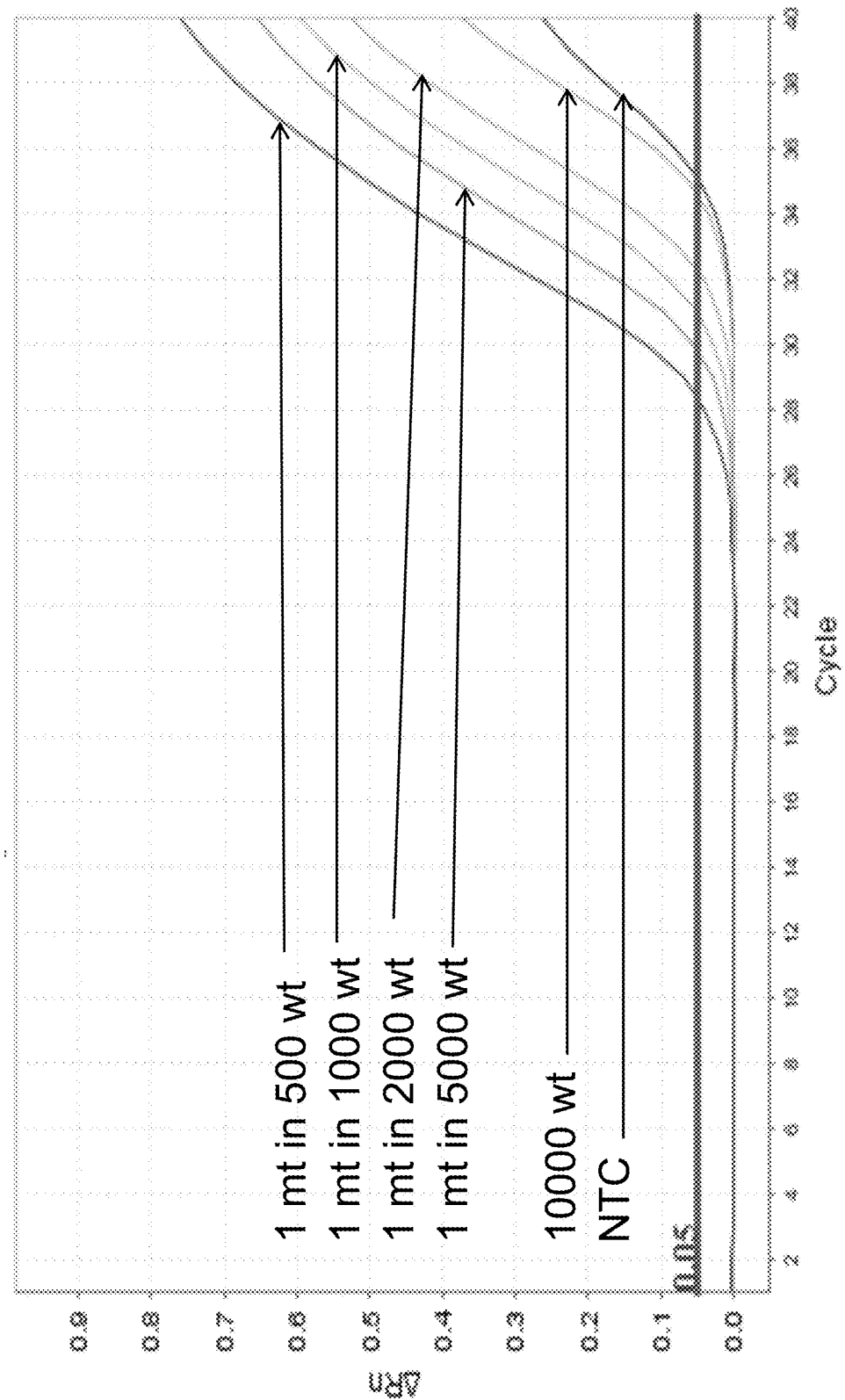

FIG. 169 illustrates the real-time PCR amplification plots obtained in the PCR-LDR-qPCR experiments to detect the KRAS G12D mutation in the presence of an excess of wild-type DNA.

Figure 170:
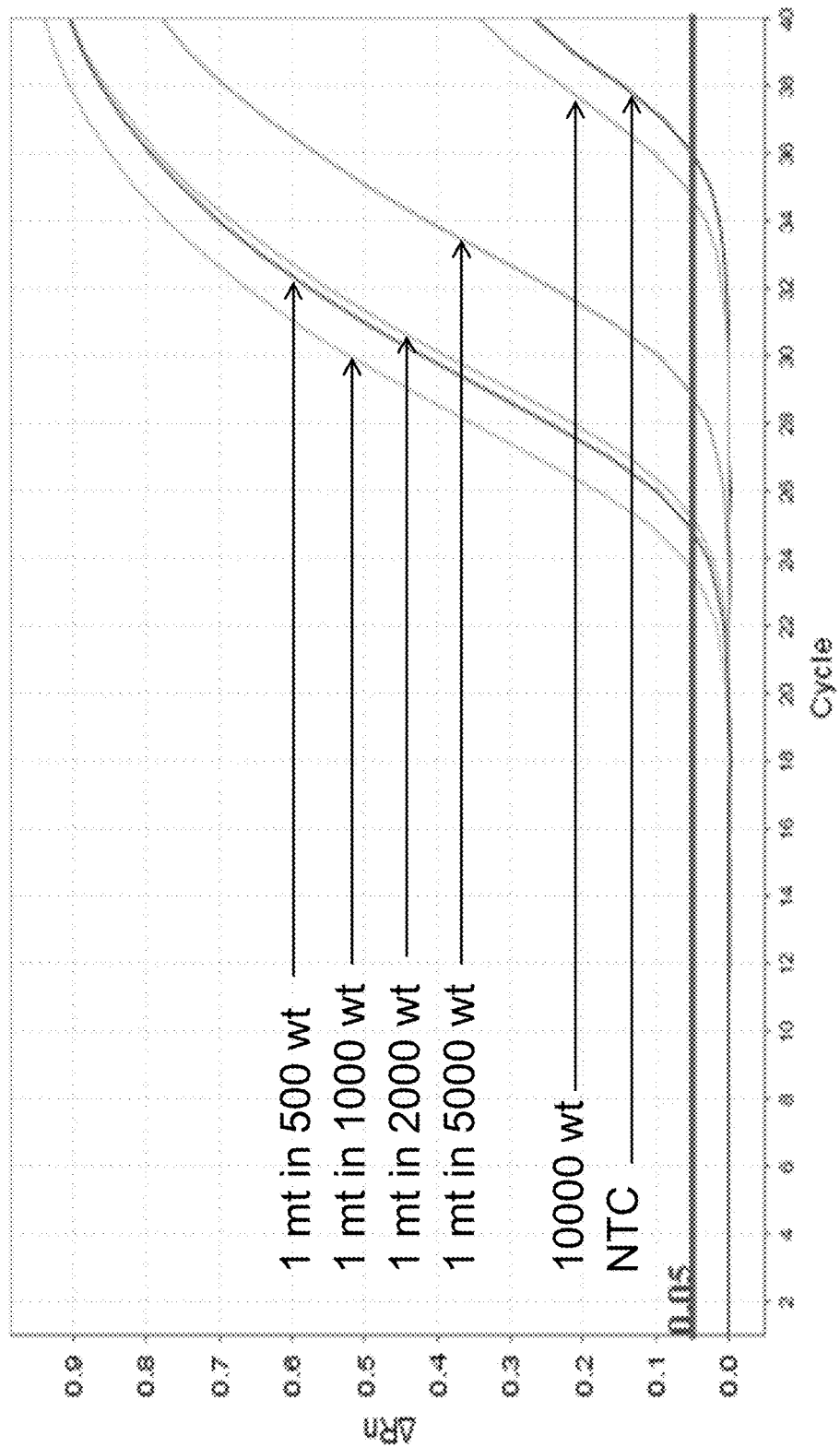

FIG. 170 illustrates the real-time PCR amplification plots obtained in the PCR-LDR-qPCR experiments to detect the KRAS G12A mutation in the presence of an excess of wild-type DNA.

Figure 171:
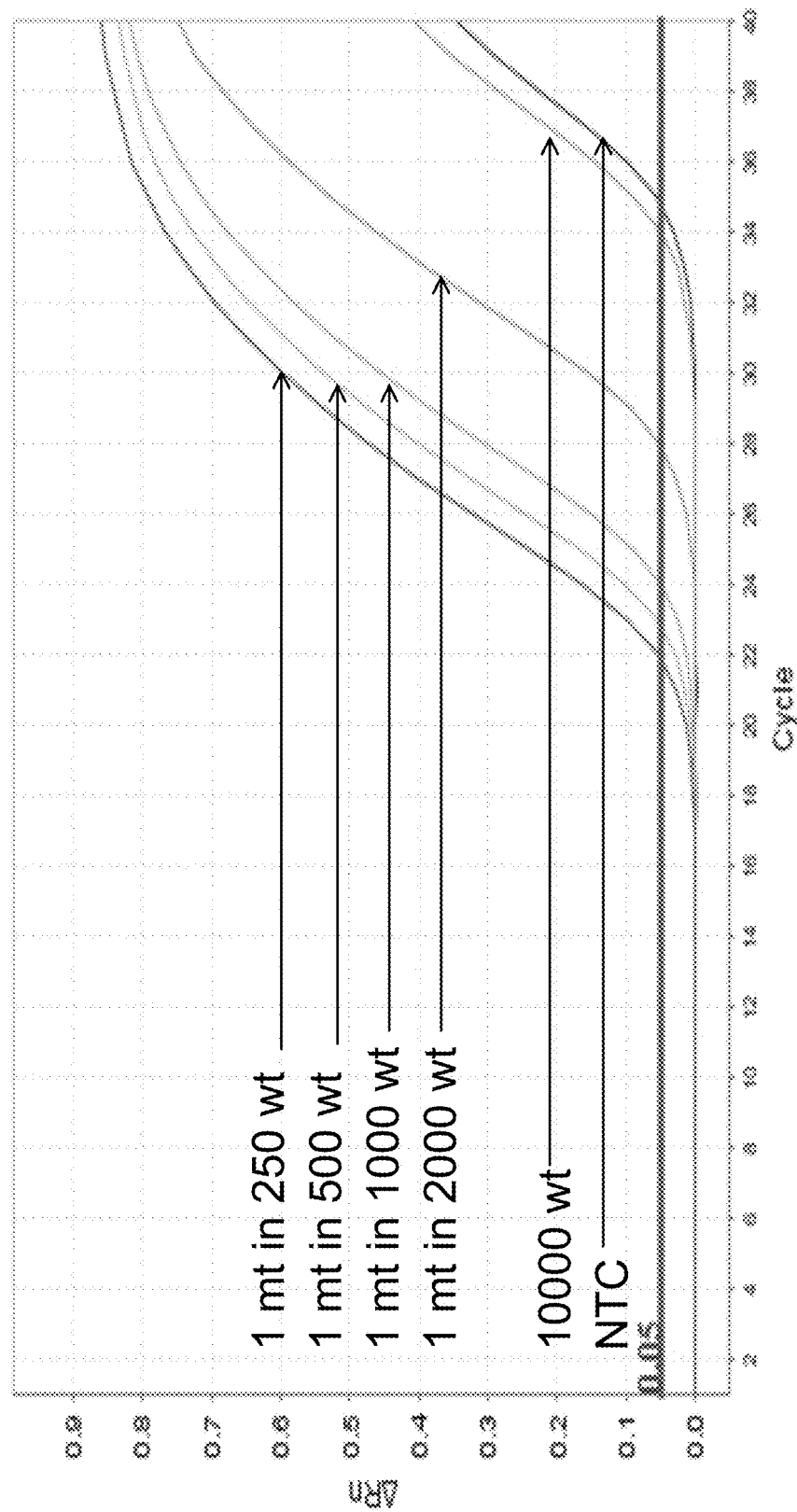

FIG. 171 illustrates the real-time PCR amplification plots obtained in the PCR-LDR-qPCR experiments to detect the KRAS G12V mutation in the presence of an excess of wild-type DNA.

Figure 172:
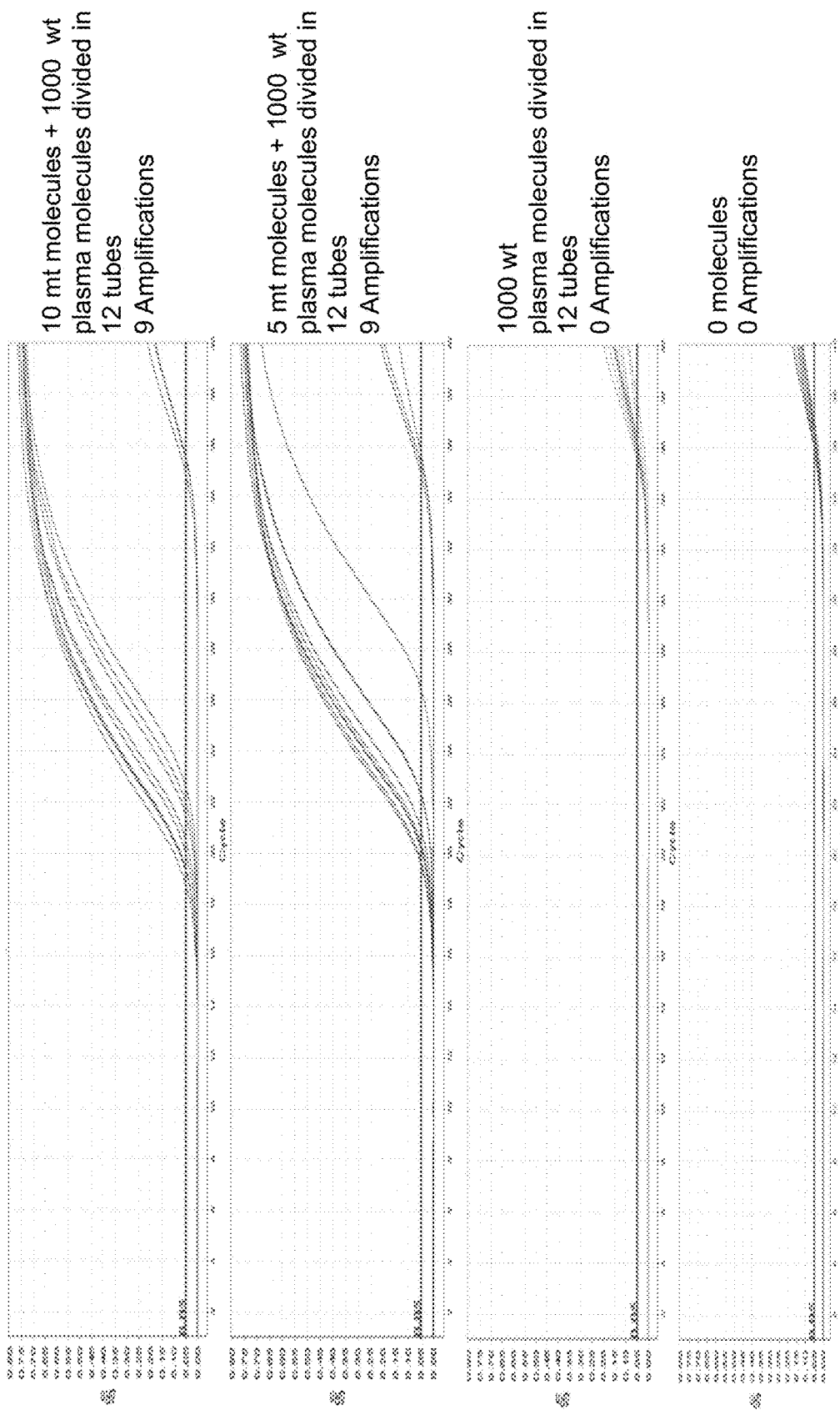

FIG. 172 illustrates the real-time PCR amplification plots obtained in the pixel PCR-LDR-qPCR experiments to enumerate single molecules of the KRAS G12V mutation in the presence of an excess of wild-type DNA in plasma.

Figure 173:
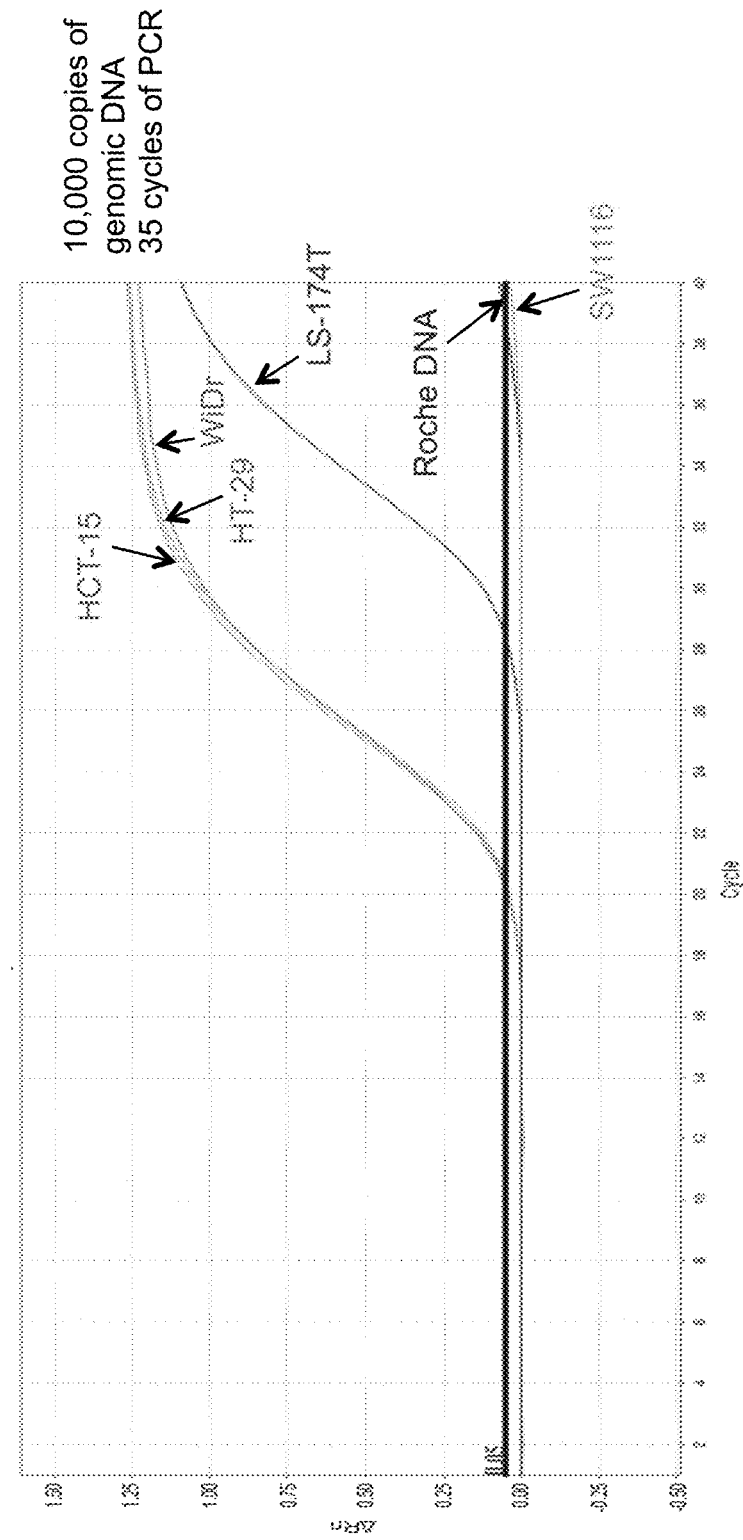

FIG. 173 illustrates the real-time PCR amplification plots obtained in the PCR-LDR-qPCR experiments to detect the presence or absence of methylation of the Vimentin gene.

Figure 174:
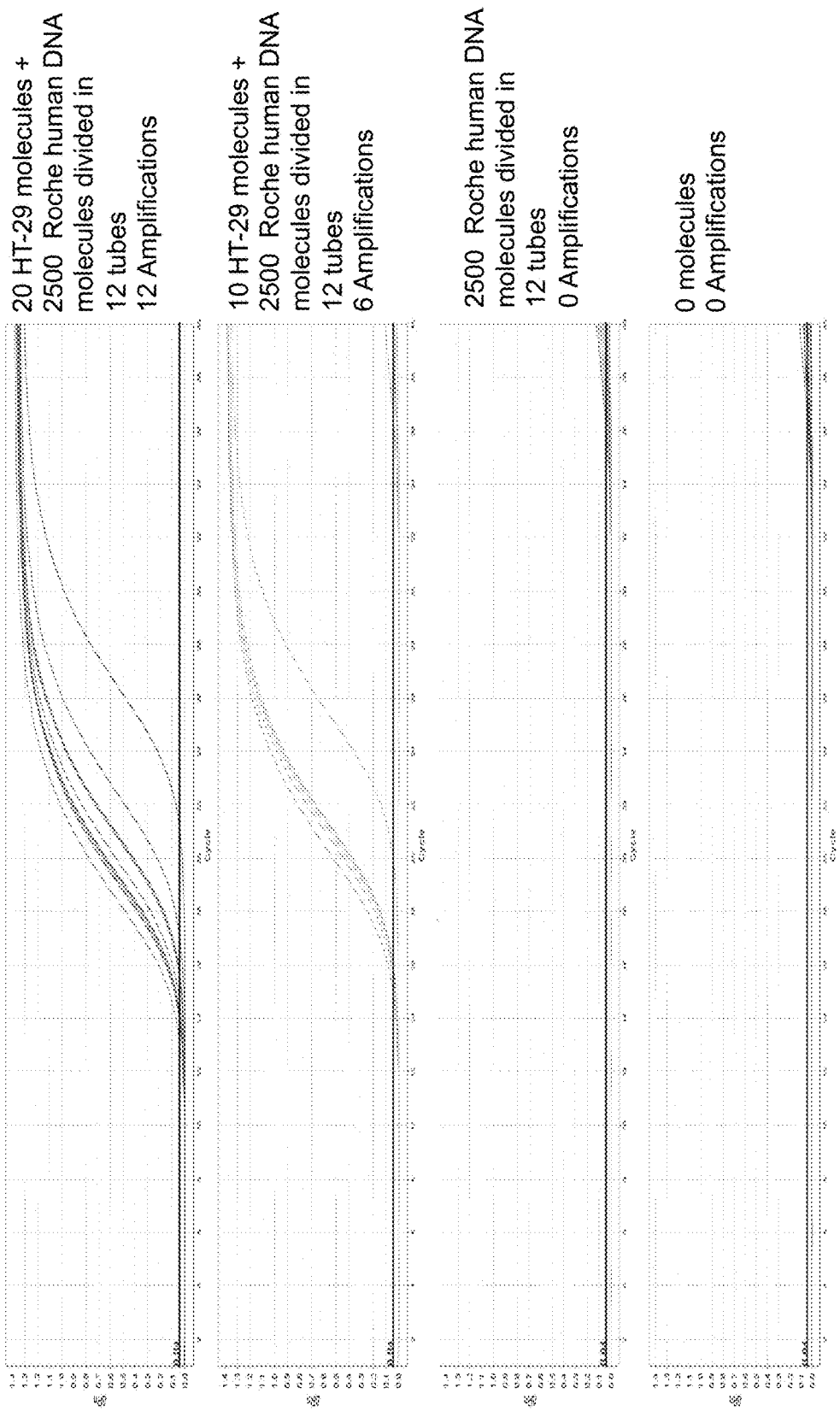

FIG. 174 illustrates the real-time PCR amplification plots obtained in the pixel PCR-LDR-qPCR experiments to enumerate single molecules of methylated DNA in the presence of an excess of unmethylated DNA (hgDNA).

Figure 175:
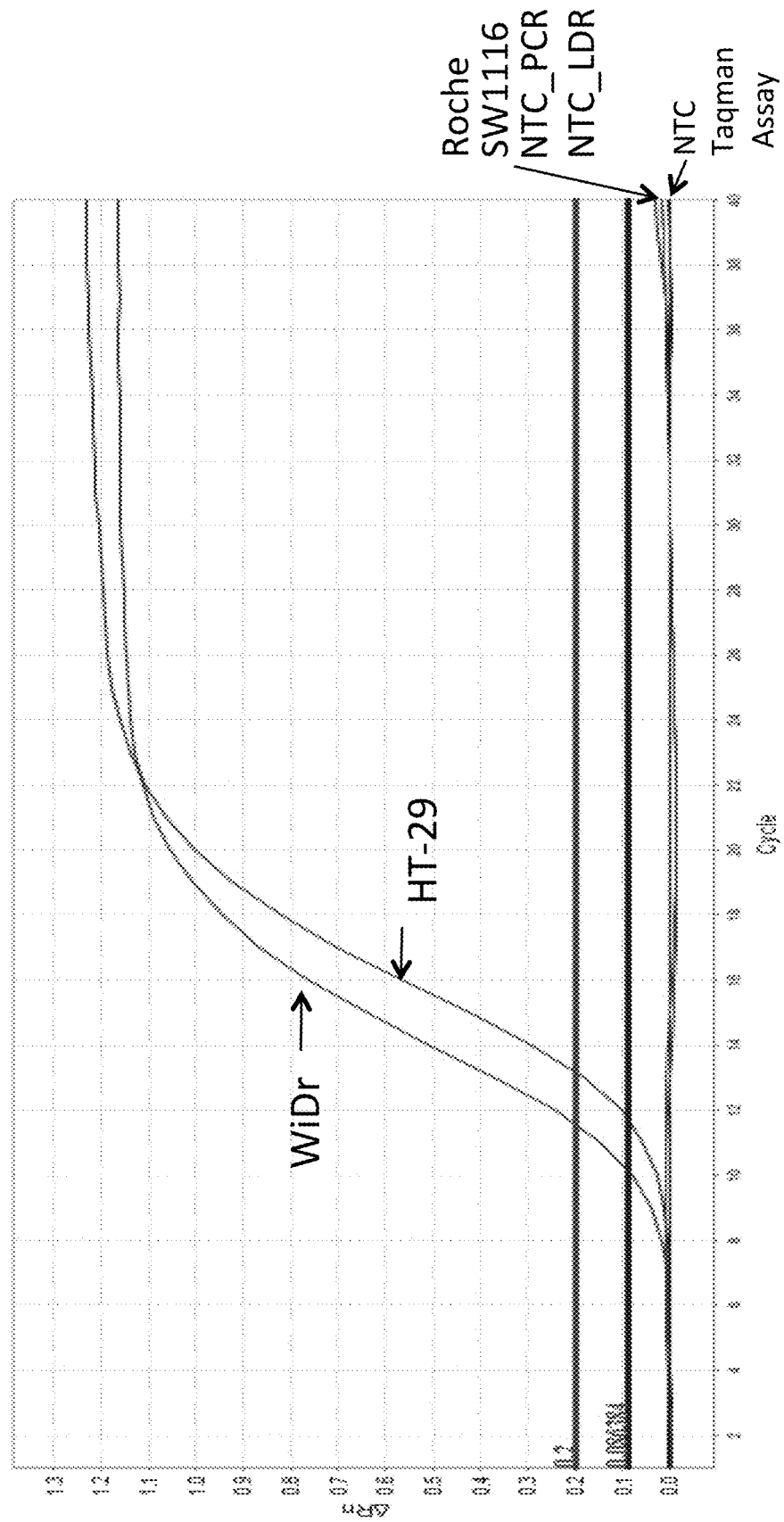

FIG. 175 illustrates the real-time PCR amplification plots obtained in the experiment to detect methylation of the VIM S3 top strand, using the Taqman probe version "A."

Figure 176:
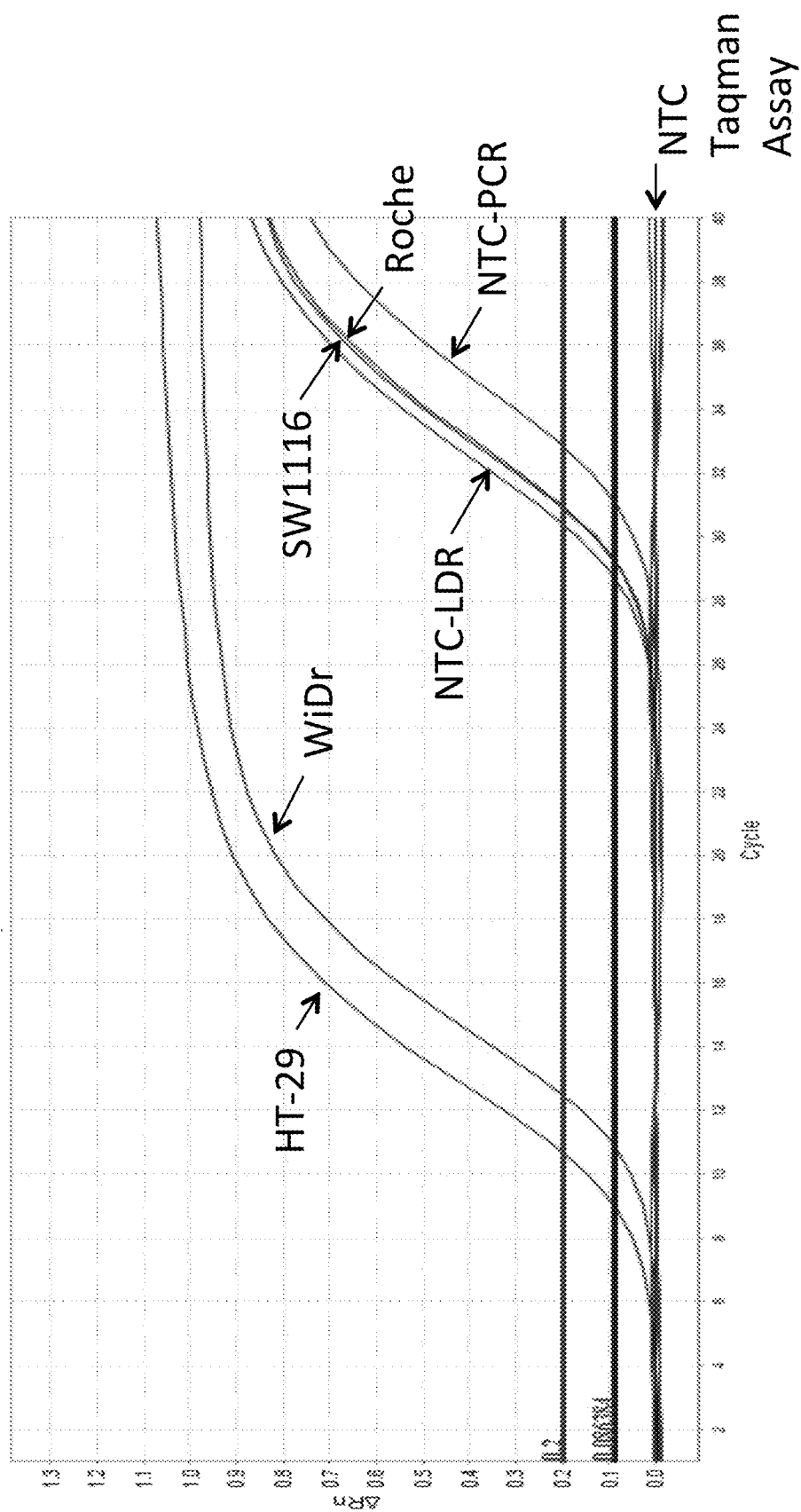

FIG. 176 illustrates the real-time PCR amplification plots obtained in the experiment to detect methylation of the VIM S3 bottom strand, using the Taqman probe version "A."

Figure 177:
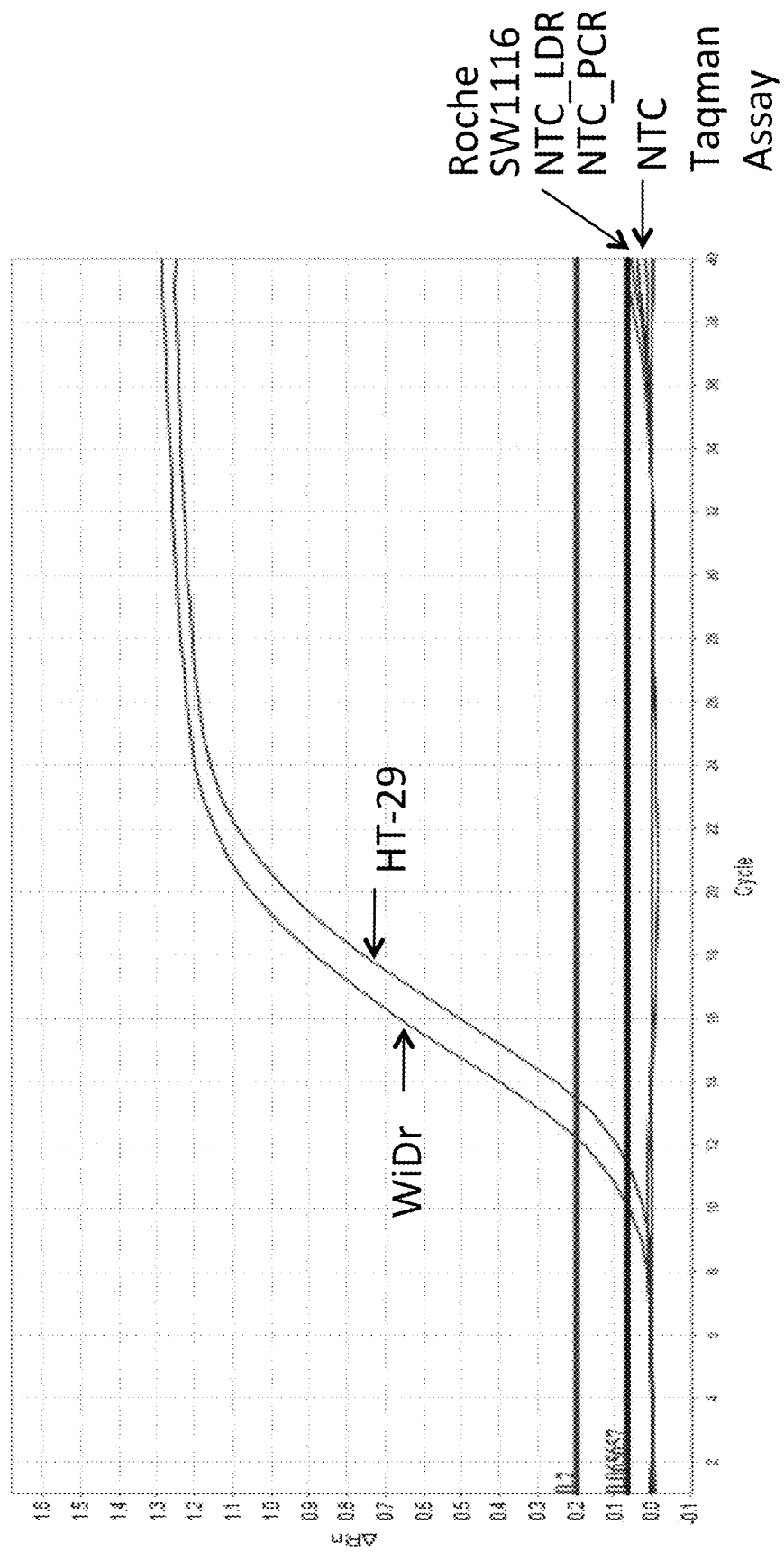

FIG. 177 illustrates the real-time PCR amplification plots obtained in the experiment to detect methylation of the VIM S3 top strand, using the Taqman probe version "B."

Figure 178:
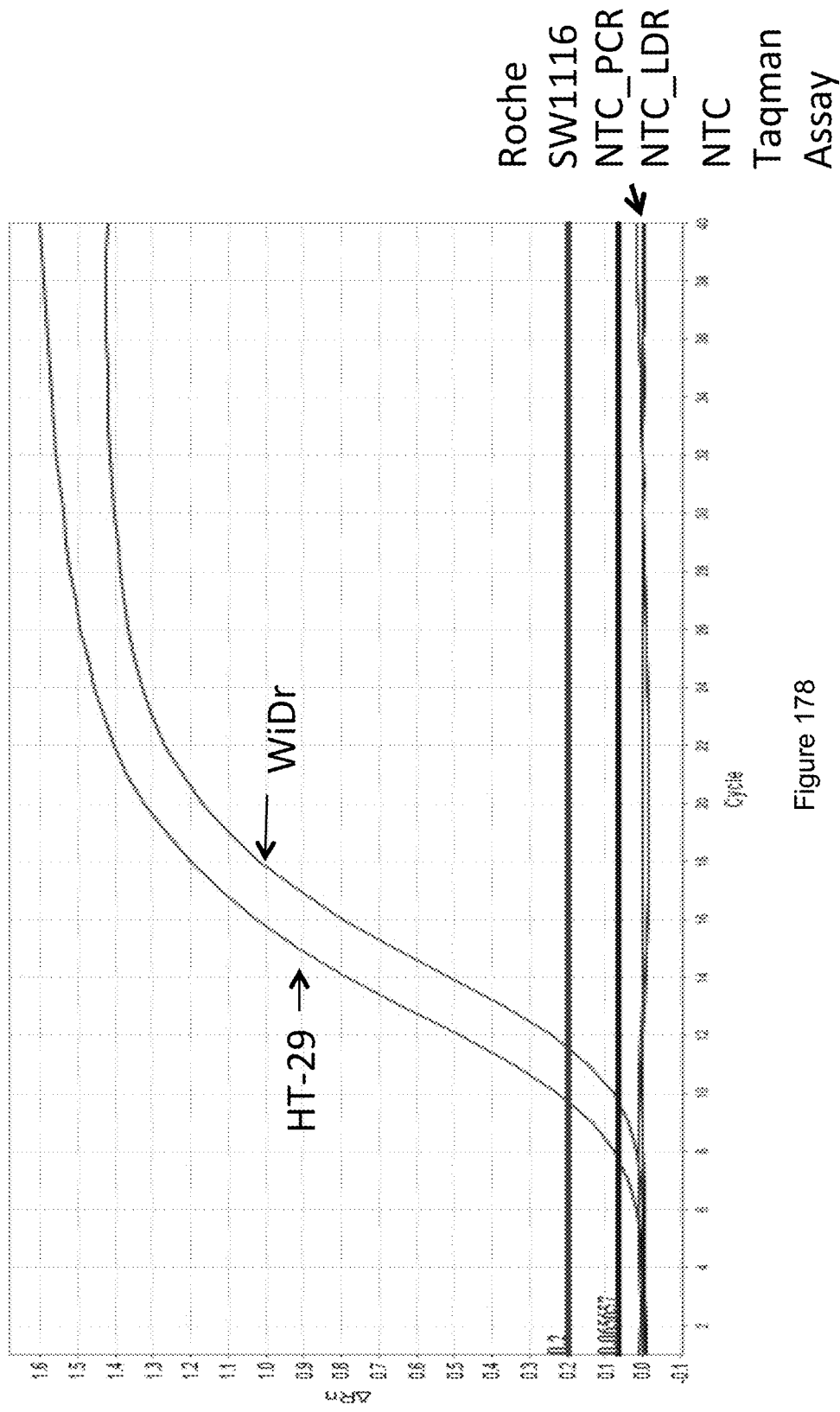

FIG. 178 illustrates the real-time PCR amplification plots obtained in the experiment to detect methylation of the VIM S3 bottom strand, using the Taqman probe version "B."

DETAILED DESCRIPTION OF THE INVENTION

A Universal Design for Early Detection of Disease Using "Disease Marker Load"

Figure 1:
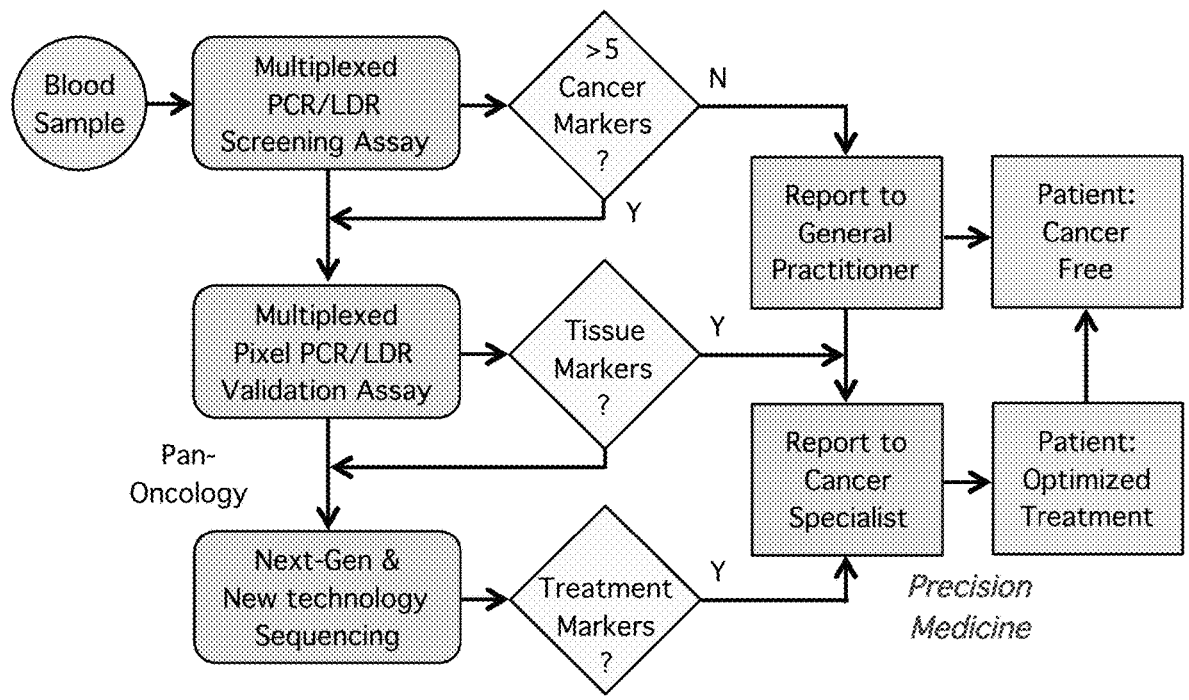
FIG. 1 illustrates a conditional logic tree for an early detection pan cancer test based on analysis of a patient's blood sample.

The most cost-effective early disease detection test may combine an initial multiplexed coupled amplification and ligation assay to determine "disease load". For cancer detection this would achieve >95% sensitivity for all cancers (pan-oncology), at >97% specificity. A flow chart for a cancer tumor load assay is illustrated in FIG. 1. An initial multiplexed PCR/LDR screening assay scoring for mutation, methylation, miRNA, mRNA, alternative splicing, and translocations identifies those samples with >5 of 24-48 markers positive. Presumptive positive samples are then assayed using "pixel" PCR/LDR with additional tissue-specific markers to validate the initial result, and identify tissue of origin. The physician may then order targeted sequencing to further guide treatment decisions for the patient.

The present invention is directed to a universal diagnostic approach that seeks to combine the best features of digital polymerase chain reaction (PCR), ligation detection reaction (LDR), and quantitative detection of multiple disease markers, e.g., cancer markers. The family of assay architecture and devices comprises three modules for PCR-LDR quantification of low-abundance disease markers from blood. Each module may be optimized independently, and may be manual, semi-automated, or fully automated. The design enables integrating the modules together, such that any module may be optimized independently to bring improved performance to the entire assay.

The first family of assay designs is based on an initial multiplexed PCR or RT-PCR amplification followed by multiplexed LDR using LDR probes having unique sequence tags containing primer-specific portions. The products are distributed and mixed with tag primer sets with target-directed TaqMan™ probes, or alternatively with Uni-Taq primer sets, and the input target nucleic acids quantified using real-time PCR The first module takes an input sample of blood, and separates plasma from red blood cells (RBCs) and white blood cells (WBCs). It separates plasma again to remove any residual cells. In addition, cell fractions containing all WBCs and circulating tumor cells (CTCs) and some RBCs are separated. Exosomes are separated or affinity captured from plasma. The module purifies (i) RNA from the WBC and CTC fraction, (ii) miRNA and RNA from exosomes, and (iii) cell free DNA (cfDNA) from plasma.

The second module enables distribution of the above components into 24 or 48 chambers or wells for spatial multiplexing with proportional multiplexed PCR or RT-PCR amplification of targeted gene, promoter, miRNA, or mRNA regions. These include: (i) specific splice-variant or gene-fusion mRNAs in the CTC containing WBC fraction, (ii) specific miRNAs from exosomes, (iii) specific mRNAs from exosomes, (iv) specific cancer gene DNA regions from cfDNA, and (v) specific (methylated) promoter regions from cfDNA.

The third module enables spatial distribution of the above products into wells of a microtiter plate, e.g., in a 24×16 or 48×32 configuration. This module enables detection and enumeration of LDR products using real-time PCR to provide quantitative results for each disease marker.

Figure 2:
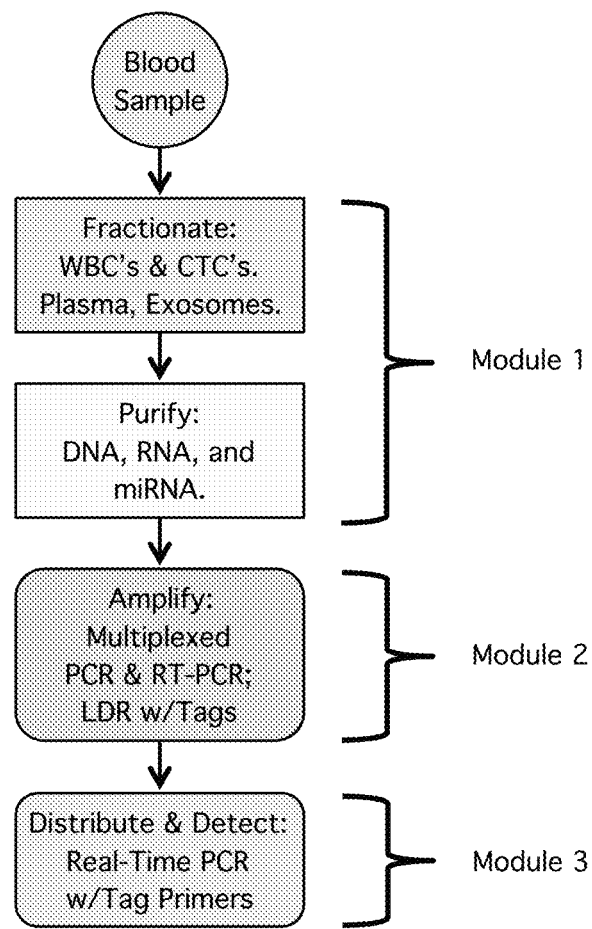
FIG. 2 illustrates a work flow for analysis of DNA, mRNA, and miRNA from plasma cfDNA, exosomes, and CTC.
Figure 3:
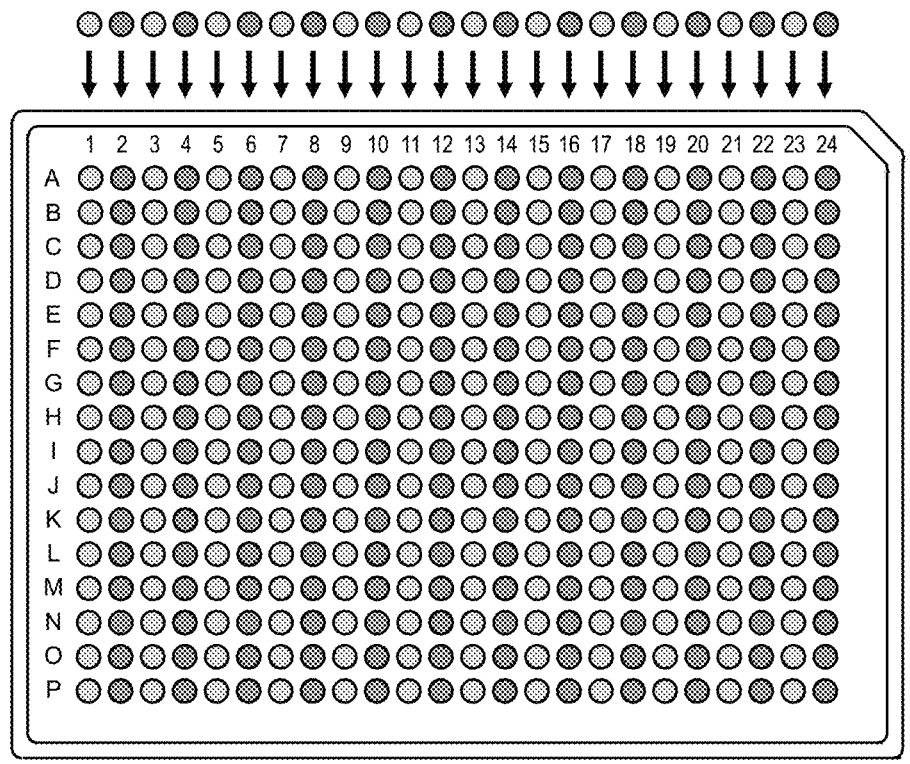
FIG. 3 illustrates the generic analysis of DNA, mRNA or miRNA by distribution of one sample, which has initially been diluted and distributed across 24 tubes for multiplexed PCR or reverse-transcriptase PCR followed by LDR with tagged probes, into 24×16 rows of a microtiter plate.
Figure 4:
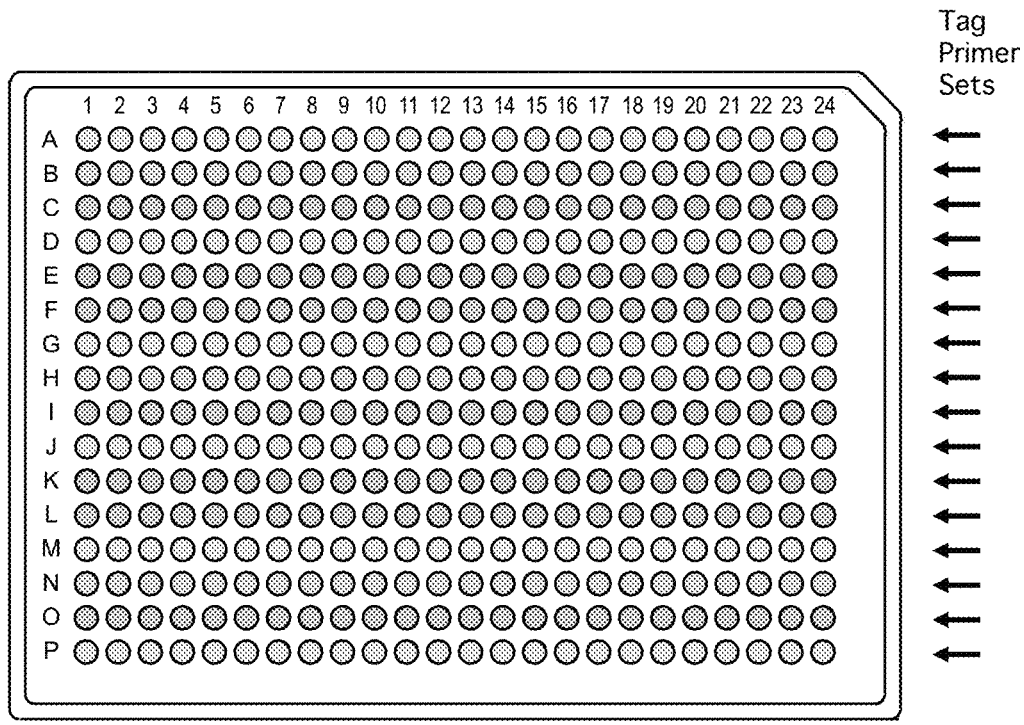
FIG. 4 illustrates the addition of 16 different tag primer sets across the 24 columns of a microtiter plate from FIG. 3.
Figure 5:
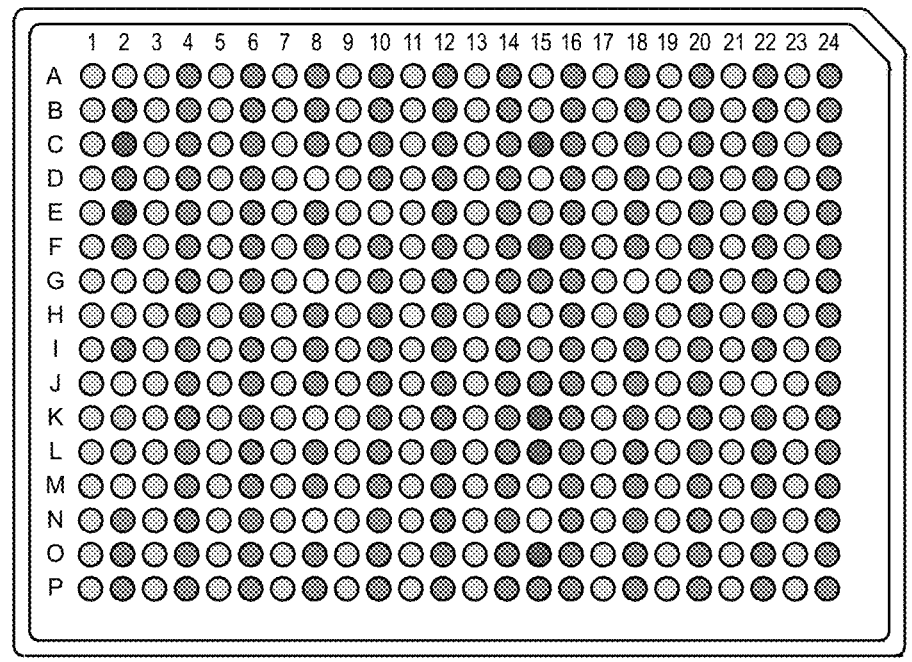
FIG. 5 illustrates a hypothetic signal pattern generated from the real-time detection of each well on a microtiter plate from FIG. 4.

The first and second modules may be configured to process multiple samples simultaneously for the screening assay mode, where the LDR products containing sequence tags provide relative quantitative results using real-time PCR readout (see FIG. 2). In this configuration, DNA and RNA isolated from various blood fractions from 24 individual samples are subjected to multiplexed PCR-LDR and RT-PCR-LDR, then distributed down a column, e.g., 16 wells in the microtiter plate as illustrated in FIG. 3. Tag primer sets with target-directed TaqMan™ probes, or alternatively with UniTaq primer sets are added across the rows as shown in FIG. 4, allowing for real-time PCR (FIG. 5). In this illustration, samples #2 & #15 have strong signal at >5 positions, so are considered potentially positive (pending additional verification as described more below), while sample #8 with 4 weak signals should also get additional workup.

Figure 6:
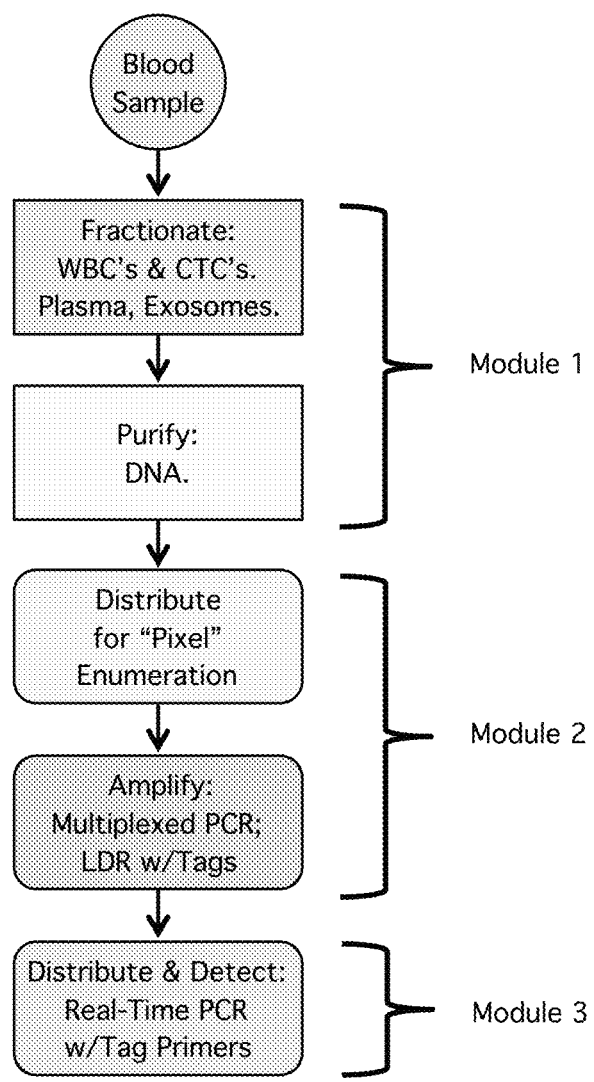
FIG. 6 illustrates the workflow for analysis of DNA from plasma cfDNA or CTC.
Figure 7:
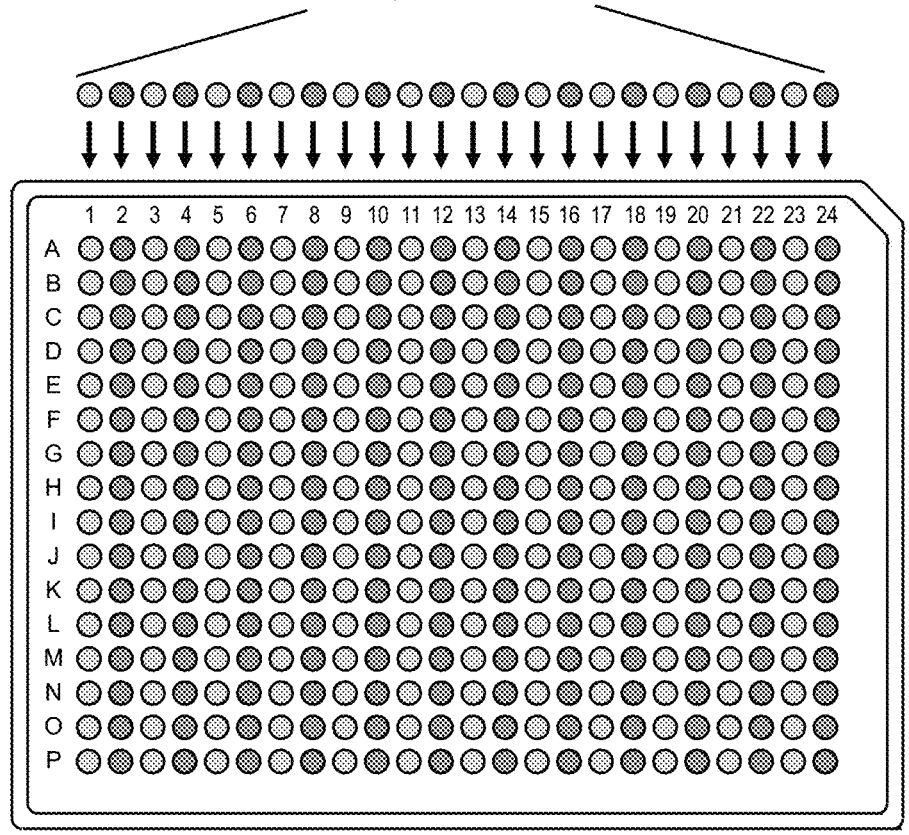
FIG. 7 illustrates the analysis of DNA, by distribution of one sample, which has initially been diluted and distributed across 24 tubes for multiplexed PCR or reverse-transcriptase PCR followed by LDR with tagged probes, into 24×16 rows of a microtiter plate.
Figure 8:
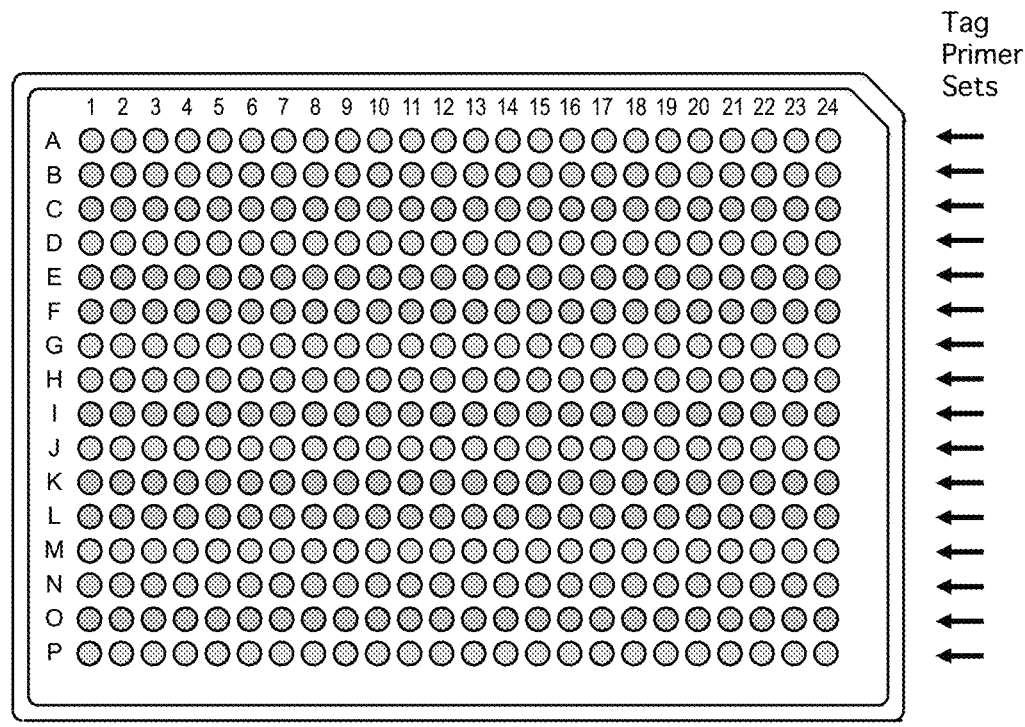
FIG. 8 illustrates the addition of 16 different tag primer sets across the 24 columns of a microtiter plate from FIG. 7.
Figure 9:
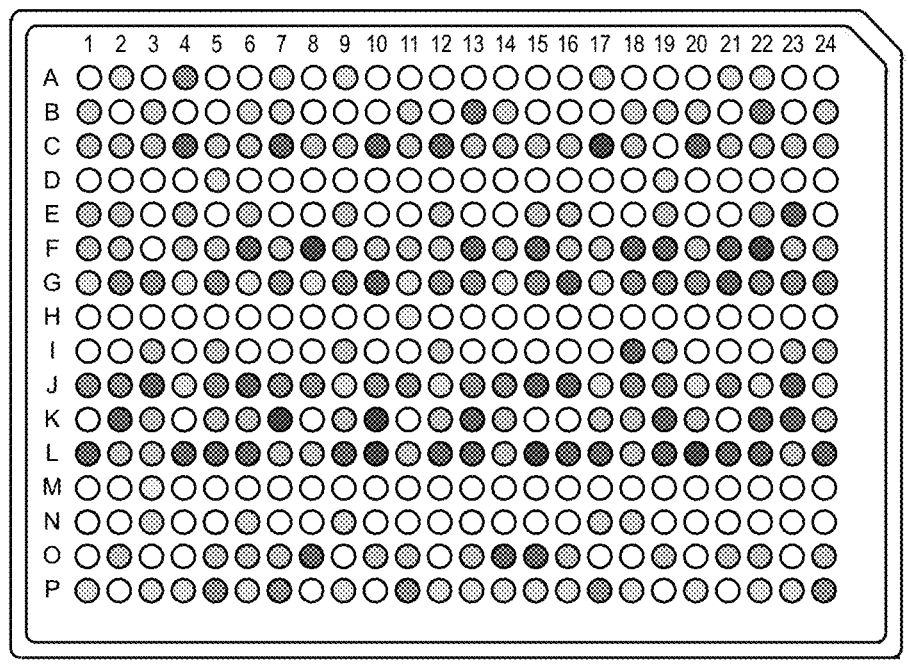
FIG. 9 illustrates a hypothetic signal pattern generated from the real-time detection of each well on a microtiter plate from FIG. 8.
Figure 10:
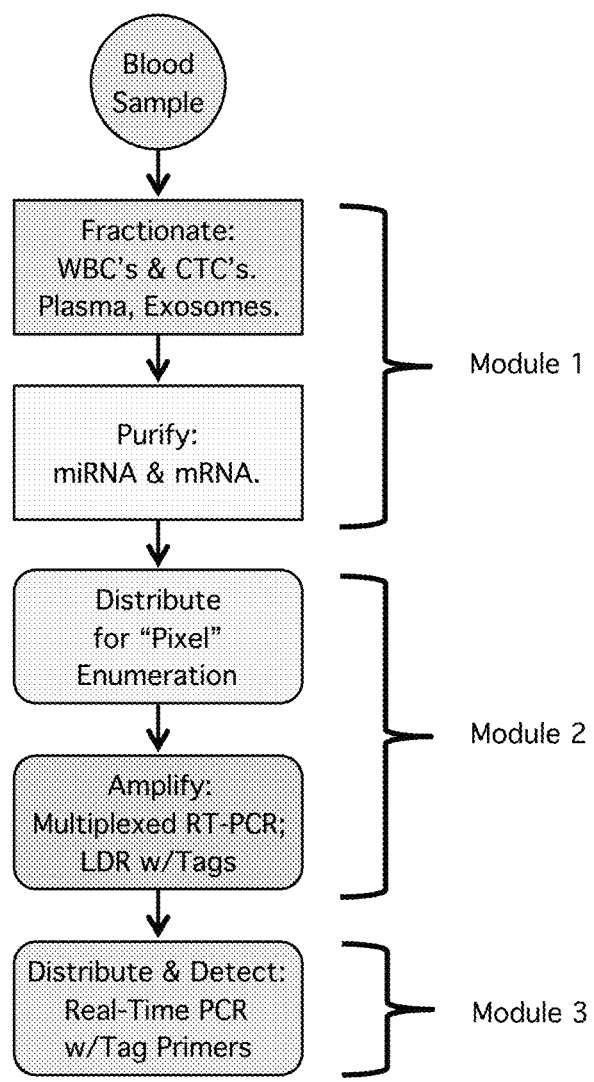
FIG. 10 illustrates a work flow for analysis of mRNA or miRNA from plasma exosomes and illustrates a work flow for analysis of DNA, mRNA, and miRNA from plasma cfDNA, exosomes and CTC.
Figure 29:
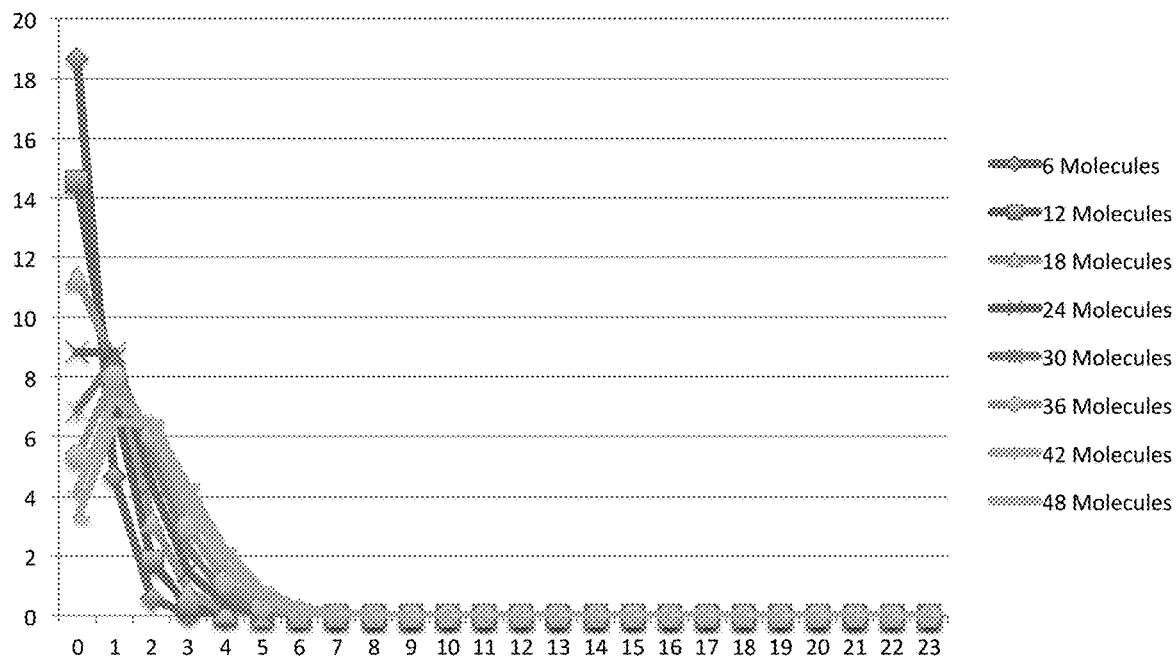
FIG. 29 illustrates a simulation of a Poisson distribution of 6 to 48 molecules distributed across 24 wells. At top is a tabular form of number of starting molecules versus molecules per well. At bottom is a histogram of # molecules (x) versus # of wells (y).
Figure 30:
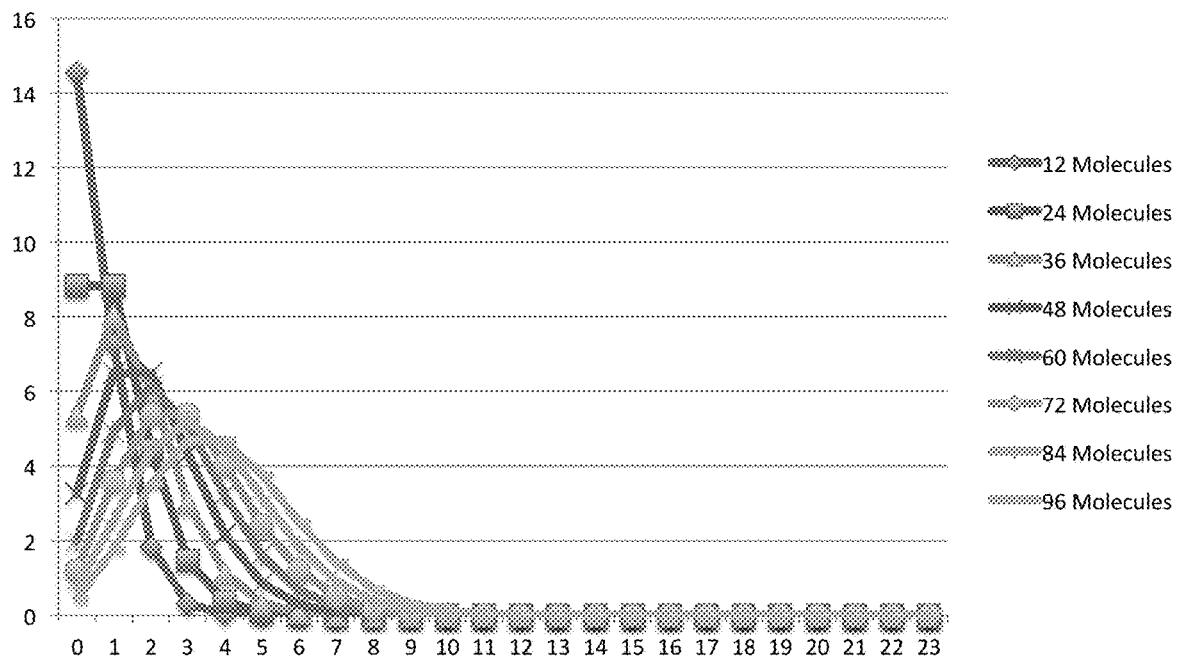
FIG. 30 illustrates a simulation of a Poisson distribution of 12 to 96 molecules distributed across 24 wells. At top is a tabular form of number of starting molecules versus molecules per well. At bottom is a histogram of # molecules (x) versus # of wells (y).
Figure 31:
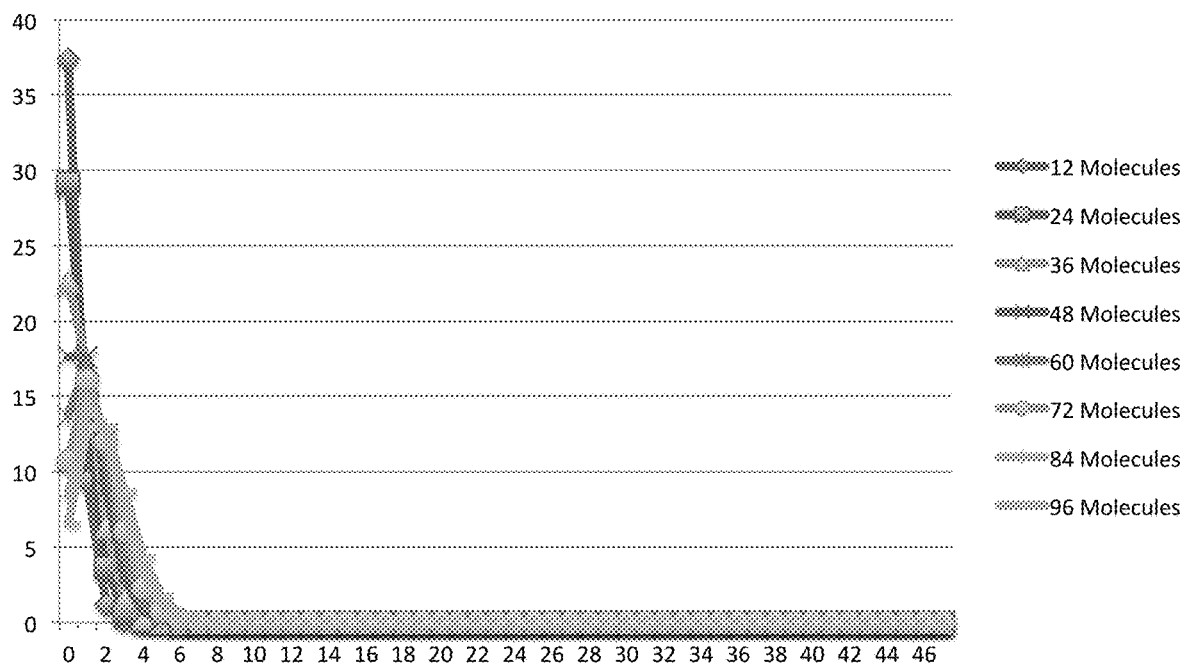
FIG. 31 illustrates a simulation of a Poisson distribution of 12 to 96 molecules distributed across 48 wells. At top is a tabular form of number of starting molecules versus molecules per well. At bottom is a histogram of # molecules (x) versus # of wells (y).
Figure 32:
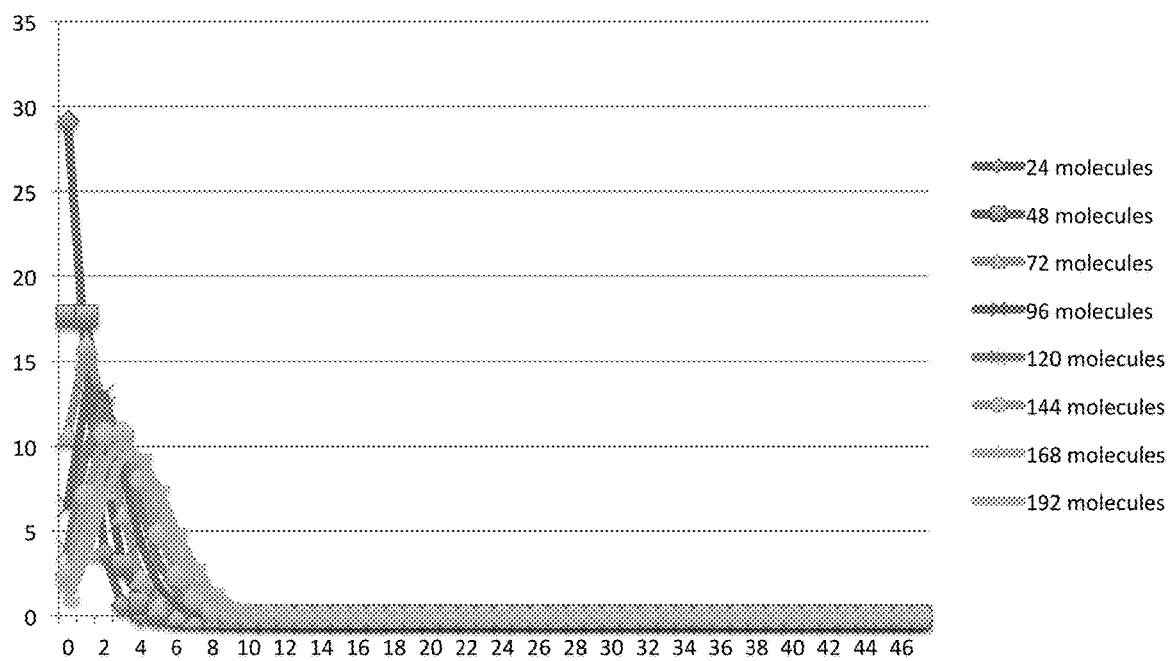
FIG. 32 illustrates a simulation of a Poisson distribution of 24 to 192 molecules distributed across 48 wells. At top is a tabular form of number of starting molecules versus molecules per well. At bottom is a histogram of # molecules (x) versus # of wells (y).
Figure 33:
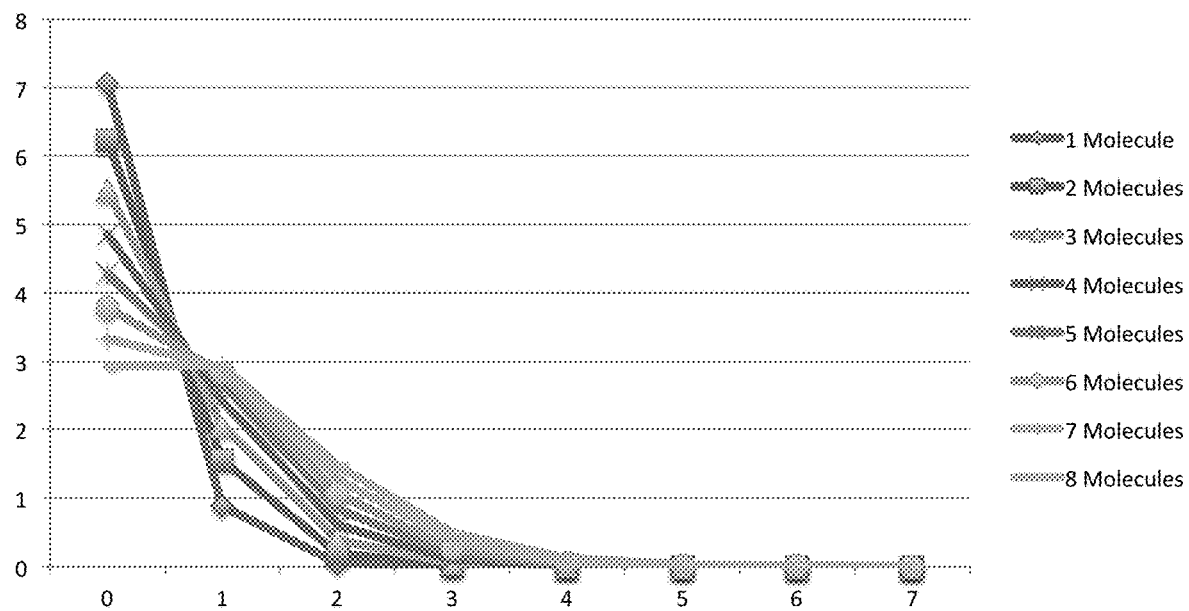
FIG. 33 illustrates a simulation of a Poisson distribution of 1 to 8 molecules distributed across 8 wells. At top is a tabular form of number of starting molecules versus molecules per well. At bottom is a histogram of # molecules (x) versus # of wells (y).
Figure 34:
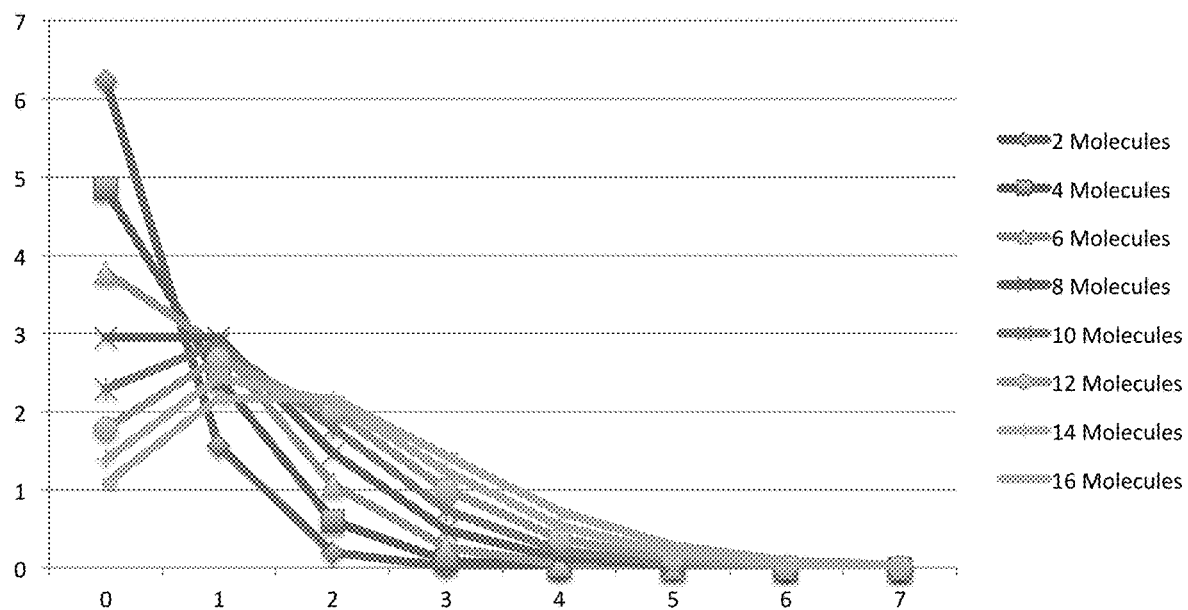
FIG. 34 illustrates a simulation of a Poisson distribution of 2 to 16 molecules distributed across 8 wells. At top is a tabular form of number of starting molecules versus molecules per well. At bottom is a histogram of # molecules (x) versus # of wells (y).
Figure 35:
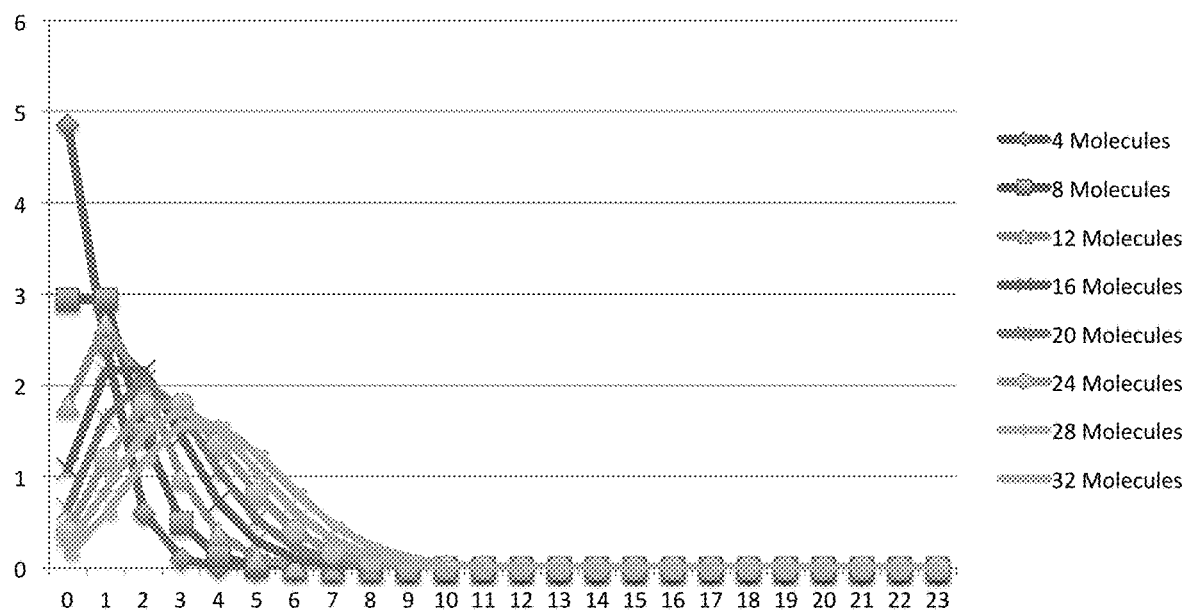
FIG. 35 illustrates a simulation of a Poisson distribution of 4 to 32 molecules distributed across 8 wells. At top is a tabular form of number of starting molecules versus molecules per well. At bottom is a histogram of # molecules (x) versus # of wells (y).
Figure 36:
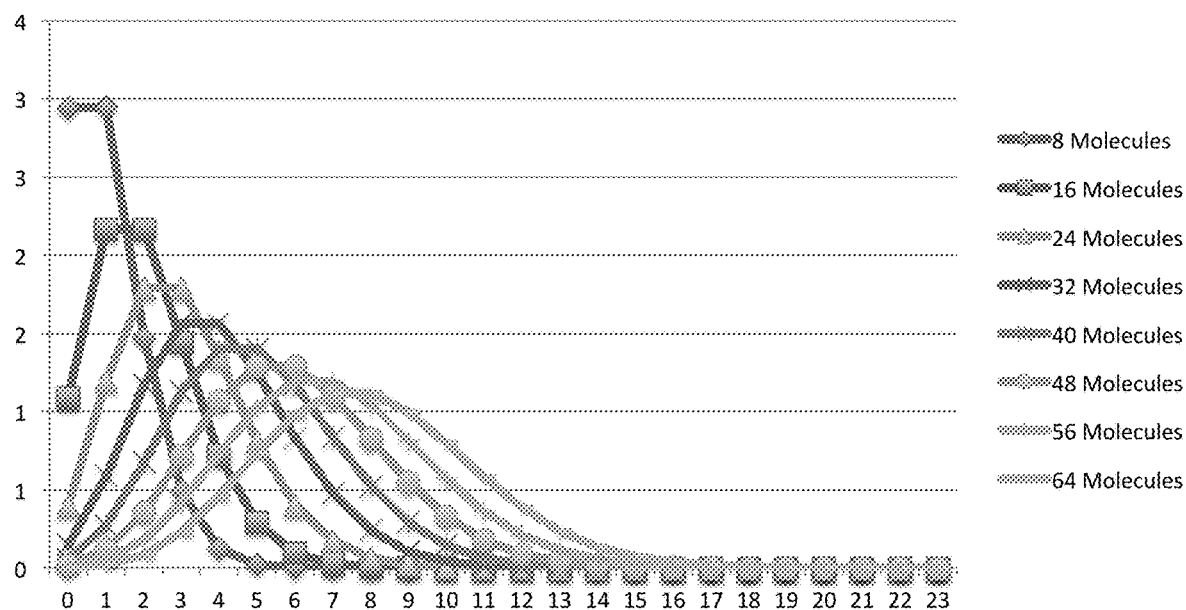
FIG. 36 illustrates a simulation of a Poisson distribution of 8 to 64 molecules distributed across 8 wells. At top is a tabular form of number of starting molecules versus molecules per well. At bottom is a histogram of # molecules (x) versus # of wells (y).
Figure 37:
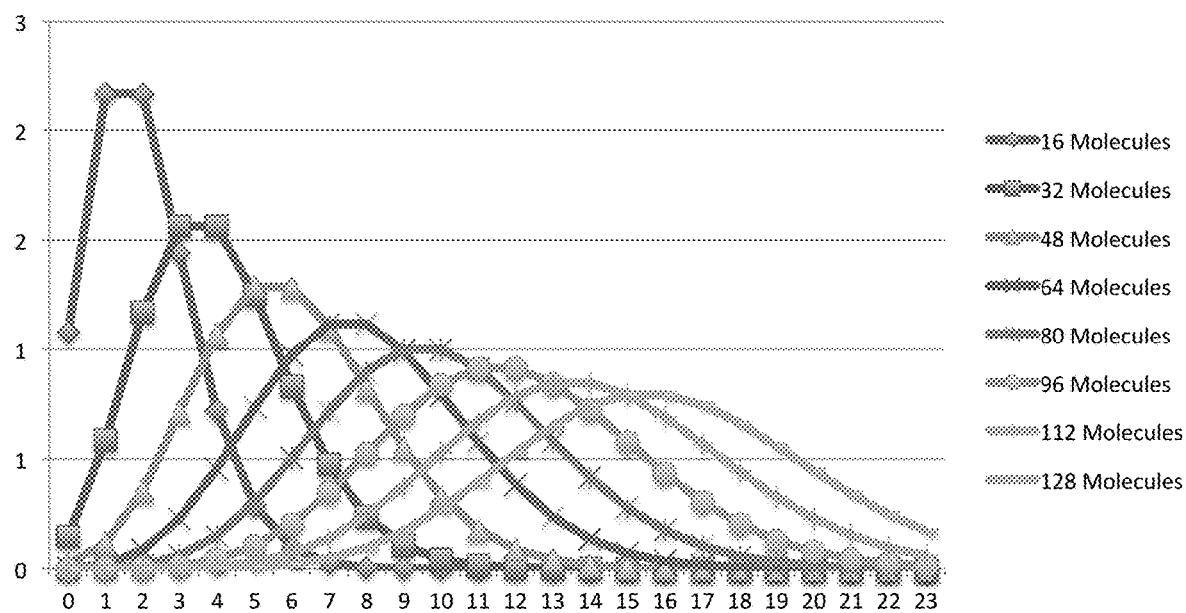
FIG. 37 illustrates a simulation of a Poisson distribution of 16 to 128 molecules distributed across 8 wells. At top is a tabular form of number of starting molecules versus molecules per well. At bottom is a histogram of # molecules (x) versus # of wells (y).

The two modules may also be configured to process a single sample, with spatial multiplexing enabling "pixel" PCR/LDR, where the LDR products enable enumeration of the original target molecules. This is analogous to digital PCR, but at a higher level of multiplexing (see FIG. 6). In this configuration the DNA and RNA from a single sample are distributed into 24 chambers prior to multiplex PCR-LDR as shown in FIG. 7. In this embodiment, some chambers have one or no target molecules. After multiplexing, the LDR products are distributed down a column, e.g., 16 wells in the microtiter plate (FIG. 7). Tag primer sets with target-directed TaqMan™ probes, or alternatively UniTaq primer sets, are added across the rows (see FIG. 8), allowing for real-time PCR (see FIG. 9). The results are interpreted based on Poisson distribution of Ct value as representing an integral multiple of a single molecule in the original mix, i.e., 0, 1, 2 etc. FIGS. 29 and 30 show a Poisson distribution of 6 to 48 and 12 to 96 molecules in 24 wells, respectively, and FIGS. 31 and 32 show a Poisson distribution of 12 to 96 and 24 to 192 molecules in 48 wells, respectively. FIG. 9, row A shows (# addresses: # initial target molecule) of (17:0; 6:1; 1:2), which corresponds to 8 molecules. FIG. 9, row K shows (7:0; 10:1; 5:2; 2:4), which corresponds to about 30 molecules.

Figure 11:
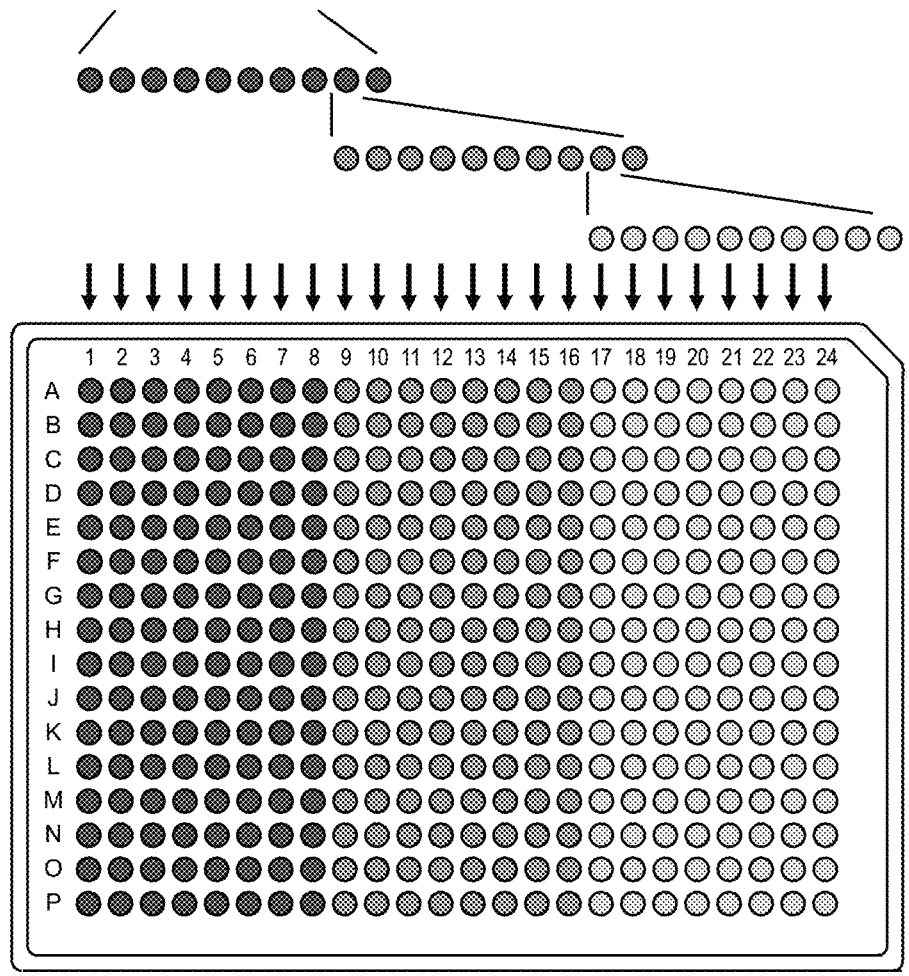
FIG. 11 illustrates the analysis of mRNA or miRNA, by distribution of one sample, which has initially been serially diluted into 24 tubes for multiplexed reverse-transcriptase PCR followed by LDR with tagged probes, into 24×16 rows of a microtiter plate.
Figure 12:
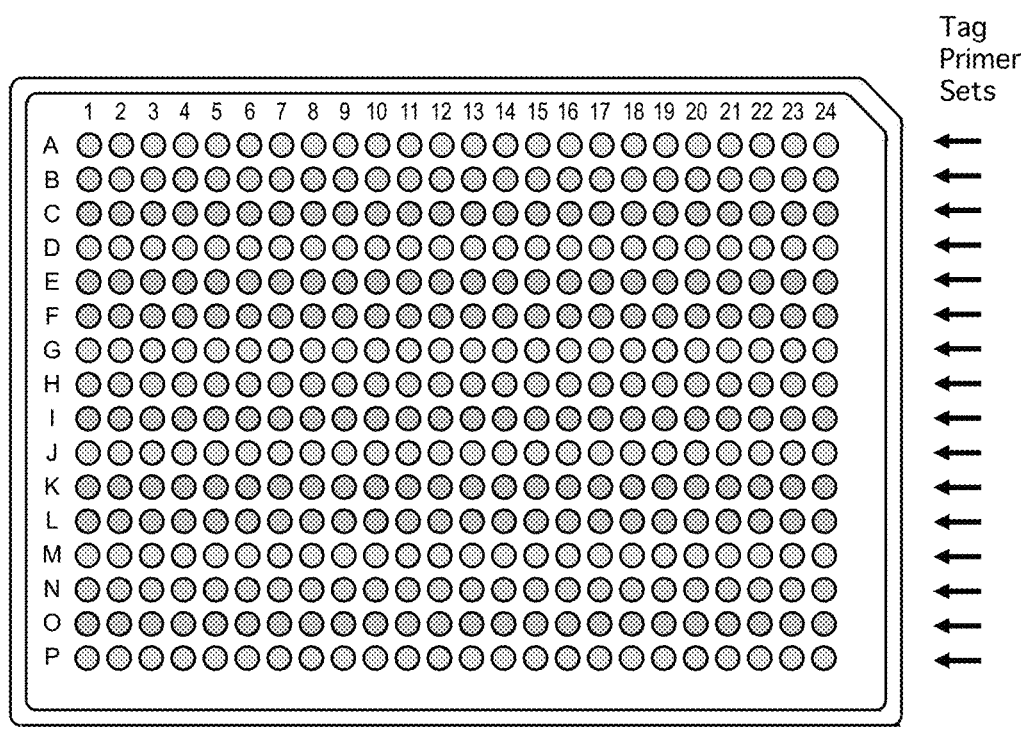
FIG. 12 illustrates the addition of 16 different tag primer sets across the 24 columns of a microtiter plate from FIG. 11.
Figure 13:
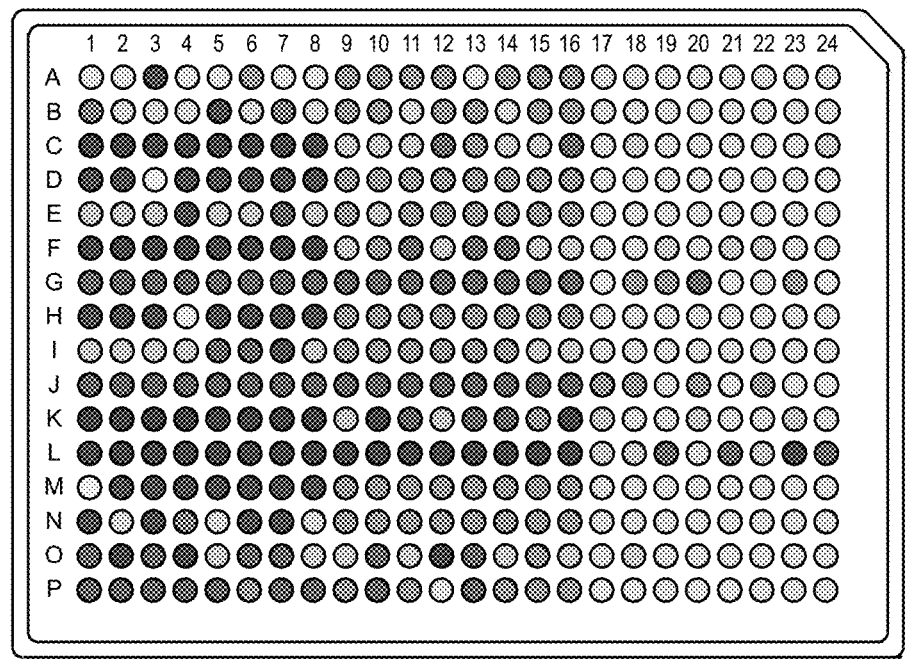
FIG. 13 illustrates a hypothetic signal pattern generated from the real-time detection of each well on a microtiter plate from FIG. 12.

A different form of dilution and distribution may be used to enumerate molecules over a wider range, as illustrated for miRNA or mRNA quantification in FIGS. 10-13. Here the initial sample is distributed into 8 chambers, diluted 10-fold and distributed into another 8 chambers, etc. (see FIG. 11). The samples are subjected to multiplexed RT-PCR and LDR, and the LDR products are individually distributed down a column (FIG. 11). Tag primer sets with target-directed TaqMan™ probes, or alternatively UniTaq primer sets, are added across the rows (see FIG. 12), allowing for real-time PCR and detection (see FIG. 13). For the example of 24 chambers, this can quantify across 3 orders of magnitude, but across 48 chambers it can cover 6 orders of magnitude differences. FIGS. 33-37 show Poisson distributions of 1 to 128 molecules in 8 wells. In the example illustrated in FIG. 13, row G, the first two dilutions give higher signal than the last 8 wells (1:0; 3:1; 3:2; 1:4), which corresponds to about 14-16×100×1.25=1,750 to 2,000 molecules. In contrast, row N of FIG. 13 gave signal only in the first 8 well distribution (4:0; 3:1; 1:2), which corresponds to about 5-6×1.25=6 to 8 molecules.

The second family of assay designs is based on an initial multiplexed PCR or RT-PCR amplification followed by distribution and capture of PCR amplified targets on the wells of a microtiter plate. A single cycle of LDR enables capture of LDR products on the correct targets on the solid support, while mis-ligations are washed away. The LDR products are quantified, either through LDR-FRET, real-time PCR, or other reporter systems.

The first module takes an input sample of blood, and separates CTCs if present, separates plasma from blood cells, and exosomes from plasma, and then purifies (i) DNA and RNA from CTCs if present, (ii) miRNA and RNA from exosomes, and (iii) cfDNA from plasma.

The second module enables distribution of the above components into 24 or 48 chambers or wells for spatial multiplexing with proportional multiplexed PCR or RT-PCR amplification of targeted gene, promoter, miRNA, or mRNA regions. These include: (i) specific chromosomal regions for copy number enumeration from CTC's, (ii) specific splice-variant or gene-fusion mRNAs from CTC's, (iii) specific miRNAs from exosomes, (iv) specific mRNAs from exosomes, (v) specific cancer gene DNA regions from cfDNA, and (vi) specific (methylated) promoter regions from cfDNA.

The third module enables spatial distribution of the above products down a column, e.g., 16 wells in the microtiter plate, followed by capture of the amplified target on the solid support, e.g., in a 24×16 or 48×32 configuration. This module enables capture of LDR products on the solid support, followed by detection and enumeration of LDR products to provide quantitative results for each marker.

Figure 14:
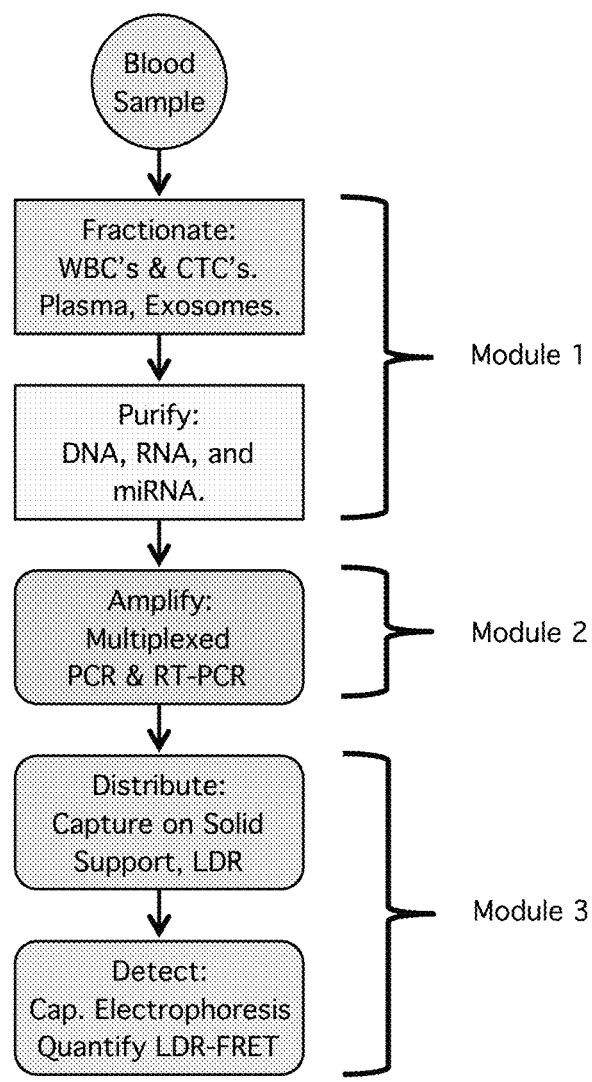
FIG. 14 illustrates the workflow for the generic analysis of DNA, mRNA or miRNA by distribution of one sample, which has initially been diluted across 24 tubes for multiplexed PCR or reverse-transcriptase PCR followed by LDR with tagged probes, for streptavidin mediated capture in 24×16 rows of a microtiter plate.
Figure 15:
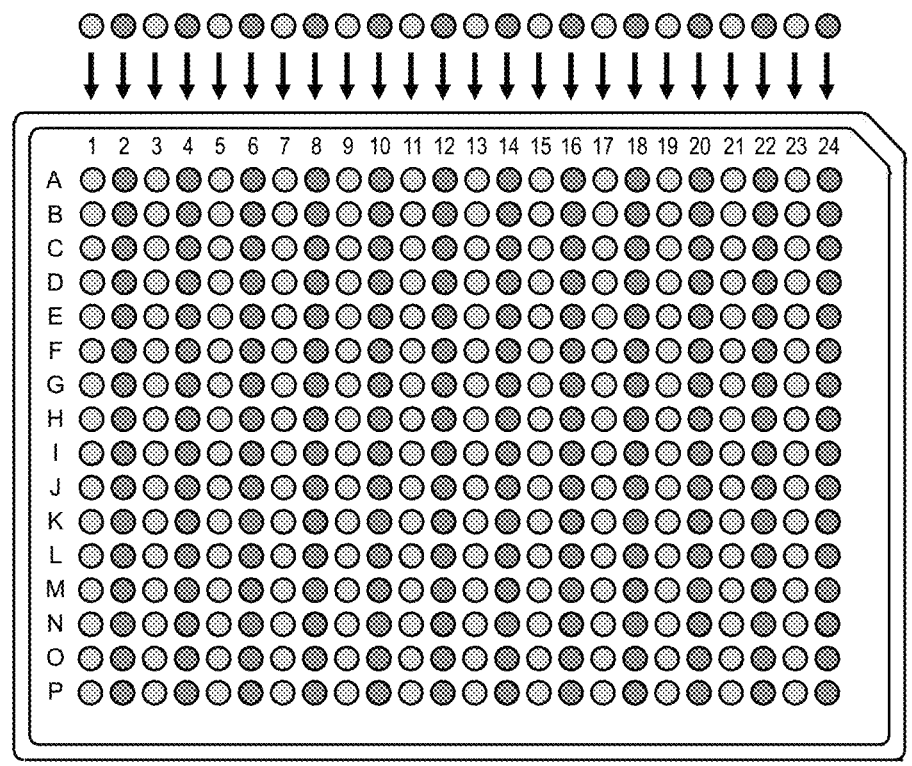
FIG. 15 illustrates the generic analysis of DNA, mRNA or miRNA by distribution of 24 samples, which have initially been diluted and distributed across 24 tubes for multiplexed PCR or reverse-transcriptase PCR followed by LDR with tagged probes, into 24×16 rows of a microtiter plate.
Figure 16:
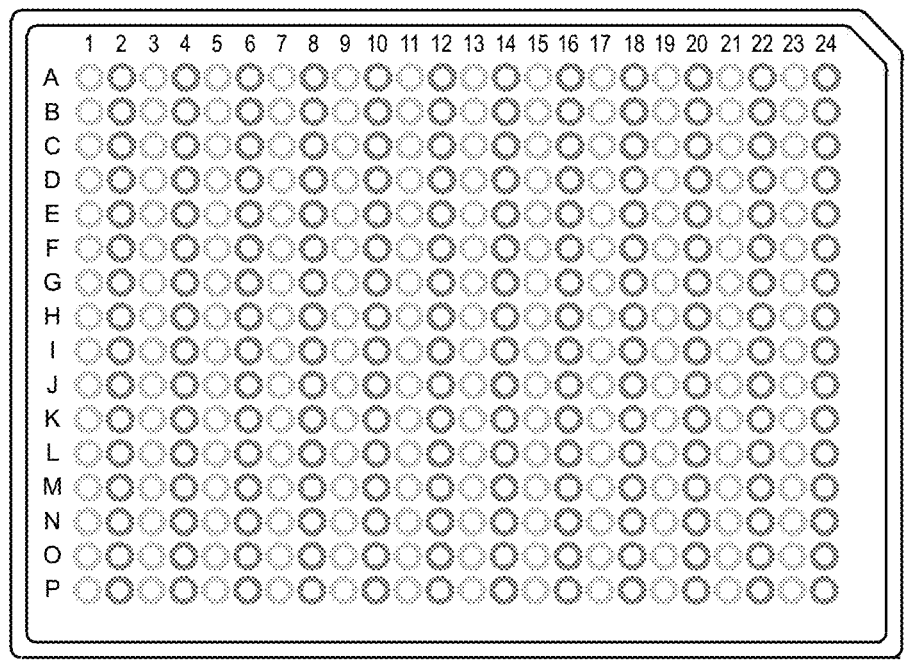
FIG. 16 illustrates the streptavidin mediated capture of the biotinylated PCR or RT-PCR amplicons in the wells of a microtiter plate from FIG. 15.
Figure 17:
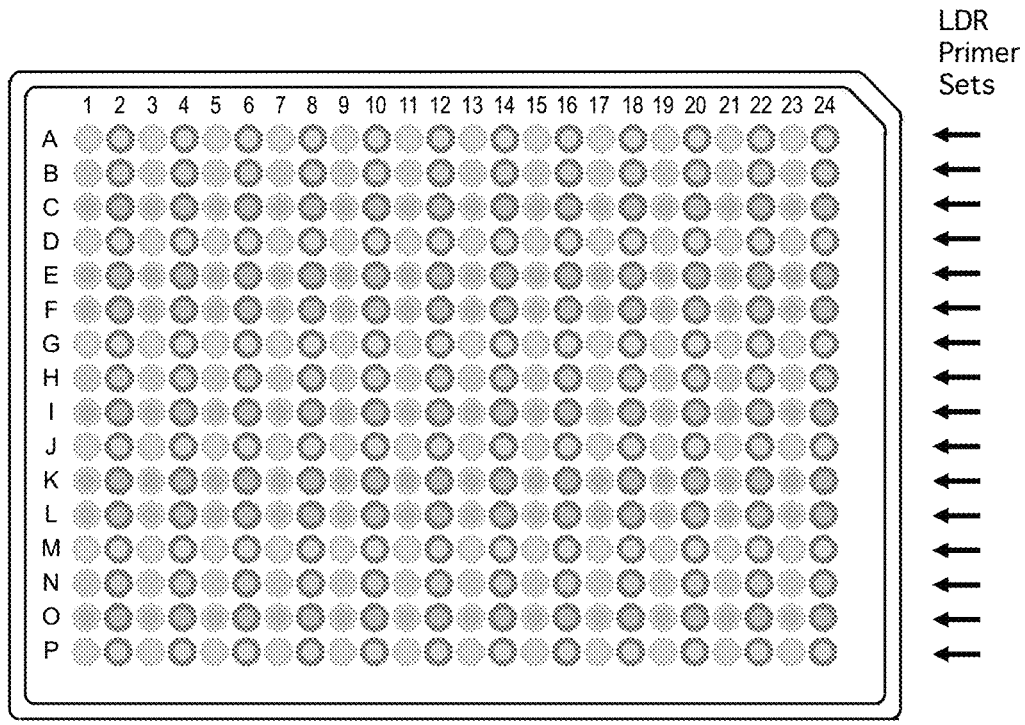
FIG. 17 illustrates the addition of 16 different tag primer sets across the 24 columns of a microtiter plate from FIG. 16.
Figure 18:
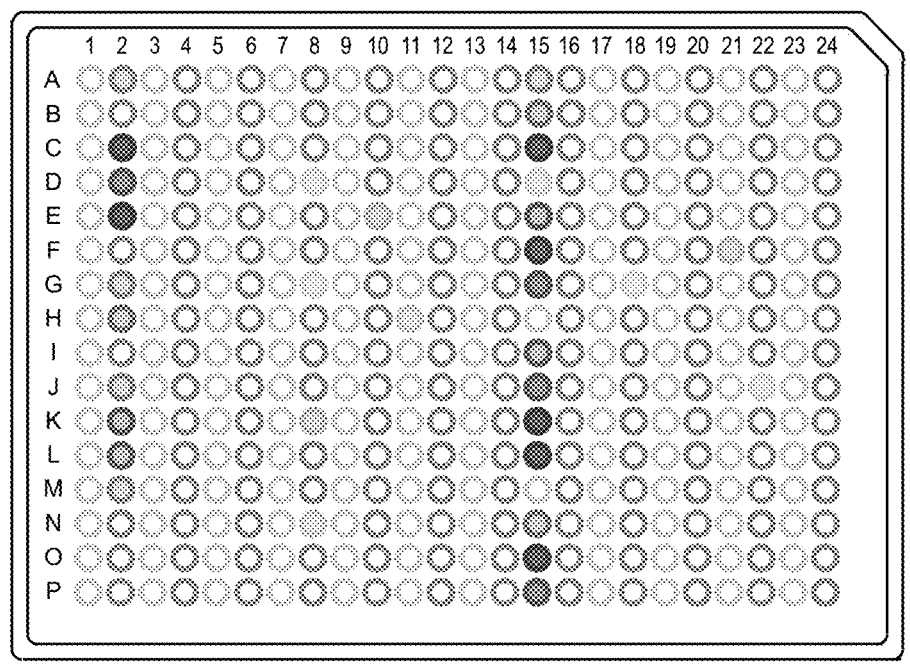
FIG. 18 illustrates a hypothetic signal pattern generated from the real-time detection of LDR-FRET in each well on a microtiter plate from FIG. 17.
Figure 19:
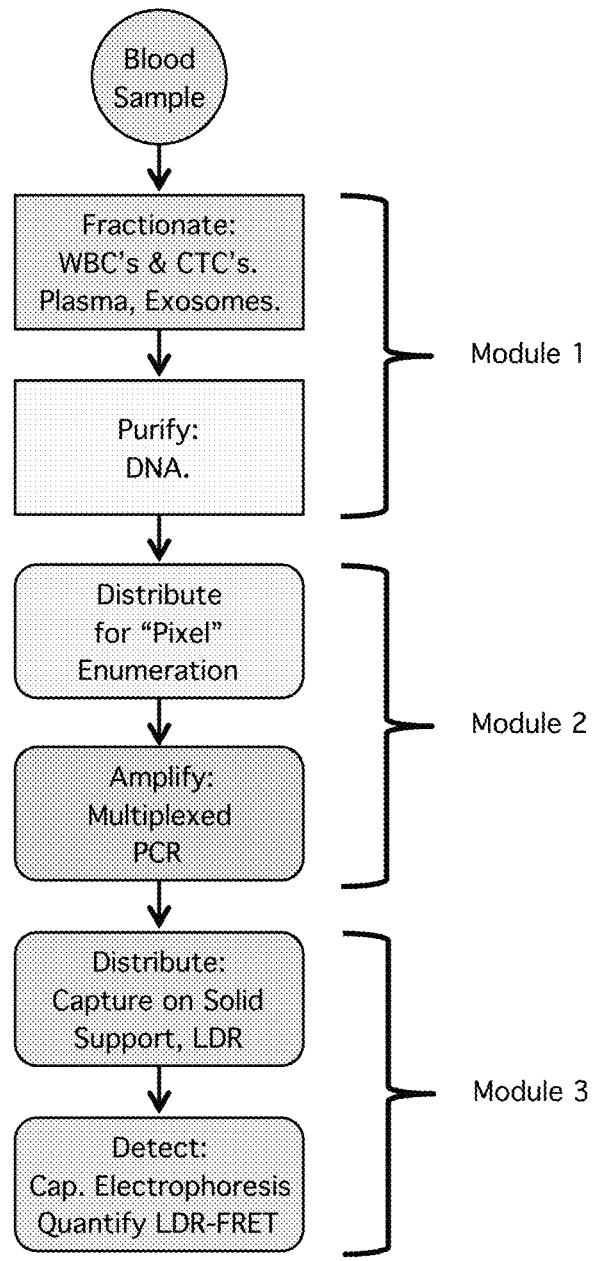
FIG. 19 illustrates the workflow for the analysis of DNA by distribution of one sample, which has initially been diluted across 24 tubes for multiplexed PCR followed by LDR with tagged probes, for streptavidin mediated capture in 24×16 rows of a microtiter plate.
Figure 20:
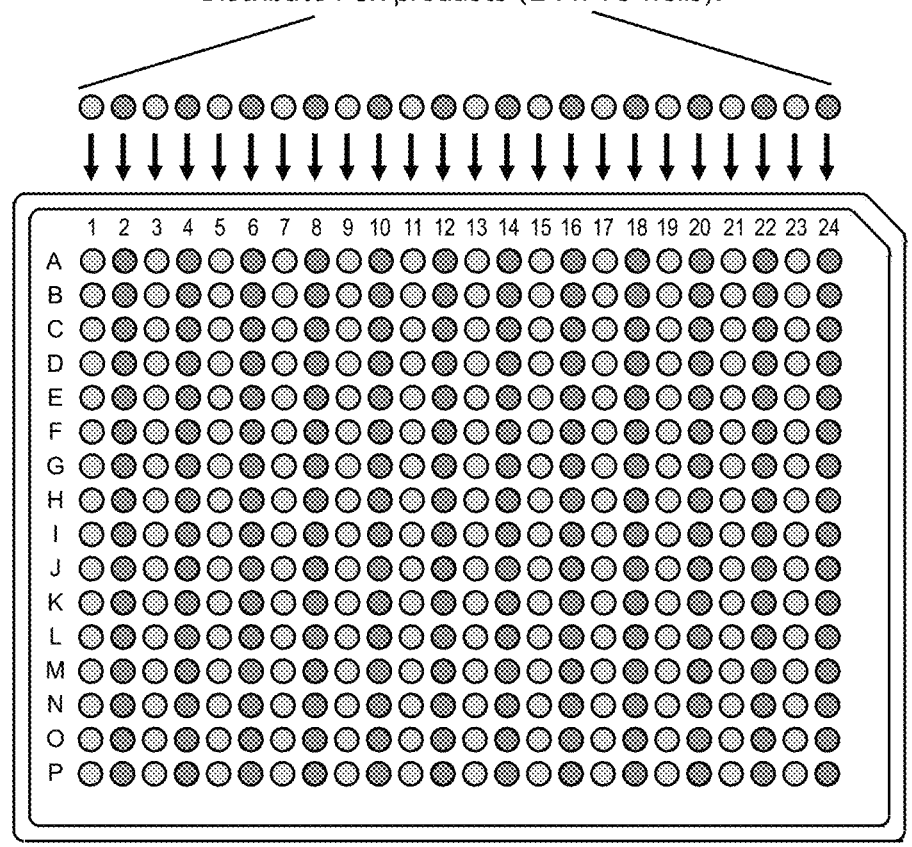
FIG. 20 illustrates the analysis of DNA by distribution of 24 samples, which have initially been diluted and distributed across 24 tubes for multiplexed PCR followed by LDR with tagged probes, into 24×16 rows of a microtiter plate.
Figure 21:
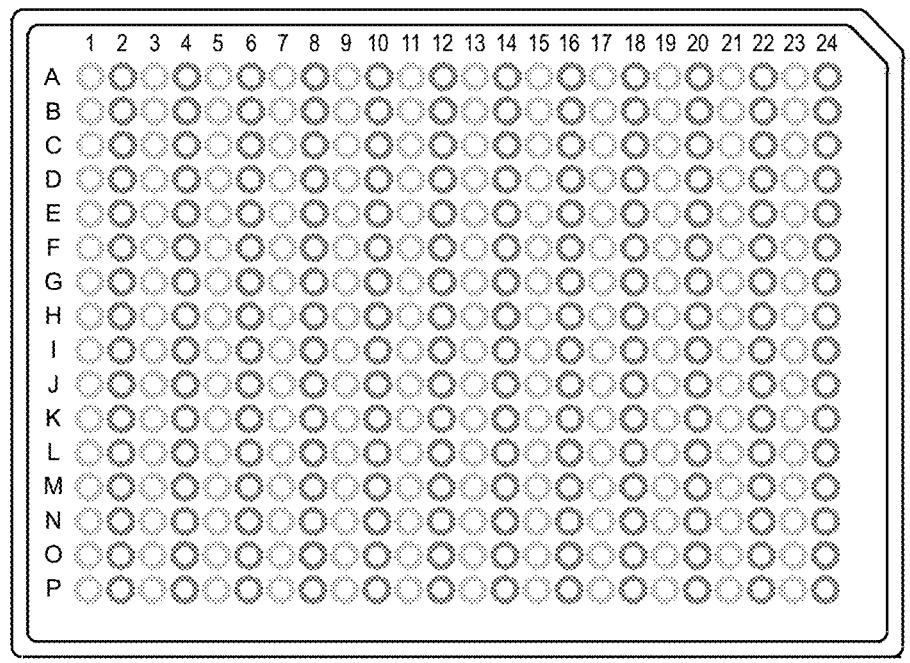
FIG. 21 illustrates the streptavidin mediated capture of the biotinylated PCR or RT-PCR amplicons in the wells of a microtiter plate from FIG. 20.
Figure 22:
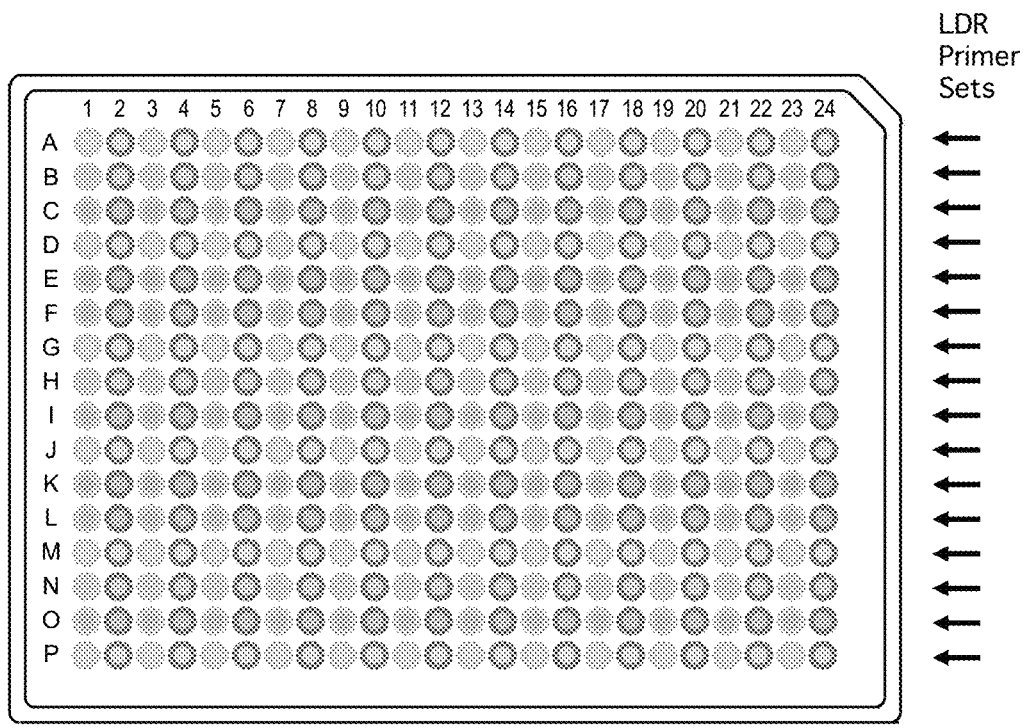
FIG. 22 illustrates the addition of 16 different tag primer sets across the 24 columns of a microtiter plate from FIG. 21.
Figure 23:
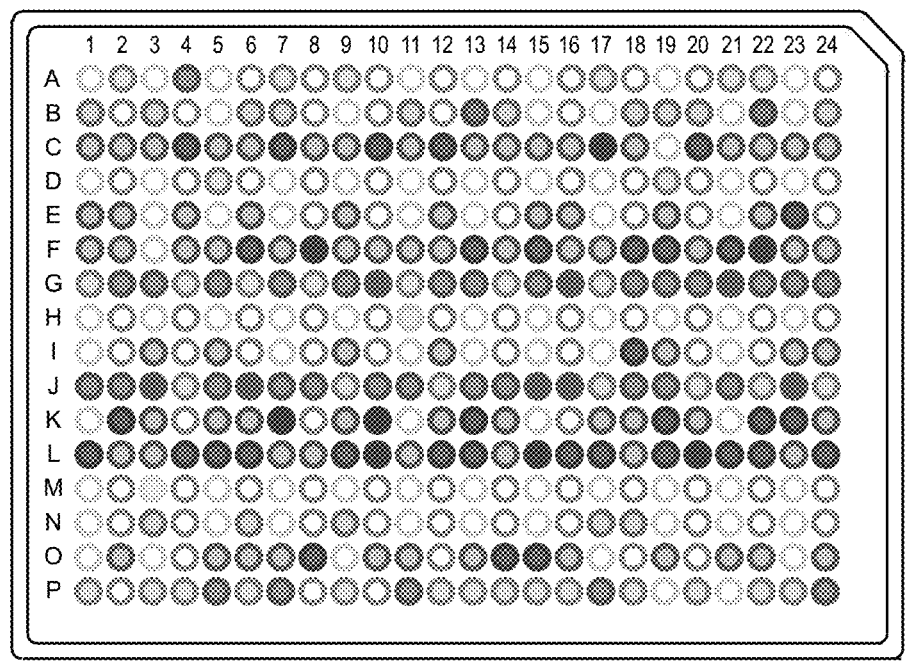
FIG. 23 illustrates a hypothetic signal pattern generated from the real-time detection of LDR-FRET in each well on a microtiter plate from FIG. 22.
Figure 24:
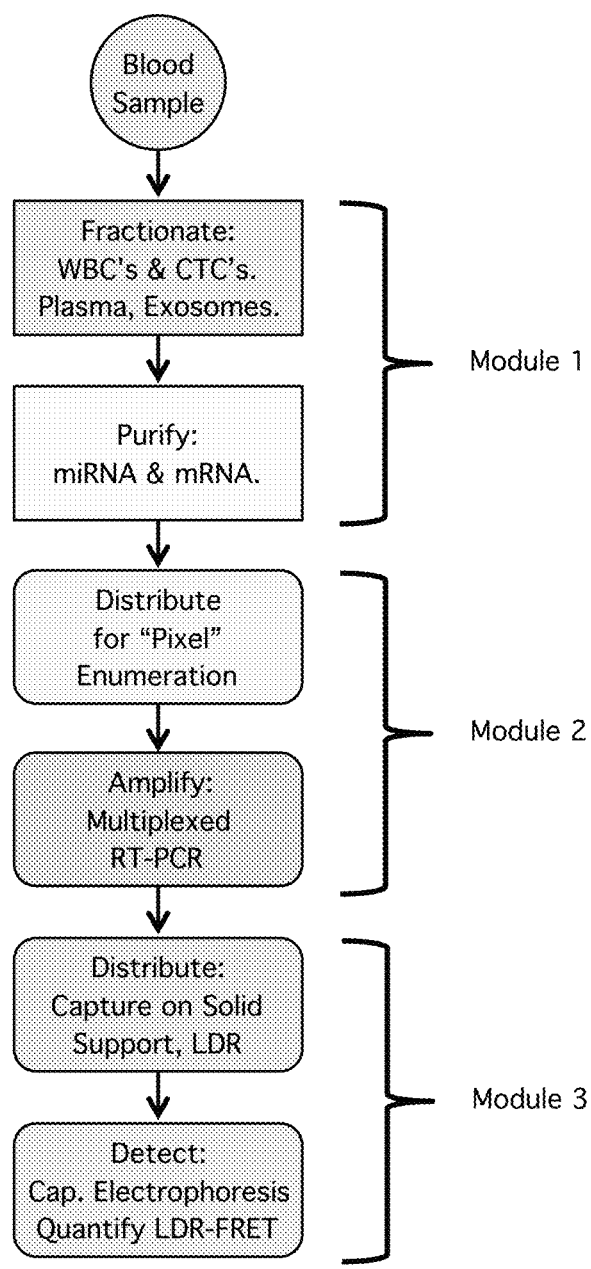
FIG. 24 illustrates the workflow for the analysis of mRNA & miRNA by distribution of one sample, which has initially been diluted across 24 tubes for multiplexed PCR followed by LDR with tagged probes, for streptavidin mediated capture in 24×16 rows of a microtiter plate.

The first and second modules may be configured to process multiple samples simultaneously for the screening assay mode, wherein the LDR products provide relative quantitative results, analogous to real-time PCR readout (see schematic overview of FIG. 14). In this configuration, DNA and RNA isolated from various blood fractions from 24 individual samples are subjected to multiplexed PCR and RT-PCR, then distributed down a column, e.g., 16 wells in the microtiter plate, and captured on the solid support (see FIGS. 15 and 16). LDR probes are added across the rows, and ligation on correct target captures the product while unreacted primer is washed away (FIG. 17). The LDR-FRET results illustrated in FIG. 18 are shown in their respective wells, although in this module, the products may also be selectively denatured and enumerated using capillary electrophoresis to provide quantitative results. In this illustration (FIG. 18), samples #2 & 15 have strong signal at >5 positions, so are presumptive positive, while sample 8 with 4 weak signals should also get additional workup The two modules may also be configured to process a single sample, with spatial multiplexing enabling "pixel" PCR/LDR, wherein the LDR products enable enumeration of the original target molecules, analogous to digital PCR, but at a higher level of multiplexing (FIG. 19). In this configuration the DNA and RNA from a single sample are distributed into 24 chambers prior to multiplex PCR (FIG. 20), such that some chambers have one or no target molecules. The amplicons are distributed down a column, e.g., 16 wells in the microtiter plate, and captured on the solid support (FIGS. 20 and 21). LDR probe addition and LDR product detection is as above (FIGS. 22 and 23). The results are interpreted based on Poisson distribution of LDR value as representing an integral multiple of a single molecule in the original mix, i.e., 0, 1, 2 etc. FIGS. 29 and 30 show the Poisson distribution of 6-48 and 12-96 molecules in 24 wells, respectively, and FIGS. 31 and 32 show the Poisson distribution of 12-96 and 24-192 molecules in 48 wells, respectively. FIG. 23, row A shows (# addresses: # initial target molecule) of (17:0; 6:1; 1:2), which corresponds to 8 molecules. FIG. 23, row K shows (7:0; 10:1; 5:2; 2:4), which corresponds to about 30 molecules.

Figure 25:
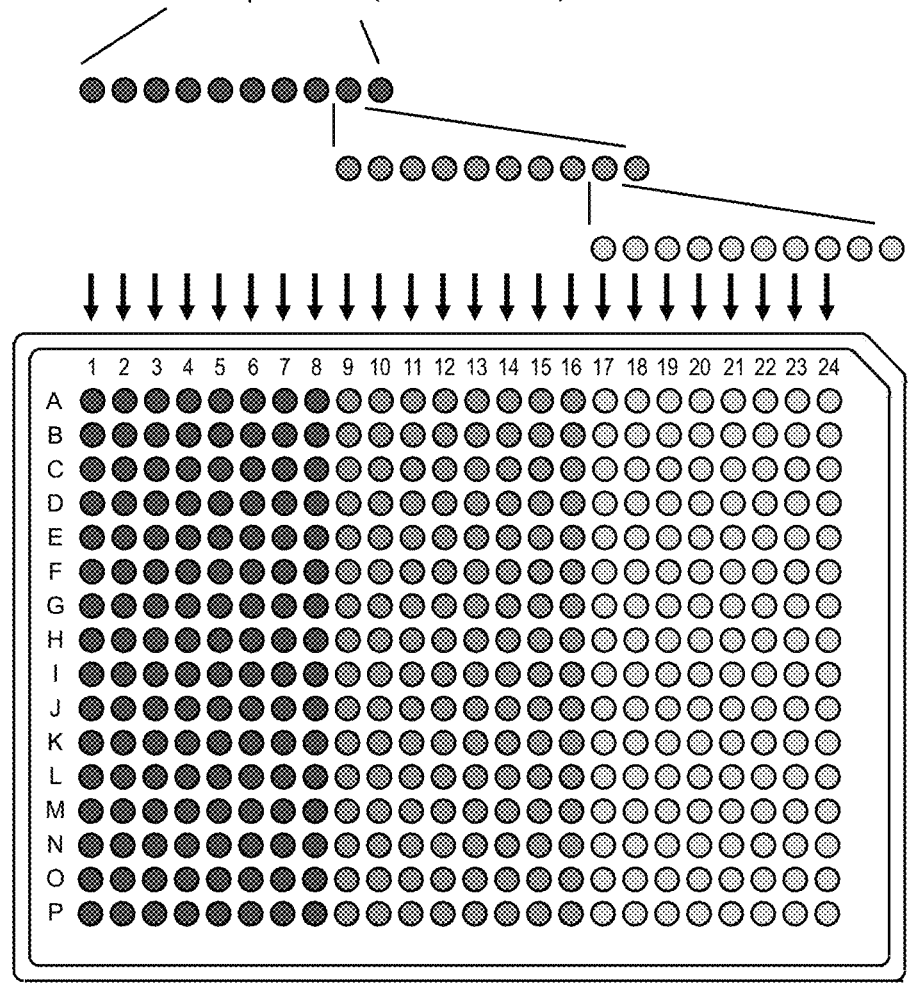
FIG. 25 illustrates the analysis of mRNA or miRNA, by distribution of one sample, which has initially been serially diluted into 24 tubes for multiplexed reverse-transcriptase PCR followed by LDR with tagged probes, into 24×16 rows of a microtiter plate.
Figure 26:
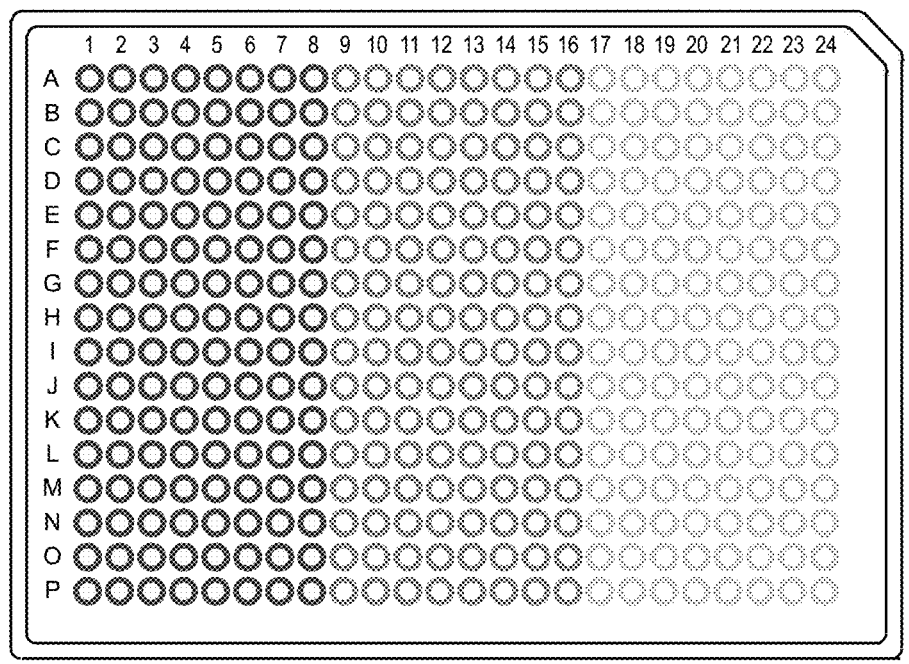
FIG. 26 illustrates the streptavidin mediated capture of RT-PCR amplicons in the wells of a microtiter plate from FIG. 25.
Figure 27:
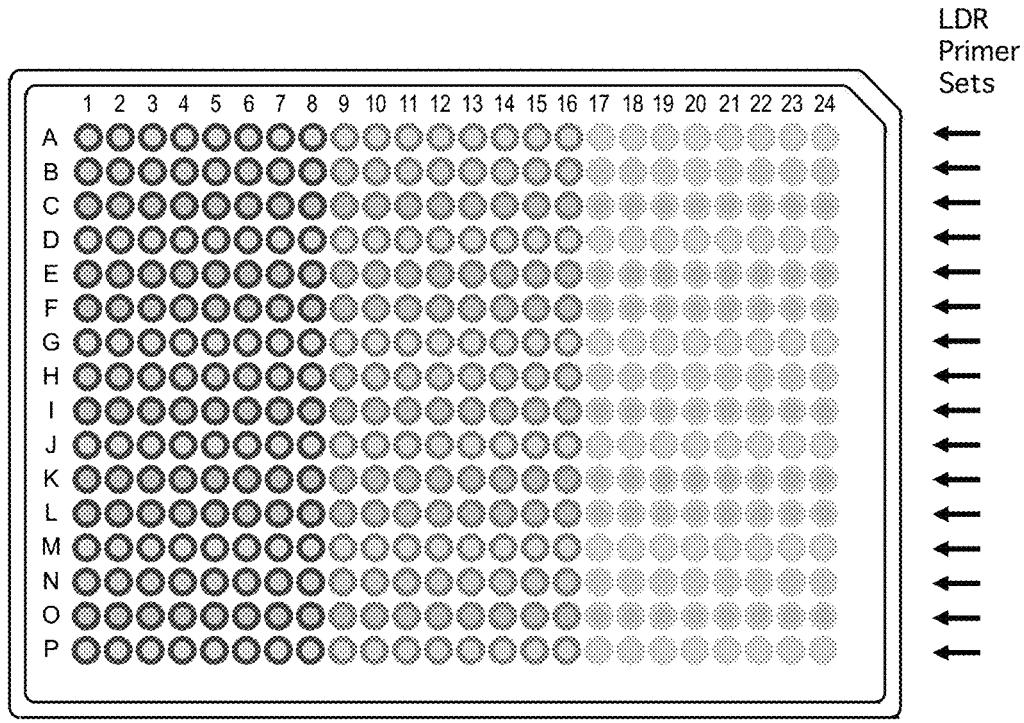
FIG. 27 illustrates the addition of 16 different tag primer sets across the 24 columns of a microtiter plate from FIG. 26.
Figure 28:
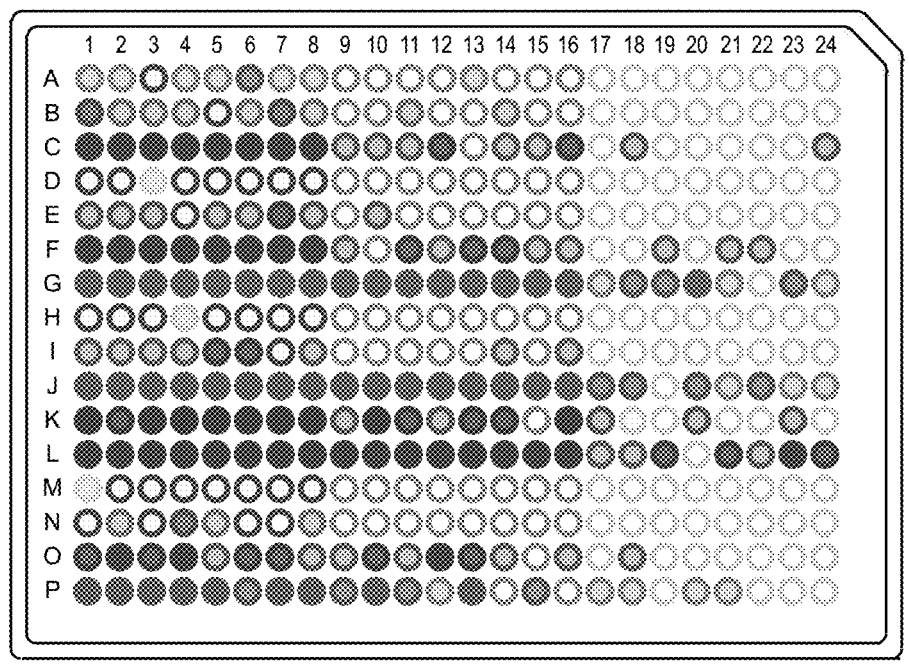
FIG. 28 illustrates a hypothetic signal pattern generated from the real-time detection of LDR-FRET in each well on a microtiter plate from FIG. 27.

A different form of dilution and distribution may be used to enumerate molecules over a wider range, as illustrated for miRNA or mRNA quantification in FIGS. 24-28. Here the initial sample is distributed into 8 chambers, diluted 10-fold and distributed into another 8 chambers, etc. (FIG. 25). The samples are subjected to multiplex RT-PCR and distributed down a column. The RT-PCR products are captured on a solid support (FIG. 26) and LDR primer sets are added across the rows (see FIG. 27). For the example of 24 chambers, this can quantify across 3 orders of magnitude, but across 48 chambers it can cover 6 orders of magnitude differences (see Poisson distributions of FIGS. 33-37). In the example illustrated in FIG. 28, row G, the first two dilutions give higher signal than the last 8 wells (1:0; 3:1; 3:2; 1:4), which corresponds to about 14-16×100×1.25=1,750 to 2,000 molecules. In contrast, FIG. 28, row N gave signal only in the first 8 well distribution (4:0; 3:1; 1:2), which corresponds to about 5-6×1.25=6 to 8 molecules.

False-Positives and Carryover Protection

There is a technical challenge of distinguishing true signal generated from the desired disease-specific nucleic acid differences vs. false signal generated from normal nucleic acids present in the sample vs. false signal generated in the absence of the disease-specific nucleic acid differences (i.e. somatic mutations).

A number of solutions to these challenges are presented below, but they share some common themes.

The first theme is multiplexing. PCR works best when primer concentration is relatively high, from 50 nM to 500 nM, limiting multiplexing. Further, the more PCR primer pairs added, the chances of amplifying incorrect products or creating primer-dimers increase exponentially. In contrast, for LDR probes, low concentrations on the order of 4 nM to 20 nM are used, and probe-dimers are limited by the requirement for adjacent hybridization on the target to allow for a ligation event. Use of low concentrations of gene-specific PCR primers or LDR probes containing universal primer sequence "tails" allows for subsequent addition of higher concentrations of universal primers to achieve proportional amplification of the initial PCR or LDR products. Another way to avoid or minimize false PCR amplicons or primer dimers is to use PCR primers containing a few extra bases and a blocking group, which is liberated to form a free 3'OH by cleavage with a nuclease only when hybridized to the target, e.g., a ribonucleotide base as the blocking group and RNase H2 as the cleaving nuclease.

The second theme is fluctuations in signal due to low input target nucleic acids. Often, the target nucleic acid originated from a few cells, either captured as CTCs, or from tumor cells that underwent apoptosis and released their DNA as small fragments (140-160 bp) in the serum. Under such conditions, it is preferable to perform some level of proportional amplification to avoid missing the signal altogether or reporting inaccurate copy number due to fluctuations when distributing small numbers of starting molecules into individual wells (for real-time, or droplet PCR quantification). As long as these initial universal amplifications are kept at a reasonable level (approximately 12 to 20 cycles), the risk of carryover contamination during opening of the tube and distributing amplicons for subsequent detection/quantification (using real-time, or droplet PCR) is minimized.

The third theme is target-independent signal, also known as "No Template Control" (NTC). This arises from either polymerase or ligase reactions that occur in the absence of the correct target. Some of this signal may be minimized by judicious primer design. For ligation reactions, the 5'→3' nuclease activity of polymerase may be used to liberate the 5' phosphate of the downstream ligation primer (only when hybridized to the target), so it is suitable for ligation. Further specificity for distinguishing presence of a low-level mutation may be achieved by: (i) using upstream LDR probes containing a mismatch in the $2^{nd}$ or $3^{rd}$ position from the 3'OH, (ii) using LDR probes to wild-type sequence that (optionally) ligate but do not undergo additional amplification, and (iii) using upstream LDR probes containing a few extra bases and a blocking group, which is liberated to form a free 3'OH by cleavage with a nuclease only when hybridized to the complementary target (e.g., RNase H2 and a ribonucleotide base).

The fourth theme is either suppressed (reduced) amplification or incorrect (false) amplification due to unused primers in the reaction. One approach to eliminate such unused primers is to capture genomic or target or amplified target DNA on a solid support, allow ligation probes to hybridize and ligate, and then remove probes or products that are not hybridized. Alternative solutions include pre-amplification, followed by subsequent nested LDR and/or PCR steps, such that there is a second level of selection in the process.

The fifth theme is carryover prevention. Carryover signal may be eliminated by standard uracil incorporation during the universal amplification step, and using UDG (and optionally AP endonuclease) in the pre-amplification workup procedure. Incorporation of carryover prevention is central to the methods of the present invention as described in more detail below. The initial PCR amplification is performed using incorporation of uracil. The LDR reaction is performed with LDR probes lacking uracil. Thus, when the LDR products are subjected to real-time PCR quantification, addition of UDG destroys the initial PCR products, but not the LDR products. Further, since LDR is a linear process and the tag primers use sequences absent from the human genome, accidental carryover of LDR products back to the original PCR will not cause template-independent amplification. Additional schemes to provide carryover prevention with methylated targets include use of restriction endonucleases before amplification, or after bisulfite treatment if using the latter approach as described infra.

Methods of Identifying Disease Markers

A first aspect of the present invention is directed to a method for identifying, in a sample, one or more nucleic acid molecules containing a target nucleotide sequence differing from nucleotide sequences in other nucleic acid molecules in the sample, or other samples, by one or more nucleotides, one or more copy numbers, one or more transcript sequences, and/or one or more methylated residues. This method involves providing a sample potentially containing one or more nucleic acid molecules containing the target nucleotide sequence differing from the nucleotide sequences in other nucleic acid molecules by one or more nucleotides, one or more copy numbers, one or more transcript sequences, and/or one or more methylated residues, and contacting the sample with one or more enzymes capable of digesting deoxyuracil (dU) containing nucleic acid molecules present in the sample. One or more primary oligonucleotide primer sets are provided, each primary oligonucleotide primer set comprising (a) a first primary oligonucleotide primer that comprises a nucleotide sequence that is complementary to a sequence adjacent to the target nucleotide sequence, and (b) a second primary oligonucleotide primer that comprises a nucleotide sequence that is complementary to a portion of an extension product formed from the first primary oligonucleotide primer. The contacted sample is blended with the one or more primary oligonucleotide primer sets, a deoxynucleotide mix including dUTP, and a DNA polymerase to form a polymerase chain reaction mixture, and the polymerase chain reaction mixture is subjected to one or more polymerase chain reaction cycles comprising a denaturation treatment, a hybridization treatment, and an extension treatment, thereby forming primary extension products comprising the target nucleotide sequence or a complement thereof. The method further involves blending the primary extension products with a ligase and one or more oligonucleotide probe sets to form a ligation reaction mixture. Each oligonucleotide probe set comprises (a) a first oligonucleotide probe having a target nucleotide sequence-specific portion, and (b) a second oligonucleotide probe having a target nucleotide sequence-specific portion, wherein the first and second oligonucleotide probes of a probe set are configured to hybridize, in a base specific manner, adjacent to one another on a complementary target nucleotide sequence of a primary extension product with a junction between them. The first and second oligonucleotide probes of the one or more oligonucleotide probe sets are ligated together to form ligated product sequences in the ligation reaction mixture, and the ligated product sequences in the sample are detected and distinguished to identify the presence of one or more nucleic acid molecules containing target nucleotide sequences differing from nucleotide sequences in other nucleic acid molecules in the sample by one or more nucleotides, one or more copy numbers, one or more transcript sequences, and/or one or more methylated residues.

FIGS. 38-44 illustrate various embodiments of this aspect of the present invention.

FIG. 38 (steps A-F) illustrates an exemplary PCR-LDR-qPCR carryover prevention reaction to detect mutations from genomic or cfDNA. This method starts by isolating genomic DNA or cell free DNA (cfDNA) as shown in step A. As shown in FIG. 38 (step B), the DNA sample is treated with an enzyme capable of digesting deoxyuracil (dU) containing nucleic acid molecules that may be present in the sample. Suitable enzymes include, without limitation, *E. coli* uracil DNA glycosylase (UDG), Antarctic Thermolabile UDG, or Human single-strand-selective monofunctional uracil-DNA Glycosylase (hSMUG1). The sample is then subject to an amplification reaction, e.g., a polymerase chain reaction (PCR) to amplify mutation containing regions of interest. The amplification reaction is carried out using locus specific primers and a deoxynucleotide mix that includes dUTP. In one embodiment, limited cycle amplification (12-20 cycles) is performed to maintain relative ratios of different amplicons being produced. In another embodiment, the regions of interest are amplified using 20-40 cycles. The amplified products contain dU as shown in FIG. 38, step C, which allows for subsequent treatment with UDG or a similar enzyme for carryover prevention.

As shown in FIG. 38 step D, target-specific oligonucleotide probes are hybridized to the amplified products and ligase (filled circle) covalently seals the two oligonucleotides together when hybridized to their complementary sequence. The upstream oligonucleotide probe contains a 5' primer-specific portion (Ai) and the downstream oligonucleotide probe contains a 3' primer-specific portion (Ci') that permits subsequent amplification of the ligation product. Following ligation, the ligation products are aliquot into separate wells containing one or more tag-specific primer pairs, each pair comprising of matched primers Ai and Ci, treated with UDG or similar enzyme to remove dU containing amplification products or contaminants, PCR amplified, and detected. As shown in FIG. 38, steps E & F, detection of the ligation product can be carried out using traditional TaqMan™ detection assay (see U.S. Pat. No. 6,270,967 to Whitcombe et al., and U.S. Pat. No. 7,601,821 to Anderson et al., which are hereby incorporated by reference in their entirety). For detection using TaqMan™ an oligonucleotide probe spanning the ligation junction is used in conjunction with primers suitable for hybridization on the primer-specific portions of the ligation products for amplification and detection. The TaqMan™ probe contains a fluorescent reporter group on one end (F1) and a quencher molecule (Q) on the other end that are in close enough proximity to each other in the intact probe that the quencher molecule quenches fluorescence of the reporter group. During amplification, the TaqMan™ probe and upstream primer hybridize to their complementary regions of the ligation product. The 5'→3' nuclease activity of the polymerase extends the hybridized primer and liberates the fluorescent group of the TaqMan™ probe to generate a detectable signal (FIG. 38, step F). Use of dUTP during the amplification reaction generates products containing dU, which can subsequently be destroyed using UDG for carryover prevention.

FIG. 39 illustrates an exemplary PCR-qLDR carryover prevention reaction to detect mutations from genomic or cfDNA. This method starts by isolating genomic DNA or cell free DNA (cfDNA) as shown in step A. As shown in FIG. 39, step B, the DNA sample is treated with a deoxyuracil (dU) digesting enzyme, such as UDG, to digest dU containing nucleic acid molecules that may be present in the sample, and then subject to an amplification reaction, e.g., a polymerase chain reaction (PCR) to amplify mutation containing regions of interest. The amplification reaction is carried out using locus specific primers and a deoxynucleotide mix that includes dUTP. In one embodiment, limited cycle amplification (12-20 cycles) is performed to maintain relative ratios of different amplicons being produced. In another embodiment, the regions of interest are amplified using 20-40 cycles. In this embodiment, the locus specific primers also contain 5' primer regions, e.g., universal primer regions, which enables a subsequent universal PCR amplification using biotin labeled primers to append a 5' biotin to the amplification products containing the region of interest (FIG. 39, step B).

As shown in FIG. 39, step C, the amplification products incorporate dU, allowing for carryover prevention, and are captured on a solid support via the appended 5' biotin moiety. The mutation of interest is detected using mutation specific ligation probes as illustrated in FIG. 39, step D. In this embodiment, the first ligation probe contains a 3' target specific region and a 5' tail sequence with a donor or acceptor moiety and the second ligation probe in a probe set contains a 5' target specific region and 3' tail sequence with an acceptor or donor moiety, respectively. The 5' and 3' tail sequences of the ligation probes in a probe set are complementary to each other and the acceptor and donor groups are capable of generating a detectable signal via Förster resonance energy transfer (FRET) when brought in close proximity to each other. Following ligation, unligated oligonucleotide probes are washed away, and the ligation product is denatured from the immobilized amplification products. Upon denaturation (FIG. 39, step E), the complementary 5' and 3' tail sequences of the ligation products hybridize to each other bringing the donor and acceptor groups in close proximity to each other to generate a detectable FRET signal.

The ligation products formed in accordance with this aspect of the present invention can be distinguished using an alternative to FRET detection. For example, the upstream probe may contain a fluorescent reporter group on the 5' end followed by the tail sequence portion, a quenching group (e.g., ZEN), and the target-specific portion as shown in FIG. 39, step F. In the single-stranded form, the fluorescent group is quenched by the Zen group. Upon ligation of the upstream and downstream ligation probes and denaturation of the resulting the ligation product, the complementary 5' and 3' tail portions of the ligation product hybridize to form a short double stranded portion. In this formation the reporter group is no longer quenched by the quenching group and a detectable signal is produced.

FIG. 39 illustrates a biotinylated universal primer-streptavidin coated surface approach for capturing extension products on a solid support. Such capture may occur prior to or subsequent to the ligation step. Other approaches for linking the product to the solid support include covalently attaching a portion of or the majority of the universal primer to the solid support prior to PCR amplification.

In addition to capture of polymerase extension products using biotin-streptavidin, the primers can be designed to include a capture sequence on the 5' end, a polymerase extension blocking group, and a universal or target-specific portion on the 3' end. After amplification, the 5' capture sequence portion of the products will be single stranded, and if it is a long and/or GC rich sequence, it may be captured on a complementary sequence under conditions which allow for denaturation of the non-captured strand, or removal by cleavage, e.g., lambda exonuclease cleavage. The capture step may be enhanced by use of PNA, LNA, or other nucleotide analogues within the primer, capture probe sequence or both.

In another embodiment, the primer may be covalently attached to the solid surface using Dibenzocyclooctyl (DBCO) for copper-free click chemistry (to an azide); 5-Octadiynyl dU for click chemistry (to an azide); Amino Modifier C6 dT (for peptide linkage); or Azide, for click chemistry to an alkene or DBCO.

FIG. 40 illustrates another exemplary PCR-LDR-qPCR carryover prevention reaction to detect mutations. Genomic or cfDNA is isolated (FIG. 40, step A), and the isolated DNA sample is treated with UDG to digest dU containing nucleic acid molecules that may be present in the sample. In this embodiment, initial amplification is carried out using locus specific PCR primers that contain a cleavable blocking group at their 3' ends. The blocking group prevents non-target specific polymerase extension and amplification. As shown in FIG. 40, step B, a suitable blocking group is an RNA base (r) that is cleaved by RNase-H (star symbol) only upon hybridization of the primer to its complementary sequence (see e.g., Dobosy et. al. "RNase H-Dependent PCR (rhPCR): Improved Specificity and Single Nucleotide Polymorphism Detection Using Blocked Cleavable Primers," *BMC Biotechnology* 11(80): 1011 (2011), which is hereby incorporated by reference in its entirety). Cleavage of the RNA base liberates a 3'OH suitable for extension by polymerase.

Following cleavage of the primer blocking groups, the region of interest is amplified and the PCR product contains dU allowing for carryover prevention (FIG. 40, step C). Target-specific oligonucleotide probes containing primer tags (Ai and Ci') are then hybridized to the amplified products in a base specific manner, and ligase (filled circle) covalently seals the two oligonucleotides together when hybridized to their complementary sequence (FIG. 40, step D). The ligation products are detected using pairs of matched primers Ai and Ci, and TaqMan™ probes that span the ligation junction as described in FIG. 38 (see FIG. 40, steps E-F).

FIG. 41 illustrates another exemplary PCR-LDR-qPCR carryover prevention reaction to detect mutations. Genomic or cfDNA is isolated (FIG. 41, step A), and the isolated DNA sample is treated with UDG to digest dU containing nucleic acid molecules that may be present in the sample (FIG. 41, step B). The region of interest is amplified using locus specific primers and a deoxynucleotide mix that includes dUTP. In one embodiment, limited cycle amplification (12-20 cycles) is performed to maintain relative ratios of different amplicons being produced. In another embodiment, the regions of interest are amplified using 20-40 cycles. The amplified products contain dU as shown in FIG. 41, step C, which allows for subsequent treatment with UDG or a similar enzyme for carryover prevention.

As shown in FIG. 41 step D, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the mutation of interest further contains a 5' primer-specific portion (Ai) to facilitate subsequent detection of the ligation product, while the upstream oligonucleotide probe having a sequence specific for detecting the wildtype (non-mutated) nucleic acid sequence does not contain a 5' primer-specific portion. The downstream oligonucleotide probe, having a sequence common to both mutant and wildtype sequences contains a 3' primer-specific portion (Ci') that, together with the 5' primer specific portion (Ai) of the upstream probe having a sequence specific for detecting the mutation, permit subsequent amplification and detection of only mutant ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 41, step D). Following ligation, the ligation products can be detected using pairs of matched primers Ai and Ci, and TaqMan™ probes that span the ligation junction as described in FIG. 38 (see FIG. 41, steps E-G), or using other suitable means known in the art.

FIG. 42 illustrates another exemplary PCR-qLDR carryover prevention reaction to detect mutations. Genomic or cfDNA is isolated (FIG. 42, step A), and the isolated DNA sample is treated with UDG to digest dU containing nucleic acid molecules that may be present in the sample (FIG. 42, step B). The region of interest is amplified using locus specific primers and a deoxynucleotide mix that includes dUTP. In this embodiment, the locus specific primers also contain 5' primer regions, e.g., universal primer regions. Such sequences enable a subsequent universal PCR amplification using biotin labeled primers to append a 5' biotin to the amplification products containing the region of interest (FIG. 42, step B). The biotinylated PCR products are immobilized to a solid support and the mutation of interest is detected using mutation specific ligation probes as illustrated in FIG. 42, step D. In this embodiment, the ligation probes of a ligation pair capable of detecting the mutant nucleic acid sequence (but not the wild-type sequence) contain complementary tail sequences and an acceptor or donor group, respectively, capable of generating a detectable signal via FRET when brought in close proximity to each other as described supra for FIG. 39. As illustrated in step D of this Figure, another layer of specificity can be incorporated into the method by including a 3' cleavable blocking group, (e.g. C3-spacer), and an RNA base (r), in the upstream ligation probe. Upon target-specific hybridization, RNase H (star symbol) removes the RNA base to generate a ligation competent 3'OH group (FIG. 42, step D). Following ligation (FIG. 42, step E), the complementary 5' and 3' tail ends of the ligation products hybridize to each other bringing their respective donor and acceptor moieties in close proximity to each other to generate a detectable FRET signal (FIG. 42, step F).

FIG. 43 illustrates another exemplary PCR-qLDR carryover prevention reaction to detect mutations. Genomic or cfDNA is isolated (FIG. 43, step A), and the isolated DNA sample is treated with UDG to digest dU containing nucleic acid molecules that may be present in the sample (FIG. 43, step B). The region of interest is amplified using locus specific primers and a deoxynucleotide mix that includes dUTP. In this embodiment, the locus specific primers also contain 5' primer regions, e.g., universal primer regions. These regions enable a subsequent universal PCR amplification using biotin labeled primers to append a 5' biotin to the amplification products containing the region of interest (FIG. 43, step B). The biotinylated PCR products are immobilized to a solid support and the mutation of interest is detected using mutation specific ligation probes as illustrated in FIG. 43, step D. In this embodiment, the oligonucleotide probes of a probe set are designed such that the 3'-most base of the first oligonucleotide probe is overlapped by the immediately flanking 5'-most base of the second oligonucleotide probe that is complementary to the target nucleic acid molecule as shown in FIG. 43, step D. The overlapping nucleotide is referred to as a "flap". When the overlapping flap nucleotide of the second oligonucleotide probe is complementary to the target nucleic acid molecule sequence and the same sequence as the terminating 3' nucleotide of the first oligonucleotide probe, the phosphodiester bond immediately upstream of the flap nucleotide of the second oligonucleotide probe is discriminatingly cleaved by an enzyme having flap endonuclease (FEN) or 5' nuclease activity (e.g. the 5'-3' exonuclease of Taq polymerase). That specific FEN activity produces a ligation competent 5' phosphate end on the second oligonucleotide probe that is precisely positioned alongside the adjacent 3' OH of the first oligonucleotide probe. As a consequence of (a) target specific annealing by oligonucleotide probes adjacent to each other, (b) selective generation of 5' phosphates only when the cleaved flap nucleotide matches the template, and (c) addition of a ligase that discriminates against non-Watson-Crick pairing for the 3'-base of the first oligonucleotide probe, very high target detection specificity and sensitivity is achieved. In accordance with this embodiment, the oligonucleotide probes for ligation also contain complementary tail sequences and an acceptor or donor group, respectively, capable of generating a detectable signal via FRET when brought in close proximity to each other as described supra for FIG. 39. Following ligation (FIG. 43, step E), the complementary 5' and 3' tail ends of the ligation products hybridize to each other bringing their respective donor and acceptor moieties in close proximity to each other to generate a detectable FRET signal (FIG. 43, step F).

FIG. 44 illustrates another PCR-LDR-qPCR carryover prevention reaction to detect mutations. Genomic or cfDNA is isolated (FIG. 44, step A), and the isolated DNA sample is treated with UDG to digest dU containing nucleic acid molecules that may be present in the sample (FIG. 44, step B). The region of interest is amplified using locus specific primers and a deoxynucleotide mix that includes dUTP. In this embodiment, the ligation probes are designed to contain UniTaq primer and tag sequences to facilitate detections. The UniTaq system is fully described in U.S. Patent Application Publication No. 2011/0212846 to Spier, which is hereby incorporated by reference in its entirety. The UniTaq system involves the use of three unique "tag" sequences, where at least one of the unique tag sequences (Ai) is present in the first oligonucleotide probe, and the second and third unique tag portions (Bi' and Ci') are in the second oligonucleotide probe sequence as shown in FIG. 44, step D. Upon ligation of oligonucleotide probes in a probe set, the resulting ligation product will contain the Ai sequence—target specific sequences—Bi' sequence—Ci' sequence. The essence of the UniTaq approach is that both oligonucleotide probes of a ligation probe set need to be correct in order to get a positive signal, which allows for highly multiplexed nucleic acid detection. For example, and as described herein, this is achieved by requiring hybridization of two parts, i.e., two of the tags, to each other.

Prior to detecting the ligation product, the sample is treated with UDG to destroy original target amplicons allowing only authentic ligation products to be detected. For detection, the ligation product containing Ai (a first primer-specific portion), Bi' (a UniTaq detection portion), and Ci' (a second primer-specific portion) is primed on both strands using a first oligonucleotide primer having the same nucleotide sequence as Ai, and a second oligonucleotide primer that is complementary to Ci' (i.e., Ci). The first oligonucleotide primer also includes a UniTaq detection probe (Bi) that has a detectable label F1 on one end and a quencher molecule (Q) on the other end (F1-Bi-Q-Ai). Optionally positioned proximal to the quencher is a polymerase-blocking unit, e.g., HEG, THF, Sp-18, ZEN, or any other blocker known in the art that is sufficient to stop polymerase extension. PCR amplification results in the formation of double stranded products as shown in FIG. 44, step F). In this example, a polymerase-blocking unit prevents a polymerase from copying the 5' portion (Bi) of the first universal primer, such that the bottom strand of product cannot form a hairpin when it becomes single-stranded. Formation of such a hairpin would result in the 3' end of the stem annealing to the amplicon such that polymerase extension of this 3' end would terminate the PCR reaction.

The double stranded PCR products are denatured, and when the temperature is subsequently decreased, the upper strand of product forms a hairpin having a stem between the 5' portion (Bi) of the first oligonucleotide primer and portion Bi' at the opposite end of the strand (FIG. 44, step G). Also during this step, the second oligonucleotide primer anneals to the 5'-primer specific portion (Ci') of the hairpinned product. Upon extension of the second universal primer in step G, 5' nuclease activity of the polymerase cleaves the detectable label D1 or the quencher molecule from the 5' end of the amplicon, thereby increasing the distance between the label and the quencher and permitting detection of the label.

FIG. 145 illustrates another exemplary PCR-LDR-qPCR carryover prevention reaction to detect low-level mutations. Genomic or cfDNA is isolated (FIG. 145, step A), and the isolated DNA sample is treated with UDG to digest dU containing nucleic acid molecules that may be present in the sample (FIG. 145, step B). The region of interest is selectively amplified using mutation-selective upstream primers, locus-specific downstream primers, and a deoxynucleotide mix that includes dUTP. As illustrated in this Figure, another layer of selectivity can be incorporated into the method by including a 3' cleavable blocking group (Blk 3', e.g. C3 spacer), and a mutation-specific RNA base (mr), in the upstream mutation-specific primer. Upon target-specific hybridization, RNase H (star symbol) removes the RNA base to liberate a 3'OH group suitable for polymerase extension (FIG. 145, step B). RNaseH will preferentially cleave the RNA base when it is perfectly matched to mutant DNA, but will be less likely to cleave the RNA base when hybridized to wild-type DNA. Once the cleavage reaction has occurred, the polymerase faithfully extends the liberated 3'OH and copies the mutant or wild-type base of the target. Thus, in contrast to allele-specific PCR, the PCR primer does not propagate a primer-derived mutation. Instead, by copying the base through repeated cycles of hybridization, cleavage, elongation, and denaturation, this PCR selectively amplifies mutant target over wild-type target during each cycle of amplification. Optional primers with wild-type sequence lack the RNA base and remain blocked, thus further reducing amplification of wild-type sequence. Optionally aliquot sample into 24, 48, or 96 wells prior to PCR. The amplified products contain dU as shown in FIG. 145, step C, which allows for subsequent treatment with UDG or a similar enzyme for carryover prevention.

As shown in FIG. 145 step D, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the mutation of interest further contains a 5' primer-specific portion (Ai) to facilitate subsequent detection of the ligation product, while the upstream oligonucleotide probe having a sequence specific for detecting the wild-type (non-mutated) nucleic acid sequence does not contain a 5' primer-specific portion. The downstream oligonucleotide probe, having a sequence common to both mutant and wild-type sequences contains a 3' primer-specific portion (Ci') that, together with the 5' primer specific portion (Ai) of the upstream probe having a sequence specific for detecting the mutation, permit subsequent amplification and detection of only mutant ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 145, step D). Following ligation, the ligation products can be detected using pairs of matched primers Ai and Ci, and TaqMan™ probes that span the ligation junction as described in FIG. 38 (see FIG. 145, steps E-G), or using other suitable means known in the art.

FIG. 146 illustrates another exemplary PCR-LDR-qPCR carryover prevention reaction to detect low-level mutations. Genomic or cfDNA is isolated (FIG. 146, step A), and the isolated DNA sample is treated with UDG to digest dU containing nucleic acid molecules that may be present in the sample (FIG. 146, step B). The region of interest is selectively amplified using mutation-selective upstream primers, locus-specific downstream primers, and a deoxynucleotide mix that includes dUTP. As illustrated in this Figure, another layer of selectivity can be incorporated into the method by including a 3' cleavable blocking group (Blk 3', e.g. C3 spacer), and a mutation-specific RNA base (mr), in the upstream mutation-specific primer. Upon target-specific hybridization, RNase H (star symbol) removes the RNA base to liberate a 3'OH group suitable for polymerase extension (FIG. 146, step B). RNaseH will preferentially cleave the RNA base when it is perfectly matched to mutant DNA, but will be less likely to cleave the RNA base when hybridized to wild-type DNA. Once the cleavage reaction has occurred, the polymerase faithfully extends the liberated 3'OH and copies the mutant or wild-type base of the target. Thus, in contrast to allele-specific PCR, the PCR primer does not propagate a primer-derived mutation. Instead, by copying the base through repeated cycles of hybridization, cleavage, elongation, and denaturation, this PCR selectively amplifies mutant target over wild-type target during each cycle of amplification. Optional primers with wild-type sequence lack the RNA base and remain blocked, thus further reducing amplification of wild-type sequence. Optionally aliquot sample into 12, 24, 48, or 96 wells prior to PCR. The amplified products contain dU as shown in FIG. 146, step C, which allows for subsequent treatment with UDG or a similar enzyme for carryover prevention.

As shown in FIG. 146 step D, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the mutation of interest further contains a 5' primer-specific portion (Ai) to facilitate subsequent detection of the ligation product, while the upstream oligonucleotide probe having a sequence specific for detecting the wild-type (non-mutated) nucleic acid sequence does not contain a 5' primer-specific portion. The downstream oligonucleotide probe, having a sequence common to both mutant and wild-type sequences contains a 3' primer-specific portion (Bi'-Ci') that, together with the 5' primer specific portion (Ai) of the upstream probe having a sequence specific for detecting the mutation, permit subsequent amplification and detection of only mutant ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 146, step D). Following ligation, the ligation products are amplified using UniTaq-specific primers (i.e., F1-Bi-Q-Ai, Ci) and detected as described supra for FIG. 44 (see FIG. 146, steps E-H), or using other suitable means known in the art.

FIG. 147 illustrates another exemplary PCR-qLDR carryover prevention reaction to detect low-level mutations. Genomic or cfDNA is isolated (FIG. 147, step A), and the isolated DNA sample is treated with UDG to digest dU containing nucleic acid molecules that may be present in the sample (FIG. 147, step B). The region of interest is selectively amplified using mutation-selective upstream primers, locus-specific downstream primers, and a deoxynucleotide mix that includes dUTP. As illustrated in step B of this Figure, another layer of selectivity can be incorporated into the method by including a 3' cleavable blocking group (Blk 3', e.g. C3 spacer), and a mutation-specific RNA base (mr), in the upstream mutation-specific primer. Upon target-specific hybridization, RNase H (star symbol) removes the RNA base to liberate a 3'OH group suitable for polymerase extension (FIG. 147, step B). RNaseH will preferentially cleave the RNA base when it is perfectly matched to mutant DNA, but will be less likely to cleave the RNA base when hybridized to wild-type DNA. Once the cleavage reaction has occurred, the polymerase faithfully extends the liberated 3'OH and copies the mutant or wild-type base of the target. Thus, in contrast to allele-specific PCR, the PCR primer does not propagate a primer-derived mutation. Instead, by copying the base through repeated cycles of hybridization, cleavage, elongation, and denaturation, this PCR selectively amplifies mutant target over wild-type target during each cycle of amplification. Optional primers with wild-type sequence lack the RNA base and remain blocked, thus further reducing amplification of wild-type sequence. In this embodiment, the downstream locus-specific primers also contain 5' primer regions, e.g., universal primer regions, that enables universal PCR amplification using biotin labeled primers to append a 5' biotin to the amplification products containing the region of interest (FIG. 146, step B). Optionally aliquot sample into 12, 24, 48, or 96 wells prior to PCR. The biotinylated PCR products are immobilized to a solid support and the mutation of interest is detected using mutation specific ligation probes as illustrated in FIG. 147, step D. In this embodiment, the ligation probes of a ligation pair capable of detecting the mutant nucleic acid sequence (but not the wild-type sequence) contain complementary tail sequences and an acceptor or donor group, respectively, capable of generating a detectable signal via FRET when brought in close proximity to each other as described supra for FIG. 39. As illustrated in this Figure, another layer of specificity can be incorporated into the method by including a 3' cleavable blocking group, (e.g. C3-spacer), and an RNA base (r), in the upstream ligation probe. Upon target-specific hybridization, RNase H (star symbol) removes the RNA base to generate a ligation competent 3'OH group (FIG. 147, step D). Following ligation (FIG. 147, step E), the complementary 5' and 3' tail ends of the ligation products hybridize to each other bringing their respective donor and acceptor moieties in close proximity to each other to generate a detectable FRET signal (FIG. 147, step F).

FIG. 148 illustrates another exemplary PCR-LDR-qPCR carryover prevention reaction to detect low-level mutations. Genomic or cfDNA is isolated (FIG. 148, step A), and the isolated DNA sample is treated with UDG to digest dU containing nucleic acid molecules that may be present in the sample (FIG. 148, step B). The region of interest is selectively amplified using locus-specific upstream primers, locus-specific downstream primers, a blocking LNA or PNA probe comprising wild-type sequence, and a deoxynucleotide mix that includes dUTP. In this embodiment, another layer of selectivity can be incorporated into the method by including a 3' cleavable blocking group (Blk 3', e.g. C3 spacer), and an RNA base (r), in the upstream primer. Upon target-specific hybridization, RNase H (star symbol) removes the RNA base to liberate a 3'OH group which is a few bases upstream of the mutation, and suitable for polymerase extension (FIG. 148, step B). A blocking LNA or PNA probe comprising wild-type sequence that partially overlaps with the upstream PCR primer will preferentially compete in binding to wild-type sequence over the upstream primer, but not as much to mutant DNA, and thus suppresses amplification of wild-type DNA during each round of PCR. Optionally aliquot sample into 12, 24, 48, or 96 wells prior to PCR. The amplified products contain dU as shown in FIG. 148, step C, which allows for subsequent treatment with UDG or a similar enzyme for carryover prevention.

As shown in FIG. 148 step D, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the mutation of interest further contains a 5' primer-specific portion (Ai) to facilitate subsequent detection of the ligation product. Once again, the presence of blocking LNA or PNA probe comprising wild-type sequence suppresses ligation to wild-type target sequence if present after the enrichment of mutant sequence during the PCR amplification step. The downstream oligonucleotide probe, having a sequence common to both mutant and wild-type sequences contains a 3' primer-specific portion (Ci') that, together with the 5' primer specific portion (Ai) of the upstream probe having a sequence specific for detecting the mutation, permit subsequent amplification and detection of only mutant ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 148, step D). Following ligation, the ligation products can be detected using pairs of matched primers Ai and Ci, and TaqMan™ probes that span the ligation junction as described supra for FIG. 38 (see FIG. 148, steps E-G), or using other suitable means known in the art.

FIG. 149 illustrates another exemplary PCR-LDR-qPCR carryover prevention reaction to detect low-level mutations. Genomic or cfDNA is isolated (FIG. 149, step A), and the isolated DNA sample is treated with UDG to digest dU containing nucleic acid molecules that may be present in the sample (FIG. 149, step B). Upstream locus-specific primers are designed a few bases upstream of the mutation, and include a 3' cleavable blocking group (Blk 3', e.g. C3 spacer), and an RNA base (r). Upon target-specific hybridization, RNase H (star symbol) removes the RNA base to liberate a 3'OH that is suitable for polymerase extension (FIG. 149, step B). A blocking LNA or PNA probe comprising wild-type sequence that partially overlaps with the upstream PCR primer will preferentially compete in binding to wild-type sequence over the upstream primer, but not as much to mutant DNA, and thus suppresses amplification of wild-type DNA during each round of PCR. Optionally aliquot sample into 12, 24, 48, or 96 wells prior to PCR. The amplified products contain dU as shown in FIG. 148, step C, which allows for subsequent treatment with UDG or a similar enzyme for carryover prevention.

As shown in FIG. 149 step D, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the mutation of interest further contains a 5' primer-specific portion (Ai) to facilitate subsequent detection of the ligation product. Once again, the presence of blocking LNA or PNA probe comprising wild-type sequence suppresses ligation to wild-type target sequence if present after the enrichment of mutant sequence during the PCR amplification step. The downstream oligonucleotide probe, having a sequence common to both mutant and wild-type sequences contains a 3' primer-specific portion (Bi-Ci') that, together with the 5' primer specific portion (Ai) of the upstream probe having a sequence specific for detecting the mutation, permit subsequent amplification and detection of only mutant ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 149, step D). Following ligation, the ligation products are amplified using UniTaq-specific primers (i.e., F1-Bi-Q-Ai, Ci) and detected as described supra for FIG. 44 (see FIG. 149, steps E-H), or using other suitable means known in the art.

FIG. 150 illustrates another exemplary PCR-qLDR carryover prevention reaction to detect low-level mutations. Genomic or cfDNA is isolated (FIG. 150, step A), and the isolated DNA sample is treated with UDG to digest dU containing nucleic acid molecules that may be present in the sample (FIG. 150, step B). Upstream locus-specific primers are designed a few bases upstream of the mutation, and include a 3' cleavable blocking group (Blk 3', e.g. C3 spacer), and an RNA base (r). Upon target-specific hybridization, RNase H (star symbol) removes the RNA base to liberate a 3'OH that is suitable for polymerase extension (FIG. 150, step B). A blocking LNA or PNA probe comprising wild-type sequence that partially overlaps with the upstream PCR primer will preferentially compete in binding to wild-type sequence over the upstream primer, but not as much to mutant DNA, and thus suppresses amplification of wild-type DNA during each round of PCR. In this embodiment, the downstream locus-specific primers also contain 5' primer regions, e.g., universal primer regions, that enables universal PCR amplification using biotin labeled primers to append a 5' biotin to the amplification products containing the region of interest (FIG. 150, step B). Optionally aliquot sample into 12, 24, 48, or 96 wells prior to PCR. The biotinylated PCR products are immobilized to a solid support and the mutation of interest is detected using mutation specific ligation probes as illustrated in FIG. 150, step D. Once again, the presence of blocking LNA or PNA probe comprising wild-type sequence suppresses ligation to wild-type target sequence if present after the enrichment of mutant sequence during the PCR amplification step. In this embodiment, the ligation probes of a ligation pair capable of detecting the mutant nucleic acid sequence (but not the wild-type sequence) contain complementary tail sequences and an acceptor or donor group, respectively, capable of generating a detectable signal via FRET when brought in close proximity to each other as described supra for FIG. 39. As illustrated in this Figure, another layer of specificity can be incorporated into the method by including a 3' cleavable blocking group, (e.g. C3-spacer), and an RNA base (r), in the upstream ligation probe. Upon target-specific hybridization, RNase H (star symbol) removes the RNA base to generate a ligation competent 3'OH group (FIG. 150, step D). Following ligation (FIG. 150, step E), the complementary 5' and 3' tail ends of the ligation products hybridize to each other bringing their respective donor and acceptor moieties in close proximity to each other to generate a detectable FRET signal (FIG. 150, step F).

In another embodiment of the this aspect of the present invention, the first primary oligonucleotide primer of the primary oligonucleotide primer set comprises a 5' portion having a nucleotide sequence that is the same as a nucleotide sequence portion in a wildtype nucleic acid molecule to which the primary oligonucleotide primer hybridizes to, but has one or more nucleotide sequence mismatches to a corresponding nucleotide sequence portion in the target nucleic acid molecule.

In accordance with this embodiment, a polymerase lacking 5' nuclease, 3' nuclease, and strand displacing activity is provided. Optionally, the primary oligonucleotide primer may also contain a cleavable nucleotide or nucleotide analog which is cleaved during the hybridization step of PCR to liberate a free 3'OH end on the oligonucleotide primer prior to said extension treatment. The polymerase chain reaction mixture is subjected to one or more additional polymerase chain reaction cycles comprising a denaturation treatment wherein the extension products from the reaction are separated from each other, a hybridization treatment wherein the first primary oligonucleotide primer hybridizes to the extension product arising from the second primary oligonucleotide primer. The extension products arising from the second primary oligonucleotide are capable of forming an intramolecular loop-hairpin between the 3' end and the complementary sequence within the extension product, which (i) comprises a mismatch at or near the 3' end that inhibits self-extension if hybridized to mutant target-sequence or (ii) comprises a match at the 3' end that enhances self-extension if self-hybridized to wild-type target-sequence. The second primary oligonucleotide primer hybridizes to the extension product arising from the first primary oligonucleotide primer. The extension product of the first primary primer forms an intramolecular loop-hairpin between the 5' portion and the complementary sequence within the extension product. During the extension step of the PCR, the first primary oligonucleotide primer (i) preferentially extends on extension product comprising mutant target sequence thereby preferentially forming primary extension products comprising the mutant target nucleotide sequence or a complement thereof, or (ii) is inhibited from forming primary extension products comprising the wild-type target nucleotide sequence or a complement thereof due to prior self-hybridization and self-extension on said target. The second primary oligonucleotide primer extends on extension product independent of target sequence, wherein the mutant sequence is preferentially amplified due to the different primary extension products arising from the hybridization of the first primary oligonucleotide primers to the target or copies thereof, resulting in enrichment of the mutant sequence extension product and complements thereof during the primary polymerase chain reaction.

FIGS. 154 and 155 illustrate the above described embodiment of this aspect of the present invention. As shown in FIG. 154, genomic or cfDNA is isolated (FIG. 154, step A), and the isolated DNA sample is treated with UDG to digest dU containing nucleic acid molecules that may be present in the sample (FIG. 154, step B). The region of interest is selectively amplified using locus-specific upstream primers that comprise a 5' portion having a nucleotide sequence that is the same as a nucleotide sequence portion of the wild-type nucleic acid molecule to which the primer hybridizes to such that the extension product is capable of forming a loop hairpin. In other words, the 5' portion of the upstream primer contains a nucleotide sequence that is the same as a sequence portion within the antisense wild-type DNA strand or complementary to a sequence portion within the sense wild-type DNA strand. The amplification reaction also contains locus-specific downstream primers and a deoxynucleotide mix that includes dUTP. As illustrated in step B of this Figure, another layer of selectivity can be incorporated into the method by including a 3' cleavable blocking group (Blk 3', e.g. C3 spacer), and an RNA base (r), in the upstream mutation-specific primer. Upon target-specific hybridization, RNase H (star symbol) removes the RNA base to liberate a 3'OH group suitable for polymerase extension (FIG. 154, step B). Optionally aliquot sample into 12, 24, 48, or 96 wells prior to PCR. The amplified products contain dU as shown in FIG. 154, step C, which allows for subsequent treatment with UDG or a similar enzyme for carryover prevention. The PCR is performed with a polymerase lacking 5' nuclease, 3' nuclease, and strand-displacement activity. FIG. 154, step D further illustrates that during subsequent rounds of PCR (i) the denatured wild-type bottom strand forms a loop-hairpin with perfect match at the 3' end, which is extended by polymerase, (ii) the denatured mutant bottom strand forms a loop-hairpin with at least one mismatched base at the 3' end, which generally is not extended by polymerase, (iii) the denatured top strand forms a loop-hairpin on 5' side, which denatures during the extension step of PCR at 72° C. FIG. 154, step E, further illustrates that: (i) after extension of the loop-hairpin on wild-type DNA, extended hairpin sequence does not denature at 72° C. and prevents upstream primer from generating full-length top strand. However, the loop-hairpin sequence of mutant DNA (ii) does not extend on account of the 3' mismatched base, and thus denatures at 72° C., enabling upstream primer to generate full-length top strand. Likewise, top strand product (iii) denatures at 72° C., allowing polymerase to generate full-length bottom strand. The difference in loop-hairpin extension preference of upstream primers with wild-type (i) and mutant (ii) template results in preferential removal of wild-type products during each cycle of amplification, and thus results in preferential amplification of mutant DNA. The differential extension efficiency of the 3' end to extend the loop hairpin when hybridized to mutant vs. wild-type DNA may be further enhanced by designing the 5' portion of the upstream primer to contain a mismatch to wild-type DNA in the $2^{nd}$ or $3^{rd}$ position from the end. The extension product from the bottom primer will generate only 1 mismatch in the $2^{nd}$ or $3^{rd}$ position from the 3' end when self-hybridizing to wild-type sequence, which will easily extend with polymerase, but will generate 2 mismatches at the 3' end when self-hybridizing to mutant sequence, which will not extend with polymerase.

As shown in FIG. 154 step G, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the mutation of interest further contains a 5' primer-specific portion (Ai) to facilitate subsequent detection of the ligation product, while the upstream oligonucleotide probe having a sequence specific for detecting the wild-type (non-mutated) nucleic acid sequence does not contain a 5' primer-specific portion. The downstream oligonucleotide probe, having a sequence common to both mutant and wild-type sequences contains a 3' primer-specific portion (Ci') that, together with the 5' primer specific portion (Ai) of the upstream probe having a sequence specific for detecting the mutation, permits subsequent amplification and detection of only mutant ligation products. As illustrated in step F of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 154, step H). Following ligation, the ligation products can be detected using pairs of matched primers Ai and Ci, and TaqMan™ probes that span the ligation junction as described in FIG. 38 (see FIG. 154, steps H-J), or using other suitable means known in the art.

FIG. 155 illustrates another exemplary PCR-LDR carryover prevention reaction to detect mutations. Genomic or cfDNA is isolated (FIG. 155, step A), and the isolated DNA sample is treated with UDG to digest dU containing nucleic acid molecules that may be present in the sample (FIG. 155, step B). The region of interest is selectively amplified using (i) locus-specific upstream primers that also comprise a 5' sequence portion that is complementary to wild-type sequence of the top strand allowing for formation of loop-hairpins after extension, (ii) locus-specific downstream primers, and (iii) a deoxynucleotide mix that includes dUTP. As illustrated in step B of this Figure, another layer of selectivity can be incorporated into the method by including a 3' cleavable blocking group (Blk 3', e.g. C3 spacer), and an RNA base (r), in the upstream mutation-specific primer.

Upon target-specific hybridization, RNase H (star symbol) removes the RNA base to liberate a 3'OH group suitable for polymerase extension (FIG. 155, step B). Optionally aliquot sample into 12, 24, 48, or 96 wells prior to PCR. The amplified products contain dU as shown in FIG. 155, step C, which allows for subsequent treatment with UDG or a similar enzyme for carryover prevention. The PCR is performed with a polymerase lacking 5' nuclease, 3' nuclease, and strand-displacement activity. FIG. 155 step D further illustrates that during subsequent rounds of PCR: (i) the denatured wild-type bottom strand forms a loop-hairpin with perfect match at the 3' end, which is extended by polymerase, (ii) the denatured mutant bottom strand forms a loop-hairpin with at least one mismatched base at the 3' end, which generally is not extended by polymerase, (iii) the denatured top strand forms a loop-hairpin on 5' side, which denatures during the extension step of PCR at 72° C. FIG. 155, step E further illustrates that after extension of the loop-hairpin on wild-type DNA (i), extended hairpin sequence does not denature at 72° C. and prevents upstream primer from generating full-length top strand. However, the loop-hairpin sequence of mutant DNA (ii) does not extend on account of the 3' mismatched base, and thus denatures at 72° C., enabling upstream primer to generate full-length top strand. Likewise, top strand product (iii) denatures at 72° C., allowing polymerase to generate full-length bottom strand. The difference in loop-hairpin extension preference of upstream primers with wild-type (i) and mutant (ii) template results in preferential removal of wild-type products during each cycle of amplification, and thus results in preferential amplification of mutant DNA.

In this embodiment, the downstream locus-specific primers also contain 5' primer regions, e.g., universal primer regions, that enables universal PCR amplification using biotin labeled primers to append a 5' biotin to the amplification products containing the region of interest (FIG. 155, step B). The biotinylated PCR products are immobilized to a solid support and the mutation of interest is detected using mutation specific ligation probes as illustrated in FIG. 155, step G. In this embodiment, the ligation probes of a ligation pair capable of detecting the mutant nucleic acid sequence (but not the wild-type sequence) contain complementary tail sequences and an acceptor or donor group, respectively, capable of generating a detectable signal via FRET when brought in close proximity to each other as described supra for FIG. 39. As illustrated in this Figure, another layer of specificity can be incorporated into the method by including a 3' cleavable blocking group, (e.g. C3-spacer), and an RNA base (r), in the upstream ligation probe. Upon target-specific hybridization, RNase H (star symbol) removes the RNA base to generate a ligation competent 3'OH group (FIG. 155, step G). Following ligation (FIG. 155, step H), the complementary 5' and 3' tail ends of the ligation products hybridize to each other bringing their respective donor and acceptor moieties in close proximity to each other to generate a detectable FRET signal (FIG. 155, step I).

The ligation reaction used in the methods of the present invention is well known in the art. Ligases suitable for ligating oligonucleotide probes of a probe set together (optionally following cleavage of a 3' ribose and blocking group on the first oligonucleotide probe, or the 5' flap on the second oligonucleotide probe) include, without limitation *Therms aquaticus* ligase, *E. coli* ligase, T4 DNA ligase, T4 RNA ligase, Taq ligase, 9 N° ligase, and *Pyrococcus* ligase, or any other thermostable ligase known in the art. In accordance with the present invention, the nuclease-ligation process of the present invention can be carried out by employing an oligonucleotide ligation assay (OLA) reaction (see Landegren, et al., "A Ligase-Mediated Gene Detection Technique," *Science* 241:1077-80 (1988); Landegren, et al., "DNA Diagnostics—Molecular Techniques and Automation," *Science* 242:229-37 (1988); and U.S. Pat. No. 4,988,617 to Landegren, et al.), a ligation detection reaction (LDR) that utilizes one set of complementary oligonucleotide probes (see e.g., WO 90/17239 to Barany et al, which is hereby incorporated by reference in their entirety), or a ligation chain reaction (LCR) that utilizes two sets of complementary oligonucleotide probes see e.g., WO 90/17239 to Barany et al, which is hereby incorporated by reference in their entirety).

The oligonucleotide probes of a probe sets can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, and mixtures thereof.

The hybridization step in the ligase detection reaction, which is preferably a thermal hybridization treatment, discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions.

Ligase discrimination can be further enhanced by employing various probe design features. For example, an intentional mismatch or nucleotide analogue (e.g., Inosine, Nitroindole, or Nitropyrrole) can be incorporated into the first oligonucleotide probe at the $2^{nd}$ or $3^{rd}$ base from the 3' junction end to slightly destabilize hybridization of the 3' end if it is perfectly matched at the 3' end, but significantly destabilize hybridization of the 3' end if it is mis-matched at the 3' end. This design reduces inappropriate misligations when mutant probes hybridize to wild-type target. Alternatively, RNA bases that are cleaved by RNases can be incorporated into the oligonucleotide probes to ensure template-dependent product formation. For example, Dobosy et. al. "RNase H-Dependent PCR (rhPCR): Improved Specificity and Single Nucleotide Polymorphism Detection Using Blocked Cleavable Primers," *BMC Biotechnology* 11(80): 1011 (2011), which is hereby incorporated by reference in its entirety, describes using an RNA-base close to the 3' end of an oligonucleotide probe with 3'-blocked end, and cutting it with RNase H2 generating a PCR-extendable and ligatable 3'-OH. This approach can be used to generate either ligation-competent 3'OH or 5'-P, or both, provided a ligase that can ligate 5'-RNA base is utilized.

Other possible modifications included abasic sites, e.g., internal abasic furan or oxo-G. These abnormal "bases" are removed by specific enzymes to generate ligation-competent 3'-OH or 5'P sites. Endonuclease IV, Tth EndoIV (NEB) will remove abasic residues after the ligation oligonucleotides anneal to the target nucleic acid, but not from a single-stranded DNA. Similarly, one can use oxo-G with Fpg or inosine/uracil with EndoV or Thymine glycol with EndoVIII.

Ligation discrimination can also be enhanced by using the coupled nuclease-ligase reaction described in WO2013/123220 to Barany et al., which is hereby incorporated by reference in its entirety. In this embodiment, the first oligonucleotide probe bears a ligation competent 3' OH group while the second oligonucleotide probe bears a ligation incompetent 5' end (i.e., an oligonucleotide probe without a 5' phosphate). The oligonucleotide probes of a probe set are designed such that the 3'-most base of the first oligonucleotide probe is overlapped by the immediately flanking 5'-most base of the second oligonucleotide probe that is complementary to the target nucleic acid molecule. The overlapping nucleotide is referred to as a "flap". When the overlapping flap nucleotide of the second oligonucleotide probe is complementary to the target nucleic acid molecule sequence and the same sequence as the terminating 3' nucleotide of the first oligonucleotide probe, the phosphodiester bond immediately upstream of the flap nucleotide of the second oligonucleotide probe is discriminatingly cleaved by an enzyme having flap endonuclease (FEN) or 5' nuclease activity. That specific FEN activity produces a novel ligation competent 5' phosphate end on the second oligonucleotide probe that is precisely positioned alongside the adjacent 3' OH of the first oligonucleotide probe to allow ligation of the two probes to occur. In accordance with this embodiment, flap endonucleases or 5' nucleases that are suitable for cleaving the 5' flap of the second oligonucleotide probe prior to ligation include, without limitation, polymerases the bear 5' nuclease activity such as *E.coli* DNA polymerase and polymerases from Taq and T thermophilus, as well as T4 RNase H and TaqExo.

For insertions or deletions, incorporation of a matched base or nucleotide analogues (e.g., -amino-dA or 5-propynyl-dC) in the first oligonucleotide probe at the $2^{nd}$ or $3^{rd}$ position from the junction improves stability and may improve discrimination of such frameshift mutations from wild-type sequences. For insertions, use of one or more thiophosphate-modified nucleotides downstream from the desired scissile phosphate bond of the second oligonucleotide probe will prevent inappropriate cleavage by the 5' nuclease enzyme when the probes are hybridized to wild-type DNA, and thus reduce false-positive ligation on wild-type target. Likewise, for deletions, use of one or more thiophosphate-modified nucleotides upstream from the desired scissile phosphate bond of the second oligonucleotide probe will prevent inappropriate cleavage by the 5' nuclease enzyme when the probes are hybridized to wild-type DNA, and thus reduce false-positive ligation on wild-type target.

The method of the present invention can also be utilized to identify one or more target nucleic acid sequences differing from other nucleic acid sequences in a sample by one or more methylated residues. In accordance with this aspect of the present invention, the method further comprises contacting the sample with at least a first methylation sensitive enzyme to form a restriction enzyme reaction mixture prior to forming a polymerase chain reaction mixture. In accordance with this aspect of the present invention, the first primary oligonucleotide primer comprises a nucleotide sequence that is complementary to a region of the target nucleotide sequence that is upstream of the one or more methylated residues and the second primary oligonucleotide primer comprises a nucleotide sequence that is the same as a region of the target nucleotide sequence that is downstream of the one or more methylated residues.

The first methylation sensitive enzyme cleaves nucleic acid molecules in the sample that contain one or more unmethylated residues within at least one methylation sensitive enzyme recognition sequence. In accordance with this embodiment, detecting involves detection of one or more nucleic acid molecules containing the target nucleotide sequence, where the nucleic acid molecule originally contained one or more methylated residues.

In accordance with this and all aspects of the present invention, a "methylation sensitive enzyme" is an endonuclease that will not cleave or has reduced cleavage efficiency of its cognate recognition sequence in a nucleic acid molecule when the recognition sequence contains a methylated residue (i.e., it is sensitive to the presence of a methylated residue within its recognition sequence). A "methylation sensitive enzyme recognition sequence" is the cognate recognition sequence for a methylation sensitive enzyme. In some embodiments, the methylated residue is a 5-methyl-C, within the sequence CpG (i.e., 5-methyl-CpG). A non-limiting list of methylation sensitive restriction endonuclease enzymes that are suitable for use in the methods of the present invention include, without limitation, AciI, HinP1I, Hpy99I, HpyCH4IV, BstUI, HpaII, HhaI, or any combination thereof.

The method of the present invention may further comprise subjecting the restriction enzyme reaction mixture to a bisulfite treatment under conditions suitable to convert unmethylated cytosine residues to uracil residues prior to forming a polymerase chain reaction mixture. In this embodiment the first primary oligonucleotide primer of the primary oligonucleotide primer set comprises a nucleotide sequence that is complementary to the bisulfite-treated target nucleotide sequence containing the one or more methylated, uncleaved restriction sites and the second primary oligonucleotide primer of the provided primary oligonucleotide primer set comprises a nucleotide sequence that is complementary to a portion of the extension product formed from the first oligonucleotide primer.

The method of the present invention may further involve providing one or more second methylation sensitive enzymes that cleave nucleic acid molecules containing unmethylated residues within a methylation sensitive enzyme recognition sequence. The at least one second methylation sensitive enzyme is blended with the polymerase chain reaction mixture comprising the bisulfite-treated restriction enzyme reaction mixture to form a second restriction enzyme reaction mixture, where the second methylation sensitive enzyme cleaves nucleic acid molecules potentially present in the sample that contain one or more unmethylated residues within at least one methylation sensitive enzyme recognition sequence during said hybridization treatment.

In one embodiment of this aspect of the present invention, one or both primary oligonucleotide primers of the primary oligonucleotide primer set have a 3' portion having a cleavable nucleotide or nucleotide analogue and a blocking group, such that the 3' end of said primer or primers is unsuitable for polymerase extension. In accordance with this embodiment, the method further involves cleaving the cleavable nucleotide or nucleotide analog of one or both oligonucleotide primers during the hybridization treatment thereby liberating free 3'OH ends on one or both oligonucleotide primers prior to said extension treatment.

In one embodiment of this aspect of the present invention, the method further involves providing one or more blocking oligonucleotides capable of hybridizing to a region of the bisulfite-treated target nucleotide sequence containing unmethylated residues. The polymerase chain reaction mixture comprising the bisulfite-treated restriction enzyme reaction mixture is contacted with the one or more blocking oligonucleotides prior to subjecting the mixture to one or more polymerase chain reaction cycles. The one or more blocking oligonucleotides hybridize to complementary target nucleic acid sequences during said hybridization treatment and impede primary oligonucleotide primer extension during said extension treatment.

FIGS. 45-53 illustrate various embodiments of the method of the present invention for detecting target nucleic acid molecules containing one or more methylated residues.

The first step of the PCR-LDR-qPCR reaction depicted in FIG. 45 involves the isolation of genomic or cfDNA. Optionally, methylated DNA can be enriched using methylation specific antibodies. The sample is then treated with methyl-sensitive restriction endonucleases, e.g., Bsh1236I (CG^CG) and/or HinP1I (G^CGC), and UNG (37° C., 30-60 minutes) to completely digest unmethylated DNA and prevent carryover (FIG. 45, step A). As shown in FIG. 45, step B, methylated regions of interest are amplified using PCR in presence of dUTP using locus-specific primers. In one embodiment, limited cycle amplification (12-20 cycles) is performed to maintain relative ratios of different amplicons being produced. In another embodiment, the regions of interest are amplified using 20-40 cycles. The PCR products incorporate dU, allowing for carryover prevention (FIG. 45, step C), and the products lack methyl groups, providing additional protection. As shown in FIG. 45, step D, the methyl region-specific ligation oligonucleotide probes contain tag primer-specific portions (Ai, Ci') suitable for subsequent PCR amplification, using pairs of tag primers Ai and Ci' and TaqMan™ probes.

Following the ligation reaction, the sample containing the ligation product can be aliquoted into separate wells for detection. Treatment with UDG destroys original target amplicons (FIG. 45, step E), allowing only authentic LDR products to be amplified and detected. The ligation products are detected in this embodiment using a traditional TaqMan™ detection assay (FIG. 45, steps E-F) as described supra.

FIG. 46 illustrates another exemplary PCR-LDR-qPCR carryover prevention reaction to detect methylation. In this embodiment, genomic DNA or cfDNA is isolated and treated with methyl-sensitive restriction endonucleases, e.g., Bsh1236I (CG^CG) and/or HinP1I (G^CGC), and UNG (37° C., 30-60 minutes) to completely digest unmethylated DNA and prevent carryover (FIG. 46, step A). As shown in FIG. 46, step B, methylated regions of interest are amplified using PCR in presence of dUTP using locus-specific primers. In one embodiment, limited cycle amplification (12-20 cycles) is performed to maintain relative ratios of different amplicons being produced. In another embodiment, the regions of interest are amplified using 20-40 cycles. Primers contain identical 8-11 base tails to prevent primer dimers. The PCR products contain dU, allowing for carryover prevention (FIG. 46, step C).

The oligonucleotide probes utilized in this embodiment are designed to contain the UniTaq primer and tag sequences to facilitate UniTaq detection as described supra. Accordingly, following the ligation reaction and treatment with UDG for carryover prevention, the ligation products are amplified using UniTaq-specific primers (i.e., F1-Bi-Q-Ai, Ci) as shown in FIG. 46, steps E and F, and the amplified products are detected as shown in FIG. 46, step G and described supra.

FIG. 47 illustrates another exemplary PCR-qLDR carryover prevention reaction to detect methylation. In this embodiment, genomic DNA or cfDNA is isolated and treated with methyl-sensitive restriction endonucleases, e.g., Bsh1236I (CG^CG) and/or HinP1I (G^CGC), and UNG (37° C., 30-60 minutes) to completely digest unmethylated DNA and prevent carryover (FIG. 47, step A). As shown in FIG. 47, step B, methylated regions of interest are amplified using PCR in presence of dUTP using locus-specific primers. In this embodiment, the locus specific primers also contain 5' primer regions, e.g., universal primer regions, which enable a subsequent universal PCR amplification using biotin labeled primers to append a 5' biotin to the amplification products containing the region of interest (FIG. 47, step B). The biotinylated PCR products are immobilized to a solid support and the mutation of interest is detected using mutation specific ligation probes as illustrated in FIG. 47, step D. In accordance with this embodiment, the oligonucleotide probes for ligation contain complementary tail sequences and an acceptor or donor group, respectively, capable of generating a detectable signal via FRET when brought in close proximity to each other as described supra for FIG. 39. Following ligation (FIG. 47, step D), the complementary 5' and 3' tail ends of the ligation products hybridize to each other bringing their respective donor and acceptor moieties in close proximity to each other to generate a detectable FRET signal (FIG. 47, step E).

FIG. 48 illustrates a nuclease-ligation-PCR-qPCR carryover prevention reaction to detect methylation. In this embodiment, genomic DNA or cfDNA is isolated and treated with HaeIII (GG^CC), methyl-sensitive restriction endonucleases, e.g., Bsh1236I (CG^CG) and/or HinP1I (G^CGC), and UNG (37° C., 30-60 minutes) to completely digest unmethylated DNA and prevent carryover (FIG. 48, step A). As shown in FIG. 48, step B, a hairpinned oligonucleotide containing tag sequence (Ai') is ligated to the newly liberated phosphate of the digested target DNA in the sample template strand. As illustrated in FIG. 48, step C, the sample is treated with HinP1I and Bsh1236I at 37° C. The methyl-sensitive restriction enzymes are then heat-inactivated while activating Taq polymerase for subsequent PCR amplification using locus-specific primers containing Ci tag sequence. As described above, the primers can contain a cleavable blocking group, (e.g. C3-spacer), and an RNA base (r), that is removed prior to amplification by an RNaseH2 (star symbol) treatment only when the primer is bound to complementary target sequence. The unblocked primer is extended with polymerase, and the 5' nuclease activity of the polymerase digests the 5' portion of the ligated hairpin to generate a product complementary to the target containing the Ci and Ai' sequence. Unligated hair-pinned oligonucleotides extend on themselves.

As shown in FIG. 48, step D, methyl-containing regions of interest are amplified using PCR including dUTP with tag-primers Ai and Ci. Perform limited cycle amplification (12-20) to maintain relative ratios of different amplicons. The PCR products incorporate dU, allowing for carryover prevention (FIG. 48, step E), and the products lack methyl groups, providing additional protection. The amplified products are aliquot into separate wells for TaqMan™ detection using locus-specific primers and TaqMan™ probe as described supra.

FIG. 49 illustrates a nuclease-ligation-PCR-qPCR carryover prevention reaction to detect methylation. PCR products containing the originally methylated residues of interest and dU are generated following the steps A-D as illustrated and described above with regard to FIG. 48. In this embodiment, subsequent amplification using UniTaq primers and tag sequences are used to detect the methylated residues of interest. As shown in step E of FIG. 49, PCR products containing dU for carryover prevention, are aliquot into separate wells and amplified using locus-specific primers tailed with Aj, and Bj-Cj, as well as UniTaq-specific primers (F1-Bj-Q-Aj, and Cj). The resulting double-stranded DNA products are shown in FIG. 49, step F. As shown in FIG. 49, step G, after the denaturation step, the temperature is cooled to allow hairpin formation between Bj and Bj'. The 5'→3' nuclease activity of Taq polymerase (filled diamonds) extends primer Ci and liberates the fluorescent group to generate signal.

FIG. 50 illustrates a PCR-LDR-qPCR carryover prevention reaction to detect methylation. In this embodiment, genomic DNA or cfDNA is isolated and treated with methyl-sensitive restriction endonucleases, e.g., Bsh1236I (CG^CG) and UNG (37° C., 30-60 minutes) to completely digest unmethylated DNA and prevent carryover (FIG. 50, step A). The digested DNA is bisulfite-treated to convert unmethylated dC residues to uracil (dU) thereby rendering the double stranded DNA non-complementary. As shown in FIG. 50B, locus-specific primers are hybridized in the presence of BstU1 (CG^CG) (filled triangles), which will cleave carryover DNA containing unmethylated residues. The locus-specific primers contain a cleavable blocker at their 3' end to prevent non-target specific extension. Once hybridized to their complementary target sequence, the blocker group (C3-spacer), and an RNA base is removed with RNaseH2 (star symbol). The methyl-containing region of interest is amplified using PCR in the presence of dUTP. Perform limited cycle amplification (12-20) to maintain relative ratios of different amplicons, and optionally aliquot digested sample into 12, 24, 48, or 96 wells prior to PCR. As shown in this embodiment, a blocking oligonucleotide (thick black bar) may be used to limit amplification of wild-type DNA.

The amplified products contain dU and lack methyl groups, allowing for carryover prevention as shown in FIG. 50, step C. As shown in FIG. 50, step D, methyl region-specific ligation oligonucleotide probes containing primer-specific sequences (Ai, Ci') suitable for subsequent PCR amplification, are hybridized to the target region of interest. Ligase (filled circles) covalently seals the two oligonucleotides together to form ligation products containing upstream and downstream primer specific portions and a portion corresponding to the methylated region of interest. The ligation products are aliquot into separate wells for detection using pairs of matched primers Ai and Ci, and TaqMan™ probes across the ligation junction as shown in FIG. 50 steps E-F. The sample mixture is treated with UDG for carryover prevention and removal of original target amplicons (FIG. 50, step E) so that only authentic LDR products are amplified and detected.

FIG. 51 illustrates another PCR-LDR-qPCR carryover prevention reaction to detect methylation. PCR products containing the originally methylated residues of interest and dU are generated following the steps A-C as illustrated and described above with regard to FIG. 50. In this embodiment, the methyl region-specific ligation oligonucleotides contain UniTaq detection primer-specific sequences (Ai and Ci') and tag sequence (Bi') for subsequent PCR amplification detection. The ligation products are amplified and detected using UniTaq-specific primers (F1-Bi-Q-Ai, Ci) as described supra (FIG. 51, steps E-G).

FIG. 52 illustrates another PCR-qLDR carryover prevention reaction to detect methylation. Similar to the embodiments shown in FIGS. 50 and 51, genomic DNA or cfDNA is isolated and treated with methyl-sensitive restriction endonucleases, e.g., Bsh1236I (CG^CG) and UNG (37° C., 30-60 minutes) to completely digest unmethylated DNA and prevent carryover (FIG. 52, step A). The digested DNA is bisulfite-treated to convert unmethylated residues to uracil thereby rendering the double stranded DNA non-complementary. As shown in FIG. 52B, locus-specific primers containing a 3' cleavable blocking group are hybridized in the presence of BstU1 (CG^CG) (filled triangles), which will cleave carryover DNA containing unmethylated residues. Once the primers hybridize to their complementary target sequence, the blocking group is removed and the methyl-containing region of interest is amplified using PCR in the presence of dUTP. In this embodiment, the locus-specific primers contain universal tails (with identical 8-11 bases to prevent primer dimers), which enables a subsequent universal primer amplification to append a 5' biotin group. A blocking oligonucleotide primer may be used during amplification to limit formation of wild-type amplicon.

Amplification products are captured on a solid support via the 5' biotin group (FIG. 52, step C). As shown in FIG. 52D, ligation products are formed using methyl region-specific ligation oligonucleotide probes, where the downstream probe contains a 5' acceptor group and sequence tail that is complementary to the 3' sequence tail of the upstream ligation probe. The upstream ligation probe also contains a 3' donor group such that upon the formation of a ligation product, the 5' and 3' complementary regions of the product hybridize bringing the acceptor and donor groups in close proximity to each other to generate FRET signal for detection of the methylated residues of interest (FIG. 52, step E).

FIG. 151 illustrates another exemplary PCR-LDR-qPCR carryover prevention reaction to detect low-level target methylation. Genomic or cfDNA is isolated (FIG. 151, step A), and the isolated DNA sample is treated with methyl-sensitive restriction endonucleases, e.g., Bsh1236I (CG^CG), and UNG to completely digest unmethylated DNA and prevent carryover (FIG. 151, step A). The digested DNA is bisulfite-treated to convert unmethylated residues to uracil thereby rendering the double stranded DNA non-complementary. The region of interest is selectively amplified using locus-specific upstream primers, locus-specific downstream primers, a blocking LNA or PNA probe comprising the bisulfate converted unmethylated sequence or its complement, and a deoxynucleotide mix that includes dUTP. In this embodiment, another layer of selectivity can be incorporated into the method by including a 3' cleavable blocking group (Blk 3', e.g. C3 spacer), and an RNA base (r), in the upstream primer, as well as the downstream primer. Upon target-specific hybridization, RNase H (star symbol) removes the RNA base to liberate a 3'OH group of the upstream primer, which is a few bases upstream of the methylation site, and suitable for polymerase extension (FIG. 151, step B). A blocking LNA or PNA probe comprising the bisulfite converted unmethylated sequence (or its complement) that partially overlaps with the upstream PCR primer will preferentially compete for binding to the bisulfite converted unmethylated sequence over the upstream primer and over the bisulfite converted methylated sequence DNA, thus suppressing amplification of bisulfite converted unmethylated sequence DNA during each round of PCR. Optionally aliquot sample into 12, 24, 48, or 96 wells prior to PCR. The amplified products contain dU as shown in FIG. 151, step C, which allows for subsequent treatment with UDG or a similar enzyme for carryover prevention.

As shown in FIG. 151 step D, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the bisulfite converted methylated target sequence of interest further contains a 5' primer-specific portion (Ai) to facilitate subsequent detection of the ligation product. Once again, the presence of blocking LNA or PNA probe comprising bisulfite converted unmethylated sequence (or its complement) suppresses hybridization of the upstream ligation probe to bisulfite converted unmethylated target sequence if present after the enrichment of bisulfite converted methylated target sequence during the PCR amplification step. The downstream oligonucleotide probe, having a sequence common to both bisulfite converted unmethylated and methylated target sequences contains a 3' primer-specific portion (Ci') that, together with the 5' primer specific portion (Ai) of the upstream probe having a sequence specific for detecting the bisulfite converted methylated target sequence. Ligation of the upstream and downstream oligonucleotide probes permits subsequent amplification and detection of only bisulfite converted methylated target sequence ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 151, step D). Following ligation, the ligation products can be detected using pairs of matched primers Ai and Ci, and TaqMan™ probes that span the ligation junction as described supra for FIG. 38 (see FIG. 151, steps E-G), or using other suitable means known in the art.

FIG. 152 illustrates another exemplary PCR-LDR-qPCR carryover prevention reaction to detect low-level target methylation. Genomic or cfDNA is isolated (FIG. 152, step A), and the isolated DNA sample is treated with methyl-sensitive restriction endonucleases, e.g., Bsh1236I (CGACG), and UNG to completely digest unmethylated DNA and prevent carryover (FIG. 152, step A). The digested DNA is bisulfite-treated to convert unmethylated residues to uracil thereby rendering the double stranded DNA non-complementary. Upstream and downstream locus-specific primers are designed to include a 3' cleavable blocking group (Blk 3', e.g. C3 spacer), and an RNA base (r). Upon target-specific hybridization, RNase H (star symbol) removes the RNA base to liberate a 3'OH, and is suitable for polymerase extension (FIG. 152, step B). A blocking LNA or PNA probe comprising the bisulfite converted unmethylated sequence (or its complement) that partially overlaps with the upstream PCR primer will preferentially compete for binding to bisulfite converted unmethylated target sequence over the upstream primer and over bisulfite converted methylated target sequence, thus suppressing amplification of bisulfite converted unmethylated target sequence during each round of PCR. Optionally aliquot sample into 12, 24, 48, or 96 wells prior to PCR. The amplified products contain dU as shown in FIG. 152, step C, which allows for subsequent treatment with UDG or a similar enzyme for carryover prevention.

As shown in FIG. 152 step D, target-specific oligonucleotide probes are hybridized to the amplified products and ligase (filled circle) covalently seals the two oligonucleotides together when hybridized to their complementary sequence. Once again, the presence of blocking LNA or PNA probe comprising bisulfite converted unmethylated sequence (or its complement) suppresses ligation to bisulfite converted unmethylated target sequence if present after the enrichment of bisulfite converted methylated target sequence during the PCR amplification step. In this embodiment, the upstream oligonucleotide probe having a sequence specific for detecting the bisulfite converted methylated target sequence of interest further contains a 5' primer-specific portion (Ai) to facilitate subsequent detection of the ligation product. The downstream oligonucleotide probe, having a sequence common to both bisulfite converted unmethylated and methylated target sequences contains a 3' primer-specific portion (Bi'-Ci') that, together with the 5' primer specific portion (Ai) of the upstream probe having a sequence specific for detecting the bisulfite converted methylated target sequence, permit subsequent amplification and detection of only bisulfite converted methylated target sequence ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 152, step D). Following ligation, the ligation products are amplified using UniTaq-specific primers (i.e., F1-Bi-Q-Ai, Ci) and detected as described supra for FIG. 44 (see FIG. 152, steps E-H), or using other suitable means known in the art.

FIG. 153 illustrates another exemplary PCR-qLDR carryover prevention reaction to detect low-level target methylation. Genomic or cfDNA is isolated (FIG. 153, step A), and the isolated DNA sample is treated with methyl-sensitive restriction endonucleases, e.g., Bsh1236I (CGACG), and UNG to completely digest unmethylated DNA and prevent carryover (FIG. 153, step A). The digested DNA is bisulfite-treated to convert unmethylated residues to uracil thereby rendering the double stranded DNA non-complementary. Upstream and downstream locus-specific primers are designed to include a 3' cleavable blocking group (Blk 3', e.g. C3 spacer), and an RNA base (r). Upon target-specific hybridization, RNase H (star symbol) removes the RNA base to liberate a 3'OH, and is suitable for polymerase extension (FIG. 153, step B). A blocking LNA or PNA probe comprising the bisulfite converted unmethylated sequence (or its complement) that partially overlaps with the upstream PCR primer will preferentially compete for binding to bisulfite converted unmethylated target sequence over the upstream primer and over the bisulfite converted methylated target sequence, thus suppressing amplification of bisulfite converted unmethylated target sequence during each round of PCR. In this embodiment, the downstream locus-specific primers also contain 5' primer regions, e.g., universal primer regions, that enables universal PCR amplification using biotin labeled primers to append a 5' biotin to the amplification products containing the region of interest (FIG. 153, step B). Optionally aliquot sample into 12, 24, 48, or 96 wells prior to PCR. The amplified products contain dU as shown in FIG. 153, step C, which allows for subsequent treatment with UDG or a similar enzyme for carryover prevention. The biotinylated PCR products are immobilized to a solid support and the bisulfite converted methylated target sequence of interest is detected using bisulfite converted methylated target sequence specific ligation probes as illustrated in FIG. 153, step D. Once again, the presence of blocking LNA or PNA probe comprising the bisulfite converted unmethylated sequence (or its complement) suppresses ligation to bisulfite converted unmethylated target sequence if present after the enrichment of bisulfite converted methylated target sequence during the PCR amplification step. In this embodiment, the ligation probes of a ligation pair capable of detecting the bisulfite converted methylated target sequence nucleic acid sequence (but not the bisulfite converted unmethylated target sequence) contain complementary tail sequences and an acceptor or donor group, respectively, capable of generating a detectable signal via FRET when brought in close proximity to each other as described supra for FIG. 39. As illustrated in this Figure, another layer of specificity can be incorporated into the method by including a 3' cleavable blocking group, (e.g. C3-spacer), and an RNA base (r), in the upstream ligation probe. Upon target-specific hybridization, RNase H (star symbol) removes the RNA base to generate a ligation competent 3'OH group (FIG. 153, step D). Following ligation (FIG. 153, step E), the complementary 5' and 3' tail ends of the ligation products hybridize to each other bringing their respective donor and acceptor moieties in close proximity to each other to generate a detectable FRET signal (FIG. 153, step F).

In another embodiment of this aspect of the present invention the first primary oligonucleotide primer of the primary oligonucleotide primer set comprises a 5' portion having a nucleotide sequence that is the same as a nucleotide sequence portion in a bisulfate-treated unmethylated target sequence to which the primary oligonucleotide primer hybridizes to, but has one or more nucleotide sequence mismatches to a corresponding nucleotide sequence portion in the bisulfate-treated methylated target sequence.

In accordance with this embodiment, the DNA polymerase is one that lacks 5' nuclease, 3' nuclease, and strand displacing activity. Optionally, the primary oligonucleotide primer also contains a cleavable nucleotide or nucleotide analog that is cleaved during the hybridization step of the polymerase chain reaction to liberate free 3'OH ends on the oligonucleotide primer suitable for extension. The polymerase chain reaction mixture is subject to one or more additional polymerase chain reaction cycles comprising a denaturation treatment wherein the extension products from the reaction are separated from each other, and a hybridization treatment wherein the first primary oligonucleotide primer hybridizes to the extension product arising from the second primary oligonucleotide primer. The extension product arising from the second primary primer forms an intramolecular loop-hairpin between the 3' end and the complementary sequence within the extension product, which (i) comprises one or more mismatches at or near the 3' end that inhibits self-extension if self-hybridized to bisulfite-treated methylated sequence or (ii) comprises a match at the 3' end that enhances self-extension if self-hybridized to bisulfate-treated unmethylated target-sequence. The second primary oligonucleotide primer hybridizes to the extension product arising from the first primary oligonucleotide primer. The extension product arising from the first primary oligonucleotide primer forms an intramolecular loop-hairpin between the 5' portion and the complementary sequence within the extension product. During the extension step of the PCR, the first primary oligonucleotide primer (i) preferentially extends on extension product comprising bisulfite-treated methylated target sequence thereby preferentially forming primary extension products comprising the bisulfite-treated methylated target nucleotide sequence or a complement thereof, or (ii) is inhibited from forming primary extension products comprising the bisulfate-treated unmethylated target nucleotide sequence or a complement thereof due to prior self-hybridization and self-extension on said target. The second primary oligonucleotide primer (iii) extends on extension product independent of target sequence, wherein the bisulfate-treated methylated sequence is preferentially amplified due to the different primary extension products arising from the hybridization of the first primary oligonucleotide primers to the target or copies thereof, resulting in enrichment of the bisulfate-treated methylated sequence extension product and complements thereof during said the primary polymerase chain reaction FIGS. 156 and 157 illustrate this embodiment of the present invention. As shown in FIG. 156, genomic DNA or cfDNA is isolated and treated with methyl-sensitive restriction endonucleases, e.g., Bsh1236I (CGACG) and UNG (37° C., 30-60 minutes) to completely digest unmethylated DNA and prevent carryover (FIG. 156, step A). The digested DNA is bisulfate-treated to convert unmethylated dC residues to uracil (dU) thereby rendering the double stranded DNA non-complementary. The region of interest is selectively amplified using (i) locus-specific upstream primers that also comprise a 5' sequence portion complementary to bisulfate-treated unmethylated sequence of the top strand allowing for formation of loop-hairpins after extension, (ii) locus-specific downstream primers, and (iii) a deoxynucleotide mix that includes dUTP. As illustrated in step B of this Figure, another layer of selectivity can be incorporated into the method by including a 3' cleavable blocking group (Blk 3', e.g. C3 spacer), and an RNA base (r), in the upstream mutation-specific primer. Upon target-specific hybridization, RNase H (star symbol) removes the RNA base to liberate a 3'OH group suitable for polymerase extension (FIG. 156, step B). Optionally aliquot digested sample into 12, 24, 48, or 96 wells prior to PCR. The amplified products contain dU as shown in FIG. 156, step C, which allows for subsequent treatment with UDG or a similar enzyme for carryover prevention. PCR is performed with a polymerase lacking 5' nuclease, 3' nuclease, and strand-displacement activity. FIG. 156, step D further illustrates that in subsequent rounds of amplification: (i) the denatured bisulfate-treated unmethylated bottom strand forms a loop-hairpin with perfect match at the 3' end, which is extended by polymerase, (ii) the denatured bisulfate-treated methylated bottom strand forms a loop-hairpin with two or more mismatches, which generally is not extended by polymerase, and (iii) the denatured top strand forms a loop-hairpin on its 5' side, which denatures during the extension step of PCR at 72° C. FIG. 156, step E further illustrates that: after extension of the loop-hairpin on bisulfate-treated unmethylated DNA (i), the extended hairpin sequence does not denature at 72° C. and prevents upstream primer from generating full-length top strand. However, the loop-hairpin sequence of bisulfate-treated methylated DNA (ii) does not extend on account of two or more mismatched bases, and thus denatures at 72° C., enabling upstream primer to generate full-length top strand. Likewise, top strand product (iii) denatures at 72° C., allowing polymerase to generate full-length bottom strand. The difference in loop-hairpin extension preference of upstream primers with (i) bisulfite-treated unmethylated and (ii) bisulfate-treated methylated template results in preferential removal of bisulfate-treated unmethylated amplification products during each cycle of amplification, and thus results in preferential amplification of bisulfate-treated methylated DNA.

As shown in FIG. 156, step G, oligonucleotide probes specific for the bisulfite-treated methylated target sequence are hybridized to the amplified products, and ligase (filled circle) covalently seals the two oligonucleotides together when hybridized to their complementary sequence. In this embodiment, the upstream oligonucleotide probe having a sequence specific for detecting the bisulfate-treated methylated sequence of interest further contains a 5' primer-specific portion (Ai) to facilitate subsequent detection of the ligation product, while the optional upstream oligonucleotide probe having a sequence specific for detecting the bisulfate-treated unmethylated nucleic acid sequence does not contain a 5' primer-specific portion. The downstream oligonucleotide probe, having a sequence specific for detecting bisulfate-treated methylated sequences contains a 3' primer-specific portion (Ci') that, together with the 5' primer specific portion (Ai) of the upstream probe having a sequence specific for detecting bisulfate-treated methylated sequence of interest, permit subsequent amplification and detection of only mutant ligation products. As illustrated in this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 156, step H). Following ligation, the ligation products can be detected using pairs of matched primers Ai and Ci, and TaqMan™ probes that span the ligation junction as described in FIG. 38 (see FIG. 156, steps H-J), or using other suitable means known in the art.

FIG. 157 illustrates another PCR-qLDR carryover prevention reaction to detect methylation. In this embodiment, genomic DNA or cfDNA is isolated and treated with methyl-sensitive restriction endonucleases, e.g., Bsh1236I (CG^CG) and UNG (37° C., 30-60 minutes) to completely digest unmethylated DNA and prevent carryover (FIG. 157, step A). The digested DNA is bisulfite-treated to convert unmethylated dC residues to uracil (dU) thereby rendering the double stranded DNA non-complementary. The region of interest is selectively amplified using (i) locus-specific upstream primers that also comprise a 5' portion having a sequence complementary to bisulfate-treated unmethylated sequence of the top strand allowing for formation of loop-hairpins after extension, (ii) locus-specific downstream primers, and (iii) a deoxynucleotide mix that includes dUTP. As illustrated in this Figure, another layer of selectivity can be incorporated into the method by including a 3' cleavable blocking group (Blk 3', e.g. C3 spacer), and an RNA base (r), in the upstream primer. Upon target-specific hybridization, RNase H (star symbol) removes the RNA base to liberate a 3'OH group suitable for polymerase extension (FIG. 157, step B). Optionally aliquot digested sample into 12, 24, 48, or 96 wells prior to PCR. The amplified products contain dU as shown in FIG. 157, step C, which allows for subsequent treatment with UDG or a similar enzyme for carryover prevention. PCR is performed with a polymerase lacking 5' nuclease, 3' nuclease, and strand-displacement activity. FIG. 157, step D further illustrates that in subsequent rounds of amplification (i) the denatured bisulfate-treated unmethylated bottom strand forms a loop-hairpin with perfect match at the 3' end, which is extended by polymerase, (ii) the denatured bisulfite-treated methylated bottom strand forms a loop-hairpin with two or more mismatches, which generally is not extended by polymerase, and (iii) the denatured top strand forms a loop-hairpin on 5' side, which denatures during the extension step of PCR at 72° C. FIG. 157, step E further illustrates that after extension of the loop-hairpin on bisulfate-treated unmethylated DNA (i), extended hairpin sequence does not denature at 72° C. and prevents upstream primer from generating full-length top strand. However, the loop-hairpin sequence of bisulfate-treated methylated DNA (ii) does not extend on account of two or more mismatched bases, and thus denatures at 72° C., enabling upstream primer to generate full-length top strand. Likewise, top strand product denatures at 72° C., allowing polymerase to generate full-length bottom strand (iii). The difference in loop-hairpin extension preference of upstream primers with (i) bisulfate-treated unmethylated and (ii) bisulfite-treated methylated template results in preferential removal of bisulfate-treated unmethylated amplification products during each cycle of amplification, and thus results in preferential amplification of bisulfate-treated methylated DNA.

In this embodiment, the downstream locus-specific primers also contain a 5' primer region, e.g., universal primer region, that enables universal PCR amplification using biotin labeled primers to append a 5' biotin to the amplification products containing the region of interest (FIG. 157, step B). The biotinylated PCR products are immobilized to a solid support and the bisulfate-treated methylated sequence of interest is detected using ligation probes specific for the bisulfate-treated methylated target sequence as illustrated in FIG. 150, step G. In this embodiment, the ligation probes of a ligation pair capable of detecting the bisulfate-treated methylated nucleic acid sequence (but not the bisulfate-treated unmethylated sequence) contain complementary tail sequences and an acceptor or donor group, respectively, capable of generating a detectable signal via FRET when brought in close proximity to each other as described supra for FIG. 39. As illustrated in step G of this Figure, another layer of specificity can be incorporated into the method by including a 3' cleavable blocking group, (e.g. C3-spacer), and an RNA base (r), in the upstream ligation probe. Upon target-specific hybridization, RNase H (star symbol) removes the RNA base to generate a ligation competent 3'OH group (FIG. 150, step G). Following ligation (FIG. 157, step H), the complementary 5' and 3' tail ends of the ligation products hybridize to each other bringing their respective donor and acceptor moieties in close proximity to each other to generate a detectable FRET signal (FIG. 157, step I).

Another aspect of the present invention is directed to a method for identifying, in a sample, one or more nucleic acid molecules containing a target nucleotide sequence differing from nucleotide sequences in other nucleic acid molecules in the sample, or other samples, by one more methylated residue. This method involves providing a sample containing one or more nucleic acid molecules potentially comprising the target nucleotide sequence differing from the nucleotide sequences in other nucleic acid molecules by one or more methylated residues and contacting the sample with one or more enzymes capable of digesting deoxyuracil (dU) containing nucleic acid molecules present in the sample. The method further involves contacting the sample with one or more methylation sensitive enzymes to form a restriction enzyme reaction mixture, wherein the one or more said methylation sensitive enzyme cleaves nucleic acid molecules in the sample that contain one or more unmethylated residues within at least one methylation sensitive enzyme recognition sequence. One or more primary oligonucleotide primer sets are provided, each primary oligonucleotide primer set comprising (a) first primary oligonucleotide primer comprising a nucleotide sequence that is complementary to a region of the target nucleotide sequence that is upstream of the one or more methylated residues and (b) a second primary oligonucleotide primer comprising a nucleotide sequence that is the same as a region of the target nucleotide sequence that is downstream of the one or more methylated residues. The restriction enzyme reaction mixture is blended with the one or more primary oligonucleotide primer sets, a deoxynucleotide mix including dUTP, and a DNA polymerase to form a primary polymerase chain reaction mixture. The method further involves subjecting the primary polymerase chain reaction mixture to one or more polymerase chain reaction cycles comprising a denaturation treatment, a hybridization treatment, and an extension treatment, thereby forming primary extension products comprising the target nucleotide sequence or a complement thereof. One or more secondary oligonucleotide primer sets are provided, each secondary oligonucleotide primer set comprising first and second nested oligonucleotide primers capable of hybridizing to the primary extension products The primary extension products are blended with the one or more secondary oligonucleotide primer sets, a deoxynucleotide mix including dUTP, and a DNA polymerase to form a secondary polymerase chain reaction mixture, and the secondary polymerase chain reaction mixture is subjected to one or more polymerase chain reaction cycles comprising a denaturation treatment, a hybridization treatment, and an extension treatment thereby forming secondary extension products. The secondary extension products in the sample are detected and distinguished to identify the presence of one or more nucleic acid molecules containing target nucleotide sequences differing from nucleotide sequences in other nucleic acid molecules in the sample by one or more methylated residues.

In accordance with this aspect of the present invention, the secondary polymerase chain reaction mixture may further comprise one or more oligonucleotide detection probes, e.g., a TaqMan™ oligonucleotide detection probe. The detection probe hybridizes to a target nucleotide sequence within the primary extension product or its complement, and has a quencher molecule and a detectable label that are separated from each other but in close enough proximity to each so that the quencher molecule quenches the detectable label. During the hybridization step of the secondary polymerase chain reaction process, the one or more oligonucleotide detection probes hybridize to complementary portions of the primary extension products and the quencher molecule and the detectable label are subsequently cleaved from the one or more oligonucleotide detection probes during the extension step. Upon cleavage, the detectable label is separated from the quencher so that the detectable label is detected.

In one embodiment, one or both primary oligonucleotide primers of the primary oligonucleotide primer set may optionally have a 3' portion comprising a cleavable nucleotide or nucleotide analogue and a blocking group, such that the 3' end of said primer or primers is unsuitable for polymerase extension until the cleavable nucleotide or nucleotide analog is cleaved. Upon cleavage, a free 3'OH end is liberated on one or both primary oligonucleotide primers prior to allow for primer extension.

In another embodiment, the primary oligonucleotide primers of the primary oligonucleotide primer set comprise an identical or substantially identical 5' nucleotide sequence portion that is between about 6 to 20 bases in length. In accordance with this embodiment, the desired extension products that are generated are of sufficient length such that primary primers preferentially hybridize to them. However, when an undesired primer dimer product forms, it will hairpin on itself via its complementary 5' ends and be unsuitable for continued amplification.

FIG. 158 illustrates an exemplary PCR-PCR carryover prevention reaction to detect methylation in accordance with this aspect of the present invention. In this embodiment, genomic DNA or cfDNA is isolated and treated with methyl-sensitive restriction endonucleases, e.g., Bsh1236I (CGACG) and/or HinP1I (GACGC), and UNG to completely digest unmethylated DNA and prevent carryover (FIG. 158, step A). As shown in FIG. 158, step B, methylated regions of interest are amplified using PCR in presence of dUTP using locus-specific primers. In one embodiment, limited cycle amplification (12-20 cycles) is performed to maintain relative ratios of different amplicons being produced. In another embodiment, the regions of interest are amplified using 20-40 cycles. Primers contain identical 8-11 base tails to prevent primer dimers. The PCR products contain dU, allowing for carryover prevention (FIG. 158, step C). Optionally, the sample is aliquoted into 12, 24, 48, or 96 wells prior to PCR. The methyl containing regions are amplified using nested or semi-nested locus-specific primers and an internal traditional TaqMan™ detection assay. PCR products incorporate dU, allowing for carryover prevention.

FIG. 53 illustrates another PCR-qPCR carryover prevention reaction to detect methylation. Similar to the other embodiments of the present invention, genomic DNA or cfDNA is isolated and treated with methyl-sensitive restriction endonucleases, e.g., Bsh1236I (CG^CG) and UNG (37° C., 30-60 minutes) to completely digest unmethylated DNA and prevent carryover (FIG. 53, step A). The digested DNA is bisulfite-treated to convert unmethylated residues to uracil thereby rendering the double stranded DNA non-complementary. As shown in FIG. 53, step B, locus-specific primers containing a 3' cleavable blocking group are hybridized in the presence of BstU1 (CG^CG) (filled triangles), which will cleave carryover DNA containing unmethylated residues. Once the primers hybridize to their complementary target sequence, the blocking group is removed. In this embodiment, the methyl-containing region of interest is amplified using PCR in the presence of dNTP. In this embodiment, a blocking oligonucleotide primer is used during amplification to limit formation of wild-type amplicon. As shown in FIG. 53, step C, the PCR products are unmethylated providing carryover protection.

As shown in FIG. 53, steps D and E, the PCR products are aliquot into separate wells for TaqMan™ detection using locus-specific primers that are optionally nested or semi-nested to the primary set of locus specific primers, and TaqMan™ probe (black bar). Optionally, a blocking oligonucleotide (thick black bar) can also be incorporated in this reaction to limit formation of wild-type amplicons. In this embodiment, the TaqMan™ reaction is carried out in the presence of dUTPs, allowing for carryover prevention.

Another aspect of the present invention is directed to a method for identifying in a sample, one or more ribonucleic acid molecules containing a target ribonucleotide sequence differing from ribonucleotide sequences in other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level. This method involves providing a sample containing one or more ribonucleic acid molecules potentially containing a target ribonucleotide sequence differing from ribonucleotide sequences in other ribonucleic acid molecules, and contacting the sample with one or more enzymes capable of digesting dU containing nucleic acid molecules potentially present in the sample. One or more oligonucleotide primers are provided, each primer being complementary to the one or more ribonucleic acid molecules containing a target ribonucleotide sequence. The contacted sample is blended with the one or more oligonucleotide primers, and a reverse-transcriptase to form a reverse-transcription mixture, and complementary deoxyribonucleic acid (cDNA) molecules are generated in the reverse transcription mixture. Each cDNA molecule comprises a nucleotide sequence that is complementary to the target ribonucleotide sequence and contains dU. The method further involves providing one or more oligonucleotide primer sets, each primer set comprising (a) a first oligonucleotide primer comprising a nucleotide sequence that is complementary to a portion of a cDNA nucleotide sequence adjacent to the target ribonucleotide sequence complement of the cDNA, and (b) a second oligonucleotide primer comprising a nucleotide sequence that is complementary to a portion of an extension product formed from the first oligonucleotide primer. The reverse transcription mixture containing the cDNA molecules is blended with the one or more oligonucleotide primer sets, and a polymerase to form a polymerase reaction mixture, and the polymerase chain reaction mixture is subjected to one or more polymerase chain reaction cycles comprising a denaturation treatment, a hybridization treatment, and an extension treatment thereby forming one or more different primary extension products. The method further involves providing one or more oligonucleotide probe sets. Each probe set comprises (a) a first oligonucleotide probe having a target sequence-specific portion, and (b) a second oligonucleotide probe having a target sequence-specific portion, wherein the first and second oligonucleotide probes of a probe set are configured to hybridize, in a base specific manner, adjacent to one another on a complementary primary extension product with a junction between them. The primary extension products are contacted with a ligase and the one or more oligonucleotide probe sets to form a ligation reaction mixture and the first and second probes of the one or more oligonucleotide probe sets are ligated together to form ligated product sequences in the ligase reaction mixture. The ligated product sequences in the sample are detected and distinguished thereby identifying the presence of one or more ribonucleic acid molecules containing the target ribonucleotide sequence differing from ribonucleotide sequences in other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level FIGS. 54-85 illustrate various embodiments of this aspect of the present invention.

FIG. 54 illustrates an overview of RT-PCR-LDR-qPCR carryover prevention reaction to detect translocations at the mRNA level. An illustration of translocations between two genes is shown at the DNA level in FIG. 54, step A. Examples of the different fusion junctions between exons 1-b (mRNA fusion 1), 2-b (mRNA fusion 2), and 3-b (mRNA fusion 3) in mRNAs are illustrated (FIG. 54, step B). This method involves isolating mRNA from whole blood cells, exosomes, or circulating tumor cells (CTCs) and generating cDNA using reverse transcriptase and a primer complementary to exon b. The generated cDNA is PCR amplified using forward primers to exons 1, 2, and 3 and the primer to exon b (FIG. 54, step B). Independent of translocation breakpoint, the primers will amplify the smallest fragment containing the exon junction region. The various products formed during PCR amplification are shown in FIG. 54, step C.

LDR is carried out using exon junction-specific ligation oligonucleotide probes. The ligation probes can be designed to contain tag primer specific portions (e.g., Ai, Ci') suitable for subsequent detection using primers (Ai, Ci) and TaqMan™ probes (FIG. 54, steps C-D, left panel). Alternatively, the ligation probes can be designed to contain UniTaq primer-specific (Ai, Ci') and tag-specific portions (Bi') (FIG. 54, steps C-D, right panel). Following the formation of exon junction specific ligation product formation, the ligation products are PCR amplified and detected (FIG. 54, step D).

When using tag-specific primers (Ai, Ci) for amplifying LDR products, each TaqMan™ probe spans the ligation junction, and can be scored individually. When using UniTaq-specific primers (F1-Bi-Q-Ai, Ci), for amplifying LDR products, the same primer set scores for the given translocation, independent of the specific exon junction.

FIG. 55 illustrates a RT-PCR-LDR-qPCR carryover prevention reaction to detect translocations at the mRNA level. In this embodiment, mRNA is isolated (FIG. 55, step A), and treated with UDG for carryover prevention (FIG. 55, step B). cDNA is generated using 3' transcript-specific primers and reverse-transcriptase in the presence of dUTP. Taq polymerase is activated to perform limited cycle PCR amplification (12-20) to maintain relative ratios of different amplicons (FIG. 55, step B). The primers contain identical 8-11 base tails to prevent primer dimers. PCR products incorporate dUTP, allowing for carryover prevention (FIG. 55, step C).

As shown in FIG. 55, step D, exon junction-specific ligation oligonucleotide probes containing primer-specific portions (Ai, Ci') suitable for subsequent PCR amplification, hybridize to their corresponding target sequence in a base-specific manner. Ligase covalently seals the two oligonucleotides together (FIG. 55, step D), and ligation products are aliquoted into separate wells for detection using tag-primers (Ai, Ci) and TaqMan™ probe (F1-Q) which spans the ligation junction (FIG. 55, step E). Treat samples with UDG for carryover prevention, which also destroys original target amplicons (FIG. 55, step E). Only authentic LDR products will amplify, when using PCR in presence of dUTP. Neither original PCR primers nor LDR probes amplify LDR products, providing additional carryover protection.

FIG. 56 illustrates another RT-PCR-LDR-qPCR carryover prevention reaction to detect translocations at the mRNA level. In this embodiment, mRNA is isolated (FIG. 56, step A), and treated with UDG for carryover prevention (FIG. 56, step B). cDNA is generated using 3' transcript-specific primers and reverse-transcriptase in the presence of dUTP. Taq polymerase is activated to perform limited cycle PCR amplification (12-20) to maintain relative ratios of different amplicons (FIG. 56, step B). The primers contain identical 8-11 base tails to prevent primer dimers. PCR products incorporate dU, allowing for carryover prevention (FIG. 56, step C).

As shown in FIG. 56, step D, exon junction-specific ligation oligonucleotide probes containing UniTaq primer-specific portions (Ai, Ci') and tag portion (Bi') suitable for subsequent PCR amplification and detection, hybridize to nucleic acid sequences corresponding to the target mRNA molecule to be detected (FIG. 56, step D). Following ligation of the oligonucleotide probes, the sample is UDG treated to remove original target amplicons, allowing selective amplification and detection of the ligation products using UniTaq-specific primers (F1-Bi-Q-Ai, Ci) as described supra (FIG. 56, steps E-F), thereby facilitating the detection of the mRNA translocation mRNA fusion. As shown in FIG. 56, steps E and F, the amplified ligation products incorporate dUTP to allow for future carry over prevention.

FIG. 57 illustrates an example of a RT-PCR-qLDR carryover prevention reaction to detect translocations at the mRNA level. In this embodiment, mRNA is isolated (FIG. 57, step A), and treated with UDG for carryover prevention (FIG. 57, step B). cDNA is generated using 3' transcript-specific primers and reverse-transcriptase in the presence of dUTP. Taq polymerase is activated to perform limited cycle PCR amplification (12-20) to maintain relative ratios of different amplicons (FIG. 57, step B). The primers contain identical 8-11 base tails to prevent primer dimers and universal primer-specific portions to enable a subsequent universal PCR amplification using biotin labeled primers to append a 5' biotin to the amplification products containing the region of interest. PCR products incorporate dU, allowing for carryover prevention (FIG. 57, step C). The biotinylated PCR products are immobilized to a solid support and the region of interest is detected using exon junction-specific ligation probes as illustrated in FIG. 57, step D. In this embodiment, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 57, step D), the complementary 5' and 3' tail ends of the ligation products hybridize to each other bringing their respective donor and acceptor moieties in close proximity to each other to generate a detectable FRET signal (FIG. 57, step E).

FIG. 58 illustrates an overview of RT-PCR-LDR-qPCR carryover prevention reaction to detect alternative splicing. FIG. 58, step A is an illustration of a gene with 5 exons shown at the DNA level, and FIG. 58, step B shows examples of normal (1-2-3a-4), and alternatively spliced (1-2-3b-4) variant mRNAs. This method involves isolating mRNA from whole blood cells, exosomes, or CTCs, and generating cDNA using reverse transcriptase with a primer complementary to exon 4 as shown in FIG. 58, step B. The cDNA is PCR amplified using the exon 4 primer and a forward primer to exon 2, to generate amplicons of both normal and alternative splice variants, if present. As shown in FIG. 58, step C, exon junction-specific ligation oligonucleotide probes containing tag-primer sequences (Ai, Ci'; left panel) or UniTaq primer and tag sequences (Ai, Bi'-Ci'; right panel) hybridize to their corresponding target sequence in the PCR products, and ligase covalently seals the two oligonucleotides together if there is perfect complementarity at the junction. The ligation products are amplified and detected using tag-specific primers (Ai, Ci) and TaqMan™ probes (F1-Q or F2-Q, FIG. 58, step D, left panel) or UniTaq primers (F1-Bi-Q-Ai, F2-Bi-Q-Ai, Ci, FIG. 58, step D, right panel), as described supra.

FIG. 59 illustrates a RT-PCR-LDR-qPCR carryover prevention reaction to quantify wild-type and alternatively spliced mRNA transcripts. FIG. 59, step A illustrates the wildtype transcript containing exon 3a (top) and alternatively spliced transcript containing exon 3b (bottom) to be detected. This method involves isolating mRNA and treating with UDG for carryover prevention (FIG. 59, step B). cDNA is generated using 3' transcript-specific primers and reverse-transcriptase in the presence of dUTP. Taq polymerase is activated to perform limited cycle PCR amplification (12-20) to maintain relative ratios of different amplicons (FIG. 59, step B). The primers contain identical 8-11 base tails to prevent primer dimers. PCR products incorporate dU, allowing for carryover prevention (FIG. 59, step C). As shown in FIG. 59, step D, exon junction-specific ligation oligonucleotide probes containing tag-primer-specific portions (Ai, Ci=) suitable for subsequent PCR amplification, hybridize to their corresponding target sequence in a base-specific manner. Ligase covalently seals the two oligonucleotides together (FIG. 59, step D), and ligation products are aliquoted into separate wells for detection using tag-primers (Ai, Ci) and TaqMan™ probes (F1-Q and F2-Q) which span the ligation junction (FIG. 59, step E-F). The wild-type and alternative splice variant are quantified and distinguished using real-time PCR and detecting the differently labeled TaqMan™ probes. Treat samples with UDG for carryover prevention, which also destroys original target amplicons (FIG. 59, step E). Only authentic LDR products will amplify, when using PCR in presence of dUTP. Neither original PCR primers nor LDR probes amplify LDR products, providing additional carryover protection.

FIG. 60 illustrates another RT-PCR-LDR-qPCR carryover prevention reaction to quantify wild-type and alternatively spliced mRNA transcripts. FIG. 60, step A illustrates the wildtype transcript containing exon 3a (top) and alternatively spliced transcript containing exon 3b (bottom) to be detected. Steps A-D of this method are essentially the same as that described for FIG. 59, except that the exon junction-specific ligation probes are designed to contain UniTaq primer sequences (Ai, Ci') and a UniTaq tag sequence (Bi'). Accordingly, in this embodiment, the ligation products corresponding to the wild-type and alternative splice variant are subsequently amplified, detected, and quantified using real time PCR with UniTaq-specific primers (F1-Bi-Q-Ai, Ci) as described above and illustrated in FIG. 60, steps E-G.

FIG. 61 illustrates a RT-PCR-qLDR carryover prevention reaction to quantify wild-type and alternatively spliced mRNA transcripts. FIG. 61, step A illustrates the wild-type transcript containing exon 3a (top) and alternatively spliced transcript containing exon 3b (bottom) to be detected. This method involves isolating mRNA and treating with UDG for carryover prevention (FIG. 61, step B). cDNA is generated using 3' transcript-specific primers and reverse-transcriptase in the presence of dUTP. The primers contain identical 8-11 base tails to prevent primer dimers and universal primer-specific portions to enable a subsequent universal PCR amplification using biotin labeled primers to append a 5' biotin to the amplification products containing the region of interest. PCR products incorporate dU, allowing for carryover prevention (FIG. 61, step C). The biotinylated PCR products are immobilized to a solid support and the region of interest is detected using exon junction-specific ligation probes as illustrated in FIG. 61, step D. In this embodiment, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 61, step D), the complementary 5' and 3' tail ends of the ligation products hybridize to each other bringing their respective donor and acceptor moieties in close proximity to each other to generate a detectable FRET signal (FIG. 61, step E).

FIG. 62 illustrates a RT-PCR-LDR-qPCR carryover prevention reaction to detect low-level alternatively spliced transcripts. FIG. 62, step A illustrates the wild-type transcript containing exon 3a (top) and the low level alternatively spliced transcript containing exon 3b (bottom) to be detected. This method involves isolating mRNA and treating with UDG for carryover prevention (FIG. 62, step B). cDNA is generated using 3' transcript-specific primers (i.e. to exon 4) and reverse-transcriptase in the presence of dUTP. Taq polymerase is activated to perform limited cycle PCR amplification (12-20) to maintain relative ratios of different amplicons (FIG. 62, step B). In this embodiment, a primer specific for the alternative splice variant (i.e., exon 3b), and which does not hybridize to the wild-type variant (i.e., exon 3a), is utilized to only generate amplification products corresponding to the alternative splice variant. PCR products incorporate dUTP, allowing for carryover prevention (FIG. 62, step C). As shown in FIG. 62, step D, exon junction-specific ligation oligonucleotide probes containing primer-specific portions (Ai, Ci') suitable for subsequent PCR amplification, hybridize to their corresponding target sequence in a base-specific manner. Ligase covalently seals the two oligonucleotides together (FIG. 62, step D), and ligation products are aliquot into separate wells for detection using tag-primers (Ai, Ci) and TaqMan™ probe (F1-Q) which span the ligation junction (FIG. 62, step E-F). The alternative splice variant is detected during real-time PCR by the liberation of fluorescent group of the TaqMan™ probe. Samples are treated with UDG for carryover prevention, which also destroys original target amplicons (FIG. 62, step E). Only authentic LDR products are amplified, when using PCR in presence of dUTP. Neither original PCR primers nor LDR probes amplify LDR products, providing additional carryover protection.

FIGS. 63 and 64 illustrate similar RT-PCR-LDR-qPCR and RT-PCR-qLDR carryover prevention reactions to detect low-level alternatively spliced transcript as described and shown with respect to FIG. 62. In the embodiment of FIG. 63, the exon junction-specific ligation probes are designed to contain UniTaq primer sequences (Ai, Ci') and a UniTaq tag sequence (Bi'). Accordingly, in this embodiment, the ligation products corresponding to the alternative splice variant are subsequently amplified, detected, and quantified using real time PCR with UniTaq-specific primers (F1-Bi-Q-Ai, Ci) as described above and as illustrated in FIG. 63, steps E-G. In the embodiment of FIG. 64, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 64, step D), the complementary 5' and 3' tail ends of the ligation products hybridize to each other bringing their respective donor and acceptor moieties (D, F2) in close proximity to each other to generate a detectable FRET signal (FIG. 64, step E).

FIG. 65 illustrates an overview of RT-PCR-LDR-qPCR carryover prevention reaction to detect alternative splicing. FIG. 65, step A shows an illustration of a gene with 3 exons, and an alternative start site and first exon at the DNA level. FIG. 65, step B shows examples of the normal (1-2-3) and the alternative splice variant (1a-2-3) mRNAs. This method involves isolating mRNA from whole blood cells, exosomes, or CTCs, and generating cDNA using reverse transcriptase with a primer complementary to exon 2 as shown in FIG. 65, step B. The cDNA is PCR amplified using the exon 2 primer and a forward primer that is complementary to either exon 1 or exon 1a to generate amplicons of both splice variants. As shown in FIG. 65, step C, exon junction-specific ligation oligonucleotide probes containing tag-primer sequences (Ai, Ci'; left panel) or UniTaq primer and tag sequences (Ai, Bi'-Ci'; right panel) hybridize to their corresponding target sequence in the PCR products, and ligase covalently seals the two oligonucleotides together if there is perfect complementarity at the junction. The ligation products are amplified and detected using tag-specific primers (Ai, Ci) and TaqMan™ probes (F1-Q or F2-Q; FIG. 58, step D, left panel) or UniTaq primers (F1-Bi-Q-Ai, F2-Bi-Q-Ai, and Ci, FIG. 58, step D, right panel), as described supra.

FIG. 66 illustrates a RT-PCR-LDR-qPCR carryover prevention reaction to quantify transcripts containing the wild-type and an alternative transcription start site. FIG. 66, step A illustrates the wildtype transcript containing exon 1 (top) and the alternative transcript having exon 1a as the start site (bottom). This method involves isolating mRNA and treating with UDG for carryover prevention (FIG. 66, step B). cDNA is generated using 3' transcript-specific primers and reverse-transcriptase in the presence of dUTP. The cDNA is PCR amplified using the exon 2-specific primer and a forward primer that is complementary to either exon 1 or exon 1a to generate amplicons of both splice variants. Limited PCR amplification (12-20 cycles) is performed to maintain relative ratios of different amplicons (FIG. 66, step B). In another embodiment, regions of interest are amplified using 20-40 PCR cycles. The primers contain identical 8-11 base tails to prevent primer dimers. PCR products incorporate dU, allowing for carryover prevention (FIG. 66, step C). As shown in FIG. 66, step D, exon junction-specific ligation oligonucleotide probes containing tag-primer-specific portions (Ai, Ci') suitable for subsequent TaqMan™ PCR amplification, hybridize to their corresponding target sequence in a base-specific manner. Ligase covalently seals the two oligonucleotides together (FIG. 66, step D), and ligation products are aliquot into separate wells for detection using tag-primers (Ai, Ci) and TaqMan™ probes (F1-Q and F2-Q) which span the ligation junction (FIG. 66, step E-F). The wild-type and alternative transcript start site variant are quantified and distinguished using real-time PCR and detecting the differently labeled TaqMan™ probes. Samples are treated with UDG for carryover prevention, which also destroys original target amplicons (FIG. 66, step E). Only authentic LDR products amplify, when using PCR in presence of dUTP. Neither original PCR primers nor LDR probes amplify LDR products, providing additional carryover protection.

FIG. 67 illustrates another RT-PCR-LDR-qPCR carryover prevention reaction to quantify wild-type and alternatively spliced mRNA transcripts. FIG. 67, step A illustrates the wildtype transcript containing exon 1 (top) and the alternative transcript having exon 1a as the start site (bottom). Steps A-D of this method are essentially the same as that described for FIG. 66, except that the exon junction-specific ligation probes are designed to contain UniTaq primer sequences (Ai, Ci') and a UniTaq tag sequence (Bi'). Accordingly, in this embodiment, the ligation products corresponding to the wildtype and variant transcripts are subsequently amplified, detected, and quantified using real time PCR with UniTaq-specific primers (F1-Bi-Q-Ai, Ci) as described above and illustrated in FIG. 67, steps E-F.

FIG. 68 illustrates RT-PCR-qLDR carryover prevention reaction to quantify wild-type and alternatively spliced mRNA transcripts. FIG. 68, step A illustrates the wildtype transcript containing exon 1 (top) and the alternative transcript having exon 1a as the start site (bottom). This method involves isolating mRNA and treating with UDG for carryover prevention (FIG. 68, step B). cDNA is generated using 3' transcript-specific primers and reverse-transcriptase in the presence of dUTP. The cDNA is PCR amplified using the exon 2 primer and a forward primer that is complementary to either exon 1 or exon 1a to generate amplicons of both splice variants. The primers contain identical 8-11 base tails to prevent primer dimers and universal primer-specific portions to enable a subsequent universal PCR amplification using biotin labeled primers to append a 5' biotin to the amplification products containing the region of interest. PCR products incorporate dU, allowing for carryover prevention (FIG. 68, step C). The biotinylated PCR products are immobilized to a solid support and the region of interest is detected using exon junction-specific ligation probes as illustrated in FIG. 68, step D. In this embodiment, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 68, step D), the complementary 5' and 3' tail ends of the ligation products hybridize to each other bringing their respective donor and acceptor moieties in close proximity to each other to generate a detectable FRET signal (FIG. 68, step E).

FIG. 69 illustrates a RT-PCR-LDR-qPCR carryover prevention reaction to detect low-level of the alternative start site transcript. FIG. 69, step A illustrates the wildtype transcript containing exon 1 (top) and the alternative transcript having exon 1a as the start site (bottom). This method involves isolating mRNA and treating with UDG for carryover prevention (FIG. 69, step B). cDNA is generated using 3' transcript-specific primers and reverse-transcriptase in the presence of dUTP. Taq polymerase is activated to perform limited cycle PCR amplification (12-20) to maintain relative ratios of different amplicons (FIG. 69, step B). In this embodiment, a primer specific for the alternative transcript (i.e., exon 1a), which does not hybridize to the wildtype variant (i.e., exon 1), is used to only generate amplification products corresponding to the alternative transcript. PCR products incorporate dUTP, allowing for carryover prevention (FIG. 69, step C). As shown in FIG. 69, step D, exon junction-specific ligation oligonucleotide probes containing primer-specific portions (Ai, Ci') suitable for subsequent PCR amplification, hybridize to their corresponding target sequence in a base-specific manner. Ligase covalently seals the two oligonucleotides together (FIG. 69, step D), and ligation products are aliquot into separate wells for detection using tag-primers (Ai, Ci) and TaqMan™ probe (F1-Q) which span the ligation junction (FIG. 69, step E-F). The alternative transcript is detected during real-time PCR by the liberation of fluorescent group of the TaqMan™ probe. Samples are treated with UDG for carryover prevention, which also destroys original target amplicons (FIG. 69, step E). Only authentic LDR products are amplified, when using PCR in presence of dUTP. Neither original PCR primers nor LDR probes amplify LDR products, providing additional carryover protection.

FIGS. 70 and 71 illustrate similar RT-PCR-LDR-qPCR and RT-PCR-qLDR carryover prevention reactions to detect low-level alternative start site transcript as described and shown with respect to FIG. 69 (steps A-C), where only primers specific for the amplification of the alternative transcript are utilized. In the embodiment of FIG. 70, the exon junction-specific ligation probes are designed to contain UniTaq primer sequences (Ai, Ci') and a UniTaq tag sequence (Bi'). Accordingly, in this embodiment, ligation products corresponding to the alternative start site transcript are subsequently amplified, detected, and quantified using real time PCR with UniTaq-specific primers (F1-Bi-Q-Ai, Ci) as described above and as illustrated in FIG. 70, steps E-G. In the embodiment of FIG. 71, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 71, step D), the complementary 5' and 3' tail ends of the ligation products hybridize to each other bringing their respective donor and acceptor moieties (D, F2) in close proximity to each other to generate a detectable FRET signal (FIG. 71, step E).

FIG. 72 illustrates an overview of RT-PCR-LDR-qPCR carryover prevention reaction to detect exon deletion. FIG. 72, step A shows an illustration of a gene with 5 exons and 4 introns at the DNA level. FIG. 72, step B shows examples of the wild-type transcript containing exons 1-5 (top) and the alternative transcript where exon 4 is deleted (bottom, i.e., exons 1-3, and 5). This method involves isolating mRNA from whole blood cells, exosomes, or CTCs, and generating cDNA using reverse transcriptase with a primer complementary to exon 5 as shown in FIG. 72, step B. The cDNA is PCR amplified using the exon 5 primer in conjunction with forward primers complementary to exon 3 and exon 4 to generate amplicons of both wild-type and the deletion variant. As shown in FIG. 72, step C, exon junction-specific ligation oligonucleotide probes containing tag-primer sequences (Ai, Ci'; left panel) or UniTaq primer and tag sequences (Ai, Bi'-Ci'; right panel), hybridize to their corresponding target sequence in the PCR products, and ligase covalently seals the two oligonucleotides together if there is perfect complementarity at the junction. The ligation products are amplified and detected using tag-specific primers (Ai, Ci), and TaqMan™ probes (F1-Q or F2-Q; FIG. 72, step D, left panel) or UniTaq primers (F1-Bi-Q-Ai, F2-Bi-Q-Ai, and Ci, FIG. 72, step D, right panel), as described supra.

FIG. 73 illustrates a RT-PCR-LDR-qPCR carryover prevention reaction to quantify wild-type transcripts and transcripts having an exon deletion. FIG. 73, step A illustrates the wild-type transcript containing exons 1-5 (top) and the alternative transcript having only exons 1-3 and 5, where exon 4 is missing (bottom). This method involves isolating mRNA and treating with UDG for carryover prevention (FIG. 73, step B). cDNA is generated using a 3' transcript-specific primer (e.g., exon 5 specific primer) and reverse-transcriptase in the presence of dUTP. The cDNA is PCR amplified using the exon 5 primer in conjunction with forward primers complementary to exon 3 and exon 4 to generate amplicons of both wild-type and the deletion variant. Limited PCR amplification (12-20 cycles) is performed to maintain relative ratios of different amplicons (FIG. 73, step B). In another embodiment, the regions of interest are amplified using 20-40 PCR cycles. The primers contain identical 8-11 base tails to prevent primer dimers. PCR products incorporate dU, allowing for carryover prevention (FIG. 73, step C). As shown in FIG. 73, step D, exon junction-specific ligation oligonucleotide probes containing primer-specific portions (Ai, Ci') suitable for subsequent PCR amplification, hybridize to their corresponding target sequence in a base-specific manner. Ligase covalently seals the two oligonucleotides together (FIG. 73, step D), and ligation products are aliquot into separate wells for detection using tag-primers (Ai, Ci) and TaqMan™ probes (F1-Q and F2-Q) which span the ligation junction (FIG. 73, step E-F). The wild-type and deletion variant are quantified and distinguished using real-time PCR and detecting the differently labeled TaqMan™ probes. Samples are treated with UDG for carryover prevention, which also destroys original target amplicons (FIG. 73, step E). Only authentic LDR products amplify, when using PCR in presence of dUTP. Neither original PCR primers nor LDR probes amplify LDR products, providing additional carryover protection.

FIG. 74 illustrates another RT-PCR-LDR-qPCR carryover prevention reaction to quantify wildtype transcripts and transcripts having an exon deletion. FIG. 74, step A illustrates the wildtype transcript containing exons 1-5 (top) and the alternative transcript having only exons 1-3 and 5, where exon 4 is missing (bottom). Steps A-D of this method are essentially the same as that described for FIG. 73, except that the exon junction-specific ligation probes are designed to contain UniTaq primer sequences (Ai, Ci') and a UniTaq tag sequence (Bi'). Accordingly, in this embodiment, the ligation products corresponding to the wildtype and variant transcripts are subsequently amplified, detected, and quantified using real time PCR with UniTaq-specific primers (F1-Bi-Q-Ai, Ci) as described above and illustrated in FIG. 74, steps E-G.

FIG. 75 illustrates RT-PCR-qLDR carryover prevention reaction to quantify wildtype transcripts and transcripts having an exon deletion. FIG. 75, step A illustrates the wildtype transcript containing exons 1-5 (top) and the alternative transcript having only exons 1-3 and 5, where exon 4 is missing (bottom). This method involves isolating mRNA and treating with UDG for carryover prevention (FIG. 75, step B). cDNA is generated using a 3' transcript-specific primer (e.g., exon 5 specific primer) and reverse-transcriptase in the presence of dUTP. The cDNA is PCR amplified using the exon 5 primer in conjunction with forward primers complementary to exon 3 and exon 4 to generate amplicons of both wildtype and the deletion variant. The primers contain identical 8-11 base tails to prevent primer dimers and universal primer-specific portions to enable a subsequent universal PCR amplification using biotin labeled primers to append a 5' biotin to the amplification products containing the region of interest. PCR products incorporate dU, allowing for carryover prevention (FIG. 75, step C). The biotinylated PCR products are immobilized to a solid support and the region of interest is detected using exon junction-specific ligation probes as illustrated in FIG. 75, step D. In this embodiment, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 75, step D), the complementary 5' and 3' tail ends of the ligation products hybridize to each other bringing their respective donor and acceptor moieties in close proximity to each other to generate a detectable FRET signal (FIG. 75, step E).

FIG. 76 illustrates a RT-PCR-LDR-qPCR carryover prevention reaction to detect low-level transcripts having an exon deletion. FIG. 76, step A illustrates the wildtype transcript containing exons 1-5 (top) and the alternative transcript having only exons 1-3 and 5, where exon 4 is missing (bottom). This method involves isolating mRNA and treating with UDG for carryover prevention (FIG. 76, step B). cDNA is generated using a 3' transcript-specific primer (e.g., an exon 5 specific primer) and reverse-transcriptase in the presence of dUTP. The cDNA is PCR amplified using the exon 5 primer in conjunction with a forward primer complementary to exon 3 and a blocking oligonucleotide. The blocking oligonucleotide hybridizes to exon 4 in the wild-type transcript, thereby preventing amplification of wild-type transcripts. Accordingly, only amplification products corresponding to the deletion transcript are generated. PCR products incorporate dUTP, allowing for carryover prevention (FIG. 76, step C). As shown in FIG. 76, step D, exon junction-specific ligation oligonucleotide probes containing tag primer-specific portions (Ai, Ci') suitable for subsequent PCR amplification, hybridize to their corresponding target sequence in a base-specific manner. Ligase covalently seals the two oligonucleotides together (FIG. 76 step D), and ligation products are aliquot into separate wells for detection using tag-primers (Ai, Ci) and TaqMan™ probe (F1-Q) which span the ligation junction (FIG. 76, step E-F). The deletion transcript is detected during real-time PCR by the liberation of fluorescent group of the TaqMan™ probe. Samples are treated with UDG for carryover prevention, which also destroys original target amplicons (FIG. 76, step E). Only authentic LDR products are amplified, when using PCR in presence of dUTP. Neither original PCR primers nor LDR probes amplify LDR products, providing additional carryover protection.

FIGS. 77 and 78 illustrate similar RT-PCR-LDR-qPCR and RT-PCR-qLDR carryover prevention reactions to detect low-level deletion transcripts as described and shown with respect to FIG. 76. In the embodiment of FIG. 77, the exon junction-specific ligation probes are designed to contain UniTaq primer sequences (Ai, Ci') and a UniTaq tag sequence (Bi'). Accordingly, in this embodiment, ligation products corresponding to the deletion transcript are subsequently amplified, detected, and quantified using real time PCR with UniTaq-specific primers (F1-Bi-Q-Ai, Ci) as described above and as illustrated in FIG. 77, steps E-G. In the embodiment of FIG. 78, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 78, step D), the complementary 5' and 3' tail ends of the ligation products hybridize to each other bringing their respective donor and acceptor moieties (D, F2) in close proximity to each other to generate a detectable FRET signal (FIG. 78, step E).

FIG. 79 illustrates an overview of RT-PCR-LDR-qPCR carryover prevention reaction to detect alternative splicing with intron insertion. FIG. 79, step A shows an illustration of a gene with 5 exons and 4 introns at the DNA level. FIG. 79, step B shows examples of the wildtype transcript containing exons 1-5 (top) and the alternatively spliced transcript containing exons 1-5 with an intron i1 insertion (bottom). This method involves isolating mRNA from whole blood cells, exosomes, or CTCs, and generating cDNA using reverse transcriptase with a primer complementary to exon 2 as shown in FIG. 79, step B. The cDNA is PCR amplified using the exon 2-specific primer in conjunction with a forward primer to exon 1, to generate amplicons of both wild-type and the intron insertion variant. As shown in FIG. 79, step C, exon junction-specific ligation oligonucleotide probes containing tag-primer sequences (Ai, Ci'; left panel) or UniTaq primer and tag sequences (Ai, Bi'-Ci'; right panel) hybridize to their corresponding target sequence in the PCR products, and ligase covalently seals the two oligonucleotides together if there is perfect complementarity at the junction. The ligation products are amplified and detected using tag-specific primers (Ai, Ci), and TaqMan™ probes (F1-Q or F2-Q; FIG. 79, step D, left panel) or UniTaq primers (F1-Bi-Q-Ai, F2-Bi-Q-Ai, and Ci, FIG. 79, step D, right panel), as described supra.

FIG. 80 illustrates a RT-PCR-LDR-qPCR carryover prevention reaction to quantify wildtype transcripts and alternatively spliced transcripts containing an intron insertion. FIG. 80, step B shows examples of the wildtype transcript containing exons 1-5 (top) and the alternatively spliced transcript containing exons 1-5 with an intron i1 insertion (bottom). This method involves isolating mRNA and treating with UDG for carryover prevention (FIG. 80, step B). cDNA is generated using a 3' transcript-specific primer (e.g., exon 2 specific primer) and reverse-transcriptase in the presence of dUTP. The cDNA is PCR amplified using the exon 2-specific primer in conjunction with a forward primer to exon 1 to generate amplicons of both wildtype and the intron insertion variant. Limited PCR amplification (12-20 cycles) is performed to maintain relative ratios of different amplicons (FIG. 80, step B). In another embodiment, the regions of interest are amplified using 20-40 cycles. The primers contain identical 8-11 base tails to prevent primer dimers. PCR products incorporate dU, allowing for carryover prevention (FIG. 80, step C). As shown in FIG. 80, step D, exon junction-specific ligation oligonucleotide probes containing tag primer-specific portions (Ai, Ci') suitable for subsequent PCR amplification, hybridize to their corresponding target sequence in a base-specific manner. Ligase covalently seals the two oligonucleotides together (FIG. 80, step D), and ligation products are aliquot into separate wells for detection using tag-primers (Ai, Ci) and TaqMan™ probes (F1-Q and F2-Q) which span the ligation junction (FIG. 80, step E-F). The wild-type and insertion variant are quantified and distinguished using real-time PCR and detecting the differently labeled TaqMan™ probes. Samples are treated with UDG for carryover prevention, which also destroys original target amplicons (FIG. 80, step E). Only authentic LDR products amplify, when using PCR in presence of dUTP. Neither original PCR primers nor LDR probes amplify LDR products, providing additional carryover protection.

FIG. 81 illustrates another RT-PCR-LDR-qPCR carryover prevention reaction to quantify wildtype transcripts and alternatively spliced transcripts containing an intron insertion. FIG. 81, step B shows examples of the wildtype transcript containing exons 1-5 (top) and the alternatively spliced transcript containing exons 1-5 with an intron i1 insertion (bottom). Steps A-D of this method are essentially the same as that described for FIG. 80, except that the exon junction-specific ligation probes are designed to contain UniTaq primer sequences (Ai, Ci') and a UniTaq tag sequence (Bi'). Accordingly, in this embodiment, the ligation products corresponding to the wildtype and variant transcripts are subsequently amplified, detected, and quantified using real time PCR with UniTaq-specific primers (F1-Bi-Q-Ai, Ci) as described above and illustrated in FIG. 81, steps E-G.

FIG. 82 illustrates RT-PCR-qLDR carryover prevention reaction to quantify wildtype transcripts and alternatively spliced transcripts containing an intron insertion. FIG. 82, step B shows examples of the wildtype transcript containing exons 1-5 (top) and the alternatively spliced transcript containing exons 1-5 with an intron i1 insertion (bottom). This method involves isolating mRNA and treating with UDG for carryover prevention (FIG. 82, step B). cDNA is generated using a 3' transcript-specific primer (e.g., exon 2 specific primer) and reverse-transcriptase in the presence of dUTP. The cDNA is PCR amplified using the exon 2-specific primer in conjunction with a forward primer to exon 1 to generate amplicons of both wildtype and the intron insertion variant. The primers contain identical 8-11 base tails to prevent primer dimers and universal primer-specific portions to enable a subsequent universal PCR amplification using biotin labeled primers to append a 5' biotin to the amplification products containing the region of interest. PCR products incorporate dU, allowing for carryover prevention (FIG. 82, step C). The biotinylated PCR products are immobilized to a solid support and the region of interest is detected using exon junction-specific ligation probes as illustrated in FIG. 82, step D. In this embodiment, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 82, step D), the complementary 5' and 3' tail ends of the ligation products hybridize to each other bringing their respective donor and acceptor moieties in close proximity to each other to generate a detectable FRET signal (FIG. 82, step E).

FIG. 83 illustrates a RT-PCR-LDR-qPCR carryover prevention reaction to detect low-level transcripts containing an intron insertion. FIG. 83, step B shows examples of the wildtype transcript containing exons 1-5 (top) and the alternatively spliced transcript containing exons 1-5 with an intron i1 insertion (bottom). This method involves isolating mRNA and treating with UDG for carryover prevention (FIG. 83, step B). cDNA is generated using a 3' transcript-specific primer (e.g., an exon 2-specific primer) and reverse-transcriptase in the presence of dUTP. The cDNA is PCR amplified using the exon 2 primer in conjunction with an intron specific forward primer. The intron specific primer does not amplify the wildtype transcript, thus only transcript containing the intron i1 insertion are amplified. PCR products incorporate dU, allowing for carryover prevention (FIG. 83, step C). As shown in FIG. 83, step D, exon junction-specific ligation oligonucleotide probes containing primer-specific portions (Ai, Ci') suitable for subsequent PCR amplification, hybridize to their corresponding target sequence in a base-specific manner. Ligase covalently seals the two oligonucleotides together (FIG. 83, step D), and ligation products are aliquot into separate wells for detection using tag-primers (Ai, Ci) and TaqMan™ probe (F1-Q) which span the ligation junction (FIG. 83, step E-F). The transcript containing the intron insertion is detected during real-time PCR by the liberation of fluorescent group of the TaqMan™ probe. Samples are treated with UDG for carryover prevention, which also destroys original target amplicons (FIG. 83, step E). Only authentic LDR products are amplified, when using PCR in presence of dUTP. Neither original PCR primers nor LDR probes amplify LDR products, providing additional carryover protection.

FIGS. 84 and 85 illustrate similar RT-PCR-LDR-qPCR and RT-PCR-qLDR carryover prevention reactions to detect low-level intron insertion transcripts as described and shown with respect to FIG. 83. In the embodiment of FIG. 84, the exon junction-specific ligation probes are designed to contain UniTaq primer sequences (Ai, Ci') and a UniTaq tag sequence (Bi'). Accordingly, in this embodiment, ligation products corresponding to the intron insertion transcript are subsequently amplified, detected, and quantified using real time PCR with UniTaq-specific primers (F1-Bi-Q-Ai, Ci) as described above and as illustrated in FIG. 84, steps E-G. In the embodiment of FIG. 85, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 85, step D), the complementary 5' and 3' tail ends of the ligation products hybridize to each other bringing their respective donor and acceptor moieties (D, F1) in close proximity to each other to generate a detectable FRET signal (FIG. 85, step E).

The methods of the present invention are suitable for quantifying or enumerating the amount of the one or more target nucleotide sequences in a sample. For example, the methods of the present invention can be utilized to enumerate the relative copy number of one or more target nucleic acid molecules in a sample as illustrated in FIGS. 86-91.

FIG. 86 illustrates PCR-LDR carryover prevention reaction to enumerate DNA copy number. This method involves isolating DNA from CTCs, tumor-specific exosomes, or another biological sample, and treating with UDG for carryover prevention (FIG. 86, step B). Chromosomal regions of interest are amplified using limited cycle PCR (12-20 cycles) to maintain relative ratios of different amplicons (FIG. 86, step B). In another embodiment, the chromosomal regions of interest are amplified using 20-40 cycles. For accurate enumeration, the sample is dispersed into 12, 24, 48, or 96 wells prior to PCR amplification. The primers contain identical 8-11 base tails to prevent primer dimers. PCR products incorporate dU, allowing for carryover prevention (FIG. 86, step C). As shown in FIG. 86, step D, locus-specific ligation oligonucleotide probes containing primer-specific portions (Ai, Ci') suitable for subsequent PCR amplification, hybridize to their corresponding target sequence in a base-specific manner. Ligase covalently seals the two oligonucleotides together (FIG. 86, step D), and ligation products are aliquot into separate wells for detection using tag-primers (Ai, Ci) and TaqMan™ probe (F1-Q) which span the ligation junction (FIG. 86, step E-F). The DNA copy number is determined based on the Poisson distribution of signal in the different wells or chambers. Samples are treated with UDG for carryover prevention, which also destroys original target amplicons (FIG. 86, step E). Only authentic LDR products will amplify, when using PCR in presence of dUTP. Neither original PCR primers nor LDR probes amplify LDR products, providing additional carryover protection.

FIG. 87 illustrates another PCR-LDR-qPCR carryover prevention reaction to enumerate DNA copy number. This method involves essentially the same steps (i.e., steps A-D) as the method illustrated in FIG. 86; however, in this embodiment, the locus specific ligation probes are designed to contain UniTaq primer sequences (Ai, Ci') and a UniTaq tag sequence (Bi'). Accordingly, in this embodiment, the ligation products are subsequently amplified, detected, and quantified using real time PCR with UniTaq-specific primers (F1-Bi-Q-Ai, Ci) as described above and illustrated in FIG. 87, steps E-G. Copy number is determined based on the Poisson distribution of signal in the different wells or chambers.

FIG. 88 also illustrates PCR-qLDR carryover prevention reaction to enumerate DNA copy number. This method involves isolating DNA from CTCs, tumor-specific exosomes, or another biological sample, and treating with UDG for carryover prevention (FIG. 88, step B). Chromosomal regions of interest are amplified using limited cycle PCR (12-20 cycles) to maintain relative ratios of different amplicons (FIG. 88, step B). In another embodiment, the chromosomal regions of interest are amplified using 20-40 cycles. For accurate enumeration, the sample is dispersed into 12, 24, 48, or 96 wells prior to PCR amplification. The primers contain identical 8-11 base tails to prevent primer dimers and universal primer-specific portions to enable a subsequent universal PCR amplification using biotin labeled primers to append a 5' biotin to the amplification products containing the region of interest. PCR products incorporate dU, allowing for carryover prevention (FIG. 88, step C). The biotinylated PCR products are immobilized to a solid support and the region of interest is detected using locus-specific ligation probes as illustrated in FIG. 88, step D. In this embodiment, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 88, step D), the complementary 5' and 3' tail ends of the ligation products hybridize to each other bringing their respective donor and acceptor moieties in close proximity to each other to generate a detectable FRET signal (FIG. 88, step E). Copy number is determined based on the Poisson distribution of signal in the different wells or chambers.

FIG. 89 illustrates RT-PCR-LDR-qPCR carryover prevention reaction to enumerate RNA copy number. This method involves isolating RNA from whole blood cells, exosomes, CTCs, or another biological sample, and treating with UDG for carryover prevention (FIG. 89, step B). cDNA is generated using 3' transcript-specific primers and reverse-transcriptase in the presence of dUTP. Taq polymerase is activated to perform limited cycle PCR amplification (12-20) to maintain relative ratios of different amplicons (FIG. 89, step B). For accurate enumeration, the sample is dispersed into 12, 24, 48, or 96 wells prior to PCR amplification. The primers contain identical 8-11 base tails to prevent primer dimers. PCR products incorporate dU, allowing for carryover prevention (FIG. 89, step C). As shown in FIG. 89, step D, locus-specific ligation oligonucleotide probes containing tag primer-specific portions (Ai, Ci') suitable for subsequent PCR amplification, hybridize to their corresponding target sequence in a base-specific manner. Ligase covalently seals the two oligonucleotides together (FIG. 89, step D), and ligation products are aliquot into separate wells for detection using tag-primers (Ai, Ci) and TaqMan™ probe (F1-Q) which span the ligation junction (FIG. 89, step E-F). The RNA copy number is quantified using real-time PCR based on the Poisson distribution of signal in the different wells or chambers. Samples are treated with UDG for carryover prevention, which also destroys original target amplicons (FIG. 89, step E). Only authentic LDR products will amplify when using PCR in presence of dUTP. Neither original PCR primers nor LDR probes amplify LDR products, providing additional carryover protection.

FIG. 90 illustrates another RT-PCR-LDR-qPCR carryover prevention reaction to enumerate RNA copy number. For accurate enumeration, the sample is dispersed into 12, 24, 48, or 96 wells prior to PCR amplification. This method involves essentially the same steps (i.e., steps A-D) as the method illustrated in FIG. 89; however, in this embodiment, the locus specific ligation probes are designed to contain UniTaq primer sequences (Ai, Ci') and a UniTaq tag sequence (Bi'). Accordingly, in this embodiment, the ligation products are subsequently amplified, detected, and quantified using real time PCR with UniTaq-specific primers (F1-Bi-Q-Ai, Ci) as described above and illustrated in FIG. 90, steps E-G. Copy number is determined based on the Poisson distribution of signal in the different wells or chambers.

FIG. 91 illustrates RT-PCR-qLDR carryover prevention reaction to enumerate RNA copy number. This method involves isolating RNA from whole blood cells, exosomes, CTCs, or another biological sample, and treating with UDG for carryover prevention (FIG. 91, step B). For accurate enumeration, the sample is dispersed into 12, 24, 48, or 96 wells prior to PCR amplification. cDNA is generated using 3' transcript-specific primers and reverse-transcriptase in the presence of dUTP. Taq polymerase is activated to perform limited cycle PCR amplification (12-20) to maintain relative ratios of different amplicons (FIG. 91, step B). The primers contain identical 8-11 base tails to prevent primer dimers and universal primer-specific portions to enable a subsequent universal PCR amplification using biotin labeled primers to append a 5' biotin to the amplification products containing the region of interest. PCR products incorporate dU, allowing for carryover prevention (FIG. 91, step C). The biotinylated PCR products are immobilized to a solid support and the region of interest is detected using locus-specific ligation probes as illustrated in FIG. 91, step D. In this embodiment, the exon junction-specific ligation probes of a ligation pair contain complementary tail sequences and an acceptor or donor group, respectively, capable of generating a detectable signal via FRET when brought in close proximity to each other as described supra. Accordingly, following ligation (FIG. 91, step D), the complementary 5' and 3' tail ends of the ligation products hybridize to each other bringing their respective donor and acceptor moieties in close proximity to each other to generate a detectable FRET signal (FIG. 91, step E). Copy number is determined based on the Poisson distribution of signal in the different wells or chambers. Another aspect of the present invention is directed to a method for identifying, in a sample, one or more micro-ribonucleic acid (miRNA) molecules containing a target micro-ribonucleotide sequence differing from micro-ribonucleotide sequences in other miRNA molecules in the sample by one or more bases. This method involves providing a sample containing one or more miRNA molecules potentially containing the target micro-ribonucleotide sequence differing from micro-ribonucleotide sequences in other miRNA molecules in the sample by one or more bases, and contacting the sample with one or more enzymes capable of digesting dU containing nucleic acid molecules potentially present in the sample. One or more oligonucleotide primer sets are provided, each primer set comprising (a) a first oligonucleotide primer having a 5' stem-loop portion, a blocking group, an internal primer-specific portion within the loop region, and a 3' nucleotide sequence portion that is complementary to a 3' portion of the miRNA molecule containing the target micro-ribonucleotide sequence, (b) a second oligonucleotide primer having a 3' nucleotide sequence portion that is complementary to a complement of the 5' end of the miRNA molecule containing the target micro-ribonucleotide sequence, and a 5' primer-specific portion, (c) a third oligonucleotide primer comprising a nucleotide sequence that is the same as the internal primer-specific portion of the first oligonucleotide primer, and (d) a fourth oligonucleotide primer comprising a nucleotide sequence that is the same as the 5' primer-specific portion of the second oligonucleotide primer. The contacted sample is blended with the one or more first oligonucleotide primers of a primer set, a deoxynucleotide mix including dUTP, and a reverse transcriptase to form a reverse transcription reaction mixture. The first oligonucleotide primer hybridizes to the miRNA molecule containing the target micro-ribonucleotide sequence, if present in the sample, and the reverse transcriptase extends the 3' end of the hybridized first oligonucleotide primer to generate an extended first oligonucleotide primer comprising the complement of the miRNA molecule containing the target micro-ribonucleotide sequence. The method further involves blending the reverse transcription reaction mixture with the second, third, and fourth oligonucleotide primers of the primer set to form a polymerase reaction mixture under conditions effective for the one or more second oligonucleotide primers of a primer set to hybridize to the region of the extended first oligonucleotide primer comprising the complement of the miRNA molecule containing the target micro-ribonucleotide sequence and extend to generate a primary extension product comprising the 5' primer-specific portion, a nucleotide sequence corresponding to the target micro-ribonucleotide sequence of the miRNA molecule, and the complement of the internal primer-specific portion. The polymerase chain reaction mixture is subjected to one or more polymerase chain reaction cycles comprising a denaturation treatment, a hybridization treatment, and an extension treatment thereby forming a plurality of primary extension products. The method further involves blending the plurality of primary extension products with a ligase and one or more oligonucleotide probe sets to form a ligation reaction mixture. Each oligonucleotide probe set comprises (a) a first oligonucleotide probe having a target-specific portion, and (b) a second oligonucleotide probe having a target-specific portion and a portion complementary to a primary extension product, wherein the first and second oligonucleotide probes of a probe set are configured to hybridize, in a base specific manner, adjacent to one another on complementary target-specific portions of a primary extension product with a junction between them. The first and second oligonucleotide probes of the one or more oligonucleotide probe sets are ligated together to form ligated product sequences in the ligation reaction mixture, and the ligated product sequences in the sample are detected and distinguished thereby identifying one or more miRNA molecules containing a target micro-ribonucleotide sequence differing from micro-ribonucleotide sequences in other miRNA molecules in the sample by one or more bases.

FIG. 92 illustrates PCR-LDR carryover prevention reaction to quantify miRNA. This method involves isolating RNA from exosomes or another biological sample, and treating with UDG for carryover prevention (FIG. 92, step B). An oligonucleotide primer having a portion that is complementary to the 3' end of the target miRNA, and containing a stem-loop, tag (Tj), and blocking group (filled circle) is hybridized to the 3' end of the target miRNA. The 3' end of the oligonucleotide primer is extended using reverse transcriptase (filled diamond) in the presence of dUTP (FIG. 92, step B). Taq polymerase is activated to perform limited cycle PCR amplification (12-20) using a bridge primer comprising a sequence that is complementary to a portion of the reverse transcribed miRNA and an upstream primer-specific sequence portion (Ti), and tag (Ti, Tj) primers as shown in FIG. 92, step B. Primers contain identical 8-11 base tails to prevent primer dimers. Optionally, the sample can be aliquot into 12, 24, 48, or 96 wells prior to PCR. PCR products incorporate dUTP, allowing for carryover prevention (FIG. 92, step C). As shown in FIG. 92, step D, miRNA sequence-specific ligation probes containing primer-specific portions (Ai, Ci') suitable for subsequent PCR amplification, hybridize to their corresponding target sequence in the PCR products in a base-specific manner. Ligase covalently seals the two oligonucleotides together (FIG. 92, step D), and ligation products are aliquot into separate wells for detection using tag-primers (Ai, Ci) and TaqMan™ probe (F1-Q) which spans the ligation junction (FIG. 92, step E-F). The presence of the miRNA in the sample is quantified using real-time PCR based on the detection of the liberated label of the TaqMan™ probe. Samples are treated with UDG for carryover prevention, which also destroys original target amplicons (FIG. 92, step E). Only authentic LDR products will amplify, when using PCR in presence of dUTP. Neither original PCR primers nor LDR probes amplify LDR products, providing additional carryover protection.

FIG. 93 illustrates another RT-PCR-LDR-qPCR carryover prevention reaction to quantify miRNA. This method involves essentially the same steps (i.e., steps A-D) as the method illustrated in FIG. 92; however, in this embodiment, the miRNA specific ligation probes are designed to contain UniTaq primer sequences (Ai, Ci') and a UniTaq tag sequence (Bi'). Accordingly, in this embodiment, the ligation products are subsequently amplified, detected, and quantified using real time PCR with UniTaq-specific primers (F1-Bi-Q-Ai, Ci) as described above and illustrated in FIG. 93, steps E-G.

FIG. 94 also illustrates RT-PCR-qLDR carryover prevention reaction to quantify miRNA. This method involves isolating RNA from exosomes or another biological sample, and treating with UDG for carryover prevention (FIG. 94, step B). An oligonucleotide primer having a portion that is complementary to the 3' end of the target miRNA, and containing a stem-loop, tag (Tj), and blocking group (filled circle) is hybridized to the 3' end of the target miRNA. The 3' end of the oligonucleotide primer is extended using reverse transcriptase (filled diamond) in the presence of dUTP (FIG. 94, step B). Taq polymerase is activated to perform limited cycle PCR amplification (12-20) using a bridge primer comprising a sequence that is complementary to a portion of the reverse transcribed miRNA and an upstream primer-specific sequence portion (Ti), and tag (Ti, Tj) primers as shown in FIG. 94, step B. The primers contain identical 8-11 base tails to prevent primer dimers and universal primer-specific portions to enable a subsequent universal PCR amplification using biotin labeled primers to append a 5' biotin to the amplification products containing the region of interest. PCR products incorporate dU, allowing for carryover prevention (FIG. 94, step C). The biotinylated PCR products are immobilized to a solid support and the region of interest is detected using miRNA sequence-specific ligation probes as illustrated in FIG. 94, step D. In this embodiment, the miRNA sequence-specific ligation probes of a ligation pair contain complementary tail sequences and an acceptor or donor group, respectively, capable of generating a detectable signal via FRET when brought in close proximity to each other as described supra. Accordingly, following ligation (FIG. 94, step D), the complementary 5' and 3' tail ends of the ligation products hybridize to each other bringing their respective donor and acceptor moieties in close proximity to each other to generate a detectable FRET signal (FIG. 94, step E).

Another aspect of the present invention is directed to a method for identifying, in a sample, one or more micro-ribonucleic acid (miRNA) molecules containing a target micro-ribonucleotide sequence differing in sequence from other miRNA molecules in the sample by one or more bases. This method involves providing a sample containing one or more miRNA molecules potentially containing a target micro-ribonucleotide sequence differing in sequence from other miRNA molecules by one or more base differences, and contacting the sample with one or more enzymes capable of digesting dU containing nucleic acid molecules potentially present in the sample. The contacted sample is blended with a ligase and a first oligonucleotide probe comprising a 5' phosphate, a 5' stem-loop portion, an internal primer-specific portion within the loop region, a blocking group, and a 3' nucleotide sequence that is complementary to a 3' portion of the miRNA molecule containing a target micro-ribonucleotide sequence to form a ligation reaction. The method further involves ligating the miRNA molecule containing a target micro-ribonucleotide sequence at its 3' end to the 5' phosphate of the first oligonucleotide probe to generate a chimeric nucleic acid molecule comprising the miRNA molecule containing a target micro-ribonucleotide sequence, if present in the sample, appended to the first oligonucleotide probe. One or more oligonucleotide primer sets are provided, each primer set comprising (a) a first oligonucleotide primer comprising a 3' nucleotide sequence that is complementary to a complement of the 5' end of the miRNA molecule containing a target micro-ribonucleotide sequence, and a 5' primer-specific portion, (b) a second oligonucleotide primer comprising a nucleotide sequence that is complementary to the internal primer-specific portion of the first oligonucleotide probe, and (c) a third oligonucleotide primer comprising a nucleotide sequence that is the same as the 5' primer-specific portion of the first oligonucleotide primer. The chimeric nucleic acid molecule is blended with the one or more second oligonucleotide primers, a deoxynucleotide mix including dUTP, and a reverse transcriptase to form a reverse transcription reaction mixture, wherein the one or more second oligonucleotide primers of a primer set hybridizes to the internal primer specific portion of the chimeric nucleic acid molecule, and extends at its 3' end to generate a complement of the chimeric nucleic acid molecule, if present in the sample. The method further involves blending the reverse transcription reaction mixture with the first and third oligonucleotide primers of a primer set to form a polymerase reaction mixture, and subjecting the polymerase chain reaction mixture to one or more polymerase chain reaction cycles comprising a denaturation treatment, a hybridization treatment, and an extension treatment thereby forming primary extension products. The primary extension products comprise the 5' primer-specific portion, a nucleotide sequence corresponding to the target micro-ribonucleotide sequence of the miRNA molecule, and the internal primer-specific portion or complements thereof. The primary extension products are blended with a ligase and one or more oligonucleotide probe sets to form a ligation reaction mixture. Each oligonucleotide probe set comprises (a) a first oligonucleotide probe having a target-specific portion, and (b) a second oligonucleotide probe having a target specific portion and a portion complementary to a primary extension product, wherein the first and second oligonucleotide probes of a probe set are configured to hybridize, in a base specific manner, adjacent to one another on complementary target-specific portions of a primary extension product with a junction between them. The first and second oligonucleotide probes of the one or more oligonucleotide probe sets are ligated together to form ligated product sequences in the ligation reaction mixture, and the ligated product sequences in the sample are detected and distinguished thereby identifying one or more miRNA molecules containing a target micro-ribonucleotide sequence differing in sequence from other miRNA molecules in the sample by one or more bases.

FIG. 95 illustrates Ligation-RT-PCR-LDR-qPCR carryover prevention reaction to quantify miRNA. This method involves isolating RNA from exosomes and treating with UDG for carryover prevention (FIG. 95, step B). An oligonucleotide probe having a portion that is complementary to the 3' end of the target miRNA, and containing a stem-loop, tag (Tj'), and blocking group (filled circle) is ligated at its 5' end to the 3' end of the target miRNA. The ligation product comprises the miRNA, Tj' tag, the blocking group, and a sequence complementary to the 3' portion of the miRNA (FIG. 95, step B). cDNA is generated using a primer to Tj' and reverse transcriptase. The cDNA is amplified by Taq polymerase in a limited cycle PCR amplification (12-20 cycles) using a bridge primer comprising a sequence that is complementary to a portion of the reverse transcribed miRNA and an upstream primer-specific sequence portion (Ti) and tag (Ti, Tj) primers as shown in FIG. 95, step B. Alternatively, the cDNA is amplified using 20-40 PCR cycles. Primers contain identical 8-11 base tails to prevent primer dimers. Optionally, the sample can be aliquot into 12, 24, 48, or 96 wells prior to PCR. PCR products incorporate dU, allowing for carryover prevention (FIG. 95, step C).

As shown in FIG. 95, step D miRNA sequence-specific ligation probes containing primer-specific portions (Ai, Ci') suitable for subsequent PCR amplification, hybridize to their corresponding target sequence in a base-specific manner. Ligase covalently seals the two oligonucleotides together (FIG. 95, step D), and ligation products are aliquot into separate wells for detection using tag-primers (Ai, Ci) and TaqMan™ probe (F1-Q) which spans the ligation junction (FIG. 95, step E-F). The presence of the miRNA in the sample is quantified using real-time PCR based on the detection of the liberated label of the TaqMan™ probe. Samples are treated with UDG for carryover prevention, which also destroys original target amplicons (FIG. 95, step E). Only authentic LDR products will amplify, when using PCR in presence of dUTP. Neither original PCR primers nor LDR probes amplify LDR products, providing additional carryover protection.

FIG. 96 illustrates another Ligation-RT-PCR-LDR-qPCR carryover prevention reaction to quantify miRNA. This method involves essentially the same steps (i.e., steps A-D) as the method illustrated in FIG. 95; however, in this embodiment, the miRNA specific ligation probes are designed to contain UniTaq primer sequences (Ai, Ci') and a UniTaq tag sequence (Bi'). Accordingly, in this embodiment, the ligation products are subsequently amplified, detected, and quantified using real time PCR with UniTaq-specific primers (F1-Bi-Q-Ai, Ci) as described above and illustrated in FIG. 96, steps E-G.

FIG. 97 illustrates Ligation-RT-PCR-qLDR carryover prevention reaction to quantify miRNA. This method involves essentially the same steps, i.e., steps A and B, as described and illustrated in FIG. 95. However, in this embodiment, the cDNA that is produced in step B is amplified using at least one biotin labeled primer to append a 5' biotin to the amplification products containing the region of interest. PCR products incorporate dU, allowing for carryover prevention (FIG. 97, step C). The biotinylated PCR products are immobilized to a solid support and the region of interest is detected using miRNA sequence-specific ligation probes as illustrated in FIG. 97, step D. In this embodiment, the miRNA sequence-specific ligation probes of a ligation pair contain complementary tail sequences and an acceptor or donor group, respectively, capable of generating a detectable signal via FRET when brought in close proximity to each other as described supra. Accordingly, following ligation (FIG. 97, step D), the complementary 5' and 3' tail ends of the ligation products hybridize to each other bringing their respective donor and acceptor moieties in close proximity to each other to generate a detectable FRET signal (FIG. 97, step E).

FIG. 98 illustrates Ligation-RT-PCR-LDR-qPCR carryover prevention reaction to quantify miRNA. This method involves isolating RNA from exosomes or another biological sample, and treating with UDG for carryover prevention (FIG. 98, step B). An oligonucleotide probe having a portion that is complementary to the 3' end of the target miRNA, and containing a stem-loop, tag (Tj'), and blocking group (filled circle) is ligated at its 5' end to the 3' end of the target miRNA. The ligation product comprises the miRNA, Tj' tag, the blocking group, and a sequence complementary to the 3' portion of the miRNA (FIG. 98, step B). cDNA is generated using primer Tj and reverse transcriptase. The cDNA is amplified by Taq polymerase in a limited cycle PCR amplification (12-20 cycles) using a bridge primer comprising a sequence that is complementary to a portion of the reverse transcribed miRNA and an upstream primer-specific sequence portion (Ti) and tag (Ti, Tj) primers, where the bridge primer contains a cleavable blocking group on its 3' end as shown in FIG. 98, step C. Alternatively, the cDNA is amplified using 20-40 PCR cycles. As described supra, C3-spacer is a suitable blocking group, and an RNA base (r) is cleaved using RNaseH (star symbol) only when the primer hybridizes to its complementary target. Primers contain identical 8-11 base tails to prevent primer dimers. Optionally, the sample can be aliquot into 24, 48, or 96 wells prior to PCR. PCR products incorporate dU, allowing for carryover prevention (FIG. 98, step D).

As shown in FIG. 98, step E, miRNA sequence-specific ligation probes containing primer-specific portions (Ai, Ci') suitable for subsequent PCR amplification, hybridize to their corresponding target sequence in a base-specific manner. Ligase covalently seals the two oligonucleotides together (FIG. 98, step E), and ligation products are aliquot into separate wells for detection using tag-primers (Ai, Ci) and TaqMan™ probe (F1-Q) which spans the ligation junction (FIG. 98, step F-G). The presence of the miRNA in the sample is quantified using real-time PCR based on the detection of the liberated label of the TaqMan™ probe. Samples are treated with UDG for carryover prevention, which also destroys original target amplicons (FIG. 98, step F). Only authentic LDR products will amplify, when using PCR in presence of dUTP. Neither original PCR primers nor LDR probes amplify LDR products, providing additional carryover protection.

FIG. 99 illustrates another Ligation-RT-PCR-LDR-qPCR carryover prevention reaction to quantify miRNA. This method involves essentially the same steps (i.e., steps A-E) as the method illustrated in FIG. 98; however, in this embodiment, the miRNA specific ligation probes are designed to contain UniTaq primer sequences (Ai, Ci') and a UniTaq tag sequence (Bi'). Accordingly, in this embodiment, the ligation products are subsequently amplified, detected, and quantified using real time PCR with UniTaq-specific primers (F1-Bi-Q-Ai, Ci) as described above and illustrated in FIG. 99, steps F-H.

FIG. 100 illustrates Ligation-RT-PCR-LDR-qPCR carryover prevention reaction to quantify miRNA. This method involves essentially the same steps, i.e., steps A and B, as described and illustrated in FIG. 98. However, in this embodiment, the cDNA that is produced in step B is amplified using at least one biotin labeled primer to form biotinylated products containing the region of interest. PCR products incorporate dU, allowing for carryover prevention (FIG. 100, step D). The biotinylated PCR products are immobilized to a solid support and the region of interest is detected using miRNA sequence-specific ligation probes as illustrated in FIG. 100, step E. In this embodiment, the miRNA sequence-specific ligation probes of a ligation pair contain complementary tail sequences and an acceptor or donor group, respectively, capable of generating a detectable signal via FRET when brought in close proximity to each other as described supra. Accordingly, following ligation (FIG. 100, step E), the complementary 5' and 3' tail ends of the ligation products hybridize to each other bringing their respective donor and acceptor moieties in close proximity to each other to generate a detectable FRET signal (FIG. 100, step F).

As described in more detail herein, the method of the present invention are capable of detecting low abundance nucleic acid molecules comprising one or more nucleotide base mutations, insertions, deletions, translocations, splice variants, miRNA variants, alternative transcripts, alternative start sites, alternative coding sequences, alternative non-coding sequences, alternative splicings, exon insertions, exon deletions, intron insertions, other rearrangement at the genome level, and/or methylated nucleotide bases.

As used herein "low abundance nucleic acid molecule" refers to a target nucleic acid molecule that is present at levels as low as 1% to 0.01% of the sample. In other words, a low abundance nucleic acid molecule with one or more nucleotide base mutations, insertions, deletions, translocations, splice variants, miRNA variants, alternative transcripts, alternative start sites, alternative coding sequences, alternative non-coding sequences, alternative splicings, exon insertions, exon deletions, intron insertions, other rearrangement at the genome level, and/or methylated nucleotide bases can be distinguished from a 100 to 10,000-fold excess of nucleic acid molecules in the sample (i.e., high abundance nucleic acid molecules) having a similar nucleotide sequence as the low abundance nucleic acid molecules but without the one or more nucleotide base mutations, insertions, deletions, translocations, splice variants, miRNA variants, alternative transcripts, alternative start sites, alternative coding sequences, alternative non-coding sequences, alternative splicings, exon insertions, exon deletions, intron insertions, other rearrangement at the genome level, and/or methylated nucleotide bases.

In some embodiments of the present invention, the copy number of one or more low abundance target nucleotide sequences are quantified relative to the copy number of high abundance nucleic acid molecules in the sample having a similar nucleotide sequence as the low abundance nucleic acid molecules. In other embodiments of the present invention, the one or more target nucleotide sequences are quantified relative to other nucleotide sequences in the sample. In other embodiments of the present invention, the relative copy number of one or more target nucleotide sequences is quantified. Methods of relative and absolute (i.e., copy number) quantitation are well known in the art.

The low abundance target nucleic acid molecules to be detected can be present in any biological sample, including, without limitation, tissue, cells, serum, blood, plasma, amniotic fluid, sputum, urine, bodily fluids, bodily secretions, bodily excretions, cell-free circulating nucleic acids, cell-free circulating tumor nucleic acids, cell-free circulating fetal nucleic acids in pregnant woman, circulating tumor cells, tumor, tumor biopsy, and exosomes.

The methods of the present invention are suitable for diagnosing or prognosing a disease state and/or distinguishing a genotype or disease predisposition.

With regard to early cancer detection, the methods of the present invention are suitable for detecting both repeat mutations in known genes (e.g., CRAF, KRAS), and uncommon mutations in known genes (e.g., p53) when present at 1% to 0.01% of the sample. The methods of the present invention can also achieve accurate quantification of tumor-specific mRNA isolated from exosomes (e.g. a dozen expression markers that differentiate colon tumor tissue from matched normal mucosa), and tumor-specific miRNA isolated from exosomes or Argonaut proteins (e.g. a dozen microRNA markers that differentiate colon tumor tissue from matched normal mucosa). The methods of the present invention also afford accurate quantification of tumor-specific copy changes in DNA isolated from circulating tumor cells (e.g. a dozen copy changes that differentiate colon tumor tissue from matched normal mucosa), and the detection of mutations in DNA isolated from circulating tumor cells. (e.g. KRAS, BRAF, AKT, p53, BRCA1 genes).

The present invention is also capable of accurately quantifying (i) tumor-specific mRNA isolated from exosomes or circulating tumor cells, (ii) tumor-specific miRNA isolated from exosomes or Argonaut proteins, and (iii) tumor-specific copy changes in DNA isolated from circulating tumor cells that can predict outcome or guide treatment. The present invention can also detect mutations in DNA isolated from circulating tumor cells, e.g. KRAS, BRAF, AKT, p53, BRCA1 or other genes that predict outcome or guide treatment.

With regard to prenatal diagnostics, the methods of the present invention are capable of detecting aneuploidy through counting copy number (e.g., Trisomy 21), inherited diseases containing common mutations in known genes (e.g. Sickle Cell Anemia, Cystic Fibrosis), inherited diseases containing uncommon mutations in known genes (e.g. familial adenomatous polyposis), inherited diseases arising from known or sporadic copy number loss or gain in known gene (e.g. Duchenne's muscular dystrophy), and paternity testing.

An important aspect of implementing the assays described above in a clinical setting is the reduction in the amount of labor required to fill rows and columns with samples, reagents and assay specific probes/primers. Ninety-six well plates are the standard in most laboratories, but 384 well plates afford a higher throughput and reduction in the cost of each assay well. Part of the hindrance of their adoption has been the increased labor associated with these plates, which can be solved by pipetting robots but at considerable capital expense. Depending upon the specific configuration of assays in the plate, significant expense is also incurred by the increased use of pipette tips. One embodiment of the assays described above requires the dispersal of 24 multiplex PCR-LDR reactions into the 24 columns of a microtiter plate followed by the dispersal of 16 different sets of LDR tag probes across the rows of the plate. This assay set-up would require 48 deliveries by an 8 tip pipettor to fill the columns and then 48 deliveries by an 8 tip pipettor to fill all of the rows. Plates having 1536 wells have the advantage of reducing the cost of an assay even further but demand automated filling as they are beyond the mechanical abilities of a human operator. Devices have been commercialized that allow the simultaneous filling of many rows and columns with a reduced number of pipetting steps by the use of microfluidic devices that use low dead volume channels that introduce liquids into each "well" but that require the added complication of valves and external valve drivers. Clearly a different approach is warranted.

Another aspect of the present invention is directed to a device for use in combination with a microtiter plate to simultaneously add liquids to two or more wells in a row and/or column of the microtiter plate having opposed top and bottom surfaces with the top surface having openings leading into the wells and the bottom surface defining closed ends of the wells. The device comprises a first layer defined by first and second boundaries with metering chambers extending between the first and second boundaries of said first layer and in fluid communication with one another. The first layer is configured to be fitted, in an operative position, proximate to the microtiter plate with the first boundary of the first layer being closest to the top surface of the microtiter plate and each of the metering chambers being in fluid communication with an individual well in a row and/or column of the microtiter plate. The first layer further comprises a filling chamber in fluid communication with one or more of the metering chambers. The device comprises a second layer defined by first and second boundaries with a filling port extending between the first and second boundaries of the second layer. The second layer is configured to be fitted, in an operative position, proximate to the first layer with the first boundary of the second layer being closest to the second boundary of the first layer and the filling port being aligned with the filling chamber. When the first layer, second layer, and microtiter plate are positioned with respect to one another in their operative positions, liquid entering the device through the filling port will pass through the filling chamber, the metering chambers, and into two or more wells in a row and/or column of the microtiter plate.

In some embodiments, the device of the present invention further comprises an intermediate layer having first and second boundaries with intermediate layer passages extending between the first and second boundaries of said intermediate layer. The intermediate layer is configured to be fitted, in an operative position, between the microtiter plate and the first layer with the first boundary of the intermediate layer adjacent to the top surface of the microtiter plate and the second boundary of the intermediate layer adjacent to the first boundary of the first layer. One of the intermediate layer passages is aligned with an individual well in a row and/or column of the microtiter plate, where, when the first layer, the second layer, the intermediate layer, and the microtiter plate are positioned with respect to one another in their operative positions, liquid entering the device through the filling port will pass through the filling chamber, the metering chambers, the intermediate layer passages, and into the wells of the microtiter plate.

The device of the present invention may further comprise a third layer having first and second boundaries with a filling port connector extending between the first and second boundaries of the third layer. The third layer is configured to be fitted, in an operative position, between the first and the second layers with the first boundary of the third layer adjacent to the second boundary of the first layer and the filling port connector being aligned with the filling port. When the first layer, the second layer, the third layer, the intermediate layer, and the microtiter plate are positioned with respect to one another in their operative positions, liquid entering the device through the filling port will pass through the filling port connector, the filling chamber, the metering chambers, the intermediate layer passages, and into the wells of the microtiter plate.

Figure 103:
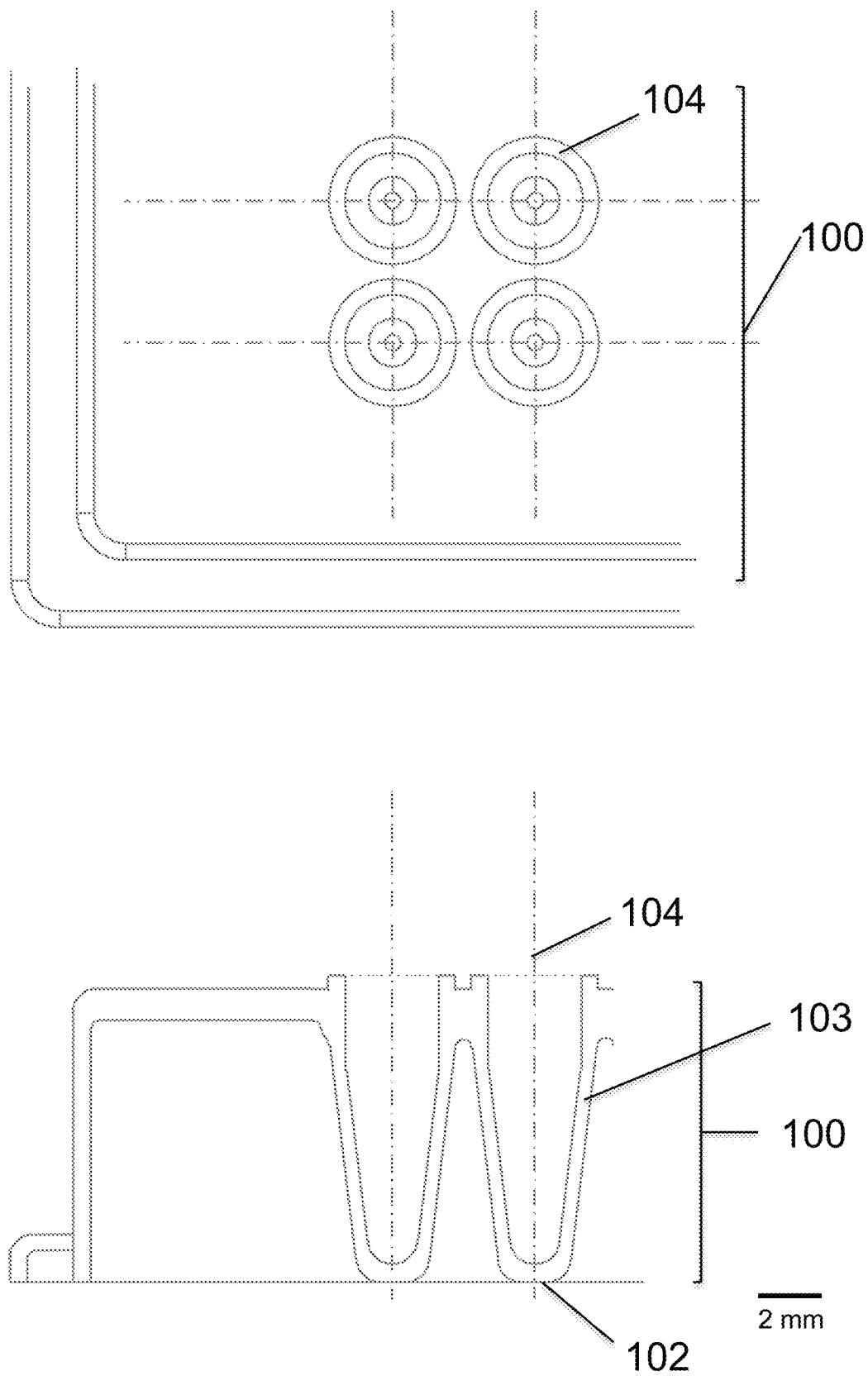
FIG. 103 shows a top and side view of a typical 384 well microtiter plate configuration.
Figure 104:
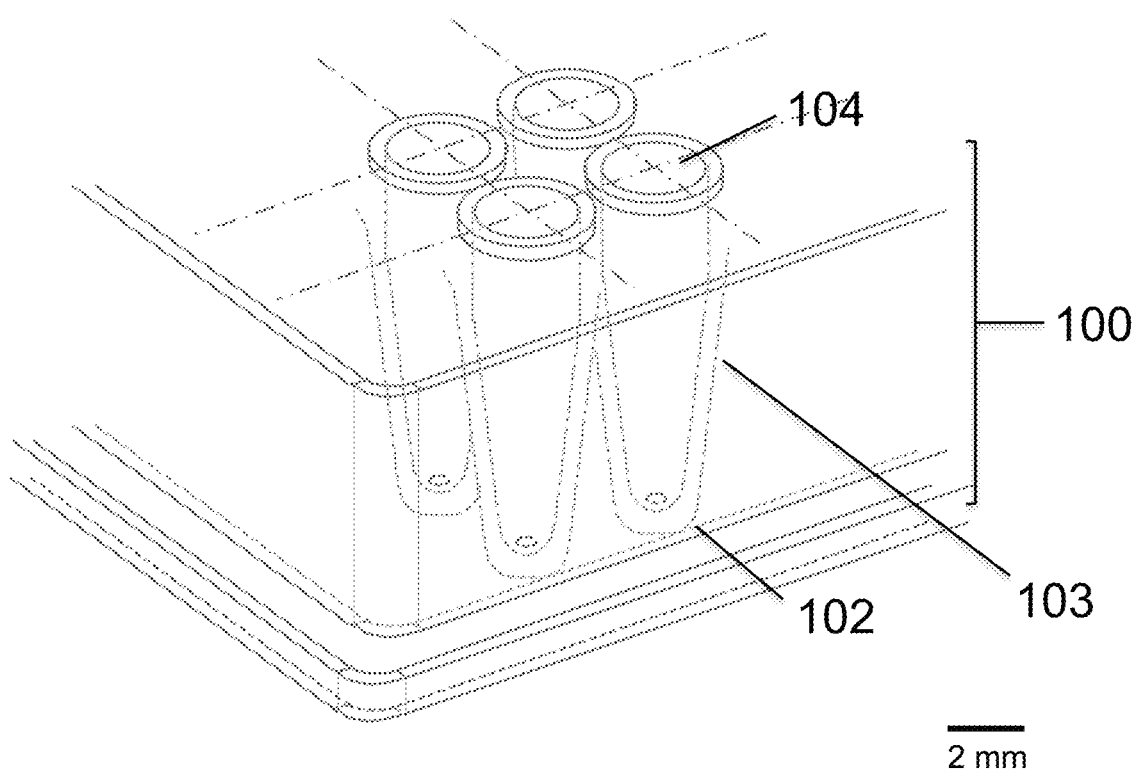
FIG. 104 shows a perspective view of a typical 384 well microtiter plate configuration.

FIGS. 103-112 depict one exemplary embodiment of the device of the invention. FIG. 103 shows a top and side view of a portion of a typical 384-well microtiter plate 100 that is used in combination with the device of the present invention. The microtiter plate is defined by several wells 103, each well having a top, open end 104 that is suitable for receiving sample and/or reaction reagents, and a closed, bottom end 102. FIG. 104 shows a perspective view of the microtiter plate of FIG. 103.

Figure 106:
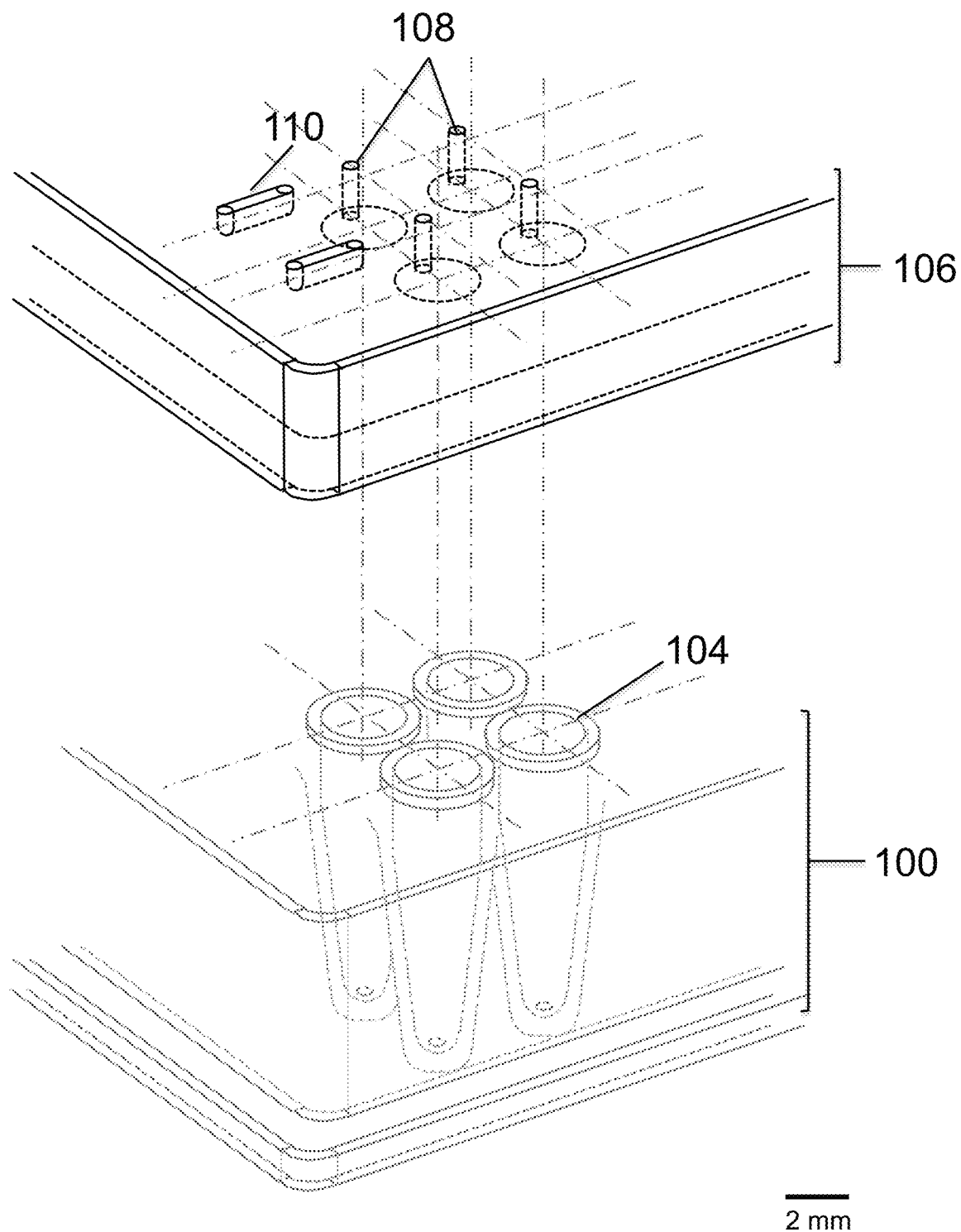
FIG. 106 illustrates an exploded perspective view of the intermediate layer of a sample dispersion device positioned above several wells of a microtiter plate.

FIGS. 105 and 106 depict top and side views and an exploded perspective view, respectively, of the intermediate layer 106 of the device positioned adjacent to the top surface of the microtiter plate 100. The intermediate layer 106 of the device contains intermediate passages 108 that extend through the intermediate layer. Each intermediate passage 108 of the intermediate layer 106 aligns with an individual well 103 of a row or column of the microtiter plate 100. In one embodiment, the intermediate layer passages function as burst valves to control or prevent the flow of liquid from the metering chamber into the wells of the microtiter plate. The diameter of the vertical channel of the intermediate layer passages 108 creates surface tension that prevents liquid from flowing out of the metering chamber 120 (see FIG. 107) until centrifugal force is applied. In some embodiments, the vertical walls of the intermediate layer passages 108 are composed of or are coated with a hydrophobic material which increases the resistance of fluid flow out of the metering chamber 120 until centrifugal force is applied. Suitable hydrophobic materials include any material with a water contact angle >90°, such as, e.g., cyclic olefin copolymer, polyethylene, polypropylene, polydimethylsiloxane, fluorinated ethylene polypropylene, polytetrafluoroethylene. Alternatively, the wall of the intermediate layer passages may be composed of a hydrophilic material having a water contact angle <90°, but treated with a hydrophobic coatings, e.g., Teflon-carbon black, to create a superhydrophobic surface having water contact angles >150°.

The ratio of the resistance of the intermediate layer passages 108 to the volume of the metering chamber 120 (see FIG. 107) is readily calculable by one skilled in the art. Other embodiments of passive valves that release the liquid under the influence of an externally applied force can alternatively be employed.

Figure 107:
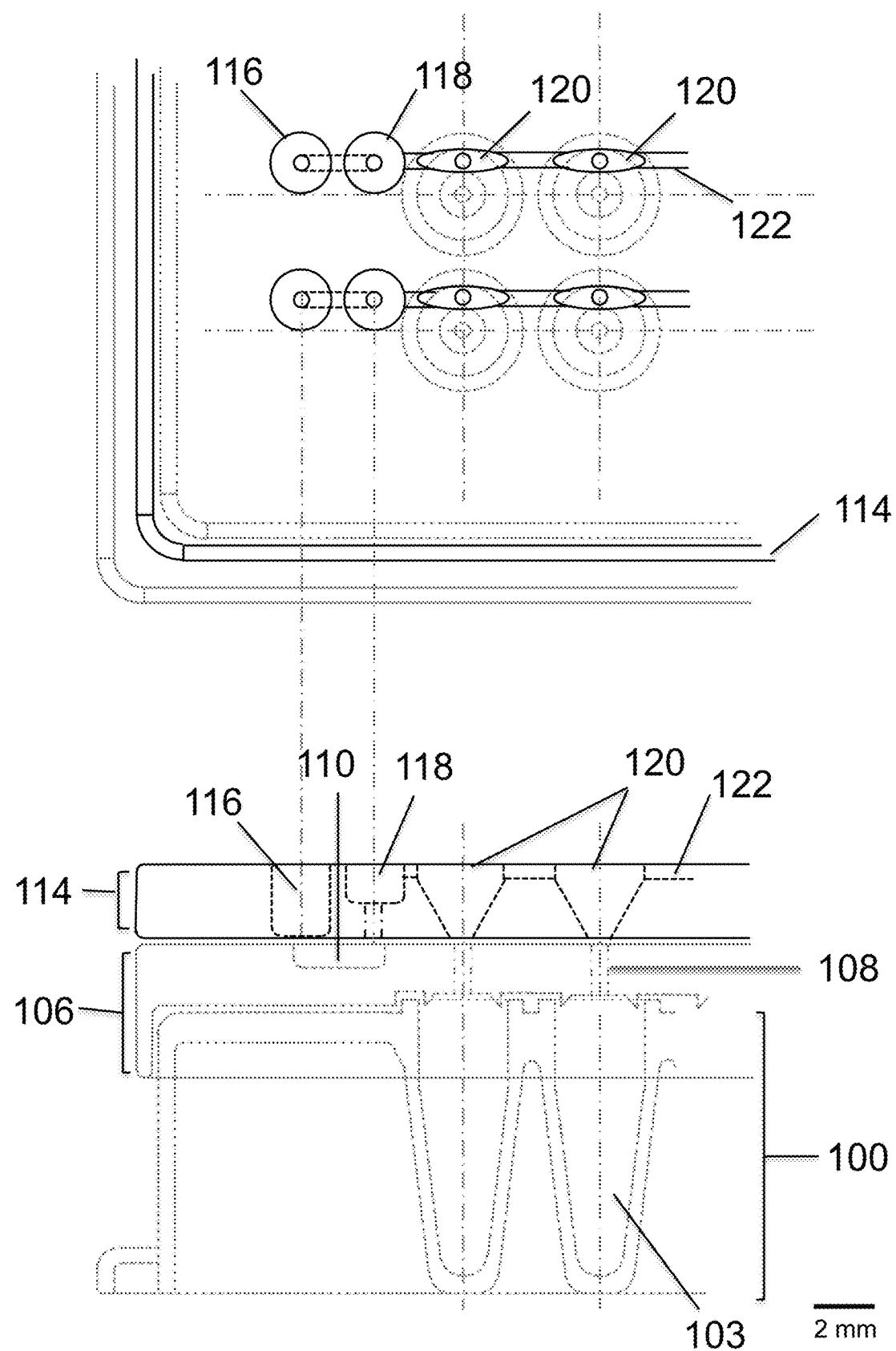
FIG. 107 illustrates a top and side view of the first and intermediate layers of a sample dispersion device positioned above several wells of a microtiter plate.

As depicted in FIGS. 105 and 106, the intermediate layer 106 also contains an overflow passage 110 that connects the overflow chamber 116 of the first layer with the filling chamber 118 of the first layer (see FIG. 107).

Figure 101:
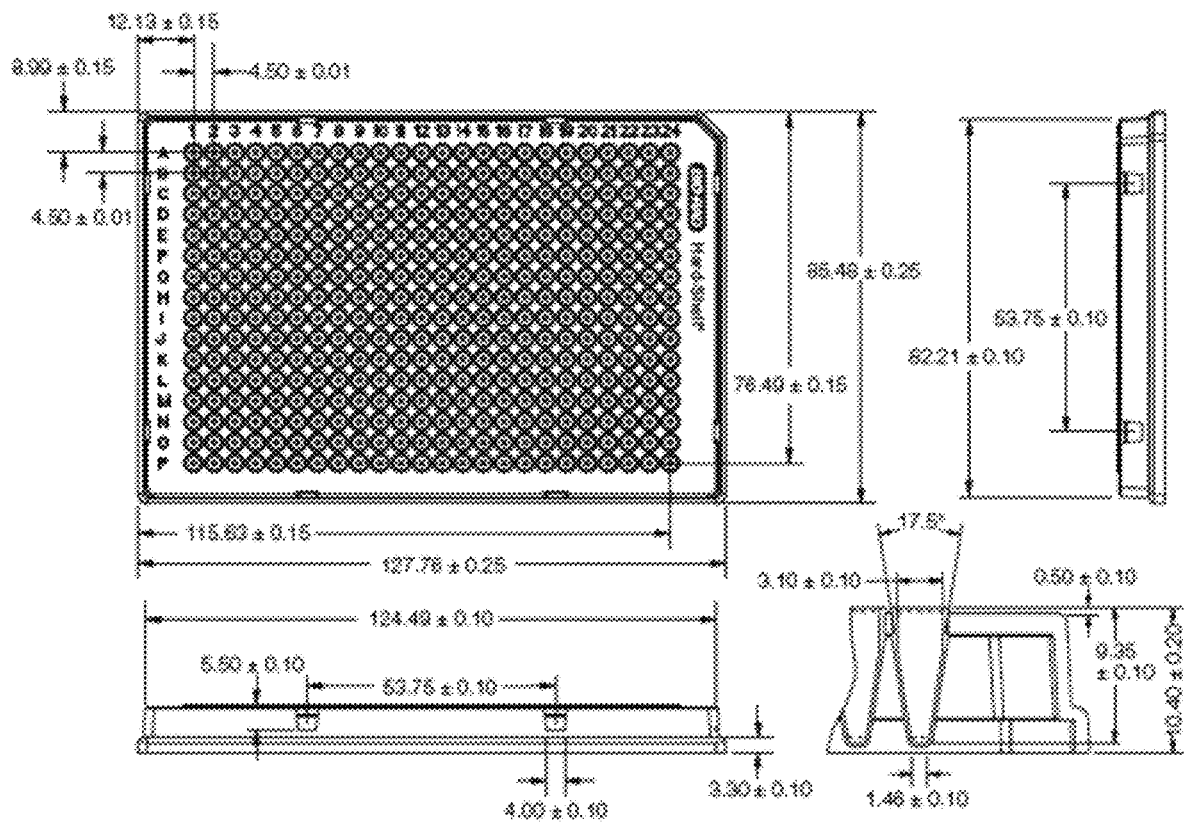
FIG. 101 illustrates the dimensions of one version of a commercially available 384 well microtiter plate.

Proper positioning and orientation of the device onto the top surface of a microtiter plate is achieved by keying the device to the perimeter of the top of the microtiter plates as shown in FIGS. 101 and 102. Further alignment of each of the metering chambers can be achieved by the use of flanges or skirts 112 in the intermediate layer 106 which interface with the open end 104 of each well 103 of the microtiter plate 100 as shown in the side view of FIG. 105. Other embodiments of positioning can be envisioned by one skilled in the art, for example based on small flanges at the top of the wells of the microtiter plate. While not meant to provide a hermetic seal, the flanges or skirts 112 of the intermediate layer 106 as depicted in FIG. 105 provide some measure of cross contamination control between adjacent wells of the microtiter plate 100.

Figure 108:
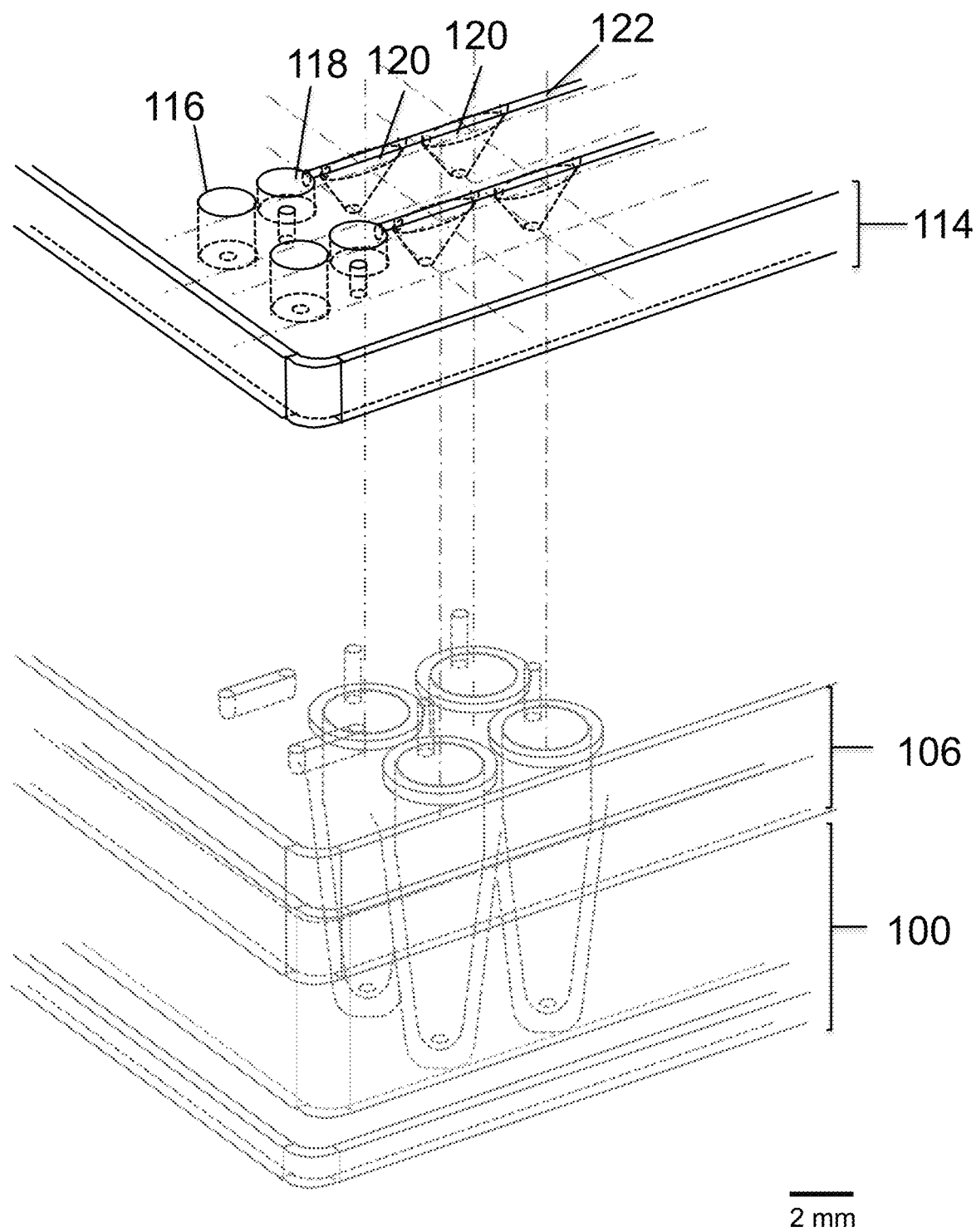
FIG. 108 illustrates an exploded perspective view of the first and intermediate layers of a sample dispersion device positioned above several wells of a microtiter plate.

FIGS. 107 and 108 depict top and side views and an exploded perspective view, respectively, of the first layer 114 of the device, operatively positioned adjacent to the second boundary of the intermediate layer 106 of the device. The first layer 114 of the device contains metering chambers 120 that are in fluid communication with each other via metering chamber channels 122, and with individual wells 103 of the microtiter plate. The metering chambers 120 have a fixed volume to control the volume of liquid delivered into each well 103 of the microtiter plate 100. The metering chambers 120 receive liquid from the filling chamber 118 by capillary action of the liquid or by mechanical force, e.g., the force of a pipettor pushing liquid into the filling chamber 118. In one embodiment, the metering chambers 120 of the device all have the same metering volume. In another embodiment, the metering chambers 120 have differing metering volumes per row and/or column. The walls of the filling chamber, metering chambers, and the metering chamber channels may be composed of or coated with a hydrophilic material.

As illustrated in FIGS. 107 and 108, each metering chamber 120 is in fluid communication with the wells 103 of the microtiter plate via the intermediate layer passages 108. As described supra, the intermediate layer passages may function as a burst valve to prevent liquid in the metering chamber 120 from flowing into the wells 103 of the microtiter plate 100 until appropriate force is applied, e.g., centrifugal force.

The first layer 114 of the device also contains an overflow chamber 116 as depicted in FIGS. 107 and 108. As noted above, the overflow chamber 116 is in fluid communication with the filling chamber 118 via the overflow passage 110 of the intermediate layer 106.

Figure 109:
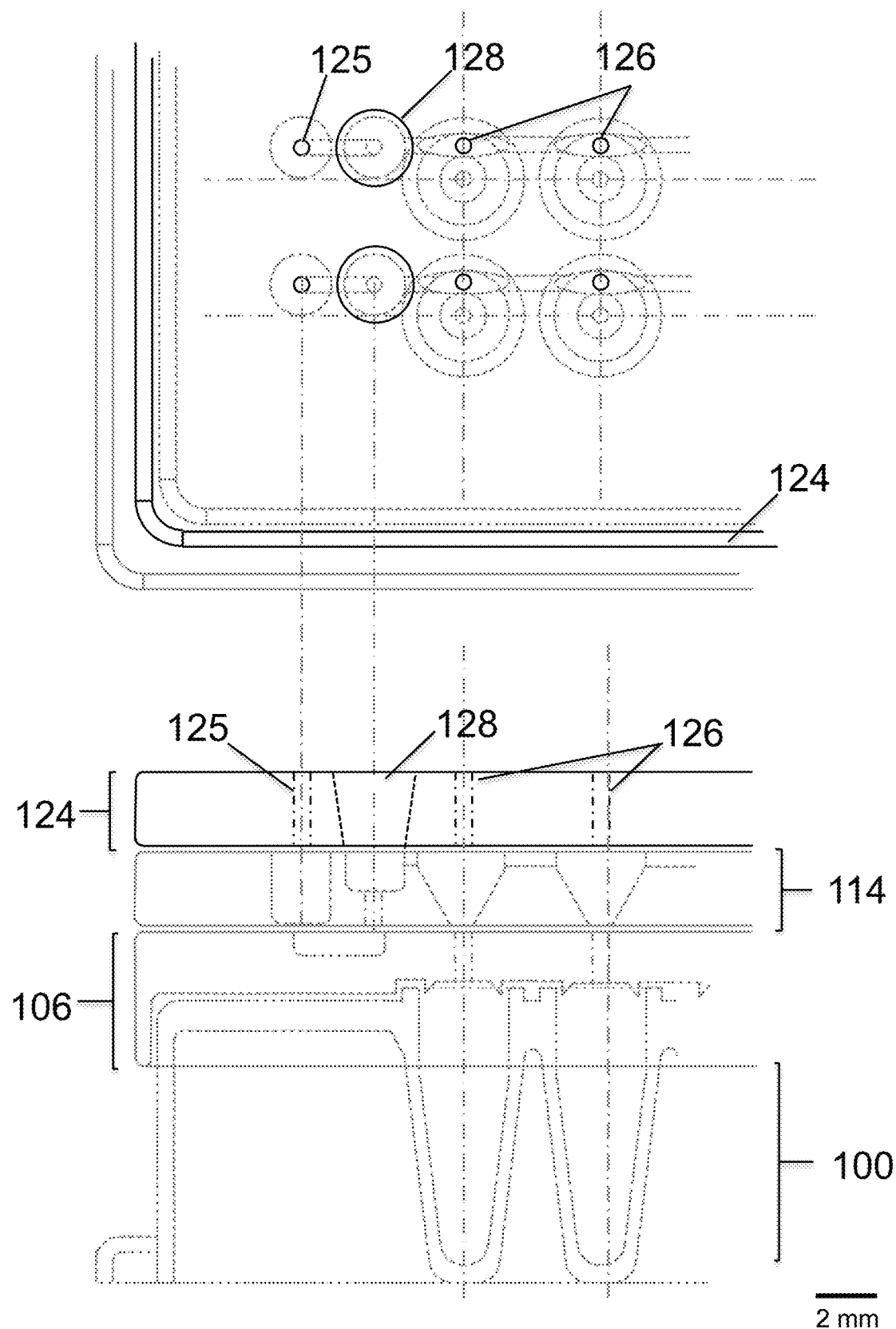
FIG. 109 illustrates a top and side view of the third, first, and intermediate layers of a sample dispersion device positioned above several wells of a microtiter plate.
Figure 110:
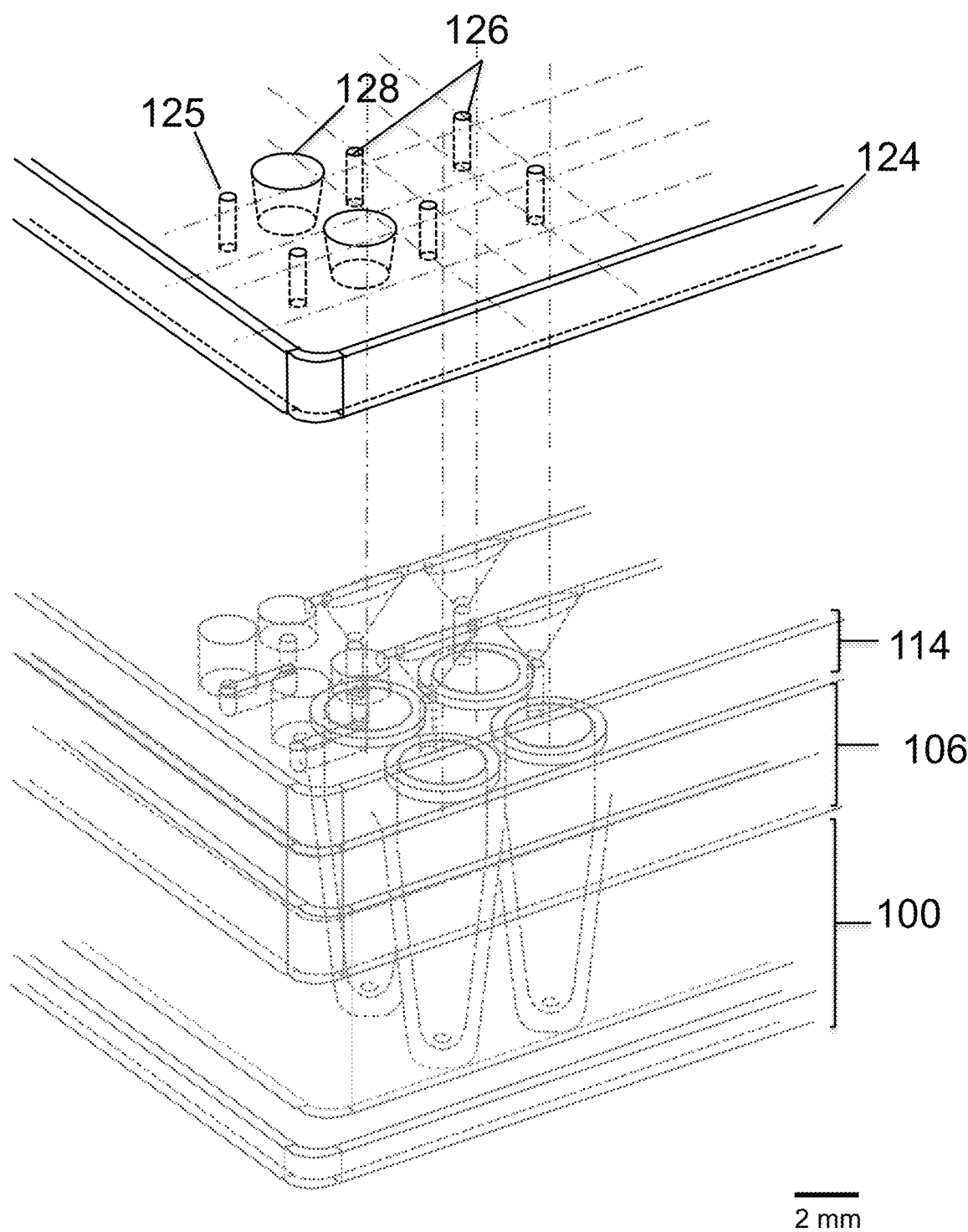
FIG. 110 illustrates an exploded perspective view of the third, first, and intermediate layers of a sample dispersion device positioned above several wells of a microtiter plate.

FIGS. 109 and 110 depict top and side views and an exploded perspective view, respectively, of the third layer 124 of the device operatively positioned adjacent to the second boundary of the first layer 114 of the device. The third layer 124 of the device contains a filling port connector 128 that extends through the third layer 124, aligning and connecting the filling port 132 of the second layer 130 (shown in FIG. 111) with the filling chamber 118 of the first layer 114. The third layer 124 also contains air passage connectors 126 that extend through the third layer 124, aligning with and connecting the metering chambers 120 of the first layer 114 with the air passages 136 of the second layer 130 (also shown in FIG. 111). The walls of the air passage connectors 126 of the third layer are composed of or coated with a hydrophobic material. The third layer 124 of the device also contains overflow air passage connectors 125 that extend through the third layer, aligning with and connecting the overflow chamber 116 of the first layer 114 to the overflow air passages 134 of the second layer 130 (shown in FIG. 111).

Figure 111:
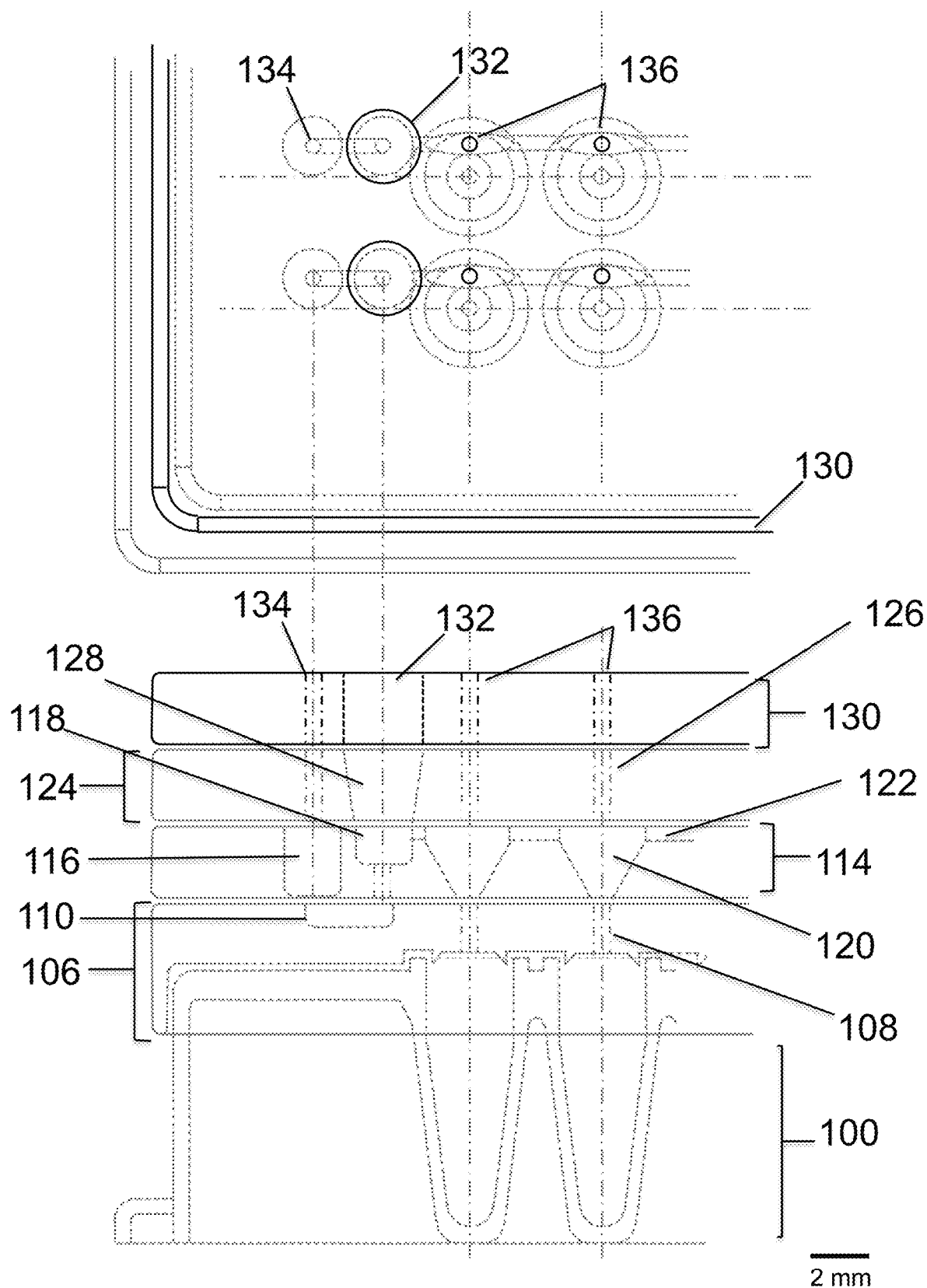
FIG. 111 illustrates a top and side view of the second, third, first, and intermediate layers of a sample dispersion device positioned above several wells of a microtiter plate.
Figure 112:
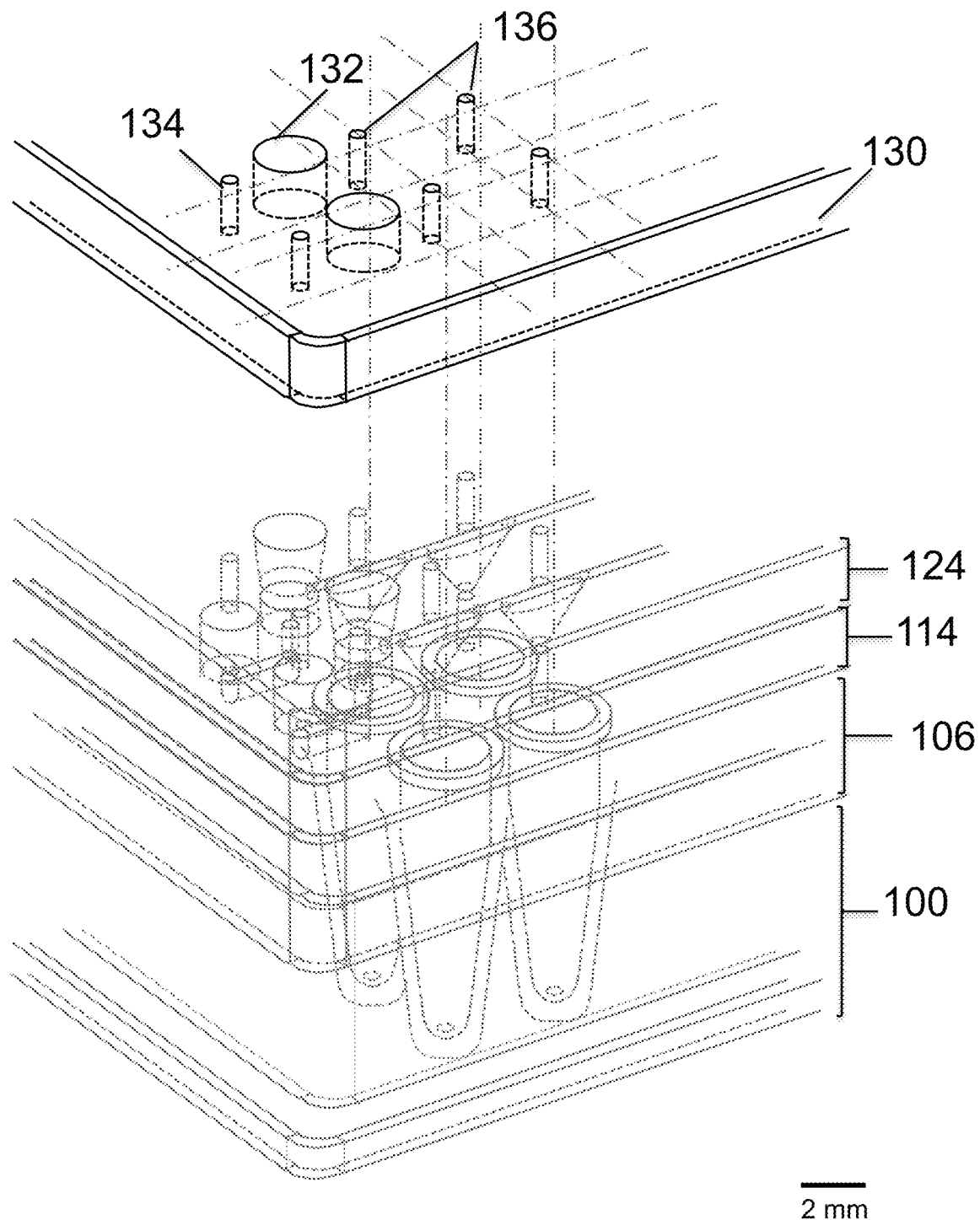
FIG. 112 illustrates an exploded perspective view of the second, third, first, and intermediate layers of a sample dispersion device positioned above several wells of a microtiter plate.
Figure 113:
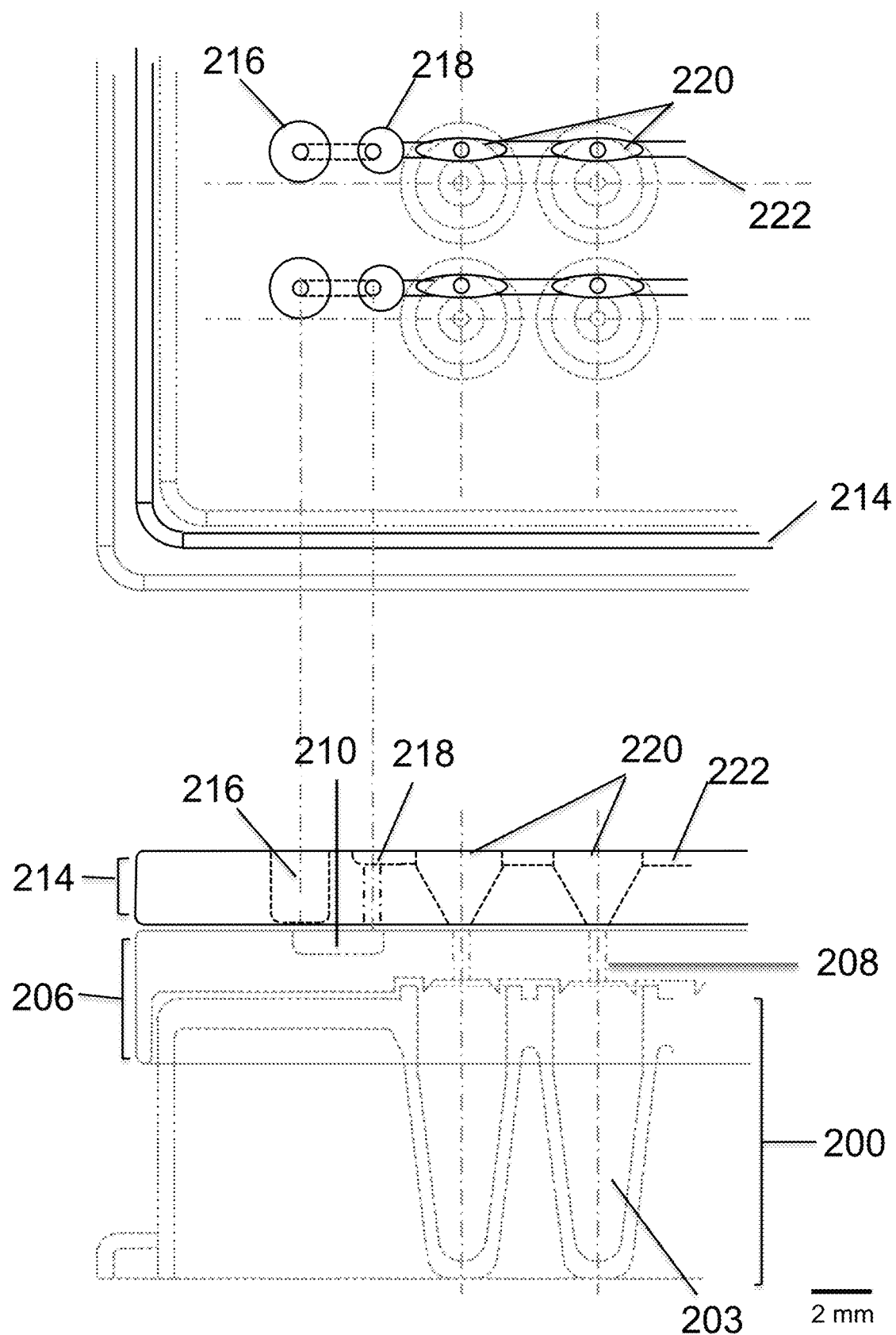
FIG. 113 illustrates a top and side view of the first and intermediate layers of a sample dispersion device that uses an alternative filling port to pressure fill the channels and metering chambers of each row of a microtiter plate.
Figure 114:
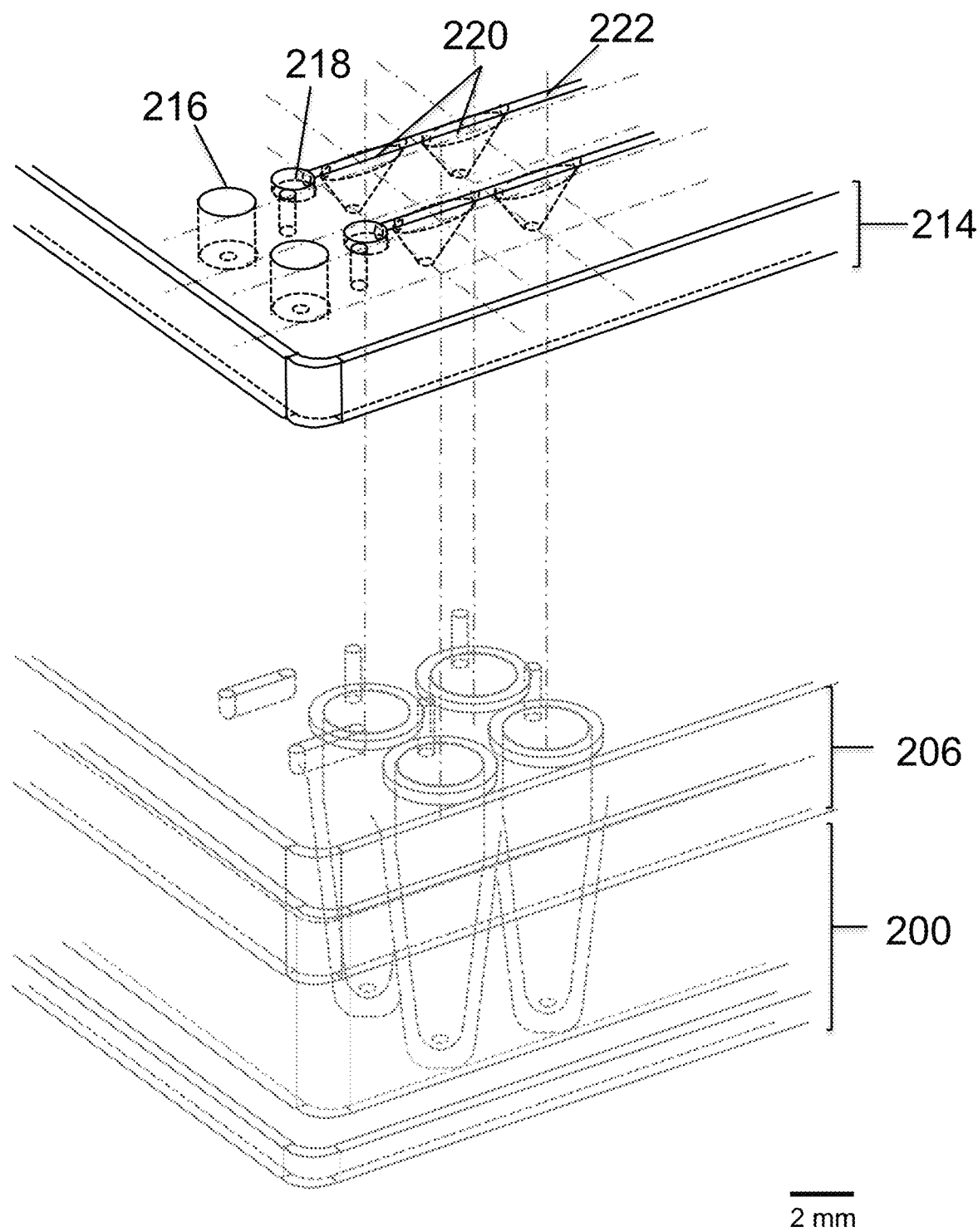
FIG. 114 illustrates an exploded perspective view of the first and intermediate layers of a sample dispersion device that uses an alternative filling port to pressure fill the channels and metering chambers of each row of a microtiter plate.
Figure 115:
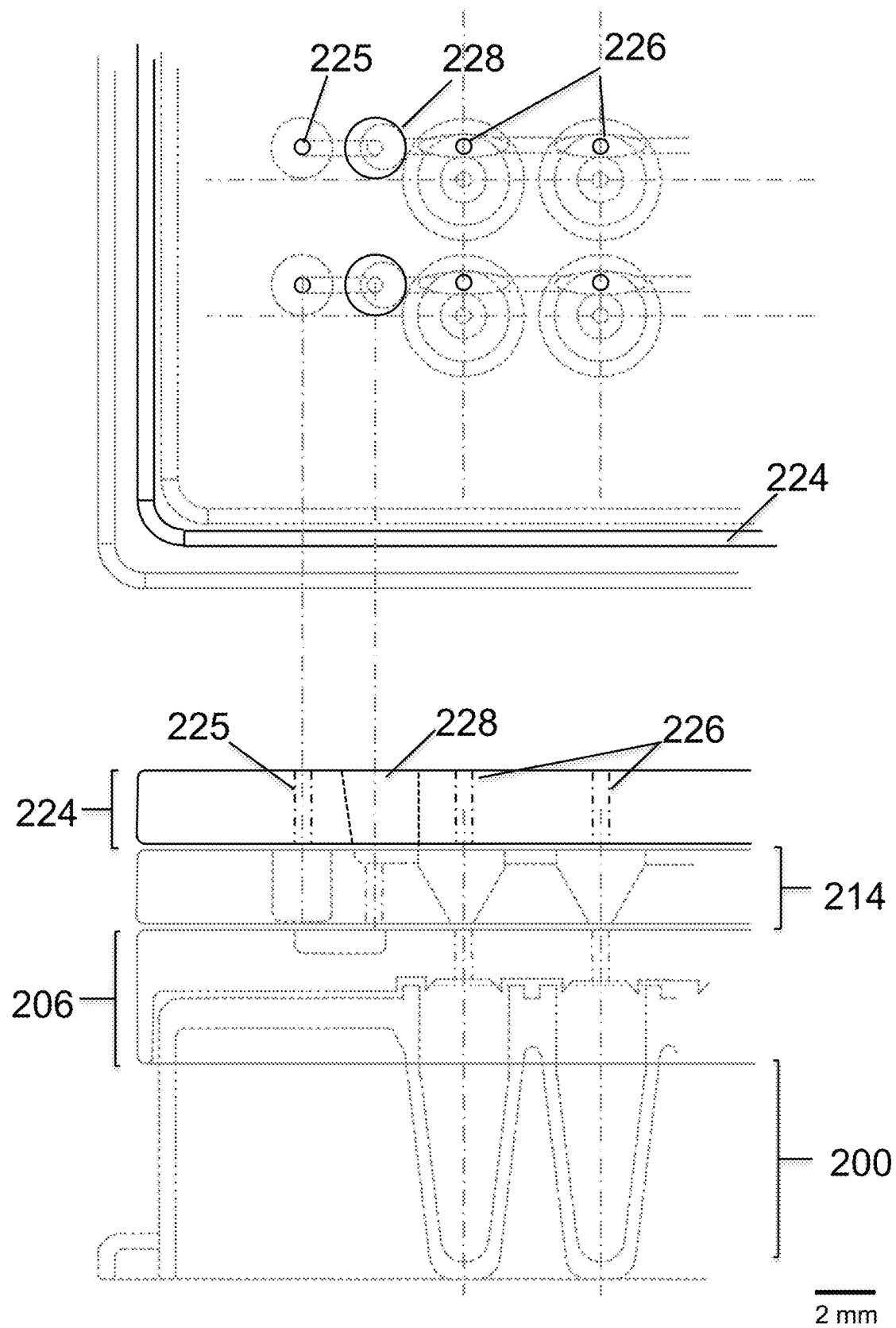
FIG. 115 illustrates a top and side view of the third, first, and intermediate layers of a sample dispersion device that uses an alternative filling port to pressure fill the channels and metering chambers of each row of a microtiter plate.
Figure 116:
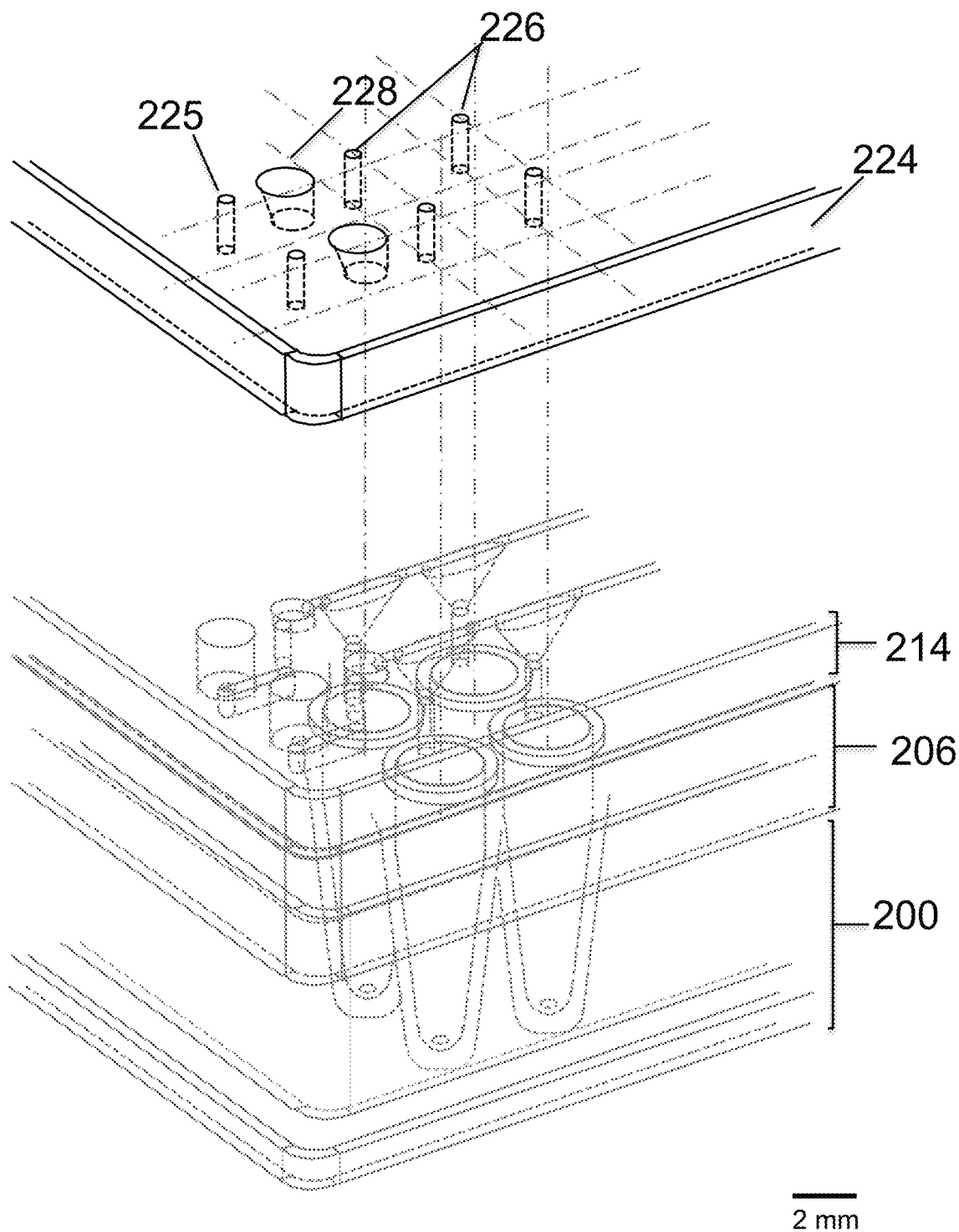
FIG. 116 illustrates an exploded perspective view of the third, first, and intermediate layers of a sample dispersion device that uses an alternative filling port to pressure fill the channels and metering chambers of each row of a microtiter plate.

FIGS. 111 and 112 depict top and side views and an exploded perspective view, respectively, of the second layer 130 of the device operatively positioned adjacent to the second boundary of the third layer 124 of the device. The second layer 130 of the device contains a filling port 132 that extends through the second layer 130, and aligns with the filling port connector 128 of the third layer 124, or in some embodiments, directly with the filling chamber 118 of the first layer 114. The second layer 130 of the device also contains air passages 136 that extend through the second layer 130 and align with the metering chambers 120 of the first layer 114. The air passages 136 of the second layer connect to the metering chambers 120 of the first layer 114 via the air passage connectors 126 of the third layer 124. As further illustrated in FIGS. 111 and 112, the second layer 130 of the device also contains an overflow air passage 134 that extends through the second layer 130 and aligns with the overflow chamber 116 of the first layer 114. The overflow air passage 134 connects to the overflow chamber 116 via the overflow air passage connectors 125 of the third layer 124.

Although the device is described in terms of individual layers, the layers of the device are integral, giving the device a monolithic structure.

In one embodiment of the present invention the first layer of the device is provided with a pair of spaced filling chambers on opposite ends of the metering chambers and the second layer is provided with a pair of spaced filling ports, each in fluid communication with one of the pair of spaced filling chambers. One of the pair of spaced filling ports provides liquid to one of the pair of spaced filling chambers and half of the metering chambers, while the other one of the pair of spaced filling ports provides liquid to the other of the pair of filling chambers and the other half of the metering chambers.

In another embodiment of the present invention, the first layer of the device is provided with a pair of spaced filling chambers on opposite ends of the metering chambers and the second layer is provided with a pair of spaced filling ports, each in fluid communication with one of the pair of spaced filling chambers. One of the pair of spaced filling ports provides liquid to one of the pair of filling chambers and all of the metering chambers, while the other one of the pair of spaced filling ports provides liquid to the other of the pair of filling chambers and all of the metering chambers.

The device of the present invention can be configured to fill two or more rows and columns of said microtiter plate with liquid.

The Figures herein illustrate different designs compatible with a 384 well microtiter plate; however the concepts described are likewise applicable to 1536 well plates by one skilled in the art. FIG. 105 thru 112 described in detail above illustrate a device for the simultaneous filling of all wells in all rows across 24 columns by use of filling ports 132 on the right side of the device-microtiter plate stack. This configuration relies on capillary action to fill each of the individual metering chambers 120 connected by channels 122 as shown in FIG. 111.

Figure 117:
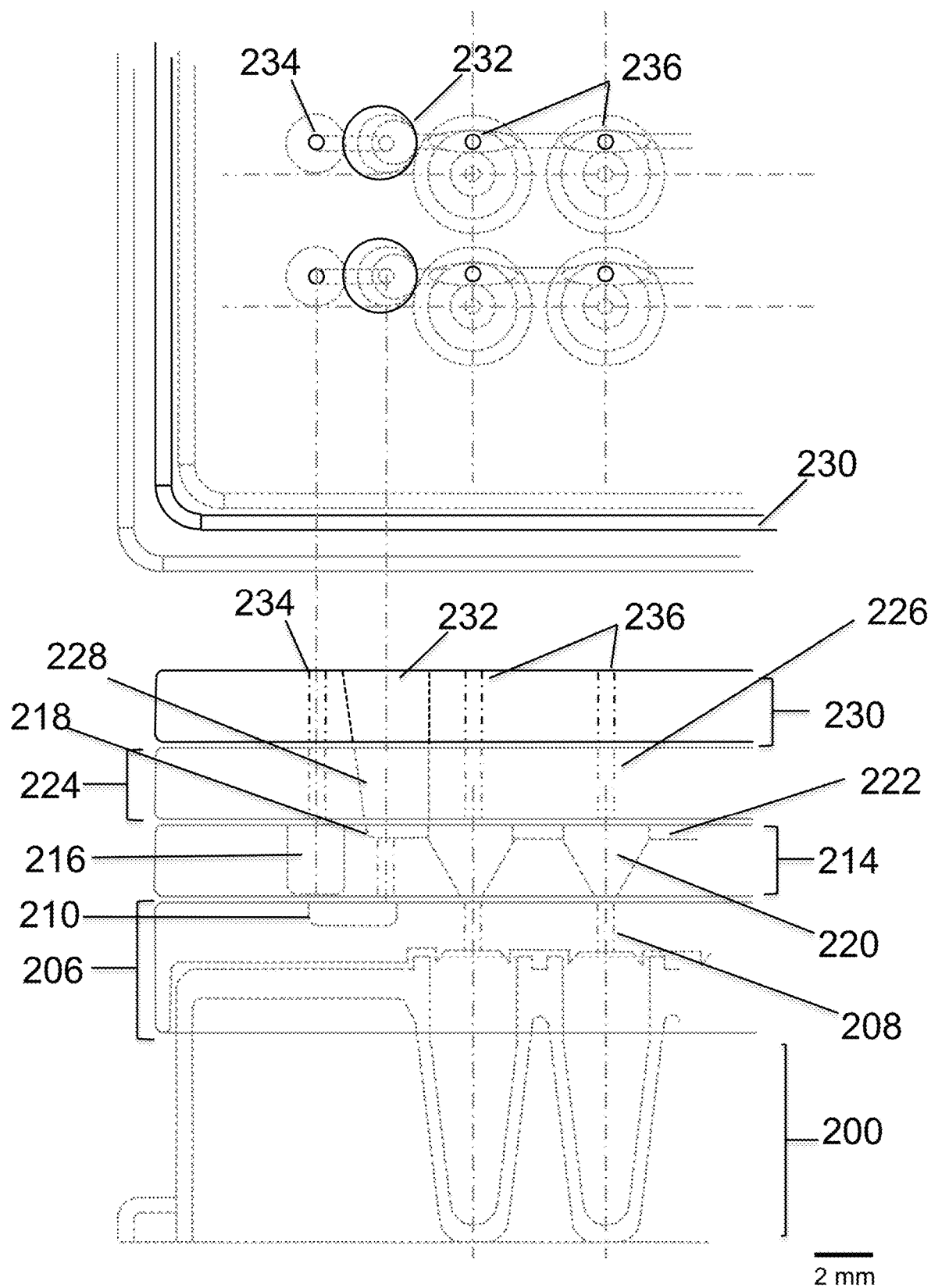
FIG. 117 illustrates a top and side view of the second, third, first, and intermediate layers of a sample dispersion device that uses an alternative filling port to pressure fill the channels and metering chambers of each row of a microtiter plate.
Figure 118:
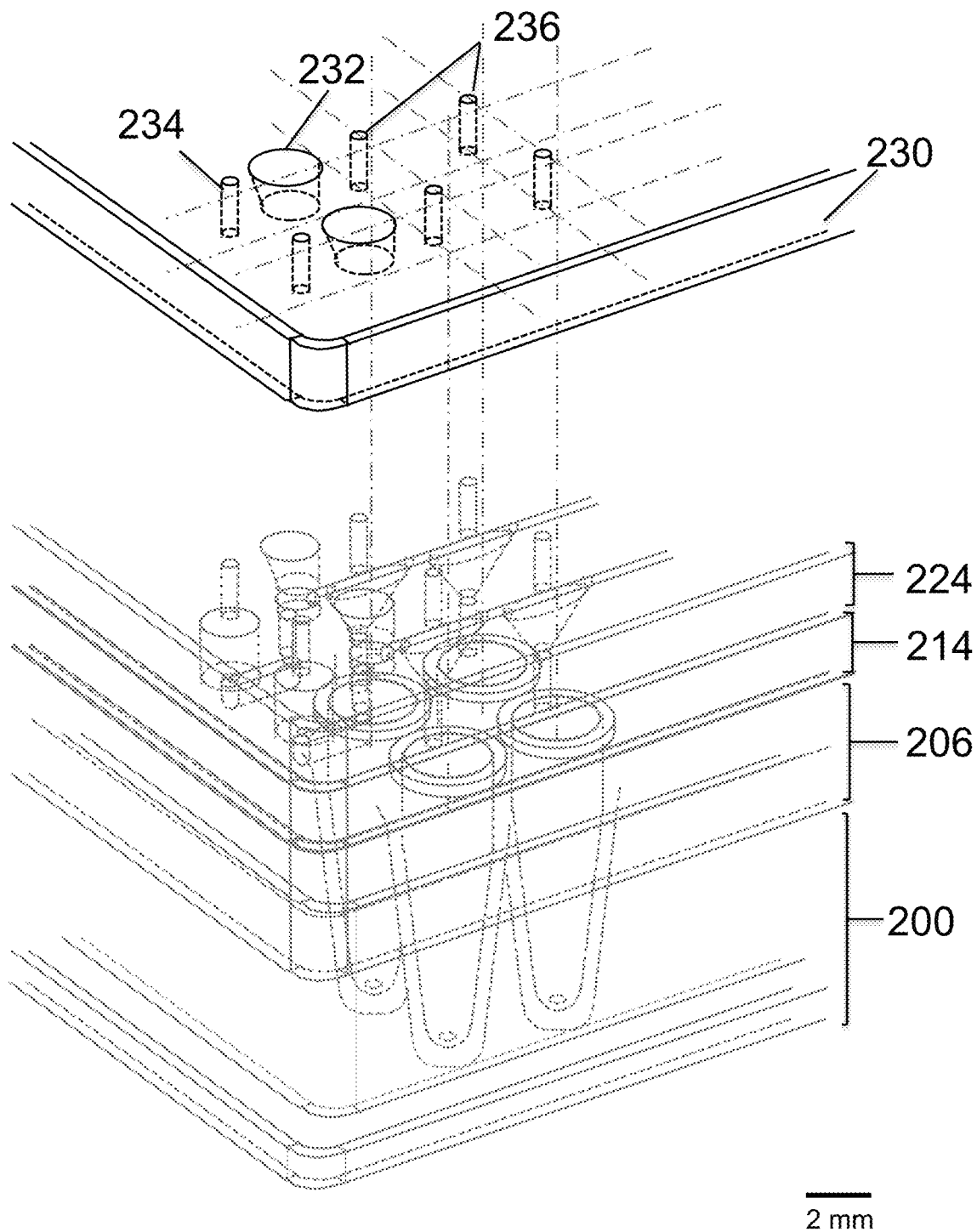
FIG. 118 illustrates an exploded perspective view of the second, third, first, and intermediate layers of a sample dispersion device that uses an alternative filling port to pressure fill the channels and metering chambers of each row of a microtiter plate.
Figure 120:
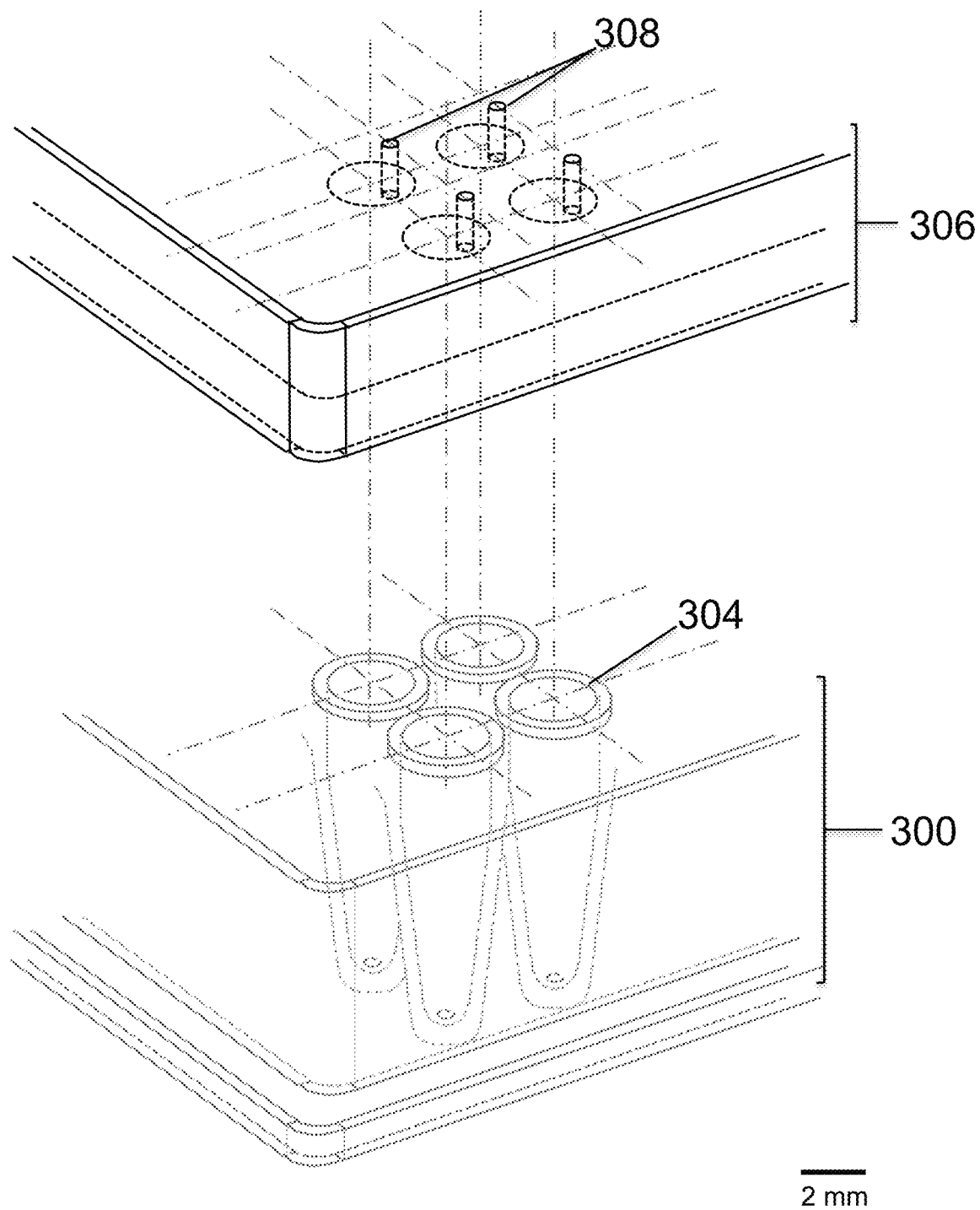
Figure 121:
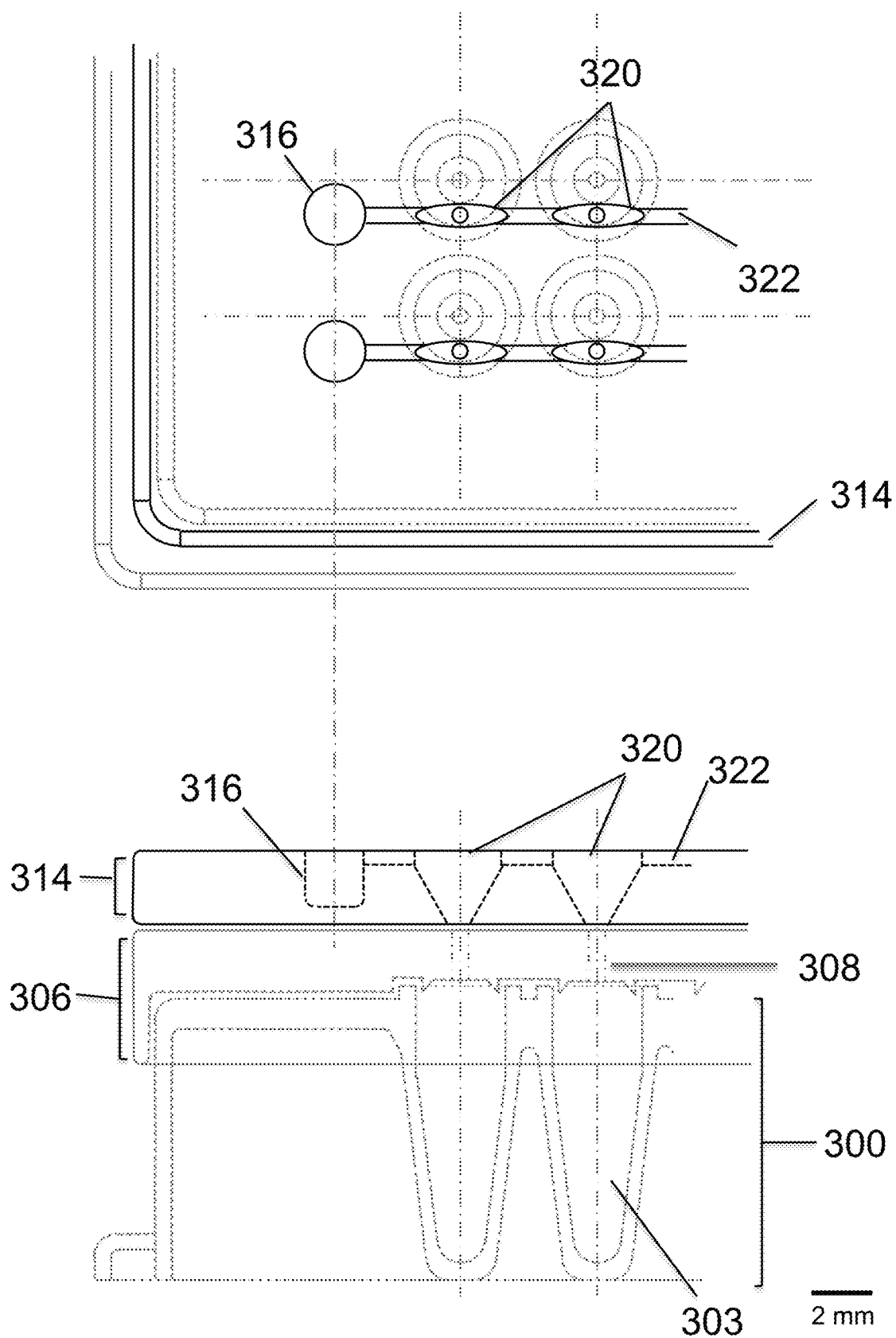
Figure 122:
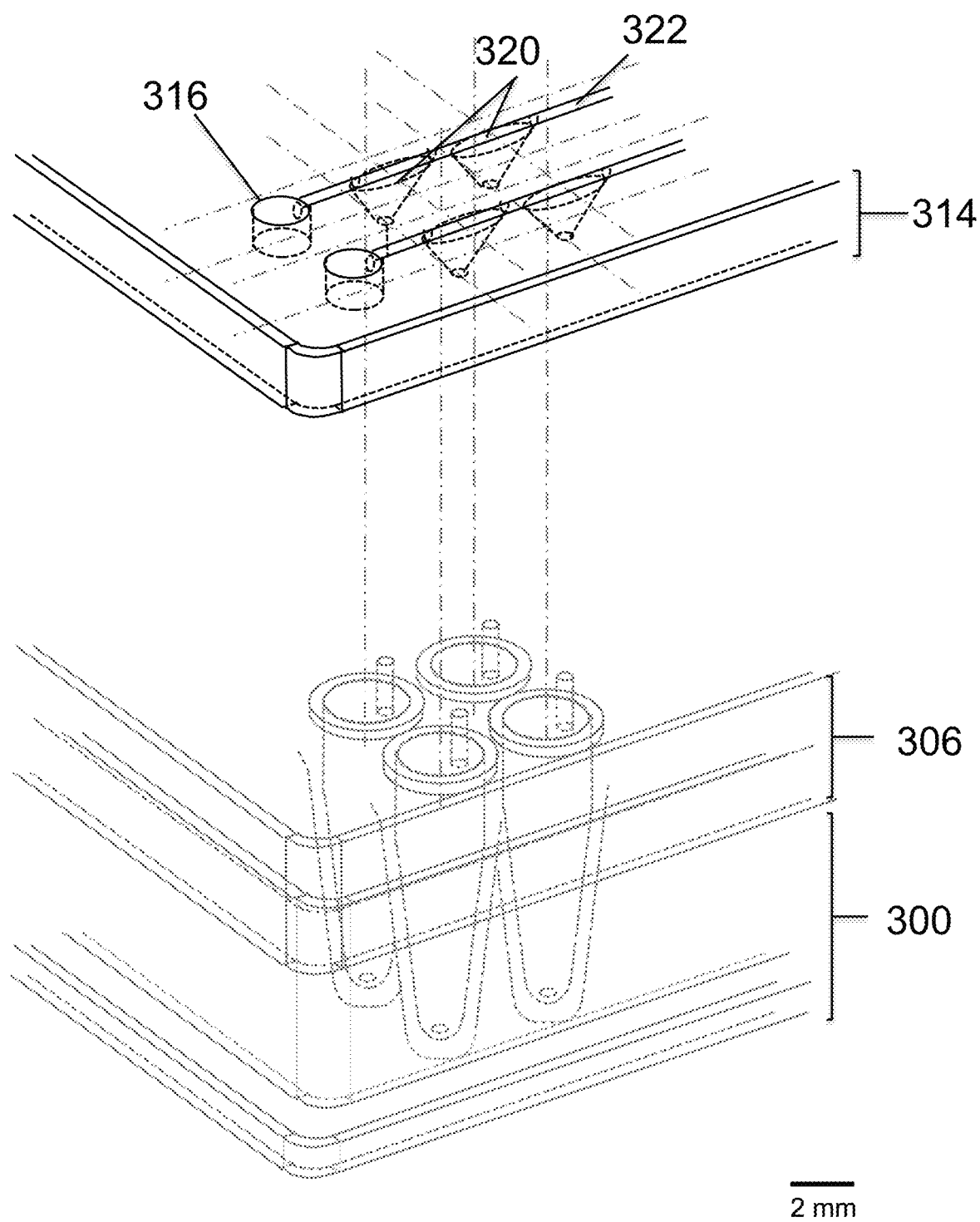
Figure 123:
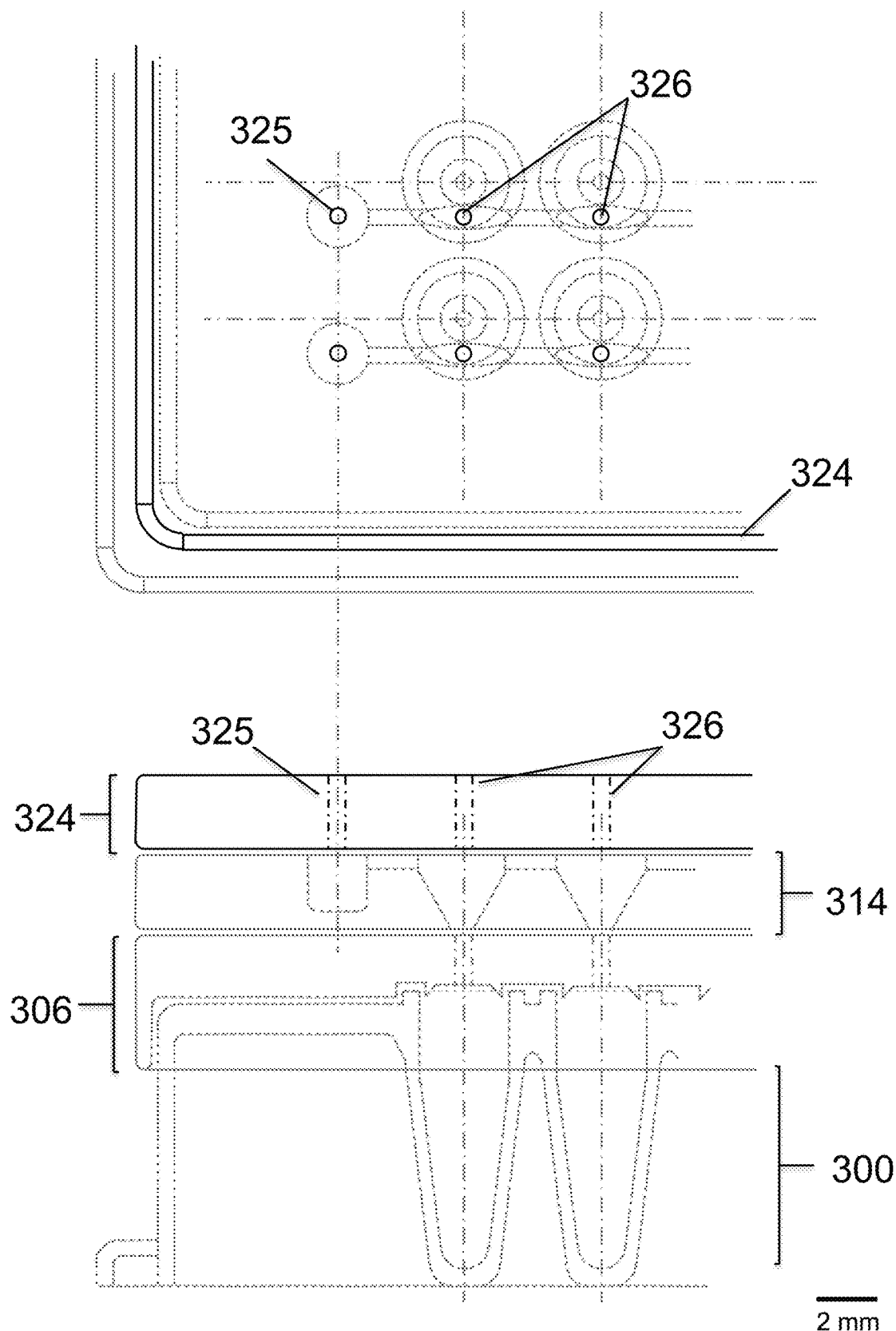
Figure 124:
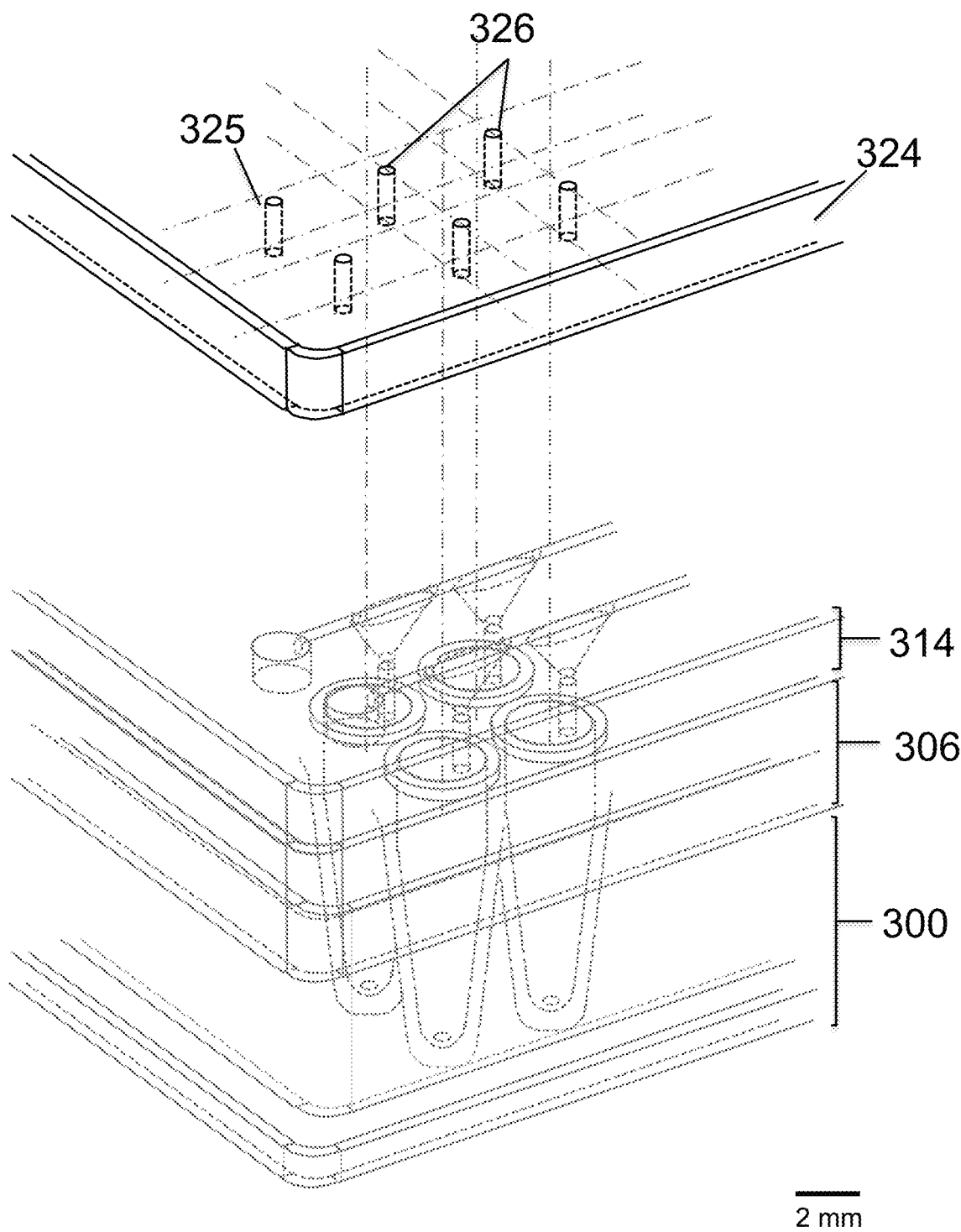
Figure 125:
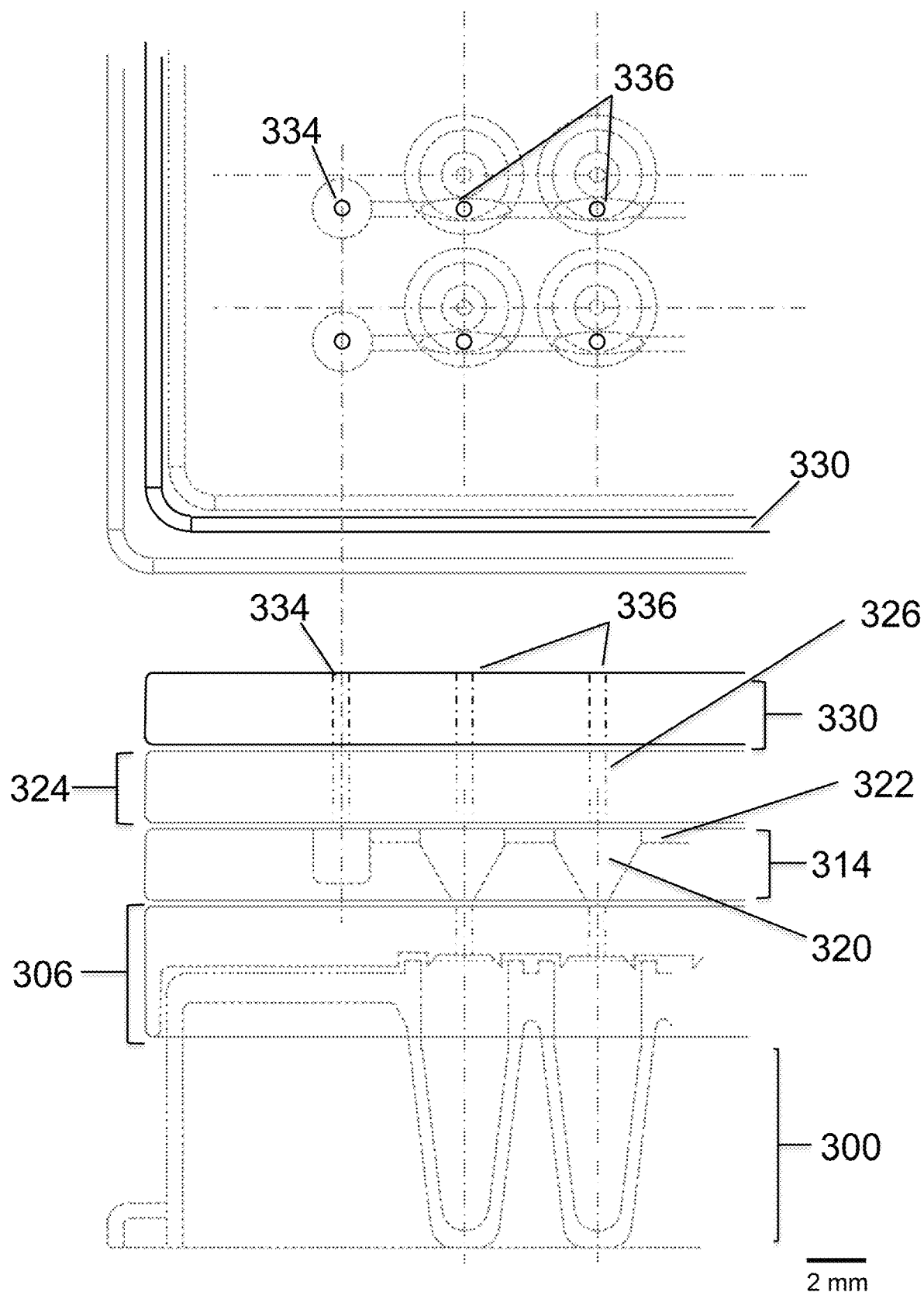
Figure 126:
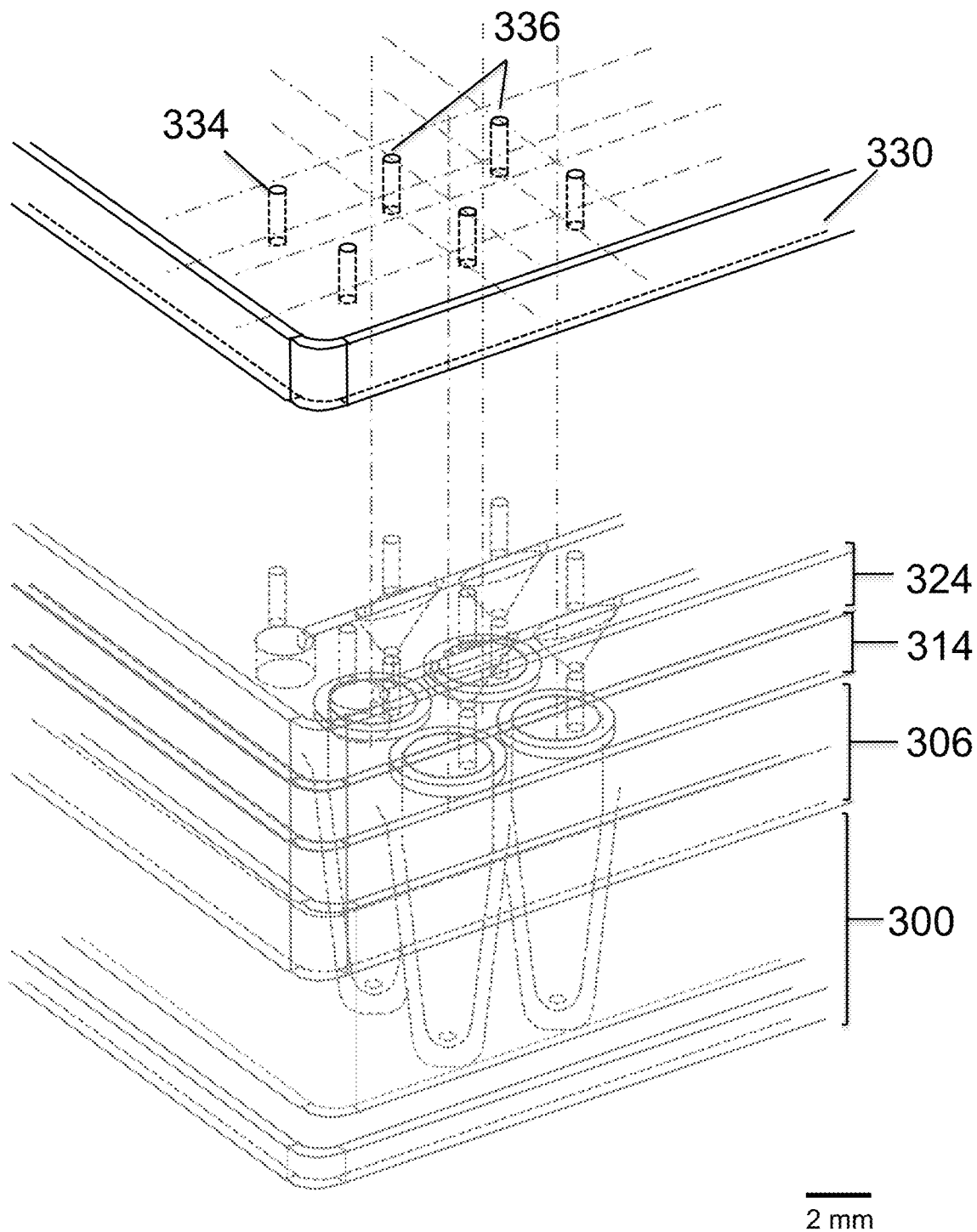
Figure 128:
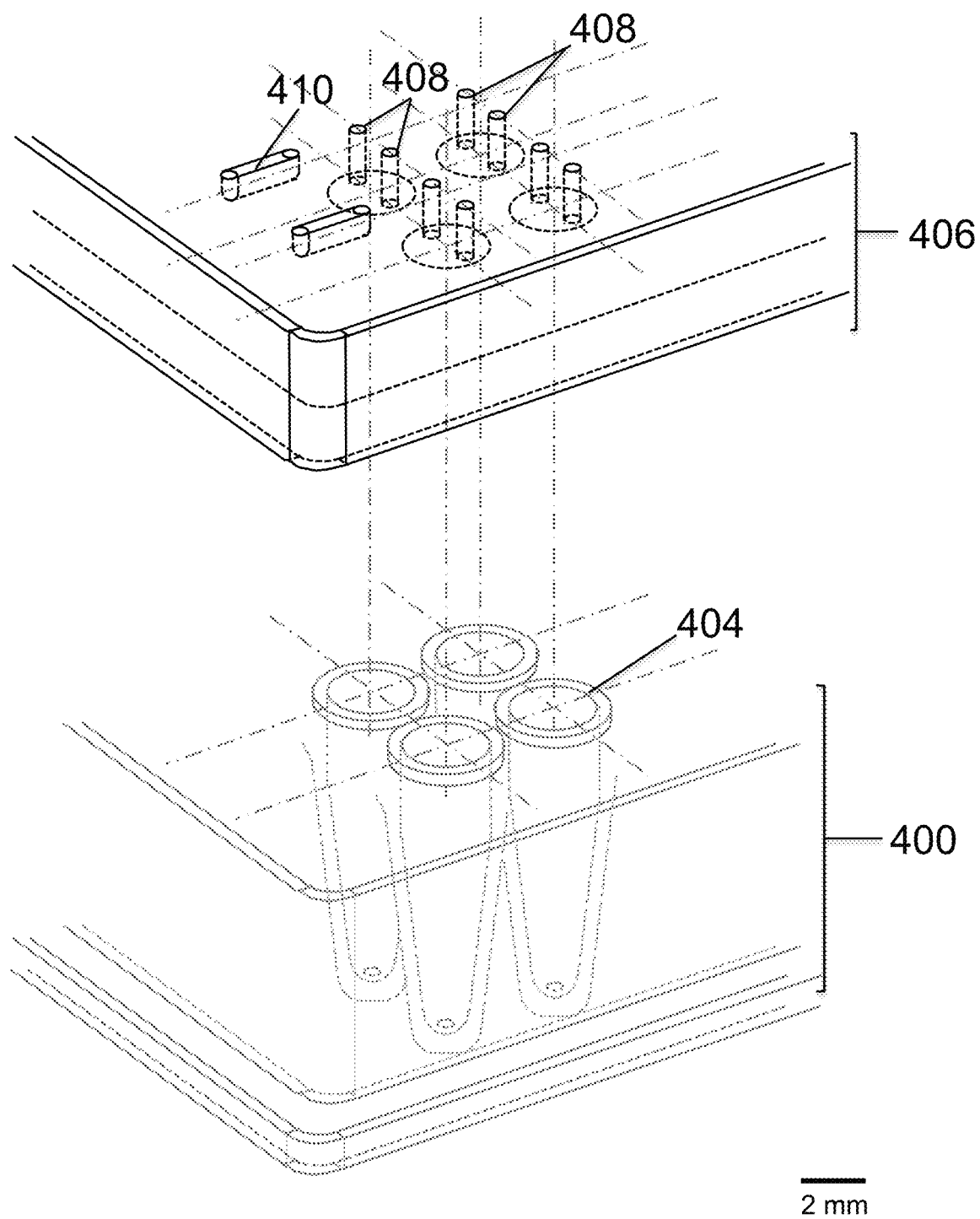
Figure 129:
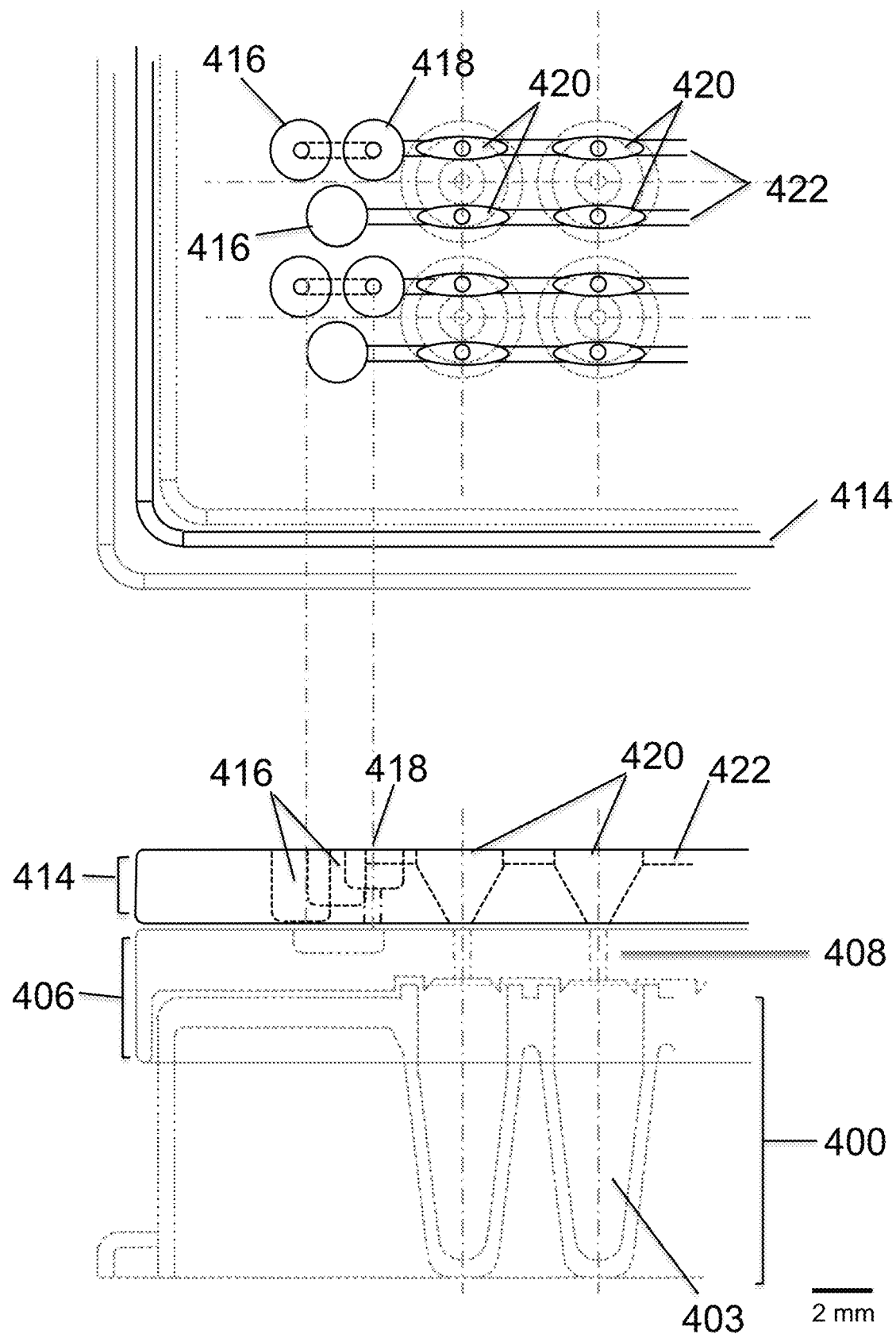
Figure 130:
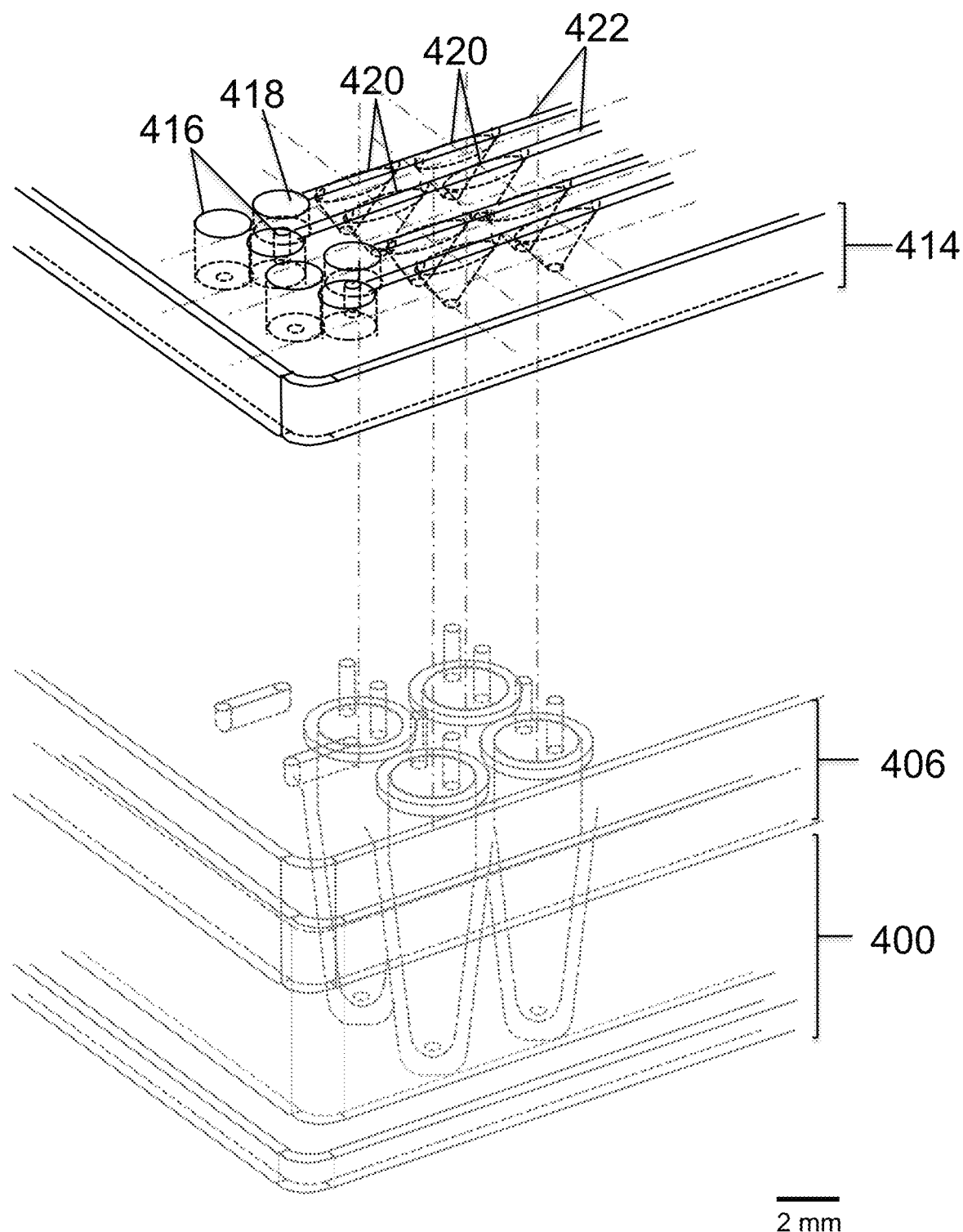
Figure 131:
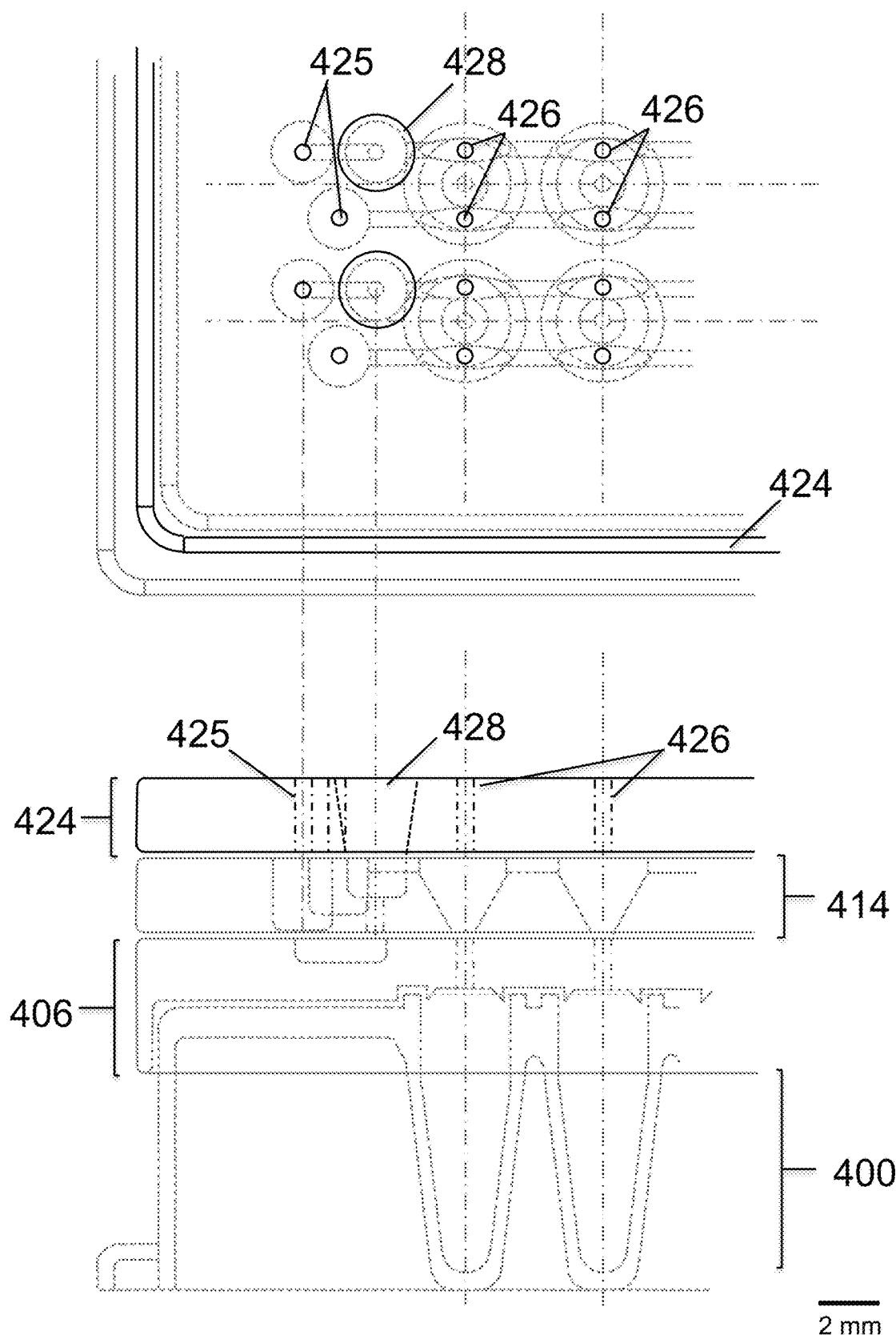

FIGS. 113 thru 118 are a series of top, side, and exploded perspective drawings that illustrate a second configuration of the device. This second configuration of the device relies on mechanical force of the pipettor to drive the liquid into the channels and metering chambers. FIGS. 113-118 depict all of the same device features as shown in FIGS. 107-112 (numbered correspondingly as 200-236), except that the filling port 232 of the second layer 230 is modified to facilitate mechanical filling of the wells with liquid as shown in FIG. 117. The filling port 232 dimensions are tapered, such that a standard disposable tip would fit snugly into the port, allowing for positive pressure to be used to fill the metering chambers. The dimensions and spacing of the filling ports are compatible with use of hand-held multichannel pipettes or multichannel robotic workstations.

FIGS. 119 thru 126 are a series of top, side, and exploded perspective drawings that show a different portion of the device as depicted in FIGS. 105 thru 118. The portion of the device depicted in FIGS. 119-126 represents the exit ends of the row and/or columns shown in FIGS. 105-118, i.e., the portion of the device that is opposite the filling ports. The device features depicted in FIGS. 119-126, labeled as 300-336, correspond to the features described and labeled in reference to FIGS. 105-112 (i.e., device features 100-136).

FIGS. 127 thru 134 are a series of top, side, and exploded perspective drawings that illustrate an alternative configuration of the device of the present invention. In this configuration of the device, filling ports 432 (see FIG. 133) for loading reagents into the wells of the microtiter plate are located on both sides of the device-microtiter plate stack. This configuration can be used to add two different sets of reagents to all wells in each row. Alternatively, each side of the fluidic channels can address 12 of the 24 columns from each side of the device thus dividing the plate into two side-by-side regions of 192 wells. This configuration retains the ability to independently address each row and each column of the two regions. The device features depicted in FIGS. 127-134, labeled as 400-436, correspond to the features described and labeled in reference to FIGS. 105-112 (i.e., device features 100-136).

FIGS. 135 thru 144 are a series of top, side, and exploded perspective drawings that illustrate an alternative configuration of the device of the present invention. This configuration of the device is suitable for the simultaneous filling of all wells by rows and all wells by columns. Alternatively, each side of the fluidic channels can address 12 of the 24 columns from each side of the device and 8 of the 16 rows from each side of the device thus dividing the plate into four different regions of 96 wells. This configuration retains the ability to independently address each row and each column of the four regions. The device features depicted in FIGS. 135-144, labeled as 500-536, correspond to the features described and labeled in reference to FIGS. 105-112 (i.e., device features 100-136).

In accordance with this configuration, FIGS. 135 and 136 depict top and side views and an exploded perspective view, respectively, of the intermediate layer 506 of the device positioned adjacent to the top surface of the microtiter plate 500. The intermediate layer 506 of the device contains intermediate passages 508 that extend through the intermediate layer. In this embodiment, each well of the microtiter plate aligns with at least two intermediate passages 508 as shown in the top, side and exploded perspective view of FIGS. 135 and 136, respectively. The intermediate layer 506 also contains the overflow passage 510.

FIGS. 137 thru 140 depict top, side, and an exploded perspective views, of the first layer 514 of the device (see FIG. 139), operatively positioned adjacent to the second boundary of the intermediate layer 506 of the device. In accordance with this embodiment, the first layer 514 of the device of the present invention has a first region 513 having the metering chambers 520 in two or more rows (see FIGS. 137 and 138), and a second region 515 having the metering chambers 520 in two or more columns (see FIGS. 139 and 140) with the first and second regions being displaced from each other. The metering chambers 520 of the first 513 and second 515 regions of the first layer 514 are in fluid communication with each other via metering chamber channels 522, and with individual wells 503 of the microtiter plate. As described supra, the metering chambers 520 have a fixed volume to control the volume of liquid delivered into each well 503 of the microtiter plate 500. The metering chambers 520 receive liquid from the filling chamber 518 by capillary action of the liquid or by mechanical force pushing liquid into the filing chamber 518. Flow of the liquid out of the metering chambers 520 into the wells of the microtiter plate is controlled by, e.g., the hydrophobic forces of the intermediate layer passages 508. In one embodiment, the metering chambers 520 of the device all have the same metering volume. In another embodiment, the metering chambers 520 have differing metering volumes per row and/or column.

The first 513 and second 515 regions of the first layer 514 of the device each contain an overflow chamber 516 as depicted in FIGS. 137-138 and FIGS. 139-140, respectively. As noted above, the overflow chamber 516 is in fluid communication with the filling chamber 518 via the overflow passage 510 of the intermediate layer 506.

FIGS. 141 and 142 depict top and side views and an exploded perspective view, respectively, of the third layer 524 of the device operatively positioned adjacent to the second boundary of the second region 515 of the first layer 514 of the device. The third layer 524 of the device contains a filling port connector 528 that extends through the third layer 524, aligning and connecting the filling port 532 of the second layer 530 (shown in FIG. 143) with the filling chamber 518 of the first layer 514. The third layer 524 also contains air passage connectors 526 that extend through the third layer 524, aligning with and connecting the metering chambers 520 of the first layer 514 with the air passages 536 of the second layer 530 (also shown in FIG. 143). The third layer 524 of the device also contains overflow air passage connectors 525 that extend through the third layer, aligning with and connecting the overflow chamber 516 of the first layer 514 to the overflow air passages 534 of the second layer 530 (shown in FIG. 143).

FIGS. 143 and 144 depict top and side views and an exploded perspective view, respectively, of the second layer 530 of the device operatively positioned adjacent to the second boundary of the third layer 524 of the device. In this embodiment, the second layer 530 of the device contains filling ports 532, one for each row and each column, that extend through the second layer 530, and align with the filling port connectors 528 of the third layer 524, or in some embodiments, directly with the filling chambers 518 of the first layer 514. The second layer 530 of the device further contains air passages 536 that extend through the second layer 530 and align with the metering chambers 520 of the first layer 514. The air passages 536 of the second layer connect to the metering chambers 520 of the first layer 514 via the air passage connectors 526 of the third layer 524. As further illustrated in FIGS. 143 and 144, the second layer 530 of the device also contains an overflow air passage 534 in each row and column that extends through the second layer 530 and aligns with the overflow chamber 516 of the first layer 514. The overflow air passage 534 connects to the overflow chamber 516 via the overflow air passage connectors 525 of the third layer 524.

While each of the different configurations described above is illustrated by a series of drawings that show top, side, and exploded views of each layer of the device, for purposes of fabrication, the device can be molded monolithically or assembled from individual layers as determined by one skilled in the art.

Another aspect of the present invention is directed to a method of adding liquids to two or more wells in a row and/or column of a microtiter plate having opposed top and bottom surfaces with the top surface having openings leading into the wells and the bottom surface defining closed ends of the wells. This method involves providing the device of the present invention as described supra, and filling the device with liquid. The liquid is discharged into two or more wells in a row and/or column of said microtiter plate of the device.

As noted above, the device of the present invention may be configured to permit the wells to be filled by capillary action or by mechanical force.

The device of the present invention, which allows the simultaneous filling of all columns and all rows of a microtiter plate either sequentially or at the same time, is fabricated out of a suitable material (e.g., polystyrene, polycarbonate, etc.) that is compatible with biological reagents and is positioned over wells of the microtiter plate. Next, reagents are introduced into the filling ports (e.g., 24 and/or 16 filling ports) and the reagents are automatically dispersed to each of the metering chambers positioned above each of the microtiter plate wells (e.g., 384 metering chambers for 384 wells in a plate). The loaded device-microtiter plate stack is placed into a swinging bucket rotor of a standard low speed centrifuge and subjected to a brief spin at a force sufficient to drive the liquid from the individual metering chambers into each of the wells. After the centrifuge has halted, the device-microtiter plate stack is removed from the centrifuge, the stack is separated and the device is disposed of while the plate is then used for the next step in the assay process. Thus the labor set-up of the assay configuration described above for a 384 well plate would be reduced to 3 each 8-tip pipettor deliveries to load the column filling ports and 2 each 8-tip pipettor deliveries to load the row filling ports compared to the 96 total 8-tip pipettor deliveries using a manual approach. In addition, the use of the device consumes only 24 pipette tips while a manual approach would consume 384 pipette tips for a considerable cost savings, which is important in a high throughput clinical laboratory. The device and process described above could easily be applied to a 1536 well microtiter plate by one skilled in the art and would result in similar benefits as described for the 384 well plate. An added benefit of the device described herein, which dramatically reduces the number of pipetting steps, is the control of cross contamination by aerosols containing PCR amplicons. This is especially critical in the detection of low copy number representation of mutant alleles. During the introduction of liquids to the loading ports of the device, each of the 384 or 1536 wells is covered by the device and the combination of the covered wells and the reduction in the number of liquid transfer steps provides some decreased probability of PCR amplicon cross contamination between wells.

Since each row and column is independently addressable, one can conceive of many assay configurations that can be fulfilled by the same device by the judicious choice of how the loading ports are filled. Thus the same liquid can be applied to all 24 columns by 3 each 8-tip pipetting steps (no tip changes) and the same liquid can be applied to all 16 rows by 2 each 8-tip pipetting steps (no tip changes); 24 different components can be applied to each of the 24 rows by 3 each 8-tip pipetting steps (3 tip changes) and 16 different components can be applied to each of the 16 rows by 2 each 8-tip pipetting steps (2 tip changes). Many other filling configurations are possible to one skilled in the art. The dispersed liquid can be any biological liquid, e.g., a biological sample, reaction reagents such as, e.g., primers, probes, enzymes, reaction products, etc.

In one embodiment, a series of dispersion devices are available with a choice of fixed metering volumes, which anticipates particular high volume molecular biology applications such as might be found in a clinical diagnostics laboratory or a pharmaceutical development laboratory. In another embodiment, custom dispersion devices are made with user specified metering volumes for their specific applications.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

EXAMPLES

Prophetic Example 1

High Sensitivity Mutation Marker (When Present at 1% to 0.01%), Single Base Mutation, Small Insertion, and Small Deletion Mutations in Known Genes in Total Plasma cfDNA Overview of approach: This approach depends on the fidelity of three enzymes: (i) Taq polymerase to faithfully copy low-level copies of DNA in the initial sample, (ii) RNase H2 enzyme removing a blocking group on the upstream LDR primer, and (iii) Ligase in discriminating a match from mismatch on the 3' side of the upstream primer. The later is enhanced further by using an intentional mismatch or nucleotide analogue in the $2^{nd}$ or $3^{rd}$ base from the 3' end that slightly destabilizes hybridization of the 3' end if it is perfectly matched at the 3' end, but significantly destabilizes hybridization of the 3' end if it is mis-matched at the 3' end. Finally, kinetic approaches, such as altering the cycling times and conditions can enhance the discrimination between wild-type and mutant template. Once a ligation event has taken place, those products will be amplified in a subsequent real-time PCR amplification step, and thus this is the key discriminatory step.

For the initial PCR step, PCR primers containing universal tails that are partially identical are used at lower concentrations (10-50 nM). The identical region may vary from 8 to 11 bases or more. Thus, if any target-independent primer dimer formed, the incorrect product will form a hairpin that will inhibit further amplification. Further, the tails enhance subsequent binding of PCR primer to the correct amplicons.

Alternatively, the fidelity of amplification and reduction of false amplicons and primer dimers is achieved by using PCR primers at lower concentrations, but containing an RNA base, 4 additional bases and a blocking group on the 3' end. Only when the primer correctly hybridizes to its intended target will RNaseH2 cleave the RNA base, liberating a free 3'OH on the DNA primer. Even if a primer is accidentally activated on an incorrect target, on the next round, the bases downstream of the primer 3' end will not be perfect matches for the bases to be removed. This significantly lowers the chance of a second cleavage and extension. In short the efficiency of amplification of incorrect targets will not produce significant background. Further, the initial PCR amplification is followed by an LDR step, essentially nesting within the initial PCR product.

When starting with cfDNA, the average length is 160 bases, thus PCR primers should be pooled in two groups when tiling across a gene region (e.g., p53) such that each group amplifies fragments of about 100 bp, which are shifted with respect to each other by about 50 bases, such that one gets "tiling" across a given region.

To protect against carryover contamination, UNG is added to the reaction prior to polymerase activation, and the initial PCR amplification is performed with dUTP. The LDR probes are comprised of the natural bases, thus the LDR product is now resistant to UNG digestion in the second real-time PCR step. Note that the LDR products contain sequence tags or UniTaq sequences on their non-ligating ends, which are lacking in the target DNA, thus accidental carryover of LDR products does not result in large-scale amplification. Unlike with PCR, an initial LDR product is not a substrate for a second LDR reaction.

The most difficult case is for KRAS mutations, where 6 changes on codon 12 and 1 change on codon 13 are all spaced together. In general, for highest fidelity, the mismatch between mutant probe and wild-type sequence should at least be C:A for the last base, not G:T. Thus, one needs to run both upper-strand and lower-strand probes, or 2 ligation sets per PCR reaction. However, more than one mutation may be given the same UniTaq sequence, or fluorescence label with a TaqMan™ probe, since the aim is to find a mutation and not necessarily distinguish different mutations from each other.

Since the different probes will compete with each other in binding the (rare) mutant sequence, it is important to allow for all the probes to hybridize to the correct sequence. There will be 3 upstream and 1 downstream primers for the KRAS codon 12 $1s^t$ position mutations. False ligation of mutant LDR probes on wild-type target sequence may be further suppressed by using blocked upstream LDR probe with the wild-type sequence at the discriminating base, but lacking the appropriate tag sequence Probes are designed to avoid false ligation/false signal of mutant probes to normal sequence, but also for correct ligations to occur in the presence of the mutant sequence.

To summarize the levels of discrimination of the above approach using both PCR primers and LDR probes for detection of each mutation:

1. Use of PCR primers with universal tails, such that if any target-independent primer dimer formed, the incorrect product will form a hairpin that will inhibit further amplification.
2. Use of UNG to prevent carryover contamination of initial PCR reaction.
3. Use of nuclease activity of RNaseH2 to liberate an unblocked 3' OH on the upstream LDR probe, only when hybridized to target.
4. Use of 3' ligation fidelity of thermostable ligase on upstream LDR probe.
5. Use of mismatch or nucleotide analogue in the $2^{nd}$ or $3^{rd}$ base from the 3' end of upstream probe.
6. Use of UniTaq or tag primers to amplify LDR products for real-time PCR readout.
7. Use of UNG to prevent carryover contamination of real-time PCR reaction.

Detailed Protocol For Highly Sensitive Detection Of Mutation Marker (when Present at 1% to 0.01%), repeat mutations in known genes:

1.1.a. Incubate genomic DNA in the presence of UNG (37° C., 15-30 minutes, to prevent carryover), dUTP, and other dNTP's, AmpliTaq Gold, and gene-specific primers containing universal tails, such that if any target-independent primer dimer formed, the incorrect product will form a hairpin that will inhibit further amplification. This initial genomic DNA—PCR reaction mixture is suitable for multiplex PCR amplification in 12, 24, 48, or 96 individual wells (spatial multiplexing), or in a single well. Denature genomic DNA from plasma, inactivate UNG, and activate AmpliTaq Gold (94° C., 5-10 minute) and multiplex PCR amplify mutation-containing fragments for a limited number of cycles (94° C., 10 sec., 60° C. 30 sec., 72° C. 30 sec. for 12-20 cycles). The PCR primers are designed to have Tm values around 64-66° C., and will hybridize robustly, even when used at concentrations 10 to 50-fold below the norm for uniplex PCR (10 nM to 50 nM each primer). The cycles are limited to retain proportional balance of PCR products with respect to each other, while still amplifying low abundant sequences about 100,000 to 1,000,000—fold. After PCR amplification, Taq polymerase is inactivated (by incubating at 99° C. for 30 minutes.)

1.1.b. Add thermostable ligase (preferably from strain AK16D), RNaseH2, buffer supplement to optimized ligation conditions, and suitable upstream and downstream LDR probes (10 nM to 20 nM each, downstream probes may be synthesized with 5' phosphate, or kinased in bulk prior to reactions; upstream probes comprise an RNA base after the desired 3' end, 4 additional bases, and a blocking group to prevent target-independent ligation.) Upstream probes comprise of a 5' tag, such as UniAi followed by target-specific sequence with a C:A or G:T mismatch at the $3^{rd}$ or penultimate base, the mutation base at the 3' end, followed by an RNA base and 4 more DNA bases that matches the target, and a C3 spacer to block ligation (or subsequent extension by polymerase). The downstream probes comprise a 5' phosphorylated end, followed by target-specific sequence, and a 3' tag, such as UniCi'. Perform 20 cycles of LDR, (94° C., 10 sec., 60° C. 4-5 minutes). This will allow for ligation events to occur on the PCR products if mutant DNA is present.

1.1.c. Open tube/wells, dilute (10- to 100-fold) and distribute aliquots to wells for Real-Time PCR reactions, each well containing the appropriate TaqMan™ master mix with UNG for carryover prevention, and the following primers: UniCi and UniAi, and a TaqMan™ probe that covers the sequence across the ligation junction. Under such conditions, the tag sequences on the LDR probes would be UniAi and UniCi respectively, and the products would be of the form:
UniAi—Upstream Target-Mutation-Downstream Target—UniCi'

This approach avoids generating background signal off wild-type DNA in the second real-time PCR reaction. First, UNG will destroy the bottom strand of the initial PCR product, such that remaining upstream LDR probe has no target to hybridize to, and thus the 3' end remains blocked and will not extend. Second, any residual PCR primer from the initial PCR reaction will be unable to bind to either initial PCR products (destroyed by UNG) or LDR products (no binding sites) and thus the 3' end remains blocked and will not extend. Finally, the TaqMan™ probe now has 2 bases differing from wild-type sequence (the mutation base, and the base in the $3^{rd}$ position from the 3' end of the ligation junction), and thus will only hybridize at a temperature below 60° C., but now the upstream PCR primer will have hybridized first, and consequently extended, thus preventing the TaqMan™ probe from hybridizing and generating signal from the 5'-3' activity of the Taq polymerase.

A second assay design is based on an initial multiplexed PCR amplification followed by distribution and capture of PCR amplified targets on the wells of a microtiter plate. A single cycle of LDR enables capture of LDR products on the correct targets on the solid support, while mis-ligations are washed away. The LDR products are quantified, either through LDR-FRET, real-time PCR, or other reporter systems.

For amplifying cfDNA for mutation detection, PCR primers containing universal tails are used. The gene-specific primers are used at low concentrations (10 to 50 nM) and contain universal tails that are partially identical. Thus, if there is any target-independent primer dimer formed, the product will form a hairpin that will inhibit further amplification. To maximize the ability to detect very low abundance mutations, after making a master mix containing all the components, the reaction mixture is distributed into 12, 24, 48, or 96 independent wells. Since a single molecule (with a mutation) can only be distributed into a given well, the process will effectively enrich the mutation-containing molecule compared to the normal wild-type DNA, and thus significantly improve signal-to-noise. One approach is to use a two-step amplification, wherein the initial amplification uses gene-specific primers with universal tails, and the second amplification uses universal primers to append a biotin group to a specific product strand. The initial amplification (with low PCR primer concentration) will still be quantitative, provided it is limited to about 8-20 cycles. The amplification products are then diluted into two new wells for each of the original wells, each containing the two universal primers (at higher concentrations of 0.5-1 pmoles), with one or the other biotinylated in the respective well. Amplification is now continued for another 8-29 cycles, for a total of about 15-40 cycles. As an optional step, the products may be separated (by electrophoresis or size) from unused primers.

Alternatively, products may be amplified in a single amplification reaction by adding the universal primers to the initial amplification well, where only one universal primer is biotinylated. Alternatively, biotinylated gene-specific primers may be used directly in a single amplification step. Only when it is prudent to design LDR probes against both the top and bottom strand (i.e. to maximize LDR discrimination of mutation) will it be necessary to capture both forward and reverse strand of a given amplicon. This may be achieved by using mixes of each primer at 50% biotinylation in the same reaction, or at 100% biotinylation in separate reactions. As long as the biotinylated products remain separated during the capture on the solid support, they may both be in the same amplification reaction. However, if the PCR product strands rehybridize after capture, they may need to be captured on separate addresses on the solid support. This spatial separation may be needed to assure there is sufficient single-stranded PCR product available for identifying mutations by subsequent LDR detection.

With cfDNA, fragment length is biologically limited to about 160 bp. Thus, in order to cover common hot-spot mutations across a larger region, primer sets will be designed to generate overlapping fragments. As such, the primers would be distributed between an "A" and "B" pool, doubling the number of wells mentioned above. With DNA isolated from CTC's exon size fragments may often be used, thus mitigating the need for two amplicon pools. Some fragments amplify more slowly than others. This problem may be overcome by including an additional multiplexed reaction with a few more amplification cycles.

FIG. 38 illustrates mutation detection on genomic or cfDNA using the basic PCR-LDR-q PCR detection protocol with carryover prevention. Products are detected using TaqMan™ probes designed across the ligation junction sequence.

FIG. 39 illustrates a variation of FIG. 38, where the PCR products are distributed (spatial multiplexing), and are captured on a solid support. The PCR primers contain universal tails to eliminate primer dimer formation, and to allow for amplification with universal primers, one of which contains a biotin, allowing for capture of products in streptavidin-coated wells. Ligation probes are hybridized to target and only form product when there is perfect complementarity at the ligation junction. Unreacted ligation probes, or target-independent ligation products are then washed away. LDR probes are designed to contain short complementary sequences that only hybridize to each other when ligated together, generating FRET signal suitable for detection.

FIG. 40 illustrates a variation of FIG. 38, where the initial gene-specific PCR primers contain an RNA base, 4 additional bases and a blocking group on the 3' end. These gene-specific primers are unblocked from the end by RNaseH2 only when hybridized to the target, liberating a 3'OH end suitable for polymerase extension.

FIG. 41 illustrates a variation of FIG. 38, where the initial gene-specific PCR primers contain identical 8-11 base tails to prevent primer dimers. The upstream and downstream LDR probes contain UniAi and UniCi' primer specific portions respectively. Further, the upstream mutation-specific LDR probes contain the mutation base at the 3' end, followed by an RNA base and 4 more DNA bases that matches the target, and a C3 spacer to block ligation (or subsequent extension by polymerase). Only in the presence of RNaseH2 and when hybridized to the correct target will the upstream blocking group be removed, liberating a 3'OH end suitable for ligation. In this illustration, the upstream LDR probe complementary to wild-type DNA also contains a blocking group, but no RNA base or 5' tag. This probe further enhances ligation specificity in discriminating mutant from wild-type target.

FIG. 42 illustrates a variation of FIG. 41, where the PCR products are distributed (spatial multiplexing), and are captured on a solid support. The PCR primers contain universal tails to eliminate primer dimer formation, and the LDR probes are designed to contain short complementary sequences that only hybridize to each other when ligated together, generating FRET signal suitable for detection.

FIG. 43 illustrates a variation of FIG. 42, where the 5' side of the downstream LDR probe contains a base the same as the 3' discriminating base on the upstream probe, said base removed by the 5' to 3' nuclease activity of Fen nuclease or Taq polymerase to liberate a 5' phosphate suitable for a subsequent ligation. The nuclease should only cleave when the downstream probe is hybridized to mutant target. Both the upstream and downstream mutation-specific LDR probes contain short complementary sequences that only hybridize to each other when ligated together, generating FRET signal suitable for detection. In this illustration, the upstream LDR probe complementary to wild-type DNA does not contain a complementary sequence, and would not generate a FRET signal even if ligated to a cleaved downstream probe.

FIG. 44 illustrates a variation of FIG. 43, where the initial gene-specific PCR primers contain identical 8-11 base tails to prevent primer dimers. The upstream and downstream LDR probes contain UniTaq Ai and UniTaq Bi'-UniTaq Ci' primer specific and sequence tag portions. After ligation, the products are diluted and distributed into wells containing UniTaq-specific primers of the format UniTaq Ci and F1-UniTaq Bi—Q—UniTaq Ai. (where F1 is a fluorescent dye that is quenched by Quencher Q). The product strand formed by the fluorescently labeled primer will hairpin, such that the UniTaq Bi sequence pairs with the UniTaq Bi' sequence. When UniTaq Primer Ci binds to the UniTaq Ci' sequence, the 5'→3' exonuclease activity of polymerase digests the UniTaq Bi sequence, liberating the F1 fluorescent dye, and generating signal detected by a real-time PCR instrument.

FIG. 145 illustrates a variation of FIG. 41, where the PCR products are selectively amplified using mutation-selective upstream primers and locus-specific downstream primers. Upon target-specific hybridization, RNaseH removes the mutant-specific RNA base to liberate a 3'OH group suitable for polymerase extension. RNaseH will preferentially cleave the RNA base when it is perfectly matched to mutant DNA, but will be less likely to cleave the RNA base when hybridized to wild-type DNA. This occurs during every cycle of the PCR amplification, thus enriching for amplification of specific mutant targets. Optional primers with wild-type sequence lack the RNA base and remain blocked, thus further reducing amplification of wild-type sequence. After the initial PCR enrichment step, this procedure continues with LDR-q PCR detection protocol with carryover prevention. Products are detected using TaqMan™ probes designed across the ligation junction sequence.

FIG. 146 illustrates a variation of FIG. 145, where the upstream and downstream LDR probes contain UniTaq Ai and UniTaq Bi'-UniTaq Ci' primer specific and sequence tag portions. After ligation, the products are diluted and distributed into wells containing UniTaq-specific primers of the format UniTaq Ci and F1-UniTaq Bi—Q—UniTaq Ai, and signal generated in the PCR is detected by a real-time PCR instrument.

FIG. 147 illustrates a variation of FIG. 145, where the PCR products are captured on a solid support. The LDR probes are designed to contain short complementary sequences that only hybridize to each other when ligated together, generating FRET signal suitable for detection.

FIG. 148 illustrates a variation of FIG. 41, where the PCR products are selectively amplified using locus-specific upstream and downstream primers. Upon target-specific hybridization, RNaseH removes the RNA base to liberate a 3'OH group suitable for polymerase extension. A blocking LNA or PNA probe comprising wild-type sequence that partially overlaps with the upstream PCR primer will preferentially compete in binding to wild-type sequence over the upstream primer, but not as much to mutant DNA, and thus suppresses amplification of wild-type DNA during each round of PCR. After the initial PCR enrichment step, this procedure continues with LDR-qPCR detection protocol with carryover prevention. Products are detected using TaqMan™ probes designed across the ligation junction sequence.

FIG. 149 illustrates a variation of FIG. 148, where the upstream and downstream LDR probes contain UniTaq Ai and UniTaq Bi'-UniTaq Ci' primer specific and sequence tag portions. After ligation, the products are diluted and distributed into wells containing UniTaq-specific primers of the format UniTaq Ci and F1-UniTaq Bi—Q—UniTaq Ai, and signal generated in the PCR is detected by a real-time PCR instrument.

FIG. 150 illustrates a variation of FIG. 148, where the PCR products are captured on a solid support. The LDR probes are designed to contain short complementary sequences that only hybridize to each other when ligated together, generating FRET signal suitable for detection.

FIG. 154 illustrates another variation where the PCR products are selectively amplified using locus-specific upstream primers that also comprise 5' portion sequences complementary to wild-type sequence of the top strand allowing for formation of loop-hairpins after extension, and locus-specific downstream primers. Upon target-specific hybridization, RNaseH removes the RNA base to liberate a 3'OH group suitable for polymerase extension. PCR is performed with a polymerase lacking 5' nuclease, 3' nuclease, and strand-displacement activity. (i) Denaturation of wild-type bottom strand results in the formation of a loop-hairpin with perfect match at 3' end, which is extended by polymerase to form a longer hairpin region. This does not denature at 72° C. and prevents upstream primer from generating a full-length top strand. (ii) Denaturation of mutant bottom strand results in the formation of a loop-hairpin with mismatch at 3' end. This is not extended by polymerase, and thus denatures at 72° C., enabling upstream primer to generate full-length top strand. (iii) Denaturation of top strand results in hairpin on 5' side, which denatures during the extend step of PCR (72° C.), allowing polymerase to generate full-length bottom strand. vThe difference in hairpin extension preference of upstream primers with (i) wild-type and (ii) mutant template results in preferential amplification of mutant DNA. This selection against amplification of wild-type DNA occurs during every cycle of the PCR, thus enriching for mutant targets. After the initial PCR enrichment step, this procedure continues with LDR-q PCR detection protocol with carryover prevention. Products are detected using TaqMan™ probes designed across the ligation junction sequence.

FIG. 155 illustrates a variation of FIG. 154, where the PCR products are captured on a solid support. The LDR probes are designed to contain short complementary sequences that only hybridize to each other when ligated together, generating FRET signal suitable for detection.

As an example of quantitative mutation enumeration using spatial multiplexing into 48 wells, consider total cfDNA in target sample that is undergoing the initial PCR amplification is about 10,000 genome equivalents, with 12 of those containing a mutation in KRAS codon 12. The initial distribution into 48 wells results in about 200 genome equivalents per well, with 1 well containing 2 mutant copies, 10 wells containing 1 mutant copy, and the remaining 37 wells containing no mutant copies. After about 20 rounds of PCR amplification, (for simplicity in calculation, say 99% efficiency of amplification, or about 960,000-fold—complete efficiency would yield 1,046,576-fold amplification), then the total number of copies for the mutation will be 960,000, and for the wild-type will be 192 million. Assuming a ligation efficiency of 50% on mutant DNA per cycle, times 20 cycles, and for ligation on wild-type DNA, a ligation fidelity of 1,000-fold, then the mutant DNA would yield 9.6 million molecules, while wild-type DNA would yield 1.9 million molecules. Spatial distribution into 48 wells would yield 200,000 and 40,000 molecules of LDR product for mutant and wild-type respectively. After addition of tag primers and TaqMan™ probe with real-time PCR, for simplicity in the calculations, the above LDR products convert to Ct values of 10 and 12.5 respectively. For any mutation-derived signal to be scored as positive, it would need to appear in at least 2 or 3 wells, and also easily distinguished from (low-level) signal arising from misligation of probes on wild-type DNA. Such mis-ligation to wild-type DNA may be even further suppressed by adding a wild-type upstream LDR probe, which would lack the fluorescent reporter, such that ligation products would be silent with no signal. The likely Poisson distribution (see e.g., FIG. 31) shows, the negative sample will have a range of distribution of (wells: molecules) (38:0; 10:1; 1:2) for 12 molecules These numbers are sufficiently different that TaqMan™ readout will give quantitative enumeration of signal, allowing us to assign a score of 0, 1, or 2 original molecules per well (represented by Ct values of 12.5, 10, and 9 respectively), for a total of 12 mutant KRAS molecules in the sample. In the case that the signal is only able to distinguish between 0 and 1 or more mutant molecules, given an initial 12 or fewer molecules enumerated in a minimum of 24 wells, the initial number of mutant copies can be enumerated.

When using LDR-FRET detection, after distribution into the individual 48 wells for solid-phase capture, assuming only 50% efficiency of capturing biotinylated products, each well will have captured 10,000 mutant and 2 million wild-type KRAS amplicons respectively. Assuming a ligation efficiency of only 50% on mutant template, at least 5,000 LDR products should be captured on the solid support if a single mutant molecule was originally present. If two mutant molecules were in the original well, then approximately 10,000 LDR products should be captured. For the wells with only wild-type product, assuming a ligation fidelity of 1:1,000 (mutant upstream LDR probe misligated on wild-type DNA), only 1,000 LDR products would be captured. For any mutation-derived signal to be scored as positive, it would need to appear in at least 2 or 3 wells, and also easily distinguished from (low-level) signal arising from misligation of probes on wild-type DNA. Such mis-ligation to wild-type DNA may be even further suppressed by adding a wild-type upstream LDR probe, which would lack the fluorescent reporter, such that ligation products would be silent with no signal. These numbers are sufficiently different that LDR-FRET readout will give quantitative enumeration of signal, allowing assignment of a score of 0, 1, or 2 original molecules per well (represented as LDR-FRET signals of about 1,000, 5,000, and 10,000, respectively), for a total of 12 mutant KRAS molecules in the sample. In the case that the signal is only able to distinguish between 0 and 1 or more mutant molecules, given an initial 12 or fewer molecules enumerated in a minimum of 24 wells, the initial number of mutant copies can be enumerated.

When using UniTaq containing LDR probes, they are of the following format: Upstream probes comprise of a 5' sequence tag, such as UniTaqAi, containing a primer specific portion, followed by target-specific sequence with a C:A or G:T mismatch at the $3^{rd}$ or penultimate base, the mutation base at the 3' end, followed by an RNA base and 4 more DNA bases that matches the target, and a C3 spacer-blocking group. The downstream primers comprise a 5' phosphorylated end, followed by target-specific sequence, and a 3' sequence tag, such as UniTaq Bi'—UniCi', also containing a primer specific portion.

The LDR products may be detected using UniTaq-specific primers of the format UniTaq Ci and F1-UniTaq Bi—Q—UniTaq Ai (where F1 is a fluorescent dye that is quenched by Quencher Q). Under these conditions, the following product will form: F1-UniTaq Bi—Q—UniTaq Ai—Upstream Target-Mutation-Downstream Target—UniTaq Bi'—UniTaq Ci'

This construct will hairpin, such that the UniTaq Bi sequence pairs with the UniTaq Bi' sequence. When UniTaq Primer Ci binds to the UniTaq Ci' sequence, the 5'→3' exonuclease activity of polymerase digests the UniTaq Bi sequence, liberating the F1 fluorescent dye.

The initial PCR primers or upstream LDR probes may also contain an RNA base, 4 additional bases and a blocking group (e.g. C3-spacer) on the 3' end. RNaseH2 is then added to the reaction. This assures that no template independent products are formed.

The downstream LDR probes may also be phosphorylated during the ligation reaction using thermophilic phage kinase (derived from bacteriophage RM378 that infects *Rhodothermus marinus*). Under these conditions the denaturation step in the LDR should be as short as possible (i.e., 94° C. or even lower for 1 second), as the thermophilic kinase is not fully thermostable—or just preincubate at 65° C. for 15 minute to achieve full primer phosphorylation. Alternatively, the 5' side of the downstream LDR probe contains a base the same as the 3' discriminating base on the upstream probe, said base removed by the 5' to 3' nuclease activity of Fen nuclease or Taq polymerase to liberate a 5' phosphate suitable for a subsequent ligation.

Prophetic Example 2

High Sensitivity Methylation Marker for Promoter Hypermethylation (When Present at 1% to 0.01%) in Total Plasma DNA. (e.g., p16 and Other Tumor Suppressor Genes, CpG "Islands" Also, Sept9, Vimentin, etc.)

Overview of approach v1: Isolated genomic DNA, or methyl enriched DNA is treated with a cocktail of methyl sensitive enzymes whose recognition elements comprise only or mostly C and G bases (e.g., Bsh1236I=CG^CG; HinP1I=G^CGC; AciI=CACGC or G^CGG; and Hpy99I=CGWCGA). Judiciously chosen PCR primers amplify uncut DNA fragments of about 100-130 bp. The fragment should have at least 2-3 methyl sensitive enzyme sites, such that cleavage would cause these fragments to dissipate. These sites are chosen such that carryover prevention may work at two levels: (i) the sites are still cleavable in DNA containing incorporated dUTP, allowing for use of UNG for carryover prevention and (ii) after amplification, the sites are unmethylated, such that products would readily be recleaved should they carryover to another reaction. Subsequent to the initial PCR amplification, LDR and UniTaq reactions with carryover protection are performed as described above. Alternatively, LDR and TaqMan™, or straight TaqMan™ reactions may be performed to identify and quantify relative amounts of methylated DNA in the initial sample.

To summarize the levels of discrimination of the above approach using both PCR primers and LDR probes for detection of low-abundance methylation:
1. Use of methylation sensitive restriction enzymes to cleave target when not methylated.
2. Use of PCR primers with universal tails, such that if any target-independent primer dimer formed, the incorrect product will form a hairpin that will inhibit further amplification.
3. Use of UNG and methylation sensitive restriction enzymes to prevent carryover contamination of initial PCR reaction.
4. Use of 3' ligation fidelity of thermostable ligase on upstream LDR probe.
5. Use of UniTaq or tag primers to amplify LDR products for real-time PCR readout.
6. Use of UNG to prevent carryover contamination of real-time PCR reaction.

Detailed Protocol for Highly Sensitive Detection of Promoter Methylation v1:

2.1.a. Incubate genomic DNA, cfDNA, or methyl enriched DNA in the presence of Bsh1236I (CG^CG) and HinP1I (GACGC), and UNG (37° C., 30-60 minutes) to completely digest unmethylated DNA and prevent carryover. Add buffer supplement to optimize multiplexed PCR amplification, dUTP, and other dNTP's, AmpliTaq Gold, and gene-specific primers containing universal tails, such that if any target-independent primer dimer formed, the incorrect product will form a hairpin that will inhibit further amplification. This initial genomic DNA—PCR reaction mixture is suitable for multiplex PCR amplification in 12, 24, 48, or 96 individual wells (spatial multiplexing), or in a single well. Denature digested genomic DNA, inactivate UNG and restriction endonucleases, and activate AmpliTaq Gold (94° C., 5-10 minute) and multiplex PCR amplify mutation containing fragments for a limited number of cycles (94° C., 10 sec., 60° C. 30 sec., 72° C. 30 sec. for 16-20 cycles). The PCR primers are designed to have Tm values around 64-66° C., and will hybridize robustly, even when used at concentrations 10 to 50-fold below the norm for uniplex PCR (10 nM to 50 nM each primer). The cycles are limited to retain relative balance of PCR products with respect to each other, while still amplifying low abundant sequences about 100,000 to 1,000,000-fold. After PCR amplification, Taq polymerase is inactivated (by incubating at 99° C. for 30 minutes.)

2.1.b. Add thermostable ligase (preferably from strain AK16D), buffer supplement to optimized ligation conditions, and suitable upstream and downstream LDR probes (10 nM to 20 nM each, downstream primers may be synthesized with 5' phosphate, or kinased in bulk prior to reactions. Upstream probes comprise of a 5' tag, such as UniAi followed by target-specific sequence. The downstream probes comprise a 5' phosphorylated end, followed by target-specific sequence, and a 3' tag, such as UniCi'. Perform 20 cycles of LDR, (94° C., 10 sec., 60° C. 4-5 minutes). This will allow for ligation events to occur on the PCR products if methylated DNA was present in the original sample.

2.1.c. Open tube/wells, dilute (10- to 100-fold) and distribute aliquots to wells for Real-Time PCR reactions, each well containing the appropriate TaqMan™ master mix with UNG for carryover prevention, and the following primers:

UniCi and UniAi, and a TaqMan™ probe that covers the sequence across the ligation junction. Under such conditions, the tag sequences on the LDR primers would be UniAi and UniCi respectively, and the products would be of the form:

UniAi—Upstream Target—Methylation Region—Downstream Target—UniCi'

Two or three fragments in a single promoter region may be interrogated at the same time using the same fluorescent dye. The number of methylated fragments per promoter may be determined by total signal for that dye. When using spatial multiplexing, the sample is distributed to 12, 24, 48, or 96 individual wells prior to the 37° C. incubation step (but after addition of enzymes). In this manner, methylation across a promoter region of a given molecule of DNA may be distinguished from methylation of three different regions on three different molecules.

Since there is no need to distinguish between a wild-type and a mutant signal, the LDR step may be eliminated, with the initial PCR reaction followed directly by a secondary real-time PCR (e.g., TaqMan™) reaction. The disadvantage of going straight to a secondary PCR is that UNG carryover protection would not be used since the initial PCR reaction products have incorporated dUTP, and thus would be destroyed by UNG. One approach to address this problem would be to use standard dNTP's in the initial PCR, and rely solely on the restriction endonucleases to destroy any potential carryover from the initial or subsequent PCR reactions, since these products are now unmethylated.

A second assay design is based on an initial restriction digestion, then multiplexed PCR amplification followed by distribution and capture of PCR amplified targets on the wells of a microtiter plate. A single cycle of LDR enables capture of LDR products on the correct targets on the solid support, while mis-ligations are washed away. The LDR products are quantified, either through LDR-FRET (qLDR), real-time PCR (qPCR), or other reporter systems.

FIG. 45 illustrates methylation detection on genomic or cfDNA using the basic restriction digestion, PCR-LDR-qPCR detection protocol with carryover prevention. Products are detected using TaqMan™ probes designed across the ligation junction sequence.

FIG. 46 illustrates a variation of FIG. 45, where the initial gene-specific PCR primers contain identical 8-11 base tails to prevent primer dimers. The upstream and downstream LDR probes contain UniTaq Ai and UniTaq Bi'-UniTaq Ci' tags respectively. After ligation, the products are diluted and distributed into wells containing UniTaq-specific primers of the format UniTaq Ci and F1-UniTaq Bi—Q—UniTaq Ai. (where F1 is a fluorescent dye that is quenched by Quencher Q). The product strand formed by the fluorescently labeled primer will hairpin, such that the UniTaq Bi sequence pairs with the UniTaq Bi' sequence. When UniTaq Primer Ci binds to the UniTaq Ci' sequence, the 5'→3' exonuclease activity of polymerase digests the UniTaq Bi sequence, liberating the F1 fluorescent dye, and generating signal detected by a real-time PCR instrument.

FIG. 47 illustrates a variation of FIG. 45, where the PCR products are distributed (spatial multiplexing), and are captured on a solid support. The PCR primers contain universal tails to eliminate primer dimer formation, and to allow for amplification with universal primers, one of which contains a biotin, allowing for capture of products in streptavidin-coated wells. Ligation probes are hybridized to target and only form product when there is perfect complementarity at the ligation junction. Unreacted ligation probes, or target-independent ligation products are then washed away. LDR probes are designed to contain short complementary sequences that only hybridize to each other when ligated together, generating FRET signal suitable for detection.

As an example of quantitative methylation enumeration using spatial multiplexing into 48 wells, consider a sample of cfDNA with 12 genome equivalents of tumor DNA, used to score for methylation on a marker on chromosome 20, which is amplified to about 4 copies per cancer cell. This would give us 48 copies of methylated DNA that is resistant to digestion. The unmethylated DNA is fragmented by the restriction enzyme, but a minority of unmethylated DNA survives, ~12 copies, for a total of 60 copies. Also, some age related methylation may occur, allow that to range to 12 copies. Accordingly, samples with no tumor-specific methylation may have a signal in the range of 12-24 copies, while those with the marker on chromosome 20 methylated in all 4 chromosomes may have a total in the range of 60-72 copies. If one looks at the likely Poisson distribution (see FIGS. 31 and 32, the negative sample will have a range of distribution of (wells: molecules) (38:0; 10:1; 1:2) for 12 molecules to (29:0; 15:1; 4:2; 1:3) for 24 molecules, while the positive samples will have a range of distribution of (14:0; 17:1; 11:2; 4:3; 1:4) for 60 molecules to (11:0; 16:1; 12:2; 6:3; 2:4; 1:5) for 72 molecules. The accuracy in distinguishing LDR signal arising from 2 molecules (e.g., for LDR-TaqMan™, a Ct value of 9, or for LDR-FRET detection 10,000 LDR products) from 3 molecules (e.g., for LDR-TaqMan™, a Ct value of 8.5, or for LDR-FRET 15,000 molecules) will depend on the standard deviation of the LDR signal from well to well. Nevertheless, even if LDR signal is variable enough that distinguishing the higher level signals becomes too difficult, as long as the signal is clean enough to distinguish 0, 1, and 2 initial molecules (represented as LDR-TaqMan™ Ct values of 12.5, 10, and 9, or LDR-FRET signals of about 1,000, 5,000, and 10,000, respectively), this approach will have no difficulty distinguishing and enumerating methylated signal arising from those individuals with authentic circulating tumor DNA, from those with age-related (but not cancerous) methylated signal in normal blood. In the case that the Ct or fluorescent signal is only able to distinguish 0 from 1 or more initial methylated molecules, given an initial 12 or fewer genome equivalents of tumor DNA, and 60 or more genome equivalents of methylated DNA for the particular region (e.g., chromsome 20) enumerated in a minimum of 48 wells, the approach should distinguish and enumerate methylated signal arising from those individuals with authentic circulating tumor DNA from those with age-related (but not cancerous) methylated signal in normal blood.

When using UniTaq containing LDR probes, they are of the following format: Upstream probes comprise of a 5' tag, such as UniTaqAi followed by target-specific sequence. The downstream probes comprise a 5' phosphorylated end, followed by target-specific sequence, and a 3' tag, such as UniTaq Bi'—UniTaq Ci'.

The LDR products may be detected using UniTaq-specific primers of the format UniTaq Ci and F1-UniTaq Bi—Q—UniTaq Ai. (where F1 is a fluorescent dye that is quenched by Quencher Q). Under these conditions, the following product will form:

F1-UniTaq Bi—Q—UniTaq Ai—Upstream Target—Methylation Region —Downstream Target—UniTaq Bi'—UniTaq Ci'

This construct will hairpin, such that the UniTaq Bi sequence pairs with the UniTaq Bi' sequence. When UniTaq Primer Ci binds to the UniTaq Ci' sequence, the 5'→3' exonuclease activity of polymerase digests the UniTaq Bi sequence, liberating the F1 fluorescent dye.

The upstream LDR probes and PCR primers may also contain an RNA base, 4 additional bases and a blocking group on the 3' end. RNaseH2 is then added to the reaction. This assures that no template independent products are formed. In some designs, a methyl sensitive restriction site is downstream of the 3' end of the PCR primer, such that cleavage with the enzyme removes the binding sequence for the 4 additional bases, and cleavage of the RNA base by RNaseH2 is significantly reduced.

The downstream LDR probes may also be phosphorylated during the ligation reaction using thermophilic phage kinase (derived from bacteriophage RM378 that infects *Rhodothermus marinus*). Under these conditions the denaturation step in the LDR should be as short as possible (e.g., 94° C. or even lower for 1 second), as the thermophilic kinase is not fully thermostable—or just preincubate at 65° C. for 15 minute to achieve full primer phosphorylation. Alternatively, the 5' side of the downstream probe may contain a base the same as the 3' discriminating base on the upstream probe, said base removed by the 5' to 3' nuclease activity of Fen nuclease or Taq polymerase to liberate a 5' phosphate suitable for a subsequent ligation.

Overview of approach v2: As above, isolated genomic DNA, or methyl enriched DNA is treated with a cocktail of methyl sensitive enzymes (HinP1I, Bsh1236I, AciI, Hpy99I, and HpyCH4IV), as well as by methyl insensitive enzymes (HaeIII and MspI). The idea is to generate a fragment of DNA of approximately 40 bases or more, wherein the 5' phosphate of the fragment originated from a methyl insensitive enzyme. The fragment should have at least 2-3 methyl sensitive enzyme sites, such that cleavage would cause these fragments to dissipate. One strand of the genomic fragment is then hybridized onto an artificial template containing a hairpin, with and upstream region, which is unrelated to genomic DNA, and can ligate to the genomic fragment at the 5' phosphate. The single-stranded portion of the hairpin also contains a region complementary to the target containing one or more methyl-sensitive restriction enzyme sites. The same methyl sensitive enzymes are then added back in, and if an unmethylated target strand accidentally escaped the initial restriction digestion step, it will be cleaved in this second step. A downstream oligonucleotide is added that hybridizes to the genomic fragment, downstream of where it hybridized to the template strand. When extending the locus-specific primer, the 5→3' exonuclease activity of polymerase destroys the template portion of the ligated oligo, creating a product containing both upstream and downstream tags and suitable for amplification. Unligated hairpin oligo will extend on itself and not amplify further. Both upstream and downstream oligonucleotides have optional Universal sequences, as well as UniTaq specific sequences, allowing for simultaneous "preamplification" for 12-20 cycles, prior to opening tube, and dividing into the appropriate UniTaq or TaqMan™ assays. For each promoter region, there will be three positions of interrogation, such that the signal appears (Ct value indicating relative quantity of methylated sequence) as well as total signal strength (i.e. =1, 2, or 3 sites methylated for that promoter). This approach is also compatible with using UNG to provide carryover protection, and RNaseH2 to provide extra fidelity during the PCR amplification steps.

To summarize the levels of discrimination of the above approach for detection of low-abundance methylation:

1. Use of methylation insensitive restriction enzyme to generate a unique 5' phosphate on double-stranded target DNA.
2. Use of methylation sensitive restriction enzymes to cleave double-stranded target when not methylated.
3. Use of UNG and methylation sensitive restriction enzymes to prevent carryover contamination of initial PCR reaction.
4. Use of ligation fidelity of thermostable ligase to ligate correct tag to target strand.
5. Use of locus specific primer and polymerase to amplify ligated target strands.
6. Use of nuclease activity of RNaseH2 to liberate an unblocked 3' OH on the PCR primers, only when hybridized to target.
7. Use of sequences on the 3' end of tag oligos, such that when they are not ligated, form hairpins and extend on themselves to form products that do not amplify.
8. Use of UniTaq or tag primers to amplify PCR or LDR products for real-time PCR readout.

Detailed Protocol for Highly Sensitive Detection of Promoter Methylation v2:

2.2a. Prepare mix containing restriction enzymes, artificial hairpin templates (see below), and thermostable ligase. Cleave isolated genomic DNA, or methyl enriched DNA with a cocktail of methyl sensitive enzymes (e.g. HinP1I, Bsh1236I, AciI, Hpy99I, and HpyCH4IV), as well as by methyl insensitive enzymes (HaeIII and MspI). Generate fragments of approximately 40 bases or more that have a 5' phosphate from a HaeIII or MspI site, and at least 3 methyl sensitive sites (that are not cleaved because they were methylated). Preferably, generate three such fragments per promoter. Heat-kill endonucleases (65° C. for 15 minutes) and denature DNA (94° C. 1 minute). Artificial templates contain upstream primer region (optional 5' Universal Primer U1Pm, followed by UniTaq Ai) as well as a region complementary to UniTaq Ai, and a region complementary to target DNA with Tm of about 72° C., and overlap with at least one methyl-sensitive restriction site). Incubate at 60° C. to allow for hybridization and ligation of hairpin oligonucleotides to 5' phosphate of target DNA if and only if it was methylated and hybridized to the correct template. This initial genomic DNA—ligation product mixture is suitable for multiplex PCR amplification in 12, 24, 48, or 96 individual wells (spatial multiplexing), or in a single well.

2.2b. Add: The methyl-sensitive restriction enzymes (incubate at 37° C. for 30 minutes), as well as Hot-start Taq polymerase, dNTPs, UniTaqAi, and downstream primers (containing 5' Universal Primer U2, followed by UniTaq Bi, followed by target locus-specific sequence complementary to the target fragment with sequence that is just downstream of the artificial template strand sequence). When extending the locus-specific primer, the 5'→3' exonuclease activity of polymerase destroys the template portion of the ligated oligonucleotide, creating a product containing both upstream and downstream tags and suitable for amplification. Unligated hairpin oligo will extend on itself and not amplify further. Ideally, the universal primer tails U1Pm and U2 on the LDR and PCR compound primers are slightly shorter than Universal primers U1 and U2. This allows initial universal amplification at a lower cycling temperature (e.g., 55° C. annealing) followed by higher cycling temperature (e.g., 65° C. annealing) such that the universal primers U1Pm and U2 bind preferentially to the desired product (compared to composite primers binding to incorrect products). In the preferred variation to minimize target independent amplifications, the downstream PCR primers contain an RNA base and a blocked 3' end, which is liberated by an RNase-H that cleaves the RNA base when the primer is hybridized to its target. These conditions amplify products of the sequence:

Univ. Primer U1Pm—UniTaq Ai —Methylation Region—UniTaq Bi'—Univ. Primer U2'

Or simply of the sequence:

UniTaq Ai—Methylation Region—UniTaq Ci'

2.2c. Open tube, dilute 10- to 100-fold and distribute aliquots to TaqMan™ wells, each well containing the following primers: Universal Primer U2 and UniTaq specific primers of the format F1-UniTaq Bi—Q—UniTaq Ai. (where F1 is a fluorescent dye that is quenched by Quencher Q). Under these conditions, the following product will form:

F1-UniTaq Bi—Q—UniTaq Ai—Methylation Region—UniTaq Bi'—Univ.Primer U2'

This construct will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

For products of the sequence UniTaq Ai—Target DNA—UniTaq Ci', they may be detected using nested PCR primers, with the optional RNaseH2 cleavage to remove blocking groups, and an internal TaqMan™ probe.

As a control for the total amount of DNA present, one can choose a nearby target fragment where the 5' phosphate is generated by a methyl insensitive enzyme (HaeIII or MspI), and the rest of the fragment is lacking in methyl sensitive enzyme sites. The upstream oligonucleotide that is ligated to the target fragment is a mixture of two oligos: (i) An oligonucleotide present at 1 in 100 with the correct UniTaq specific sequence, and (ii) an oligonucleotide present at 99 in 100 with a sequence that has about 8-10 bases complementary to its 3' end. After the ligation event and destroying template with UNG and AP endonuclease, the universal primers are added for PCR amplification. The ligation product containing the UniTaq sequences amplifies and will give a signal equivalent to 1 in 100 of the original template. The majority ligation product lacks the universal sequence on the 5' end, and does not amplify exponentially. Unligated upstream probe will form a hairpin back on itself, and extend its own 3' sequence on itself, taking it out of contention for becoming part of another PCR amplicon. Alternatively or in addition, the control may use a different ratio of the two oligonucleotides, for example 1:10 or 1:1,000 to allow for accurate comparisons to low-levels of the methylated DNA present at the promoter site of interest.

An alternative control uses a mixture of two oligos: (i) A hairpin oligonucleotide present at 1 in 100 with the correct UniTaq specific sequence, and (ii) A hairpin oligonucleotide present at 99 in 100 without the UniTaq sequence. After the ligation event, the universal primers are added for PCR amplification. When extending the locus-specific primer, the 5'→3' exonuclease activity of polymerase destroys the template portion of the ligated oligo, creating a product containing both upstream and downstream tags and suitable for amplification. Unligated hairpin oligo will extend on itself and not amplify further. The ligation product containing the UniTaq sequences amplifies and will give a signal equivalent to 1 in 100 of the original template. The majority ligation product lacks the universal sequence on the 5' end, and does not amplify exponentially.

FIG. 48 illustrates methylation detection on genomic or cfDNA using the restriction digestion, hairpin ligation, locus-specific extension, with PCR amplification protocol with carryover prevention. Products are detected using nested PCR primers with TaqMan™ probes designed across the methylated sequence.

FIG. 49 illustrates a variation of FIG. 48, where the initial gene-specific PCR primers contain tags UniAi and UniCi. The products are diluted and distributed into wells for a nested amplification. The upstream and downstream nested PCR primers contain UniTaq Aj and UniTaq Bj-UniTaq Cj tags on their 5' ends, respectively. In addition, UniTaq-specific primers of the format UniTaq Cj and F1-UniTaq Bj—Q≥UniTaq Aj are present in the amplification mix at higher concentration, and thus become the dominant primers incorporating into the amplification products. The product strand formed by the fluorescently labeled primer will hairpin, such that the UniTaq Bj sequence pairs with the UniTaq Bj' sequence. When UniTaq Primer Cj binds to the UniTaq Cj' sequence, the 5'→3' exonuclease activity of polymerase digests the UniTaq Bj sequence, liberating the F1 fluorescent dye, and generating signal detected by a real-time PCR instrument.

The products of the sequence UniTaq Ai—Target DNA—UniTaq Ci' may also be detected using primers nested inside the UniTaq Ci and UniTaq Ai sequence, and a standard TaqMan™ probe.

Two or three fragments in a single promoter region may be interrogated at the same time using the same fluorescent dye. The number of methylated fragments per promoter may be determined by total signal for that dye. When using spatial multiplexing, the sample is distributed to 12, 24, 48, or 96 individual wells prior to the 37° C. incubation step (but after addition of enzymes). In this manner, methylation across a promoter region of a given molecule of DNA may be distinguished from methylation of three different regions on three different molecules.

Since there is an initial ligation step, a subsequent LDR step is not necessary, with the initial PCR reaction followed directly by a secondary real-time PCR (e.g., TaqMan™) reaction. The disadvantage of going straight to a secondary PCR is that UNG carryover protection would not be used since the initial PCR reaction products have incorporated dUTP, and thus would be destroyed by UNG. One approach to address this problem would be to use standard dNTP's in the initial PCR, and rely solely on the restriction endonucleases to destroy any potential carryover from the initial or subsequent PCR reactions, since these products are now unmethylated.

The PCR primers may also contain an RNA base, 4 additional bases and a blocking group on the 3' end. RNaseH2 is then added to the reaction. This assures that no template independent products are formed with the UniTaq primer sets. In some designs, a methyl sensitive restriction site is downstream of the 3' end of the PCR primer, such that cleavage with the enzyme removes the binding sequence for the 4 additional bases, and cleavage of the RNA base by RNaseH2 is significantly reduced.

Overview of approach v3: Isolated genomic DNA, or methyl enriched DNA is treated with a methyl sensitive enzymes whose recognition elements comprise only of CpG dinucleotide pairs (i.e. Bsh1236I=CG^CG; and Hpy99I=CGWCGA). Treat with bisulfite, which converts "dC" to "dU", and renders the strands non-complementary. Hybridize locus-specific primers in the presence of BstU1 (CGACG), which will cleave carryover DNA. Primers and target that were not cleaved are unblocked with RNaseH2 only when bound to target. Unblocked PCR primers then amplify uncut bisulfite-converted DNA fragments of about 100-130 bp. The fragment should have at least 2 methyl sensitive enzyme sites, such that cleavage would cause these fragments to dissipate. These sites are chosen such that carryover prevention may work at two levels: (i) the sites are still cleavable in DNA containing incorporated dUTP, allowing for use of UNG for carryover prevention and (ii) after amplification, the sites are unmethylated, such that products would readily be recleaved should they carryover to another reaction. Further, the fragment should have additional internal methylated CpG pairs, such that a blocking primer would enrich for amplification of initially methylated target, and further the LDR probes would also select for detection of initially methylated target. Subsequent to the initial PCR amplification, LDR and UniTaq reactions with carryover protection are performed as described above. Alternatively, LDR and TaqMan™, or straight TaqMan™ reactions may be performed to identify and quantify relative amounts of methylated DNA in the initial sample.

To summarize the levels of discrimination of the above approach using both PCR and LDR primers for detection of low-abundance methylation:
1. Use of methylation sensitive restriction enzymes to cleave target when not methylated.
2. Use of nuclease activity of RNaseH2 to liberate an unblocked 3' OH on the PCR primers, only when hybridized to target.
3. Use of UNG and methylation sensitive restriction enzymes to prevent carryover contamination of initial PCR reaction.
4. Use of 3' ligation fidelity of thermostable ligase on upstream LDR probe.
5. Use of UniTaq or tag primers to amplify LDR products for real-time PCR readout.
6. Use of UNG to prevent carryover contamination of real-time PCR reaction.

Detailed Protocol for Highly Sensitive Detection of Promoter Methylation v3

2.3.a. Incubate genomic DNA, or methyl enriched DNA in the presence of Bsh1236I (CGACG) and UNG (37° C., 30-60 minutes) to completely digest unmethylated DNA and prevent carryover. Treat with bisulfite, which renders the strands non-complementary, and purify DNA strands using a commercially available kit (i.e. from Zymo Research or Qiagen). Add buffer supplement to optimize multiplexed PCR amplification, dUTP, and other dNTP's, AmpliTaq Gold, RNaseH2, BstU1 (CG^CG), and gene-specific primers containing an RNA base after the desired 3' end, 4 additional bases, and a blocking group to prevent extension on incorrect targets. This initial genomic DNA—PCR reaction mixture is suitable for multiplex PCR amplification in 12, 24, 48, or 96 individual wells (spatial multiplexing), or in a single well. BstU1 will cleave any carryover DNA from an earlier amplification. Denature digested genomic DNA and the restriction endonuclease, and activate AmpliTaq Gold (94° C., 5-10 minute) and multiplex PCR amplify mutation containing fragments for a limited number of cycles (94° C., 10 sec., 60° C. 30 sec., 72° C. 30 sec. for 16-20 cycles). The PCR primers are designed to have Tm values around 60° C., but with the 5 extra bases they are closer to 65-68° C., and will hybridize robustly, even when used at concentrations 10 to 50-fold below the norm for uniplex PCR (10 nM to 50 nM each primer). In addition, a blocking oligonucleotide is used to limit amplification of unmethylated DNA. The cycles are limited to retain relative balance of PCR products with respect to each other, while still amplifying low abundant sequences about 100,000 to 1,000,000—fold. After PCR amplification, Taq polymerase is inactivated (by incubating at 99° C. for 30 minutes.)

2.3.b. Add thermostable ligase (preferably from strain AK16D), buffer supplement to optimized ligation conditions, and suitable upstream and downstream LDR probes (10 nM to 20 nM each, downstream probes may be synthesized with 5' phosphate, or phosphorylated with kinase in bulk prior to reactions. Upstream probes comprise of a 5' tag, such as UniAi followed by target-specific sequence. The downstream probes comprise a 5' phosphorylated end, followed by target-specific sequence, and a 3' tag, such as UniCi'. Perform 20 cycles of LDR, (94° C., 10 sec., 60° C. 4-5 minutes). This will allow for ligation events to occur on the PCR products if methylated DNA was present in the original sample.

2.3.c. Open tube/wells, dilute (10- to 100-fold) and distribute aliquots to wells for Real-Time PCR reactions, each well containing the appropriate TaqMan™ master mix with UNG for carryover prevention, and the following primers: UniCi and UniAi, and a TaqMan™ probe that covers the sequence across the ligation junction. Under such conditions, the tag sequences on the LDR probes would be UniAi and UniCi respectively, and the products would be of the form:
UniAi—Upstream Target—Bisulfite-converted Methylation—egion —Downstream Target—UniCi'

Two or three fragments in a single promoter region may be interrogated at the same time using the same fluorescent dye. The number of methylated fragments per promoter may be determined by total signal for that dye. When using spatial multiplexing, the sample is distributed to 12, 24, 48, or 96 individual wells prior to the 37° C. incubation step (but after addition of enzymes). In this manner, methylation across a promoter region of a given molecule of DNA may be distinguished from methylation of three different regions on three different molecules.

FIG. 50 illustrates methylation detection on genomic or cfDNA using restriction digestion, and bisulfate treatment. The initial bisulfite-converted methylated region PCR primers contain an RNA base, 4 additional bases and a blocking group on the 3' end. Hybridization of these primers in the presence of BstU1 will cleave carryover DNA. These gene-specific primers are unblocked from the end by RNaseH2 only when hybridized to the target, liberating a 3'OH end suitable for polymerase extension. A blocking oligonucleotide is used to limit amplification of bisulfate-converted, unmethylated DNA. LDR probes for bisulfate-converted methylated DNA target provide additional specificity. Products are detected using TaqMan™ probes designed across the ligation junction sequence.

FIG. 51 illustrates a variation of FIG. 50. The upstream and downstream LDR probes contain UniTaq Ai and UniTaq Bi'-UniTaq Ci' tags respectively. After ligation, the products are diluted and distributed into wells containing UniTaq-specific primers of the format UniTaq Ci and F1-UniTaq Bi—Q—UniTaq Ai (where F1 is a fluorescent dye that is quenched by Quencher Q). The product strand formed by the fluorescently labeled primer will hairpin, such that the UniTaq Bi sequence pairs with the UniTaq Bi' sequence. When UniTaq Primer Ci binds to the UniTaq Ci' sequence, the 5'→3' exonuclease activity of polymerase digests the UniTaq Bi sequence, liberating the F1 fluorescent dye, and generating signal detected by a real-time PCR instrument.

FIG. 52 illustrates a variation of FIG. 50, where the PCR products are distributed (spatial multiplexing), and are captured on a solid support. The PCR primers contain universal tails to eliminate primer dimer formation, and to allow for amplification with universal primers, one of which contains a biotin, allowing for capture of products in streptavidin-coated wells. Ligation probes are hybridized to target and only form product when there is perfect complementarity at the ligation junction. Unreacted ligation probes, or target-independent ligation products are then washed away. LDR probes are designed to contain short complementary sequences that only hybridize to each other when ligated together, generating FRET signal suitable for detection.

FIG. 151 illustrates a variation of FIG. 50, where after initial restriction endonuclease digestion and bisulfite conversion, the PCR products are selectively amplified using locus-specific upstream and downstream primers. Upon target-specific hybridization, RNaseH removes the RNA base to liberate a 3'OH group suitable for polymerase extension. A blocking LNA or PNA probe comprising bisulfite converted unmethylated sequence (or its complement) that partially overlaps with the upstream PCR primer will preferentially compete in binding to bisulfite converted unmethylated target sequence over the upstream primer, but not as much to bisulfite converted methylated target sequence, and thus suppresses amplification of bisulfite converted unmethylated target sequence during each round of PCR. After the initial PCR enrichment step, this procedure continues with LDR-qPCR detection protocol with carryover prevention. Products are detected using TaqMan™ probes designed across the ligation junction sequence.

FIG. 152 illustrates a variation of FIG. 151, where the upstream and downstream LDR probes contain UniTaq Ai and UniTaq Bi'-UniTaq Ci' primer specific and sequence tag portions. After ligation, the products are diluted and distributed into wells containing UniTaq-specific primers of the format UniTaq Ci and F1-UniTaq Bi—Q—UniTaq Ai, and signal generated in the PCR is detected by a real-time PCR instrument.

FIG. 153 illustrates a variation of FIG. 151, where the PCR products are captured on a solid support. The LDR probes are designed to contain short complementary sequences that only hybridize to each other when ligated together, generating FRET signal suitable for detection.

FIG. 156 illustrates a variation of FIG. 50, where the PCR products are selectively amplified using locus-specific upstream primers that also comprise 5' portion sequences complementary to bisulfite-treated unmethylated sequence of the top strand allowing for formation of loop-hairpins after extension, and locus-specific downstream primers. Upon target-specific hybridization, RNaseH removes the RNA base to liberate a 3'OH group suitable for polymerase extension. PCR is performed with a polymerase lacking 5' nuclease, 3' nuclease, and strand-displacement activity. (i) Denaturation of bisulfite-treated unmethylated bottom strand results in loop-hairpin with perfect match at 3' end, which is extended by polymerase to form a longer hairpin region. This does not denature at 72° C. and prevents upstream primer from generating full-length top strand. (ii) Denaturation of bisulfite-treated methylated bottom strand results in loop-hairpin with two or more mismatches. This is not extended by polymerase, and thus denatures at 72° C., enabling upstream primer to generate full-length top strand. (iii) Denaturation of top strand results in hairpin on 5' side, which denatures during the extend step of PCR (72° C.), allowing polymerase to generate full-length bottom strand. The difference in hairpin extension preference of upstream primers with (i) bisulfite-treated unmethylated template and (ii) bisulfite-treated methylated template results in preferential amplification of mutant DNA. This selection against amplification of bisulfate-treated unmethylated target occurs during every cycle of the PCR, thus enriching for bisulfate-treated methylated targets. After the initial PCR enrichment step, this procedure continues with LDR-q PCR detection protocol with carryover prevention. Products are detected using TaqMan™ probes designed across the ligation junction sequence.

Figure illustrates a variation of FIG. 148, where the PCR products are captured on a solid support. The LDR probes are designed to contain short complementary sequences that only hybridize to each other when ligated together, generating FRET signal suitable for detection.

The upstream LDR probes and PCR primers may also contain an RNA base, 4 additional bases and a blocking group on the 3' end. RNaseH2 is then added to the reaction. This assures that no template independent products are formed. In some designs, a methyl sensitive restriction site is downstream of the 3' end of the PCR primer, such that cleavage with the enzyme removes the blocking group.

The downstream LDR probes may also be phosphorylated during the ligation reaction using thermophilic phage kinase (derived from bacteriophage RM378 that infects *Rhodothermus marinus*). Under these conditions the denaturation step in the LDR should be as short as possible (e.g., 94° C. or even lower for 1 second), as the thermophilic kinase is not fully thermostable—or just preincubate at 65° C. for 15 minute to achieve full primer phosphorylation. Alternatively, the 5' side of the downstream primer may contain a base the same as the 3' discriminating base on the upstream primer, said base removed by the 5' to 3' nuclease activity of Fen nuclease or Taq polymerase to liberate a 5' phosphate suitable for a subsequent ligation.

FIG. 53 illustrates a variation of FIG. 50, where the PCR products are distributed (spatial multiplexing), and then subjected to a second nested PCR using a TaqMan™ probe as well as a blocking oligonucleotide to limit amplification of bisulfite-converted, unmethylated DNA.

FIG. 151 158 illustrates a variation of FIG. 45, where the primary PCR products are detected directly using nested locus-specific primers and internal TaqMan™ probes. PCR products incorporate dU, and are unmethylated, allowing for carryover prevention.

Prophetic Example 3

High Sensitivity Detection of Gene Translocation or Splice-Site Variation in mRNA Isolated from Total Plasma mRNA, Exosomes, Circulating Tumor Cells (CTC's) or Total Blood Cells Containing CTC's Overview of approach: This approach depends on the fidelity of three enzymes: (i) reverse transcriptase and faithfully copy low-level copies of aberrant RNA transcripts in the initial sample, (ii) Taq polymerase to proportionally amplify the cDNA, and (iii) thermostable ligase in discriminating primers hybridized adjacent to each other. Once a ligation event has taken place, those products will be amplified in a subsequent Real-time PCR amplification step, and thus this is the key discriminatory step.

One advantage of using LDR is that it can discriminate a translocation event independent of the precise breakpoints. Further, when a translocation or alternative splicing creates new exon-exon junctions, LDR is ideally suited to precisely distinguish these junctions, down to the exact bases at the junctions.

There are at least two sources of aberrantly spliced transcripts in tumors. Tumors may undergo global dysregulation of gene expression through overall hypo-methylation.

One consequence of hypomethylation is the degradation of control of transcription start sites in promoter regions, allowing for alternative sequences in the 5' end of transcripts. Such alternatively spliced leader sequences may then be accurately identified and quantified using LDR-based assays. A second source of aberrantly spliced transcripts arises from dysregulation of the splicing machinery. Some such transcripts are translated into proteins that facilitate or even drive tumor growth. Again, these alternatively spliced transcripts may then be accurately identified and quantified using LDR-based assays, including providing relative levels of both the aberrant and wild-type transcript in the same LDR reaction.

To protect against carryover contamination, UNG is added to the reaction prior to polymerase activation, and the initial PCR amplification is performed with dUTP. The LDR probes are comprised of the natural bases, thus the LDR product is now resistant to UNG digestion in the second real-time PCR step. Note that the LDR products contain tags or UniTaq sequences on their non-ligating ends, which are lacking in the target DNA, thus accidental carryover of LDR products does not result in large-scale amplification. Unlike with PCR, an initial LDR product is not a substrate for a second LDR reaction.

To summarize the levels of discrimination of the above approach for high sensitivity detection of translocation or splice-site variation in mRNA:
1. Use of PCR primers with universal tails, such that if any target-independent primer dimer formed, the incorrect product will form a hairpin that will inhibit further amplification.
2. Use of UNG to prevent carryover contamination of initial PCR reaction.
3. Use of 3' ligation fidelity of thermostable ligase on upstream LDR probe.
4. Use of UniTaq or tag primers to amplify LDR products for real-time PCR readout.
5. Use of UNG to prevent carryover contamination of real-time PCR reaction.

Detailed Protocol for Highly Sensitive Detection of Gene Translocation or Splice-Site Variation in mRNA 3.1.a. Incubate isolated mRNA (or even total isolated nucleic acids) in the presence of UNG (37° C., 15-30 minutes, to prevent carryover), dUTP, and other dNTP's, MMLV reverse transcriptase, AmpliTaq Gold, and transcript-specific primers. (MMLV reverse transcriptase may be engineered to synthesize cDNA at 50-60° C., from total input RNA (Invitrogen Superscript III). Alternatively, Tth or Tma DNA polymerases have been engineered to improve their reverse-transcriptase activity (may require addition of Mn cofactor). Finally, thermophilic PyroPhage 3173 DNA Polymerase has both strand-displacement and reverse-transcription activity, and may also be used.) This initial cDNA—PCR reaction mixture is suitable for multiplex reverse-transcription PCR amplification in 12, 24, 48, or 96 individual wells (spatial multiplexing), or in a single well. After extension of reverse primers on their cognate RNA transcripts to generate cDNA, inactivate UNG and MMLV reverse transcriptase, and activate AmpliTaq Gold (94° C., 5-10 minute) and multiplex PCR amplify transcript-containing fragments for a limited number of cycles (94° C., 10 sec., 60° C. 30 sec., 72° C. 30 sec. for 16-20 cycles). The PCR primers are designed to have Tm values around 64-66° C., and will hybridize robustly, even when used at concentrations 10 to 50-fold below the norm for uniplex PCR (10 nM to 50 nM each primer). The cycles are limited to retain relative balance of PCR products with respect to each other, while still amplifying low abundant sequences about 100,000 to 1,000,000—fold. After PCR amplification, Taq polymerase is inactivated (by incubating at 99° C. for 30 minutes.)

3.1.b. Add thermostable ligase (preferably from strain AK16D), buffer supplement to optimized ligation conditions, and suitable upstream and downstream LDR probes (10 nM to 20 nM each, downstream probes may be synthesized with 5' phosphate, or phosphorylated with kinase in bulk prior to reactions; upstream probes comprise of a 5' tag, such as UniAi followed by transcript-specific sequence. The downstream probes comprise a 5' phosphorylated end, followed by target-specific sequence, and a 3' tag, such as UniCi'. Perform 20 cycles of LDR, (94° C., 10 sec., 60° C. 4-5 minutes). This will allow for ligation events to occur on the cDNA PCR products if the desired exon-exon junction is present. For detection of translocations where the precise junction is unknown, three LDR probes are used. The middle probe (s) contains sequence complementary to the known upstream and downstream regions of the (various) spliced transcripts. The upstream and downstream probes contain tags as described above to enable subsequent UniTaq or TaqMan™ amplification and detection of the desired ligation products.

3.1.c. Open tube/wells, dilute (10- to 100-fold) and distribute aliquots to wells for Real-Time PCR reactions, each well containing the appropriate TaqMan™ master mix with UNG for carryover prevention, and the following primers: UniCi and UniAi, and a TaqMan™ probe that covers the sequence across the ligation junction. Under such conditions, the tag sequences on the LDR probes would be UniAi and UniCi respectively, and the products would be of the form:

UniTaq Ai—Upstream Exon—Downstream Exon Junction—UniTaq Ci'

For products using three LDR probes to detect transcripts with unknown junctions, the following product will form:
UniTaq Ai—Upstream Exon—Bridge sequence—Downstream Exon—UniTaq Ci'

FIG. 54 illustrates an overview of the approach to use PCR-LDR reaction with carryover prevention to detect translocation at the mRNA level. An illustration of a translocation between two genes is shown, with the crossover allowing exons 1, 2, or 3 of the upstream gene to fuse with exon b of the downstream gene. LDR probes are designed to detect all the possible exon junctions (1-b, 2-b, and 3-b).

FIG. 55 illustrates a close up of translocation detection (overview in FIG. 54) on a fusion gene using the basic RT-PCR-LDR-qPCR detection protocol with carryover prevention. The initial gene-specific reverse-transcription and PCR primers contain identical 8-11 base tails to prevent primer dimers. Products are detected using TaqMan™ probes designed across the ligation junction sequence.

FIG. 56 illustrates a variation of FIG. 55, where upstream and downstream LDR probes contain UniTaq Ai and UniTaq Bi'-UniTaq Ci' tags respectively, and products are detected using fluorescently labeled UniTaq primers.

FIG. 57 illustrates a variation of FIG. 55, where the PCR products are distributed (spatial multiplexing), and are captured on a solid support. The LDR probes are designed to contain short complementary sequences that only hybridize to each other when ligated together, generating FRET signal suitable for detection.

FIG. 58 illustrates an overview of the approach to use PCR-LDR reaction with carryover prevention to detect alternative splicing. An illustration of an example of normal (1-2-3a-4) and alternative splice variant (1-2-3b-4) mRNA's are illustrated. LDR probes are designed to detect both the normal and/or the alternative splice variant (3a-4, and 3b-4).

FIG. 59 illustrates a close up of alternative splice variant detection (overview in FIG. 58) using the basic RT-PCR-LDR-qPCR detection protocol with carryover prevention. The initial gene-specific reverse-transcription and PCR primers contain identical 8-11 base tails to prevent primer dimers. Products are detected using differently labeled TaqMan™ probes designed across the ligation junction sequences, for the normal transcript 3a-4 (F1), and for the alternative splice variant 3b-4 (F2).

FIG. 60 illustrates a variation of FIG. 59, where upstream and downstream LDR probes contain UniTaq Ai or UniTaq Aj and UniTaq Bi'-UniTaq Ci' tags respectively, and products are detected using fluorescently labeled UniTaq primers F1-UniTaq Bi—Q—UniTaq Ai and F2-UniTaq Bi—Q—UniTaq Aj to detect signals F1 and F2, representing normal transcript 3a-4, and for the alternative splice variant 3b-4, respectively.

FIG. 61 illustrates a variation of FIG. 59, where the PCR products are distributed (spatial multiplexing), and are captured on a solid support. The LDR probes are designed to contain short complementary sequences that only hybridize to each other when ligated together, generating FRET signal F1 and F2 suitable for detection, representing normal transcript 3a-4, and for the alternative splice variant 3b-4, respectively.

FIG. 62 illustrates a close up of low-level alternative splice variant detection (overview in FIG. 58) using the basic RT-PCR-LDR-q PCR detection protocol with carryover prevention. The initial gene-specific reverse-transcription and PCR primers contain identical 8-11 base tails to prevent primer dimers, and are designed to amplify only the minority transcript containing the 3b-4 junction. Products are detected using TaqMan™ probes designed across the ligation junction sequence for the low-abundant alternative splice variant 3b-4.

FIG. 63 illustrates a variation of FIG. 62, where upstream and downstream LDR probes contain UniTaq Ai and UniTaq Bi'-UniTaq Ci' tags respectively, and products are detected using fluorescently labeled UniTaq primer F1-UniTaq Bi—Q—UniTaq Ai to detect signal F1, representing low-abundant alternative splice variant 3b-4.

FIG. 64 illustrates a variation of FIG. 62, where the PCR products are distributed (spatial multiplexing), and are captured on a solid support. The LDR probes are designed to contain short complementary sequences that only hybridize to each other when ligated together, generating FRET signal F1 suitable for detection, representing the low-abundant alternative splice variant 3b-4.

FIG. 65 illustrates an overview of the approach to use PCR-LDR reaction with carryover prevention to detect alternative splicing, with an alternative start site for the first exon. An illustration of an example of normal (1-2-3) and alternative splice variant (1a-2-3) mRNAs are shown. LDR probes are designed to detect both the normal and/or the alternative splice variant (1-2, and 1a-2).

FIG. 66 illustrates a close up of alternative splice variant detection (overview in FIG. 65) using the basic RT-PCR-LDR-qPCR detection protocol with carryover prevention. The initial gene-specific reverse-transcription and PCR primers contain identical 8-11 base tails to prevent primer dimers. Products are detected using differently labeled TaqMan™ probes designed across the ligation junction sequences, for the normal transcript 1-2 (F1), and for the alternative start site variant 1a-2 (F2).

FIG. 67 illustrates a variation of FIG. 66, where upstream and downstream LDR probes contain UniTaq Ai or UniTaq Aj and UniTaq Bi'-UniTaq Ci' tags respectively, and products are detected using fluorescently labeled UniTaq primers F1-UniTaq Bi—Q—UniTaq Ai and F2-UniTaq Bi—Q—UniTaq Aj to detect signals F1 and F2, representing normal transcript 1-2, and for the alternative start site variant 1a-2, respectively.

FIG. 68 illustrates a variation of FIG. 66, where the PCR products are distributed (spatial multiplexing), and are captured on a solid support. The LDR probes are designed to contain short complementary sequences that only hybridize to each other when ligated together, generating FRET signal F1 and F2 suitable for detection, representing normal transcript 1-2, and for the alternative start site variant 1a-2, respectively.

FIG. 69 illustrates a close up of low-level alternative splice variant detection (overview in FIG. 58) using the basic RT-PCR-LDR-q PCR detection protocol with carryover prevention. The initial gene-specific reverse-transcription and PCR primers contain identical 8-11 base tails to prevent primer dimers, and are designed to amplify only the minority transcript containing the 1a-2 junction. Products are detected using TaqMan™ probes designed across the ligation junction sequence for the low-abundant alternative start site variant 1a-2.

FIG. 70 illustrates a variation of FIG. 69, where upstream and downstream LDR probes contain UniTaq Ai and UniTaq Bi'-UniTaq Ci' tags respectively, and products are detected using fluorescently labeled UniTaq primer F1-UniTaq Bi—Q—UniTaq Ai to detect signal F1, representing low-abundant alternative start site variant 1a-2.

FIG. 71 illustrates a variation of FIG. 69, where the PCR products are distributed (spatial multiplexing), and are captured on a solid support. The LDR probes are designed to contain short complementary sequences that only hybridize to each other when ligated together, generating FRET signal F1 suitable for detection, representing the low-abundant alternative start site variant 1a-2.

FIG. 72 illustrates an overview of the approach to use PCR-LDR reaction with carryover prevention to detect alternative splicing with exon deletion. An illustration of an example of normal (e1-e2-e3-e4-e5) and alternative splice variant (e1-e2-e3-e5) mRNA's are illustrated. LDR probes are designed to detect both the normal and/or the alternative splice exon-deletion variant (e4-e5, and e3-e5).

FIG. 73 illustrates a close up of alternative splice variant (exon deletion) detection (overview in FIG. 58) using the basic RT-PCR-LDR-q PCR detection protocol with carryover prevention. The initial gene-specific reverse-transcription and PCR primers contain identical 8-11 base tails to prevent primer dimers. Products are detected using differently labeled TaqMan™ probes designed across the ligation junction sequences, for the normal transcript e4-e5 (F1), and for the alternative splice exon-deletion variant e3-e5 (F2).

FIG. 74 illustrates a variation of FIG. 73, where upstream and downstream LDR probes contain UniTaq Ai or UniTaq Aj and UniTaq Bi'-UniTaq Ci' tags respectively, and products are detected using fluorescently labeled UniTaq primers F1-UniTaq Bi—Q—UniTaq Ai and F2-UniTaq Bi—Q—UniTaq Aj to detect signals F1 and F2, representing normal transcript e4-e5, and for the alternative splice exon-deletion variant e3-e5, respectively.

FIG. 75 illustrates a variation of FIG. 73, where the PCR products are distributed (spatial multiplexing), and are captured on a solid support. The LDR probes are designed to contain short complementary sequences that only hybridize to each other when ligated together, generating FRET signal F1 and F2 suitable for detection, representing normal transcript e4-e5, and for the alternative splice exon-deletion variant e3-e5, respectively.

FIG. 76 illustrates a close up of low-level alternative splice variant (exon deletion) detection (overview in FIG. 58) using the basic RT-PCR-LDR-q PCR detection protocol with carryover prevention. The initial gene-specific reverse-transcription and PCR primers contain identical 8-11 base tails to prevent primer dimers, and are designed to amplify only the minority transcript containing the e3-e4 junction by using a blocking oligonucleotide with e4 sequence to suppress amplification of wild-type transcript. Products are detected using TaqMan™ probes designed across the ligation junction sequence for the low-abundant alternative splice exon-deletion variant e3-e5.

FIG. 77 illustrates a variation of FIG. 76, where upstream and downstream LDR probes contain UniTaq Ai and UniTaq Bi'-UniTaq Ci' tags respectively, and products are detected using fluorescently labeled UniTaq primer F1-UniTaq Bi—Q—UniTaq Ai to detect signal F1, representing low-abundant alternative splice exon-deletion variant e3-e5.

FIG. 78 illustrates a variation of FIG. 76, where the PCR products are distributed (spatial multiplexing), and are captured on a solid support. The LDR probes are designed to contain short complementary sequences that only hybridize to each other when ligated together, generating FRET signal F1 suitable for detection, representing the low-abundant alternative splice exon-deletion variant e3-e5.

FIG. 79 illustrates an overview of the approach to use PCR-LDR reaction with carryover prevention to detect alternative splicing with intron insertion. An illustration of an example of normal (e1-e2-e3-e4-e5) and alternative splice variant (e1-i1-e2-e3-e4-e5) mRNA's are shown. LDR probes are designed to detect both the normal and/or the alternative splice variant with intron insertion (e1-e2, and i1-e2).

FIG. 80 illustrates a close up of alternative splice variant detection (overview in FIG. 79) using the basic RT-PCR-LDR-real-time PCR detection protocol with carryover prevention. The initial gene-specific reverse-transcription and PCR primers contain identical 8-11 base tails to prevent primer dimers. Products are detected using differently labeled TaqMan™ probes designed across the ligation junction sequences, for the normal transcript e1-e2 (F1), and for the alternative splice variant with intron insertion i1-e2 (F2).

FIG. 81 illustrates a variation of FIG. 80, where upstream and downstream LDR probes contain UniTaq Ai or UniTaq Aj and UniTaq Bi'-UniTaq Ci' tags respectively, and products are detected using fluorescently labeled UniTaq primers F1-UniTaq Bi—Q—UniTaq Ai and F2-UniTaq Bi—Q—UniTaq Aj to detect signals F1 and F2, representing normal transcript e1-e2, and for the alternative splice variant with intron insertion i1-e2, respectively.

FIG. 82 illustrates a variation of FIG. 80, where the PCR products are distributed (spatial multiplexing), and are captured on a solid support. The LDR probes are designed to contain short complementary sequences that only hybridize to each other when ligated together, generating FRET signal F1 and F2 suitable for detection, representing normal transcript e1-e2, and for the alternative splice variant with intron insertion i1-e2, respectively.

FIG. 83 illustrates a close up of low-level alternative splice variant (intron insertion) detection (overview in FIG. 79) using the basic RT-PCR-LDR-qPCR detection protocol with carryover prevention. The initial gene-specific reverse-transcription and PCR primers contain identical 8-11 base tails to prevent primer dimers, and are designed to amplify only the minority transcript containing the i1-e2 junction. This may be achieved by (i) digesting nucleic acids with pancreatic DNaseI, to digest all genomic DNA while leaving the mRNA intact, or (ii) using primer sets that span intron i2 as well, e.g., reverse-transcribe from e3, in the presence of blocking primer to i2. Products are detected using TaqMan™ probes designed across the ligation junction sequence for the low-abundant alternative splice variant with intron insertion i1-e2.

FIG. 84 illustrates a variation of FIG. 83, where upstream and downstream LDR probes contain UniTaq Ai and UniTaq Bi'-UniTaq Ci' tags respectively, and products are detected using fluorescently labeled UniTaq primer F1-UniTaq Bi—Q—UniTaq Ai to detect signal F1, representing low-abundant alternative splice variant with intron insertion i1-e2.

FIG. 85 illustrates a variation of FIG. 83, where the PCR products are distributed (spatial multiplexing), and are captured on a solid support. The LDR probes are designed to contain short complementary sequences that only hybridize to each other when ligated together, generating FRET signal F1 suitable for detection, representing the low-abundant alternative splice variant with intron insertion i1-e2.

When using UniTaq containing LDR probes, they are of the following format: upstream probes comprise of a 5' tag, such as UniTaqAi followed by target-specific sequence. The downstream probes comprise a 5' phosphorylated end, followed by target-specific sequence, and a 3' tag, such as UniTaq Bi'—UniTaq Ci'.

The LDR products may be detected using UniTaq-specific primers of the format UniTaq Ci and F1-UniTaq Bi—Q—UniTaq Ai. (where F1 is a fluorescent dye that is quenched by Quencher Q). Under these conditions, the following product will form:
F1-UniTaq Bi—Q—UniTaq Ai—Upstream Exon-Downstream Exon Junction—UniTaq Bi'—UniTaq Ci'

This construct will hairpin, such that the UniTaq Bi sequence pairs with the UniTaq Bi' sequence. When UniTaq Primer Ci binds to the UniTaq Ci' sequence, the 5'→3' exonuclease activity of polymerase digests the UniTaq Bi sequence, liberating the F1 fluorescent dye.

For products using three LDR probes to detect transcripts with unknown junctions, the following product will form:
F1-UniTaq Bi—Q—UniTaq Ai—Upstream Exon—Bridge sequence—Downstream Exon—UniTaq Bi'—UniTaq Ci'

One of the initial PCR primers or upstream LDR probes may also contain an RNA base, 4 additional bases and a blocking group on the 3' end. RNaseH2 is added to the reaction after the reverse-transcription step for the PCR, and/or during the LDR reaction. This assures that no template independent products are formed.

The downstream LDR probes may also be phosphorylated during the ligation reaction using thermophilic phage kinase (derived from bacteriophage RM378 that infects *Rhodothermus marinus*). Under these conditions the denaturation step in the LDR should be as short as possible (e.g., 94° C. or even lower for 1 second), as the thermophilic kinase is not fully thermostable—or just preincubate at 65° C. for 15 minute to achieve full primer phosphorylation. Alternatively, the 5' side of the downstream probe may contain a base the same as the 3' discriminating base on the upstream primer, said base removed by the 5' to 3' nuclease activity of Fen nuclease or Taq polymerase to liberate a 5' phosphate suitable for a subsequent ligation.

Prophetic Example 4

Accurate Quantification of Tumor-Specific Copy Changes in DNA Isolated from Circulating Tumor Cells Overview of approach: Since there may be only a few CTC's present in the purified sample, it is important to use spatial multiplexing to accurately count every chromosome copy in the sample. This approach depends on the fidelity of two enzymes: (i) Taq polymerase to faithfully copy low-level copies of DNA regions in the initial sample, and (ii) ligase in discriminating primers that hybridize adjacent to each other. Once a ligation event has taken place, those products will be amplified in a subsequent Real-time PCR amplification step, and thus this is the key discriminatory step.

To protect against carryover contamination, UNG is added to the reaction prior to polymerase activation, and the initial PCR amplification is performed with dUTP. The LDR probes are comprised of the natural bases, thus the LDR product is now resistant to UNG digestion in the second real-time PCR step. Note that the LDR products contain tags or UniTaq sequences on their non-ligating ends, which are lacking in the target DNA, thus accidental carryover of LDR products does not result in large-scale amplification. Unlike with PCR, an initial LDR product is not a substrate for a second LDR reaction.

To summarize the levels of discrimination of the above approach using both PCR and LDR primers for the determination of copy number detection of specific regions:
1. Use of PCR primers with universal tails, such that if any target-independent primer dimer formed, the incorrect product will form a hairpin that will inhibit further amplification.
2. Use of UNG to prevent carryover contamination of initial PCR reaction.
3. Use of 3' ligation fidelity of thermostable ligase on upstream LDR probe.
4. Use of UniTaq or tag primers to amplify LDR products for real-time PCR readout.
5. Use of UNG to prevent carryover contamination of real-time PCR reaction.

Detailed protocol for Highly Accurate Quantification of Tumor-Specific Copy Changes in DNA or RNA Isolated from Circulating Tumor Cells.

4.1.a. Incubate genomic DNA in the presence of UNG (37° C., 15-30 minutes, to prevent carryover), dUTP, and other dNTP's, AmpliTaq Gold, and gene-specific primers containing universal tails, such that if any target-independent primer dimer formed, the incorrect product will form a hairpin that will inhibit further amplification. This initial genomic DNA—PCR reaction mixture is distributed in 12, 24, 48, or 96 individual wells (spatial multiplexing) for multiplex PCR amplification. Denature genomic DNA from plasma, inactivate UNG, and activate AmpliTaq Gold (94° C., 5-10 minute) and multiplex PCR amplify chromosomal regions for a limited number of cycles (94° C., 10 sec., 60° C. 30 sec., 72° C. 30 sec. for 12-20 cycles). The PCR primers are designed to have Tm values around 64-66° C., and will hybridize robustly, even when used at concentrations 10 to 50-fold below the norm for uniplex PCR (10 nM to 50 nM each primer). The cycles are limited to retain proportional balance of PCR products with respect to each other, while still amplifying low abundant sequences about 100,000 to 1,000,000—fold. After PCR amplification, Taq polymerase is inactivated (by incubating at 99° C. for 30 minutes.)

4.1.b. Add thermostable ligase (preferably from strain AK16D), buffer supplement to optimized ligation conditions, and suitable upstream and downstream LDR probes (10 nM to 20 nM each, downstream probes may be synthesized with 5' phosphate, or kinased in bulk prior to reactions; Upstream probes comprise of a 5' tag, such as UniAi followed by target-specific sequence. The downstream probes comprise a 5' phosphorylated end, followed by target-specific sequence, and a 3' tag, such as UniCi'. Perform 20 cycles of LDR, (94° C., 10 sec., 60° C. 4-5 minutes). This will allow for ligation events to occur on the PCR products if chromosomal DNA is present.

4.1.c. Open tube/wells, dilute (10- to 100-fold) and distribute aliquots to wells for Real-Time PCR reactions, each well containing the appropriate TaqMan™ master mix with UNG for carryover prevention, and the following primers: UniCi and UniAi, and a TaqMan™ probe that covers the sequence across the ligation junction. Under such conditions, the tag sequences on the LDR primers would be UniAi and UniCi respectively, and the products would be of the form:
UniAi—Chromosomal Target Region—UniCi'

FIG. 86 illustrates DNA copy number enumeration with spatial multiplexing (see FIGS. 6-9), using the basic PCR-LDR-q PCR detection protocol with carryover prevention. The initial gene-specific PCR primers contain identical 8-11 base tails to prevent primer dimers. Products are detected using TaqMan™ probes designed across the ligation junction sequence for each chromosomal region, and total copy number enumerated.

FIG. 87 illustrates a variation of FIG. 86, where upstream and downstream LDR probes contain UniTaq Ai and UniTaq Bi'-UniTaq Ci' tags respectively, and products are detected using fluorescently labeled UniTaq primer F1-UniTaq Bi—Q—UniTaq Ai to detect signal for each chromosomal region, and total copy number enumerated.

FIG. 88 illustrates a variation of FIG. 86, where the PCR products are distributed (spatial multiplexing), and are captured on a solid support (see FIGS. 19-23). The LDR probes are designed to contain short complementary sequences that only hybridize to each other when ligated together, generating FRET signal suitable for detection of each chromosomal region, and total copy number enumerated.

FIG. 89 illustrates mRNA transcript number enumeration with spatial multiplexing (see FIGS. 10-13), using the basic reverse-transcription PCR-LDR-qPCR detection protocol with carryover prevention. The initial gene-specific reverse-transcription and PCR primers contain identical 8-11 base tails to prevent primer dimers. Products are detected using TaqMan™ probes designed across the ligation junction sequence for each mRNA transcript, to enable accurate enumeration.

FIG. 90 illustrates a variation of FIG. 89, where upstream and downstream LDR probes contain UniTaq Ai and UniTaq Bi'-UniTaq Ci' tags respectively, and products are detected using fluorescently labeled UniTaq primer F1-UniTaq Bi—Q—UniTaq Ai to detect signal for each mRNA transcript, to enable accurate enumeration.

FIG. 91 illustrates a variation of FIG. 89, where the PCR products are distributed (spatial multiplexing), and are captured on a solid support (see FIGS. 24-28). The LDR probes are designed to contain short complementary sequences that only hybridize to each other when ligated together, generating FRET signal suitable for detection of each mRNA transcript, to enable accurate enumeration.

As an example of spatial multiplexing across 48 wells, consider DNA isolated from 12 CTC's, with probes prepared for various copy regions with prognostic or therapeutic value, such as loss of heterozygosity of chromosomal arm 8p (LOH at 8p; predicts worse outcome), or amplification of the Her2 gene at 17q12 (predicts responsiveness to Herceptin therapy). Multiple LDR probe sets may be employed to determine copy number across the genome, with additional pairs at focal points known to undergo significant amplification. For this example, the diploid regions of the genome would produce signal from 24 copies (i.e. 2×12 cells), an LOH event at 8p would produce 12 copies, and for example if the Her2 gene was amplified 8-fold, it would produce signal from 96 copies (i.e. 8×12). The likely Poisson distribution (FIGS. 31 & 32) show the LOH region will have a distribution of about (wells: molecules) (38:0; 10:1; 1:2) for 12 molecules, the diploid regions will have a distribution of about (29:0; 15:1; 4:2; 1:3) for 24 molecules, while the amplified region will have a distribution of about (6:0; 13:1; 13:2; 9:3; 4:4; 2:5; 1:6) for 96 molecules. Note that even if a region has undergone only mild amplification, for example from 2 copies per cell to 3 copies, trisomy regions will have a distribution of about (23:0; 17:1; 6:2; 2:3) for 36 molecules, and thus distinguishable from diploid regions. As before, even if LDR-TaqMan™ LDR signal is variable enough that distinguishing the higher level signals becomes too difficult, as long as the signal is clean enough to distinguish 0, 1, and 2 initial molecules (represented as LDR-TaqMan™ Ct values of 12.5, 10, and 9, or LDR signals of about 1,000, 5,000, and 10,000, respectively), this approach will have no difficulty distinguishing and enumerating regions that have undergone LOH, regions that are diploid, and regions that have undergone amplification. The CT or fluorescent signal is variable enough only to distinguish between 0 and 1 or more initial chromosomal molecules, given 24 copies of diploid chromosomes in a minimum of 48 wells, this approach should distinguish and enumerate regions that have undergone LOH, regions that are diploid, and regions that have undergone amplification.

For cfDNA samples with higher tumor DNA load, or with mRNA or miRNA, where the starting target is present in higher amounts, the LDR signal will be proportionally stronger. A large dynamic range of initial molecules may also be achieved by using a different strategy for diluting the initial signal. For example, after a reverse-transcription step for mRNA isolated from exosomes, instead of dividing the sample equally among 48 wells, the sample is distributed into 10 aliquots, the first 8 are distributed into wells, and one of the remaining aliquots is diluted into10 aliquots, with 8 distributed into wells, etc. This allows for 6 orders of magnitude of dilution: (i.e. 8×6=48). Examination of Poisson distributions shows that as long as 1 well in the last dilution represents 0 molecules, a given set of 8 wells can provide a semi-quantitative estimate of starting molecules over a 2 order of magnitude dynamic range, from 1 to 128 molecules, even while the LDR readout only needs to provide a 20-fold dynamic range, or Ct range of 4-5 (see FIGS. 33-37 that show Poisson distribution of from 1 to 128 molecules in 8 wells). Since the dilutions are only 10-fold, at least 2 sets of 8 wells may be used to determine the number of original molecules of multiple different transcripts in the sample, even if some mRNA molecules were on the order of 10 molecules, while others were on the order of 1×10$^6$ molecules.

The same approach may be used for quantifying RNA copy, but reverse transcriptase is added in the first step, and the spatial distribution of initial reaction mix may be dilution & distribution as outlined above.

When using UniTaq containing LDR probes, they are of the following format: upstream probes comprise of a 5' tag, such as UniTaqAi followed by target-specific sequence with a C:A or G:T mismatch at the 3$^{rd}$ or penultimate base, the mutation base at the 3' end, followed by an RNA base and 4 more DNA bases that matches the target, and a C3 spacer-blocking group. The downstream probes comprise a 5' phosphorylated end, followed by target-specific sequence, and a 3' tag, such as UniTaq Bi'—UniCi'.

The LDR products may be detected using UniTaq-specific primers of the format UniTaq Ci and F1-UniTaq Bi—Q—UniTaq Ai. (where F1 is a fluorescent dye that is quenched by Quencher Q). Under these conditions, the following product will form:

F1-UniTaq Bi—Q—UniTaq Ai—Chromosomal Target Region—UniTaq Bi'—UniTaq Ci'

This construct will hairpin, such that the UniTaq Bi sequence pairs with the UniTaq Bi' sequence. When UniTaq Primer Ci binds to the UniTaq Ci' sequence, the 5'→3' exonuclease activity of polymerase digests the UniTaq Bi sequence, liberating the F1 fluorescent dye.

One of the initial PCR primers (with RNA) or both initial PCR primers (with DNA) or upstream LDR probes may also contain an RNA base, 4 additional bases and a blocking group on the 3' end. When quantifying DNA copy, RNaseH2 is added with the PCR reaction, and/or with the LDR reaction. When quantifying RNA, RNaseH2 is added to the reaction after the reverse-transcription step with the PCR, and/or with the LDR reaction. This assures that no template independent products are formed.

The downstream LDR probes may also be phosphorylated during the ligation reaction using thermophilic phage kinase (derived from bacteriophage RM378 that infects *Rhodothermus marinus*). Under these conditions the denaturation step in the LDR should be as short as possible (e.g. 94° C. or even lower for 1 second), as the thermophilic kinase is not fully thermostable—or just preincubate at 65° C. for 15 minute to achieve full primer phosphorylation. Alternatively, the 5' side of the downstream primer may contain a base the same as the 3' discriminating base on the upstream primer, said base removed by the 5' to 3' nuclease activity of Fen nuclease or Taq polymerase to liberate a 5' phosphate suitable for a subsequent ligation.

Prophetic Example 5

Accurate Quantification of miRNA, lncRNA, or mRNA Changes from Isolated Exosomes, or from Circulating Tumor Cells Overview of approach: This approach depends on the fidelity of two enzymes: (i) Reverse Transcriptase and Taq polymerase to faithfully copy low-level copies of miRNA in the initial sample, and (ii) the ligase in discriminating probes hybridized adjacent to each other. Once a ligation event has taken place, those products will be amplified in a subsequent Real-time PCR amplification step, and thus this is the key discriminatory step.

MicroRNA (miRNA) have been identified as potential tissue-specific markers of the presence of tumors, their classification and prognostication. miRNA exist in serum and plasma either as complexes with Ago2 proteins or by encapsulation as exosomes.

To protect against carryover contamination, UNG is added to the reaction prior to reverse transcription by MMLV, and the initial PCR amplification is performed with dUTP. The LDR probes are comprised of the natural bases, thus the LDR product is now resistant to UNG digestion in the second real-time PCR step. Note that the LDR products contain tags or UniTaq sequences on their non-ligating ends, which are lacking in the target miRNA, thus accidental carryover of LDR products does not result in large-scale amplification. Unlike with PCR, an initial LDR product is not a substrate for a second LDR reaction.

A miRNA specific hairpin loop containing a universal reverse primer region and an 6-8 base miRNA specific region is hybridized to the 3' end of the miRNA and extended with MMLV in the presence of dUTP. Under the right conditions, MMLV will add 2-3 C nucleotides past the 5' end of the miRNA template in a template-independent extension reaction.

After the initial cDNA generation, add a universal reverse primer and universal-tailed forward primer that hybridize to the 2-3 additional C nucleotides and from 12 to 14 specific bases of the miRNA. Taq polymerase is used to perform 16-20 cycles of universal amplification; the universal reverse primer is located to eliminate most of the hairpin region during the cDNA generation.

To summarize the levels of discrimination of the above approach for high sensitivity detection of miRNA:
1. Use of UNG to prevent carryover contamination of initial reverse transcription and PCR reactions.
2. Use of 3' ligation fidelity of thermostable ligase on upstream LDR probe.
3. Use of UniTaq or tag primers to amplify LDR products for real-time PCR readout.
4. Use of UNG to prevent carryover contamination of real-time PCR reaction.

Detailed Protocol for Highly Sensitive Detection of miRNA:

5.1.a. Incubate isolated miRNA (or even total isolated nucleic acids) in the presence of UNG (37° C., 15-30 minutes, to prevent carryover), dUTP, and other dNTP's, MMLV reverse transcriptase, AmpliTaq Gold, and transcript-specific primers. This initial cDNA—PCR reaction mixture is suitable for multiplex reverse-transcription PCR amplification in 12, 24, 48, or 96 individual wells (spatial multiplexing), or in a single well. After extension of hairpin reverse primers on their cognate miRNA to generate cDNA, inactivate UNG and MMLV reverse transcriptase, and activate AmpliTaq Gold (94° C., 5-10 minute) and multiplex PCR amplify transcript-containing fragments using bridge and tag primers Ti, and Tj for a limited number of cycles (94° C., 10 sec., 60° C. 30 sec., 72° C. 30 sec. for 16-20 cycles). After PCR amplification, Taq polymerase is inactivated (by incubating at 99° C. for 30 minutes.)

5.1.b. Add thermostable ligase (preferably from strain AK16D), buffer supplement to optimized ligation conditions, and suitable upstream and downstream LDR probes (10 nM to 20 nM each, downstream probes may be synthesized with 5' phosphate, or kinased in bulk prior to reactions; Upstream probes comprise of a 5' tag, such as UniAi followed by target-specific sequence. The downstream probes comprise a 5' phosphorylated end, followed by target-specific sequence, and a 3' tag, such as UniCi'. Perform 20 cycles of LDR, (94° C., 10 sec., 60° C. 4-5 minutes). This will allow for ligation events to occur on the PCR products if chromosomal DNA is present.

5.1.c. Open tube/wells, dilute (10- to 100-fold) and distribute aliquots to wells for Real-Time PCR reactions, each well containing the appropriate TaqMan™ master mix with UNG for carryover prevention, and the following primers: UniCi and UniAi, and a TaqMan™ probe that covers the sequence across the ligation junction. Under such conditions, the tag sequences on the LDR probes would be UniAi and UniCi respectively, and the products would be of the form:

UniAi—Upstream miRNA—Downstream miRNA Junction—UniCi'

In one variation of the above theme, the hairpin oligonucleotide is ligated to the 3' end of the miRNA in a base-specific manner, appending an artificial loop sequence, which contains a tag-primer binding site (Tj). This enables extension to copy the entire miRNA sequence, as well as initiating a PCR reaction using miRNA target-specific bridge primers (comprising of (Ti) and miRNA-specific sequence), and the two tag primer (Ti, Tj). The PCR product is now suitable for subsequent LDR step as described above.

FIG. 92 illustrates miRNA detection, using reverse transcription of a loop primer, followed by tag and bridge primer PCR protocol with carryover prevention. Subsequent LDR-q PCR detection protocol is used with carryover prevention. The initial miRNA-specific PCR primers contain identical 8-11 base tails as part of the tag primers to prevent primer dimers. Products are detected using TaqMan™ probes designed across the ligation junction sequence for each miRNA detected.

FIG. 93 illustrates a variation of FIG. 92, where upstream and downstream LDR probes contain UniTaq Ai and UniTaq Bi'-UniTaq Ci' tags respectively, and products are detected using fluorescently labeled UniTaq primer F1-UniTaq Bi—Q—UniTaq Ai to detect signal for each miRNA.

FIG. 94 illustrates a variation of FIG. 92, where the PCR products are distributed (spatial multiplexing), and are captured on a solid support. The LDR probes are designed to contain short complementary sequences that only hybridize to each other when ligated together, generating FRET signal suitable for detection of each miRNA.

FIG. 95 illustrates miRNA detection, using ligation of a loop primer directly to miRNA, followed reverse transcription using a tag primer complementary to the loop with carryover prevention. The procedure uses a tag and bridge primer for PCR-LDR-q PCR detection, with carryover prevention. The initial miRNA-specific PCR primers contain identical 8-11 base tails as part of the tag primers to prevent primer dimers. Products are detected using TaqMan™ probes designed across the ligation junction sequence for each miRNA detected.

FIG. 96 illustrates a variation of FIG. 95, where upstream and downstream LDR primers contain UniTaq Ai and UniTaq Bi'-UniTaq Ci' tags respectively, and products are detected using fluorescently labeled UniTaq primer F1-UniTaq Bi—Q—UniTaq Ai to detect signal for each miRNA.

FIG. 97 illustrates a variation of FIG. 95, where the PCR products are distributed (spatial multiplexing), and are captured on a solid support. The LDR probes are designed to contain short complementary sequences that only hybridize to each other when ligated together, generating FRET signal suitable for detection of each miRNA.

FIG. 98 illustrates a variation of FIG. 95, where the bridge PCR primer contains an RNA base, 4 additional bases and a blocking group on the 3' end. RNaseH2 is added to the reaction after the reverse-transcription step to unblock the PCR primer. This assures that no template independent products are formed.

FIG. 99 illustrates a variation of FIG. 98, where upstream and downstream LDR probes contain UniTaq Ai and UniTaq Bi'-UniTaq Ci' tags respectively, and products are detected using fluorescently labeled UniTaq primer F1-UniTaq Bi—Q—UniTaq Ai to detect signal for each miRNA.

FIG. 100 illustrates a variation of FIG. 98, where the PCR products are distributed (spatial multiplexing), and are captured on a solid support. The LDR probes are designed to contain short complementary sequences that only hybridize to each other when ligated together, generating FRET signal suitable for detection of each miRNA.

When using UniTaq containing LDR probes, they are of the following format: upstream probes comprise of a 5' tag, such as UniTaqAi followed by target-specific sequence. The downstream probes comprise a 5' phosphorylated end, followed by target-specific sequence, and a 3' tag, such as UniTaq Bi'—UniTaq Ci'.

The LDR products may be detected using UniTaq-specific primers of the format UniTaq Ci and F1-UniTaq Bi—Q—UniTaq Ai. (where F1 is a fluorescent dye that is quenched by Quencher Q). Under these conditions, the following product will form: F1-UniTaq Bi—Q—UniTaq Ai—Upstream miRNA—Downstream miRNA Junction—UniTaq Bi'—UniTaq Ci'

This construct will hairpin, such that the UniTaq Bi sequence pairs with the UniTaq Bi' sequence. When UniTaq Primer Ci binds to the UniTaq Ci' sequence, the 5'→3' exonuclease activity of polymerase digests the UniTaq Bi sequence, liberating the F1 fluorescent dye.

For products using three LDR probes to detect transcripts with unknown junctions, the following product will form: F1-UniTaq Bi—Q—UniTaq Ai—Upstream Exon—Bridge Sequence—Downstream Exon—UniTaq Bi'—UniTaq Ci'

One of the initial PCR primers or upstream LDR probes may also contain an RNA base, 4 additional bases and a blocking group on the 3' end. RNaseH2 is added to the reaction after the reverse-transcription step for the PCR, and/or during the LDR reaction. This assures that no template independent products are formed.

The downstream LDR probes may also be phosphorylated during the ligation reaction using thermophilic phage kinase (derived from bacteriophage RM378 that infects *Rhodothermus marinus*). Under these conditions the denaturation step in the LDR should be as short as possible (e.g., 94° C. or even lower for 1 second), as the thermophilic kinase is not fully thermostable—or just preincubate at 65° C. for 15 minute to achieve full primer phosphorylation. Alternatively, the 5' side of the downstream probe may contain a base the same as the 3' discriminating base on the upstream probe, said base removed by the 5' to 3' nuclease activity of Fen nuclease or Taq polymerase to liberate a 5' phosphate suitable for a subsequent ligation.

Empirical Examples

Detection of Cancer-Related Mutations and Methylation by PCR-LDR-qPCR

General Methods for Empirical Examples 1-4.

The cell lines used were: HT-29 colon adenocarcinoma cell line, which harbors the V600E (1799T>A) BRAF heterozygotic mutation; HEC-1 (A) endometrium adenocarcinoma cell line, which harbors the R248Q (743G>A) TP53 heterozygotic mutation and the G12D (35G>A) KRAS heterozygotic mutation; LS123 colon adenocarcinoma cell line, which harbors the G12S (34G>A) KRAS heterozygotic mutation; SW1463 colon adenocarcinoma cell line, which harbors the G12C (34G>T) KRAS homozygotic mutation; SW480 colon adenocarcinoma cell line, which harbors the G12V (35G>T) KRAS homozygotic mutation; and SW1116 colon adenocarcinoma cell line, which harbors the G12A (35G>C) KRAS heterozygotic mutation. All cell lines were seeded in 60 cm$^2$ culture dishes in McCoy's 5a medium containing 4.5 g/l glucose, supplemented with 10% fetal calf serum and kept in a humidified atmosphere containing 5% $CO_2$. Once cells reached 80-90% confluence they were washed in Phosphate Buffered Saline (×3) and collected by centrifugation (500×g). DNA was isolated using the DNeasy Blood & Tissue Kit (Qiagen; Valencia, Calif.). DNA concentration was determined with Quant-iT Picogreen Assay Life Technologies/ThermoFisher;Waltham, Mass.). Human Genomic DNA (0.2 mg/ml) containing high molecular weight (>50 kb) genomic DNA isolated from human blood (buffy coat) (Roche hgDNA) was purchased from Roche (Indianapolis, Ind.). Its accurate concentration was determined to be 39 ng/µl by Quant-iT PicoGreen dsDNA Assay Kit.

Human plasma (with K2 EDTA as an anti-coagulant) from cancer-free donors, 21-61 years of age was purchased from BioreclamationIVT (Nassau, N.Y.). DNA was isolated from individual plasma samples (5 mL) using the QIAamp Circulating Nucleic Acid Kit according to manufacturer's instructions, and quantified with Quant-iT Picogreen Assay Life Technologies/ThermoFisher; Waltham, Mass.).

Empirical Example 1

Detection of V600E (1799T>A) BRAF Mutation

All primers used are listed in Table 1. All primers were purchased from Integrated DNA Technologies Inc. (IDT, Coralville, Iowa), except for primer iCDx-315-BRAF_FLW, which was purchased from Exiqon Inc. (Woburn, Mass.).

TABLE 1

Primers for PCR-LDR-qPCR detection of BRAF V600E mutation

| Primer Name | Step | Primer Sequence |
|---|---|---|
| iCDx-328-Braf_PF_WT_blk2 | PCR | CCTCACAGTAAAAATAGGTGATTTT GGTCTArGCTAT/3SpC3/ (SEQ ID NO: 1) |
| iCDx-284-Br600-PR | PCR | GGTGTCGTGGTCAAAATGGATCCAG ACAACTGTTCAAAC (SEQ ID NO: 2) |
| iCDx-315-BRAF_FLW | PCR | /5Phos/GCTA+C+AG+T+G-FAAAT+ CTCG/3SpC3/ (SEQ ID NO: 3) |

TABLE 1 -continued

Primers for PCR-LDR-qPCR detection of
BRAF V600E mutation

| Primer Name | Step | Primer Sequence |
|---|---|---|
| iCDx-308-Br600_(3)-L_Up_Rm | LDR | TAGCGATAGTACCGACAGTCACGTCCTA AATAGGTGATTTTGGTCTAGCTACGGAr GAAAC/3SPC3/ (SEQ ID NO: 4) |
| iCDx-276-Br600-L_Dn_P | LDR | /5Phos/GAAATCTCGATGGAGTGGGT CCCATTTGGTGTGCGGAAACCTATCGT CGA (SEQ ID NO: 5) |
| iCDx-277_A4 | qPCR | TAGCGATAGTACCGACAGTCAC (SEQ ID NO: 6) |
| iCDx-279_C4 | qPCR | TCGACGATAGGTTTCCGCAC (SEQ ID NO: 7) |
| iCDx-281-Br600_(3)_Probe | qPCR | 5'-/56-TAMN/TA CGG AGA AAT CTC GAT GGA GTG GGT/ 3IAbRQSp/-3' (SEQ ID NO: 8) |

/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher, green to pink spectral range,
"+"-Locked Nucleic Acid base,
"rA"-ribonucleotide base riboadenosine;
"rT"-ribonucleotide base ribothymidine;
"rG"-ribonucleotide base riboguanosine;
"rC"-ribonucleotide base ribocytosine Dilution experiments. The PCR step was performed in a 10 µl reaction prepared by adding: 1.58 µl of nuclease free water (IDT), 2 µl of Gotaq Flexi buffer 5× without Magnesium (Promega, Madison, Wis.), 0.8 µl of MgCl$_2$ at 25 mM (Promega, Madison, Wis.), 0.2 µl of dNTPs (with dATP, dCTP, dGTP and dUTP, 10 mM each) (Promega, Madison, Wis.), 0.25 µl of iCDx-328-Braf PF WT blk2 forward primer at 2 µM, 0.25 µl of iCDx-284-Br600-PR reverse primer at 2 µM, 1.25 µl of iCDx-284-Br600-PR LNA blocking primer at 2 µM, 0.25 µl of RNAseH2 (IDT) at 20 mU/µl (diluted in RNAseH2 dilution buffer from IDT), 0.2 µl of Antarctic thermolabile UDG (New England Biolabs (NEB), Ipswich, Mass.) at 1 U/µl, and 0.22 µl of Klentaql polymerase (DNA Polymerase Technology, St. Louis, Mo.) mixed with Platinum Taq Antibody (Invitrogen/ThermoFisher Waltham, Mass.) (the mix is prepared by adding 0.02 µl of Klentaql polymerase at 50 U/µl to 0.2 µl of Platinum Taq Antibody at 5 U/µl), and 3 µl of corresponding template. Templates were: nuclease free water for the NTC—Non Template Control—, Roche hgDNA at 11.7 ng/µl (thus, 35 ng or 10000 Genome Equivalents (GE) in 3 µl)—wild type—, and HT-29 wcDNA mixed with Roche hgDNA as follows: 1) 0.047 ng/µl of wcDNA HT-29 in 11.7 ng/µl of Roche hgDNA, thus 0.14 ng of wcDNA HT-29 and 35 ng of Roche hgDNA in 3 µl, which corresponds to 40 GE HT-29 (only 20 GE are mutated) and 10000 GE of Roche human genomic DNA (i.e. 1 mutant (mt) in 500 wild type (wt)); 2) 0.023 ng/µl of wcDNA HT-29 in 11.7 ng/µl of Roche hgDNA, thus 0.07 ng of wcDNA HT-29 and 35 ng of Roche hgDNA in 3 µl, which corresponds to 20 GE HT-29 (only 10 GE are mutated) and 10000 GE of Roche hgDNA; (i.e. 1 mt in 1000 wt) 3) 0.0117 ng/µl of wcDNA HT-29 in 11.7 ng/µl of Roche hgDNA, thus 0.0035 ng of wcDNA HT-29 and 35 ng of Roche hgDNA in 3 µl, which corresponds to 10 GE HT-29 (only 5 GE are mutated) and 10000 GE of Roche hgDNA (i.e. 1 mt in 2000 wt); 4) 0.006 ng/µl of wcDNA HT-29 in 11.7 ng/µl of Roche hgDNA, thus 0.00175 ng of wcDNA HT-29 and 35 ng of Roche hgDNA in 3 µl, which corresponds to 5 GE HT-29 (only 2 or 3 GE are mutated) and 10000 GE of Roche hgDNA (i.e. 1 mt in 5000 wt). Note: after preparing the 0.047 ng/µl of wcDNA HT-29 in 11.7 ng/µl of Roche hgDNA mix (40 GE of mutant in 10000 GE of Roche hgDNA), rest of mutant plus Roche hgDNA mixes are prepared by serial dilutions mixing 0.5 volumes of the preceding mutant-Roche hgDNA mix plus 0.5 volumes of Roche hgDNA at 11.7 ng/µl, so the mutant GE are diluted ½ while Roche hgDNA GE remains undiluted (10000 GE). PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler (Applied Biosystems/ThermoFisher; Waltham, Mass.) and the following program: 30 min at 37° C., 2 min at 95° C., 40 cycles of (10 sec at 94° C., 30 sec at 60° C. and 30 sec at 72° C.), 10 min at 99.5° C., and a final hold at 4° C.

The LDR step was performed in a 10 µl reaction prepared by adding: 5.82 µl of nuclease free water (IDT), 1 µl of 10× AK16D ligase reaction buffer [1× buffer contains 20 mM Tris-HCl pH 8.5 (Bio-Rad, Hercules, Calif.), 5 mM MgCl$_2$ (Sigma-Aldrich, St. Louis, Mo.), 50 mM KCl (Sigma-Aldrich, St. Louis, Mo.), 10 mM DTT (Sigma-Aldrich, St. Louis, Mo.) and 20 ug/ml of BSA (Sigma-Aldrich, St. Louis, Mo.)], 0.25 µl of DTT (Sigma-Aldrich, St. Louis, Mo.) at 40 mM, 0.25 µl of NAD$^+$(Sigma-Aldrich, St. Louis, Mo.) at 40 mM, 0.25 µl of RNAseH2 (IDT) at 20 mU/µl, 0.2 µl of iCDx-308-Br600_(3)-L_Up_Rm Up primer at 500 nM, 0.2 µl of iCDx-276-Br600-L_Dn_P Down primer at 500 nM, 0.028 µl of purified AK16D ligase at 8.8 µM, and 2 µl of PCR reaction. LDR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler (Applied Biosystems/ThermoFisher; Waltham, Mass.) and the following program: 20 cycles of (10 sec at 94° C., and 4 min at 60° C.) followed by a final hold at 4° C.

The qPCR step was performed in a 10 µl reaction prepared by adding: 1.5 µl of nuclease free water (IDT), 5 µl of 2× TaqMan® Fast Universal PCR Master Mix (fast amplitaq, UDG and dUTP) from Applied Biosystems (Applied Biosystems/ThermoFisher; Waltham, Mass.), 1 µl of iCDx-277 A4 forward primer at 2.5 µM, 1 µl of iCDx-279_C4 reverse primer at 2.5 µM, 0.5 µl of iCDx-281-Br600_(3)_Probe Taqman probe at 5 µM, and 1 µl of LDR reaction. qPCR reactions were run in a ViiA7 real-time thermocycler from Applied Biosystems (Applied Biosystems/ThermoFisher; Waltham, Mass.), using MicroAmp® Fast-96-Well Reaction 0.1 ml plates sealed with MicroAmp™ Optical adhesive film Applied Biosystems/ThermoFisher; Waltham, Ma, and the following setting: fast block, Standard curve as experiment type, ROX as passive reference, Ct as quantification method (automatic threshold, but adjusted to 0.04 when needed), TAMRA as reporter, and NFQ-MGB as quencher; and using the following program: 2 min at 50° C., and 40 cycles of (1 sec at 95° C., and 20 sec at 60° C.). Results are shown in FIG. 159 and Table 2.

TABLE 2

Results of dilution experiments to detect BRAF V600E.

| Templates | Starting Genome Equivalents (per 10 µl of PCR) | Ct | Ct Difference vs 10000 GE of Roche hgDNA |
|---|---|---|---|
| HT-29_1 (BRAF V600E, het) + Roche hgDNA (WT) | 40 (20 mt) + 10,000 wt (i.e. 1 mt/ 500 wt) | 16.1 | 16.7 |
| HT-29_1 (BRAF V600E, het) + Roche hgDNA (WT) | 20 (10 mt) + 10,000 wt (i.e. 1 mt/ 1,000 wt) | 22.4 | 10.4 |
| HT-29_1 (BRAF V600E, het) + Roche hgDNA (WT) | 10 (5 mt) + 10,000 wt (i.e. 1 mt/ 2,000 wt) | 22.7 | 10.2 |
| HT-29_1 (BRAF V600E, het) + Roche hgDNA (WT) | 5 (2 or 3 mt) + 10,000 wt (i.e. 1 mt/ 5,000 wt) | 22.0 | 10.9 |
| Roche hgDNA (WT) | 10,000 wt | 32.8 | |
| NTC | N/A | Undetermined | |

Mt = mutant BRAF V600E.
WT = wild-type BRAF.
Het = heterozygote.
UD = Undetermined.
Ct values in bold correspond to Cts obtained from "true curves", and values in normal font type correspond to values obtained from "flat curves," i.e. non-baseline curves that appear in the late amplification cycles (generally after a Ct value of 36).

Pixel experiments using hgDNA from Roche. The PCR step was performed in a 130 µl mixture prepared by adding: 56.54 µl of nuclease free water (IDT), 26 µl of Gotaq Flexi buffer 5× without Magnesium (Promega, Madison, Wis.), 10.4 µl of $MgCl_2$ at 25 mM (Promega, Madison, Wis.), 2.6 µl of dNTPs (with dATP, dCTP, dGTP and dUTP, 10 mM each) (Promega, Madison, Wis.), 3.25 µl of iCDx-328-Braf PF WT blk2 forward primer at 2 µM, 3.25 µl of iCDx-284-Br600-PR reverse primer at 2 µM, 16.25 µl of iCDx-284-Br600-PR LNA blocking primer at 2 µM, 3.25 µl of RNAseH2 (IDT) at 20 mU/µl (diluted in RNAseH2 dilution buffer from IDT), 2.6 µl of Antarctic thermolabile UDG (New England Biolabs (NEB), Ipswich, Mass.) at 1 U/µl, and 2.86 µl of Klentaql polymerase (DNA Polymerase Technology, St. Louis, Mo.) mixed with Platinum Taq Antibody (Invitrogen, Carlsbad, Calif.) (the mix is prepared by adding 0.3 µl of Klentaql polymerase at 50 U/µl to 3 µl of Platinum Taq Antibody at 5 U/µl), and 3 µl of corresponding template. Templates were: nuclease free water for the NTC—Non Template Control—, Roche hgDNA at 2.925 ng/µl (thus, 8.75 ng of Roche hgDNA or 2500 Genome Equivalents (GE) in 3 µl)—wild type—, and HT-29 wcDNA mixed with Roche hgDNA as follows: 1) 0.023 ng/µl of wcDNA HT-29 in 2.925 ng/µl of Roche hgDNA, thus 0.07 ng of wcDNA HT-29 and 8.75 ng of Roche hgDNA in 3 µl, which corresponds to 20 GE HT-29 (only 10 GE are mutated) and 2500 GE of Roche hgDNA; 2) 0.0117 ng/µl of wcDNA HT-29 in 2.925 ng/µl of Roche hgDNA, thus 0.0035 ng of wcDNA HT-29 and 8.75 ng of Roche hgDNA in 3 µl, which corresponds to 10 GE HT-29 (only 5 GE are mutated) and 2500 GE of Roche hgDNA. Note: the 0.0117 ng/µl of wcDNA HT-29 in 2.925 ng/µl of Roche hgDNA mix is prepared by serial dilution mixing 0.5 volume of the 0.023 ng/µl of wcDNA HT-29 in 2.925 ng/µl of Roche hgDNA mix (20 GE of mutant, 10 GE mutated, in 2500 GE of Roche hgDNA) plus 0.5 volume of Roche hgDNA at 2.925 ng/µl, so the mutant is diluted to 10 GE (5 GE mutated) while Roche hgDNA GE remains undiluted (2500 GE).

Each 130 µl PCR mixture was divided into 12 tubes, 10 µl each, and then the PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Mass. and the following program: 30 min at 37° C., 2 min at 95° C., 40 cycles of (10 sec at 94° C., 30 sec at 60° C. and 30 sec at 72° C.), 10 min at 99.5° C., and a final hold at 4° C. The subsequent LDR and qPCR step were performed as described above, in the Dilution experiments section. Results are shown in FIG. 160 and Table 3.

TABLE 3

Results of pixel experiments to detect BRAF V600E diluted in Roche hgDNA.

| Templates | GE per 130 µl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| HT-29_1 (BRAF V600E, het) + Roche hgDNA (wt) | 20 GE (10 mt) + 2500 GE (wt) | 27.7 | 23.0 | 25.2 | 27.5 | 27.4 | 26.0 | 35.7 | 22.6 | 24.9 | 27.1 | 25.8 | 26.4 | 11 |

TABLE 3-continued

Results of pixel experiments to detect BRAF V600E diluted in Roche hgDNA.

| Templates | GE per 130 μl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| HT-29_1 (BRAF V600E, het )+ Roche hgDNA (wt) | 10 GE (5 mt) + 2500 GE (wt) | 35.8 | 31.8 | 27.5 | 36.0 | 26.5 | 31.1 | 31.3 | 23.1 | 35.9 | 23.7 | 36.3 | 35.7 | 7 |
| Roche hgDNA (wt) | 2500 GE (wt) | 36.5 | 37.5 | 36.3 | 36.4 | 35.8 | 37.2 | 36.0 | 36.9 | 37.0 | 36.8 | 36.8 | 36.0 | 0 |
| NTC | N/A | UD | 39.8 | 39.1 | 38.1 | UD | UD | 39.5 | UD | 39.1 | 35.5 | UD | 38.8 | 0 |

Mt = mutant BRAF V600E.
wt = wild-type BRAF.
Het = heterozygote.
UD = Undetermined.
Columns 1-12 correspond to the Cts obtained from tubes 1-12, respectively, with values in bold corresponding to Cts obtained from "true curves", and values in normal font type corresponding to values obtained from "flat curves," i.e. non-baseline curves that appear in the late amplification cycles (generally after a Ct value of 36).

Pixel experiments using human plasma DNA (plasma #8). The PCR step was performed in a 130 μl mixture prepared by adding: 46.54 μl of nuclease free water (IDT), 26 μl of Gotaq Flexi buffer 5× without Magnesium (Promega, Madison, Wis.), 10.4 μl of $MgCl_2$ at 25 mM (Promega, Madison, Wis.), 2.6 μl of dNTPs (with dATP, dCTP, dGTP and dUTP, 10 mM each) (Promega, Madison, Wis.), 3.25 μl of iCDx-328-Braf_PF_WT_blk2 forward primer at 2 μM, 3.25 μl of iCDx-284-Br600-PR reverse primer at 2 μM, 16.25 μl of iCDx-284-Br600-PR LNA blocking primer at 2 μM, 3.25 μl of RNAseH2 (IDT) at 20 mU/μl (diluted in RNAseH2 dilution buffer from IDT), 2.6 μl of Antarctic thermolabile UDG (New England Biolabs (NEB), Ipswich, Mass.) at 1 U/μl, and 2.86 μl of Klentaq1 polymerase (DNA Polymerase Technology, St. Louis, Mo.) mixed with Platinum Taq Antibody (Invitrogen, Carlsbad, Calif.) (the mix is prepared by adding 0.3 μl of Klentaq1 polymerase at 50 U/μl to 3 μl of Platinum Taq Antibody at 5 U/μl), and 13 μl of corresponding template. Templates were: nuclease free water for the NTC—Non Template Control—, Plasma DNA (prepared as 6.9 μl nuclease free $H_2O$ plus 6.1 μl of plasma DNA at 0.714 ng/μl thus, 4.375 ng of plasma DNA or 1250 Genome Equivalents (GE) in the PCR reaction)—wild type—and HT-29 wcDNA mixed with Plasma DNA as follows: 1) 4.9 μl nuclease free H2O, plus 6.1 μl, Plasma DNA at 0.714 ng/μl, plus 2 μl of 0.035 ng/μl of wcDNA HT-29, thus, 4.375 ng of plasma DNA or 1250 Genome Equivalents (GE) plus 0.07 ng of wcDNA HT-29 which corresponds to 20 GE HT-29 (only 10 GE are mutated) in the PCR reaction; 2) 5.9 μl nuclease free H2O, plus 6.1 μl Plasma DNA at 0.714 ng/μl, plus 1 μl of 0.035 ng/μl of wcDNA HT-29, thus, 4.375 ng of plasma DNA or 1250 Genome Equivalents (GE) plus 0.035 ng of wcDNA HT-29 which corresponds to 10 GE HT-29 (only 5 GE are mutated) in the PCR reaction. Note: The mix with 4.375 ng of plasma DNA or 1250 Genome Equivalents (GE) plus 0.035 ng of wcDNA (10 GE of mutant, 5 mutated) is prepared by serial dilution mixing 0.5 volumes of the previous mix with 4.375 ng of plasma DNA or 1250 Genome Equivalents (GE) and 0.07 ng of wcDNA (20 GE of mutant, 10 mutated) with 0.5 volumes of the 4.375 ng of plasma DNA mix.

Each 130 μl PCR mixture was divided into 12 tubes, 10 μl each, and then the PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Mass. and the following program: 30 min at 37° C., 2 min at 95° C., 45 cycles of (10 sec at 94° C., 30 sec at 60° C. and 30 sec at 72° C.), 10 min at 99.5° C., and a final hold at 4° C. The subsequent LDR and qPCR step were performed as described above, in the Dilution experiments section. Results are shown in FIG. 161 and Table 4.

TABLE 4

Results of pixel experiments to detect BRAF V600E diluted in human plasma DNA.

| Templates | GE per 130 μl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| HT-29_1 (BRAF V600E, het) + Human plasma DNA (wt) | 20 GE (10 mt) + 1250 GE (wt) | 35.7 | 22.4 | 19.4 | 34.3 | 21.1 | 19.1 | 28.2 | 16.4 | 34.4 | 29.1 | 34.7 | 18.0 | 8 |
| HT-29_1 (BRAF V600E, het) + Human plasma DNA (wt) | 10 GE (5 mt) + 1250 GE (wt) | 20.3 | 35.5 | 16.6 | 35.0 | 34.8 | 19.3 | 34.3 | 34.2 | 35.3 | 34.3 | 36.0 | 34.9 | 3 |
| Human plasma DNA (wt) | 1250 GE (wt) | 36.4 | UD | 25.6 | 36.0 | 35.1 | 35.7 | 34.7 | 35.3 | 35.8 | 36.2 | 36.2 | 33.0 | 1 |
| NTC | N/A | UD | 39.9 | UD | UD | 38.2 | UD | UD | UD | UD | UD | UD | UD | 0 |

Mt = mutant BRAF V600E.
wt = wild-type BRAF.
Het = heterozygote.
UD = Undetermined.
Columns 1-12 correspond to the Cts obtained from tubes 1-12, respectively, with values in bold corresponding to Cts obtained from "true curves", and values in normal font type corresponding to values obtained from "flat curves," i.e. non-baseline curves that appear in the late amplification cycles (generally after a Ct value of 36).

Empirical Example 2

Detection of R248Q (743G>A) TP53 Mutation

All primers used are listed in Table 5. All primers were purchased from Integrated DNA Technologies Inc. ((IDT), Coralville, Iowa), except for PNA primers, which were purchased from PNABio Inc. (Thousand Oaks, Calif.).

TABLE 5

Primers for PCR-LDR-qPCR detection of TP53 R248Q mutation

| Primer Name | Step | Primer Sequence |
| --- | --- | --- |
| iCDx-326-p53-248_PF_WT_blk2 | PCR | CCTGCATGGGCGGCATGrAACCG/3SpC3/ (SEQ ID NO: 9) |
| iCDx-248-p53-248_PR | PCR | GGTGTCGTGGAAGTGGCAAGTGGCTCC TGAC (SEQ ID NO: 10) |
| PNA-p53-248-10 | PCR | GAACCGGAGG (SEQ ID NO: 11) |
| PNA-p53-248-11L | PCR | TGAACCGGAGG (SEQ ID NO: 12) |
| iCDx-305-P53-248(3)-L_Up_Rm | LDR | TCACTATCGGCGTAGTCACCACAGACGCA TGGGCGGCATGAATCArGAGGT/3SPC3/ (SEQ ID NO: 13) |
| iCDx-202-P53-248-L_Dn_P | LDR | /5Phos/GAGGCCCATCCTCACCATCATCA CGTTGTTGGTGACTTTACCCGGAGGA (SEQ ID NO: 14) |
| iCDx-82_GTT-GCGC_A2 | qPCR | TCACTATCGGCGTAGTCACCA (SEQ ID NO: 15) |
| iCDx-244-C2 | qPCR | TCCTCCGGGTAAAGTCACCA (SEQ ID NO: 16) |
| iCDx-228-p53-248_Probe_s | qPCR | 5'-/56-FAM/CG GCA TGA A/ZEN/T CAG AGG CCC ATC C/3IABkFQ/ (SEQ ID NO: 17) |

PNA = Peptide nucleic acid,
/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher,
green to pink spectral range,
"+"-Locked Nucleic Acid base,
"rA"-ribonucleotide base riboadenosine;
"rT"-ribonucleotide base ribothymidine;
"rG"-ribonucleotide base riboguanosine;
"rC"-ribonucleotide base ribocytosine Dilution experiments. The PCR step was performed in a 10 µl reaction prepared by adding: 1.58 µl of nuclease free water (IDT), 2 µl of Gotaq Flexi buffer 5× without Magnesium (Promega, Madison, Wis.), 0.8 µl of MgCl₂ at 25 mM (Promega, Madison, Wis.), 0.2 µl of dNTPs (with dATP, dCTP, dGTP and dUTP, 10 mM each) (Promega, Madison, Wis.), 0.25 µl of iCDx-326-p53-248_PF_WT_blk2 forward primer at 2 µM, 0.25 µl of iCDx-248-p53-248_PR reverse primer at 2 µM, 1.25 µl of PNA-p53-248-10 PNA blocking primer (or PNA-p53-248-11L in the latest experiments) at 2 µM, 0.25 µl of RNAseH2 (IDT) at 20 mU/µl (diluted in RNAseH2 dilution buffer from IDT), 0.2 µl of Antarctic thermolabile UDG (New England Biolabs (NEB), Ipswich, Mass.) at 1 U/µl, and 0.22 µl of Klentaql polymerase (DNA Polymerase Technology, St. Louis, Mo.) mixed with Platinum Taq Antibody (Invitrogen, Carlsbad, Calif.) (the mix is prepared by adding 0.02 µl of Klentaql polymerase (stock at 50 U/µl) to 0.2 µl of Platinum Taq Antibody (stock at 5 U/µl), and 3 µl of corresponding template. Templates were: nuclease free water for the NTC—Non Template Control —, Roche hgDNA at 11.7 ng/µl (thus, 35 ng or 10000 Genome Equivalents (GE) in 3 µl)—wild type—, and HEC-1(A) wcDNA mixed with Roche hgDNA as follows: 1) 0.047 ng/µl of wcDNA HEC-1(A) in 11.7 ng/µl of Roche hgDNA, thus 0.14 ng of wcDNA HEC-1(A) and 35 ng of Roche hgDNA in 3 µl, which corresponds to 40 GE HEC-1(A) (only 20 GE are mutated) and 10000 GE of Roche human genomic DNA (i.e. 1 mt in 500 wt); 2) 0.023 ng/µl of wcDNA HEC-1(A) in 11.7 ng/µl of Roche hgDNA, thus 0.07 ng of wcDNA HEC-1(A) and 35 ng of Roche hgDNA in 3 µl, which corresponds to 20 GE HEC-1(A) (only 10 GE are mutated) and 10000 GE of Roche hgDNA (i.e. 1 mt in 1000 wt); 3) 0.0117 ng/µl of wcDNA HEC-1(A) in 11.7 ng/µl of Roche hgDNA, thus 0.0035 ng of wcDNA HEC-1(A) and 35 ng of Roche hgDNA in 3 µl, which corresponds to 10 GE HEC-1(A) (only 5 GE are mutated) and 10000 GE of Roche hgDNA (i.e. 1 mt in 2000 wt); 4) 0.006 ng/µl of wcDNA HEC-1(A) in 11.7 ng/µl of Roche hgDNA, thus 0.00175 ng of wcDNA HEC-1(A) and 35 ng of Roche hgDNA in 3 µl, which corresponds to 5 GE HEC-1(A) (only 2 or 3 GE are mutated) and 10000 GE of Roche hgDNA (i.e. 1 mt in 5000 wt). Note: after preparing the 0.047 ng/µl of wcDNA HEC-1(A) in 11.7 ng/µl of Roche hgDNA mix (40 GE of mutant in 10000 GE of Roche hgDNA), rest of mutant plus Roche hgDNA mixes are prepared by serial dilutions mixing 0.5 volumes of the preceding mutant-Roche hgDNA mix plus 0.5 volumes of Roche hgDNA at 11.7 ng/µl, so the mutant GE are diluted ½ while Roche hgDNA GE remains undiluted (10000 GE). PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Mass. and the following program: 30 min at 37° C., 2 min at 95° C., 35 cycles of (10 sec at 94° C., 30 sec at 60° C. and 30 sec at 72° C.), 10 min at 99.5° C., and a final hold at 4° C.

The LDR step was performed in a 10 µl reaction prepared by adding: 5.82 µl of nuclease free water (IDT), 1 µl of 10× AK16D ligase reaction buffer [1× buffer contains 20 mM Tris-HCl pH 8.5 (Bio-Rad, Hercules, Calif.), 5 mM MgCl₂ (Sigma-Aldrich, St. Louis, Mo.), 50 mM KCl (Sigma-Aldrich, St. Louis, Mo.), 10 mM DTT (Sigma-Aldrich, St. Louis, Mo.) and 20 ug/ml of BSA (Sigma-Aldrich, St. Louis, Mo.)], 0.25 µl of DTT (Sigma-Aldrich, St. Louis, Mo.) at 40 mM, 0.25 µl of NAD⁺(Sigma-Aldrich, St. Louis, Mo.) at 40 mM, 0.25 µl of RNAseH2 (IDT) at 20 mU/µl, 0.2 µl of iCDx-305-P53-248(3)-L Up Rm Up primer at 500 nM, 0.2 µl of iCDx-202-P53-248-L Dn P Dn primer at 500 nM, 0.028 µl of purified AK16D ligase at 8.8 µM, and 2 µl of PCR reaction. LDR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Mass. and the following program: 20 cycles of (10 sec at 94° C., and 4 min at 60° C.) followed by a final hold at 4° C.

The qPCR step was performed in a 10 µl reaction prepared by adding: 1.5 µl of nuclease free water (IDT), 5 µl of 2× TaqMan® Fast Universal PCR Master Mix (fast amplitaq, UDG and dUTP) from Applied Biosystems (Applied Biosystems/ThermoFisher; Waltham, Mass.), 1 µl of iCDx-82 GTT-GCGC A2 forward primer at 2.5 µM, 1 µl of iCDx- 244-C2 reverse primer at 2.5 µM, 0.5 µl of iCDx-228-p53-248_Probe_s Taqman probe at 5 µM, and 1 µl of LDR reaction. qPCR reactions were run in a ViiA7 real-time thermocycler from Applied Biosystems (Applied Biosystems/ThermoFisher; Waltham, Mass.), using MicroAmp® Fast-96-Well Reaction 0.1 ml plates sealed with MicroAmp™ Optical adhesive film Applied Biosystems/ThermoFisher; Waltham, Mass., and the following setting: fast block, Standard curve as experiment type, ROX as passive reference, Ct as quantification method (automatic threshold, but adjusted to 0.04 when needed), FAM as reporter, and NFQ-MGB as quencher; and using the following program: 2 min at 50° C., and 40 cycles of (1 sec at 95° C., and 20 sec at 60° C.). Results for the experiment using PNA-p53-248-10 blocking primer in the PCR step are shown in FIG. 162 and Table 6, and results for the experiment using PNA-p53-248-11L blocking primer in the PCR step are shown in FIG. 163 and Table 7.

TABLE 6

Results of dilution experiments to detect TP53 R248Q using PNA-p53-248-10 as blocking primer in the PCR step

| Templates | Starting Genome Equivalents (per 10 µl of PCR) | Ct | Ct Difference vs 10000 GE of Roche hgDNA |
|---|---|---|---|
| HEC-1(A)_1 (TP53 R248Q, het) + Roche hgDNA (WT) | 40 (20 mt) + 10,000 wt (i.e. 1 mt/ 500 wt) | 6.4 | 7.3 |
| HEC-1(A)_1 (TP53 R248Q, het) + Roche hgDNA (WT) | 20 (10 mt) + 10,000 wt (i.e. 1 mt/ 1,000 wt) | 7.6 | 6.0 |
| HEC-1(A)_1 (TP53 R248Q, het) + Roche hgDNA (WT) | 10 (5 mt) + 10,000 wt (i.e. 1 mt/ 2,000 wt) | 10.6 | 3.0 |
| HEC-1(A)_1 (TP53 R248Q, het) + Roche hgDNA (WT) | 5 (2 or 3 mt) + 10,000 wt (i.e. 1 mt/ 5,000 wt) | 11.2 | 2.5 |
| Roche hgDNA (WT) | 10,000 wt | 13.7 | |
| NTC | N/A | UD | |

Mt = mutant TP53 R248Q.
WT = wild-type TP53.
Het = heterozygote.
UD = Undetermined.
Ct values in bold correspond to Cts obtained from "true curves", and values in normal font type correspond to values obtained from "flat curves," i.e. non-baseline curves that appear in the late amplification cycles (generally after a Ct value of 36).

TABLE 7

Results of dilution experiments to detect TP53 R248Q using PNA-p53-248-11L as blocking primer in the PCR step

| Templates | Starting Genome Equivalents (per 10 µl of PCR) | Ct | Ct Difference vs 10000 GE of Roche hgDNA |
|---|---|---|---|
| HEC-1(A)_1 (TP53 R248Q, het) + Roche hgDNA (WT) | 40 (20 mt) + 10,000 wt (i.e. 1 mt/ 500 wt) | 6.2 | 14.5 |
| HEC-1(A)_1 (TP53 R248Q, het) + Roche hgDNA (WT) | 20 (10 mt) + 10,000 wt (i.e. 1 mt/ 1,000 wt) | 15.7 | 5.0 |
| HEC-1(A)_1 (TP53 R248Q, het) + Roche hgDNA (WT) | 10 (5 mt) + 10000 (i.e. 1 mt/ 2,000 wt) | 14.5 | 6.3 |
| HEC-1(A)_1 (TP53 R248Q, het) + Roche hgDNA (WT) | 5 (2 or 3 mt) + 10,000 wt (i.e. 1 mt/ | 16.6 | 4.1 |

TABLE 7-continued

Results of dilution experiments to detect TP53 R248Q using PNA-p53-248-11L as blocking primer in the PCR step

| Templates | Starting Genome Equivalents (per 10 µl of PCR) | Ct | Ct Difference vs 10000 GE of Roche hgDNA |
|---|---|---|---|
| Roche hgDNA (WT) | 5,000 wt) | | |
| Roche hgDNA (WT) | 10,000 wt | 20.7 | |
| NTC | N/A | UD | |

Mt = mutant TP53 R248Q.
WT = wild-type TP53.
Het = heterozygote.
UD = Undetermined.
Ct values in bold correspond to Cts obtained from "true curves", and values in normal font type correspond to values obtained from "flat curves," i.e. non-baseline curves that appear in the late amplification cycles (generally after a Ct value of 36).

Pixel experiments using hgDNA from Roche. The PCR step was performed in a 130 µl mixture prepared by adding: 56.54 µl of nuclease free water (IDT), 26 µl of Gotaq Flexi buffer 5× without Magnesium (Promega, Madison, Wis.), 10.4 µl of MgCl$_2$ at 25 mM (Promega, Madison, Wis.), 2.6 µl of dNTPs (with dATP, dCTP, dGTP and dUTP, 10 mM each) (Promega, Madison, Wis.), 3.25 µl of iCDx-326-p53-248 PF WT blk2 forward primer at 204, 3.25 µl of iCDx-248-p53-248_PR reverse primer at 204, 16.25 µl of PNA-p53-248-10 PNA blocking primer at 204, 3.25 µl of RNAseH2 (IDT) at 20 mU/µl (diluted in RNAseH2 dilution buffer from IDT), 2.6 µl of Antarctic thermolabile UDG (New England Biolabs (NEB), Ipswich, Mass.) at 1 U/µl, and 2.86 µl of Klentaql polymerase (DNA Polymerase Technology, St. Louis, Mo.) mixed with Platinum Taq Antibody (Invitrogen, Carlsbad, Calif.) (the mix is prepared by adding 0.3 µl of Klentaql polymerase at 50 U/µ1 to 3 µl of Platinum Taq Antibody at 5 U/µl), and 3 µl of corresponding template. Templates were: nuclease free water for the NTC—Non Template Control—, Roche hgDNA at 2.925 ng/µl (thus, 8.75 ng of Roche hgDNA or 2500 Genome Equivalents (GE) in 3 µl)—wild type—, and HEC-1(A) wcDNA mixed with Roche hgDNA as follows: 1) 0.023 ng/µl of wcDNA HEC-1(A) in 2.925 ng/µl of Roche hgDNA, thus 0.07 ng of wcDNA HEC-1(A) and 8.75 ng of Roche hgDNA in 3 µl, which corresponds to 20 GE HEC-1(A) (only 10 GE are mutated) and 2500 GE of Roche hgDNA; 2) 0.0117 ng/µl of wcDNA HEC-1(A) in 2.925 ng/µl of Roche hgDNA, thus 0.0035 ng of wcDNA HEC-1 (A) and 8.75 ng of Roche hgDNA in 3 µl, which corresponds to 10 GE HEC-1(A) (only 5 GE are mutated) and 2500 GE of Roche hgDNA. Note: the 0.0117 ng/µl of wcDNA HEC-1(A) in 2.925 ng/µl of Roche hgDNA mix is prepared by serial dilution mixing 0.5 volume of the 0.023 ng/µl of wcDNA HEC-1(A) in 2.925 ng/µl of Roche hgDNA mix (20 GE of mutant, 10 GE mutated, in 2500 GE of Roche hgDNA) plus 0.5 volume of Roche hgDNA at 2.925 ng/µl, so the mutant is diluted to 10 GE (5 GE mutated) while Roche hgDNA GE remains undiluted (2500 GE).

Each 130 µl PCR mixture was divided into 12 tubes, 10 µl each, and then the PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Mass. and the following program: 30 min at 37° C., 2 min at 95° C., 35 cycles of (10 sec at 94° C., 30 sec at 60° C. and 30 sec at 72° C.), 10 min at 99.5° C., and a final hold at 4° C. The subsequent LDR and qPCR step were performed as described above, in the Dilution experiments section. Results are shown in FIG. 164 and Table 8.

TABLE 8

Results of pixel experiments to detect TP53 R248Q diluted in Roche hgDNA.

| Templates | GE per 130 μl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| HEC-1(A)_1 (TP53 R248Q, het) + Roche hgDNA (wt) | 20 GE (10 mt) + 2500 GE (wt) | 34.8 | 18.6 | 30.0 | 27.5 | 20.3 | 18.3 | 18.7 | 17.4 | 21.8 | 17.0 | 19.5 | 19.0 | 9 |
| HEC-1(A)_1 (TP53 R248Q, het) + Roche hgDNA (wt) | 10 GE (5 mt) + 2500 GE (wt) | 19.9 | 20.2 | 22.2 | UD | 19.2 | UD | 18.0 | 34.7 | 34.4 | 19.7 | 31.3 | 18.8 | 7 |
| Roche hgDNA (wt) | 2500 GE (wt) | 37.0 | 28.8 | 33.4 | 28.8 | 33.2 | UD | 32.4 | 34.8 | UD | 34.2 | 20.5 | 34.1 | 1 |
| NTC | N/A | UD | UD | UD | UD | UD | UD | UD | UD | UD | UD | UD | UD | 0 |

Mt = mutant TP53 R24Q.
WT = wild-type TP53.
Het = heterozygote.
UD = Undetermined.

Columns 1-12 correspond to the Cts obtained from tubes 1-12, respectively, with values in bold corresponding to Cts obtained from "true curves", and values in normal font type corresponding to values obtained from "flat curves," i.e. non-baseline curves that appear in the late amplification cycles (generally after a Ct value of 36).

Pixel experiments using human plasma DNA (plasma #10). The PCR step was performed in a 130 μl mixture prepared by adding: 46.54 μl of nuclease free water (IDT), 26 μl of Gotaq Flexi buffer 5× without Magnesium (Promega, Madison, Wis.), 10.4 μl of MgCl$_2$ at 25 mM (Promega, Madison, Wis.), 2.6 μl of dNTPs (with dATP, dCTP, dGTP and dUTP, 10 mM each) (Promega, Madison, Wis.), 3.25 μl of iCDx-326-p53-248_PF_WT_blk2 forward primer at 2 μM, 3.25 μl of iCDx-248-p53-248_PR reverse primer at 2 μM, 16.25 μl of PNA-p53-248-11L PNA blocking primer at 2 μM, 3.25 μl of RNAseH2 (IDT) at 20 mU/μl (diluted in RNAseH2 dilution buffer from IDT), 2.6 μl of Antarctic thermolabile UDG (New England Biolabs (NEB), Ipswich, Mass.) at 1 U/μl, and 2.86 μl of Klentaql polymerase (DNA Polymerase Technology, St. Louis, Mo.) mixed with Platinum Taq Antibody (Invitrogen, Carlsbad, Calif.) (the mix is prepared by adding 0.3 μl of Klentaql polymerase at 50 U/μl to 3 μl of Platinum Taq Antibody at 5 U/μl), and 13 μl of corresponding template. Templates were: nuclease free water for the NTC—Non Template Control—; Plasma DNA (prepared as 7.6 μl nuclease free H2O plus 5.4 μl of plasma DNA at 0.811 ng/μl thus, 4.375 ng of plasma DNA or 1250 Genome Equivalents (GE) in the PCR reaction)—wild type—; and HEC-1(A) wcDNA mixed with Plasma DNA as follows: 1) 5.6 μl nuclease free H2O, plus 5.4 μl Plasma DNA at 0.811 ng/μl, plus 2 μl of 0.035 ng/μl of wcDNA HEC-1(A), thus, 4.375 ng of plasma DNA or 1250 Genome Equivalents (GE) plus 0.07 ng of wcDNA HEC-1(A) which corresponds to 20 GE HEC-1(A) (only 10 GE are mutated) in the PCR reaction; 2) 6.6 μl nuclease free H2O, plus 5.4 μl Plasma DNA at 0.811 ng/μl, plus 1 μl of 0.035 ng/μl of wcDNA HEC-1(A), thus, 4.375 ng of plasma DNA or 1250 Genome Equivalents (GE) plus 0.035 ng of wcDNA HEC-1(A) which corresponds to 10 GE HEC-1(A) (only 5 GE are mutated) in the PCR reaction. Note: The mix with 4.375 ng of plasma DNA or 1250 Genome Equivalents (GE) plus 0.035 ng of wcDNA (10 GE of mutant, 5 mutated) is prepared by serial dilution mixing 0.5 volumes of the previous mix with 4.375 ng of plasma DNA or 1250 Genome Equivalents (GE) and 0.07 ng of wcDNA (20 GE of mutant, 10 mutated) with 0.5 volumes of the 4.375 ng of plasma DNA mix.

Each 130 μl PCR mixture was divided into 12 tubes, 10 μl each, and then the PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler (Applied Biosystems/ThermoFisher; Waltham, Mass.) and the following program: 30 min at 37° C., 2 min at 95° C., 35 cycles of (10 sec at 94° C., 30 sec at 60° C. and 30 sec at 72° C.), 10 min at 99.5° C., and a final hold at 4° C. The subsequent LDR and qPCR step were performed as described above, in the Dilution experiments section. Results are shown in FIG. 165 and Table 9.

TABLE 9

Results of pixel experiments to detect TP53 R248Q diluted in human plasma DNA.

| Templates | GE per 130 μl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| HEC-1(A)_1 (TP53 R248Q, het) + Human plasma DNA (WT) | 20 GE (10 mt) + 1250 GE (wt) | 19.7 | 19.5 | 22.9 | 24.0 | 20.4 | 18.7 | 22.7 | 23.0 | 19.3 | 19.7 | 20.8 | UD | 11 |
| HEC-1(A)_1 (TP53 R248Q, het) + | 10 GE (5 mt) + 1250 GE | UD | UD | 19.9 | UD | 37.1 | UD | 19.7 | 25.9 | 22.9 | UD | 37.4 | UD | 4 |

TABLE 9-continued

Results of pixel experiments to detect TP53 R248Q diluted in human plasma DNA.

| Templates | GE per 130 μl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| Human plasma DNA (WT) | (wt) 1250 GE | UD | UD | UD | UD | UD | UD | UD | UD | UD | UD | UD | UD | 0 |
| Human plasma DNA (WT) | (wt) | | | | | | | | | | | | | |
| NTC | N/A | UD | UD | UD | UD | UD | UD | UD | UD | UD | UD | UD | UD | 0 |

Mt = mutant TP53 R248Q.
WT = wild-type TP53.
Het = heterozygote.
UD = Undetermined.
Columns 1-12 correspond to the Cts obtained from tubes 1-12, respectively, with values in bold corresponding to Cts obtained from "true curves", and values in normal font type corresponding to values obtained from "flat curves," i.e. non-baseline curves that appear in the late amplification cycles (generally after a Ct value of 36).

Empirical Example 3

Detection of KRAS Codon 12 First Position Mutations: G12C (34G>T) and G12S (34G>A)

All primers used are listed in Table 10. All primers were purchased from Integrated DNA Technologies Inc. ((IDT), Coralville, Iowa), except for the PNA primer, which was purchased from PNABio Inc. (Thousand Oaks, Calif.).

TABLE 10

Primers for PCR-LDR-qPCR detection of KRAS G12C and G12S mutations

| Primer Name | Step | Primer Sequence |
|---|---|---|
| iCDx-327-Kr_12_2_PF_WT_blk2 | PCR | TGACTGAATATAAACTTGTGGTAGT TGGArGCTGG/3SpC3/ (SEQ ID NO: 18) |
| iCDx-303-Kr-12_1&2_PR | PCR | GGTGTCGTGGCGTCCACAAAATGAT TCTGAATTAGCTGTA (SEQ ID NO: 19) |
| PNA-Kras 12_2-11L | PCR | GAGCTGGTGGC (SEQ ID NO: 20) |
| PNA-Kras 12_2-11R | PCR | AGCTGGTGGCG (SEQ ID NO: 21) |
| iCDx-393-Kr-12_1 (3)-L_Up_Rm | LDR | TTCGTACCTCGGCACACCAACATAACTG AATATAAACTTGTGGTAGTTGGAGTTHr GTGAT/3SpC3/ (SEQ ID NO: 22) |
| iCDx-222-Kr-12_1-L_Dn_P | LDR | /5Phos/GTGGCGTAGGCAAGAGTGCCT TGACGGCGTGTGGCTCCGTTACTCTGTC GA (SEQ ID NO: 23) |
| iCDx-245_A3 | qPCR | TTCGTACCTCGGCACACCA (SEQ ID NO: 24) |
| iCD x-246-C3 | qPCR | TCGACAGAGTAACGGAGCCA (SEQ ID NO: 25) |
| iCDx-259-T-Kr-12_1_Probe | qPCR | 5'-/5HEX/TT GGA GTT H/ZEN/ GT GGC GTA GGC AAG A/3IABk FQ/-3' (SEQ ID NO: 26) |

PNA = Peptide nucleic acid,
/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Flourescent Dye,
/ZEN/-ZEN ™ Flourescent Quencher ™,
/3IABkFQ/-3' Iowa Black ® Flourescent Quencher, green to pink spectral range,
"+"-Locked Nucleic Acid base,
"rA"-ribonucleotide base riboadenosine;
"rT"-ribonucleotide base ribothymidine;
"rG"-ribonucleotide base riboguanosine;
"rC"-ribonucleotide base ribocytosine Dilution experiments. The PCR step was performed in a 10 μl reaction prepared by adding: 1.58 μl of nuclease free water (IDT), 2 μl of Gotaq Flexi buffer 5× without Magnesium (Promega, Madison, Wis.), 0.8 μl of $MgCl_2$ at 25 mM (Promega, Madison, Wis.), 0.2 μl of dNTPs (with dATP, dCTP, dGTP and dUTP, 10 mM each) (Promega, Madison, Wis.), 0.25 μl of iCDx-327-Kr_12_2 PF_WT_blk2 forward primer at 2 μM, 0.25 μl of iCDx-303-Kr-12_1&2_PR reverse primer at 2 μM, 1.25 μl of PNA-Kras 12_2-11L (or PNA-Kras 12_2-11R) PNA blocking primer at 2 μM, 0.25 μl of RNAseH2 (IDT) at 20 mU/μl (diluted in RNAseH2 dilution buffer from IDT), 0.2 μl of Antarctic thermolabile UDG (New England Biolabs (NEB), Ipswich, Mass.) at 1 U/μl, and 0.22 μl of Klentaql polymerase (DNA Polymerase Technology, St. Louis, Mo.) mixed with Platinum Taq Antibody (Invitrogen, Carlsbad, Calif.) (the mix is prepared by adding 0.02 μl of Klentaql polymerase at 50 U/μl to 0.2 μl of Platinum Taq Antibody at 5 U/μl), and 3 μl of corresponding template. Templates were: nuclease free water for the NTC—Non Template Control—, Roche hgDNA at 11.7 ng/μl (thus, 35 ng or 10000 Genome Equivalents (GE) in 3 μl)—wild type—, and SW1463 (G12C, 34G>T, homozygotic) or LS123 (G125, 34G>A, heterozygotic) wcDNA mixed with Roche hgDNA as follows: 1) 0.047 ng/μl of SW1463 or LS123 wcDNA in 11.7 ng/μl of Roche hgDNA, thus 0.14 ng of SW1463 or LS123 wcDNA and 35 ng of Roche hgDNA in 3 μl, which corresponds to 40 GE of SW1463 or LS123 wcDNA (40 GE are mutated for SW1463, and 20 GE are mutated for LS123) and 10000 GE of Roche human genomic DNA (i.e. 1 mt in 250 wt for SW1463 and 1 mt in 500 wt for LS123); 2) 0.023 ng/µl of SW1463 or LS123 wcDNA in 11.7 ng/µl of Roche hgDNA, thus 0.07 ng of SW1463 or LS123 wcDNA and 35 ng of Roche hgDNA in 3 µl, which corresponds to 20 GE of SW1463 or LS123 wcDNA (20 GE are mutated for SW1463, and 10 GE are mutated for LS123) and 10000 GE of Roche hgDNA (i.e. 1 mt in 500 wt for SW1463 and 1 mt in 1000 for LS123); 3) 0.0117 ng/µl of SW1463 or LS123 wcDNA in 11.7 ng/µl of Roche hgDNA, thus 0.0035 ng of SW1463 or LS123 wcDNA and 35 ng of Roche hgDNA in 3 µl, which corresponds to 10 GE of SW1463 or LS123 wcDNA (10 GE are mutated for SW1463, and 5 GE are mutated for LS123) and 10000 GE of Roche hgDNA (i.e. 1 mt in 1000 wt for SW1463 and 1 mt in 2000 wt for LS123); 4) 0.006 SW1463 or LS123 ng/µl of wcDNA in 11.7 ng/µl of Roche hgDNA, thus 0.00175 ng of SW1463 or LS123 wcDNA and 35 ng of Roche hgDNA in 3 µl, which corresponds to 5 GE of SW1463 or LS123 wcDNA (5 GE are mutated for SW1463, and 2 or 3 GE are mutated for LS123) and 10000 GE of Roche hgDNA (i.e. 1 mt in 2000 wt for SW1463 and 1 mt in 5000 wt for LS123). Note: after preparing the 0.047 ng/µl of SW1463 or LS123 wcDNA in 11.7 ng/µl of Roche hgDNA mix (40 GE of mutant in 10000 GE of Roche hgDNA), rest of mutant plus Roche hgDNA mixes are prepared by serial dilutions mixing 0.5 volumes of the preceding mutant-Roche hgDNA mix plus 0.5 volumes of Roche hgDNA at 11.7 ng/µl so the mutant GE are diluted ½ while Roche hgDNA GE remains undiluted (10000 GE). PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Mass. and the following program: 30 min at 37° C., 2 min at 95° C., 50 cycles of (10 sec at 94° C., 30 sec at 60° C. and 30 sec at 72° C.), 10 min at 99.5° C., and a final hold at 4° C.

The LDR step was performed in a 10 µl reaction prepared by adding: 5.82 µl of nuclease free water (IDT), 1 µl of 10× AK16D ligase reaction buffer [1× buffer contains 20 mM Tris-HCl pH 8.5 (Bio-Rad, Hercules, Calif.), 5 mM MgCl$_2$ (Sigma-Aldrich, St. Louis, Mo.), 50 mM KCl (Sigma-Aldrich, St. Louis, Mo.), 10 mM DTT (Sigma-Aldrich, St. Louis, Mo.) and 20 ug/ml of BSA (Sigma-Aldrich, St. Louis, Mo.)], 0.25 µl of DTT (Sigma-Aldrich, St. Louis, Mo.) at 40 mM, 0.25 µl of NAD$^+$(Sigma-Aldrich, St. Louis, Mo.) at 40 mM, 0.25 µl of RNAseH2 (IDT) at 20 mU/µl, 0.2 µl of iCDx-393-Kr-12_1(3)-L_Up_Rm Up primer at 500 nM, 0.2 µl of iCDx-222-Kr-12_1-L_Dn_P Dn primer at 500 nM, 0.028 µl of purified AK16D ligase at 8.8 µM, and 2 µl of PCR reaction. LDR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Mass. and the following program: 20 cycles of (10 sec at 94° C., and 4 min at 60° C.) followed by a final hold at 4° C.

The qPCR step was performed in a 10 µl reaction prepared by adding: 1.5 µl of nuclease free water (IDT), 5 µl of 2× TaqMan® Fast Universal PCR Master Mix (fast amplitaq, UDG and dUTP) from Applied Biosystems (Applied Biosystems/ThermoFisher; Waltham, Mass.), 1 µl of iCDx-245_A3 forward primer at 2.5 µM, 1 µl of iCDx-246-C3 reverse primer at 2.5 µM, 0.5 µl of iCDx-259-T-Kr-12_1 Probe Taqman probe at 504, and 1 µl of LDR reaction. qPCR reactions were run in a ViiA7 real-time thermocycler from Applied Biosystems (Applied Biosystems/ThermoFisher; Waltham, Mass.), using MicroAmp® Fast-96-Well Reaction 0.1 ml plates sealed with MicroAmp™ Optical adhesive film Applied Biosystems/ThermoFisher; Waltham, Mass., and the following setting: fast block, Standard curve as experiment type, ROX as passive reference, Ct as quantification method (automatic threshold, but adjusted to 0.04 when needed), HEX as reporter, and NFQ-MGB as quencher; and using the following program: 2 min at 50° C., and 40 cycles of (1 sec at 95° C., and 20 sec at 60° C.). Results of the experiment using PNA-Kras 12_2-11L PNA blocking primer in the PCR step are shown in FIG. 166 and Table 11. Results of the experiment using PNA-Kras 12_2-11R PNA blocking primer in the PCR step are shown in FIG. 167 and Table 12.

TABLE 11

Results of dilution experiments to detect KRAS G12C (34G > T) mutation using PNA-Kras 12_2-11L PNA blocking primer in the PCR step.

| Templates | Starting Genome Equivalents (per 10 µl of PCR) | Ct | Ct Difference vs 10000 GE of Roche hgDNA |
|---|---|---|---|
| SW1463_1 (KRAS G12C, hom) + Roche hgDNA (WT) | 40 (40 mt) + 10,000 wt (i.e. 1 mt/250 wt) | 26.0 | 4.9 |
| SW1463_1 (KRAS G12C, hom) + Roche hgDNA (WT) | 20 (20 mt) + 10,000 wt (i.e. 1 mt/500 wt) | 22.1 | 8.8 |
| SW1463_1 (KRAS G12C, hom) + Roche hgDNA (WT) | 10 (10 mt) + 10,000 wt (i.e. 1 mt/1,000 wt) | 24.2 | 6.7 |
| SW1463_1 (KRAS G12C, hom) + Roche hgDNA (WT) | 5 (5 mt) + 10,000 wt (i.e. 1 mt/2,000 wt) | 26.3 | 4.6 |
| Roche hgDNA (WT) | 10,000 wt | 30.9 | |
| NTC | N/A | Undetermined | |

Mt = mutant KRAS G12C.
WT = wild-type KRAS.
Hom = homozygote.
UD = Undetermined.
Ct values in bold correspond to Cts obtained from "true curves", and values in normal font type correspond to values obtained from "flat curves," i.e. non-baseline curves that appear in the late amplification cycles (generally after a Ct value of 36).

TABLE 12

Results of dilution experiments to detect KRAS G12S (34G > A) mutation using PNA-Kras 12_2-11R PNA blocking primer in the PCR step.

| Templates | Starting Genome Equivalents (per 10 µl of PCR) | Ct | Ct Difference vs 10000 GE of Roche hgDNA |
|---|---|---|---|
| LS123_1 (KRAS G12S, het) + Roche hgDNA (WT) | 40 (20 mt) + 10,0000 wt (i.e. 1 mt/500 wt) | 30.5 | 1.6 |
| LS123_1 (KRAS G12S, het) + Roche hgDNA (WT) | 20 (10 mt) + 10,000 wt (i.e. 1 mt/1,000 wt) | 31.2 | 0.9 |
| LS123_1 (KRAS G12S, het) + Roche hgDNA (WT) | 10 (5 mt) + 10,000 wt (i.e. 1 mt/2,000 wt) | 31.4 | 0.7 |
| LS123_1 (KRAS G12S, het) + | 5 (2 or 3 mt) + 10,000 wt (i.e. 1 mt/ | 30.5 | 1.6 |

TABLE 12-continued

Results of dilution experiments to detect KRAS G12S (34G > A) mutation using PNA-Kras 12_2-11R PNA blocking primer in the PCR step.

| Templates | Starting Genome Equivalents (per 10 μl of PCR) | Ct | Ct Difference vs 10000 GE of Roche hgDNA |
|---|---|---|---|
| Roche hgDNA (WT) | 5,000 wt) | | |
| Roche hgDNA (WT) | 10,000 wt | 32.1 | |
| NTC | N/A | 38.4 | |

Mt = mutant KRAS G12S.
WT = wild-type KRAS.
Het = heterozygote.
UD = Undetermined.
Ct values in bold correspond to Cts obtained from "true curves", and values in normal font type correspond to values obtained from "flat curves," i.e. non-baseline curves that appear in the late amplification cycles (generally after a Ct value of 36).

Pixel experiments using human plasma DNA (plasma #9). The PCR step was performed in a 130 μl mixture prepared by adding: 46.54 μl of nuclease free water (IDT), 26 μl of Gotaq Flexi buffer 5× without Magnesium (Promega, Madison, Wis.), 10.4 μl of MgCl$_2$ at 25 mM (Promega, Madison, Wis.), 2.6 μl of dNTPs (with dATP, dCTP, dGTP and dUTP, 10 mM each) (Promega, Madison, Wis.), 3.25 μl of iCDx-327-Kr 12 2 PF WT blk2 forward primer at 2 μM, 3.25 μl of iCDx-303-Kr-12_1&2_PR reverse primer at 2 μM, 16.25 μl of PNA-Kras 12_2-11L PNA blocking primer at 2 μM, 3.25 μl of RNAseH2 (IDT) at 20 mU/μl (diluted in RNAseH2 dilution buffer from IDT), 2.6 μl of Antarctic thermolabile UDG (New England Biolabs (NEB), Ipswich, Mass.) at 1 U/μl, and 2.86 μl of Klentaq1 polymerase (DNA Polymerase Technology, St. Louis, Mo.) mixed with Platinum Taq Antibody (Invitrogen, Carlsbad, Calif.) (the mix is prepared by adding 0.3 μl of Klentaq1 polymerase at 50 U/μl to 3 μl of Platinum Taq Antibody at 5 U/μl), and 13 μl of corresponding template. Templates were: nuclease free water for the NTC—Non Template Control—; Plasma DNA (prepared as 8.3 μl nuclease free H2O plus 4.7 μl of plasma DNA at 0.743 ng/μl thus, 3.5 ng of plasma DNA or 1000 Genome Equivalents (GE) in the PCR reaction)—wild type—; and SW1463 wcDNA mixed with Plasma DNA as follows: 1) 6.3 μl nuclease free H2O, plus 4.7 μl Plasma DNA at 0.743 ng/μl, plus 2 μl of 0.0175 ng/μl of wcDNA SW1463, thus, 3.5 ng of plasma DNA or 1000 Genome Equivalents (GE) plus 0.035 ng of wcDNA SW1463 which corresponds to 10 GE SW1463 (all 10 GE are mutated) in the PCR reaction; 2) 7.3 μl nuclease free H2O, plus 4.7 μl Plasma DNA at 0.743 ng/μl, plus 1 μl of 0.0175 ng/μl of wcDNA SW1463, thus, 3.5 ng of plasma DNA or 1000 Genome Equivalents (GE) plus 0.0175 ng of wcDNA SW1463 which corresponds to 5 GE SW1463 (all 5 GE are mutated) in the PCR reaction. Note: The mix with 3.5 ng of plasma DNA or 1000 Genome Equivalents (GE) plus 0.0175 ng of wcDNA (5 GE of mutant, 5 mutated) is prepared by serial dilution mixing 0.5 volumes of the previous mix with 3.5 ng of plasma DNA or 1000 Genome Equivalents (GE) and 0.035 ng of wcDNA (10 GE of mutant, 10 mutated) with 0.5 volumes of the 3.5 ng of plasma DNA mix.

Each 130 μl PCR mixture was divided into 12 tubes, 10 μl each, and then the PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Mass. and the following program: 30 min at 37° C., 2 min at 95° C., 50 cycles of (10 sec at 94° C., 30 sec at 60° C. and 30 sec at 72° C.), 10 min at 99.5° C., and a final hold at 4° C. The subsequent LDR and qPCR step were performed as described above, in the Dilution experiments section. Results are shown in FIG. 168 and Table 13.

TABLE 13

Results of pixel experiments to detect KRAS G12C diluted in human plasma DNA.

| Templates | GE per 130 μl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| SW1463_1 (KRAS G12C, hom) + Human plasma DNA (WT) | 10 GE (10 mt) + 1000 GE (wt) | UD | 22.4 | UD | UD | 18.9 | UD | 38.1 | 38.8 | 19.6 | 37.8 | 39.6 | 37.6 | 3 |
| SW1463_1 (KRAS G12C, hom) + Human plasma DNA (WT) | 5 GE (5 mt) + 1000 GE (wt) | 38.8 | 39.7 | 19.3 | 25.9 | 37.2 | 39.0 | 17.9 | UD | UD | 39.6 | UD | UD | 3 |
| Human plasma DNA (WT) | 1000 GE | 39.1 | 38.4 | UD | 38.4 | 39.4 | UD | 38.3 | 38.0 | UD | 39.4 | UD | UD | 0 |
| NTC | N/A | UD | 39.4 | UD | UD | UD | 37.8 | UD | UD | UD | UD | 38.7 | UD | 0 |

Mt = mutant KRAS G12C.
WT = wild-type KRAS.
Hom = homozygote
UD = Undetermined.

Columns 1-12 correspond to the Cts obtained from tubes 1-12, respectively, with values in bold corresponding to Cts obtained from "true curves", and values in normal font type corresponding to values obtained from "flat curves," i.e. non-baseline curves that appear in the late amplification cycles (generally after a Ct value of 36).

Empirical Example 4

Detection of KRAS Codon 12 Second Position Mutations: G12D (35G>A), G12A (35G>C) and G12V (35G>T)

All primers used are listed in Table 14. All primers were purchased from Integrated DNA Technologies Inc. ((IDT), Coralville, Iowa), except for the PNA primer, which was purchased from PNABio Inc. (Thousand Oaks, Calif.).

TABLE 14

Primers for PCR-LDR-qPCR detection of KRAS G12D, G12A and G12V mutations

| Primer Name | Step | Primer Sequence |
|---|---|---|
| iCDx-327-Kr_12_2_PF_WT_blk2 | PCR | TGACTGAATATAAACTTGTGGTAGTT GGArGCTGG/3SpC3/ (SEQ ID NO: 18) |
| iCDx-303-Kr-12_1&2_PR | PCR | GGTGTCGTGGCGTCCACAAAATGATTCT GAATTAGCTGTA (SEQ ID NO: 19) |
| PNA-Kras_12_2-11L | PCR | GAGCTGGTGGC (SEQ ID NO: 20) |
| iCDx-307-Kr-12_2(3)-L_Up_Rm | LDR | TTCGTACCTCGGCACACCAACATATG AATATAAACTTGTGGTAGTTGGAGCCGH rUGGCA/3SpC3/ (SEQ ID NO: 27) |
| iCDx-394-Kr-12_2(3)-L_Up_Rm | LDR | TTCGTACCTCGGCACACCAACATATG AATATAAACTTGTGGTAGTTGGAGCCGH rUGGTA/3SpC3/ (SEQ ID NO: 28) |
| iCDx-269-Kr-12_2-L_Dn_P | LDR | /5Phos/ TGGCGTAGGCAAGAGTGCCTTG ACGGCGTGTGGCTCCGTTACTCTGTCG A (SEQ ID NO: 29) |
| iCDx-245 A3 | qPCR | TTCGTACCTCGGCACACCA (SEQ ID NO: 24) |
| iCDx-246-C3 | qPCR | TCGACAGAGTAACGGAGCCA (SEQ ID NO: 25) |
| iCDx-270-Kr-e 12_2(3)_Prob | qPCR | 5'-/5HEX/TAG TTG GAG/ZEN/CCG HTG GCG TAG G/3IABkFQ/-3' (SEQ ID NO: 30) |

PNA = Peptide nucleic acid,
/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher,
green to pink spectral range,
"+"-Locked Nucleic Acid base,
"rA"-ribonucleotide base riboadenosine;
"rT"-ribonucleotide base ribothymidine;
"rG"-ribonucleotide base riboguanosine;
"rC"-ribonucleotide base ribocytosine Dilution experiments. The PCR step was performed in a 10 µl reaction prepared by adding: 1.58 µl of nuclease free water (IDT), 2 µl of Gotaq Flexi buffer 5× without Magnesium (Promega, Madison, Wis.), 0.8 µl of MgCl$_2$ at 25 mM (Promega, Madison, Wis.), 0.2 µl of dNTPs (with dATP, dCTP, dGTP and dUTP, 10 mM each) (Promega, Madison, Wis.), 0.25 µl of iCDx-327-Kr_12_2_PF_WT_blk2 forward primer at 2 µM, 0.25 µl of iCDx-303-Kr-12_1&2_PR reverse primer at 2 µM, 1.25 µl of PNA-Kras 12_2-11L PNA blocking primer at 2 µM, 0.25 µl of RNAseH2 (IDT) at 20 mU/µl (diluted in RNAseH2 dilution buffer from IDT), 0.2 µl of Antarctic thermolabile UDG (New England Biolabs (NEB), Ipswich, Mass.) at 1 U/µl, and 0.22 µl of Klentaq1 polymerase (DNA Polymerase Technology, St. Louis, Mo.) mixed with Platinum Taq Antibody (Invitrogen, Carlsbad, Calif.) (the mix is prepared by adding 0.02 µl of Klentaq1 polymerase at 50 U/µl to 0.2 µl of Platinum Taq Antibody at 5 U/µl), and 3 µl of corresponding template. Templates were: nuclease free water for the NTC—Non Template Control—, Roche hgDNA at 11.7 ng/µl (thus, 35 ng or 10000 Genome Equivalents (GE) in 3 µl)—wild type—, HEC-1(A) (G12D, 35G>A, heterozygotic) or SW1116 (G12A, 35G>C, heterozygotic) or SW480 (G12V, 35G>T, homozygotic) wcDNA mixed with Roche hgDNA as follows: 1) 0.047 ng/µl of HEC-1(A), SW1116 or SW480 wcDNA in 11.7 ng/µl of Roche hgDNA, thus 0.14 ng of HEC-1(A), SW1116 or SW480 and 35 ng of Roche hgDNA in 3 µl, which corresponds to 40 GE of HEC-1(A), SW1116 or SW480 (20 GE are mutated for HEC-1(A) or SW1116, and 40 GE are mutated for SW480) and 10000 GE of Roche human genomic DNA (i.e. 1 mt in 500 wt for HEC-1(A) or SW1116 and 1 mt in 250 for SW480; 2) 0.023 ng/µl of wcDNA of HEC-1(A), SW1116 or SW480 in 11.7 ng/µl of Roche hgDNA, thus 0.07 ng of HEC-1(A), SW1116 or SW480 wcDNA and 35 ng of Roche hgDNA in 3 µl, which corresponds to 20 GE of HEC-1(A), SW1116 or SW480 (10 GE are mutated for HEC-1(A) or SW1116, and 20 GE are mutated for SW480) and 10000 GE of Roche hgDNA (i.e. 1 mt in 1000 wt for HEC-1(A) or SW1116 and 1 mt in 500 wt for SW480); 3) 0.0117 ng/µl of HEC-1(A), SW1116 or SW480 wcDNA in 11.7 ng/µl of Roche hgDNA, thus 0.0035 ng of HEC-1(A), SW1116 or SW480 wcDNA and 35 ng of Roche hgDNA in 3 µl, which corresponds to 10 GE of HEC-1(A), SW1116 or SW480 (5 GE are mutated for HEC-1(A) or SW1116, and 10 GE are mutated for SW480) and 10000 GE of Roche hgDNA (i.e. 1 mt in 2000 for HEC-1(A) or SW1116 and 1 mt in 1000 for SW480); 4) 0.006 ng/µl of HEC-1(A), SW1116 or SW480 wcDNA in 11.7 ng/µl of Roche hgDNA, thus 0.00175 ng of HEC-1(A), SW1116 or SW480 wcDNA and 35 ng of Roche hgDNA in 3 µl, which corresponds to 5 GE of HEC-1(A), SW1116 or SW480 (2 or 3 GE are mutated for HEC-1(A) or SW1116, and 5 GE are mutated for SW480) and 10000 GE of Roche hgDNA (i.e. 1 mt in 5000 wt for HEC-1(A) or SW1116 and 1 mt in 2000 wt for SW480). Note: after preparing the 0.047 ng/µl of HEC-1(A), SW1116 or SW480 wcDNA in 11.7 ng/µl of Roche hgDNA mix (40 GE of mutant in 10000 GE of Roche hgDNA), rest of mutant plus Roche hgDNA mixes are prepared by serial dilutions mixing 0.5 volumes of the preceding mutant-Roche hgDNA mix plus 0.5 volumes of Roche hgDNA at 11.7 ng/µl so the mutant GE are diluted ½ while Roche hgDNA GE remains undiluted (10000 GE). PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler (Applied Biosystems/ThermoFisher; Waltham, Mass.) and the following program: 30 min at 37° C., 2 min at 95° C., 50 cycles of (10 sec at 94° C., 30 sec at 60° C. and 30 sec at 72° C.), 10 min at 99.5° C., and a final hold at 4° C.

The LDR step was performed in a 10 µl reaction prepared by adding: 5.82 µl of nuclease free water (IDT), 1 µl of 10× AK16D ligase reaction buffer [1× buffer contains 20 mM Tris-HCl pH 8.5 (Bio-Rad, Hercules, Calif.), 5 mM MgCl$_2$ (Sigma-Aldrich, St. Louis, Mo.), 50 mM KCl (Sigma-Aldrich, St. Louis, Mo.), 10 mM DTT (Sigma-Aldrich, St. Louis, Mo.) and 20 ug/ml of BSA (Sigma-Aldrich, St. Louis, Mo.)], 0.25 μl of DTT (Sigma-Aldrich, St. Louis, Mo.) at 40 mM, 0.25 μl of NAD+ (Sigma-Aldrich, St. Louis, Mo.) at 40 mM, 0.25 μl of RNAseH2 (IDT) at 20 mU/μl, 0.2 μl of iCDx-307-Kr-12_2(3)-L_Up_Rm or iCDx-394-Kr-12_2(3)-L_Up_Rm Up primer at 500 nM, 0.2 μl of iCDx-269-Kr-12_2-L_Dn_P Dn primer at 500 nM, 0.028 μl of purified AK16D ligase at 8.8 μM, and 2 μl of PCR reaction. LDR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Ma and the following program: 20 cycles of (10 sec at 94° C., and 4 min at 60° C.) followed by a final hold at 4° C.

The qPCR step was performed in a 10 μl reaction prepared by adding: 1.5 μl of nuclease free water (IDT), 5 μl of 2× TaqMan® Fast Universal PCR Master Mix (fast amplitaq, UDG and dUTP) from Applied Biosystems (Applied Biosystems/ThermoFisher; Waltham, Mass.), 1 μl of iCDx-245 A3 forward primer at 2.5 μM, 1 μl of iCDx-246-C3 reverse primer at 2.5 μM, 0.5 μl of iCDx-270-Kr-12_2(3) Probe Taqman probe at 5 μM, and 1 μl of LDR reaction. qPCR reactions were run in a ViiA7 real-time thermocycler from Applied Biosystems (Applied Biosystems/ThermoFisher; Waltham, Mass.), using MicroAmp® Fast-96-Well Reaction 0.1 ml plates sealed with MicroAmp™ Optical adhesive film Applied Biosystems/ThermoFisher; Waltham, Mass., and the following setting: fast block, Standard curve as experiment type, ROX as passive reference, Ct as quantification method (automatic threshold, but adjusted to 0.04 when needed), HEX as reporter, and NFQ-MGB as quencher; and using the following program: 2 min at 50oC, and 40 cycles of (1 sec at 95° C., and 20 sec at 60° C.). Results of the experiment to detect KRAS G12D (35G>A) mutation using iCDx-307-Kr-12_2(3)-L up Rm UP LDR primer are shown in FIG. 169 and Table 15. Results of the experiment to detect KRAS G12A (G>C) mutation using iCDx-307-Kr-12_2(3)-L up Rm UP LDR primer are shown in FIG. 170 and Table 16. Results of the experiment to detect KRAS G12V (35G>T) mutation using iCDx-307-Kr-12_2(3)-L up Rm UP LDR primer are shown in FIG. 171 and Table 17.

TABLE 15

Results of dilution experiments to detect KRAS G12D (35G > A) mutation using iCDx-307-Kr-12_2(3)-L_Up_Rm UP LDR primer.

| Templates | Starting Genome Equivalents (per 10 μl of PCR) | Ct | Ct Difference vs 10000 GE of Roche hgDNA |
|---|---|---|---|
| HEC-1(A)_1 (KRAS G12D, het) + Roche hgDNA | 40 (20 mt) + 10,000 wt (i.e. 1 mt/500 wt) | 28.4 | 6.0 |
| HEC-1(A)_1 (KRAS G12D, het) + Roche hgDNA | 20 (10 mt) + 10,000 wt (i.e. 1 mt/1,000 wt) | 31.0 | 3.5 |
| HEC-1(A)_1 (KRAS G12D, het) + Roche hgDNA | 10 (5 mt) + 10,000 wt (i.e. 1 mt/2,000 wt) | 32.2 | 2.2 |
| HEC-1(A)_1 (KRAS G12D, het) + | 5 (2 or 3 mt) + 10,000 wt (i.e. 1 | 29.8 | 4.6 |

TABLE 15-continued

Results of dilution experiments to detect KRAS G12D (35G > A) mutation using iCDx-307-Kr-12_2(3)-L_Up_Rm UP LDR primer.

| Templates | Starting Genome Equivalents (per 10 μl of PCR) | Ct | Ct Difference vs 10000 GE of Roche hgDNA |
|---|---|---|---|
| Roche hgDNA (WT) | mt/5,000 wt) | | |
| Roche hgDNA (WT) | 10,000 wt | 34.4 | |
| NTC | N/A | 35.1 | |

Mt = mutant KRAS G12D.
WT = wild-type KRAS.
Het = heterozygote.
UD = Undetermined.
Ct values in bold correspond to Cts obtained from "true curves", and values in normal font type correspond to values obtained from "flat curves," i.e. non-baseline curves that appear in the late amplification cycles (generally after a Ct value of 36).

TABLE 16

Results of dilution experiments to detect KRAS G12A (35G > C) mutation using iCDx-307-Kr-12_2(3)-L_Up_Rm UP LDR primer.

| Templates | Starting Genome Equivalents (per 10 μl of PCR) | Ct | Ct Difference vs 10000 GE of Roche hgDNA |
|---|---|---|---|
| SW1116 (KRAS G12A, het) + Roche hgDNA (WT) | 40 (20 mt) + 10,000 wt (i.e. 1 mt/500 wt) | 24.8 | 9.6 |
| SW1116 (KRAS G12A, het) + Roche hgDNA (WT) | 20 (10 mt) + 10,000 wt (i.e. 1 mt/1,000 wt) | 23.6 | 10.8 |
| SW1116 (KRAS G12A, het) + Roche hgDNA (WT) | 10 (5 mt) + 10,000 wt (i.e. 1 mt/2,000 wt) | 25.2 | 9.2 |
| SW1116 (KRAS G12A, het) + Roche hgDNA (WT) | 5 (2 or 3 mt) + 10,000 wt (i.e. 1 mt/5,000 wt) | 28.9 | 5.6 |
| Roche hgDNA (WT) | 10,000 wt | 34.4 | |
| NTC | N/A | 36.0 | |

Mt = mutant KRAS G12A.
WT = wild-type KRAS.
Het = heterozygote.
UD = Undetermined.
Ct values in bold correspond to Cts obtained from "true curves", and values in normal font type correspond to values obtained from "flat curves," i.e. non-baseline curves that appear in the late amplification cycles (generally after a Ct value of 36).

TABLE 17

Results of dilution experiments to detect KRAS G12V (35G > T) mutation using iCDx-307-Kr-12_2(3)-L_Up_Rm UP LDR primer.

| Templates | Starting Genome Equivalents (per 10 μl of PCR) | Ct | Ct Difference vs 10000 GE of Roche hgDNA |
|---|---|---|---|
| SW480 (KRAS G12V, hom) + Roche hgDNA (WT) | 40 (40 mt) + 10,000 wt (i.e. 1 mt/ 250 wt) | 21.9 | 12.6 |
| SW480 (KRAS G12V, hom) + Roche hgDNA (WT) | 20 (20 mt) + 10,000 wt (i.e. 1 mt/ 500 wt) | 22.8 | 11.6 |
| SW480 (KRAS G12V, hom) + Roche hgDNA (WT) | 10 (10 mt) + 10,000 wt (i.e. 1 mt/ 1,000 wt) | 24.0 | 10.5 |
| SW480 (KRAS G12V, hom) + | 5 (5 mt) + 10,000 wt (i.e. 1 mt/ | 27.9 | 6.5 |

TABLE 17-continued

Results of dilution experiments to detect KRAS G12V (35G > T) mutation using iCDx-307-Kr-12_2(3)-L_Up_Rm UP LDR primer.

| Templates | Starting Genome Equivalents (per 10 µl of PCR) | Ct | Ct Difference vs 10000 GE of Roche hgDNA |
|---|---|---|---|
| Roche hgDNA (WT) | 2,000 wt | | |
| Roche hgDNA (WT) | 10,000 wt | 34.4 | |
| NTC | N/A | 34.8 | |

Mt = mutant KRAS G12V.
WT = wild-type KRAS.
Hom = homozygote.
UD = Undetermined.
Ct values in bold correspond to Cts obtained from "true curves", and values in normal font type correspond to values obtained from "flat curves," i.e. non-baseline curves that appear in the late amplification cycles (generally after a Ct value of 36).

Pixel experiments using human plasma DNA (plasma #9). The PCR step was performed in a 130 µl mixture prepared by adding: 46.54 µl of nuclease free water (IDT), 26 µl of Gotaq Flexi buffer 5× without Magnesium (Promega, Madison, Wis.), 10.4 µl of $MgCl_2$ at 25 mM (Promega, Madison, Wis.), 2.6 µl of dNTPs (with dATP, dCTP, dGTP and dUTP, 10 mM each) (Promega, Madison, Wis.), 3.25 µl of iCDx-327-Kr_12_2_PF_WT_blk2 forward primer at 2 µM, 3.25 µl of iCDx-303-Kr-12_1&2_PR reverse primer at 2 µM, 16.25 µl of PNA-Kras 12_2-11L PNA blocking primer at 2 µM, 3.25 µl of RNAseH2 (IDT) at 20 mU/µl (diluted in RNAseH2 dilution buffer from IDT), 2.6 µl of Antarctic thermolabile UDG (New England Biolabs (NEB), Ipswich, Mass.) at 1 U/µl, and 2.86 µl of Klentaql polymerase (DNA Polymerase Technology, St. Louis, Mo.) mixed with Platinum Taq Antibody (Invitrogen, Carlsbad, Calif.) (the mix is prepared by adding 0.3 µl of Klentaql polymerase at 50 U/µl to 3 µl of Platinum Taq Antibody at 5 U/µl), and 13 µl of corresponding template. Templates were: nuclease free water for the NTC—Non Template Control—; Plasma DNA (prepared as 8.3 µl nuclease free H2O plus 4.7 µl of plasma DNA at 0.743 ng/µl thus, 3.5 ng of plasma DNA or 1000 Genome Equivalents (GE) in the PCR reaction)—wild type—; and SW480 wcDNA mixed with Plasma DNA as follows: 1) 6.3 µl nuclease free H2O, plus 4.7 µl Plasma DNA at 0.743 ng/µl, plus 2 µl of 0.0175 ng/µl of SW480 wcDNA, thus, 3.5 ng of plasma DNA or 1000 Genome Equivalents (GE) plus 0.035 ng of SW480 wcDNA which corresponds to 10 GE of SW480 wcDNA (all 10 GE are mutated) in the PCR reaction; 2) 7.3 µl nuclease free H2O, plus 4.7 µl Plasma DNA at 0.743 ng/µl, plus 1 µl of 0.0175 ng/µl of SW480 wcDNA, thus, 3.5 ng of plasma DNA or 1000 Genome Equivalents (GE) plus 0.0175 ng of SW480 wcDNA which corresponds to 5 GE of SW480 (all 5 GE are mutated) in the PCR reaction. Note: The mix with 3.5 ng of plasma DNA or 1000 Genome Equivalents (GE) plus 0.0175 ng of SW480 wcDNA (5 GE of mutant, 5 mutated) is prepared by serial dilution mixing 0.5 volumes of the previous mix with 3.5 ng of plasma DNA or 1000 Genome Equivalents (GE) and 0.035 ng of SW480 wcDNA (10 GE of mutant, 10 mutated) with 0.5 volumes of the 3.5 ng of plasma DNA mix.

Each 130 µl PCR mixture was divided into 12 tubes, 10 µl each, and then the PCR reactions were run in BioExcell Clear 96 Well PCR 0.2 ml plates (Worldwide Medical Products, Inc., Bristol, Pa.) sealed with MicroAmp® clear adhesive film from Applied Biosystems (Applied Biosystems/ThermoFisher; Waltham, Mass.), using a Proflex PCR system thermocycler Applied Biosystems/ThermoFisher; Waltham, Ma and the following program: 30 min at 37° C., 2 min at 95° C., 50 cycles of (10 sec at 94° C., 30 sec at 60° C. and 30 sec at 72° C.), 10 min at 99.5° C., and a final hold at 4° C. The subsequent LDR and qPCR step were performed as described above, in the Dilution experiments section, using iCDx-394-Kr-12_2(3)-L_Up_Rm as Upstream primer for the LDR step. Results are shown in FIG. 172 and Table 18.

TABLE 18

Results of pixel experiments to detect KRAS G12V diluted in human plasma DNA.

| Templates | GE per 130 µl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| SW480_1 (KRAS G12V, hom) + Human plasma DNA (WT) | 10 GE (10 mt) + 1000 GE (wt) | 35.5 | 19.4 | 21.5 | 35.6 | 18.8 | 19.3 | 19.4 | 34.9 | 22.6 | 22.0 | 20.0 | 20.5 | 9 |
| SW480_1 (KRAS G12V, hom) + Human plasma DNA (WT) | 5 GE (5 mt) + 1000 GE (wt) | 22.4 | 21.0 | 20.3 | 22.3 | 20.2 | 35.3 | 35.0 | 19.6 | 19.8 | 26.5 | 35.7 | 20.4 | 9 |
| Human plasma DNA (WT) | 1000 GE (wt) | 37.9 | 36.1 | 36.3 | 36.2 | 35.7 | 36.2 | 36.4 | 35.5 | 36.0 | 37.1 | 36.3 | 35.9 | 0 |
| NTC | N/A | 36.0 | 36.6 | 35.9 | 36.9 | 36.2 | 36.2 | 36.7 | 36.5 | 37.2 | 36.5 | 36.8 | 35.9 | 0 |

Mt = mutant KRAS G12V.
WT = wild-type KRAS.
Hom = homozygote.
UD = Undetermined.
Columns 1-12 correspond to the Cts obtained from tubes 1-12, respectively, with values in bold corresponding to Cts obtained from "true curves", and values in normal font type corresponding to values obtained from "flat curves," i.e. non-baseline curves that appear in the late amplification cycles (generally after a Ct value of 36).

Empirical Example 5

Detection of Methylation in Cell Line Genomic DNA

General Methods. The cell lines used were: LS-174T, HCT-15, HT-29, WiDi, SW1116, colon adenocarcinoma cell line. All cell lines were seeded in 60 $cm^2$ culture dishes in McCoy's 5a medium containing 4.5 g/l glucose, supplemented with 10% fetal calf serum and kept in a humidified atmosphere containing 5% $CO_2$. Once cells reached 80-90% confluence they were washed in Phosphate Buffered Saline (×3) and collected by centrifugation (500×g). DNA was isolated using the DNeasy Blood & Tissue Kit (Qiagen; Valencia, Calif.). DNA concentration was determined with Quant-iT Picogreen Assay (Life Technologies/ThermoFisher; Waltham, Mass.).

Human Genomic DNA (0.2 mg/ml) containing high molecular weight (>50 kb) genomic DNA isolated from human blood (buffy coat) (Roche human genomic DNA) was purchased from Roche (Indianapolis, Ind.). Its concentration was determined to be 39 ng/µl by Quant-iT PicoGreen dsDNA Assay Kit.

Restriction Digestion of Genomic DNA with Enzyme Bsh1236I. Genomic DNA (500 ng) from the cell lines listed above were digested with 10 units of the restriction enzyme Bsh1236I in 20 µl of reaction mixture containing 1×CutSmart buffer (50 mM Potassium Acetate, 20 mM TrisAcetate, 10 mM Magnesium Acetate, 100 µg/ml BSA, pH7.9 @ 25° C.). The digestion reactions were carried out at 37° C. for 1 hour and subsequent enzyme inactivation by heating to 80° C. for 20 min.

Bisulfite conversion of digested genomic DNA. Bisulfite conversion was carried out using the EZ DNA MethylationLightning kit from Zymo Research Corporation (Irvine, Calif.). 130 µl of Lightning Conversion Reagent was added to 20 µl of the Bsh1236I digested genomic DNA. The conversion reaction was incubated at 98° C. for 8 minutes, followed by 54° C. for one hour and then cooled down to 4° C. 600 µl of M-Binding Buffer was added to a Zymo-Spin™ Column followed by column placement into a collection tube. The 150 µl reaction mixture containing digested DNA and lightning conversion reagent was loaded into the ZymoSpin IC Column containing the 600 µl of M-Binding Buffer. The cap of the column was sealed, and the solution was mixed by inverting the column several times. The column was centrifuged at full speed (≥10,000×g) for 30 sec with the flow through discarded. 100 µl of M-washing buffer was added to the column and the column was centrifuged at full speed for 30 seconds and the flow through was discarded. 200 µl of L-Desulphonation Buffer was added into the column, and the column was allowed to stand at room temperature for 15-20 minutes. After the incubation, the column was centrifuged at full speed for 30 seconds. 200 µl of M-Wash Buffer was added to the column and the column was centrifuged at full speed for 30 seconds with the flow through discarded. This wash step was repeated one more time. Finally, the column was placed into a 1.5 ml micro centrifuge tube, and 10 µl of M-Elution buffer was added to the column matrix and centrifuged at full speed for 30 second to elute the Bisulfite converted DNA.

PCR and LDR primers. All primers used are listed in Table 19. All primers were purchased from Integrated DNA Technologies Inc. ((IDT), Coralville, Iowa), except for LNA1 and LNA2, which was purchased from Exiqon Inc. (Woburn, Mass.), and PNA, which was purchased from PNA Bio (Thousand Oaks, Calif.).

TABLE 19

Primers for PCR-LDR-qPCR methylation.

| Primer Name | Step | Primer Sequence |
|---|---|---|
| iCDx-2031-Vim-S3-FP | PCR | GAACTCCAACCGAAACTACGTA ArCTACA/3SpC3/ (SEQ ID NO: 31) |

TABLE 19-continued

Primers for PCR-LDR-qPCR methylation.

| Primer Name | Step | Primer Sequence |
|---|---|---|
| iCDx-2032A-Vim-S3-RP | PCR | GGTGTCGTGGACGAGGCGTAGA GGTTGCrGGTTA/3SpC/ (SEQ ID NO: 32) |
| VIM-53-LNA1 | PCR | CA+TAA+CT+AC+AT+CC+AC+ CCA (SEQ ID NO: 33) |
| VIM-S3-LNA2 | PCR | CA+TAA+CT+AC+AT+C+C+AC+ CCA (SEQ ID NO: 34) |
| VIM-S3-PNA2 | PCR | ACATAACTACATCCACCCA (SEQ ID NO: 35) |
| iCDx-2033A-Vim-53-Up | LDR | TAGACACGAGCGAGGTCACAACT CCAACCGAAACTACGTAACTGCG rUCCGT/3SpC3/ (SEQ ID NO: 36) |
| iCDx-2034A-Vim-53-Dn | LDR | /5Phos/TCCACCCGCACCTACA ACCTAAACAACGCGTGCAAAATT CAGGCTGTGCA (SEQ ID NO: 37) |
| iCDx-2035A-Vim-53-RT-Pb | qPCR | TAACTGCGTCCACCCGCACCTAC (SEQ ID NO: 38) |
| iCDx-2036-Vim-53-RT-FP | qPCR | TAGACACGAGCGAGGTCAC (SEQ ID NO: 39) |
| iCDx-2037-Vim-53-RT-RP | qPCR | TGCACAGCCTGAATTTTGCAC (SEQ ID NO: 40) |

/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher,
green to pink spectral range,
"+"-Locked Nucleic Acid base,
"rA"-ribonucleotide base riboadenosine;
"rT"-ribonucleotide base ribothymidine;
"rG"-ribonucleotide base riboguanosine;
"rC"-ribonucleotide base ribocytosine PCR-LDR-qPCR experiments. The PCR step was performed in a 10 µl reaction prepared by adding: 2 µl of Gotaq Flexi buffer 5× without Magnesium (Promega, Madison, Wis.), 0.8 µl of MgCl$_2$ at 25 mM (Promega, Madison, Wis.), 0.4 l of dNTPs (with dATP, dCTP, dGTP and dUTP, 10 mM each) (Promega, Madison, Wis.), 0.25 µl of iCDx-2031-Vim-S3-FP forward primer at 2 µM, 0.25 µl of iCDx-2032A-Vim-S3-RP reverse primer at 2 µM, 1.25 µl of VIM-S3-LNA or VIM-S3-PNA2 blocking primer at 2 µM, 0.25 µl of RNAseH2 (IDT) at 20 mU/µl (diluted in RNAseH2 dilution buffer from IDT), and 0.22 µl of Klentaql polymerase (DNA Polymerase Technology, St. Louis, Mo.) mixed with Platinum Taq Antibody (Invitrogen/Thermo Fisher, Waltham, Mass.) (the mixture is prepared by adding 0.02 µl of Klentaql polymerase at 50 U/µl to 0.2 µl of Platinum Taq Antibody at 5 U/µl), and 4.78 µl of corresponding template containing 35 ng genomic DNA. Templates were: LS-174T, HCT-15, HT-29, WiDr, SW1116 cell line genomic DNA, and Roche human genomic DNA. PCR reactions were run in a ProFlex PCR system thermocycler (Applied Biosystems/ThermoFisher, Waltham, Mass.) and run with the following program: 2 min at 95° C., 40 cycles of (10 sec at 94° C., 30 sec at 60° C. and 30 sec at 72° C.), 10 min at 99.5° C., and a final hold at 4° C.

The LDR step was performed in a 10 μl reaction prepared by adding: 5.82 μl of nuclease free water (IDT), 1 μl of 10× AK16D ligase reaction buffer [1× buffer contains 20 mM Tris-HCl pH 8.5 (Bio-Rad, Hercules, Calif.), 5 mM MgCl$_2$ (Sigma-Aldrich, St. Louis, Mo.), 50 mM KCl (Sigma-Aldrich, St. Louis, Mo.), 10 mM DTT (Sigma-Aldrich, St. Louis, Mo.) and 20 ug/ml of BSA (Sigma-Aldrich, St. Louis, Mo.)], 0.25 μl of DTT (Sigma-Aldrich, St. Louis, Mo.) at 40 mM, 0.25 μl of NAD$^+$ (Sigma-Aldrich, St. Louis, Mo.) at 40 mM, 0.25 μl of RNAseH2 (IDT) at 20 mU/μl, 0.2 μl of iCDx-2033A-Vim-S3-Up primer at 500 nM, 0.2 μl of iCDx-2034A-Vim-S3-Dn primer at 500 nM, 0.028 μl of purified AK16D ligase at 8.8 μM, and 2 μl of PCR reaction. LDR reactions were run in a ProFlex PCR system thermocycler (Applied Biosystems/ThermoFisher; Waltham, Mass.) and the following program: 20 cycles of (10 sec at 94° C., and 4 min at 60° C.) followed by a final hold at 4° C.

The qPCR step was performed in a 10 μl reaction mixture prepared by adding: 1.5 μl of nuclease free water (IDT), 5 μl of 2× TaqMan® Fast Universal PCR Master Mix (Fast amplitaq, UDG and dUTP from Applied Biosystems (Applied Biosystems/ThermoFisher; Waltham, Mass.), 1 μl of iCDx-2036-Vim-S3-RT-FP forward primer at 2.5 μM, 1 μl of iCDx-2037-Vim-S3-RT-RP reverse primer at 2.5 μM, 0.5 μl of iCDx-2035A-Vim-S3-RT-Pb Taqman probe at 5 μM, and 1 μl of LDR reaction products. qPCR reactions were run in a ViiA7 real-time thermo-cycler from Applied Biosystems (Applied Biosystems/ThermoFisher; Waltham, Mass.), using MicroAmp® Fast-96-Well Reaction 0.1 ml plates sealed with MicroAmp™ Optical adhesive film (Applied Biosystems/ThermoFisher; Waltham, Mass.), and the following setting: fast block, Standard curve as experiment type, ROX as passive reference, Ct as quantification method (automatic threshold, but adjusted to 0.05 when needed), TAMRA as reporter, and NFQ-MGB as quencher; and using the following program: 2 min at 50° C., and 40 cycles of (1 sec at 95° C., and 20 sec at 60° C.). Results are shown in FIG. 173 and Table 20.

TABLE 20

Results of experiments to detect methylation in cell line genomic DNA.

| Templates | Starting Genome Equivalents (per 10 μl of PCR) | Ct | Ct Difference vs 10000 GE of Roche hgDNA |
|---|---|---|---|
| LS-174T | 10,000 | 28.5 | 10.1 |
| HCT-15 | 10,000 | 20.2 | 18.6 |
| HT-29 | 10,000 | 20.4 | 18.2 |
| WiDr | 10,000 | 20.3 | 18.3 |
| SW1116 | 10,000 | UD | 0 |
| Roche DNA | 10,000 | 38.6 | 0 |

Pixel experiments. The PCR step was setup in a 130 μl mixture prepared by adding: 59.14 μl of nuclease free water (IDT), 26 μl of Gotaq Flexi buffer 5× without Magnesium (Promega, Madison, Wis.), 10.4 μl of MgCl$_2$ at 25 mM (Promega, Madison, Wis.), 2.6 μl of dNTPs (with dATP, dCTP, dGTP and dUTP, 10 mM each) (Promega, Madison, Wis.), 3.25 μl of iCDx-2031-VIM-S3-FP forward primer at 2 μM, 3.25 μl of iCDx-2032-VIM-S3-PR reverse primer at 2 μM, 16.25 μl of iCDx-VIM-S3-LNA2 blocking primer at 2 μM, 3.25 μl of RNAseH2 (IDT) at 20 mU/μl (diluted in RNAseH2 dilution buffer from IDT), 2.6 μl of Antarctic thermolabile UDG (New England Biolabs (NEB), Ipswich, Mass.) at 1 U/μl, and 2.86 μl of Klentaql polymerase (DNA Polymerase Technology, St. Louis, Mo.) mixed with Platinum Taq Antibody (Invitrogen, Carlsbad, Calif.) (the mixture is prepared by adding 0.3 μl of Klentaq1 polymerase at 50 U/μl to 3 μl of Platinum Taq Antibody at 5 U/μl), and 3 μl of corresponding template. 3 μl of templates contains: (1) 0.070 ng (20 GE) HT-29 DNA mixed with 9 ng (2500 GE) Roche hgDNA. (2) 0.035 ng (10 GE) HT-29 cell line DNA mixed with 9 ng (2500 GE) Roche hgDNA. (3) 9 ng (2500 GE) Roche DNA, (4) nuclease free water for the Non Template Control (NTC).

Each 130 μl PCR mixture was divided into 12 tubes, 10 μl each, and then the PCR reactions were run in a Proflex PCR system thermo-cycler (Applied Biosystems/ThermoFisher; Waltham, Mass.) and the following program: 2 min at 95° C., 40 cycles of (10 sec at 94° C., 30 sec at 60° C. and 30 sec at 72° C.), 10 min at 99.5° C., and a final hold at 4° C. The subsequent LDR and qPCR step were performed as described above. Results are shown in FIG. 174 and Table 25.

The PCR-LDR-qPCR procedure for methylation detection in VIM-S3 top and bottom strands was repeated as described above using a modified version of the LDR and Taqman probes (i.e., version B) probes. A comparison of results for methylation detection is shown in the amplification plots of FIGS. 175-178. FIG. 175 provides the real-time PCR plots for cell-line and wild-type (Roche) DNA using the VIM-S3 top-strand primer design and the Taqman probe version "A" (Table 21). Results show a Ct value of about 10 and 11.5 for WiDr and HT-29 cell line DNA respectively, indicating methylation at the S3 site in the VIM promoter region. Cell lines SW1116, Roche DNA, no-template control (NTC) for the initial PCR step, the following LDR step, and the final Taqman step are all base-line (i.e. flat). The same experiment was repeated using version "A" probes designed for the bottom strand (FIG. 176 and Table 22). As expected, results show a Ct value of about 11 and 9 for WiDr and HT-29 cell line DNA respectively, indicating methylation at the S3 site in the VIM promoter region. However, results with SW1116, Roche DNA, no-template control (NTC) for the initial PCR step, and NTC for the following LDR step al give Ct values of around 28.5 to 31, even though we know from the prior experiment that there is no methylation at the S3 site in the VIM promoter region. This discrepancy was resolved by designing the Taqman probes to overlap the upstream LDR probe portion of the LDR product by about 9 bases, and the downstream LDR probe portion of the LDR product by the remaining bases in the probe. Further, two non-complementary bases on the 5' side were added to the Taqman probe to assure that any accidental cross-polymerase extension would not be able to extend on the upstream LDR probe in a subsequent round. FIG. 177 provides the real-time PCR plots for cell-line and wild-type (Roche) DNA using the WIM-S3 top-strand primer design and the Taqman probe version "B" (Table 23). Results show a Ct value of about 12 and 13.5 for WiDr and HT-29 cell line DNA respectively, indicating methylation at the S3 site in the VIM promoter region. Cell lines SW1116, Roche DNA, no-template control (NTC) for the initial PCR step, the following LDR step, and the final Taqman step are all base-line (i.e. flat). The same experiment was repeated using version "B" probes designed for the bottom strand (FIG. 178 and Table 24). As expected, results show a Ct value of about 11.5 and 9.5 for WiDr and HT-29 cell line DNA respectively, indicating methylation at the S3 site in the VIM promoter region. Now, results with cell lines SW1116, Roche DNA, no-template control (NTC) for the initial PCR step, the following LDR step, and the final Taqman step are all base-line (i.e. flat), indicating the new probe design version "B" solved the problem of false signal from NTC or samples without methylation in the VIM-site 3 region.

TABLE 21

Methylation Primers for VIM_S3_Top Strand using Taqman Probe version "A"

| Primer Type | Primer Name | Sequences |
|---|---|---|
| PCR | iCDx_2031 | GAACTCCAACCGAAACTACGTAArCTACA/3SpC3/ (SEQ ID NO: 31) |
| PCR | iCDx_2032 | GGTGTCGTGGACGAGGCGTAGAGGTTGCrGGTTA/3SpC3/ (SEQ ID NO: 32) |
| LDR | iCDx_2033 | AAAACTACGTATAGACACGAGCGAGGTCACAACTCCAACCGACTGCGrUCCGT/3SpC3/ (SEQ ID NO: 36) |
| LDR | iCDx_2034 | /5Phos/TCCACCCGCACCTACAACCTAAACAACGCGTGCAAAATTCAGGCTGTGCA (SEQ ID NO: 37) |
| Taqman Probe | iCDx_2035 | /5HEX/TAACTGCGT/ZEN/CCACCCGCACCTAC/3IABkFQ/ (SEQ ID NO: 38) |
| Taqman Primer | iCDx_2036 | TAGACACGAGCGAGGTCAC (SEQ ID NO: 39) |
| Taqman Primer | iCDx_2037 | TGCACAGCCTGAATTTTGCAC (SEQ ID NO: 40) |
| PCR Blocker | VIM-S3-LNA2 | CA+TAA+CT+AC+AT+C+C+AC+CCA (SEQ D NO: 34) |

/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher,
green to pink spectral range,
"+"-Locked Nucleic Acid base,
"rA"-ribonucleotide base riboadenosine;
"rT"-ribonucleotide base ribothymidine;
"rG"-ribonucleotide base riboguanosine;
"rC"-ribonucleotide base ribocytosine

TABLE 22

Methylation Primers for VIM_S3_Bottom Strand using Taqman Probe version "A"

| Primer Type | Primer Name | Sequences |
|---|---|---|
| PCR | iCDx_2081 | GTCGAGTTTTAGTCGGAGTTACGTGrATTAA/3SpC3/ (SEQ ID NO: 92) |
| PCR | iCDx_2082 | GGTGTCGTGGGAAAACGAAACGTAAAAACTACGACTAArUACTG/3SpC3/ (SEQ ID NO: 93) |
| LDR | iCDx_2083 | TGGATCGAGACGGAATGCAACCGAGTTTTAGTCGGAGTTACGTGATCACrGTTCG/3SpC3/ (SEQ ID NO: 94) |
| LDR | iCDx_2084 | /5Phos/GTTTATTCGTATTTATAGTTTGGGTAGCGCGTTGCGGTTTCCCTGATTGATACCCGCA (SEQ ID NO: 98) |
| Taqman Probe | iCDx_2085 | /5HEX/AGTCGGAGT/ZEN/TACGTGATCACGTTTATTCGTATTTATAG/3IABkFQ/ (SEQ ID NO: 101) |
| Taqman Primer | iCDx_2086 | TGGATCGAGACGGAATGCAAC (SEQ ID NO: 102) |
| Taqman Primer | iCDx_2087 | TGCGGGTATCAATCAGGGAAAC (SEQ ID NO: 103) |
| PCR Blocker | iCDx_2088 | GTT+A+T+GT+G+ATT+A+T+GT+TT+AT+T+T+GT+ATTT (SEQ ID NO: 104) |

/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher,
green to pink spectral range,
"+"-Locked Nucleic Acid base,
"rA"-ribonucleotide base riboadenosine;
"rT"-ribonucleotide base ribothymidine;
"rG"-ribonucleotide base riboguanosine;
"rC"-ribonucleotide base ribocytosine

TABLE 23

Methylation Primers for VIM_S3_Top Strand using Taqman Probe version "B"

| Primer Type | Primer Name | Sequences |
|---|---|---|
| PCR | iCDx_2031 | GAACTCCAACCGAAACTACGTAArCTACA/3SpC3/ (SEQ ID NO: 31) |
| PCR | iCDx_2032 | GGTGTCGTGGACGAGGCGTAGAGGTTGCrGGTTA/3SpC3/ (SEQ ID NO: 32) |
| LDR | iCDx_2033A | TAGACACGAGCGAGGTCACAACTCCAACCGAAACTACGTAACTGCGrUCCGT/3SpC3/ (SEQ ID NO: 36) |
| LDR | iCDx_2034 | /5Phos/TCCACCCGCACCTACAACCTAAACAACGCGTGCAAAATTCAGGCTGTGCA (SEQ ID NO: 37) |
| Taqman Probe | iCDx_2035B | /5HEX/TTTAACTGC/ZEN/GTCCACCCGCACCTAC/3IABkFQ/ (SEQ ID NO: 44) |
| Taqman Primer | iCDx_2036 | TAGACACGAGCGAGGTCAC (SEQ ID NO: 39) |
| Taqman Primer | iCDx_2037 | TGCACAGCCTGAATTTTGCAC (SEQ ID NO: 40) |
| PCR Blocker | VIM-S3-LNA2 | CA+TAA+CT+AC+AT+C+C+AC+CCA (SEQ ID NO: 34) |

/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher,
green to pink spectral range,
"+"-Locked Nucleic Acid base,
"rA"-ribonucleotide base riboadenosine;
"rT"-ribonucleotide base ribothymidine;
"rG"-ribonucleotide base riboguanosine;
"rC"-ribonucleotide base ribocytosine

TABLE 24

Methylation Primers for VIM_S3_Bottom Strand using Taqman Probe version

| Primer Type | Primer Name | Sequences |
|---|---|---|
| PCR | iCDx_2081 | GTCGAGTTTTAGTCGGAGTTACGTGrATTAA/3SpC3/ (SEQ ID NO: 92) |
| PCR | iCDx_2082 | GGTGTCGTGGGAAAACGAAACGTAAAAACTACGACTAArUACTG/3SpC3/ (SEQ ID NO: 93) |
| LDR | iCDx_2083 | TGGATCGAGACGGAATGCAACCGAGTTTTAGTCGGAGTTACGTGATCACrGTTCG/3SpC3/ (SEQ ID NO: 94) |
| LDR | iCDx_2084 | /5Phos/GTTTATTCGTATTTATAGTTTGGGTAGCGCGTTGCGGTTTCCCTGATTGATACCCGCA (SEQ ID NO: 98) |
| Taqman Probe | iCDx_2085B | /5HEX/TTTGATCAC/ZEN/GTTTATTCGTATTTATAGTTTGGGTAGCGC/3IABkFQ/ (SEQ ID NO: 99) |
| Taqman Primer | iCDx_2086 | TGGATCGAGACGGAATGCAAC (SEQ ID NO: 102) |
| Taqman Primer | iCDx_2087 | TGCGGGTATCAATCAGGGAAAC (SEQ ID NO: 103) |
| PCR Blocker | iCDx_2088 | GTT+A+T+GT+G+ATT+A+T+GT+TT+AT+T+T+GT+ATTT (SEQ ID NO: 104) |

/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher,
green to pink spectral range,
"+"-Locked Nucleic Acid base,
"rA"-ribonucleotide base riboadenosine;
"rT"-ribonucleotide ribocytosine ribothymidine;
"rG"-ribonucleotide base riboguanosine;
"rC"-ribonucleotide base

Empirical Example 6

Methylation and Mutation Detection Primer Design

Methylation Assay design was accomplished by first performing computerized analysis of the genomic DNA sequence of the Vimentin (VIM) and TMEM90B genes to identify prospective highly methylated CG sites. After the computer analysis and identification of multiple methylation sites, three to four sites within each gene were selected for assay development. To aid in assay development, a computerized bisulfite conversion is performed on the bisulfite converted genomic DNA of the respective genes. This is done for both the top and bottom strand to design oligonucleotides off of the expected bisulfite converted sequences. The computerized conversion is performed on the top strand by converting the G bases that are not following an immediate 5'C base into A bases (G-A Conversion for all G's that are not CG) and for the bottom strand converting a C base next to an immediate 3'G base into T bases (C-T conversion for all C bases that are not CG). The design criteria for the ligation assay, starts by identifying the discriminating base that is either the methylated C or adjacent G (wherein the C of the complementary strand is methylated), as the identification of a number of additional features in the sequence that would aid our design criteria, including avoiding sequences with very high GC content after bisulfite conversion. Once the methylated sites for assay development are selected, the same site in both the top and bottom strands is assayed. A four step approach was utilized to design oligonucleotides for this assay. The first step is to design the upstream and downstream Ligase Detection Reaction (LDR) oligonucleotides. Second, design a gene specific forward and reverse oligonucleotide to cover the LDR site and the LDR oligonucleotides within a gene-specific amplicon between 100 to 140 bases in total length. Third, design fluorescent dyed labeled probes (FAM and HEX™) that cover the ligation site and bind specifically to the ligated LDR product. And the final step is to design a corresponding WT Locked Nucleic Acid (LNA™) probe to block amplification of the bisulfite-converted un-methylated promoter region.

TABLE 25

Results of pixel experiments to detect methylation in HT-29 DNA in the background of Roche hgDNA.

| Templates | GE per 130 μl of PCR | 1 | 2 | 3 | 4 | 5 | 6 | 7 | 8 | 9 | 10 | 11 | 12 | Total Amplifications |
|---|---|---|---|---|---|---|---|---|---|---|---|---|---|---|
| HT-29 + Roche hgDNA | 20 GE (Meth) + 2500 GE (wt) | 21.5 | 17.5 | 14.5 | 16.0 | 15.9 | 14.4 | 15.0 | 14.5 | 14.3 | 14.2 | 16.1 | 13.5 | 12 |
| HT-29 + Roche hgDNA | 10 GE (Meth) + 2500 GE (wt) | UD | 15.2 | UD | 16.2 | UD | 15.8 | 16.3 | UD | 20.3 | 16.1 | UD | UD | 6 |
| Roche hgDNA | 2500 GE (wt) | UD | UD | UD | UD | UD | 38.5 | UD | 36.8 | UD | UD | 37.6 | 36.6 | 0 |
| NTC | 0 | UD | 37.6 | UD | 37.9 | 38.3 | UD | UD | UD | 36.8 | 38.0 | 39.5 | UD | 0 |

(SEQ ID NO: 137)
...AGCCGGCCGAGCTCCAGCCGGAGCTACGT<u>GACTA</u>C̄<u>GTCCACCC</u>GCAC

CTACAGCCTGGGCAG<u>CGCG</u>CTGCGCCCCAGCACCAGCCGCAGCCTCTACGC

CTCGTCCCCGGGCGGCGTGTATGCCA<u>CGCG</u>CTCCTCTGC...

(SEQ ID NO: 131)
...AACCGACCGAACTCCAACCGAAACTACGTAACTA<u>CG</u>TCCACCCGCACC

TACAACCTAAACAACGCGCTACGCCCCAACACCAACCGCAACCTCTACGCC

TCGTCCCCGAACGACGTATATACCACGCGCTCCTCTAC...

Top VIM Site 3 (S3) genomic sequence before bisulfite conversion and after bisulfite conversion. (Red bold nucleotide represents the S3 site of methylation)

The LDR upstream (Up) oligonucleotide probes are designed with a $T_m$ of 64-66° C., with the 3' end at the discriminating base of interest either the C or G in in methylated CG. Once the primer sequence is selected and within the required $T_m$ range a technique of blocking non-specific extension, based off of the IDT (Coralville, Iowa) RNaseH2™ cleavage method, is utilized to add a complementary RNA base immediate to the 3' side of the discriminating base followed by two matched DNA bases at the second and third position and two mismatched DNA bases (preferably either G-T or A-C mismatches) at the fourth and fifth (or the third and fifth) positions followed by the addition of a 3' C3 Spacer. The overall five base tail and spacer is used to block non-specific extension off of the upstream LDR probe. For the upstream LDR oligonucleotide probe, an additional mismatch (preferably either G-T or A-C mismatch) is also utilized at the adjacent, second, or third position on the 5' side of the discriminating base. Additional modifications include an optional 5' C3 Spacer to block lambda exonuclease digestion of ligation products. After the selection and modification of the upstream oligonucleotide, a tag-sequence corresponding to a forward oligonucleotide for a subsequent real-time PCR experiment is added to the 5' side of the sequence. The tag sequences are chosen from a list of qPCR oligonucleotide forward and reverse primer pairs that were designed previously.

Upstream LDR probe sequence
(SEQ ID NO: 132)
AACTCCAACCGAAACTACGTAACTGCGrUCCgt/3SpC3/

5' Tag sequence + Uptream LDR probe sequence:
(SEQ ID NO: 133)
TAGACACGAGCGAGGTCACAACTCCAACCGAAACTACGTAACTGCGrUCC gt/3SpC3/

5' Tag sequence ++ Uptream LDR probe sequence with 5' Spacer and fourth and fifth cleavage position mismatch:
(SEQ ID NO: 36)
/5SpC3/TAGACACGAGCGAGGTCACAACTCCAACCGAAACTACGTAACT GCGrUCCgt/3SpC3/

5' Tag sequence + Uptream LDR probe sequence with 5' Spacer and third and fifth cleavage position mismatch:
(SEQ ID NO: 42)
/5SpC3/TAGACACGAGCGAGGTCACAACTCCAACCGAAACTACGTAACT GCGrUCtAt/3SpC3/ qPCR Forward Primer:
(SEQ ID NO: 39)
5'-TAGACACGAGCGAGGTCAC 3'

(SEQ ID NO: 131)
... AACCGACCGAACTCCAACCGAAACTACGTAACTa<u>CG</u>TCCACCCG

CACCTACAACCTAAACAACGCGCTACGCCCCAACACCAACCGCAACCTCT

ACGCCTCGTCCCCGAACGACGTATATACCACGCGCTCCTCTAC...

VIM S3 bisulfite converted genomic DNA-Upstream LDR location in Bold, lowercase "a" site of third position mismatch, and the RNA cleavage site underlined.

The downstream (Dn) LDR oligonucleotide probe was designed at the base immediately following the 3' side of the discriminating base. The oligonucleotide probes were designed with a $T_m$ of 70-72° C. degrees. Like the upstream probe, a selected tag-sequence is added to the 3' end of the sequence. Additional modifications made to the design involve the addition of a mismatch at the fourth position closest to the 5' side and the inclusion of additional mismatched bases to the 3' end of the oligonucleotide right before the real-time tag sequence.

Downstream LDR probe sequence:
(SEQ ID NO: 134)
/5Phos/TCCACCCGCACCTACAACCTAAACAACGC Downstream LDR probe + 3' complementary tag-primer sequence:
(SEQ ID NO: 37)
/5Phos/TCCACCCGCACCTACAACCTAAACAACGCGTGCAAAATTC

AGGCTGTGCA

Downstream oligo with fourth position mismatch and additional bases spacing the bisulfite converted genomic sequence from the qPCR sequence:

(SEQ ID NO: 135)
/5Phos/TCCaCCCGCACCTACAACCTAAACAACGCGCTGTGCAAAATTC

AGGCTGTGCA qPCR Reverse Primer:
(SEQ ID NO: 40)
5'-TGCACAGCCTGAATTTTGCAC-3'

(SEQ ID NO: 131)
... AACCGACCGAACTCCAACCGAAACTACGTAACTA<u>CG</u>TCCACCCG

CACCTACAACCTAAACAACGCGCTACGCCCCAACACCAACCGCAACCTCT

ACGCCTCGTCCCCGAACGACGTATATACCACGCGCTCCTCTAC...

VIM S3 bisulfite converted genomic DNA-Downstream (Dn) LDR location in bold, CG site of methylation is underlined Gene specific forward (FP) and reverse (RP) oligonucleotide primers were designed immediately upstream of the LDR oligonucleotide probes with significant overlap of the upstream LDR oligonucleotide probe with a total amplicon length between about 100-140 bases. The forward and reverse gene-specific oligonucleotide primers were designed with a $T_m$ of 62-64° C. The reverse primer was designed further downstream and with no overlap of the Dn LDR oligonucleotide probe, to incorporate additional CGCG restriction sites when present for further discrimination of methylated sites. Preferably, one or more Bsh1236I (CGCG) restriction sites are present in the target DNA to allow for an optional cleaving of un-methylated DNA prior to bisulfite conversion. Optionally, the reverse primer has a non-specific 10 base tail added to the 5' end to prevent primer-dimer formation with the other reverse primers. Both the forward and reverse primers also utilize the RNA cleavage trick at the 3' end of the primer, but unlike the LDR oligonucleotide probes the primers only have one mismatch at the 3' end adjacent to the blocking group.

Forward primer:
(SEQ ID NO: 31)
5'-GAACTCCAACCGAAACTACGTAArCTACa/3SpC3/

Reverse primer:
(SEQ ID NO: 136)
5'-ACGAGGCGTAGAGGTTGCrGGTTa/3SpC3/

Reverse primer + 10 Base Tail
(SEQ ID NO: 32)
5' GGTGTCGTGGACGAGGCGTAGAGGTTGCrGGTTA/3SpC3/

Forward and Reverse Primer containing the one base mismatch (lowercase and bold) in the RNA cleavage portion of the primer (SEQ ID NO: 131)
. . . AACCGACCGAACTCCAACCGAAACTACGTAACTACGTCCACCCG

CACCTACAACCTAAACAACGCGCTACGCCCCAACACCAACCGCAACCTCT

ACGCCTCGTCCCCGAACGACGTATATACCACGCGCTCCTCTAC . . .

VIM S3 bisulfite converted genomic DNA-Gene specific Forward (FP) and Reverse (RP) Primers in bold, CG site of methylation is enlarged, RNA cleavage site regions are underlined Of the three to four sites identified by the above analysis two sites were selected for assay development on both the top and bottom strand. To differentiate between the two sites, strand specific real-time probes were designed to cover the ligation product with site-specific 5' FAM- or 5' HEX™ labeled probes. Real-time probes were designed to incorporate the third position mismatch that was incorporated into the upstream LDR probe on the 5' side of the discriminating base, and an additional probe was designed to cover the 5' mismatch and the optional fourth position mismatch on the 3' side of the discriminating base in the downstream probe. The $T_m$ of the probes are designed for 68-70° C. Initially, the probes were designed to have equal coverage of the 5' and 3' sides of the ligation site, but additional probes were designed with a coverage bias of ⅓ on the (5') side followed by ⅔ on the downstream side (3') of the ligation site, which was in most cases 7 bases upstream and 15 bases downstream of the ligation site for most probes. To avoid problems with low FAM-dye fluorescence when coupled to a G base, all probes were designed avoiding a G base at its first 5' base so dyes can be interchanged as needed without the need for sequence modification. Additional modifications involve the addition of mismatches immediately following the fluorescent dye. The probes were synthesized from IDT and utilize a ZEN™ (IDT) quencher nine bases from the 5' side, and Iowa Black® FQ (IDT) fluorescent quencher at the 3' end.

Real-time probe with matching third position mismatch (Bold):

(SEQ ID NO: 38)
/5HEX/TAACTGCGT/ZEN/CCACCCGCACCTAC/3IABkFQ/

Real-Time Probe With Matching Third Position Mismatch (Bold) and Two Additional Bases:

(SEQ ID NO: 44)
/5HEX/ttTAACTGC/ZEN/GTCCACCCGCACCTAC/3IABkFQ/

(SEQ ID NO: 45)
/5HEX/ttTAACTGC/ZEN/GTCCGCCCGCACCTAC/3IABkFQ/

(SEQ ID NO: 131)
. . . AACCGACCGAACTCCAACCGAAACTACGTAACTaCGTCCACCCG

CACCTACAACCTAAACAACGCGCTACGCCCCAACACCAACCGCAACCTCT

ACGCCTCGTCCCCGAACGACGTATATACCACGCGCTCCTCTAC . . .

VIM S3 bisulfite converted genomic DNA-Site of the Real-time probe, lowercase "a" site of the third position mismatch upstream and underlined A site of the fourth position mismatch downstream Locked Nucleic Acid (LNA™) blocking primers were designed to reduce amplification of bisulfite converted un-methylated target, by having a perfectly matched LNA probe binds to the bisulfite converted un-methylated target and utilizing between 5-10 locked (LNA) bases to prevent amplification. The LNA blocking probes, are synthesized by Exiqon (Woburn, Mass.) with a $T_m$ of 72-75° C.

TABLE 26

Methylation Detection Oligo List

| | |
|---|---|
| iCDx-2031-VIM-S3-FP,GAACTCCAACCGAAACTACGTAArCTACA/3SpC3/ (SEQ ID NO. 31) | PCR Amplification Forward oligo |
| iCDx-2032A-VIM-S3-RP, GGTGTCGTGGACGAGGCGTAGAGGTTGCrGGTTA/3SpC3/ (SEQ ID NO. 32) | PCR Amplification Reverse oligo |
| iCDx-2033A-VIM-S3-Up, TAGACACGAGCGAGGTCAC AACTCCAACCGAAACT ACGTAACTBCGrUCCBT/3SpC3/ (SEQ ID NO. 36) | Upstream LDR oligo with third position mismatch and 4th and 5th cleavage site mismatches (bold) |
| iCDx-2033B-VIM-S3-Up, /5SpC3/TAGACACGAGCGAGGTCAC AACTCCAACCGAAACTACGTAACTGCGrUCCGT/3SpC3/ (SEQ ID NO. 41) | Upstream LDR oligo with third position and cleavage site mismatches in 4th and 5th position (bold) and 5' C3 Spacer |

TABLE 26-continued

Methylation Detection Oligo List

| Oligo | Description |
|---|---|
| iCDx-2033D-VIM-S3-Up, /5SpC3/TAGACACGAGCGAGGTCACAACTCCAACCGAAACTACGTAACTGCGrUCTAT/3SpC3/ (SEQ ID NO. 42) | Upstream LDR oligo with third position and cleavage site mismatches in third and fifth position (bold) and 5' C3 Spacer |
| iCDx-2034A-VIM-S3-Dn, /5Phos/TCCACCCGCACCTACAACCTAAACAACGCGTGCAAAATTCAGGCTGTGCA (SEQ ID NO. 37) | Downstream LDR oligo |
| iCDx-2034D-VIM-S3-Dn, /5Phos/TCCGCCCGCACCTACAACCTAAACAACGCGCTGTGCAAAATTCAGGCTGTGCA (SEQ ID NO. 43) | Downstream LDR oligo with fourth position mismatch (bold) |
| iCDx-2035A-VIM-S3-RT-Pb, /5HEX/TAACTGCGT/ZEN/CCACCCGCACCTAC/3IABkFQ/ (SEQ. ID NO. 38) | Real-time probe with matching third position mismatch (bold) |
| iCDx-2035B-VIM-S3-RT-Pb, /5HEX/ttTAACTGC/ZEN/GTCCACCCGCACCTAC/3IABkFQ/ (SEQ ID NO. 44) | Real-time probe with matching third position mismatch (bold) and pre-sequence mismatches (lowercase) |
| iCDx-2035D-VIM-S3-RT-Pb, 5HEX/ttTAACTGC/ZEN/GTCCGCCCGCACCITAC/3IABkFQ/ (SEQ ID NO. 45) | Real-time probe with matching third position mismatch (Upstream bold) and fourth position (downstream bold) and pre-sequence mismatches (lowercase) |
| iCDx-2036-VIM-S3-RT-FP, TAGACACGAGCGAGGTCAC (SEQ ID NO. 39) | Real-time Forward Primer |
| iCDx-2037-VIM-S3-RT-RP, TGCACAGCCTGAATTTTGCAC (SEQ ID NO. 40) | Real-time Reverse Primer |
| VIM-S3-LNA1, CA + TAA + CT + AC + AT + CC + AC + CCA (SEQ ID NO. 33) | LNA probe ("+" =locked nucleic base) |
| VIM-S3-LNA2, CA + TAA + CT + AC + AT + CC + AC + CCA (SEQ ID NO. 34) | LNA probe ("+" =locked nucleic base) |

/5SpC3/ - 5' C3 Spacer,
/3SpC3/ - 3' C3 Spacer,
/5Phos/ - 5' Phosphate,
/56-FAM/ - 5' Fam Flourescent Dye,
/5HEX/ - HEX ™ Fluorescent Dye,
/ZEN/ - ZEN ™ Flourescent Quencher ™,
/3IABkFQ/ - 3' Iowa Black ® Flourescent Quencher, green to pink spectral range,
"+" - Locked Nucleic Acid base,
"rA" - ribonucleotide base riboadenosine;
"rT" - ribonucleotide base ribothymidine;
"rG" - ribonucleotide base riboguanosine;
"rC" - ribonucleotide base ribocytosine Mutation detection was performed on a number of different cancer oncogenes and tumor suppressors harboring known hot-spot mutations including KRAS (G12A, G12D, G12S, G12C, and G12V), BRAF (V600E, 1799T>A), and Tp53 (R248Q, 743G>A). The assay is performed similarly to the methylation assay using a quantitative Ligase Detection Reactions (LDR) approach except the discriminating base is located at the mutation of interest.

The LDR upstream (Up) oligonucleotide probes are designed with a $T_m$ of 64-66° C. 5' upstream of and ending at the mutation (discriminating base of interest). Once the primer is selected off of this base and within the required $T_m$ range, the technique of blocking nonspecific extension based off of the IDT (Coralville, Ia) RNaseH2™ cleavage method is utilized to add a complementary RNA base immediate to the 3' side of the discriminating base followed by two matched DNA bases at the second and third position and two mismatched DNA bases (G-A, C-T) at the fourth and fifth position followed by the addition of a 3' C3 Spacer. The overall five base tail and spacer is used to block non-specific extension off of the upstream LDR probe. For the upstream LDR oligonucleotide probe an additional mismatch (preferably either G-T or A-C mismatch) is also utilized at the adjacent, second, or preferably third position on the 5' side of the discriminating base. After the selection and modification of the upstream oligonucleotide, a tag-sequence corresponding to a forward primer for a subsequent real-time PCR experiment is added to the 5' side of the upstream LDR probe sequence. The tag sequences are chosen from a list of qPCR oligonucleotide forward and reverse primer pairs that were designed previously.

iCDx-308-Br600_(3)-L_Up_Rm:

(SEQ ID NO: 4)
5'TAGCGATAGTACCGACAGTCACGtcct**AAATAGGTGATTTTGGTCTAG
CTACGGArGAAAc**/3SpC3/

Example of an Upstream LDR Oligo (from 5': Tag in uppercase and bold, short linker sequence in lowercase italics, upstream LDR probe sequence in uppercase with mismatch in position 3 prior to mutation in bold, and mismatch in last position of five base tail in bold and lowercase)

Additional upstream LDR probes were designed as described above, with the following modifications: for "A" version LDR probes, the RNA base immediate to the 3' side of the discriminating base followed by three matched DNA bases at the second, third, and fourth position and one mismatched DNA base (G-A, C-T) at the fifth position followed by the addition of a 3' C3 Spacer; for "B" version LDR probes, the RNA base immediate to the 3' side of the discriminating base followed by two matched DNA bases at the second and third position and two mismatched DNA bases (G-A, C-T) at the fourth and fifth position followed by the addition of a 3' C3 Spacer; for "D" versions of the LDR probes, the RNA base immediate to the 3' side of the discriminating base followed by two matched DNA bases at the second and fourth position and two mismatched DNA bases (G-A, C-T) at the third and fifth position followed by the addition of a 3' C3 Spacer. In addition, the "A", "B" and "D" version of the upstream LDR probes had a mismatched DNA base (G-A, C-T) at the third position from the ligation junction (i.e. 3' end after cleavage with RNaseH) and the "D" version of the downstream LDR probes had a mismatched DNA base (G-A, C-T) at the fourth position from the ligation junction (i.e. 5' end).

The downstream (Dn) LDR oligonucleotide probe was designed at the base immediately following the 3' side of the discriminating base. The oligonucleotides were designed with a $T_m$ of 68° C. degrees. A tag-sequence corresponding to the reverse complement of the reverse primer for a subsequent real-time PCR experiment is added to the 3' side of the LDR specific sequence. Like the upstream LDR oligonucleotide probe, these sequences were also selected from a predetermined list of optimal qPCR primer pairs.

iCDx-276-Br600-L_Dn_P:

(SEQ ID NO: 5)
/5Phos/GAAATCTCGATGGAGTGGGTCCCATttggt**GTGCGGAAACCTA
TCGTCGA**

Example of a Downstream LDR Oligo (from 5': upstream LDR probe sequence in uppercase, short linker sequence in lowercase italics, and followed by Tag for real time PCR in uppercase and bold)

Gene-specific forward (FP) and reverse (RP) primers for the PCR step were designed immediately upstream or downstream, respectively, of the LDR oligonucleotide probes. There is significant overlap between the FP and the upstream LDR oligonucleotide probe, and there is no overlap between the RP and downstream LDR probe. The forward and reverse gene-specific oligonucleotide primers were designed with a $T_m$ of 64-66° C., and with a total amplicon length of 74-94 bases. Additionally, the reverse primer has a non-specific 10 base tail added to the 5' end to prevent primer-dimer formation of the downstream primers. Optionally, both the forward and reverse primers also utilize the 5-base RNaseH2™ cleavage method at the 3' end of the primer, but unlike the LDR oligonucleotide probes, they had zero or one mismatch at the 3' end (when that 3' end is the mutated base to be discriminated, it matched the wild type sequence and mismatched the mutant sequence).

iCDx-328-Braf_PF_WT_blk2 (gene-specific FP wit 5-base RNaseH2 ™ cleavage method and mismatch at 3' end):

(SEQ ID NO: 1)
CCTCACAGTAAAAATAGGTGATTTTGGTCTArGCTAt/3SpC3/ iCDx-284-Br600-PR (gene-specific RP with 10-base tail in bold, one extra linker base in italics, and gene-specific sequence in uppercase):

(SEQ ID NO: 2)
ggtgtcgtggtTCAAAATGGATCCAGACAACTGTTCAAAC

Example of a gene-specific forward and reverse PCR primers

For the real time PCR step, strand specific real-time probes labeled with FAM, HEX™ or TAMRA at the 5' end were designed to cover the ligation product across the junction between the upstream and downstream LDR primers. Different probes were designed to incorporate either the adjacent, second, or third position mismatch positioned on the 5' side of the discriminating base that was incorporated into the corresponding upstream oligos. The probes were designed with a $T_m$ of 68° C. To avoid problems with low FAM dye fluorescence when coupled to a G base, all probes were designed without using a G base at its first 5' starting base so dyes can be interchanged as needed without the need for sequence modification. Additional modifications involve the addition of mismatches immediately following the fluorescent probe. The probes were synthesized from IDT and most utilize a ZEN™ quencher nine bases from the 5' side, and Iowa Black® FQ or Iowa Black® RQ (IDT) fluorescent quencher at the 3' end. iCDx-277_A4: TAGCGA-TAGTACCGACAGTCAC (SEQ ID NO: 6) iCDx-279_C4: TCGACGATAGGTTTCCGCAC (SEQ ID NO: 7) iCDx-281-Br600_(3)_Probe: 5'—/56-TAMN/TA CGG AGA AAT CTC GAT GGA GTG GGT/3IAbRQSp/-3' (SEQ ID NO: 8) Example of the Oligos Used in a Real-Time PCR Experiment Locked Nucleic Acid (LNA™) blocking primers were designed to reduce amplification of wild-type target, as well as ligation of upstream and downstream LDR probes on amplified wild-type target. To accomplish this a perfectly matched to Wild-type LNA probe utilizing between 3-6 locked bases was synthesized by Exiqon (Woburn, Mass.) with a $T_m$ of 71-76° C. The LNAs also contain a 5' phosphate group and a three prime C3 Spacer to prevent false-positive results arising from probe extension on Wild-type DNA. iCDx-315-BRAF FLW: /5Phos/GCTA+C+AG+T+G+AAAT+CTCG/3SpC3/(SEQ ID NO: 3)
Example of the LNA Oligo Used to Block Wild-Type Signal (LNA Bases are Those Preceded by a + Sign)

Alternatively, Peptide nucleic acid (PNA™) blocking primers were designed to reduce amplification of wild-type target, as well as ligation of upstream and downstream LDR probes on amplified wild-type target. To do this, a perfectly matched to Wild-type PNA oligo was designed to include 4-8 bases on each side of the discriminating base, and to have a Tm of 70-76° C. PNA oligos were synthesized by PNA Bio (Thousand Oaks, Calif.).

(SEQ ID NO: 12)
PNA-p53-248-11L: TGAACCGGAGG

Example of a PNA oligo used to block wild-type signal (the discriminating base is in bold, and it matches the wild-type target)

TABLE 27

Mutation Detection Primer List

| Step | Primer Name | Primer Sequence |
|---|---|---|
| BRAF | | |
| Forward Primer PCR | iCDx-328-Braf_PF_WT_blk2 | CCTCACAGTAAAAATAGGTGATTTTGGTCTArGCTAT/3SpC3/ (SEQ ID NO: 1) |
| Reverse Primer PCR | iCDx-284-Br600-PR | GGTGTCGTGGTCAAAATGGATCCAGACAACTGTTCAAAC (SEQ ID NO: 2) |
| LNA Blocking Probe 1 | iCDx-315-BRAF_FLW | /5Phos/GCTA+C+AG+T+G+AAAT+CTCG/3SpC3/ (SEQ ID NO: 3) |
| Upstream LDR | iCDx-308-Br600_(3)-L_Up_Rm | TAGCGATAGTACCGACAGTCACGTCCTAAATAGGTGATTTTGGTCTAGCTACGGArGAAAC/3SPC3/ (SEQ ID NO: 4) |
| Downstream LDR | iCDx-276-Br600-L_Dn_P | /5Phos/GAAATCTCGATGGAGTGGGTCCCATTTGGTGTGCGGAAACCTATCGTCGA (SEQ ID NO: 5) |
| Tag Forward Primer | iCDx-277_A4 | TAGCGATAGTACCGACAGTCAC (SEQ ID NO: 6) |
| Tag Reverse Primer | iCDx-279_C4 | TCGACGATAGGTTTCCGCAC (SEQ ID NO: 7) |
| Real-Time Probe | iCDx-281-Br600_(3)_Probe | 5'-/56-TAMN/TA CGG AGA AAT CTC GAT GGA GTG GGT/3IAbRQSp/-3 (SEQ ID NO: 8) |
| p53 | | |
| Forward Primer PCR | iCDx-326-p53-248_PF_WT_blk2 | CCTGCATGGGCGGCATGrAACCG/3SpC3/ (SEQ ID NO: 9) |
| Reverse Primer PCR | iCDx-248-p53-248_PR | GGTGTCGTGGAAGTGGCAAGTGGCTCCTGAC (SEQ ID NO: 10) |
| PNA Blocking Probe 1 | PNA-p53-248-10 | GAACCGGAGG (SEQ ID NO: 11) |
| PNA Blocking Probe 2 | PNA-p53-248-11L | TGAACCGGAGG (SEQ ID NO: 12) |
| Upstream LDR | iCDx-305-P53-248(3)-L_Up_Rm | TCACTATCGGCGTAGTCACCACAGACGCATGGGCGGCATGAATCArGAGGT (SEQ ID NO: 13) /3SPC3/ |
| Downstream LDR | iCDx-202-P53-248-L_Dn_P | /5Phos/GAGGCCCATCCTCACCATCATCACGTTGTTGGTGACTTTACCCGGAGGA (SEQ ID NO: 14) |
| Tag Forward Primer | iCDx-82_GTT-GCGC_A2 | TCACTATCGGCGTAGTCACCA (SEQ ID NO: 15) |
| Tag Reverse Primer | iCDx-244-C2 | TCCTCCGGGTAAAGTCACCA (SEQ ID NO: 16) |
| Real-Time Probe | iCDx-228-p53-248_Probe_s | 5'-/56-FAM/CG CAT GAA /ZEN/T CAG AGG CCC ATC C/3IABkFQ/ (SEQ ID NO: 17) |
| KRAS | | |
| Forward Primer PCR | iCDx-327-Kr_12_2_PF_WT_blk2 | TGACTGAATATAAACTTGTGGTAGTTGGArGCTGG/3SpC3/ (SEQ ID NO: 18) |
| Reverse Primer PCR | iCDx-303-Kr-12_1&2_PR | GGTGTCGTGGCGTCCACAAAATGATTCTGAATTAGCTGTA (SEQ ID NO: 19) |
| PNA Blocking Probe 1 | PNA-Kras_12_2-11L | GAGCTGGTGGC (SEQ ID NO: 20) |
| PNA Blocking Probe 2 | PNA-Kras_12_2-11R | AGCTGGTGGCG (SEQ ID NO: 21) |
| Upstream LDR | iCDx-393-Kr-12_1(3)-L_Up_Rm | TTCGTACCTCGGCACACCAACATAACTGAATATAAACTTGTGGTAGTTGGAGTTHrGTGAT/3SpC3/ (SEQ ID NO: 22) |
| Downstream LDR | iCDx-222-Kr-12_1-L_Dn_P | /5Phos/GTGGCGTAGGCAAGAGTGCCTTGACGGCGTGTGGCTCCGTTACTCTGTCGA (SEQ ID NO: 23) |
| Upstream LDR ver-B | iCDx-307-Kr-12_2(3)-L_Up_Rm | TTCGTACCTCGGCACACCAACATATGAATATAAACTTGTGGTAGTTGGAGCCGHrUGGCA/3SpC3/ (SEQ ID NO: 27) |
| Upstream LDR ver-C | iCDx-394-Kr-12_2(3)-L_Up_Rm | TTCGTACCTCGGCACACCAACATATGAATATAAACTTGTGGTAGTTGGAGCCGHrUGGTA/3SpC3/ (SEQ ID NO: 28) |
| Downstream LDR ver-B | iCDx-269-Kr-12_2-L_Dn_P | /5Phos/TGGCGTAGGCAAGAGTGCCTTGACGGCGTGTGGCTCCGTTACTCTGTCGA (SEQ ID NO: 29) |
| Tag Forward Primer | iCDx-245_A3 | TTCGTACCTCGGCACACCA (SEQ ID NO: 24) |
| Tag Reverse Primer | iCDx-246-C3 | TCGACAGAGTAACGGAGCCA (SEQ ID NO: 25) |
| Real-Time Probe 1 | iCDx-259-T-Kr-12_1_Probe | 5'-/5HEX/TT GGA GTT H/ZEN/GT GGC GTA GGC AAG A/3IABkFQ/-3' (SEQ ID NO: 26) |

TABLE 27 -continued

Mutation Detection Primer List

| Step | Primer Name | Primer Sequence |
|---|---|---|
| Real-Time Probe 2 | iCDx-270-Kr-12_2(3)_Probe | 5'-/5HEX/TAG TTG GAG/ZEN/ CCG HTG GCG TAG G/3IABkFQ/-3' (SEQ ID NO: 30) |

/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher, green to pink spectral range,
"+"-Locked Nucleic Acid base,
"rA"-ribonucleotide base riboadenosine;
"rT"-ribonucleotide ribocytosine ribothymidine;
"rG"-ribonucleotide base riboguanosine;
"rC"-ribonucleotide base

TABLE 28

Methylation Detection Oligonucleotides

| Step | Name | Sequence |
|---|---|---|
| VIM-S2 Top Strand | | |
| Forward Primer PCR | iCDx-2021-Vim-S2-FP | ACCACTCTCGCTCCGAAATrCCCCA/3SpC3/ (SEQ ID NO. 46) |
| Reverse Primer PCR | iCDx-2022A-Vim-S2-RP | GGTGTCGTGGCGGATTGGTTTTCGGAGAAGAGGrCGAAT/3SpC3/ (SEQ ID NO. 47) |
| Upstream LDR ver-A | iCDx-2023A-Vim-S2-Up | TACCCTCCTAGCTCCGTACATCTCGCTCCGAAATCCTCGrCGCTG/3SpC3/ (SEQ ID NO: 48) |
| Upstream LDR ver-B | iCDx-2023B-Vim-S2-Up | /5SpC3/TACCCTCCTAGCTCCGTACATCTCGCTCCGAAATCCTCGrCGCTG/3SpC3/ (SEQ ID NO. 48) |
| Downstream LDR ver-A | iCDx-2024A-Vim-S2-Dn | /5Phos/CGCCAAAAACGCAACCGCGCTGTGTTGTCTGGTGGTGCA (SEQ ID NO. 49) |
| Real Time probe ver-B | iCDx-2025B-Vim-S2-RT-Pb | /56-FAM/AT CCT CGC G/ZEN/C CAA AAA CGC /3IABkF0/ (SEQ ID NO. 50) |
| Real-Time Probe ver-A | iCDx-2025A-Vim-S2-RT-Pb | /56-FAM/CCGAAATCC/ZEN/ TCGCGCCAAAAACG/3IABkFQ/ (SEQ ID NO. 51) |
| Tag Forward Primer | iCDx-2026-Vim-S2-RT-FP | TACCCTCCTAGCTCCGTACA (SEQ ID NO. 52) |
| Tag Reverse Primer | iCDx-2027-Vim-S2-RT-RP | TGCACCACCAGACAACACA (SEQ ID NO. 53) |
| LNA Blocking Probe 1 | VIM-S2-LNA1 | A+AT+CC+CC+AC+AC+CA+A (SEQ ID NO. 54) |
| LNA Blocking Probe 2 | VIM-S2-LNA2 | A+AT+CC+CC+A+C+AC+CA+A (SEQ ID NO. 55) |
| PNA Blocking Probe 2 | VIM-S2-PNA2 | AATCCCCACACCAAA (SEQ ID NO. 56) |
| VIM-S3 Top Strand | | |
| Forward Primer PCR | iCDx-2031-VIM-S3-FP | GAACTCCAACCGAAACTACGTAArCTACA/3SpC3/ (SEQ ID NO. 31) |
| Reverse Primer PCR | iCDx-2032A-VIM-S3-RP | GGTGTCGTGGACGAGGCGTAGAGGTTGCrGGTTA/3SpC3/ (SEQ ID NO. 32) |
| Upstream LDR ver-A | iCDx-2033A-VIM-S3-Up | TAGACACGAGCGAGGTCACAACTCCAACCGAAACTACGTAACTGCGrUCCGT/3SpC3/ (SEQ ID NO. 36) |
| Upstream LDR ver-B | iCDx-2033B-VIM-S3-Up | /5SpC3/TAGACACGAGCGAGGTCACAACTCCAACCGAAACTACGTAACTGCGrUCCGT/3SpC3/ (SEQ ID NO. 41) |
| Upstream LDR ver-D | iCDx-2033D-VIM-S3-Up | /5SpC3/TAGACACGAGCGAGGTCACAACTCCAACCGAAACTACGTAACTGCGrUCTAT/3SpC3/ (SEQ ID NO. 42) |
| Downstream LDR ver-A | iCDx-2034A-VIM-S3-Dn | /5Phos/TCCACCCGCACCTACAACCTAAACAACGCGTGCAAAATTCAGGCTGTGCA (SEQ ID NO. 37) |
| Downstream LDR ver-D | iCDx-2034D-VIM-S3-Dn | /5Phos/TCCGCCCGCACCTACAACCTAAACAACGCGCTGTGCAAAATTCAGGCTGTGCA (SEQ ID NO. 43) |
| Real Time probe ver-B | iCDx-2035B-VIM-S3-RT-Pb | /5HEX/TTTAACTGC/ZEN/GTCCACCCGCACCTAC/3IABkFQ/ (SEQ ID NO. 44) |
| Real Time Probe ver-D | iCDx-2035D-VIM-S3-RT-Pb | /5HEX/TTTAACTGC/ZEN/GTCCGCCCGCACCTAC/3IABkFQ/ (SEQ ID NO. 45) |

TABLE 28 -continued

Methylation Detection Oligonucleotides

| Step | Name | Sequence |
|---|---|---|
| Real-Time Probe ver-A | iCDx-2035A-VIM-S3-RT-Pb | /5HEX/TAACTGCGT/ZEN/CCACCCGCACCTAC/3IABkFQ/ (SEQ ID NO. 38) |
| Tag Forward Primer | iCDx-2036-VIM-S3-RT-FP | TAGACACGAGCGAGGTCAC (SEQ ID NO. 39) |
| Tag Reverse Primer | iCDx-2037-VIM-S3-RT-RP | TGCACAGCCTGAATTTTGCAC (SEQ ID NO. 40) |
| LNA Blocking Probe 1 | VIM-S3-LNA1 | CA+TAA+CT+AC+AT+CC+AC+CCA (SEQ ID NO. 33) |
| LNA Blocking Probe 2 | VIM-S3-LNA2 | CA+TAA+CT+AC+AT+C+C+AC+CCA (SEQ ID NO. 34) |
| PNA Blocking Probe 2 | VIM-S3-PNA2 | ACATAACTACATCCACCCA (SEQ ID NO. 35) |

TMEM-S1
Bottom Strand

| Step | Name | Sequence |
|---|---|---|
| Forward Primer PCR | iCDx-2051-TMEM90B-REV-S1-FP | GTTAGATATTGGTCGCGGGTTATTATTTGrGACGA/3SpC3/ (SEQ ID NO. 57) |
| Reverse Primer PCR | iCDx-2052-TMEM90B-REV-S1-RP | GGTGTCGTGGGCAACCCGCGCGAAAArTAACT/3SpC3/ (SEQ ID NO. 58) |
| Upstream LDR ver-B | iCDx-2053B-TMEM90B-REV-S1-Up | /5SpC3/TGCTTACCCACGATGCACCCGCGGGTTATTATTTGGAAGCrGATCC/3SpC3/ (SEQ ID NO. 59) |
| Upstream LDR ver-D | iCDx-2053D-TMEM90B-REV-S1-Up | /5SpC3/TGCTTACCCACGATGCACCCGCGGGTTATTATTTGGAAGCrGACTC/3SpC3/ (SEQ ID NO. 60) |
| Upstream LDR ver-A | iCDx-2053A-TMEM90B-REV-S1-Up | TGCTTACCCACGATGCACCCGCGGGTTATTATTTGGAAGCrGATCC/3SpC3/ (SEQ ID NO. 61) |
| Downstream LDR ver-D | iCDx-2054D-TMEM90B-REV-S1-Dn | /5Phos/GATCTTTCGTTAGGGTTTTTTTGGTTTGGGTTAAGTTGGTGGGTCGTATGACTTGCTCGCA (SEQ ID NO. 62) |
| Downstream LDR ver-A | iCDx-2054A-TMEM90B-REV-S1-Dn | /5Phos/GATTTTTCGTTAGGGTTTTTTTGGTTTGGGTTAAGTTGGTCGTATGACTTGCTCGCA (SEQ ID NO. 63) |
| Real Time probe ver-B | iCDx-2055B-TMEM90B-REV-S1-RT-Pb | /56-FAM/AATGGAAGC/ZEN/GATTTTTCGTTAGGGTTTTTTG/3IABkF0/ (SEQ ID NO: 138) |
| Real Time Probe ver-D | iCDx-2055D-TMEM90B-REV-S1-RT-Pb | /56-FAM/AATGGAAGC/ZEN/GATCTTTCGTTAGGGTTTTTTG/3IABkF0/ (SEQ ID NO. 64) |
| Real-Time Probe ver-A | iCDx-2055A-TMEM90B-REV-S1-RT-Pb | /56-FAM/ATTTGGAAG/ZEN/CGATTTTTCGTTAGGGTTTT/3IABkFQ/ (SEQ ID NO. 65) |
| Tag Forward Primer | iCDx-2056-TMEM90B-REV-S1-RT-FP | TGCTTACCCACGATGCACC (SEQ ID NO. 66) |
| Tag Reverse Primer | iCDx-2057-TMEM90B-REV-S1-RT-RP | TGCGAGCAAGTCATACGACC (SEQ ID NO. 67) |
| LNA Blocking Probe 1 | iCDx-2058-TMEM90B-REV-S1-LNA | AT+TT+GG+A+T+G+T+GA+TTTTT+T+GTT+AG (SEQ ID NO. 68) |

TMEM-S3
Bottom Strand

| Step | Name | Sequence |
|---|---|---|
| Forward Primer PCR | iCDx-2061-TMEM90B-REV-S3-FP | TTTGGGTTGTATTTTGGTGTTTTGTTrATTTA/3SpC3/ (SEQ ID NO. 69) |
| Reverse Primer PCR | iCDx-2062-TMEM90B-REV-S3-RP | GGTGTCGTGGCTAACTCCGCTACGCTCTCAArUTCTA/3SpC3/ (SEQ ID NO. 70) |
| Upstream LDR ver-B | iCDx-2063B-TMEM90B-REV-S3-Up | /5SpC3/TTCGCCTACCGCAGTGAACTGGGTTGTATTTTGGTGTTTTGTTATCTCrGGGGA/3SpC3/ (SEQ ID NO. 71) |
| Upstream LDR ver-D | iCDx-2063D-TMEM90B-REV-S3-Up | /5SpC3/TTCGCCTACCGCAGTGAACTGGGTTGTATTTTGGTGTTTTGTTATCTCrGGAAA/3SpC3/ (SEQ ID NO. 72) |
| Upstream LDR ver-A | iCDx-2063A-TMEM90B-REV-S3-Up | TTCGCCTACCGCAGTGAACTGGGTTGTATTTTGGTGTTTTGTTATCTCrGGGGA/3SpC3/ (SEQ ID NO. 73) |
| Downstream LDR ver-D | iCDx-2064D-TMEM90B-REV-S3-Dn | /5Phos/GGGTGACGCGAAGGGGTTGTTGTGCGAAGTTGAGACATGGGCTCGCA (SEQ ID NO. 74) |
| Downstream LDR ver-A | iCDx-2064A-TMEM90B-REV-S3-Dn | /5Phos/GGGAGACGCGAAGGGGTTGTTGTGGTTGAGACATGGGCTCGCA (SEQ ID NO. 75) |
| Real Time probe ver-B | iCDx-2065B-TMEM90B-REV-S3-RT-Pb | /5HEX/AATTATCTC/ZEN/GGGAGACGCGAAGGG/3IABkFQ/ (SEQ ID NO. 76) |
| Real Time Probe ver-D | iCDx-2065D-TMEM90B-REV-S3-RT-Pb | /5HEX/AATTATCTC/ZEN/GGGTGACGCGAAGGG/3IABkFQ/ (SEQ ID NO. 77) |
| Real-Time Probe ver-A | iCDx-2065A-TMEM90B-REV-S3-RT-Pb | /5HEX/TTTTGTTAT/ZEN/CTCGGGAGACGCGAAGGG/3IABkFQ/ (SEQ ID NO. 78) |
| Tag Forward Primer | iCDx-2066-TMEM90B-REV-S3-RT-FP | TTCGCCTACCGCAGTGAAC (SEQ ID NO. 79) |
| Tag Reverse Primer | iCDx-2067-TMEM90B-REV-S3-RT-RP | TGCGAGCCCATGTCTCAAC (SEQ ID NO. 80) |
| LNA Blocking Probe 1 | iCDx-2068-TMEM90B-REV-S3-LNA | TTGTTATT+T+T+GGGAGA+T+G+T+GAAG (SEQ ID NO. 81) |

TABLE 28 -continued

Methylation Detection Oligonucleotides

| Step | Name | Sequence |
|---|---|---|
| VIM-S2 Bottom Strand | | |
| Forward Primer PCR | iCDx-2071-VIM-REV-S2-FP | GGTTTAGTTTTTGTTATTTTCGTTTCGAGGrUTTTA/3SpC3/ (SEQ ID NO. 82) |
| Reverse Primer PCR | iCDx-2072-VIM-REV-S2-RP | GGTGTCGTGGGACGATAACGCGAACTAACTCrCCGAG/3SpC3/ (SEQ ID NO. 83) |
| Upstream LDR ver-B | iCDx-2073B-VIM-REV-S2-Up | /5SpC3/TTGCAACAGGCTACCGACCGTTTTTTGTTATTT TCGTTTCGAGGTTCTCrGCGCC/3SpC3/ (SEQ ID NO. 84) |
| Upstream LDR ver-A | iCDx-2073A-VIM-REV-S2-Up | TTGCAACAGGCTACCGACCGTTTTTTGTTATTTTCGTTT CGAGGTTCTCrGCGCC/3SpC3/ (SEQ ID NO. 85) |
| Downstream LDR | iCDx-2074-VIM-REV-S2-Dn | /5Phos/GCGTTAGAGACGTAGTCGCGTTTTATTATTTA TATTTATCGCGGGTAGGTAAGGAAGTCACGCA (SEQ ID NO. 86) |
| Real Time probe ver-B | iCDx-2075B-VIM-REV-S2-RT-Pb | /56-FAM/AG GTT CTC G/ZEN/C GTT AGA GAC GTA GTC G/3IABkFQ/ (SEQ ID NO. 87) |
| Real-Time Probe ver-A | iCDx-2075A-VIM-REV-S2-RT-Pb | /56-FAM/ATTTTCGTT/ZEN/TCGAGGTTCTCGCGTTAGAGA/3IABkFQ/ (SEQ ID NO. 88) |
| Tag Forward Primer | iCDx-2076-VIM-REV-S2-RT-FP | TTGCAACAGGCTACCGACC (SEQ ID NO. 89) |
| Tag Reverse Primer | iCDx-2077-VIM-REV-S2-RT-RP | TGCGTGACTTCCTTACCTACC (SEQ ID NO. 90) |
| LNA Blocking Probe 1 | iCDx-2078-VIM-REV-S2-LNA | TTT+T+GAG+GTTTT+T+G+T+GTTAGAGA+T+GTA (SEQ ID NO. 91 |
| VIM-S3 Bottom Strand | | |
| Forward Primer PCR | iCDx-2081-VIM-REV-S3-FP | GTCGAGTTTTAGTCGGAGTTACGTGrATTAA/3SpC3/ (SEQ ID NO. 92) |
| Reverse Primer PCR | iCDx-2082-VIM-REV-S3-RP | GGTGTCGTGGGAAAACGAAACGTAAAAACTACGACTA ArUACTG/3SpC3/ (SEQ ID NO. 93) |
| Upstream LDR ver-B | iCDx-2083B-VIM-REV-S3-Up | /5SpC3/TGGATCGAGACGGAATGCAACCGAGTTTTAGT CGGAGTTACGTGATCACrGTTCG/3SpC3/ (SEQ ID NO. 94) |
| Upstream LDR ver-D | iCDx-2083D-VIM-REV-S3-Up | /5SpC3/TGGATCGAGACGGAATGCAACCGAGTTTTAGT CGGAGTTACGTGATCACrGTCTG/3SpC3/ (SEQ ID NO. 95) |
| Upstream LDR ver-A | iCDx-2083A-VIM-REV-S3-Up | TGGATCGAGACGGAATGCAACCGAGTTTTAGTCGGAG TTACGTGATCACrGTTCG/3SpC3/ (SEQ ID NO. 96) |
| Downstream LDR ver-D | iCDx-2084D-VIM-REV-S3-Dn | /5Phos/GTTCATTCGTATTTATAGTTTGGGTAGCGCGTT GCGTTTTGTTTCCCTGATTGATACCCGCA (SEQ ID NO. 97) |
| Downstream LDR ver-A | iCDx-2084A-VIM-REV-S3-Dn | /5Phos/GTTTATTCGTATTTATAGTTTGGGTAGCGCGTT GCGGTTTCCCTGATTGATACCCGCA (SEQ ID NO. 98) |
| Real Time probe ver-B | iCDx-2085B-VIM-REV-S3-RT-Pb | /5HEX/TTTGATCAC/ZEN/GTTTATTCGTATTTATAGTTT GGGTAGCGC/3IABkFQ/ (SEQ ID NO. 99) |
| Real Time Probe ver-D | iCDx-2085D-VIM-REV-S3-RT-Pb | /5HEX/TTTGATCAC/ZEN/GTTCATTCGTATTTATAGTTT GGGTAGCGC/3IABkFQ/ (SEQ ID NO. 100) |
| Real-Time Probe ver-A | iCDx-2085A-VIM-REV-S3-RT-Pb | /5HEX/AGTCGGAGT/ZEN/TACGTGATCACGTTTATTCG TATTTATAG/3IABkFQ/ (SEQ ID NO. 101) |
| Tag Forward Primer | iCDx-2086-VIM-REV-S3-RT-FP | TGGATCGAGACGGAATGCAAC (SEQ ID NO. 102) |
| Tag Reverse Primer | iCDx-2087-VIM-REV-S3-RT-RP | TGCGGGTATCAATCAGGGAAAC (SEQ ID NO. 103) |
| LNA Blocking Probe 1 | iCDx-2088-VIM-REV-S3-LNA | GTT+A+T+GT+G+ATT+A+T+GT+TT+AT+T+GT+ATTT (SEQ ID NO. 104) |
| TMEM90B-S1 Top Strand | | |
| Forward Primer PCR | iCDx-2101-TMEM90B-F-S1-FP | CTAACCGCGAACCACCATCTAArACGCT/3SpC3/ (SEQ ID NO. 105) |
| Reverse Primer PCR | iCDx-2102-TMEM90B-F-S1-RP | GGTGTCGTGGTTCGCGCGAAGGTGGTTArUTAAC/3SpC3/ (SEQ ID NO. 106) |
| Upstream LDR ver-B | iCDx-2103B-TMEM90B-F-S1-Up | /5SpC3/TTGCATTTCGTTAGCGACACAGCGAACCACCA TCTAAACACGrATCTT/3SpC3/ (SEQ ID NO. 107) |
| Upstream LDR ver-D | iCDx-2103D-TMEM90B-F-S1-Up | /5SpC3/TTGCATTTCGTTAGCGACACAGCGAACCACCA TCTAAACACGrATTCT/3SpC3/ (SEQ ID NO. 108) |
| Upstream LDR ver-A | iCDx-2103A-TMEM90B-F-S1-Up | TTGCATTTCGTTAGCGACACAGCGAACCACCATCTAAA CACGrATCTT/3SpC3/ (SEQ ID NO. 109) |

TABLE 28 -continued

Methylation Detection Oligonucleotides

| Step | Name | Sequence |
|---|---|---|
| Downstream LDR ver-D | iCDx-2104D-TMEM90B-F-S1-Dn | /5Phos/ATCTCCCGCTAAAACCTCCCTAATCTAAACCAA AATTAATGTGAGTCGATCTACCCGCA (SEQ ID NO. 110) |
| Downstream LDR ver-A | iCDx-2104A-TMEM90B-F-S1-Dn | /5Phos/ATCCCCCGCTAAAACCTCCCTAATCTAAACCTG TGAGTCGATCTACCCGCA (SEQ ID NO. 111) |
| Real Time probe ver-B | iCDx-2105B-TMEM90B-F-S1-RT-Pb | /56-FAM/AAAAACACG/ZEN/ATCCCCGCTAAAACCT/3IABkFQ/ (SEQ ID NO. 112) |
| Real Time Probe ver-D | iCDx-2105D-TMEM90B-F-S1-RT-Pb | /56-FAM/AAAAACACG/ZEN/ATCTCCCGCTAAAACCTCC/3IABkFQ/ (SEQ ID NO. 113) |
| Real-Time Probe ver-A | iCDx-2105A-TMEM90B-F-S1-RT-Pb | /56-FAM/CATCTAAAC/ZEN/ACGATCCCCGCTAA/3IABkFQ/ (SEQ ID NO. 114) |
| Tag Forward Primer | iCDx-2106-TMEM90B-F-S1-RT-FP | TTGCATTTCGTTAGCGACACA (SEQ ID NO. 115) |
| Tag Reverse Primer | iCDx-2107-TMEM90B-F-S1-RT-RP | TGCGGGTAGATCGACTCACA (SEQ ID NO. 116) |
| LNA Blocking Probe 1 | iCDx-2108-TMEM90B-F-S1-LNA | CTAAA+C+A+C+A+ATCCCC+C+A+CT (SEQ ID NO. 117) |

TMEM90B-53
Top Strand

| Step | Name | Sequence |
|---|---|---|
| Forward Primer PCR | iCDx-2111-TMEM90B-F-53-FP | CTAACCTAAACTACACCTTAATACCTTACCArCCCCT/3SpC3/ (SED ID NO. 118) |
| Reverse Primer PCR | iCDx-2112-TMEM90B-F-53-RP | GGTGTCGTGGTTTTGTTGGGTAGTTTGGTTTCGTTArCGTTC/3SpC3/ (SEQ ID NO. 119) |
| Upstream LDR ver-B | iCDx-2113B-TMEM90B-F-53-Up | /5SpC3/TGGATCGAGACGGAATGCAACCTACACCTTAATACCTTACCACCTCGrAAAGG/3SpC3/ (SEQ ID NO. 120) |
| Upstream LDR ver-D | iCDx-2113D-TMEM90B-F-53-Up | /5SpC3/TGGATCGAGACGGAATGCAACCTACACCTTAATACCTTACCACCTCGrAAGAG/3SpC3/ (SEQ ID NO. 121) |
| Upstream LDR ver-A | iCDx-2113A-TMEM90B-F-53-Up | TGGATCGAGACGGAATGCAACCTACACCTTAATACCTTACCACCTCGrAAAGG/3SpC3/ (SEQ ID NO. 122) |
| Downstream LDR ver-D | iCDx-2114D-TMEM90B-F-53-Dn | /5Phos/AAAGACGCGAAAAAACTACTATACGAATTCGATAAAAACTAATAAAACCGAAAACTGTTTCCCTGATTGATACCCGCA (SEQ ID NO. 123) |
| Downstream LDR ver-A | iCDx-2114A-TMEM90B-F-53-Dn | /5Phos/AAAAACGCGAAAAAACTACTATACGAATTCGATAAAAACTAATAAAACCGTTTCCCTGATTGATACCCGCA (SEQ ID NO. 124) |
| Real Time probe ver-B | iCDx-2115B-TMEM90B-F-53-RT-Pb | /5HEX/TTCACCTCG/ZEN/AAAAACGCGAAAAAACTACT/3IABkFQ/ (SEQ ID NO. 125) |
| Real Time Probe ver-D | iCDx-2115D-TMEM90B-F-53-RT-Pb | /5HEX/TTCACCTCG/ZEN/AAAGACGCGAAAAAACTACTATACG/3IABkFQ/ (SEQ ID NO. 126) |
| Real-Time Probe ver-A | iCDx-2115A-TMEM90B-F-53-RT-Pb | /5HEX/CCTTACCAC/ZEN/CTCGAAAAACGCGAA/3IABkFQ/ (SEQ ID NO. 127) |
| Tag Forward Primer | iCDx-2116-TMEM90B-F-53-RT-FP | TGGATCGAGACGGAATGCAAC (SEQ ID NO. 128) |
| Tag Reverse Primer | iCDx-2117-TMEM90B-F-53-RT-RP | TGCGGGTATCAATCAGGGAAAC (SEQ ID NO. 129) |
| LNA Blocking Probe 1 | iCDx-2118-TMEM90B-F-S3-LNA | ACCACCC+C+A+AAAAA+C+A+C+AA (SEQ ID NO. 130) |

/5SpC3/-5' C3 Spacer,
/3SpC3/-3' C3 Spacer,
/5Phos/-5' Phosphate,
/56-FAM/-5' Fam Flourescent Dye,
/5HEX/-HEX ™ Fluorescent Dye,
/ZEN/-ZEN ™ Flourescent Quencher ™,
/3IABkFQ/-3' Iowa Black ® Flourescent Quencher, green to pink spectral range,
"+"-Locked Nucleic Acid base,
"rA"-ribonucleotide base riboadenosine;
"rT"-ribonucleotide ribocytosine ribothymidine;
"rG"-ribonucleotide base riboguanosine;
"rC"-ribonucleotide base

What is claimed is:

1. A method for identifying in a sample, one or more target ribonucleic acid molecules differing in sequence from other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level, said method comprising:

providing a sample containing one or more target ribonucleic acid molecules potentially differing in sequence from other ribonucleic acid molecules;

contacting the sample with one or more enzymes capable of digesting dU containing nucleic acid molecules potentially present in the sample;

providing one or more oligonucleotide primers, each primer being complementary to the one or more target ribonucleic acid molecules;

blending the contacted sample, the one or more oligonucleotide primers, a deoxynucleotide mix including dUTP, and a reverse-transcriptase to form a reverse-transcription mixture;

generating complementary deoxyribonucleic acid (cDNA) molecules in the reverse transcription mixture, each cDNA molecule comprising a nucleotide sequence that is complementary to the target ribonucleic acid molecule and contains dU;

providing one or more oligonucleotide primer sets, each primer set comprising (a) a first oligonucleotide primer comprising a nucleotide sequence that is complementary to a portion of a cDNA nucleotide sequence adjacent to the target ribonucleic acid molecule sequence complement of the cDNA, and (b) a second oligonucleotide primer comprising a nucleotide sequence that is complementary to a portion of an extension product formed from the first oligonucleotide primer;

blending the reverse transcription mixture containing the cDNA molecules, the one or more oligonucleotide primer sets, a deoxynucleotide mix including dUTP, and a polymerase to form a polymerase reaction mixture;

subjecting the polymerase chain reaction mixture to one or more polymerase chain reaction cycles comprising a denaturation treatment, a hybridization treatment, and an extension treatment thereby forming one or more different primary extension products;

providing one or more oligonucleotide probe sets, each probe set comprising (a) a first oligonucleotide probe having a 5' primer-specific portion and a 3' target sequence-specific portion, and (b) a second oligonucleotide probe having a 5' target sequence-specific portion and a 3' primer-specific portion, wherein the first and second oligonucleotide probes of a probe set are configured to hybridize, in a base specific manner, on complementary portions of a primary extension product corresponding to the target ribonucleic acid molecule sequence;

contacting the primary extension products with a ligase and the one or more oligonucleotide probe sets to form a ligation reaction mixture;

subjecting the ligation reaction mixture to one or more ligation reaction cycles whereby the first and second probes of the one or more oligonucleotide probe sets are ligated together to form ligated product sequences in the ligase reaction mixture, wherein each ligated product sequence comprises the 5' primer-specific portion, the target-specific portions, and the 3' primer-specific portion;

providing one or more secondary oligonucleotide primer sets, each secondary oligonucleotide primer set comprising (a) a first secondary oligonucleotide primer comprising the same nucleotide sequence as the 5' primer-specific portion of the ligated product sequence and (b) a second secondary oligonucleotide primer comprising a nucleotide sequence that is complementary to the 3' primer-specific portion of the ligated product sequence;

blending the ligated product sequences, the one or more secondary oligonucleotide primer sets with one or more enzymes capable of digesting deoxyuracil (dU) containing nucleic acid molecules, a deoxynucleotide mix including dUTP, and a DNA polymerase to form a second polymerase chain reaction mixture;

subjecting the second polymerase chain reaction mixture to conditions suitable for digesting deoxyuracil (dU) containing nucleic acid molecules present in the second polymerase chain reaction mixture, and one or more polymerase chain reaction cycles comprising a denaturation treatment, a hybridization treatment, and an extension treatment thereby forming secondary extension products; and detecting and distinguishing the secondary extension products in the sample thereby identifying the presence of one or more ribonucleic acid molecules differing in sequence from other ribonucleic acid molecules in the sample due to alternative splicing, alternative transcript, alternative start site, alternative coding sequence, alternative non-coding sequence, exon insertion, exon deletion, intron insertion, translocation, mutation, or other rearrangement at the genome level.

2. The method of claim 1, wherein the second oligonucleotide probe of the oligonucleotide probe set further comprises a unitaq detection portion, thereby forming ligated product sequences comprising the 5' primer-specific portion, the target-specific portions, the unitaq detection portion, and the 3' primer-specific portion, said method further comprising:

providing one or more unitaq detection probes, wherein each unitaq detection probe hybridizes to a complementary unitaq detection portion and said detection probe comprises a quencher molecule and a detectable label that are separated from each other;

adding the one or more unitaq detection probes to the second polymerase chain reaction mixture; and hybridizing the one or more unitaq detection probes to complementary unitaq detection portions on the ligated product sequence or complement thereof during said subjecting the second polymerase chain reaction mixture to conditions suitable for one or more polymerase chain reaction cycles, whereby the quencher molecule and the detectable label are cleaved from the one or more unitaq detection probes during the extension treatment, whereby said detecting involves the detection of the cleaved detectable label.

3. The method of claim 1, said method further comprising:

providing one or more oligonucleotide detection probes, wherein each oligonucleotide detection probe hybridizes to a ligation product junction portion or its complement, and said detection probe comprises a quencher molecule and a detectable label that are separated from each other;

adding the one or more oligonucleotide detection probes to the second polymerase chain reaction mixture; and hybridizing the one or more oligonucleotide detection probes to complementary detection portions on the ligated product sequence or complement thereof during said subjecting the second polymerase chain reaction mixture to conditions suitable for one or more polymerase chain reaction cycles, whereby the quencher molecule and the detectable label are cleaved from the one or more oligonucleotide detection probes during said extension treatment, whereby said detecting involves the detection of the cleaved detectable label.

* * * * *